United States Patent
Qian et al.

(10) Patent No.: US 11,530,222 B2
(45) Date of Patent: Dec. 20, 2022

(54) SUBSTITUTED PYRROLOPYRIMIDINE AND PYRAZOLOPYRIMIDINE AS BRUTON'S TYROSINE KINASE (BTK) DEGRADERS

(71) Applicant: ACCUTAR BIOTECHNOLOGY INC., Brooklyn, NY (US)

(72) Inventors: Yimin Qian, Plainsboro, NJ (US); Wei He, Zionsville, IN (US); Robert Luo, New City, NY (US); Jie Su, New York, NY (US); Hui Zhang, New York, NY (US); Ke Liu, Shanghai (CN); Jie Fan, New York, NY (US)

(73) Assignee: Accutar Biotechnology Inc., Brooklyn, NY (US)

( * ) Notice: Subject to any disclaimer, the term of this patent is extended or adjusted under 35 U.S.C. 154(b) by 35 days.

(21) Appl. No.: 17/591,051

(22) Filed: Feb. 2, 2022

(65) Prior Publication Data

US 2022/0259207 A1     Aug. 18, 2022

Related U.S. Application Data

(60) Provisional application No. 63/145,126, filed on Feb. 3, 2021.

(51) Int. Cl.
    *A61K 31/45*     (2006.01)
    *C07D 211/40*    (2006.01)
    *C07D 487/04*    (2006.01)

(52) U.S. Cl.
    CPC ................. *C07D 487/04* (2013.01)

(58) Field of Classification Search
    CPC ........................ A61K 31/45; C07D 211/40
    USPC ........................... 514/326; 546/243
    See application file for complete search history.

(56) References Cited

FOREIGN PATENT DOCUMENTS

CN     112812100     *   5/2021

OTHER PUBLICATIONS

Jordan, V. C. Nature Reviews: Drug Discovery, 2, 2003, 205.*
Vippagunta, et al. Advanced Drug Delivery Reviews, 48, 2001, 18.*

* cited by examiner

*Primary Examiner* — Douglas M Willis
(74) *Attorney, Agent, or Firm* — Finnegan, Henderson, Farabow, Garrett & Dunner, LLP

(57) ABSTRACT

The present disclosure relates to novel compounds of Formula (I) that degrade Bruton's tyrosine kinase (BTK), pharmaceutical compositions containing such compounds, and their use in prevention and treatment of conditions modulated by BTK.

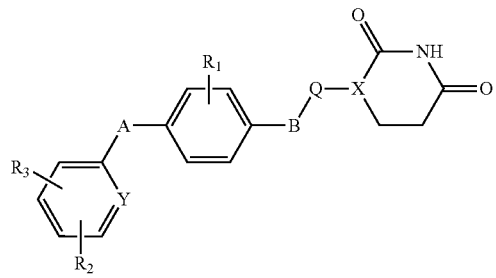

(I)

30 Claims, 2 Drawing Sheets

SUBSTITUTED PYRROLOPYRIMIDINE AND PYRAZOLOPYRIMIDINE AS BRUTON'S TYROSINE KINASE (BTK) DEGRADERS

This application claims priority from U.S. Provisional Patent Application No. 63/145,126, filed Feb. 3, 2021, which is hereby incorporated by reference in its entirety.

FIELD OF THE DISCLOSURE

The present invention relates to compounds that modulate Bruton's tyrosine kinase (BTK). In particular, the present invention relates to compounds that have a degrading effect on BTK, pharmaceutical compositions comprising the compounds and methods of use therefor.

BACKGROUND OF THE DISCLOSURE

Signaling through the B-cell receptor (BCR) can lead to a range of biological outputs depending upon, in part, the developmental stage of the B-cell. Faulty signaling through the BCR can cause dysregulation of the B-cell function and/or the formation of auto-antibodies which may lead to the auto-immune and/or inflammatory diseases. Therapeutics, such as Rituxan, which deplete B-cells are effective in the treatment of inflammatory diseases such as rheumatoid arthritis.

BTK is a Tec family non-receptor protein kinase, expressed in most hematopoietic cells such as B cells, mast cells, and macrophages but not in T cells, natural killer cells, and plasma cells. See, Smith, C. I. et al. *J Immunology*, 152 (2), 557-65 (1994). BTK is a crucial part of the BCR and FcR signaling pathway, and the targeted inhibition of BTK is a novel approach for treating many different human diseases such as B-cell malignancies, autoimmune disease, and inflammatory disorders. See, e.g., Uckun, Fatih M. et al, *Anti-Cancer Agents in Med Chem.* 7(6):624-632 (2007); Shinohara et al, *Cell* 132(5):794-806 (2008); Pan, Z., *Drug News & Perspectives*, 21(7):357-362 (2008); Gilfillan et al, *Immuno. Rev.* 228(1):149-169 (2009); Davis R E et al, *Nature*, 463:88-92 (2010). BTK plays a role in the development and activation of B cells and has been implicated in multiple signaling pathways across a wide range of immune-mediated diseases. BTK activity has been implicated in the pathogenesis of several disorders and conditions, such as B cell-related hematological cancers (e.g., non-Hodgkin lymphoma and B cell chronic lymphocytic leukemia) and auto-immune diseases (e.g., rheumatoid arthritis, Sjogren's syndrome, pemphigus, inflammatory bowel disease, lupus, and asthma).

SUMMARY OF THE DISCLOSURE

In some embodiments, the present disclosure is directed to a compound of Formula (I), or a tautomer, stereoisomer or a mixture of stereoisomers, or a pharmaceutically acceptable salt, or hydrate, or deuterated derivative thereof:

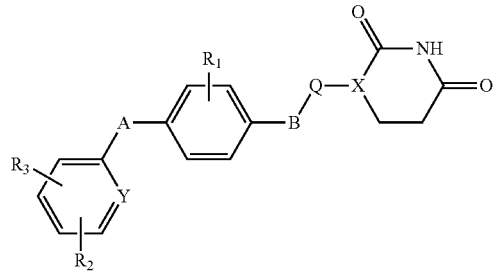

wherein:

X is CH or N;

Y is CH or N;

A is chosen from —C(O)—, —SO$_2$—, —S(O)—, —O—, —S—, —NH—, —N(C$_1$-C$_5$alkyl)-, and —C(O)NH(C$_1$-C$_5$alkyl)-;

B is

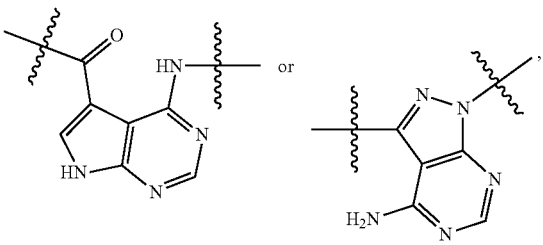 [SMILES: *Nc1ncnc2[nH]cc(C(*)=O)c12 ; *c1nn(*)c2ncnc(N)c12]

with the proviso that when B is

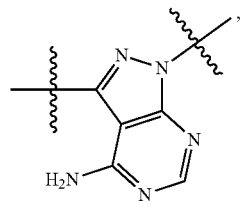 [SMILES: *c1nn(*)c2ncnc(N)c12]

A is not O—;

R$_1$ is chosen from H, C$_1$-C$_3$ alkyl, C$_1$-C$_3$haloalkyl, dialkylamino group, amino group, —CN, hydroxyl, C$_1$-C$_4$alkoxy, and halogen;

each R$_2$ and R$_3$ is independently chosen from H, halogen, —CN, hydroxyl, dialkylamino group, C$_1$-C$_5$alkyl, C$_1$-C$_5$alkoxy, deuterated C$_1$-C$_5$ alkyl, deuterated C$_1$-C$_5$alkoxy, and C$_1$-C$_5$haloalkyl;

Q is L-W$_1$ or L-W$_2$;

wherein

L is a linker of 2 to 20 carbon atoms in length, wherein one or more carbon atoms are optionally and independently replaced by a group chosen from C(=O), O, N(R$_6$), S, S(O), SO$_2$, C(O)NH, C(O)NCH$_3$, C(O)NCH$_2$CH$_3$, C$_2$-alkenyl, C$_2$-alkynyl, cycloalkyl, heterocycloalkyl, heterocycle, aryl, or heteroaryl, wherein each are independently substituted with 0, 1, 2 or 3 R$_7$;

$W_1$ is chosen from

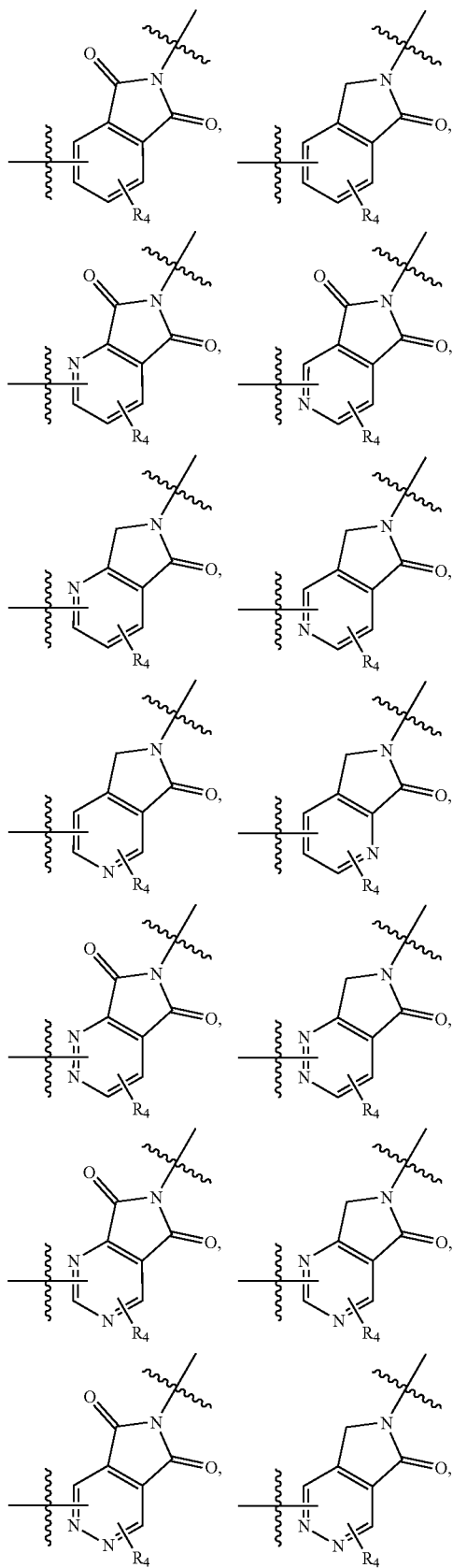

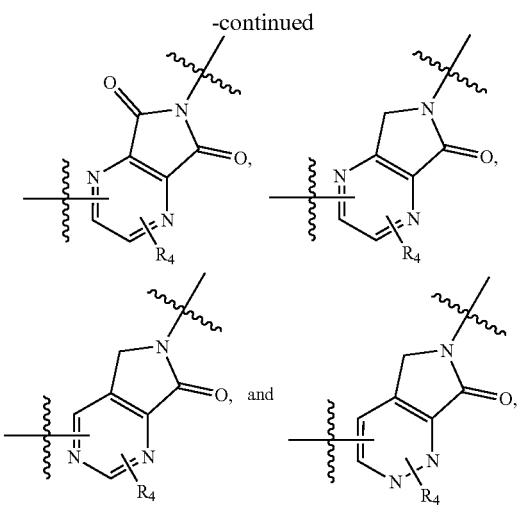

wherein $R_4$ is chosen from H, halogen, —CN, $C_1$-$C_5$alkyl, $C_1$-$C_5$alkoxy, and $C_1$-$C_5$haloalkyl; and $W_2$ is

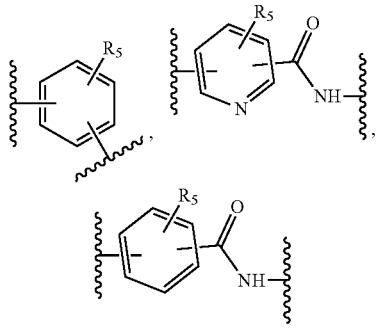

or is absent, wherein $R_5$ is chosen from H, halogen, —CN, $C_1$-$C_5$alkyl, deuterated $C_1$-$C_5$ alkyl, $C_1$-$C_5$alkoxy, deuterated $C_1$-$C_5$alkoxy, and $C_1$-$C_5$haloalkyl;

each $R_6$ is independently chosen from H, $C_1$-$C_3$alkyl, —C(=O)—($C_1$-$C_3$alkyl), —C(=O)—O—($C_1$-$C_3$alkyl), and —C(=O)—NH—($C_1$-$C_3$alkyl), each of which is substituted with 0, 1, 2, or 3 $R_7$; each $R_7$ is independently chosen from halogen, hydroxyl, amino group, $C_1$-$C_3$alkyl, $C_1$-$C_3$alkoxy, $C_1$-$C_3$haloalkyl, —N($R_6$)$_2$, and —CN.

In some embodiments, the compound of Formula (I) may be a compound of Formula (IA):

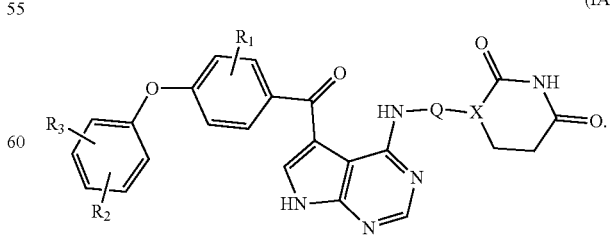

(IA)

In some embodiments, the compound of Formula (I) may be a compound of Formula (IB):

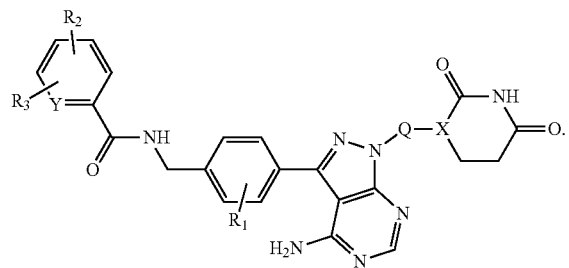

(IB)

In some embodiments, A is —O— or —C(O)—NH—CH$_2$—.

In some embodiments, R$_1$ is chosen from H, C$_1$-C$_3$ alkyl, C$_1$-C$_3$haloalkyl, and halogen.

In some embodiments, R$_2$ and R$_3$ are each independently chosen from H, —OCD$_3$, —CD$_3$, halogen, C$_1$-C$_4$alkyl, and C$_1$-C$_4$alkoxy.

In some embodiments, R$_4$ is chosen from H, halogen, —CN, and C$_1$-C$_4$haloalkyl.

In some embodiments, R$_5$ is chosen from H, halogen, deuterated C$_1$-C$_5$alkoxy, and C$_1$-C$_5$alkoxy.

In some embodiments, L is a linker of 2 to 12 carbon atoms in length, wherein one or more carbon atoms are optionally and independently replaced by a group selected from C(=O), O, S, S(O), SO$_2$, C(O)NH, C(O)NCH$_3$, C(O)NCH$_2$CH$_3$, NH, NCH$_3$, NCH$_2$CH$_3$, C$_2$-alkynyl,

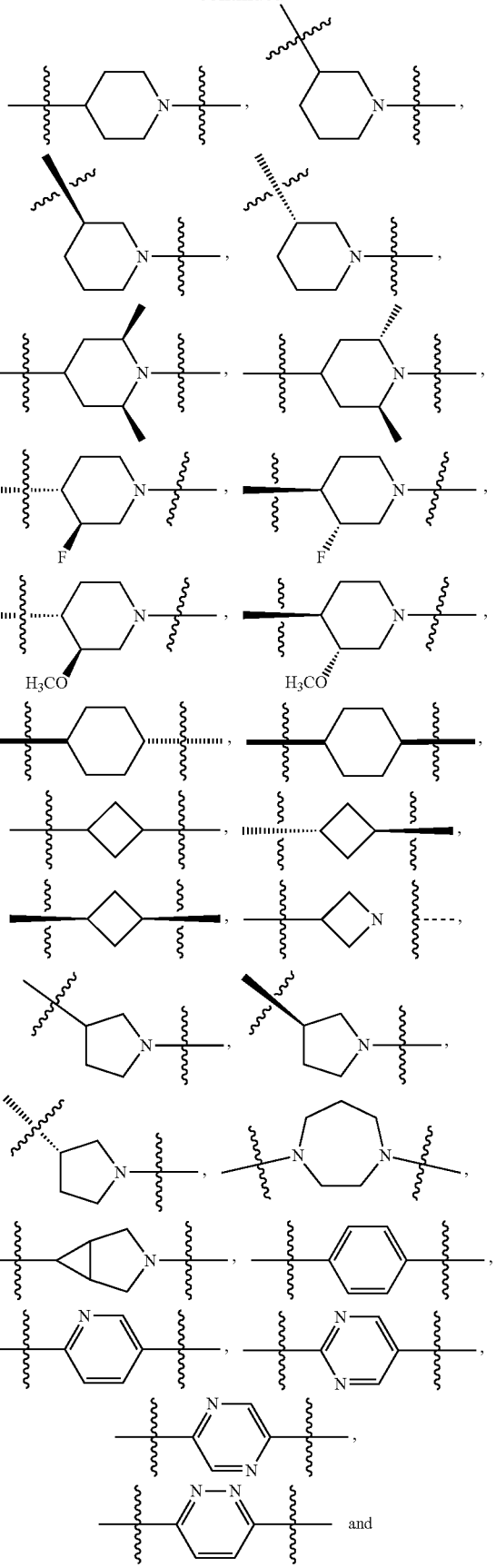

-continued

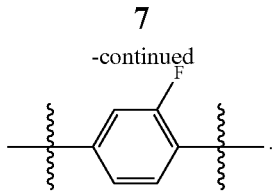

In some embodiments, the compound of Formula (I) (e.g. Formula (IA), Formula (IB)) may encompass both stereoisomers and a mixture of stereoisomers. In some embodiments, the compound of Formula (I) may encompass both racemic isomers and enantiomeric isomers.

Also disclosed herein is a method of treating a condition which is modulated by Bruton's tyrosine kinase (BTK) in a subject in need thereof, comprising administering to the subject a compound of Formula (I) (e.g. Formula (IA), Formula (IB)) or pharmaceutically acceptable salt thereof, or a pharmaceutical composition comprising a compound of Formula (I) or a pharmaceutically acceptable salt thereof. In at least one embodiment, the pharmaceutical composition of the present disclosure may be for use in (or in the manufacture of medicaments for) the treatment of cancer, immunological disease, autoimmune diseases, and inflammatory diseases in the subject in need thereof.

In at least one embodiment, a therapeutically effective amount of a pharmaceutical composition of the present disclosure may be administered to a subject suffering from a condition modulated by BTK. In some embodiments, the condition modulated by BTK is chosen from cancer, immunological disease, autoimmune diseases, and inflammatory disorders. In some embodiments, the condition is chosen from B-cell malignancy, B-cell lymphoma, diffuse large B cell lymphoma, chronic lymphocyte leukemia, non-Hodgkin lymphoma, mantle cell lymphoma, follicular lymphoma, hairy cell leukemia B-cell non-Hodgkin lymphoma, Waldenström's macroglobulinemia, multiple myeloma, bone cancer, bone metastasis, arthritis, multiple sclerosis osteoporosis, irritable bowel syndrome, inflammatory bowel disease, Crohn's disease, lupus, Sjogren's syndrome, and disorders associated with renal transplant.

BRIEF DESCRIPTION OF THE FIGURES

The foregoing summary, as well as the following detailed description of the disclosure, will be better understood when read in conjunction with the appended drawings. For the purpose of illustrating the present disclosure, the attached drawings illustrate some, but not all, alternative embodiments. It should be understood, however, that the disclosure is not limited to the precise arrangements and instrumentalities shown. These figures, which are incorporated into and constitute part of the specification, assist in explaining the principles of the disclosures.

DETAILED DESCRIPTION OF THE DISCLOSURE

Definitions

Figure 1:
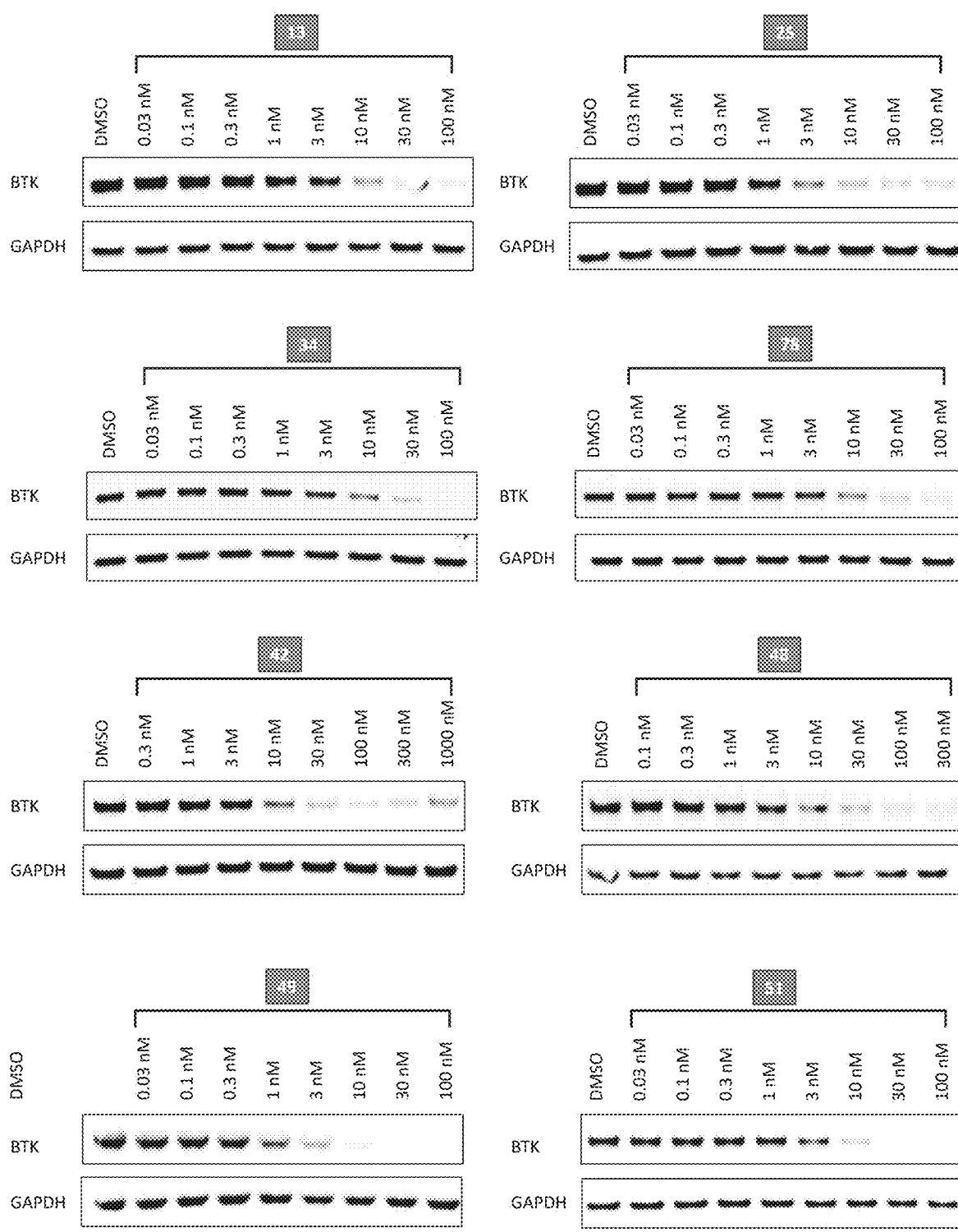
FIG. 1 illustrates the BTK degradative activity of compounds 13, 25, 34, 42, 48, 49, 51, and 78 in a RAMOS cell line 6 hours after administration.

A dash ("-") that is not between two letters or symbols is used to indicate a point of attachment for a substituent. For example, —CN is attached through the carbon atom.

When a range of values is listed, it is intended to encompass each value and sub-range within the range. For example, "$C_1$-$C_6$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "acyl" as used herein refers to R—C(O)— groups such as, but not limited to, (alkyl)-C(O)—, (alkenyl)-C(O)—, (alkynyl)-C(O)—, (aryl)-C(O)—, (cycloalkyl)-C(O)—, (heteroaryl)-C(O)—, and (heterocyclyl)-C(O)—, wherein the group is attached to the parent molecular structure through the carbonyl functionality. In some embodiments, it is a $C_{1-10}$ acyl radical which refers to the total number of chain or ring atoms of the, for example, alkyl, alkenyl, alkynyl, aryl, cycloalkyl, or heteroaryl, portion plus the carbonyl carbon of acyl. For example, a $C_4$-acyl has three other ring or chain atoms plus carbonyl.

The term "alkenyl" as used herein refers to an unsaturated straight or branched hydrocarbon having at least one carbon-carbon double bond, such as a straight or branched group of 2-8 carbon atoms, referred to herein as ($C_2$-$C_8$)alkenyl. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkyl" as used herein refers to a saturated straight or branched hydrocarbon, such as a straight or branched group of 1-8 carbon atoms, referred to herein as $C_{1-8}$ alkyl. Exemplary alkyl groups include, but are not limited to, methyl, ethyl, propyl, isopropyl, 2-methyl-1-propyl, 2-methyl-2-propyl, 2-methyl-1-butyl, 3 methyl-1-butyl, 2-methyl-3-butyl, 2,2-dimethyl-1-propyl, 2-methyl-1-pentyl, 3 methyl-1-pentyl, 4-methyl-1-pentyl, 2-methyl-2-pentyl, 3-methyl-2-pentyl, 4 methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl. In some embodiments, "alkyl" is a straight-chain hydrocarbon. In some embodiments, "alkyl" is a branched hydrocarbon.

The term "alkoxy" means a straight or branched chain saturated hydrocarbon containing 1-12 carbon atoms containing a terminal "O" in the chain, e.g., —O(alkyl). Examples of alkoxy groups include, without limitation, methoxy, ethoxy, propoxy, butoxy, t-butoxy, or pentoxy groups.

The term "alkylene" as used herein refers to a divalent alkyl radical. Representative examples of $C_{1-10}$ alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene.

The term "alkynyl" as used herein refers to an unsaturated straight or branched hydrocarbon having at least one carbon-carbon triple bond, such as a straight or branched group of 2-8 carbon atoms, referred to herein as ($C_2$-$C_8$)alkynyl. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "aryl" as used herein refers to a mono-, bi-, or other multi carbocyclic, aromatic ring system with 5 to 14 ring atoms. The aryl group can optionally be fused to one or more rings selected from aryls, cycloalkyls, heteroaryls, and heterocyclyls. The aryl groups of this present disclosure can be substituted with groups selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include but are not limited to a monocyclic aromatic ring system, wherein the ring comprises 6 carbon atoms, referred to herein as "$C_6$-aryl."

The term "cyano" as used herein refers to —CN.

The term "cycloalkyl" as used herein refers to a saturated or unsaturated cyclic, bicyclic, or bridged bicyclic hydrocarbon group of 3-16 carbons, or 3-8 carbons, referred to herein as "($C_3$-$C_8$)cycloalkyl," derived from a cycloalkane. Exemplary cycloalkyl groups include, but are not limited to, cyclohexanes, cyclohexenes, cyclopentanes, and cyclopentenes. Cycloalkyl groups may be substituted with alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Cycloalkyl groups can be fused to other cycloalkyl (saturated or partially unsaturated), aryl, or heterocyclyl groups, to form a bicycle, tetracycle, etc. The term "cycloalkyl" also includes bridged and spiro-fused cyclic structures which may or may not contain heteroatoms.

The terms "halo" or "halogen" as used herein refer to —F, —Cl, —Br, and/or —I.

"Haloalkyl" means an alkyl group substituted with one or more halogens. Examples of haloalkyl groups include, but are not limited to, trifluoromethyl, difluoromethyl, pentafluoroethyl, trichloromethyl, etc.

The term "heteroaryl" as used herein refers to a mono-, bi-, or multi-cyclic, aromatic ring system containing one or more heteroatoms, for example 1 3 heteroatoms, such as nitrogen, oxygen, and sulfur. Heteroaryls can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heteroaryls can also be fused to non-aromatic rings. Exemplary heteroaryl groups include, but are not limited to, a monocyclic aromatic ring, wherein the ring comprises 2-5 carbon atoms and 1-3 heteroatoms, referred to herein as "($C_2$-$C_5$)heteroaryl." Illustrative examples of heteroaryl groups include, but are not limited to, pyridinyl, pyridazinyl, pyrimidyl, pyrazyl, triazinyl, pyrrolyl, pyrazolyl, imidazolyl, (1,2,3)- and (1,2,4)-triazolyl, pyrazinyl, pyrimidilyl, tetrazolyl, furyl, thienyl, isoxazolyl, thiazolyl, furyl, phenyl, isoxazolyl, and oxazolyl. Exemplary heteroaryl groups also include, but are not limited to, a bicyclic aromatic ring, wherein the ring comprises 5-14 carbon atoms and 1-3 heteroatoms, referred to herein as "($C_5$-$C_{14}$)heteroaryl." Representative examples of heteroaryl include, but not limited to, indazolyl, indolyl, azaindolyl, indolinyl, benzotriazolyl, benzoxadiazolyl, imidazolyl, cinnolinyl, imidazopyridyl, pyrazolopyridyl, pyrrolopyridyl, quinolinyl, isoquinolinyl, quinazolinyl, quinazolinonyl, indolinonyl, isoindolinonyl, tetrahydronaphthyl, tetrahydroquinolinyl, tetrahydroisoquinolinyl, and the like.

The terms "heterocycle," "heterocyclyl," or "heterocyclic" as used herein each refer to a saturated or unsaturated 3- to 18-membered ring containing one, two, three, or four heteroatoms independently selected from nitrogen, oxygen, phosphorus, and sulfur. Heterocycles can be aromatic (heteroaryls) or non-aromatic. Heterocycles can be substituted with one or more substituents including alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide and thioketone. Heterocycles also include bicyclic, tricyclic, and tetracyclic groups in which any of the above heterocyclic rings is fused to one or two rings independently selected from aryls, cycloalkyls, and heterocycles. Exemplary heterocycles include acridinyl, benzimidazolyl, benzofuryl, benzothiazolyl, benzothienyl, benzoxazolyl, biotinyl, cinnolinyl, dihydrofuryl, dihydroindolyl, dihydropyranyl, dihydrothienyl, dithiazolyl, furyl, homopiperidinyl, imidazolidinyl, imidazolinyl, imidazolyl, indolyl, isoquinolyl, isothiazolidinyl, isothiazolyl, isoxazolidinyl, isoxazolyl, morpholinyl, oxadiazolyl, oxazolidinyl, oxazolyl, piperazinyl, piperidinyl, pyranyl, pyrazolidinyl, pyrazinyl, pyrazolyl, pyrazolinyl, pyridazinyl, pyridyl, pyrimidinyl, pyrimidyl, pyrrolidinyl, pyrrolidin-2-onyl, pyrrolinyl, pyrrolyl, quinolinyl, quinoxaloyl, tetrahydrofuryl, tetrahydroisoquinolyl, tetrahydropyranyl, tetrahydroquinolyl, tetrazolyl, thiadiazolyl, thiazolidinyl, thiazolyl, thienyl, thiomorpholinyl, thiopyranyl, and triazolyl.

The terms "hydroxy" and "hydroxyl" as used herein refer to —OH.

"Spirocycloalkyl" or "spirocyclyl" means carbogenic bicyclic ring systems with both rings connected through a single atom. The rings can be different in size and nature, or identical in size and nature. Examples include spiropentane, spriohexane, spiroheptane, spirooctane, spirononane, or spirodecane. One or both of the rings in a spirocycle can be fused to another ring carbocyclic, heterocyclic, aromatic, or heteroaromatic ring. A ($C_{3-12}$)spirocycloalkyl is a spirocycle containing between 3 and 12 carbon atoms.

"Spiroheterocycloalkyl" or "spiroheterocyclyl" means a spirocycle wherein at least one of the rings is a heterocycle one or more of the carbon atoms can be substituted with a heteroatom (e.g., one or more of the carbon atoms can be substituted with a heteroatom in at least one of the rings). One or both of the rings in a spiroheterocycle can be fused to another ring carbocyclic, heterocyclic, aromatic, or heteroaromatic ring.

"Isomers" means compounds having the same number and kind of atoms, and hence the same molecular weight, but differing with respect to the arrangement or configuration of the atoms in space.

"Stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the disclosure which may give rise to stereoisomerism, the disclosure contemplates stereoisomers and mixtures thereof. The compounds of the disclosure and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the disclosure from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more. In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

Individual stereoisomers of compounds of the present disclosure can be prepared synthetically from commercially available starting materials that contain asymmetric or stereogenic centers, or by preparation of racemic mixtures followed by resolution methods well known to those of ordinary skill in the art. These methods of resolution are exemplified by: (1) attachment of a mixture of enantiomers to a chiral auxiliary, separation of the resulting mixture of diastereomers by recrystallization or chromatography and liberation of the optically pure product from the auxiliary; (2) salt formation employing an optically active resolving agent; or (3) direct separation of the mixture of optical enantiomers on chiral chromatographic columns. Stereoisomeric mixtures can also be resolved into their component stereoisomers by well-known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well-known asymmetric synthetic methods.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

The term "pharmaceutically acceptable carrier" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutically acceptable composition" as used herein refers to a composition comprising at least one compound as disclosed herein formulated together with one or more pharmaceutically acceptable carriers.

The term "pharmaceutically acceptable prodrugs" as used herein represents those prodrugs of the compounds of the present disclosure that are, within the scope of sound medical judgment, suitable for use in contact with the tissues of humans and lower animals without undue toxicity, irritation, allergic response, commensurate with a reasonable benefit/risk ratio, and effective for their intended use, as well as the zwitterionic forms, where possible, of the compounds of the present disclosure. A discussion is provided in Higuchi et al., "Prodrugs as Novel Delivery Systems," ACS Symposium Series, Vol. 14, and in Roche, E. B., ed. Bioreversible Carriers in Drug Design, American Pharmaceutical Association and Pergamon Press, 1987, both of which are incorporated herein by reference.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

As used herein, nomenclature for compounds including organic compounds, can be given using common names, IUPAC, IUBMB, or CAS recommendations for nomenclature. One of skill in the art can readily ascertain the structure of a compound if given a name, either by systemic reduction of compound structure using naming conventions, or by commercially available software, such as CHEMDRAW™ (Cambridgesoft Corporation, U.S.A.). Chemical names were generated using PerkinElmer ChemDraw® Professional, version 17.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbol "R" or "S," depending on the configuration of substituents around the stereogenic carbon atom. The present disclosure encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. In some embodiments, an enantiomer or stereoisomer may be provided substantially free of the corresponding enantiomer.

As used herein, "cancer" refers to diseases, disorders, and conditions that involve abnormal cell growth with the potential to invade or spread to other parts of the body. Exemplary cancers include, but are not limited to, breast cancer, lung cancer, ovarian cancer, endometrial cancer, prostate cancer, and esophageal cancer.

As used herein, the term "subject" refers to an animal. Typically, the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit," "inhibition," or "inhibiting" refers to the reduction or suppression of a given condition, symptom, or disorder, or disease, or a significant decrease in the baseline activity of a biological activity or process.

As used herein, the term "treat," "treating," or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those which may not be discernible by the patient. In yet another embodiment, "treat," "treating," or "treatment" refers to modulating the disease or disorder, either physically (e.g., through stabilization of a discernible symptom), physiologically, (e.g., through stabilization of a physical parameter), or both. In yet another embodiment, "treat," "treating," or "treatment" refers to preventing or delaying the onset or development or progression of the disease or disorder.

As used herein, a subject is "in need of" a treatment if such subject would benefit biologically, medically or in quality of life from such treatment.

Additionally, unless otherwise stated, structures described herein are also meant to include compounds that differ only in the presence of one or more isotopically enriched atoms. For example, compounds having the present structures except for the replacement of hydrogen by deuterium (2H) or tritium (3H), or the replacement of a carbon by a $^{13}$C- or $^{14}$C-carbon atom are within the scope of this disclosure. Such compounds may be useful as, for example, analytical tools, probes in biological assays, or therapeutic agents.

Compounds

In some embodiments, provided herein are compounds of Formula (I) or a tautomer, stereoisomer or a mixture of stereoisomers, or a pharmaceutically acceptable salt, or hydrate, or deuterated derivative thereof:

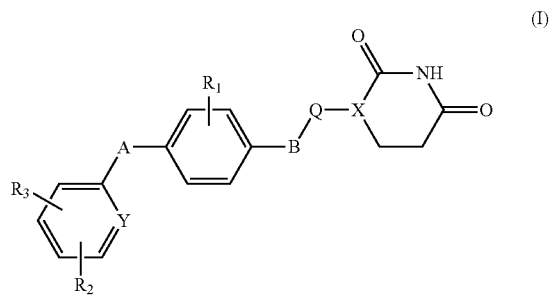

(I)

wherein:

X is CH or N;

Y is CH or N;

A is chosen from —C(O)—, —SO$_2$—, —S(O)—, —O—, —S—, —NH—, —N(C$_1$-C$_5$alkyl)-, and —C(O)NH(C$_1$-C$_5$alkyl)-;

B is

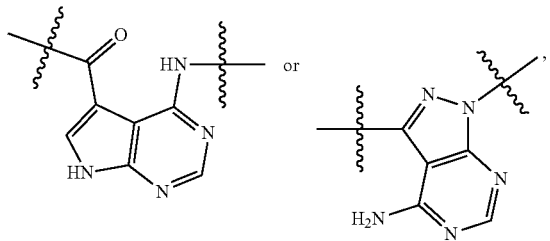 [SMILES: *Nc1ncnc2[nH]cc(C(*)=O)c12 ; *c1nn(*)c2ncnc(N)c12] or with the proviso that when B is

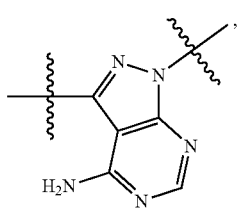 [SMILES: *c1nn(*)c2ncnc(N)c12]

A is not —O—;

R$_1$ is chosen from H, C$_1$-C$_3$ alkyl, C$_1$-C$_3$haloalkyl, dialkylamino group, amino group, —CN, hydroxyl, C$_1$-C$_4$alkoxy, and halogen;

each R$_2$ and R$_3$ is independently chosen from H, halogen, —CN, hydroxyl, dialkylamino group, C$_1$-C$_5$alkyl, C$_1$-C$_5$alkoxy, deuterated C$_1$-C$_5$alkyl, deuterated C$_1$-C$_5$alkoxy, and C$_1$-C$_5$haloalkyl;

Q is L-W$_1$ or L-W$_2$;

wherein

L is a linker of 2 to 20 carbon atoms in length, wherein one or more carbon atoms are optionally and independently replaced by a group chosen from C(=O), O, N(R$_6$), S, S(O), SO$_2$, C(O)NH, C(O)NCH$_3$, C(O)NCH$_2$CH$_3$, C$_2$-alkenyl, C$_2$-alkynyl, cycloalkyl, heterocycloalkyl, heterocycle, aryl, or heteroaryl, wherein each are independently substituted with 0, 1, 2 or 3 R$_7$;

W$_1$ is chosen from

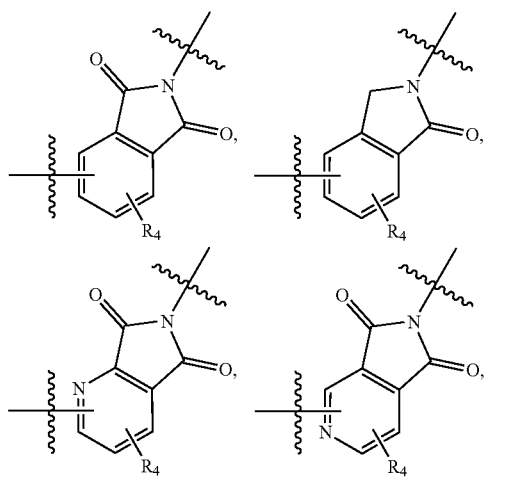

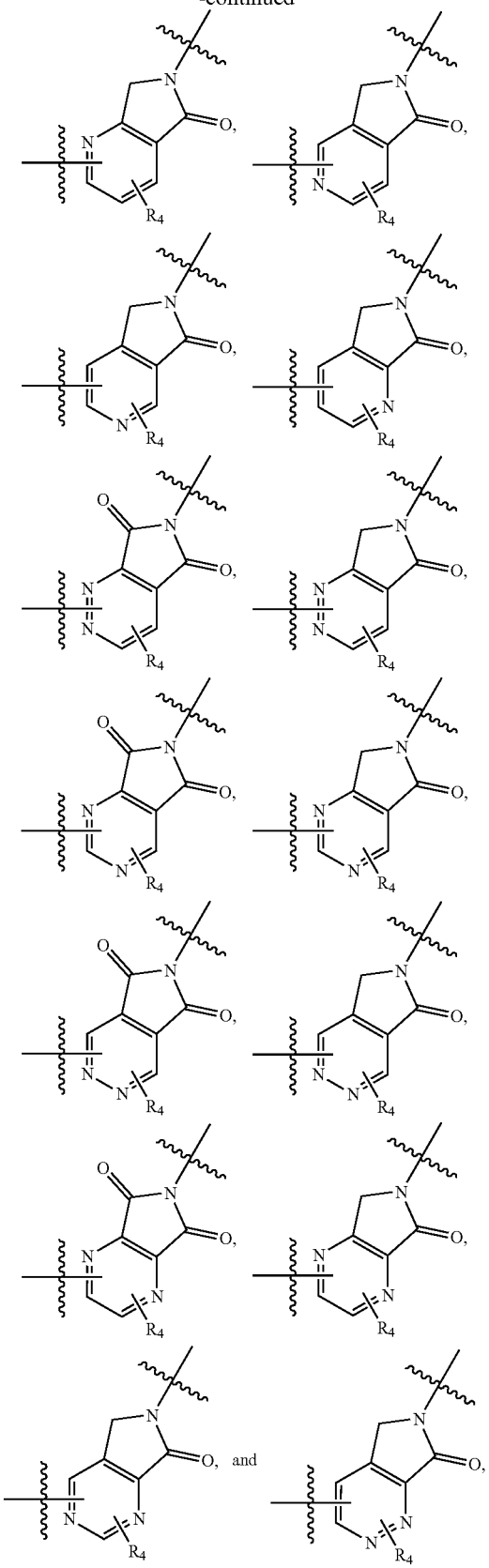

wherein R$_4$ is chosen from H, halogen, —CN, C$_1$-C$_5$alkyl, C$_1$-C$_5$alkoxy, and C$_1$-C$_5$haloalkyl; and $W_2$ is

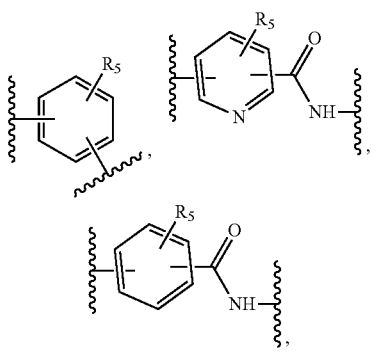

or is absent, wherein $R_5$ is chosen from H, halogen, —CN, $C_1$-$C_5$alkyl, $C_1$-$C_5$alkoxy, and $C_1$-$C_5$haloalkyl;

each $R_6$ is independently chosen from H, $C_1$-$C_3$alkyl, —C(=O)—($C_1$-$C_3$alkyl), —C(=O)—O—($C_1$-$C_3$alkyl), and —C(=O)—NH—($C_1$-$C_3$alkyl), each of which is substituted with 0, 1, 2, or 3 $R_7$;

each $R_7$ is independently chosen from halogen, hydroxyl, amino group, $C_1$-$C_3$alkyl, $C_1$-$C_3$alkoxy, $C_1$-$C_3$haloalkyl, —N($R_6$)$_2$, and —CN. In some embodiments, the compound of Formula (I) may be a compound of Formula (IA):

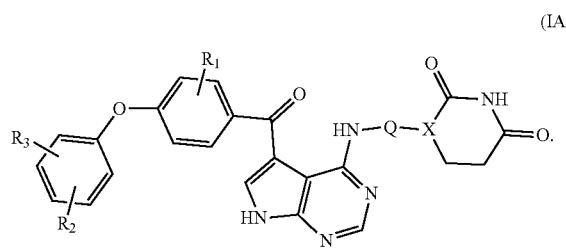

In some embodiments, the compound of Formula (I) may be a compound of Formula (IB):

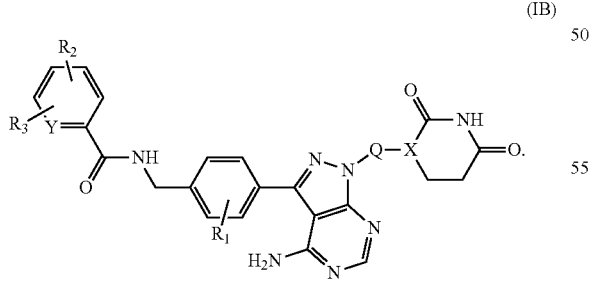

In some embodiments, A is —O— or —C(O)—NH—CH$_2$. In some embodiments, A is —O—. In some embodiments, A is —C(O)—NH—CH$_2$.

In some embodiments, $R_1$ is chosen from H, $C_1$-$C_3$ alkyl, $C_1$-$C_3$haloalkyl, and halogen. In some embodiments, $R_1$ is chosen from H, F, Cl, Br, I, —CF$_3$, —CH$_3$, and

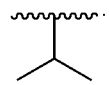

In some embodiments, $R_1$ is H. In some embodiments, $R_1$ is Br. In some embodiments, $R_1$ is Cl. In some embodiments, $R_1$ is F. In some embodiments, $R_1$ is I.

In some embodiments, $R_2$ and $R_3$ are each independently chosen from H, —OCD$_3$, —CD$_3$, halogen, $C_1$-$C_4$alkyl, and $C_1$-$C_4$alkoxy. In some embodiments, $R_2$ and $R_3$ are each H. In some embodiments, $R_2$ is H and $R_3$ is F. In some embodiments, $R_2$ is F and $R_3$ is H. In some embodiments, $R_2$ is —OCH$_3$ and $R_3$ is F. In some embodiments, $R_2$ is F and $R_3$ is —OCH$_3$. In some embodiments, $R_2$ is —OCD$_3$ and $R_3$ is F. In some embodiments, $R_2$ is —F and $R_3$ is or —OCD$_3$. In some embodiments, $R_2$ is —CD$_3$ and $R_3$ is F. In some embodiments, $R_2$ is —F and $R_3$ is —CD$_3$.

In some embodiments, $R_4$ is chosen from H, halogen, —CN, and $C_1$-$C_4$haloalkyl. In some embodiments, $R_4$ is H. In some embodiments, $R_4$ is halogen. In some embodiments, $R_4$ is F. In some embodiments, $R_4$ is Cl. In some embodiments, $R_4$ is Br.

In some embodiments, $R_5$ is chosen from H, halogen, deuterated $C_1$-$C_5$alkoxy, and $C_1$-$C_5$alkoxy. In some embodiments, $R_5$ is —OCH$_3$ or —OCD$_3$. In some embodiments, $R_5$ is —OCH$_3$.

In some embodiments, L is a linker of 2 to 12 carbon atoms in length, wherein one or more carbon atoms are optionally and independently replaced by a group selected from C(=O), O, S, S(O), SO$_2$, C(O)NH, C(O)NCH$_3$, C(O)NCH$_2$CH$_3$, NH, NCH$_3$, NCH$_2$CH$_3$, $C_2$-alkynyl

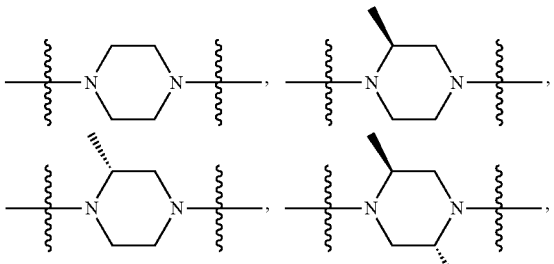

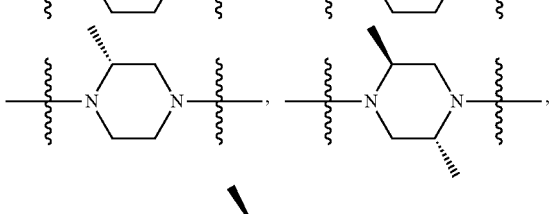

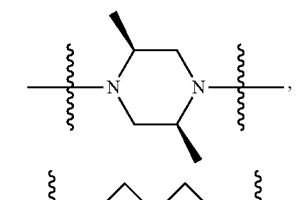

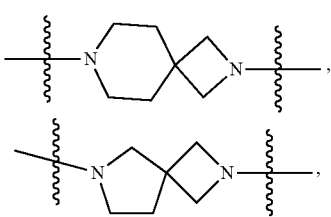

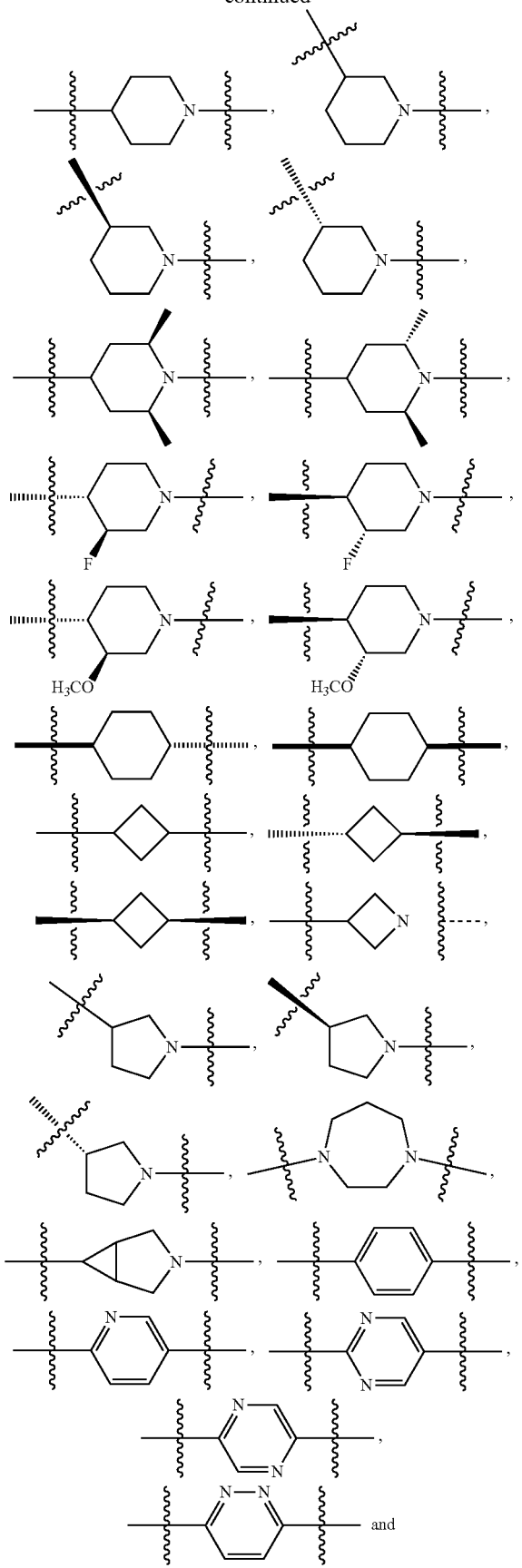
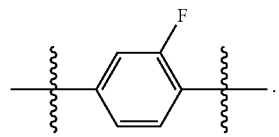
In some embodiments, W₂ is
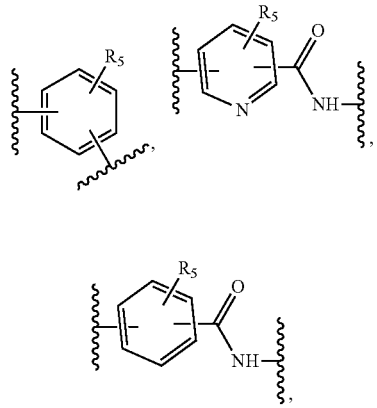
or is absent. In some embodiments, W₂ is
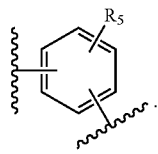
In some embodiments, W₂ is
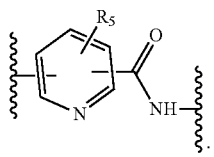
In some embodiments, W₂ is
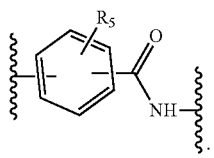
In some embodiments, W₂ is absent.
In some embodiments, provided herein is a compound, or pharmaceutically acceptable salt thereof, chosen from the compounds listed in Table 1.

TABLE 1

Exemplary Compounds of the Present Disclosure

| Compound No. | Chemical Structure and IUPAC Nomenclature |
|---|---|
| 1 | 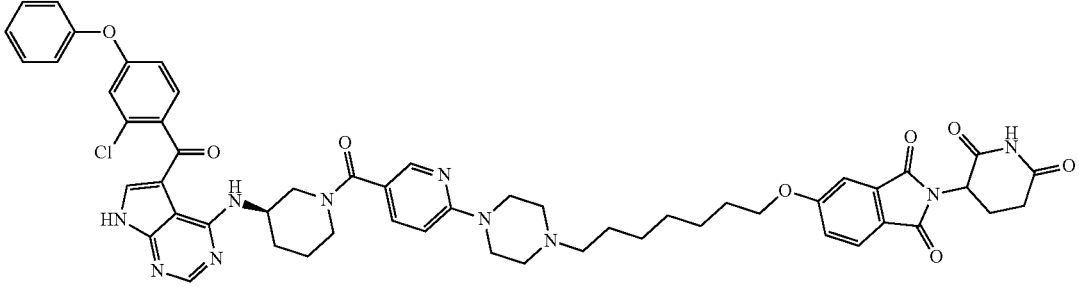 [SMILES: O=C1CCC(N2C(=O)c3ccc(OCCCCCCCN4CCN(c5ccc(C(=O)N6CCC[C@@H](Nc7ncnc8[nH]cc(C(=O)c9ccc(Oc%10ccccc%10)cc9Cl)c78)C6)cn5)CC4)cc3C2=O)C(=O)N1]<br>5-((7-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)heptyl)oxy)-2-(2,6-dioxopiperidin-3-yl)isoindoline-1,3-dione |
| 2 | 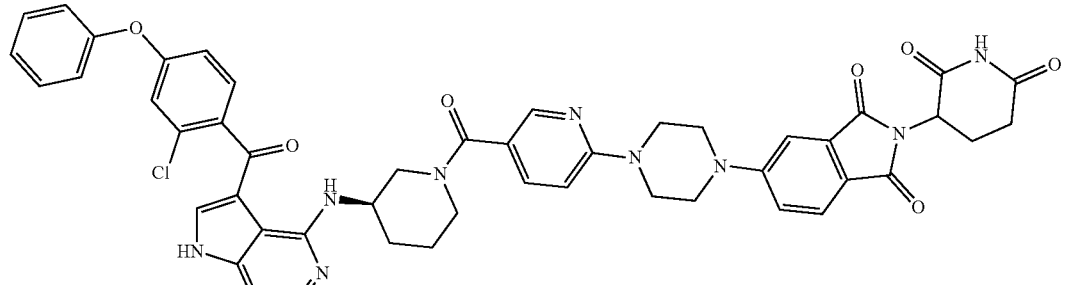<br>5-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)-2-(2,6-dioxopiperidin-3-yl)isoindoline-1,3-dione |
| 3 | 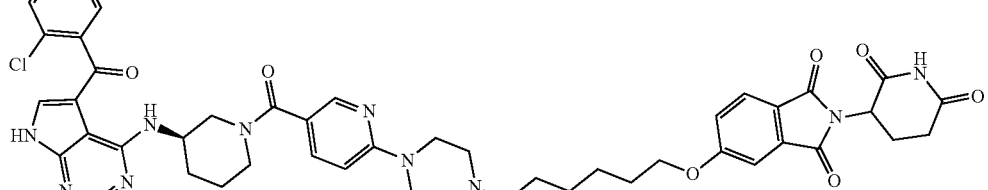<br>5-((6-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)hexyl)oxy)-2-(2,6-dioxopiperidin-3-yl)isoindoline-1,3-dione |
| 4 | 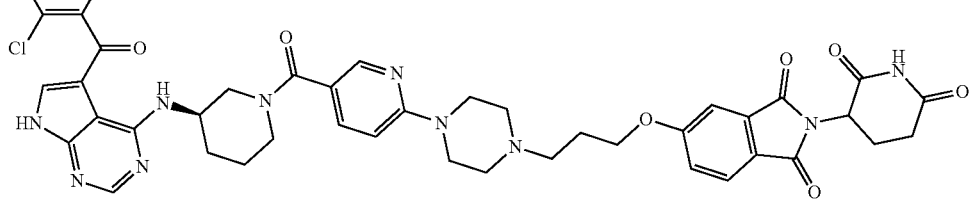<br>5-(3-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)propoxy)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
|---|---|
| 5 | 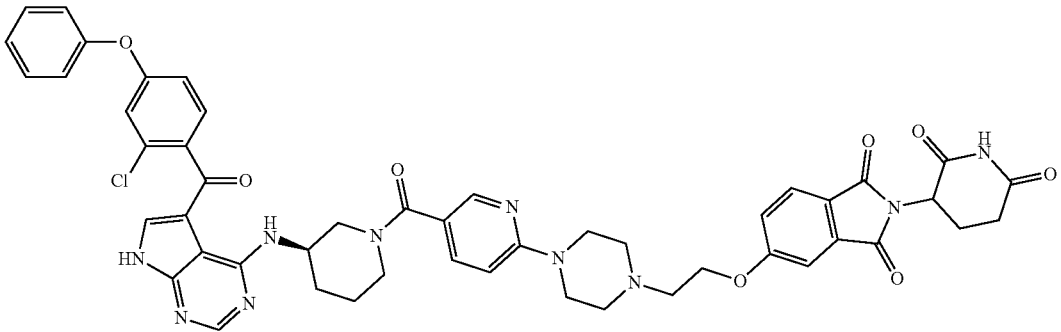 [SMILES: O=C1CCC(N2C(=O)c3ccc(OCCN4CCN(c5ccc(C(=O)N6CCC[C@@H](Nc7ncnc8[nH]cc(C(=O)c9ccc(Oc%10ccccc%10)cc9Cl)c78)C6)cn5)CC4)cc3C2=O)C(=O)N1]<br>5-(2-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)ethoxy)-2-(2,6-dioxopiperidin-3-yl)isoindoline-1,3-dione |
| 6 | 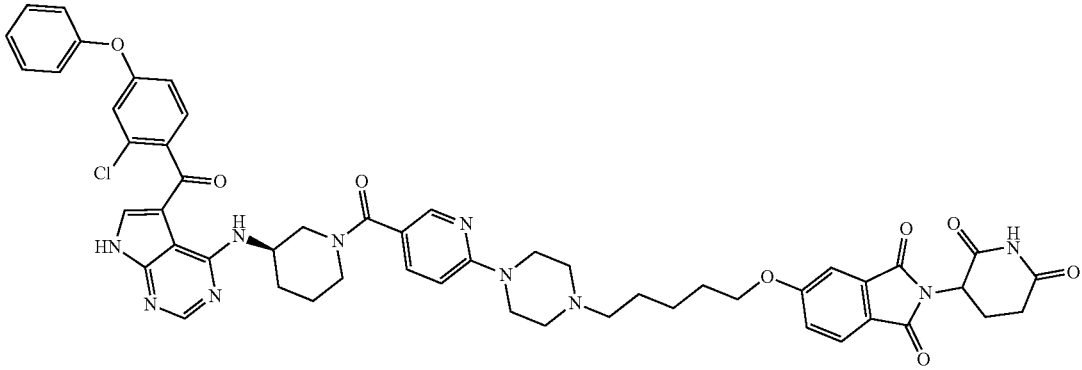 [SMILES: O=C1CCC(N2C(=O)c3ccc(OCCCCCN4CCN(c5ccc(C(=O)N6CCC[C@@H](Nc7ncnc8[nH]cc(C(=O)c9ccc(Oc%10ccccc%10)cc9Cl)c78)C6)cn5)CC4)cc3C2=O)C(=O)N1]<br>5-((5-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)pentyl)oxy)-2-(2,6-dioxopiperidin-3-yl)isoindoline-1,3-dione |
| 7 | 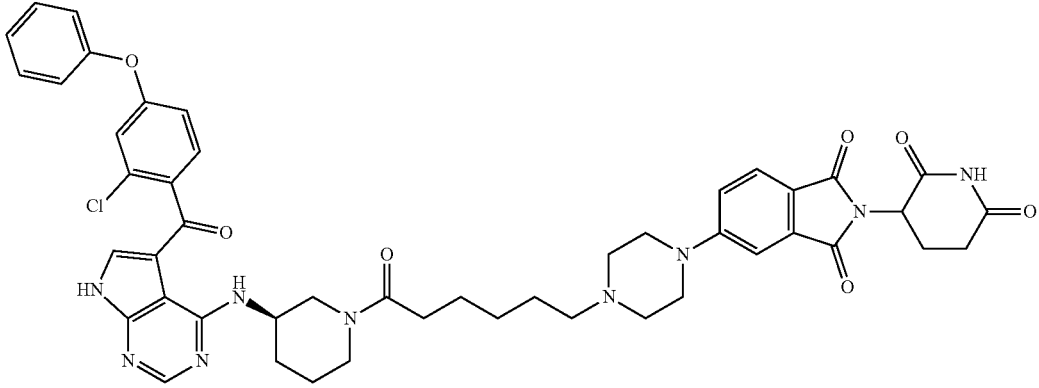 [SMILES: O=C1CCC(N2C(=O)c3ccc(N4CCN(CCCCCC(=O)N5CCC[C@@H](Nc6ncnc7[nH]cc(C(=O)c8ccc(Oc9ccccc9)cc8Cl)c67)C5)CC4)cc3C2=O)C(=O)N1]<br>5-(4-(6-((R)-3-((5-(2-chloro-4-phenoxybenzoyl)-7H-pyrrolo[2,3-d]pyrimidin-4-yl)amino)piperidin-1-yl)-6-oxohexyl)piperazin-1-yl)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
|---|---|
| 8 | 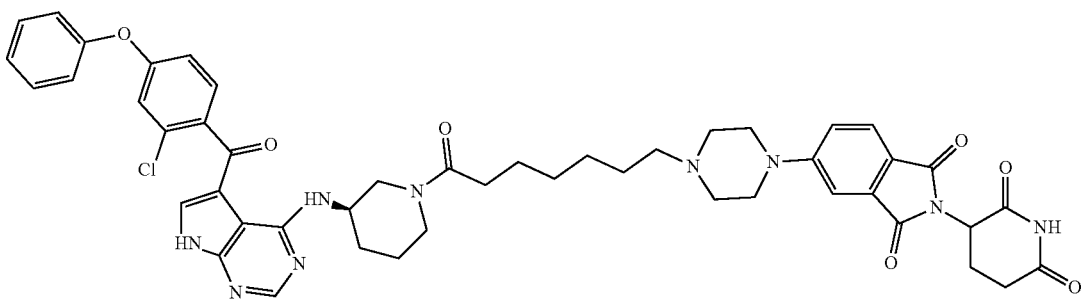 [SMILES: O=C1CCC(N2C(=O)c3ccc(N4CCN(CCCCCCC(=O)N5CCC[C@@H](Nc6ncnc7[nH]cc(C(=O)c8ccc(Oc9ccccc9)cc8Cl)c67)C5)CC4)cc3C2=O)C(=O)N1]
5-(4-(7-((R)-3-((5-(2-chloro-4-phenoxybenzoyl)-7H-pyrrolo[2,3-d]pyrimidin-4-yl)amino)piperidin-1-yl)-7-oxoheptyl)piperazin-1-yl)-2-(2,6-dioxopiperidin-3-yl)isoindoline-1,3-dione |
| 9 | 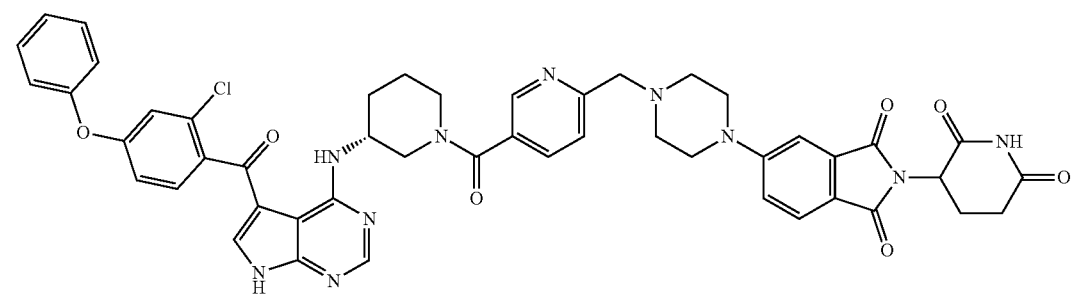 [SMILES: O=C1CCC(N2C(=O)c3ccc(N4CCN(Cc5ccc(C(=O)N6CCC[C@@H](Nc7ncnc8[nH]cc(C(=O)c9ccc(Oc%10ccccc%10)cc9Cl)c78)C6)cn5)CC4)cc3C2=O)C(=O)N1]
5-(4-((5-((R)-3-((5-(2-chloro-4-phenoxybenzoyl)-7H-pyrrolo[2,3-d]pyrimidin-4-yl)amino)piperidine-1-carbonyl)pyridin-2-yl)methyl)piperazin-1-yl)-2-(2,6-dioxopiperidin-3-yl)isoindoline-1,3-dione |
| 10 | 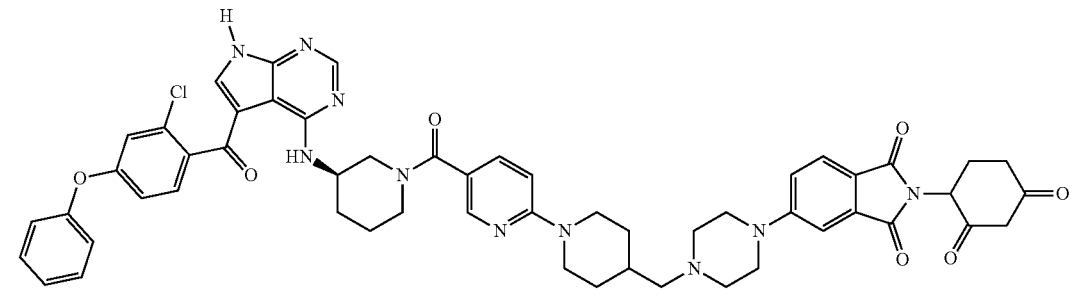 [SMILES: O=C1CCC(N2C(=O)c3ccc(N4CCN(CC5CCN(c6ccc(C(=O)N7CCC[C@@H](Nc8ncnc9[nH]cc(C(=O)c%10ccc(Oc%11ccccc%11)cc%10Cl)c89)C7)cn6)CC5)CC4)cc3C2=O)C(=O)C1]
5-(4-(((1-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperidin-4-yl)methyl)piperazin-1-yl)-2-(2,6-dioxopiperidin-3-yl)isoindoline-1,3-dione |
| 11 | 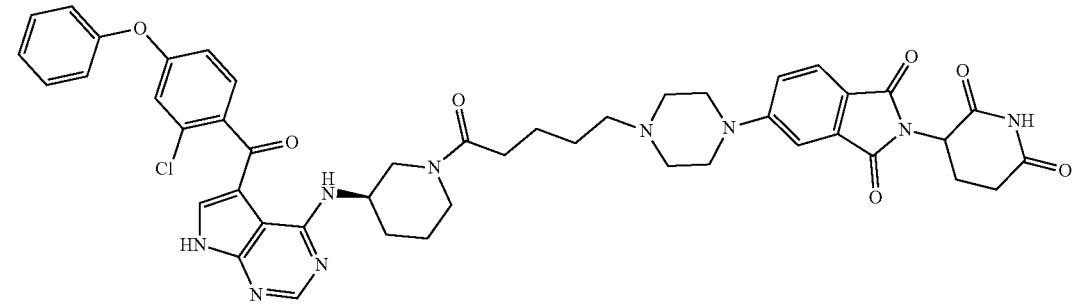 [SMILES: O=C1CCC(N2C(=O)c3ccc(N4CCN(CCCCC(=O)N5CCC[C@@H](Nc6ncnc7[nH]cc(C(=O)c8ccc(Oc9ccccc9)cc8Cl)c67)C5)CC4)cc3C2=O)C(=O)N1]
5-(4-(5-((R)-3-((5-(2-chloro-4-phenoxybenzoyl)-7H-pyrrolo[2,3-d]pyrimidin-4-yl)amino)piperidin-1-yl)-5-oxopentyl)piperazin-1-yl)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
|---|---|
| 12 | 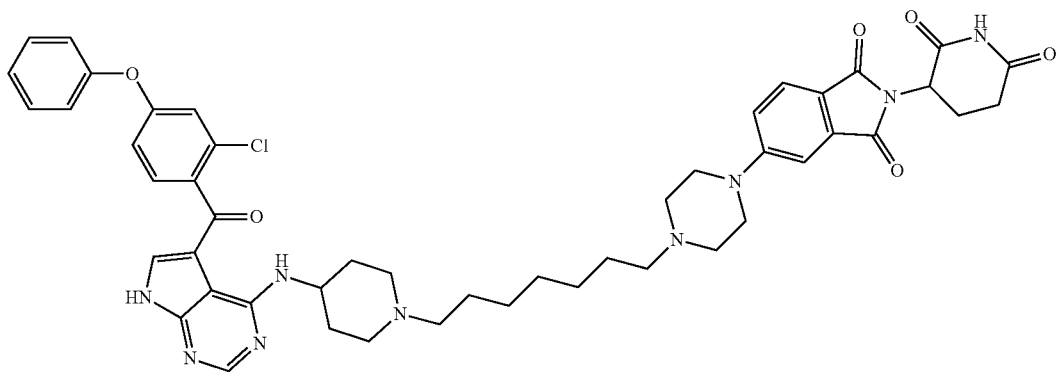 [SMILES: O=C1CCC(N2C(=O)c3ccc(N4CCN(CCCCCCCN5CCC(Nc6ncnc7[nH]cc(C(=O)c8ccc(Oc9ccccc9)cc8Cl)c67)CC5)CC4)cc3C2=O)C(=O)N1]<br>5-(4-(7-(4-((5-(2-chloro-4-phenoxybenzoyl)-7H-pyrrolo[2,3-d]pyrimidin-4-yl)amino)piperidin-1-yl)heptyl)piperazin-1-yl)-2-(2,6-dioxopiperidin-3-yl)isoindoline-1,3-dione |
| 13 | 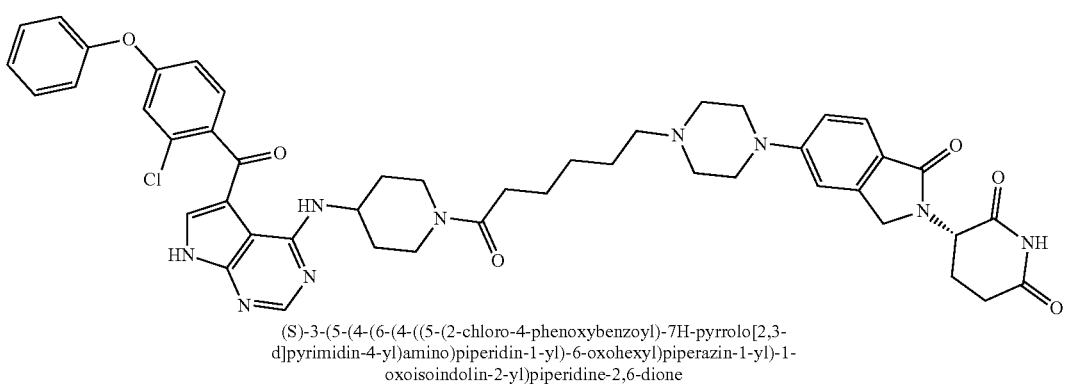<br>(S)-3-(5-(4-(6-(4-((5-(2-chloro-4-phenoxybenzoyl)-7H-pyrrolo[2,3-d]pyrimidin-4-yl)amino)piperidin-1-yl)-6-oxohexyl)piperazin-1-yl)-1-oxoisoindolin-2-yl)piperidine-2,6-dione |
| 14 | 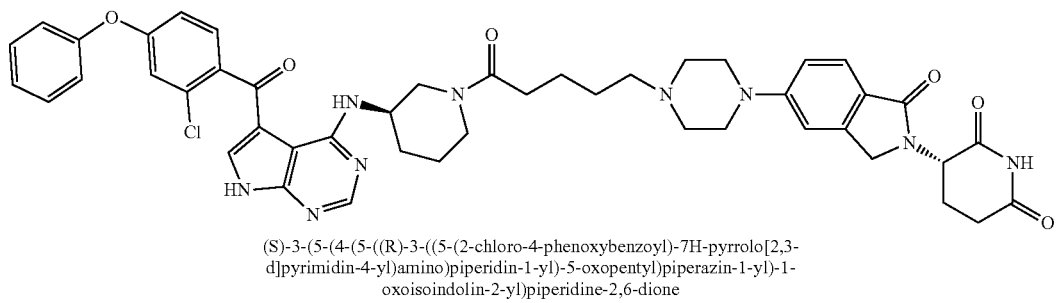<br>(S)-3-(5-(4-(5-((R)-3-((5-(2-chloro-4-phenoxybenzoyl)-7H-pyrrolo[2,3-d]pyrimidin-4-yl)amino)piperidin-1-yl)-5-oxopentyl)piperazin-1-yl)-1-oxoisoindolin-2-yl)piperidine-2,6-dione |
| 15 | 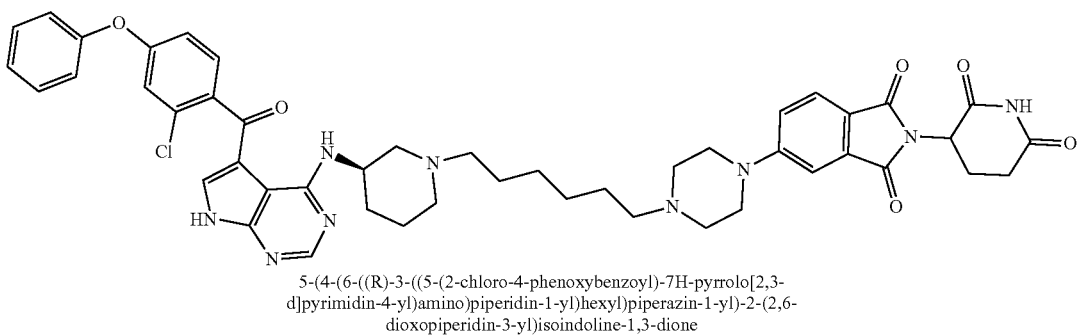<br>5-(4-(6-((R)-3-((5-(2-chloro-4-phenoxybenzoyl)-7H-pyrrolo[2,3-d]pyrimidin-4-yl)amino)piperidin-1-yl)hexyl)piperazin-1-yl)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
|---|---|
| 16 | 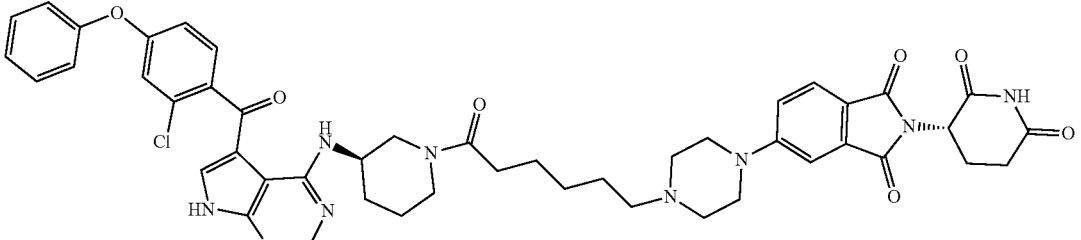<br>(S)-3-(5-(4-(6-((R)-3-((5-(2-chloro-4-phenoxybenzoyl)-7H-pyrrolo[2,3-d]pyrimidin-4-yl)amino)piperidin-1-yl)-6-oxohexyl)piperazin-1-yl)-1-oxoisoindolin-2-yl)piperidine-2,6-dione |
| 17 | 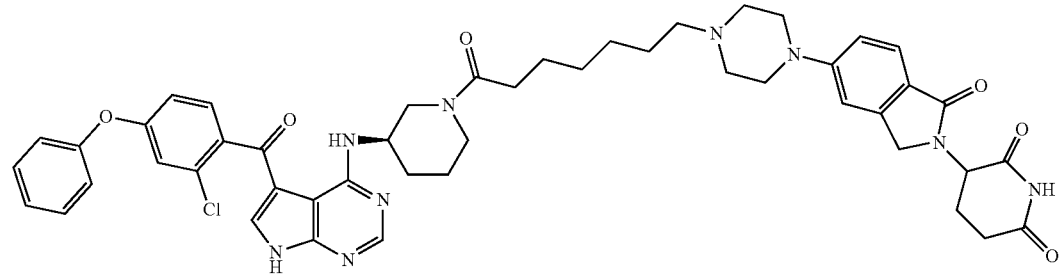 [SMILES: O=C1CCC(N2Cc3cc(N4CCN(CCCCCCC(=O)N5CCC[C@@H](Nc6ncnc7[nH]cc(C(=O)c8ccc(Oc9ccccc9)cc8Cl)c67)C5)CC4)ccc3C2=O)C(=O)N1]<br>3-(5-(4-(7-((R)-3-((5-(2-chloro-4-phenoxybenzoyl)-7H-pyrrolo[2,3-d]pyrimidin-4-yl)amino)piperidin-1-yl)-7-oxoheptyl)piperazin-1-yl)-1-oxoisoindolin-2-yl)piperidine-2,6-dione |
| 18 | 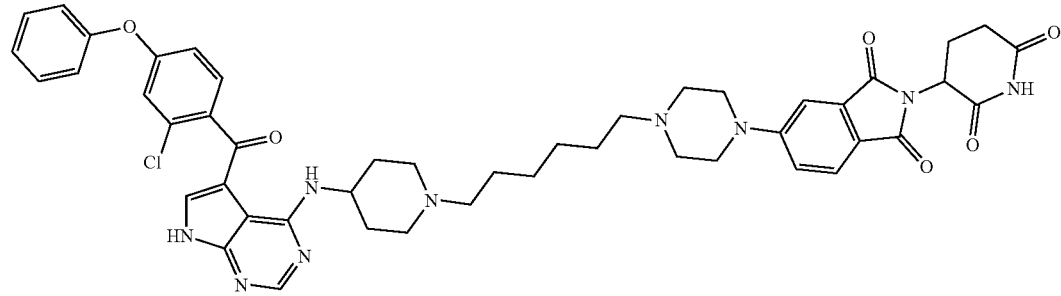 [SMILES: O=C1CCC(N2C(=O)c3ccc(N4CCN(CCCCCCN5CCC(Nc6ncnc7[nH]cc(C(=O)c8ccc(Oc9ccccc9)cc8Cl)c67)CC5)CC4)cc3C2=O)C(=O)N1]<br>5-(4-(6-(4-((5-(2-chloro-4-phenoxybenzoyl)-7H-pyrrolo[2,3-d]pyrimidin-4-yl)amino)piperidin-1-yl)hexyl)piperazin-1-yl)-2-(2,6-dioxopiperidin-3-yl)isoindoline-1,3-dione |
| 19 | 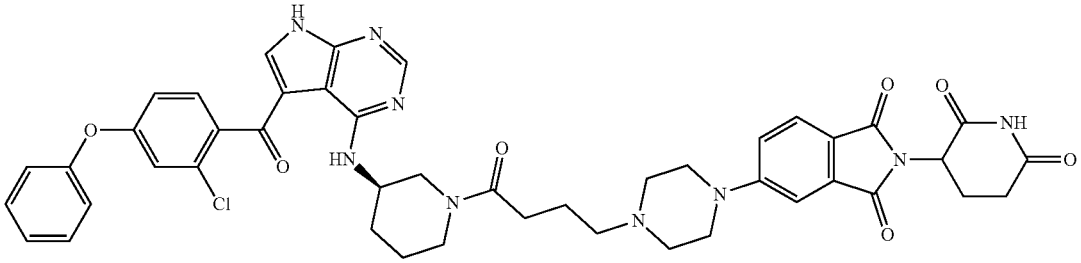 [SMILES: O=C1CCC(N2C(=O)c3ccc(N4CCN(CCCC(=O)N5CCC[C@@H](Nc6ncnc7[nH]cc(C(=O)c8ccc(Oc9ccccc9)cc8Cl)c67)C5)CC4)cc3C2=O)C(=O)N1]<br>5-(4-(4-((R)-3-((5-(2-chloro-4-phenoxybenzoyl)-7H-pyrrolo[2,3-d]pyrimidin-4-yl)amino)piperidin-1-yl)-4-oxobutyl)piperazin-1-yl)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
|---|---|
| 20 | 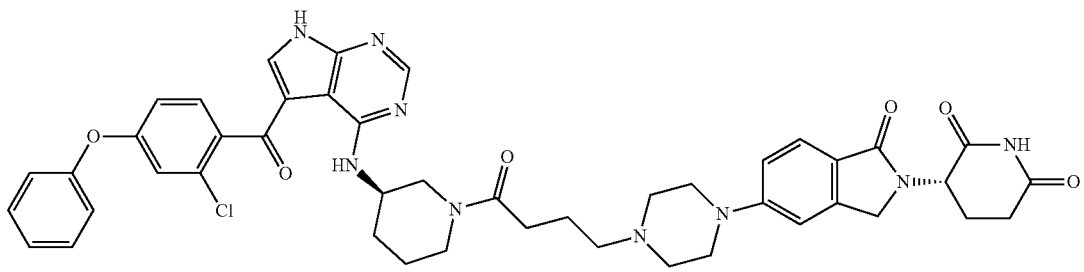 [SMILES: O=C1CC[C@H](N2Cc3cc(N4CCN(CCCC(=O)N5CCC[C@@H](Nc6ncnc7[nH]cc(C(=O)c8ccc(Oc9ccccc9)cc8Cl)c67)C5)CC4)ccc3C2=O)C(=O)N1]<br>(S)-3-(5-(4-(4-((R)-3-((5-(2-chloro-4-phenoxybenzoyl)-7H-pyrrolo[2,3-d]pyrimidin-4-yl)amino)piperidin-1-yl)-4-oxobutyl)piperazin-1-yl)-1-oxoisoindolin-2-yl)piperidine-2,6-dione |
| 21 | 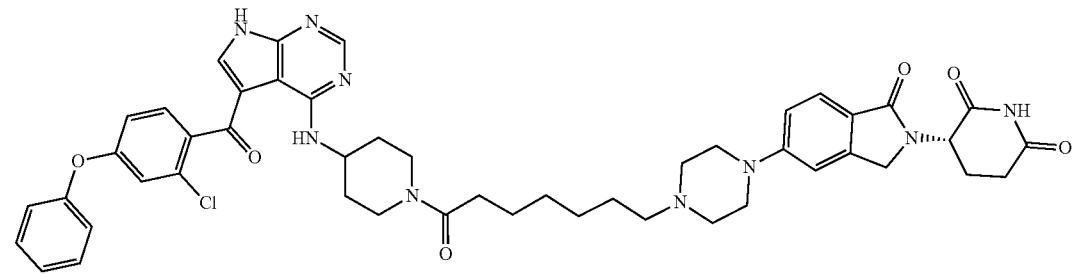 [SMILES: O=C1CC[C@H](N2Cc3cc(N4CCN(CCCCCCC(=O)N5CCC(Nc6ncnc7[nH]cc(C(=O)c8ccc(Oc9ccccc9)cc8Cl)c67)CC5)CC4)ccc3C2=O)C(=O)N1]<br>(S)-3-(5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazin-1-yl)-1-oxoisoindolin-2-yl)piperidine-2,6-dione |
| 22 | 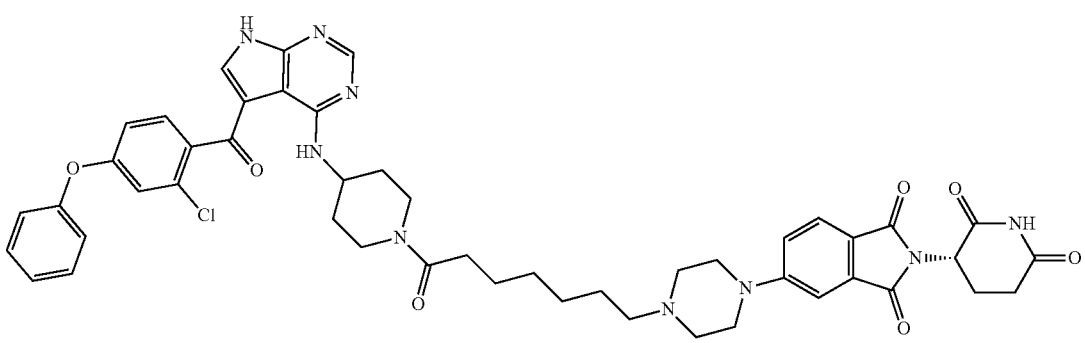 [SMILES: O=C1CC[C@H](N2C(=O)c3ccc(N4CCN(CCCCCCC(=O)N5CCC(Nc6ncnc7[nH]cc(C(=O)c8ccc(Oc9ccccc9)cc8Cl)c67)CC5)CC4)cc3C2=O)C(=O)N1]<br>5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazin-1-yl)-2-(2,6-dioxopiperidin-3-yl)isoindoline-1,3-dione |
| 23 | 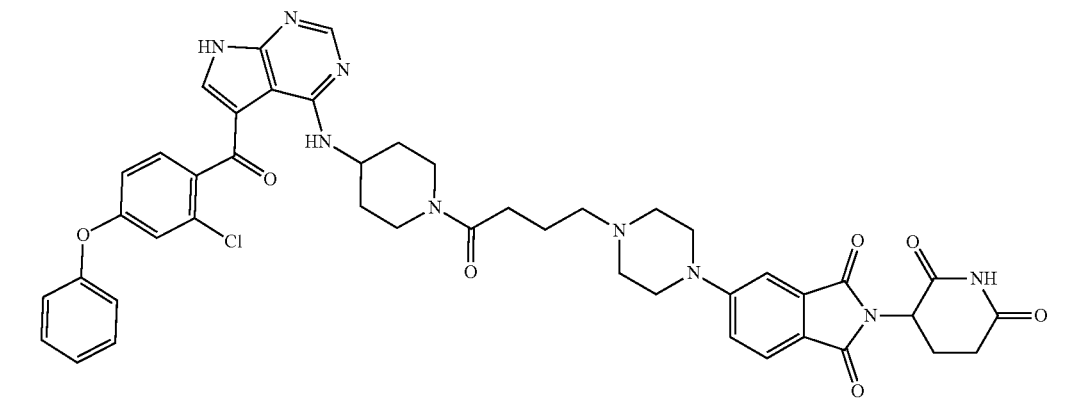 [SMILES: O=C1CCC(N2C(=O)c3ccc(N4CCN(CCCC(=O)N5CCC(Nc6ncnc7[nH]cc(C(=O)c8ccc(Oc9ccccc9)cc8Cl)c67)CC5)CC4)cc3C2=O)C(=O)N1]<br>5-(4-(4-(4-((5-(2-chloro-4-phenoxybenzoyl)-7H-pyrrolo[2,3-d]pyrimidin-4-yl)amino)piperidin-1-yl)-4-oxobutyl)piperazin-1-yl)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
| --- | --- |

24

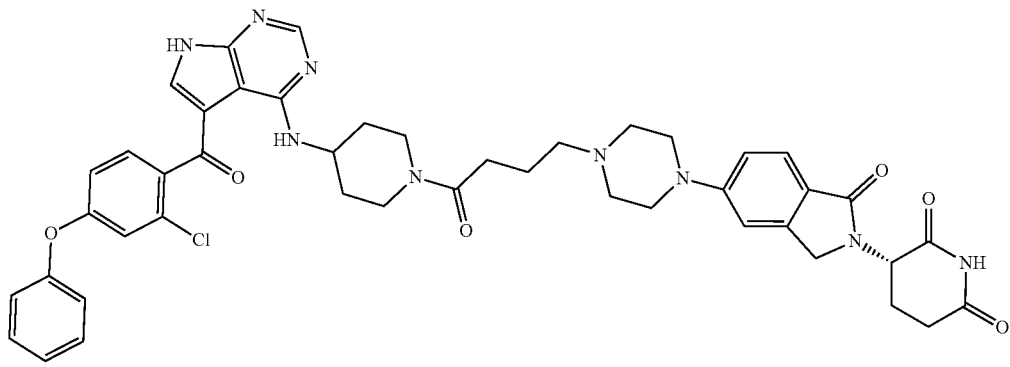 [SMILES: O=C1CC[C@H](N2Cc3cc(N4CCN(CCCC(=O)N5CCC(Nc6ncnc7[nH]cc(C(=O)c8ccc(Oc9ccccc9)cc8Cl)c67)CC5)CC4)ccc3C2=O)C(=O)N1]

(S)-3-(5-(4-(4-(4-((5-(2-chloro-4-phenoxybenzoyl)-7H-pyrrolo[2,3-d]pyrimidin-4-yl)amino)piperidin-1-yl)-4-oxobutyl)piperazin-1-yl)-1-oxoisoindolin-2-yl)piperidine-2,6-dione

25

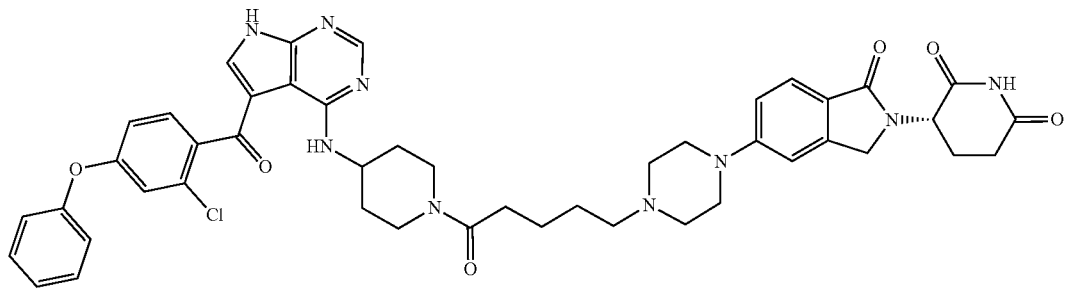 [SMILES: O=C1CC[C@H](N2Cc3cc(N4CCN(CCCCC(=O)N5CCC(Nc6ncnc7[nH]cc(C(=O)c8ccc(Oc9ccccc9)cc8Cl)c67)CC5)CC4)ccc3C2=O)C(=O)N1]

(S)-3-(5-(4-(5-(4-((5-(2-chloro-4-phenoxybenzoyl)-7H-pyrrolo[2,3-d]pyrimidin-4-yl)amino)piperidin-1-yl)-5-oxopentyl)piperazin-1-yl)-1-oxoisoindolin-2-yl)piperidine-2,6-dione

26

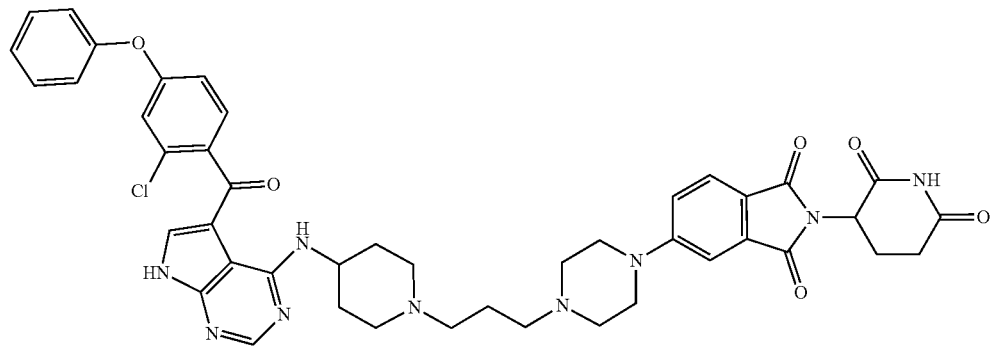 [SMILES: O=C1CCC(N2C(=O)c3ccc(N4CCN(CCCN5CCC(Nc6ncnc7[nH]cc(C(=O)c8ccc(Oc9ccccc9)cc8Cl)c67)CC5)CC4)cc3C2=O)C(=O)N1]

5-(4-(3-(4-((5-(2-chloro-4-phenoxybenzoyl)-7H-pyrrolo[2,3-d]pyrimidin-4-yl)amino)piperidin-1-yl)propyl)piperazin-1-yl)-2-(2,6-dioxopiperidin-3-yl)isoindoline-1,3-dione TABLE 1-continued Exemplary Compounds of the Present Disclosure

| Compound No. | Chemical Structure and IUPAC Nomenclature |
|---|---|
| 27 | 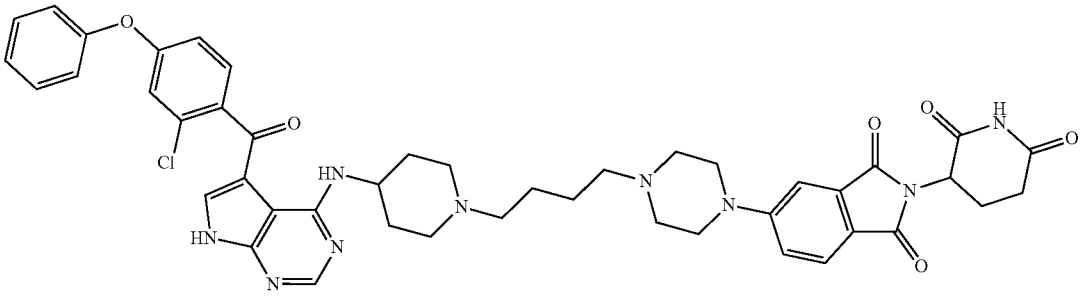 [SMILES: O=C1CCC(N2C(=O)c3ccc(N4CCN(CCCCN5CCC(Nc6ncnc7[nH]cc(C(=O)c8ccc(Oc9ccccc9)cc8Cl)c67)CC5)CC4)cc3C2=O)C(=O)N1]<br>5-(4-(4-(4-((5-(2-chloro-4-phenoxybenzoyl)-7H-pyrrolo[2,3-d]pyrimidin-4-yl)amino)piperidin-1-yl)butyl)piperazin-1-yl)-2-(2,6-dioxopiperidin-3-yl)isoindoline-1,3-dione |
| 28 | 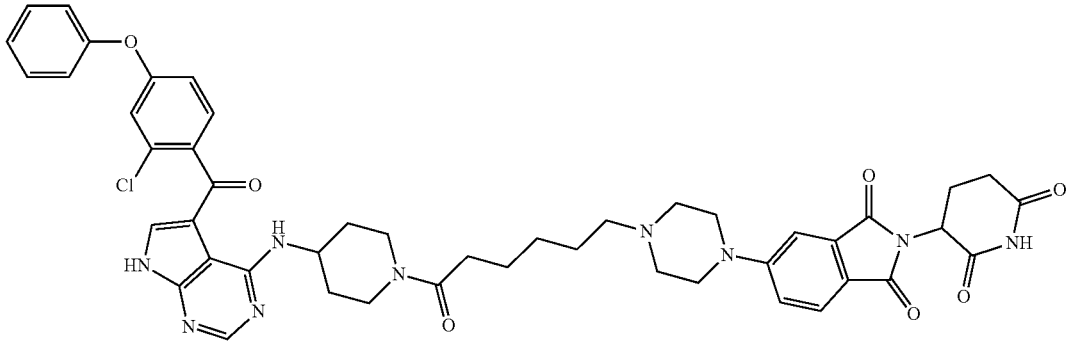 [SMILES: O=C1CCC(N2C(=O)c3ccc(N4CCN(CCCCCC(=O)N5CCC(Nc6ncnc7[nH]cc(C(=O)c8ccc(Oc9ccccc9)cc8Cl)c67)CC5)CC4)cc3C2=O)C(=O)N1]<br>5-(4-(6-(4-((5-(2-chloro-4-phenoxybenzoyl)-7H-pyrrolo[2,3-d]pyrimidin-4-yl)amino)piperidin-1-yl)-6-oxohexyl)piperazin-1-yl)-2-(2,6-dioxopiperidin-3-yl)isoindoline-1,3-dione |
| 29 | 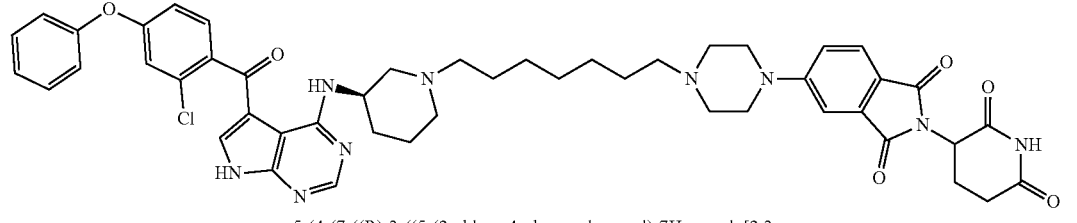<br>5-(4-(7-((R)-3-((5-(2-chloro-4-phenoxybenzoyl)-7H-pyrrolo[2,3-d]pyrimidin-4-yl)amino)piperidin-1-yl)heptyl)piperazin-1-yl)-2-(2,6-dioxopiperidin-3-yl)isoindoline-1,3-dione |
| 30 | 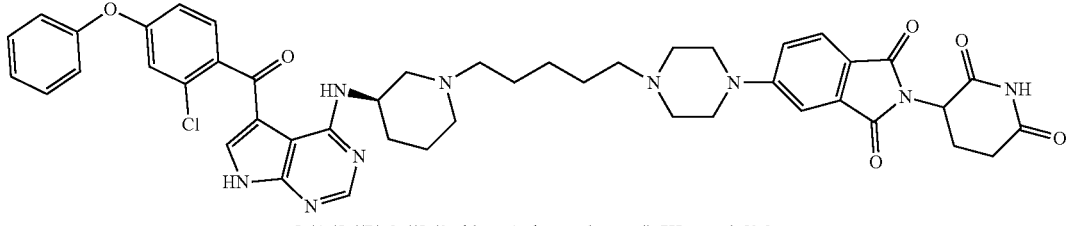<br>5-(4-(5-((R)-3-((5-(2-chloro-4-phenoxybenzoyl)-7H-pyrrolo[2,3-d]pyrimidin-4-yl)amino)piperidin-1-yl)pentyl)piperazin-1-yl)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
|---|---|
| 31 | 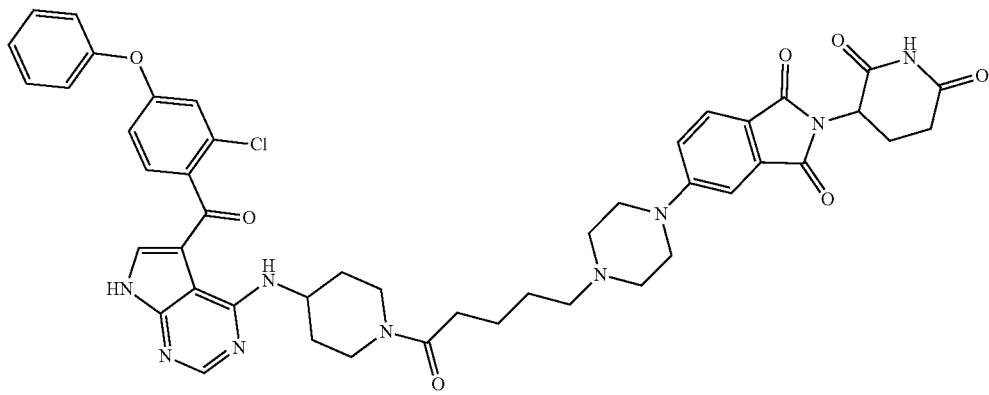 [SMILES: O=C1CCC(N2C(=O)c3ccc(N4CCN(CCCCC(=O)N5CCC(Nc6ncnc7[nH]cc(C(=O)c8ccc(Oc9ccccc9)cc8Cl)c67)CC5)CC4)cc3C2=O)C(=O)N1]<br>5-(4-(5-(4-((5-(2-chloro-4-phenoxybenzoyl)-7H-pyrrolo[2,3-d]pyrimidin-4-yl)amino)piperidin-1-yl)-5-oxopentyl)piperazin-1-yl)-2-(2,6-dioxopiperidin-3-yl)isoindoline-1,3-dione |
| 32 | 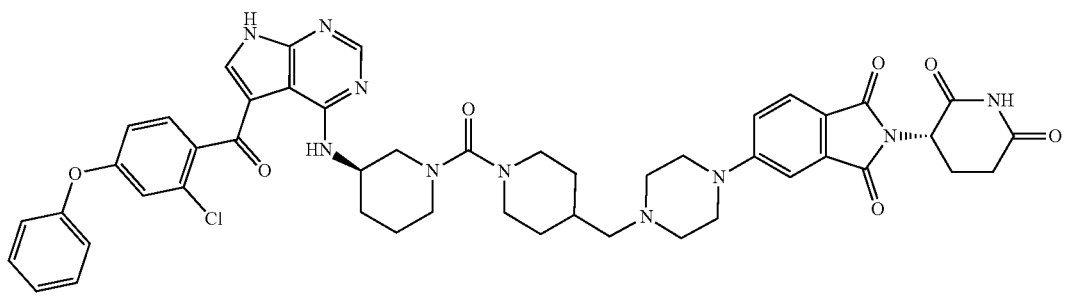 [SMILES: O=C1CC[C@H](N2C(=O)c3ccc(N4CCN(CC5CCN(C(=O)N6CCC[C@@H](Nc7ncnc8[nH]cc(C(=O)c9ccc(Oc%10ccccc%10)cc9Cl)c78)C6)CC5)CC4)cc3C2=O)C(=O)N1]<br>(S)-3-(5-(4-((1-((R)-3-((5-(2-chloro-4-phenoxybenzoyl)-7H-pyrrolo[2,3-d]pyrimidin-4-yl)amino)piperidine-1-carbonyl)piperidin-4-yl)methyl)piperazin-1-yl)-1-oxoisoindolin-2-yl)piperidine-2,6-dione |
| 33 | 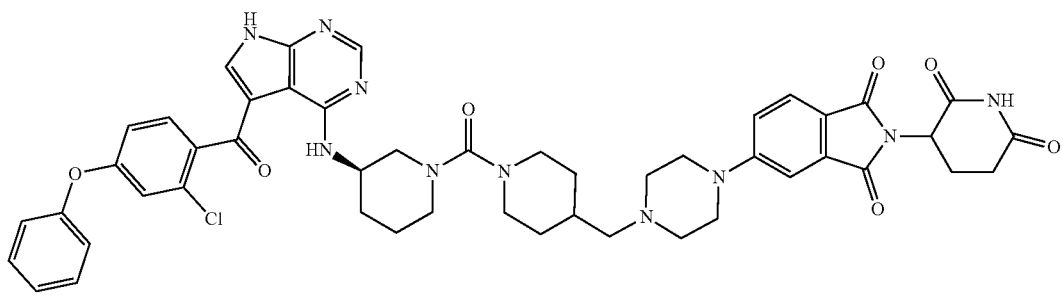 [SMILES: O=C1CCC(N2C(=O)c3ccc(N4CCN(CC5CCN(C(=O)N6CCC[C@@H](Nc7ncnc8[nH]cc(C(=O)c9ccc(Oc%10ccccc%10)cc9Cl)c78)C6)CC5)CC4)cc3C2=O)C(=O)N1]<br>5-(4-((1-((R)-3-((5-(2-chloro-4-phenoxybenzoyl)-7H-pyrrolo[2,3-d]pyrimidin-4-yl)amino)piperidine-1-carbonyl)piperidin-4-yl)methyl)piperazin-1-yl)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
|---|---|
| 34 | 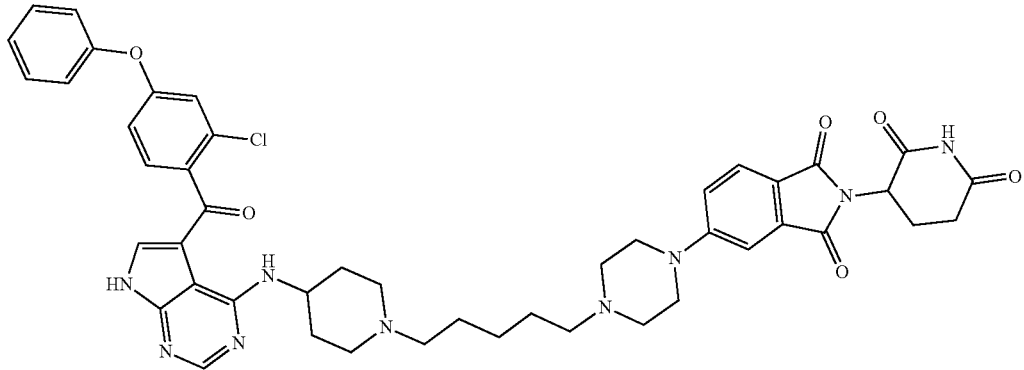<br>5-(4-(5-(4-((5-(2-chloro-4-phenoxybenzoyl)-7H-pyrrolo[2,3-d]pyrimidin-4-yl)amino)piperidin-1-yl)pentyl)piperazin-1-yl)-2-(2,6-dioxopiperidin-3-yl)isoindoline-1,3-dione |
| 35 | 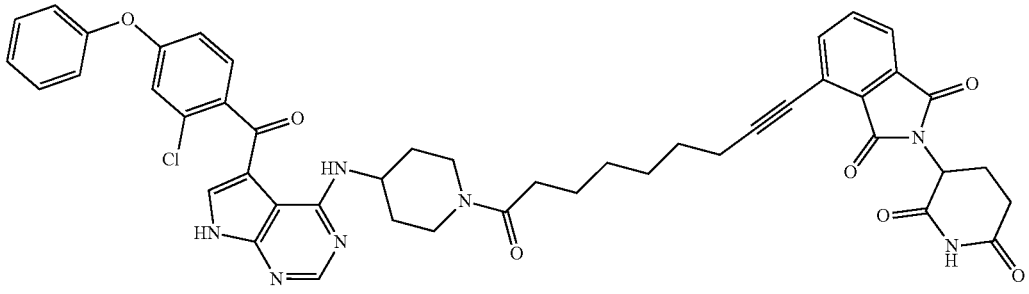<br>4-(9-(4-((5-(2-chloro-4-phenoxybenzoyl)-7H-pyrrolo[2,3-d]pyrimidin-4-yl)amino)piperidin-1-yl)-9-oxonon-1-yn-1-yl)-2-(2,6-dioxopiperidin-3-yl)isoindoline-1,3-dione |
| 36 | 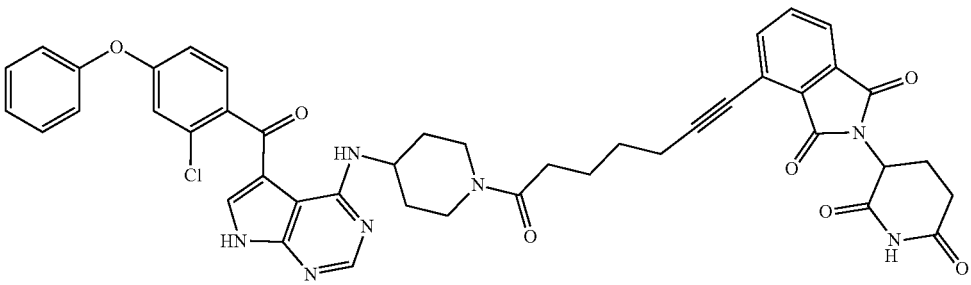<br>4-(7-(4-((5-(2-chloro-4-phenoxybenzoyl)-7H-pyrrolo[2,3-d]pyrimidin-4-yl)amino)piperidin-1-yl)-7-oxohept-1-yn-1-yl)-2-(2,6-dioxopiperidin-3-yl)isoindoline-1,3-dione |
| 37 | 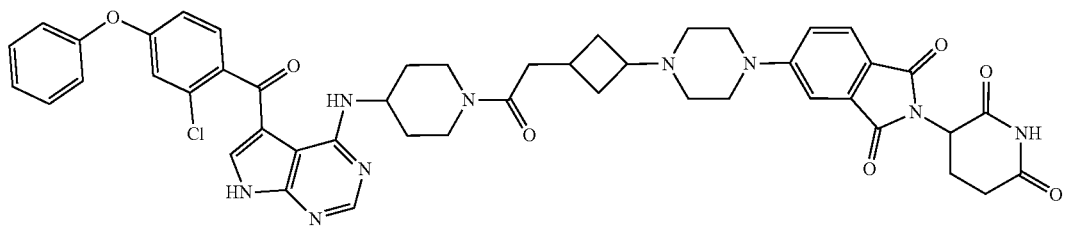 [SMILES: O=C1CCC(N2C(=O)c3ccc(N4CCN(C5CC(CC(=O)N6CCC(Nc7ncnc8[nH]cc(C(=O)c9ccc(Oc%10ccccc%10)cc9Cl)c78)CC6)C5)CC4)cc3C2=O)C(=O)N1]<br>5-(4-(3-(2-(4-((5-(2-chloro-4-phenoxybenzoyl)-7H-pyrrolo[2,3-d]pyrimidin-4-yl)amino)piperidin-1-yl)-2-oxoethyl)cyclobutyl)piperazin-1-yl)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
|---|---|
| 38 | 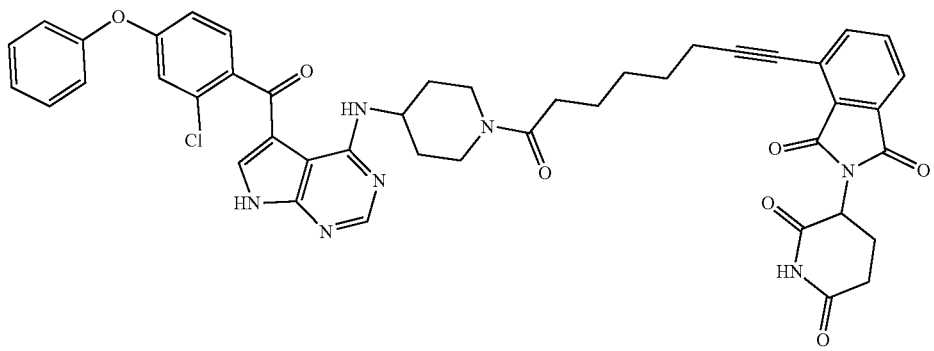 [SMILES: O=C1CCC(N2C(=O)c3cccc(C#CCCCCCC(=O)N4CCC(Nc5ncnc6[nH]cc(C(=O)c7ccc(Oc8ccccc8)cc7Cl)c56)CC4)c3C2=O)C(=O)N1]<br>4-(8-(4-((5-(2-chloro-4-phenoxybenzoyl)-7H-pyrrolo[2,3-d]pyrimidin-4-yl)amino)piperidin-1-yl)-8-oxooct-1-yn-1-yl)-2-(2,6-dioxopiperidin-3-yl)isoindoline-1,3-dione |
| 39 | 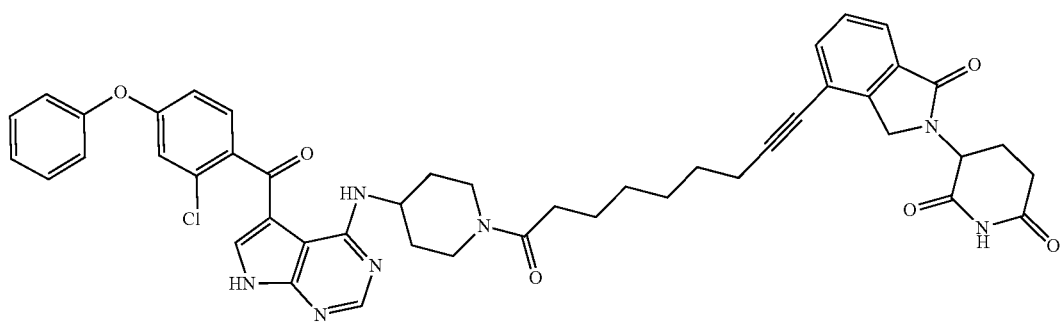<br>3-(4-(9-(4-((5-(2-chloro-4-phenoxybenzoyl)-7H-pyrrolo[2,3-d]pyrimidin-4-yl)amino)piperidin-1-yl)-9-oxonon-1-yn-1-yl)-1-oxoisoindolin-2-yl)piperidine-2,6-dione |
| 40 | 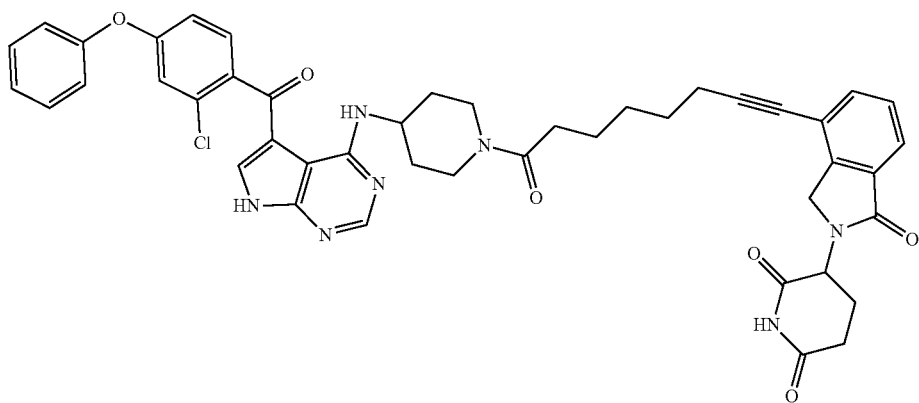 [SMILES: O=C1CCC(N2Cc3c(C#CCCCCCC(=O)N4CCC(Nc5ncnc6[nH]cc(C(=O)c7ccc(Oc8ccccc8)cc7Cl)c56)CC4)cccc3C2=O)C(=O)N1]<br>3-(4-(8-(4-((5-(2-chloro-4-phenoxybenzoyl)-7H-pyrrolo[2,3-d]pyrimidin-4-yl)amino)piperidin-1-yl)-8-oxooct-1-yn-1-yl)-1-oxoisoindolin-2-yl)piperidine-2,6-dione |

TABLE 1-continued

Exemplary Compounds of the Present Disclosure

| Compound No. | Chemical Structure and IUPAC Nomenclature |
|---|---|
| 41 | 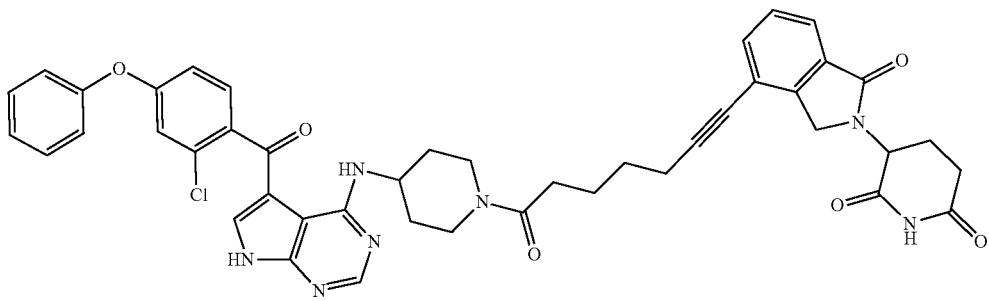<br>3-(4-(7-(4-(((5-(2-chloro-4-phenoxybenzoyl)-7H-pyrrolo[2,3-d]pyrimidin-4-yl)amino)piperidin-1-yl)-7-oxohept-1-yn-1-yl)-1-oxoisoindolin-2-yl)piperidine-2,6-dione |
| 42 | 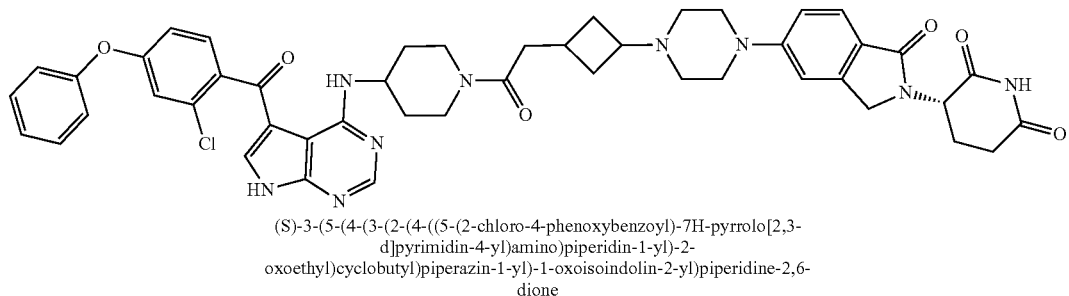<br>(S)-3-(5-(4-(3-(2-(4-((5-(2-chloro-4-phenoxybenzoyl)-7H-pyrrolo[2,3-d]pyrimidin-4-yl)amino)piperidin-1-yl)-2-oxoethyl)cyclobutyl)piperazin-1-yl)-1-oxoisoindolin-2-yl)piperidine-2,6-dione |
| 43 | 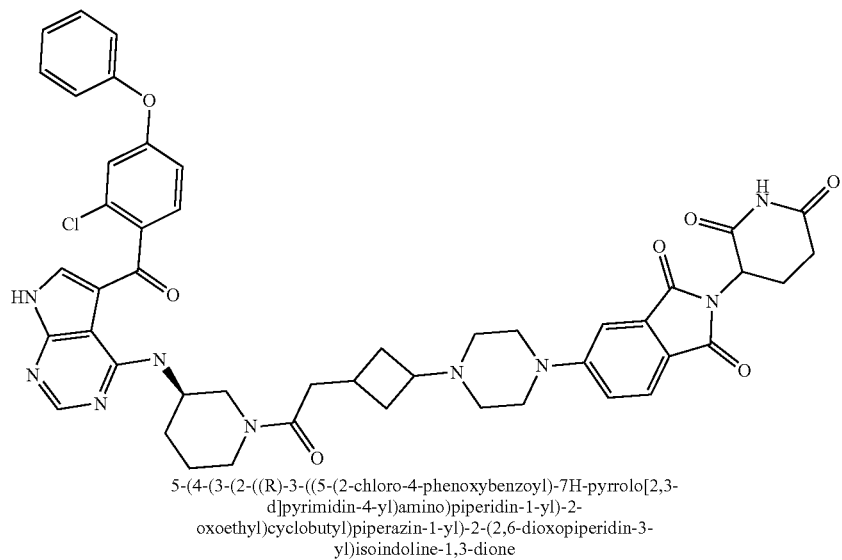<br>5-(4-(3-(2-((R)-3-((5-(2-chloro-4-phenoxybenzoyl)-7H-pyrrolo[2,3-d]pyrimidin-4-yl)amino)piperidin-1-yl)-2-oxoethyl)cyclobutyl)piperazin-1-yl)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
|---|---|
| 44 | 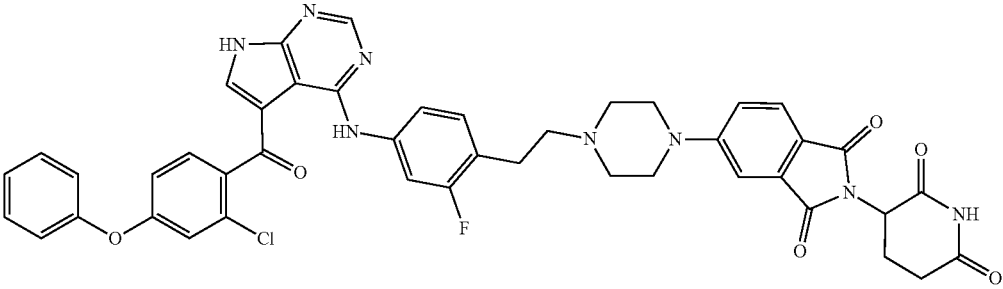 [SMILES: O=C1CCC(N2C(=O)c3ccc(N4CCN(CCc5ccc(Nc6ncnc7[nH]cc(C(=O)c8ccc(Oc9ccccc9)cc8Cl)c67)cc5F)CC4)cc3C2=O)C(=O)N1]<br>5-(4-(2-(1-(4-((5-(2-chloro-4-phenoxybenzoyl)-7H-pyrrolo[2,3-d]pyrimidin-4-yl)amino)-2-fluorophenyl)piperidin-4-yl)ethyl)piperazin-1-yl)-2-(2,6-dioxopiperidin-3-yl)isoindoline-1,3-dione |
| 45 | 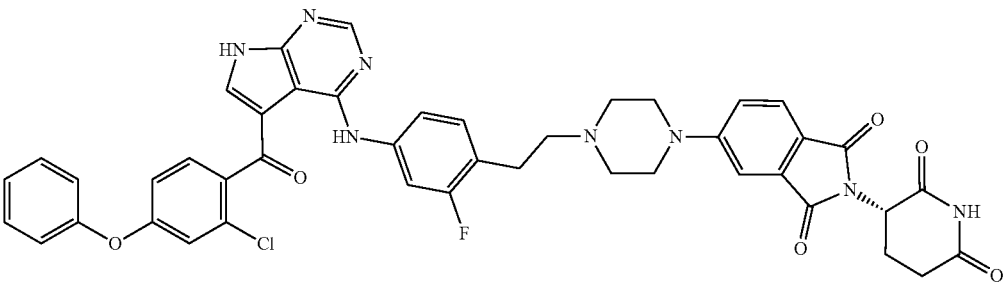 [SMILES: O=C1CC[C@H](N2C(=O)c3ccc(N4CCN(CCc5ccc(Nc6ncnc7[nH]cc(C(=O)c8ccc(Oc9ccccc9)cc8Cl)c67)cc5F)CC4)cc3C2=O)C(=O)N1]<br>(S)-3-(5-(4-(2-(1-(4-((5-(2-chloro-4-phenoxybenzoyl)-7H-pyrrolo[2,3-d]pyrimidin-4-yl)amino)-2-fluorophenyl)piperidin-4-yl)ethyl)piperazin-1-yl)-1-oxoisoindolin-2-yl)piperidine-2,6-dione |
| 46 | 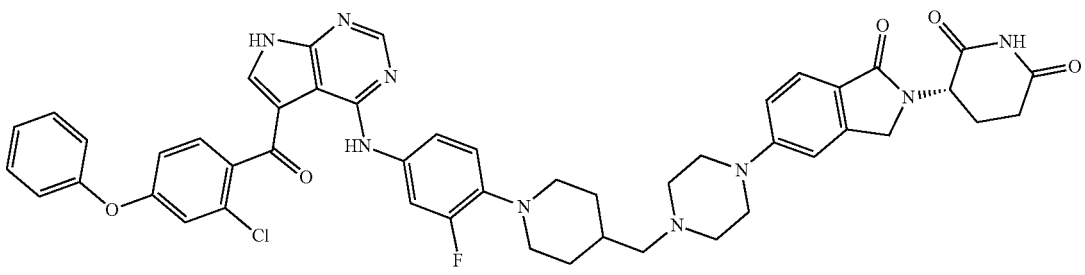 [SMILES: O=C1CC[C@H](N2Cc3cc(N4CCN(CC5CCN(c6ccc(Nc7ncnc8[nH]cc(C(=O)c9ccc(Oc%10ccccc%10)cc9Cl)c78)cc6F)CC5)CC4)ccc3C2=O)C(=O)N1]<br>(S)-3-(5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)piperazin-1-yl)-1-oxoisoindolin-2-yl)piperidine-2,6-dione |
| 47 | 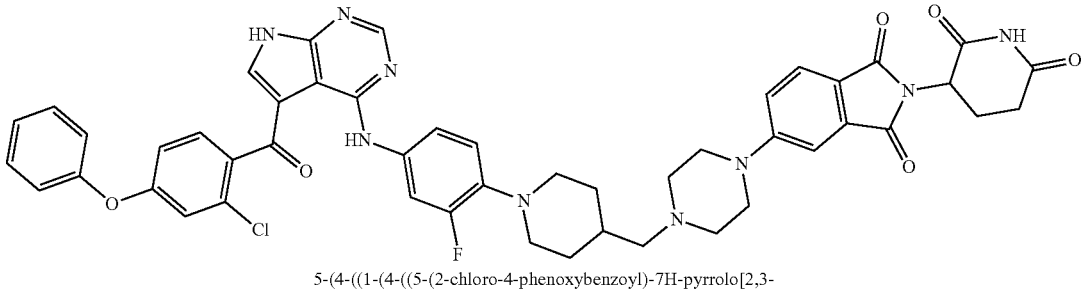<br>5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)piperazin-1-yl)-2-(2,6-dioxopiperidin-3-yl)isoindoline-1,3-dione |

TABLE 1-continued

Exemplary Compounds of the Present Disclosure

| Compound No. | Chemical Structure and IUPAC Nomenclature |
|---|---|
| 48 | 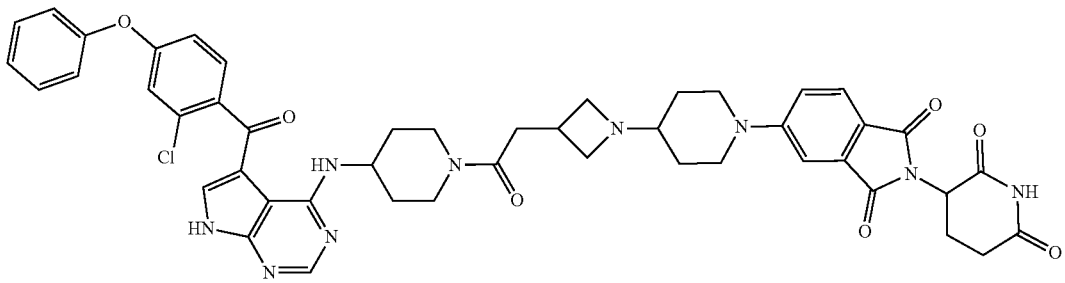 [SMILES: O=C1CCC(N2C(=O)c3ccc(N4CCC(N5CC(CC(=O)N6CCC(Nc7ncnc8[nH]cc(C(=O)c9ccc(Oc%10ccccc%10)cc9Cl)c78)CC6)C5)CC4)cc3C2=O)C(=O)N1]
5-(4-(3-(2-(4-((5-(2-chloro-4-phenoxybenzoyl)-7H-pyrrolo[2,3-d]pyrimidin-4-yl)amino)piperidin-1-yl)-2-oxoethyl)azetidin-1-yl)piperidin-1-yl)-2-(2,6-dioxopiperidin-3-yl)isoindoline-1,3-dione |
| 49 | 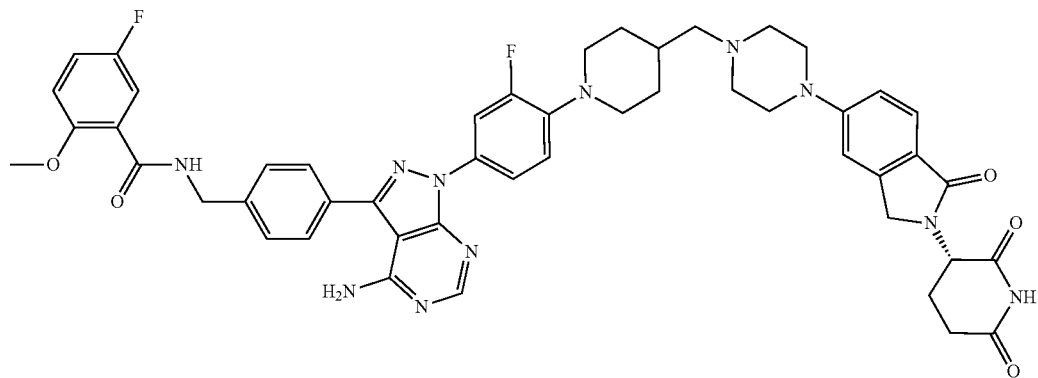 [SMILES: COc1ccc(F)cc1C(=O)NCc1ccc(-c2nn(-c3ccc(N4CCC(CN5CCN(c6ccc7c(c6)CN([C@H]6CCC(=O)NC6=O)C7=O)CC5)CC4)c(F)c3)c3ncnc(N)c23)cc1]
(S)-N-(4-(4-amino-1-(4-(4-((4-(2-(2,6-dioxopiperidin-3-yl)-1-oxoisoindolin-5-yl)piperazin-1-yl)methyl)piperidin-1-yl)-3-fluorophenyl)-1H-pyrazolo[3,4-d]pyrimidin-3-yl)benzyl)-5-fluoro-2-methoxybenzamide |
| 50 | 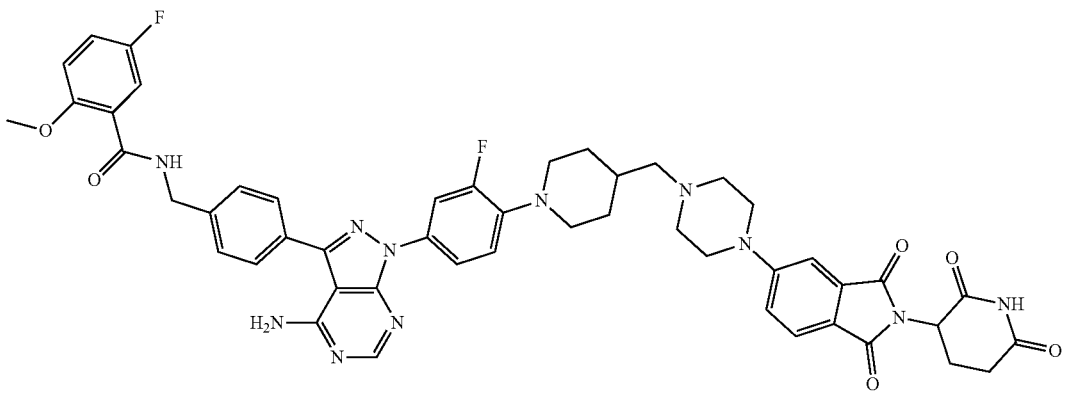 [SMILES: COc1ccc(F)cc1C(=O)NCc1ccc(-c2nn(-c3ccc(N4CCC(CN5CCN(c6ccc7c(c6)C(=O)N(C6CCC(=O)NC6=O)C7=O)CC5)CC4)c(F)c3)c3ncnc(N)c23)cc1]
N-(4-(4-amino-1-(4-(4-((4-(2-(2,6-dioxopiperidin-3-yl)-1,3-dioxoisoindolin-5-yl)piperazin-1-yl)methyl)piperidin-1-yl)-3-fluorophenyl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 51 | 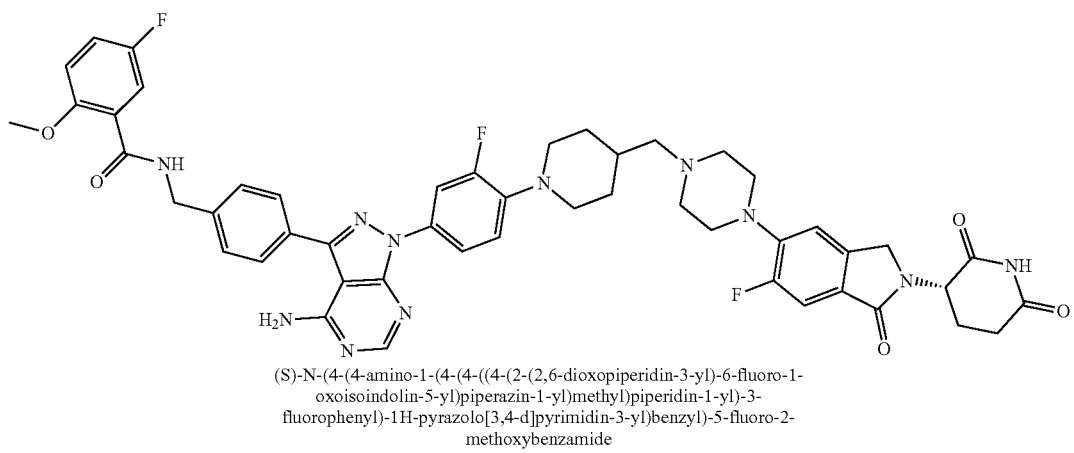
(S)-N-(4-(4-amino-1-(4-(4-((4-(2-(2,6-dioxopiperidin-3-yl)-6-fluoro-1-oxoisoindolin-5-yl)piperazin-1-yl)methyl)piperidin-1-yl)-3-fluorophenyl)-1H-pyrazolo[3,4-d]pyrimidin-3-yl)benzyl)-5-fluoro-2-methoxybenzamide |
| 52 | 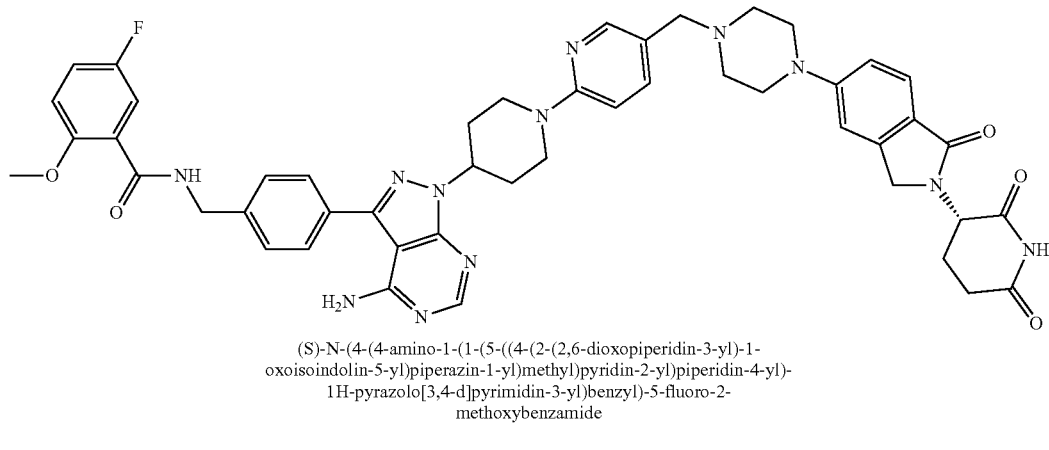
(S)-N-(4-(4-amino-1-(1-(5-((4-(2-(2,6-dioxopiperidin-3-yl)-1-oxoisoindolin-5-yl)piperazin-1-yl)methyl)pyridin-2-yl)piperidin-4-yl)-1H-pyrazolo[3,4-d]pyrimidin-3-yl)benzyl)-5-fluoro-2-methoxybenzamide |
| 53 | 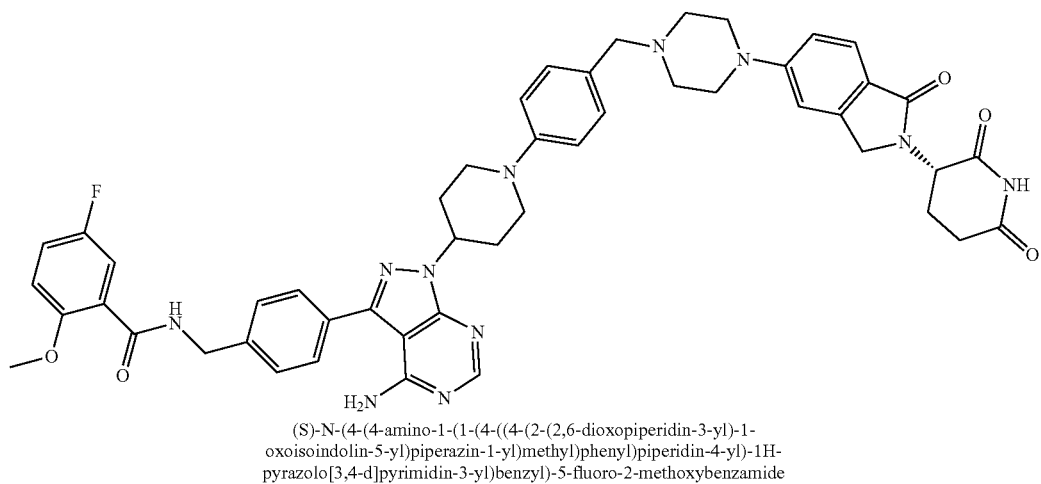
(S)-N-(4-(4-amino-1-(1-(4-((4-(2-(2,6-dioxopiperidin-3-yl)-1-oxoisoindolin-5-yl)piperazin-1-yl)methyl)phenyl)piperidin-4-yl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 54 | 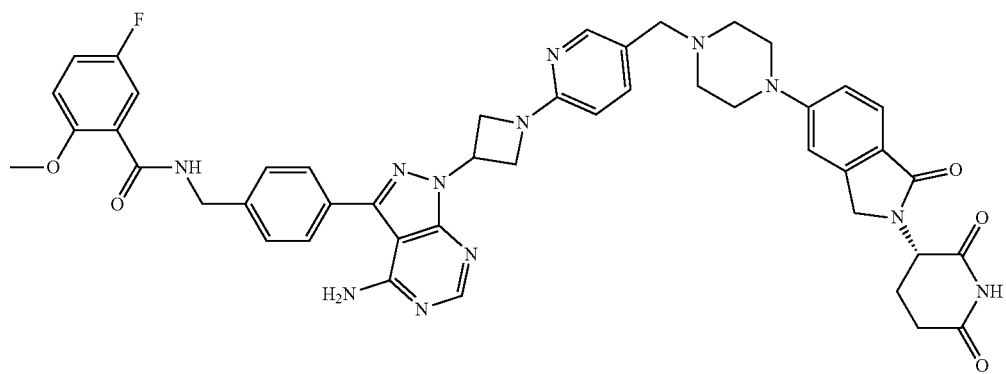 [SMILES: COc1ccc(F)cc1C(=O)NCc1ccc(-c2nn(C3CN(c4ccc(CN5CCN(c6ccc7c(c6)CN([C@H]6CCC(=O)NC6=O)C7=O)CC5)cn4)C3)c3ncnc(N)c23)cc1]<br>(S)-N-(4-(4-amino-1-(1-(5-((4-(2-(2,6-dioxopiperidin-3-yl)-1-oxoisoindolin-5-yl)piperazin-1-yl)methyl)pyridin-2-yl)azetidin-3-yl)-1H-pyrazolo[3,4-d]pyrimidin-3-yl)benzyl)-5-fluoro-2-methoxybenzamide |
| 55 | 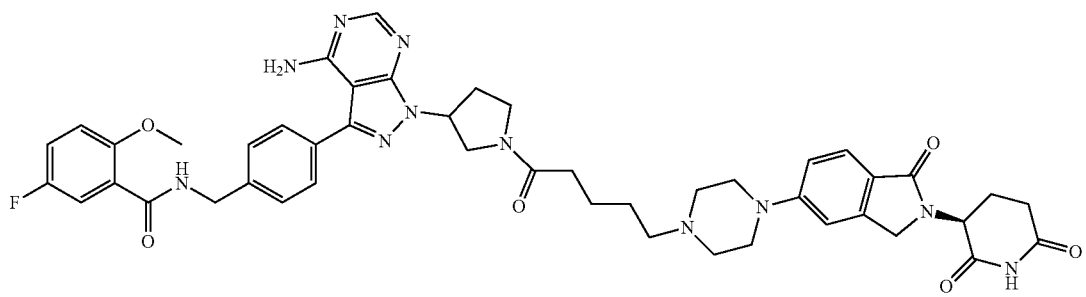 [SMILES: COc1ccc(F)cc1C(=O)NCc1ccc(-c2nn(C3CCN(C(=O)CCCCN4CCN(c5ccc6c(c5)CN([C@H]5CCC(=O)NC5=O)C6=O)CC4)C3)c3ncnc(N)c23)cc1]<br>N-(4-(4-amino-1-(1-(5-(4-(2-((S)-2,6-dioxopiperidin-3-yl)-1-oxoisoindolin-5-yl)piperazin-1-yl)pentanoyl)pyrrolidin-3-yl)-1H-pyrazolo[3,4-d]pyrimidin-3-yl)benzyl)-5-fluoro-2-methoxybenzamide |
| 56 | 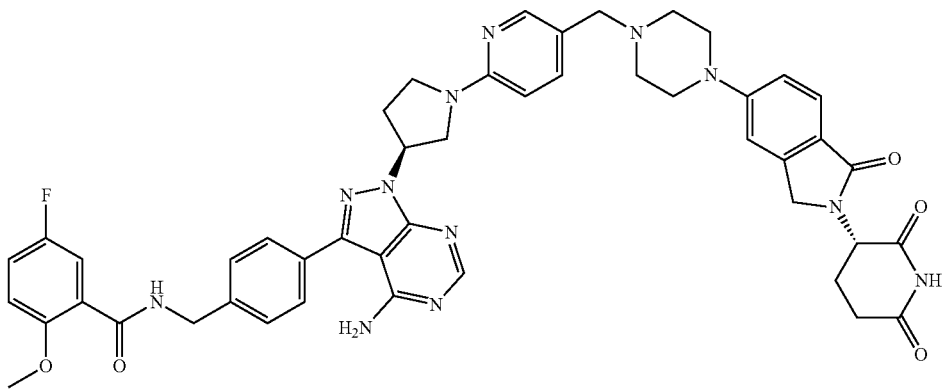 [SMILES: COc1ccc(F)cc1C(=O)NCc1ccc(-c2nn([C@H]3CCN(c4ccc(CN5CCN(c6ccc7c(c6)CN([C@H]6CCC(=O)NC6=O)C7=O)CC5)cn4)C3)c3ncnc(N)c23)cc1]<br>N-(4-(4-amino-1-((S)-1-(5-((4-(2-((S)-2,6-dioxopiperidin-3-yl)-1-oxoisoindolin-5-yl)piperazin-1-yl)methyl)pyridin-2-yl)pyrrolidin-3-yl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 57 | 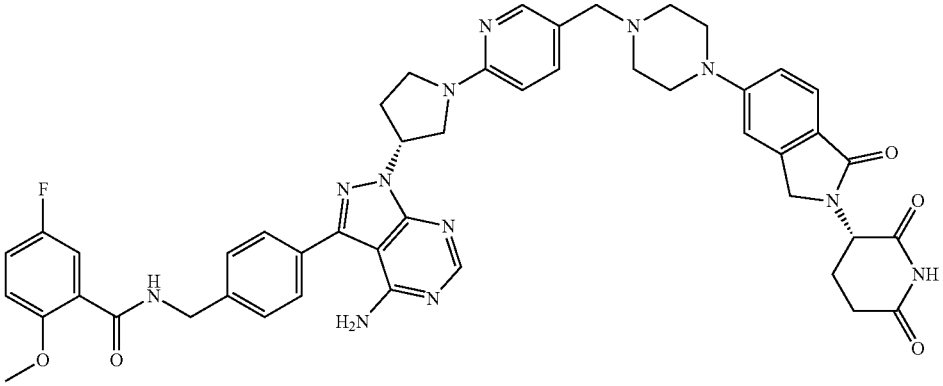 [SMILES: COc1ccc(F)cc1C(=O)NCc1ccc(-c2nn([C@@H]3CCN(c4ccc(CN5CCN(c6ccc7c(c6)CN([C@H]6CCC(=O)NC6=O)C7=O)CC5)cn4)C3)c3ncnc(N)c23)cc1] N-(4-(4-amino-1-((R)-1-(5-((4-(2-((S)-2,6-dioxopiperidin-3-yl)-1-oxoisoindolin-5-yl)piperazin-1-yl)methyl)pyridin-2-yl)pyrrolidin-3-yl)-1H-pyrazolo[3,4-d]pyrimidin-3-yl)benzyl)-5-fluoro-2-methoxybenzamide |
| 58 | 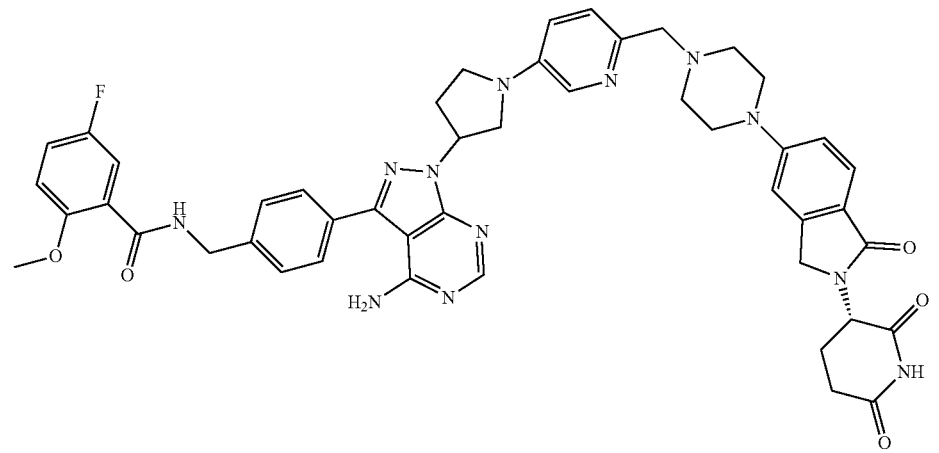 [SMILES: COc1ccc(F)cc1C(=O)NCc1ccc(-c2nn(C3CCN(c4ccc(CN5CCN(c6ccc7c(c6)CN([C@H]6CCC(=O)NC6=O)C7=O)CC5)nc4)C3)c3ncnc(N)c23)cc1] N-(4-(4-amino-1-(1-(6-((4-(2-((S)-2,6-dioxopiperidin-3-yl)-1-oxoisoindolin-5-yl)piperazin-1-yl)methyl)pyridin-3-yl)pyrrolidin-3-yl)-1H-pyrazolo[3,4-d]pyrimidin-3-yl)benzyl)-5-fluoro-2-methoxybenzamide |
| 59 | 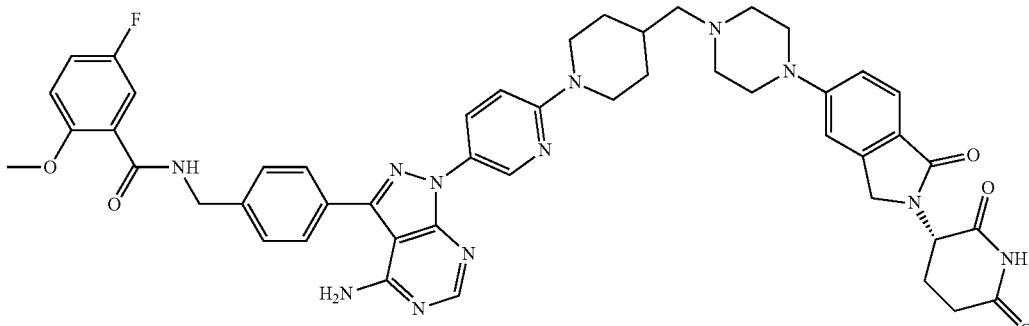 (S)-N-(4-(4-amino-1-(6-(4-((4-(2-(2,6-dioxopiperidin-3-yl)-1-oxoisoindolin-5-yl)piperazin-1-yl)methyl)piperidin-1-yl)pyridin-3-yl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 60 | 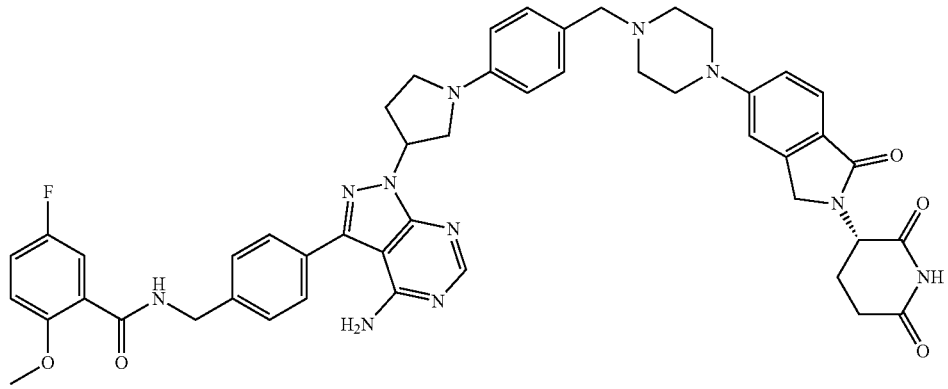
N-(4-(4-amino-1-(1-(4-((4-(2-((S)-2,6-dioxopiperidin-3-yl)-1-oxoisoindolin-5-yl)piperazin-1-yl)methyl)phenyl)pyrrolidin-3-yl)-1H-pyrazolo[3,4-d]pyrimidin-3-yl)benzyl)-5-fluoro-2-methoxybenzamide |
| 61 | 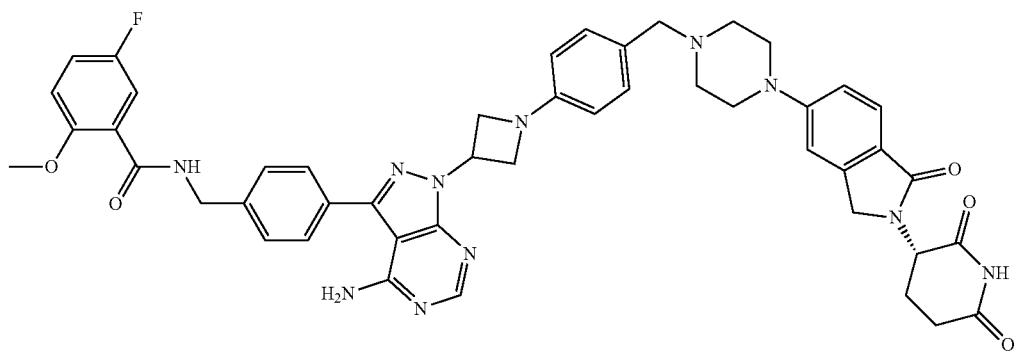 [SMILES: COc1ccc(F)cc1C(=O)NCc1ccc(-c2nn(C3CN(c4ccc(CN5CCN(c6ccc7c(c6)CN([C@H]6CCC(=O)NC6=O)C7=O)CC5)cc4)C3)c3ncnc(N)c23)cc1]
(S)-N-(4-(4-amino-1-(1-(4-((4-(2-(2,6-dioxopiperidin-3-yl)-1-oxoisoindolin-5-yl)piperazin-1-yl)methyl)phenyl)azetidin--yl)-1H-pyrazolo[3,4-d]pyrimidin-3-yl)benzyl)-5-fluoro-2-methoxybenzamide |
| 62 | 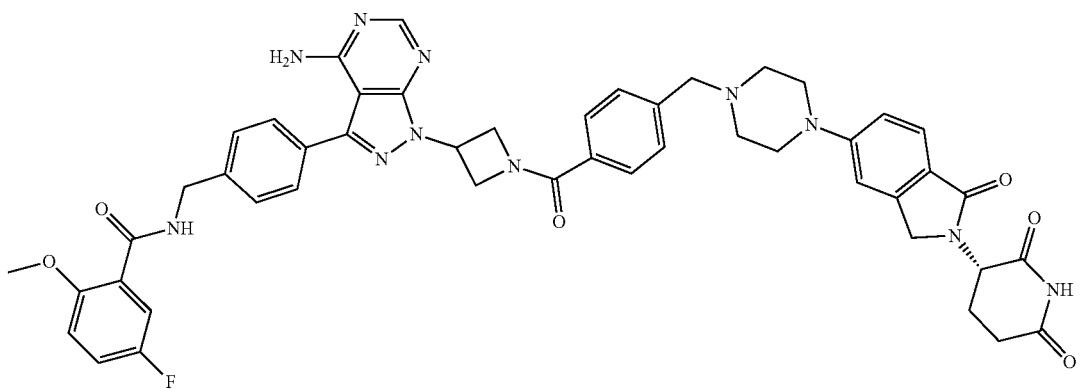 [SMILES: COc1ccc(F)cc1C(=O)NCc1ccc(-c2nn(C3CN(C(=O)c4ccc(CN5CCN(c6ccc7c(c6)CN([C@H]6CCC(=O)NC6=O)C7=O)CC5)cc4)C3)c3ncnc(N)c23)cc1]
(S)-N-(4-(4-amino-1-(1-(4-((4-(2-(2,6-dioxopiperidin-3-yl)-1-oxoisoindolin-5-yl)piperazin-1-yl)methyl)benzoyl)azetidin-3-yl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 63 | 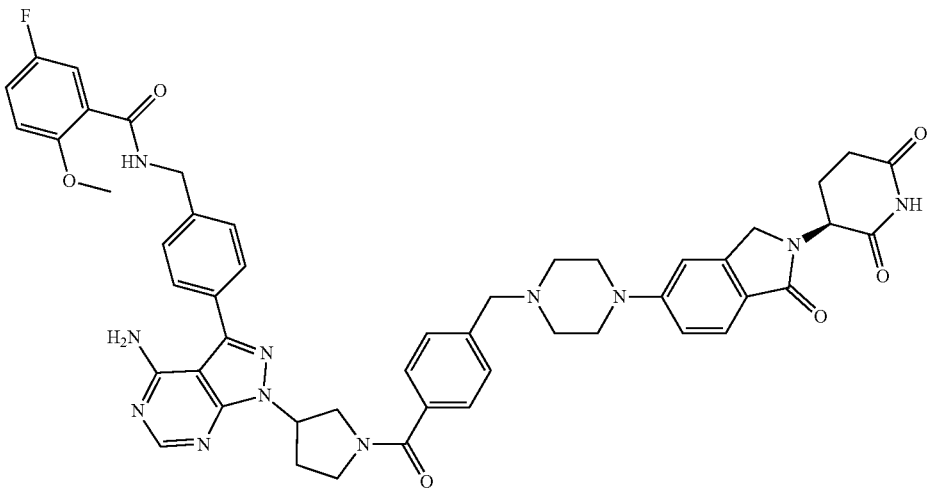 [SMILES: COc1ccc(F)cc1C(=O)NCc1ccc(-c2nn(C3CCN(C(=O)c4ccc(CN5CCN(c6ccc7c(c6)CN([C@H]6CCC(=O)NC6=O)C7=O)CC5)cc4)C3)c3ncnc(N)c23)cc1]<br>N-(4-(4-amino-1-(1-(4-((4-(2-((S)-2,6-dioxopiperidin-3-yl)-1-oxoisoindolin-5-yl)piperazin-1-yl)methyl)benzoyl)pyrrolidin-3-yl)-1H-pyrazolo[3,4-d]pyrimidin-3-yl)benzyl)-5-fluoro-2-methoxybenzamide |
| 64 | 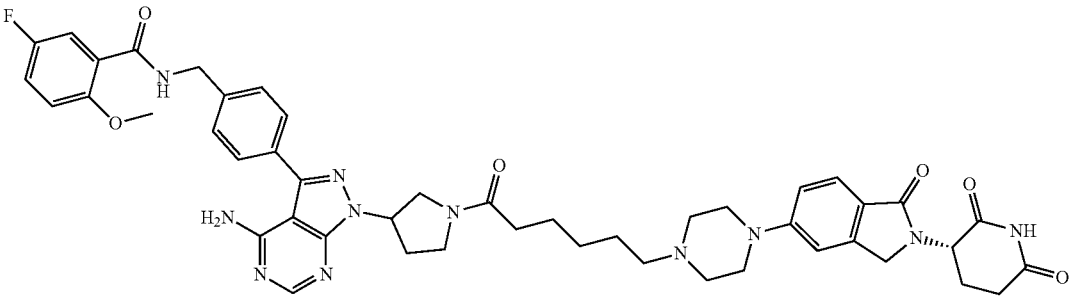 [SMILES: COc1ccc(F)cc1C(=O)NCc1ccc(-c2nn(C3CCN(C(=O)CCCCCN4CCN(c5ccc6c(c5)CN([C@H]5CCC(=O)NC5=O)C6=O)CC4)C3)c3ncnc(N)c23)cc1]<br>N-(4-(4-amino-1-(1-(6-(4-(2-((S)-2,6-dioxopiperidin-3-yl)-1-oxoisoindolin-5-yl)piperazin-1-yl)hexanoyl)pyrrolidin-3-yl)-1H-pyrazolo[3,4-d]pyrimidin-3-yl)benzyl)-5-fluoro-2-methoxybenzamide |
| 65 | 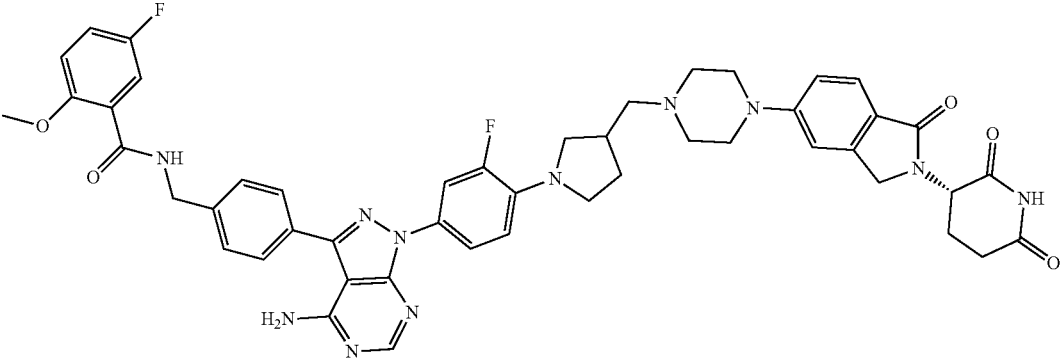 [SMILES: COc1ccc(F)cc1C(=O)NCc1ccc(-c2nn(-c3ccc(N4CCC(CN5CCN(c6ccc7c(c6)CN([C@H]6CCC(=O)NC6=O)C7=O)CC5)C4)c(F)c3)c3ncnc(N)c23)cc1]<br>N-(4-(4-amino-1-(4-(3-((4-(2-((S)-2,6-dioxopiperidin-3-yl)-1-oxoisoindolin-5-yl)piperazin-1-yl)methyl)pyrrolidin-1-yl)-3-fluorophenyl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 66 | 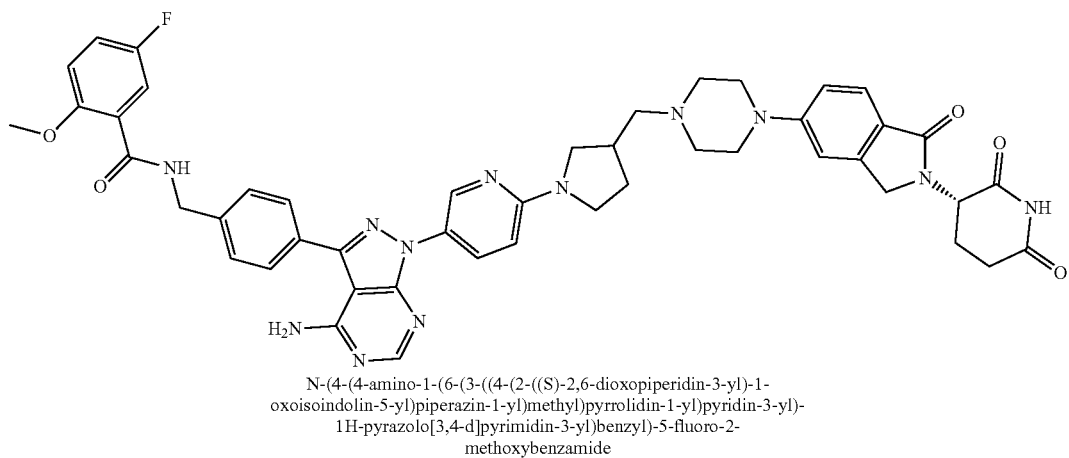
N-(4-(4-amino-1-(6-(3-((4-(2-((S)-2,6-dioxopiperidin-3-yl)-1-oxoisoindolin-5-yl)piperazin-1-yl)methyl)pyrrolidin-1-yl)pyridin-3-yl)-1H-pyrazolo[3,4-d]pyrimidin-3-yl)benzyl)-5-fluoro-2-methoxybenzamide |
| 67 | 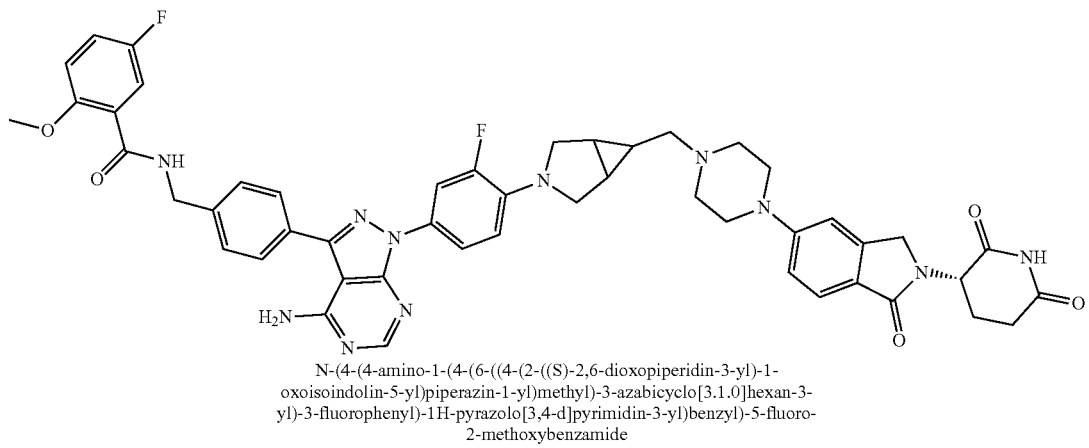
N-(4-(4-amino-1-(4-(6-((4-(2-((S)-2,6-dioxopiperidin-3-yl)-1-oxoisoindolin-5-yl)piperazin-1-yl)methyl)-3-azabicyclo[3.1.0]hexan-3-yl)-3-fluorophenyl)-1H-pyrazolo[3,4-d]pyrimidin-3-yl)benzyl)-5-fluoro-2-methoxybenzamide |
| 68 | 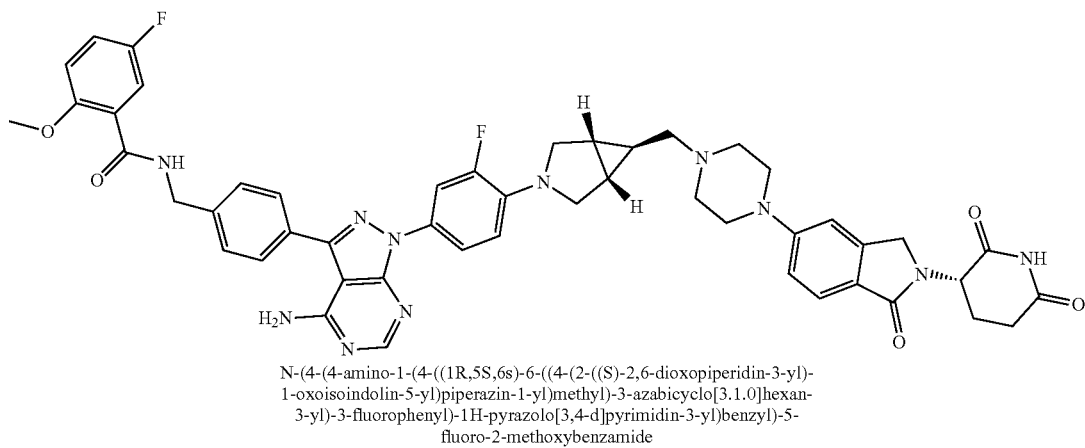
N-(4-(4-amino-1-(4-((1R,5S,6s)-6-((4-(2-((S)-2,6-dioxopiperidin-3-yl)-1-oxoisoindolin-5-yl)piperazin-1-yl)methyl)-3-azabicyclo[3.1.0]hexan-3-yl)-3-fluorophenyl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 69 | 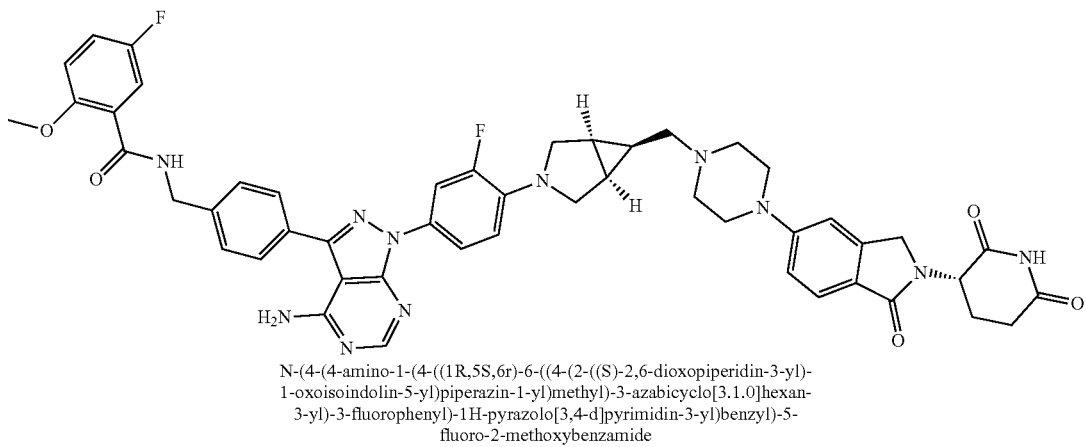<br>N-(4-(4-amino-1-(4-(((1R,5S,6r)-6-((4-(2-((S)-2,6-dioxopiperidin-3-yl)-1-oxoisoindolin-5-yl)piperazin-1-yl)methyl)-3-azabicyclo[3.1.0]hexan-3-yl)-3-fluorophenyl)-1H-pyrazolo[3,4-d]pyrimidin-3-yl)benzyl)-5-fluoro-2-methoxybenzamide |
| 70 | 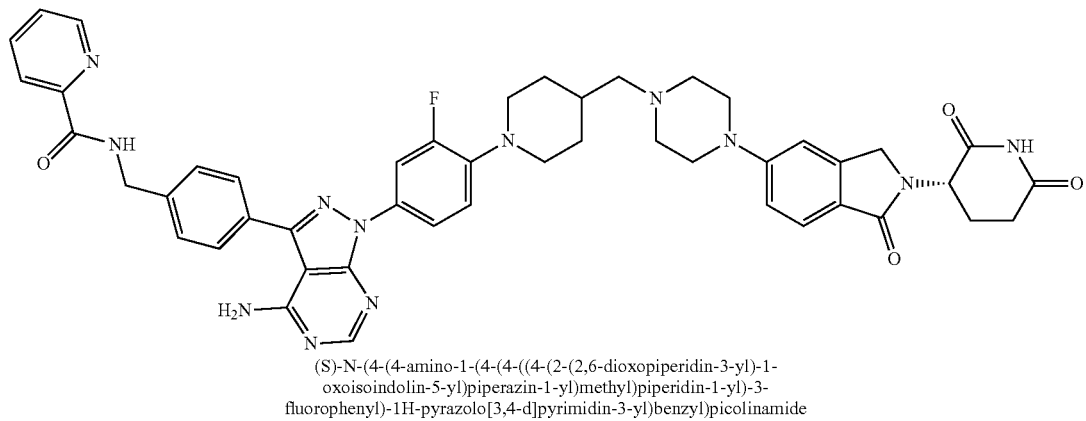<br>(S)-N-(4-(4-amino-1-(4-(4-((4-(2-(2,6-dioxopiperidin-3-yl)-1-oxoisoindolin-5-yl)piperazin-1-yl)methyl)piperidin-1-yl)-3-fluorophenyl)-1H-pyrazolo[3,4-d]pyrimidin-3-yl)benzyl)picolinamide |
| 71 | 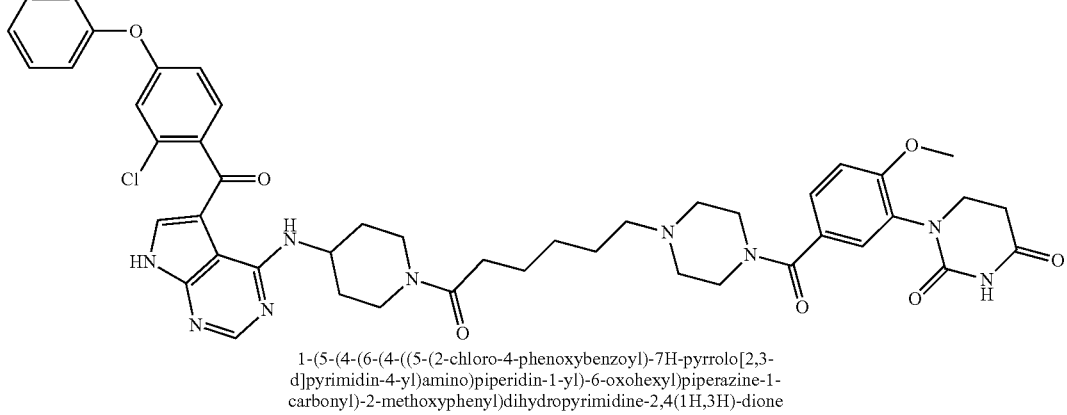<br>1-(5-(4-(6-(4-((5-(2-chloro-4-phenoxybenzoyl)-7H-pyrrolo[2,3-d]pyrimidin-4-yl)amino)piperidin-1-yl)-6-oxohexyl)piperazine-1-carbonyl)-2-methoxyphenyl)dihydropyrimidine-2,4(1H,3H)-dione |

TABLE 1-continued

Exemplary Compounds of the Present Disclosure

| Compound No. | Chemical Structure and IUPAC Nomenclature |
|---|---|

72

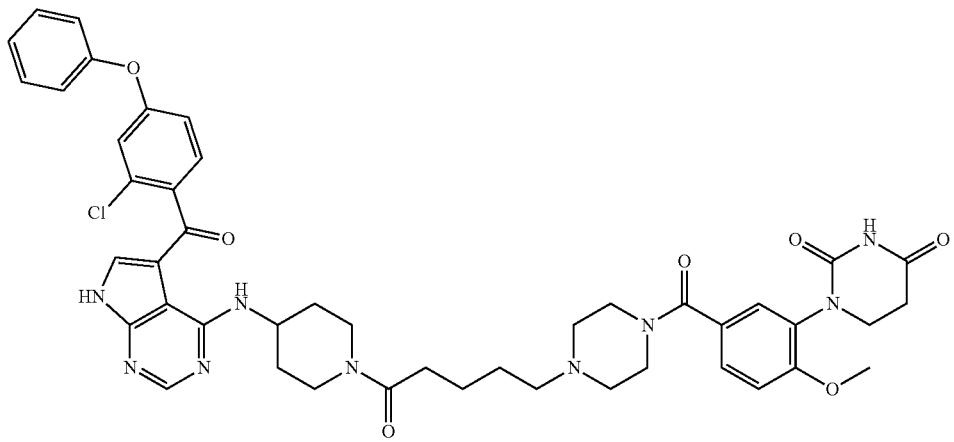 [SMILES: COc1ccc(C(=O)N2CCN(CCCCC(=O)N3CCC(Nc4ncnc5[nH]cc(C(=O)c6ccc(Oc7ccccc7)cc6Cl)c45)CC3)CC2)cc1N1CCC(=O)NC1=O]

1-(5-(4-(5-(4-((5-(2-chloro-4-phenoxybenzoyl)-7H-pyrrolo[2,3-d]pyrimidin-4-yl)amino)piperidin-1-yl)-5-oxopentyl)piperazine-1-carbonyl)-2-methoxyphenyl)dihydropyrimidine-2,4(1H,3H)-dione

73

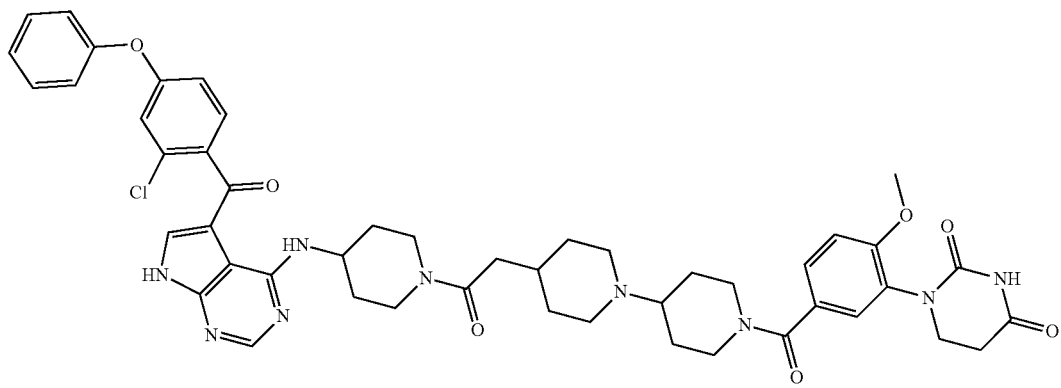 [SMILES: COc1ccc(C(=O)N2CCC(N3CCC(CC(=O)N4CCC(Nc5ncnc6[nH]cc(C(=O)c7ccc(Oc8ccccc8)cc7Cl)c56)CC4)CC3)CC2)cc1N1CCC(=O)NC1=O]

1-(5-(4-(2-(4-((5-(2-chloro-4-phenoxybenzoyl)-7H-pyrrolo[2,3-d]pyrimidin-4-yl)amino)piperidin-1-yl)-2-oxoethyl)-[1,4'-bipiperidine]-1'-carbonyl)-2-methoxyphenyl)dihydropyrimidine-2,4(1H,3H)-dione

74

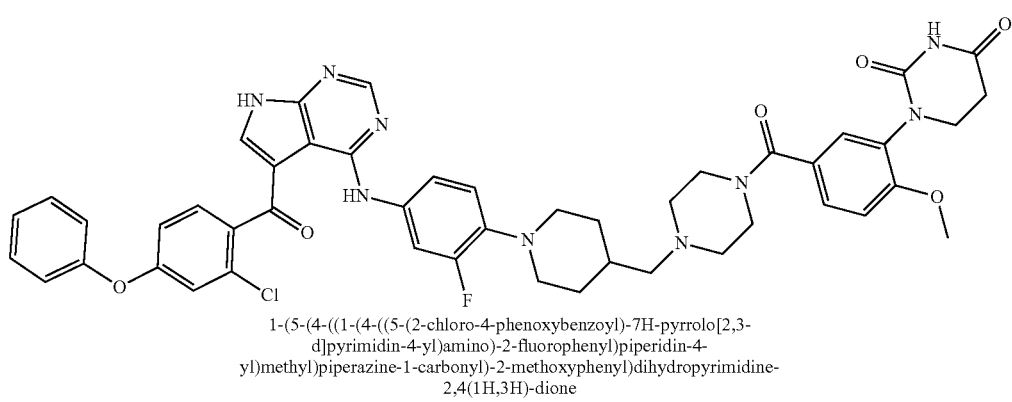

1-(5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)piperazine-1-carbonyl)-2-methoxyphenyl)dihydropyrimidine-2,4(1H,3H)-dione TABLE 1-continued Exemplary Compounds of the Present Disclosure

| Compound No. | Chemical Structure and IUPAC Nomenclature |
| --- | --- |
| 75 | 1-(5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)-1,4-diazepane-1-carbonyl)-2-methoxyphenyl)dihydropyrimidine-2,4(1H,3H)-dione |
| 76 | 1-(5-(4-(2-(1-(4-((5-(2-chloro-4-phenoxybenzoyl)-7H-pyrrolo[2,3-d]pyrimidin-4-yl)amino)-2-fluorophenyl)piperidin-4-yl)ethyl)piperazine-1-carbonyl)-2-methoxyphenyl)dihydropyrimidine-2,4(1H,3H)-dione |
| 77 | (R)-1-(5-(4-(2-(3-((5-(2-chloro-4-phenoxybenzoyl)-7H-pyrrolo[2,3-d]pyrimidin-4-yl)amino)piperidin-1-yl)-2-oxoethyl)-[1,4'-bipiperidine]-1'-carbonyl)-2-methoxyphenyl)dihydropyrimidine-2,4(1H,3H)-dione |

TABLE 1-continued

Exemplary Compounds of the Present Disclosure

| Compound No. | Chemical Structure and IUPAC Nomenclature |
|---|---|
| 78 | 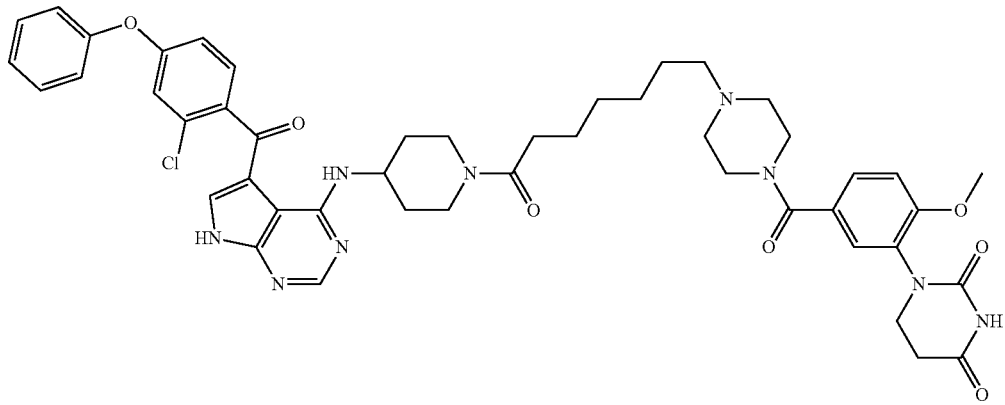 [SMILES: COc1ccc(C(=O)N2CCN(CCCCCCC(=O)N3CCC(Nc4ncnc5[nH]cc(C(=O)c6ccc(Oc7ccccc7)cc6Cl)c45)CC3)CC2)cc1N1CCC(=O)NC1=O]<br>1-(5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazine-1-carbonyl)-2-methoxyphenyl)dihydropyrimidine-2,4(1H,3H)-dione |
| 79 | 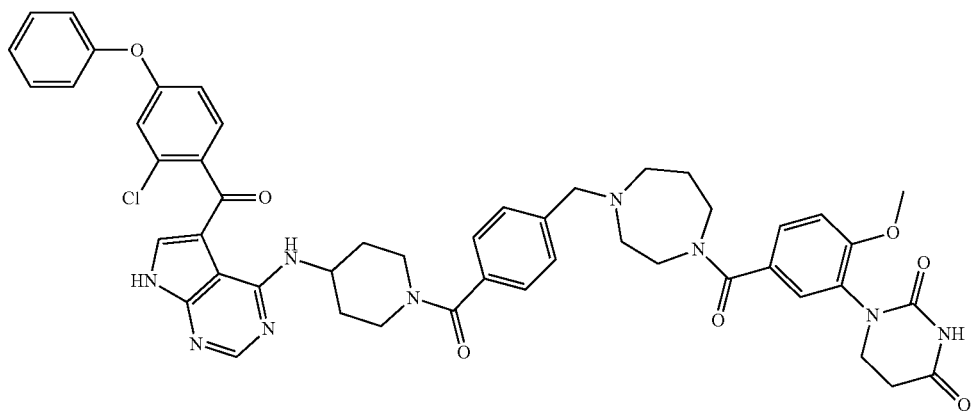 [SMILES: COc1ccc(C(=O)N2CCCN(Cc3ccc(C(=O)N4CCC(Nc5ncnc6[nH]cc(C(=O)c7ccc(Oc8ccccc8)cc7Cl)c56)CC4)cc3)CC2)cc1N1CCC(=O)NC1=O]<br>1-(5-(4-(4-(4-((5-(2-chloro-4-phenoxybenzoyl)-7H-pyrrolo[2,3-d]pyrimidin-4-yl)amino)piperidine-1-carbonyl)benzyl)-1,4-diazepane-1-carbonyl)-2-methoxyphenyl)dihydropyrimidine-2,4(1H,3H)-dione |
| 80 | 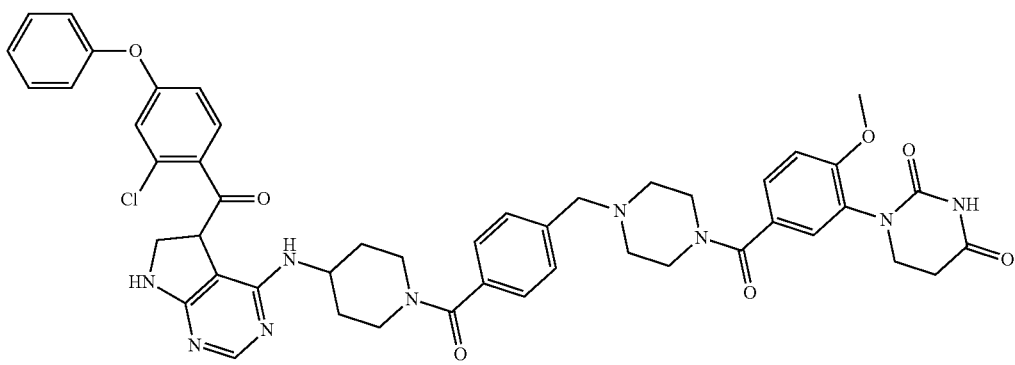 [SMILES: COc1ccc(C(=O)N2CCN(Cc3ccc(C(=O)N4CCC(Nc5ncnc6c5C(C(=O)c5ccc(Oc7ccccc7)cc5Cl)CN6)CC4)cc3)CC2)cc1N1CCC(=O)NC1=O]<br>1-(5-(4-(4-(4-((5-(2-chloro-4-phenoxybenzoyl)-7H-pyrrolo[2,3-d]pyrimidin-4-yl)amino)piperidine-1-carbonyl)benzyl)piperazine-1-carbonyl)-2-methoxyphenyl)dihydropyrimidine-2,4(1H,3H)-dione |

TABLE 1-continued

Exemplary Compounds of the Present Disclosure

| Compound No. | Chemical Structure and IUPAC Nomenclature |
| --- | --- |

81

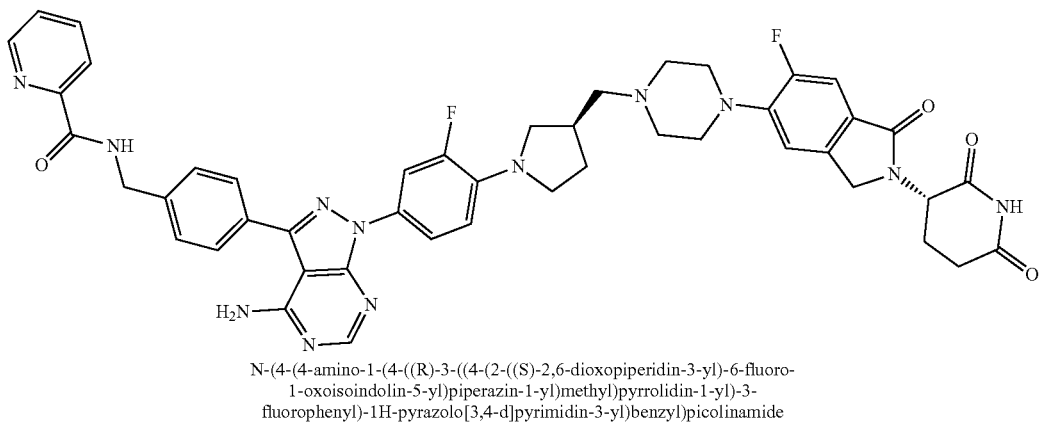

N-(4-(4-amino-1-(4-((R)-3-((4-(2-((S)-2,6-dioxopiperidin-3-yl)-6-fluoro-1-oxoisoindolin-5-yl)piperazin-1-yl)methyl)pyrrolidin-1-yl)-3-fluorophenyl)-1H-pyrazolo[3,4-d]pyrimidin-3-yl)benzyl)picolinamide

82

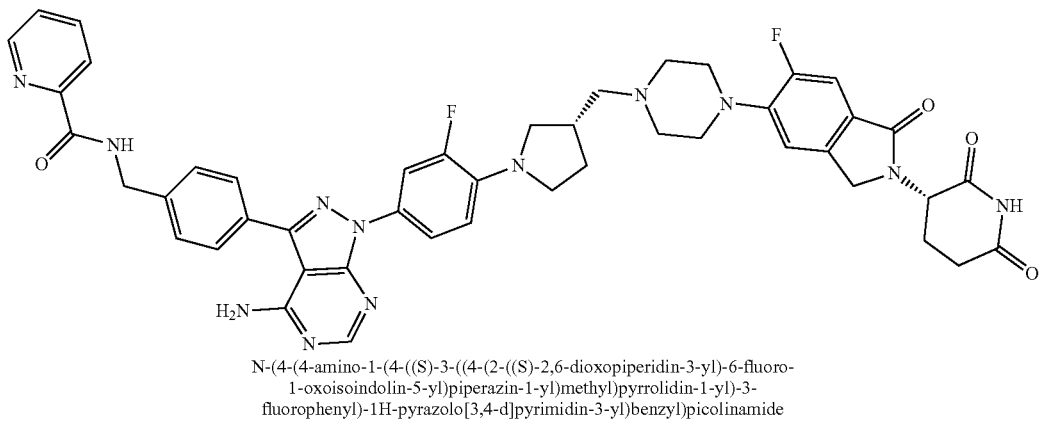

N-(4-(4-amino-1-(4-((S)-3-((4-(2-((S)-2,6-dioxopiperidin-3-yl)-6-fluoro-1-oxoisoindolin-5-yl)piperazin-1-yl)methyl)pyrrolidin-1-yl)-3-fluorophenyl)-1H-pyrazolo[3,4-d]pyrimidin-3-yl)benzyl)picolinamide

83

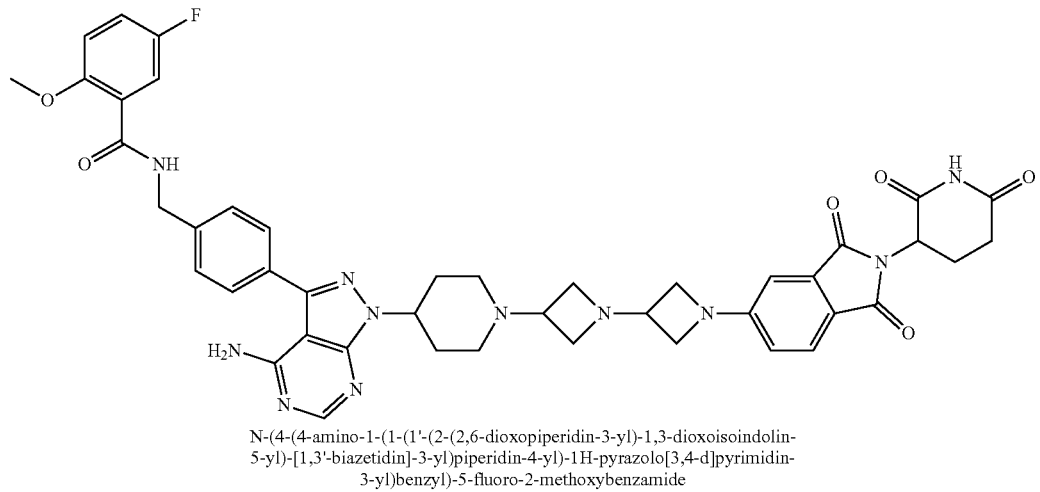

N-(4-(4-amino-1-(1-(1'-(2-(2,6-dioxopiperidin-3-yl)-1,3-dioxoisoindolin-5-yl)-[1,3'-biazetidin]-3-yl)piperidin-4-yl)-1H-pyrazolo[3,4-d]pyrimidin-3-yl)benzyl)-5-fluoro-2-methoxybenzamide

TABLE 1-continued

Exemplary Compounds of the Present Disclosure

| Compound No. | Chemical Structure and IUPAC Nomenclature |
|---|---|
| 84 | N-(4-(4-amino-1-(1'-(1-(2-(2,6-dioxopiperidin-3-yl)-1,3-dioxoisoindolin-5-yl)azetidin-3-yl)-[1,4'-bipiperidin]-4-yl)-1H-pyrazolo[3,4-d]pyrimidin-3-yl)benzyl)-5-fluoro-2-methoxybenzamide |
| 85 | (S)-N-(4-(4-amino-1-(4-(3-((4-(2-(2,6-dioxopiperidin-3-yl)-1-oxoisoindolin-5-yl)piperazin-1-yl)methyl)azetidin-1-yl)-3-fluorophenyl)-1H-pyrazolo[3,4-d]pyrimidin-3-yl)benzyl)-5-fluoro-2-methoxybenzamide |
| 86 | (S)-N-(4-(4-amino-1-(1-(1-(2-(4-(2-(2,6-dioxopiperidin-3-yl)-1-oxoisoindolin-5-yl)piperazin-1-yl)ethyl)azetidin-3-yl)piperidin-4-yl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 87 | 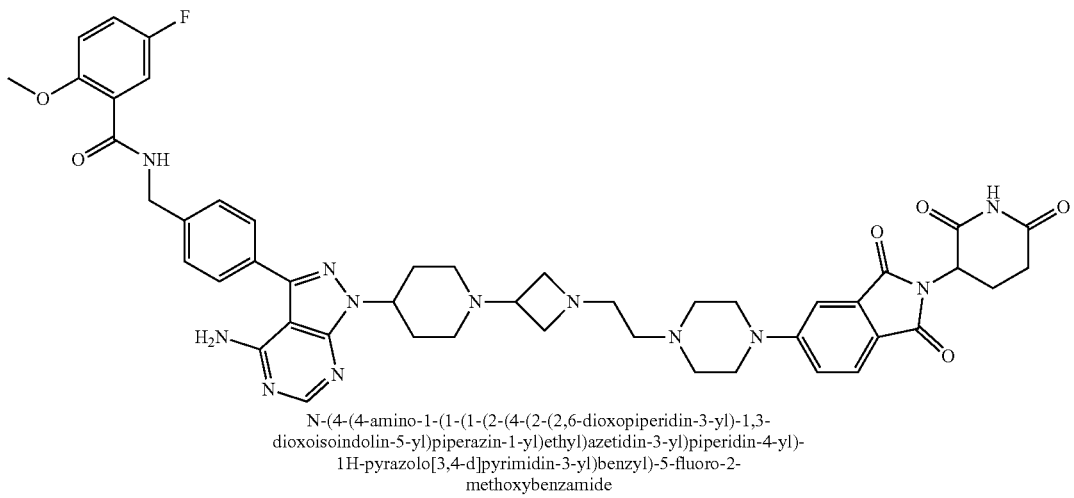<br>N-(4-(4-amino-1-(1-(1-(2-(4-(2-(2,6-dioxopiperidin-3-yl)-1,3-dioxoisoindolin-5-yl)piperazin-1-yl)ethyl)azetidin-3-yl)piperidin-4-yl)-1H-pyrazolo[3,4-d]pyrimidin-3-yl)benzyl)-5-fluoro-2-methoxybenzamide |
| 88 | 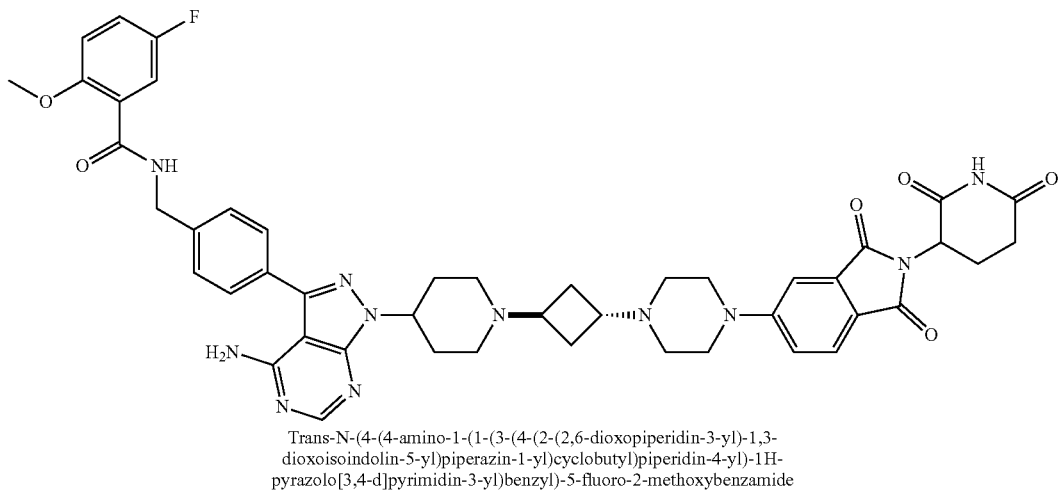<br>Trans-N-(4-(4-amino-1-(1-(3-(4-(2-(2,6-dioxopiperidin-3-yl)-1,3-dioxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide |
| 89 | 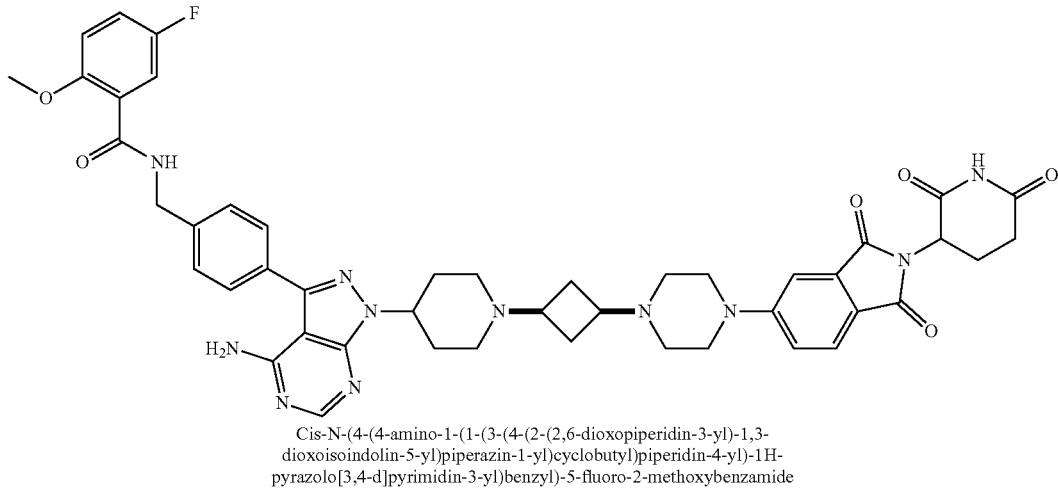<br>Cis-N-(4-(4-amino-1-(1-(3-(4-(2-(2,6-dioxopiperidin-3-yl)-1,3-dioxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 90 | Trans-N-(4-(4-amino-1-(1-((1S,3r)-3-(4-(2-((S)-2,6-dioxopiperidin-3-yl)-1-oxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide |
| 91 | Cis-N-(4-(4-amino-1-(1-(3-(4-(2-((S)-2,6-dioxopiperidin-3-yl)-1-oxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide |
| 92 | N-(4-(4-amino-1-(1-(5-((4-(2-((S)-2,6-dioxopiperidin-3-yl)-1-oxoisoindolin-5-yl)piperazin-1-yl)methyl)pyridin-2-yl)pyrrolidin-3-yl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 93 | 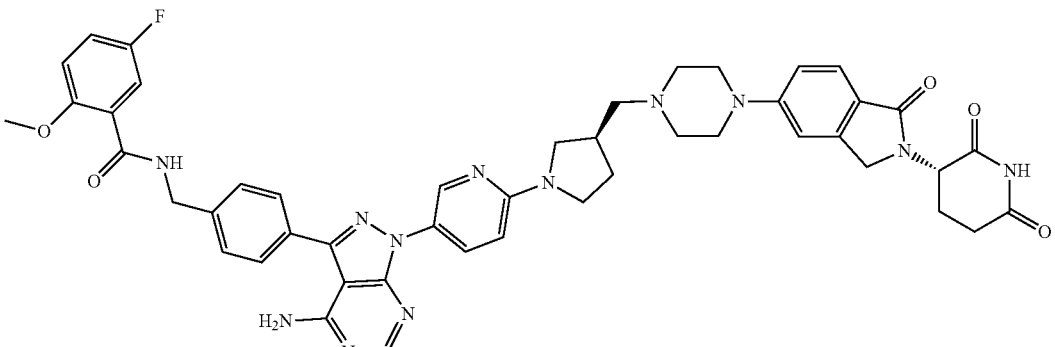<br>N-(4-(4-amino-1-(6-((R)-3-((4-(2-((S)-2,6-dioxopiperidin-3-yl)-1-oxoisoindolin-5-yl)piperazin-1-yl)methyl)pyrrolidin-1-yl)pyridin-3-yl)-1H-pyrazolo[3,4-d]pyrimidin-3-yl)benzyl)-5-fluoro-2-methoxybenzamide |
| 94 | 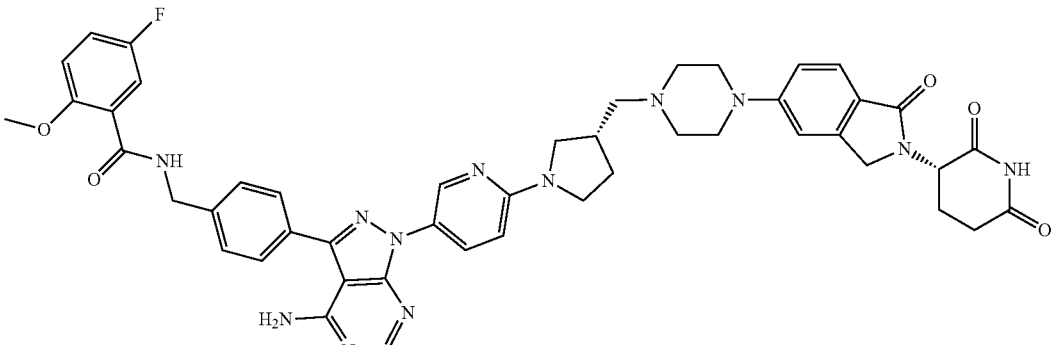<br>N-(4-(4-amino-1-(6-((S)-3-((4-(2-((S)-2,6-dioxopiperidin-3-yl)-1-oxoisoindolin-5-yl)piperazin-1-yl)methyl)pyrrolidin-1-yl)pyridin-3-yl)-1H-pyrazolo[3,4-d]pyrimidin-3-yl)benzyl)-5-fluoro-2-methoxybenzamide |
| 95 | 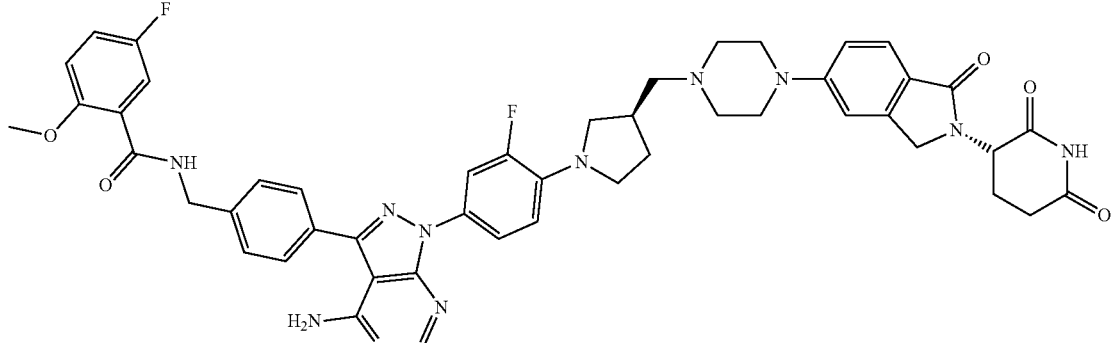<br>N-(4-(4-amino-1-(4-((R)-3-((4-(2-((S)-2,6-dioxopiperidin-3-yl)-1-oxoisoindolin-5-yl)piperazin-1-yl)methyl)pyrrolidin-1-yl)-3-fluorophenyl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 96 | 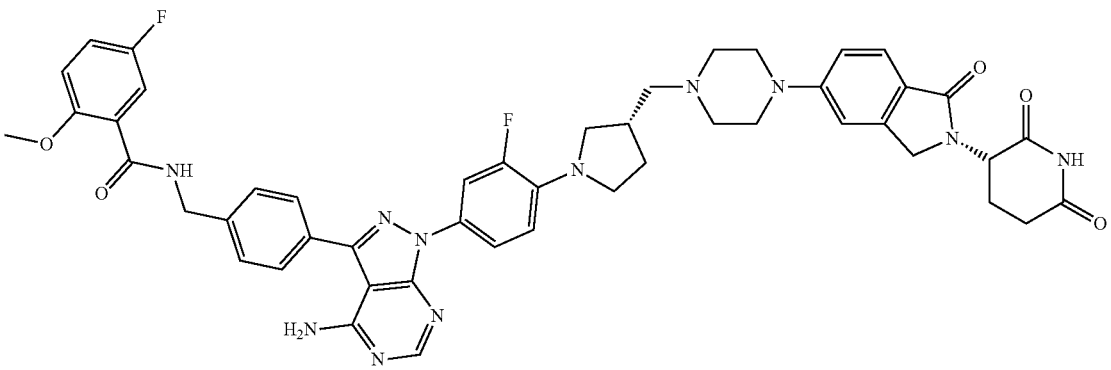<br>N-(4-(4-amino-1-(4-((S)-3-((4-(2-((S)-2,6-dioxopiperidin-3-yl)-1-oxoisoindolin-5-yl)piperazin-1-yl)methyl)pyrrolidin-1-yl)-3-fluorophenyl)-1H-pyrazolo[3,4-d]pyrimidin-3-yl)benzyl)-5-fluoro-2-methoxybenzamide |
| 97 | 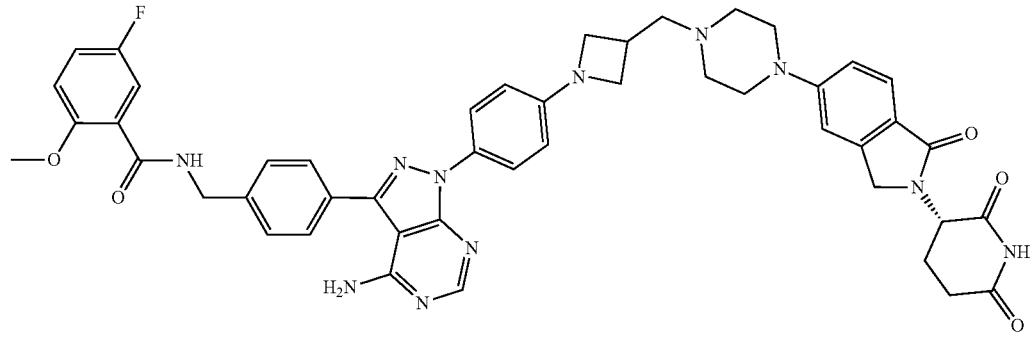 [SMILES: COc1ccc(F)cc1C(=O)NCc1ccc(-c2nn(-c3ccc(N4CC(CN5CCN(c6ccc7c(c6)CN([C@H]6CCC(=O)NC6=O)C7=O)CC5)C4)cc3)c3ncnc(N)c23)cc1]<br>(S)-N-(4-(4-amino-1-(6-(3-((4-(2-(2,6-dioxopiperidin-3-yl)-1-oxoisoindolin-5-yl)piperazin-1-yl)methyl)azetidin-1-yl)pyridin-3-yl)-1H-pyrazolo[3,4-d]pyrimidin-3-yl)benzyl)-5-fluoro-2-methoxybenzamide |
| 98 | 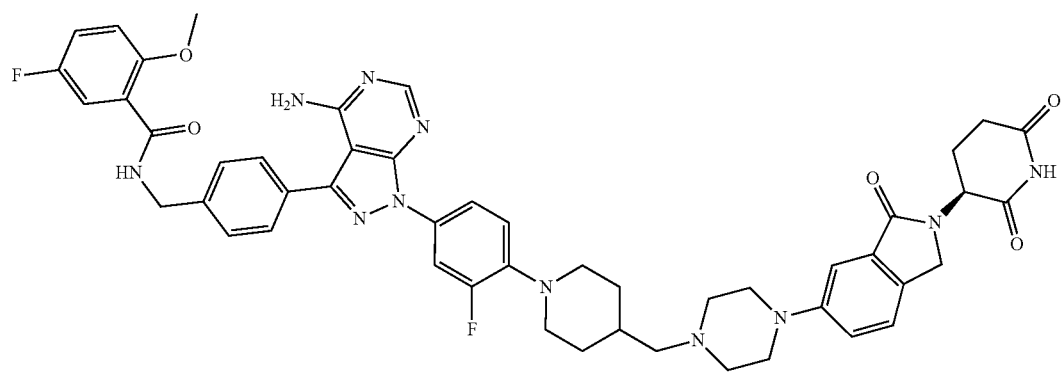 [SMILES: COc1ccc(F)cc1C(=O)NCc1ccc(-c2nn(-c3ccc(N4CCC(CN5CCN(c6ccc7c(c6)C(=O)N([C@H]6CCC(=O)NC6=O)C7)CC5)CC4)c(F)c3)c3ncnc(N)c23)cc1]<br>(S)-N-(4-(4-amino-1-(4-(4-((4-(2-(2,6-dioxopiperidin-3-yl)-3-oxoisoindolin-5-yl)piperazin-1-yl)methyl)piperidin-1-yl)-3-fluorophenyl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 99 | 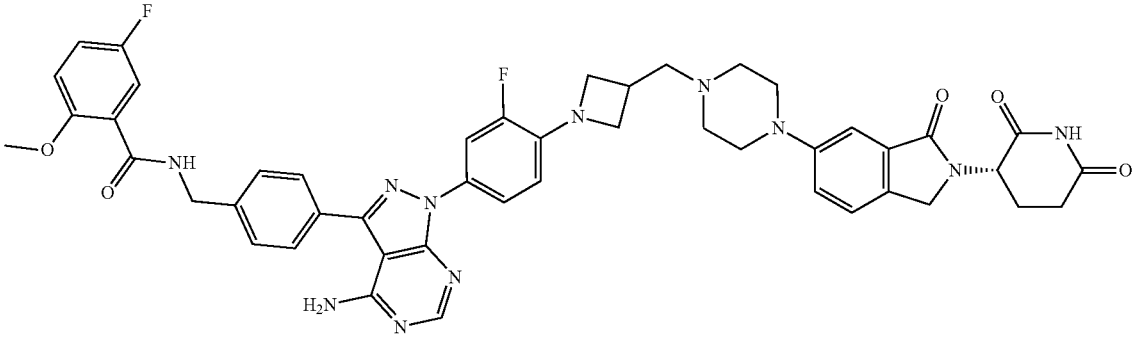 [SMILES: COc1ccc(F)cc1C(=O)NCc1ccc(-c2nn(-c3ccc(N4CC(CN5CCN(c6ccc7c(c6)C(=O)N([C@H]6CCC(=O)NC6=O)C7)CC5)C4)c(F)c3)c3ncnc(N)c23)cc1]<br>(S)-N-(4-(4-amino-1-(4-(3-((4-(2-(2,6-dioxopiperidin-3-yl)-3-oxoisoindolin-5-yl)piperazin-1-yl)methyl)azetidin-1-yl)-3-fluorophenyl)-1H-pyrazolo[3,4-d]pyrimidin-3-yl)benzyl)-5-fluoro-2-methoxybenzamide |
| 100 | 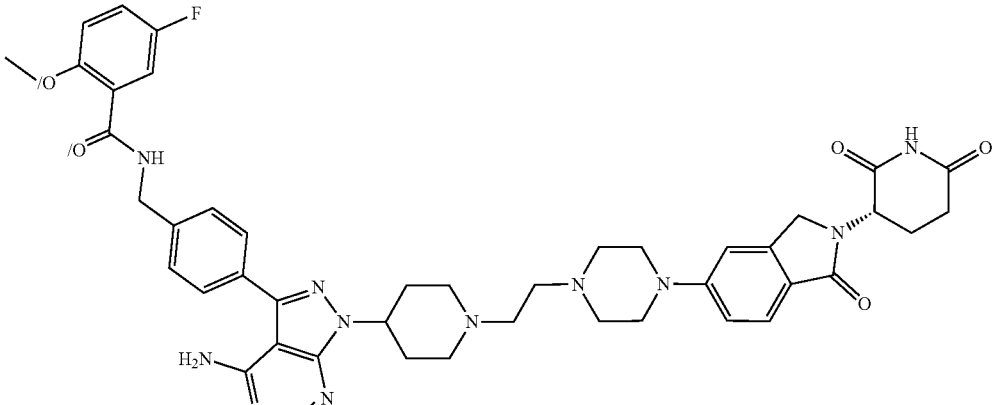<br>(S)-N-(4-(4-amino-1-(1-(2-(4-(2-(2,6-dioxopiperidin-3-yl)-1-oxoisoindolin-5-yl)piperazin-1-yl)ethyl)piperidin-4-yl)-1H-pyrazolo[3,4-d]pyrimidin-3-yl)benzyl)-5-fluoro-2-methoxybenzamide |
| 101 | 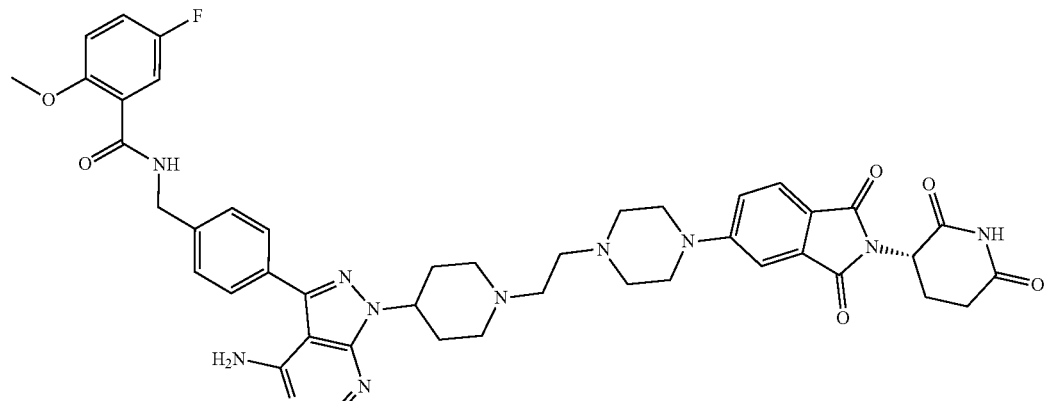<br>(S)-N-(4-(4-amino-1-(1-(2-(4-(2-(2,6-dioxopiperidin-3-yl)-3-oxoisoindolin-5-yl)piperazin-1-yl)ethyl)piperidin-4-yl)-1H-pyrazolo[3,4-d]pyrimidin-3-yl)benzyl)-5-fluoro-2-methoxybenzamide |

TABLE 1-continued

Exemplary Compounds of the Present Disclosure

| Compound No. | Chemical Structure and IUPAC Nomenclature |
|---|---|
| 102 | 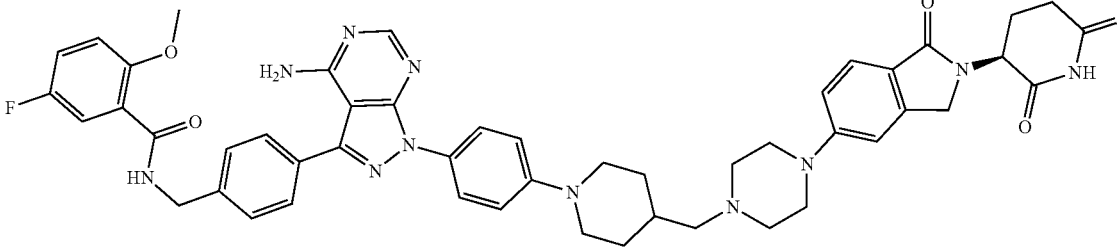<br>(S)-N-(4-(4-amino-1-(4-(4-((4-(2-(2,6-dioxopiperidin-3-yl)-1-oxoisoindolin-5-yl)piperazin-1-yl)methyl)piperidin-1-yl)phenyl)-1H-pyrazolo[3,4-d]pyrimidin-3-yl)benzyl)-5-fluoro-2-methoxybenzamide |
| 103 | 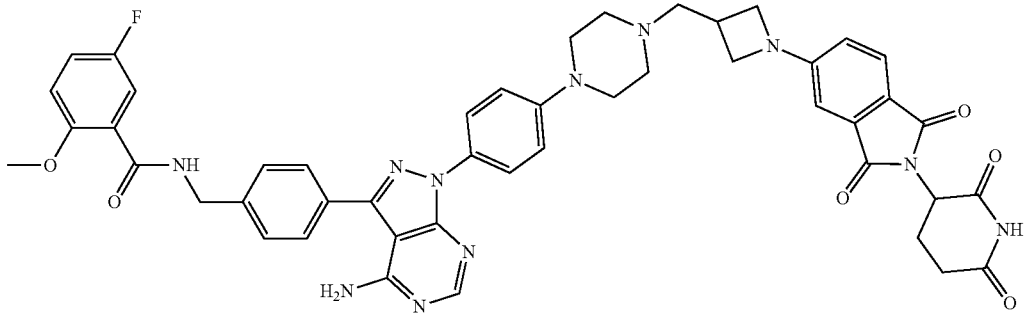 [SMILES: COc1ccc(F)cc1C(=O)NCc1ccc(-c2nn(-c3ccc(N4CCN(CC5CN(c6ccc7c(c6)C(=O)N(C6CCC(=O)NC6=O)C7=O)C5)CC4)cc3)c3ncnc(N)c23)cc1]<br>N-(4-(4-amino-1-(4-(4-((1-(2-(2,6-dioxopiperidin-3-yl)-1,3-dioxoisoindolin-5-yl)azetidin-3-yl)methyl)piperazin-1-yl)phenyl)-1H-pyrazolo[3,4-d]pyrimidin-3-yl)benzyl)-5-fluoro-2-methoxybenzamide |
| 104 | 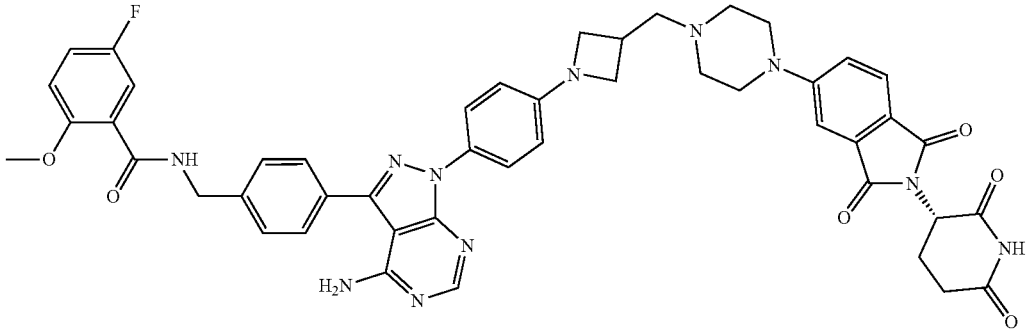 [SMILES: COc1ccc(F)cc1C(=O)NCc1ccc(-c2nn(-c3ccc(N4CC(CN5CCN(c6ccc7c(c6)C(=O)N([C@H]6CCC(=O)NC6=O)C7=O)CC5)C4)cc3)c3ncnc(N)c23)cc1]<br>(S)-N-(4-(4-amino-1-(4-(3-((4-(2-(2,6-dioxopiperidin-3-yl)-1-oxoisoindolin-5-yl)piperazin-1-yl)methyl)azetidin-1-yl)phenyl)-1H-pyrazolo[3,4-d]pyrimidin-3-yl)benzyl)-5-fluoro-2-methoxybenzamide |
| 105 | 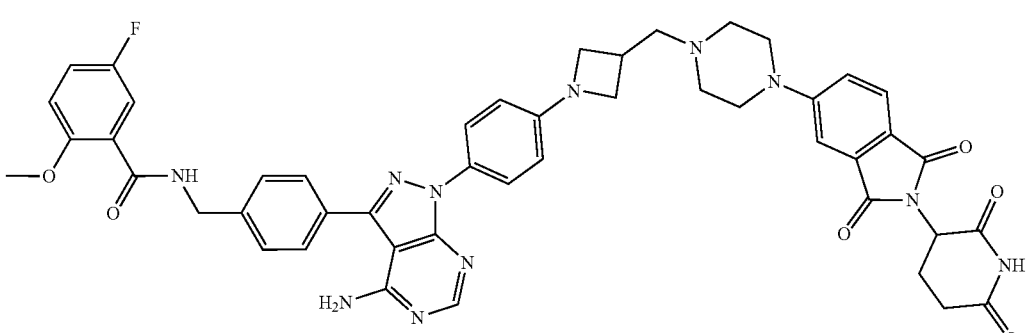<br>5-(4-((1-(4-(4-amino-3-(4-((5-fluoro-2-methoxybenzamido)methyl)phenyl)-1H-pyrazolo[3,4-d]pyrimidin-1-yl)phenyl)azetidin-3-yl)methyl)piperazin-1-yl)-N-(2,6-dioxopiperidin-3-yl)picolinamide |

TABLE 1-continued

Exemplary Compounds of the Present Disclosure

| Compound No. | Chemical Structure and IUPAC Nomenclature |
| --- | --- |

106

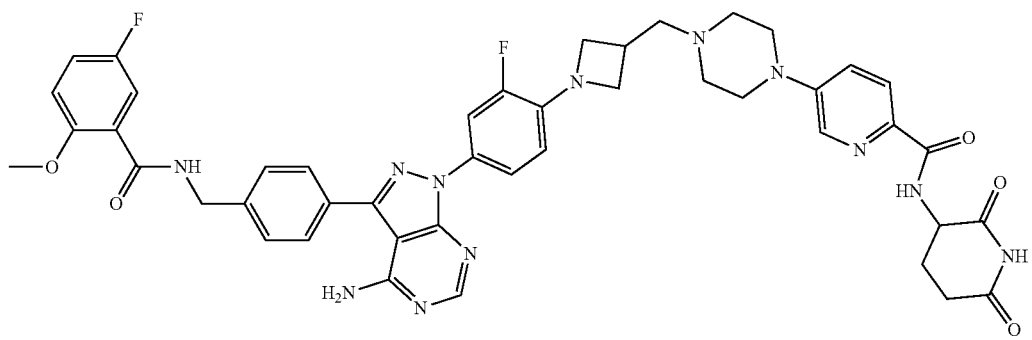 [SMILES: COc1ccc(F)cc1C(=O)NCc1ccc(-c2nn(-c3ccc(N4CC(CN5CCN(c6ccc(C(=O)NC7CCC(=O)NC7=O)nc6)CC5)C4)c(F)c3)c3ncnc(N)c23)cc1]

5-(4-((1-(4-(4-amino-3-(4-((5-fluoro-2-methoxybenzamido)methyl)phenyl)-1H-pyrazolo[3,4-d]pyrimidin-1-yl)-2-fluorophenyl)azetidin-3-yl)methyl)piperazin-1-yl)-N-(2,6-dioxopiperidin-3-yl)picolinamide

107

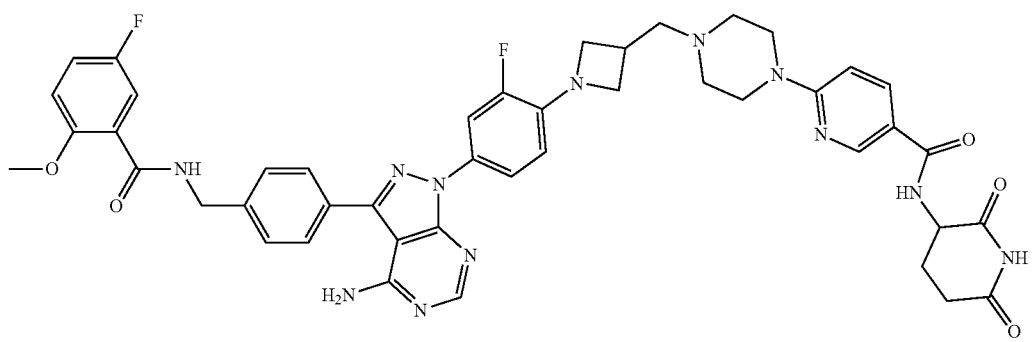 [SMILES: COc1ccc(F)cc1C(=O)NCc1ccc(-c2nn(-c3ccc(N4CC(CN5CCN(c6ccc(C(=O)NC7CCC(=O)NC7=O)cn6)CC5)C4)c(F)c3)c3ncnc(N)c23)cc1]

6-(4-((1-(4-(4-amino-3-(4-((5-fluoro-2-methoxybenzamido)methyl)phenyl)-1H-pyrazolo[3,4-d]pyrimidin-1-yl)-2-fluorophenyl)azetidin-3-yl)methyl)piperazin-1-yl)-N-(2,6-dioxopiperidin-3-yl)nicotinamide

108

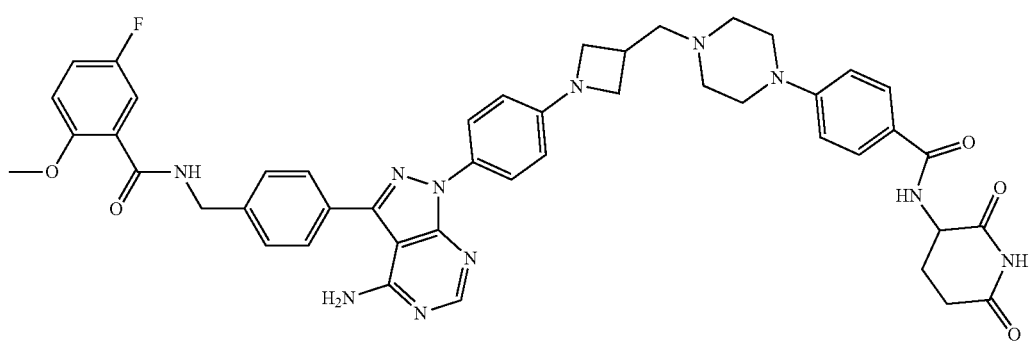 [SMILES: COc1ccc(F)cc1C(=O)NCc1ccc(-c2nn(-c3ccc(N4CC(CN5CCN(c6ccc(C(=O)NC7CCC(=O)NC7=O)cc6)CC5)C4)cc3)c3ncnc(N)c23)cc1]

N-(4-(4-amino-1-(4-(3-((4-(4-((2,6-dioxopiperidin-3-yl)carbamoyl)phenyl)piperazin-1-yl)methyl)azetidin-1-yl)phenyl)-1H-pyrazolo[3,4-d]pyrimidin-3-yl)benzyl)-5-fluoro-2-methoxybenzamide TABLE 1-continued Exemplary Compounds of the Present Disclosure

| Compound No. | Chemical Structure and IUPAC Nomenclature |
|---|---|
| 109 | 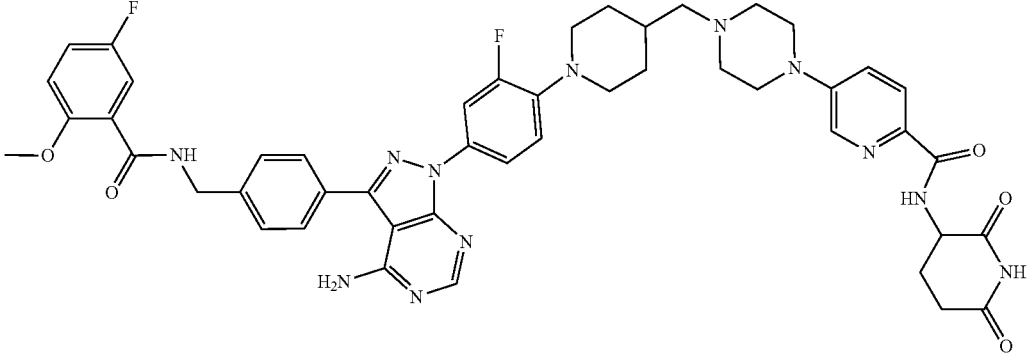 [SMILES: COc1ccc(F)cc1C(=O)NCc1ccc(-c2nn(-c3ccc(N4CCC(CN5CCN(c6ccc(C(=O)NC7CCC(=O)NC7=O)nc6)CC5)CC4)c(F)c3)c3ncnc(N)c23)cc1]<br>5-(4-((1-(4-(4-amino-3-(4-((5-fluoro-2-methoxybenzamido)methyl)phenyl)-1H-pyrazolo[3,4-d]pyrimidin-1-yl)-2-fluorophenyl)piperidin-4-yl)methyl)piperazin-1-yl)-N-(2,6-dioxopiperidin-3-yl)picolinamide |

Pharmaceutical Compositions

Pharmaceutical compositions of the present disclosure comprise at least one compound of Formula (I) (e.g. Formula (IA), Formula (IB)), or tautomer, stereoisomer or a mixture of stereoisomers, or a pharmaceutically acceptable salt, or hydrate, or deuterated derivative thereof formulated together with one or more pharmaceutically acceptable carriers. These formulations include those suitable for oral, rectal, topical, buccal and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, or tablets, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from about 0.05% to about 95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by, for example, dissolving or dispersing, at least one active compound of the present disclosure as described herein and optional pharmaceutical adjuvants in an excipient, such as, for example, water, saline, aqueous dextrose, glycerol, ethanol, and the like, to thereby form a solution or suspension. In general, suitable formulations may be prepared by uniformly and intimately admixing the at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound of Formula (I) (e.g. Formula (IA), Formula (IB)), or a tautomer, stereoisomer or a mixture of stereoisomers, or a pharmaceutically acceptable salt, or hydrate, or deuterated derivative thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from about 0.1 to about 5% w/w of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, or oil. Carriers and excipients which may be used include Vaseline, lanoline, polyethylene glycols, alcohols, and combinations of two or more thereof. The active compound (i.e., at least one compound of Formula (I) (e.g. Formula (IA), Formula (IB)), or a tautomer, stereoisomer or a mixture of stereoisomers, or a pharmaceutically acceptable salt, or hydrate, or deuterated derivative thereof) is generally present at a concentration of from about 0.1% to about 15% w/w of the composition, for example, from about 0.5 to about 2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of about 1 μg to about 1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following Table for Equivalent Surface Area Dosage Factors).

TABLE 2

Equivalent Surface Area Dosage Factors.

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | 1/2 | 1/4 | 1/6 | 1/12 |
| Rat | 2 | 1 | 1/2 | 1/4 | 1/7 |
| Monkey | 4 | 2 | 1 | 3/5 | 1/3 |
| Dog | 6 | 4 | 3/5 | 1 | 1/2 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

Methods of Treatment

In some embodiments, a compound of Formula (I) (e.g. Formula (IA), Formula (IB)), or a tautomer, stereoisomer or a mixture of stereoisomers, or a pharmaceutically acceptable salt, or hydrate, or deuterated derivative thereof, is administered to treat a condition which is modulated by BTK in a subject in need thereof. In some embodiments, the condition modulated by BTK is chosen from cancer, immunological disease, autoimmune diseases, and inflammatory diseases.

In some embodiments, the disease is inflammatory disease such as arthritis, kidney disease, or cancer, such as leukemia and lymphoma, for example chronic lymphocytic leukemia (CLL), multiple myeloma, and small lymphocytic lymphoma (SLL), and B-cell non-Hodgkin lymphoma.

In some embodiments, the disease is an autoimmune disease. In some embodiments, the disease is rheumatoid arthritis. In some embodiments, the autoimmune disease is lupus.

In one embodiment, the subject in need is suffering from a heteroimmune condition or disease, e.g., graft versus host disease, transplantation, transfusion, anaphylaxis, allergy, type I hypersensitivity, allergic conjunctivitis, allergic rhinitis, or atopic dermatitis.

In some embodiments, the subject in need is suffering from an inflammatory disease, e.g., asthma, appendicitis, blepharitis, bronchiolitis, bronchitis, bursitis, cervicitis, cholangitis, cholecystitis, colitis, conjunctivitis.

In some embodiments, the subject in need is suffering from a cancer. In one embodiment, the cancer is a B-cell proliferative disorder, e.g., diffuse large B cell lymphoma, follicular lymphoma, lymphoma, chronic lymphocytic leukemia, B-cell prolymphocytic leukemia, lymphoplamascytic lymphoma, Waldenström macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis. In some embodiments, the condition is chosen from B-cell malignancy, B-cell lymphoma, diffuse large B cell lymphoma, chronic lymphocyte leukemia, non-Hodgkin lymphoma, mantle cell lymphoma, follicular lymphoma, hairy cell leukemia B-cell non-Hodgkin lymphoma, marginal zone lymphoma, Waldenström's macroglobulinemia, multiple myeloma, bone cancer, bone metastasis, arthritis, multiple sclerosis, osteoporosis, irritable bowel syndrome, inflammatory bowel disease, Crohn's disease, lupus, Sjogren's syndrome, and disorders associated with renal transplant. In some embodiments, the condition is mantle cell lymphoma. In some embodiments, the condition is chronic lymphocytic leukemia and small lymphocytic lymphoma. In some embodiments, the condition is Waldenström's macroglobulinemia. In some embodiments, the condition is marginal zone lymphoma.

In some embodiments, the subject in need is suffering from a heteroimmune condition or disease, e.g., graft versus host disease (GVHD). In some embodiments, the GVHD is acute GVHD. In some embodiments, the GVHD is chronic GVHD.

In some embodiments, a compound of Formula (I) (e.g. Formula (IA), Formula (IB)), or a tautomer, stereoisomer, pharmaceutically acceptable salt, or hydrate thereof, or deuterated derivative thereof, is administered as a pharmaceutical composition.

In some embodiments, the invention provides for methods for degrading BTK in a cell, comprising contacting the cell with an effective amount of a compound of Formula (I) (e.g. Formula (IA), Formula (IB)), pharmaceutically acceptable salts thereof or pharmaceutical compositions containing the compound or pharmaceutically acceptable salt thereof. In one embodiment, the contacting is in vitro. In one embodiment, the contacting is in vivo.

As used herein, the term "contacting" refers to the bringing together of indicated moieties in an in vitro system or an in vivo system. For example, "contacting" a BTK with a compound provided herein includes the administration of a compound provided herein to an individual or patient, such as a human, having a condition which is modulated by BTK, as well as, for example, introducing a compound provided herein into a sample containing a cellular or purified preparation containing the BTK.

The concentration and route of administration to the patient will vary depending on the condition to be treated.

In one embodiment, a compound of Formula (I) (e.g. Formula (IA), Formula (IB)), or a tautomer, stereoisomer, pharmaceutically acceptable salt, or hydrate thereof, or deuterated derivatives thereof, is administered in combination with other therapeutic agent. In one embodiment, these therapeutic agents comprise chemotherapeutic agents, steroids, immunotherapeutic agents, targeted therapies, antibody drug conjugates, B cell receptor pathway inhibitors, antibodies, B cell receptor signaling inhibitors, PI3K inhibitors, IAP inhibitors, mTOR inhibitors, radio immunotherapeutics, DNA damaging agents, proteosome inhibitors, histone deacetylase inhibitors, protein kinase inhibitors, hedgehog inhibitors, Hsp90 inhibitors, telomerase inhibitors, Jak1/2 inhibitors, protease inhibitors, BCL2 inhibitors, PKC inhibitors and PARP inhibitors. In some embodiments, these therapeutic agents are chlorambucil, ifosphamide, doxorubicin, mesalazine, thalidomide, lenalidomide, temsirolimus, everolimus, fludarabine, fostamatinib, paclitaxel, docetaxel, ofatumumab, rituximab, dexamethasone, prednisone, CAL-101, ibritumomab, tositumomab, bortezomib, pentostatin, endostatin, bendamustine, cyclophosphamide, vincristine, Venetoclax and lenalidomide.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The examples and preparations provided below further illustrate and exemplify the compounds as disclosed herein and methods of preparing such compounds. It is to be understood that the scope of the present disclosure is not limited in any way by the scope of the following examples and preparations.

The chemical entities described herein can be synthesized according to one or more illustrative schemes herein and/or techniques well known in the art. Unless specified to the contrary, the reactions described herein take place at atmospheric pressure, generally within a temperature range from about −10° C. to about 200° C. Further, except as otherwise specified, reaction times and conditions are intended to be approximate, e.g., taking place at about atmospheric pressure within a temperature range of about −10° C. to about 200° C. over a period that can be, for example, about 1 to about 24 hours; reactions left to run overnight in some embodiments can average a period of about 16 hours.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. See, e.g., Carey et al. Advanced Organic Chemistry, $3^{rd}$ Ed., 1990 New York: Plenum Press; Mundy et al., Name Reaction and Reagents in Organic Synthesis, $2^{nd}$ Ed., 2005 Hoboken, N.J.: J. Wiley & Sons. Specific illustrations of suitable separation and isolation procedures are given by reference to the examples hereinbelow. However, other equivalent separation or isolation procedures can also be used.

In all of the methods, it is well understood that protecting groups for sensitive or reactive groups may be employed where necessary, in accordance with general principles of chemistry. Protecting groups are manipulated according to standard methods of organic synthesis (T. W. Greene and P. G. M. Wuts (1999) Protective Groups in Organic Synthesis, $3^{rd}$ Ed., John Wiley & Sons). These groups may be removed at a convenient stage of the compound synthesis using methods that are readily apparent to those skilled in the art.

When desired, the (R)- and (S)-isomers of the nonlimiting exemplary compounds, if present, can be resolved by methods known to those skilled in the art, for example, by formation of diastereoisomeric salts or complexes which can be separated, e.g., by crystallization; via formation of diastereoisomeric derivatives which can be separated, e.g., by crystallization, gas-liquid or liquid chromatography; selective reaction of one enantiomer with an enantiomer-specific reagent, e.g., enzymatic oxidation or reduction, followed by separation of the modified and unmodified enantiomers; or gas-liquid or liquid chromatography in a chiral environment, e.g., on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well-known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Millipore Sigma or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein. The skilled artisan will understand that standard atom valencies apply to all compounds disclosed herein in genus or named compound for unless otherwise specified.

The following abbreviations have the definitions set forth below:

| 1. | ACN: | Acetonitrile |
| 2. | DCM: | Dichloromethane |
| 3. | DIEA: | Diisopropylethylamine |
| 4. | DMF: | Dimethylformamide |
| 5. | EA: | Ethyl acetate |
| 6. | EDCI: | 1-Ethyl-3-(3-dimethylaminopropyl)carbodiimide |
| 7. | FA: | Formic acid |
| 8. | HATU: | 1-[Bis(dimethylamino)methylene]-1H-1,2,3-triazolo[4,5-b]pyridinium 3-oxid hexafluorophosphate |
| 9. | HPLC: | High pressure liquid chromatography |
| 10. | LC/MS: | Liquid chromatography/Mass spectroscopy |
| 11. | NMM: | N-Methylmorpholine |
| 12. | NMR: | Nuclear magnetic resonance |
| 13. | PE: | Petroleum ether |
| 14. | TEA: | Triethylamine |
| 15. | TFA: | Trifluoroacetic acid |
| 16. | THF: | Tetrahydrofuran |
| 17. | TLC: | Thin layer chromatography |
| 18. | TsCl: | p-Toluenesulfonyl chloride |

General Synthetic Schemes

The claimed compounds can be prepared according to the following schemes. The following schemes represent the general methods used in preparing these compounds. However, the synthesis of these compounds is not limited to these representative methods, as they can also be prepared through various other methods by those skilled in the art of synthetic chemistry.

Scheme 1: Method for the preparation of compounds 1,3,4,5 and 6

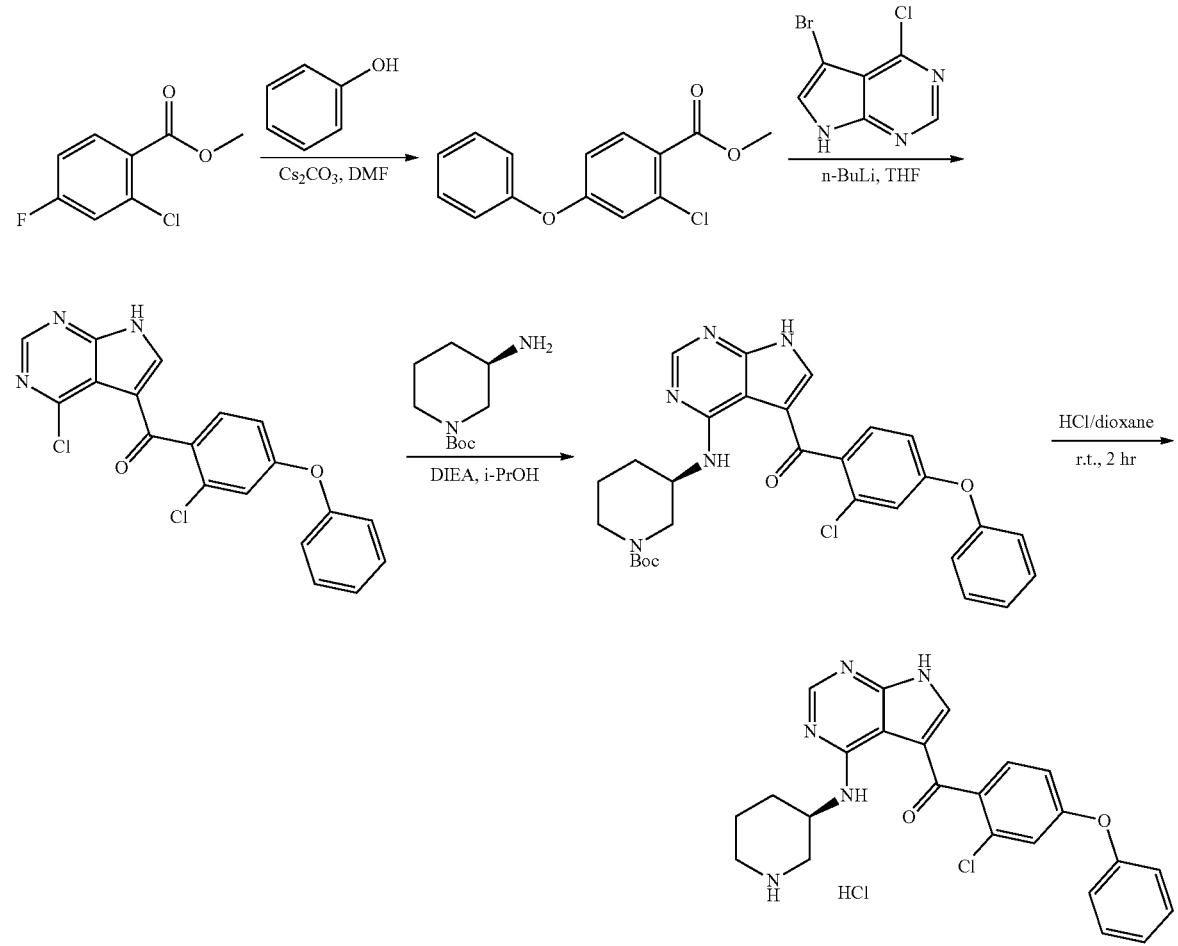

Intermediate A

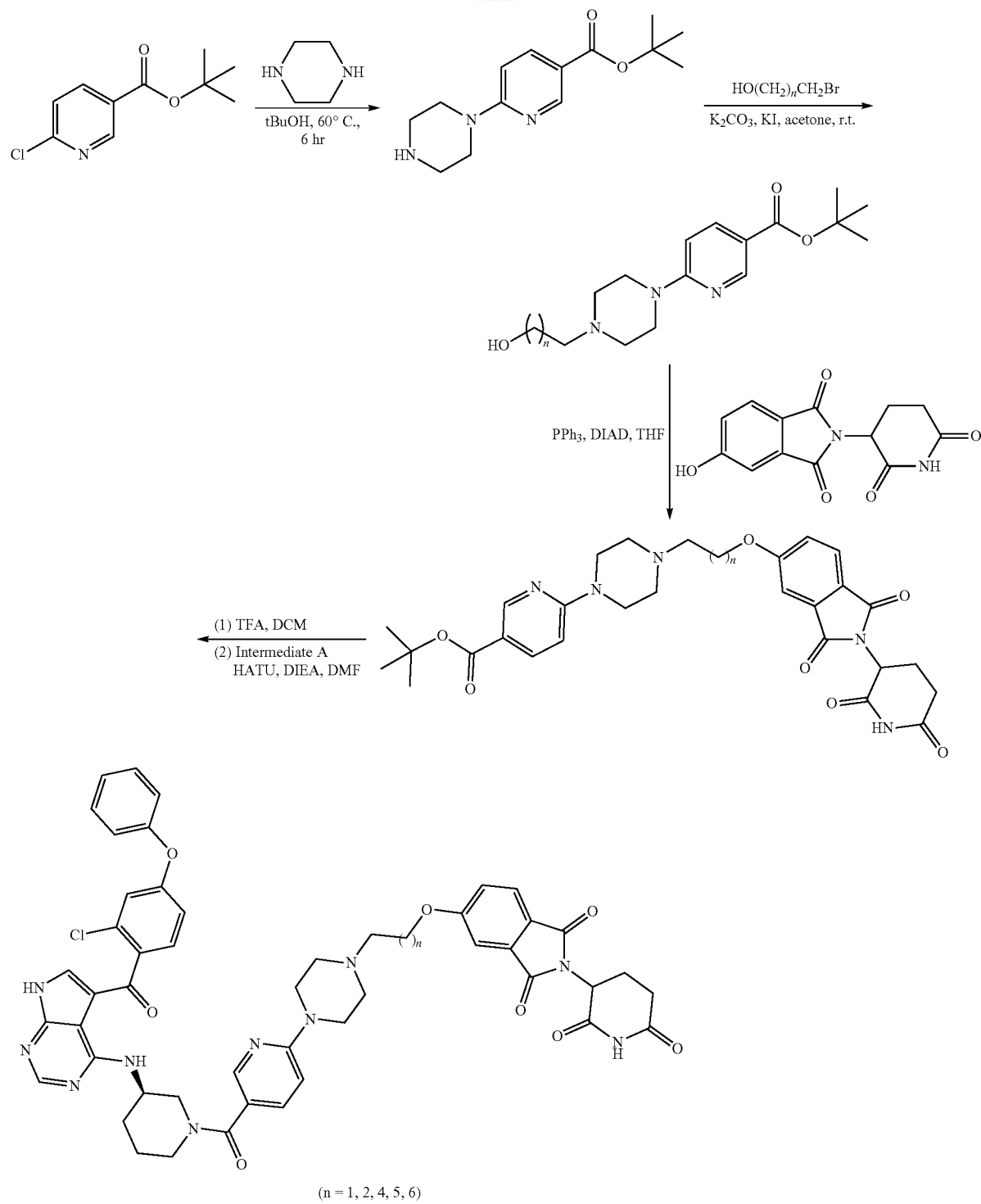
(n = 1, 2, 4, 5, 6)
Scheme 2: Method for preparation of compound 2
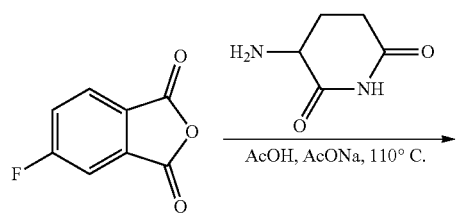

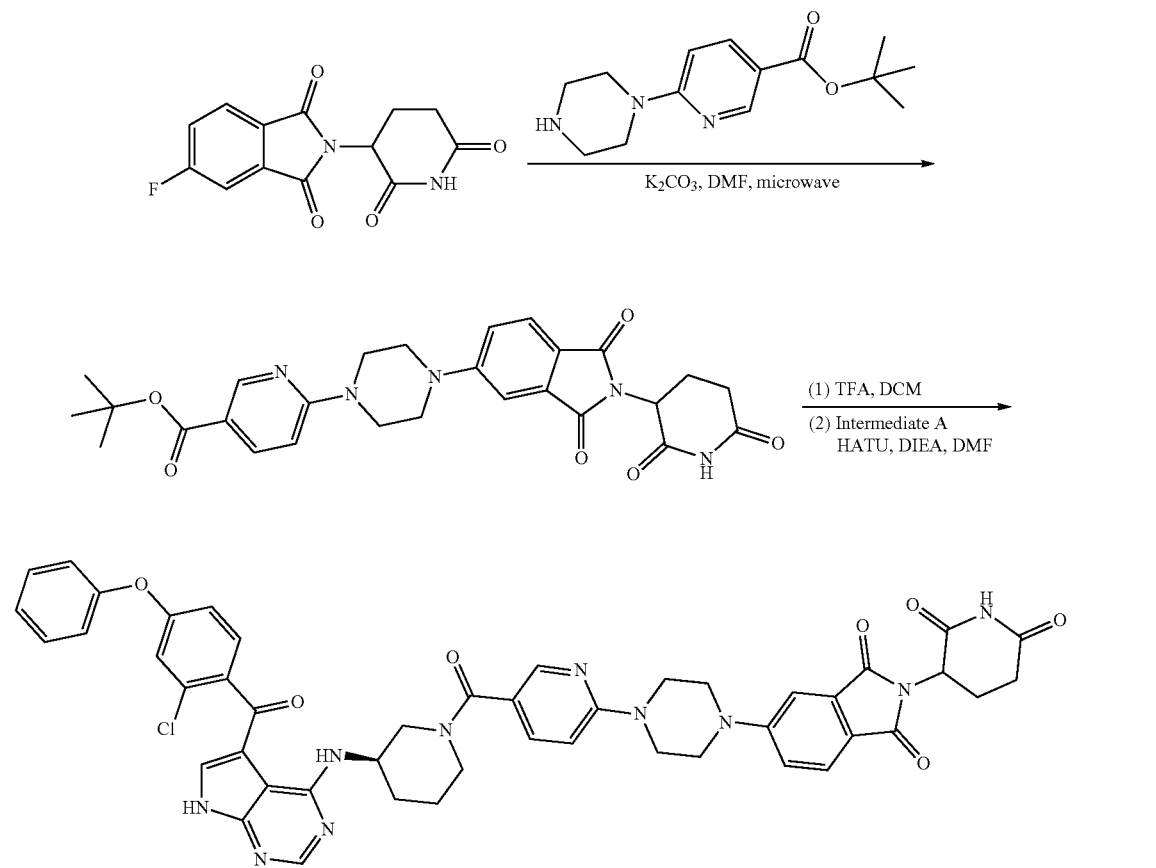
Scheme 3: Method for the preparation of compounds 7, 8, 11, and 19
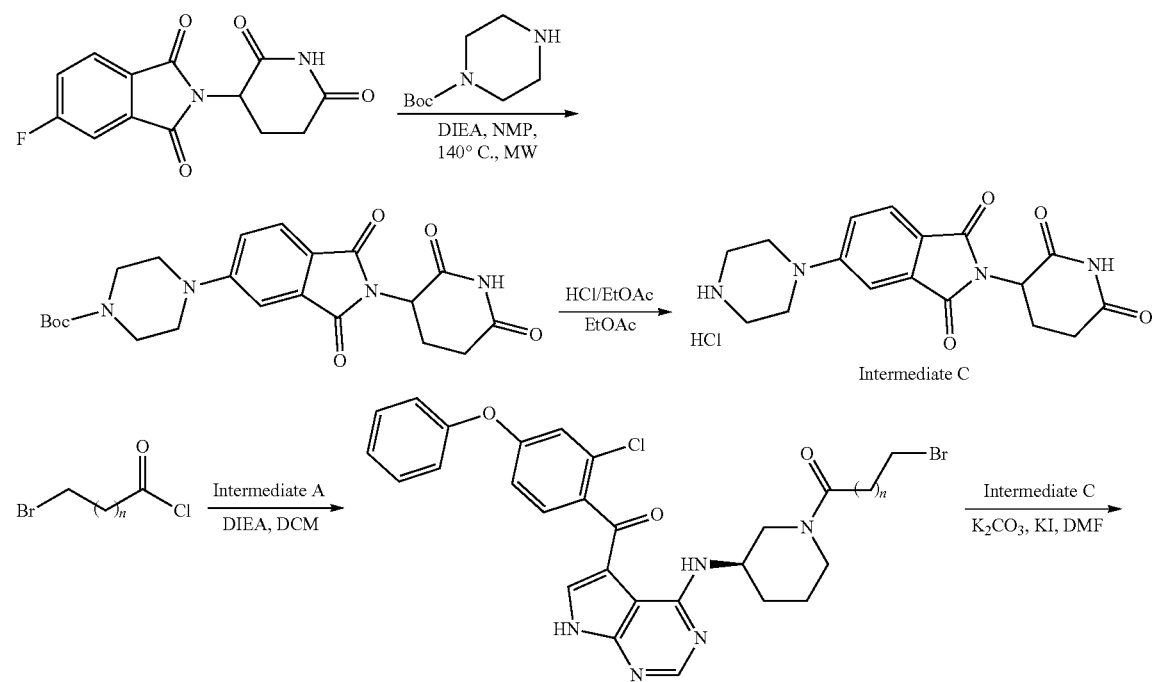

-continued
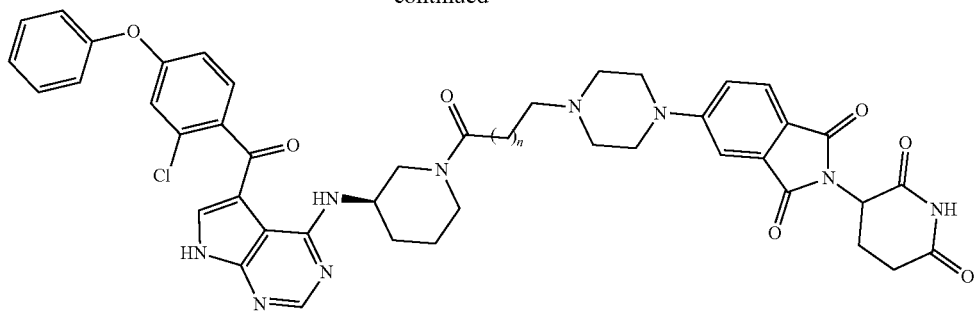
(n = 2, 3, 4, 5)
Scheme 4: Method for the preparation of compounds 14, 16, 17 and 20
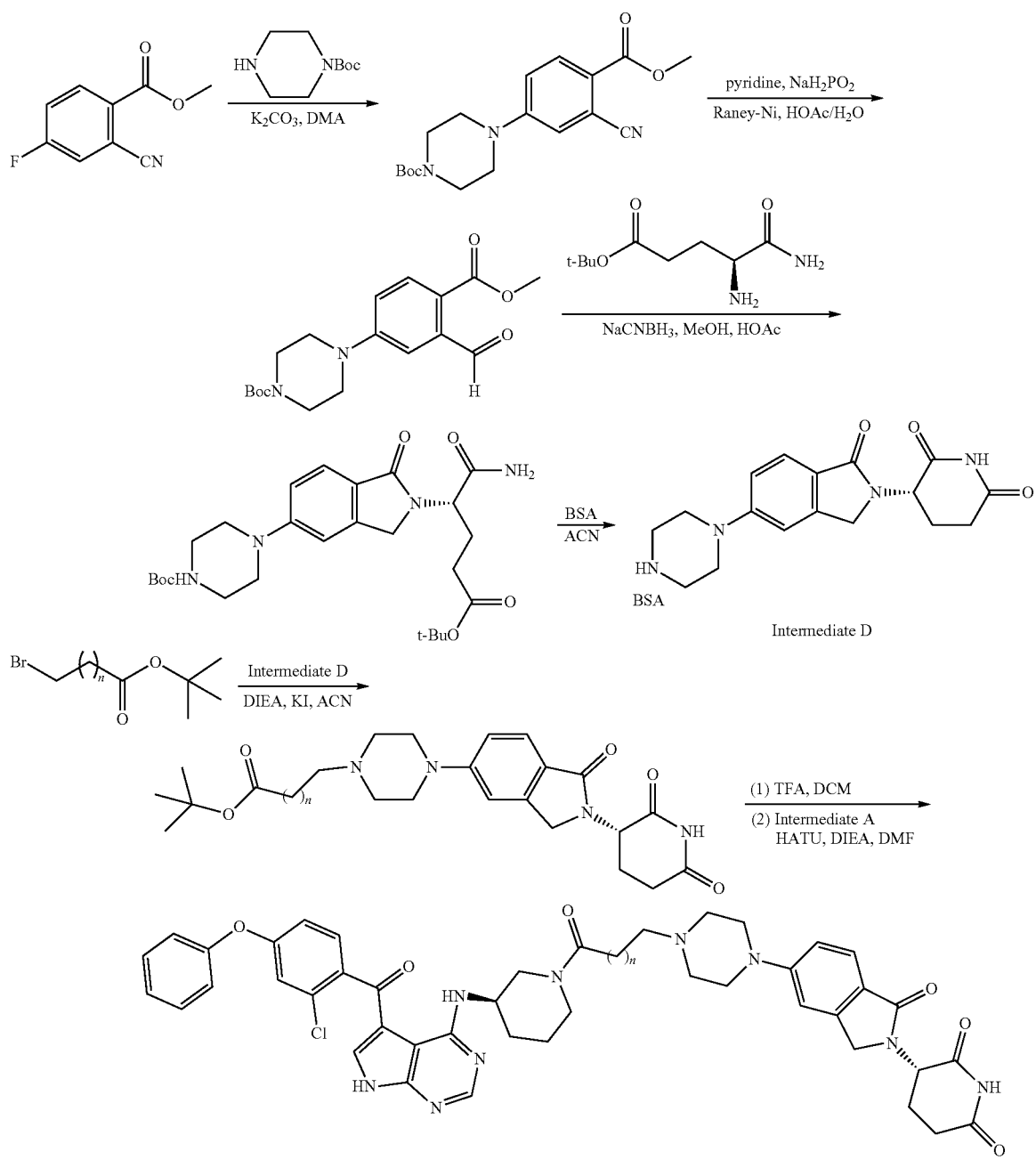
(n = 2, 3, 4, 5)

-continued
Scheme 5: Method for the preparation for compounds 9 and 10
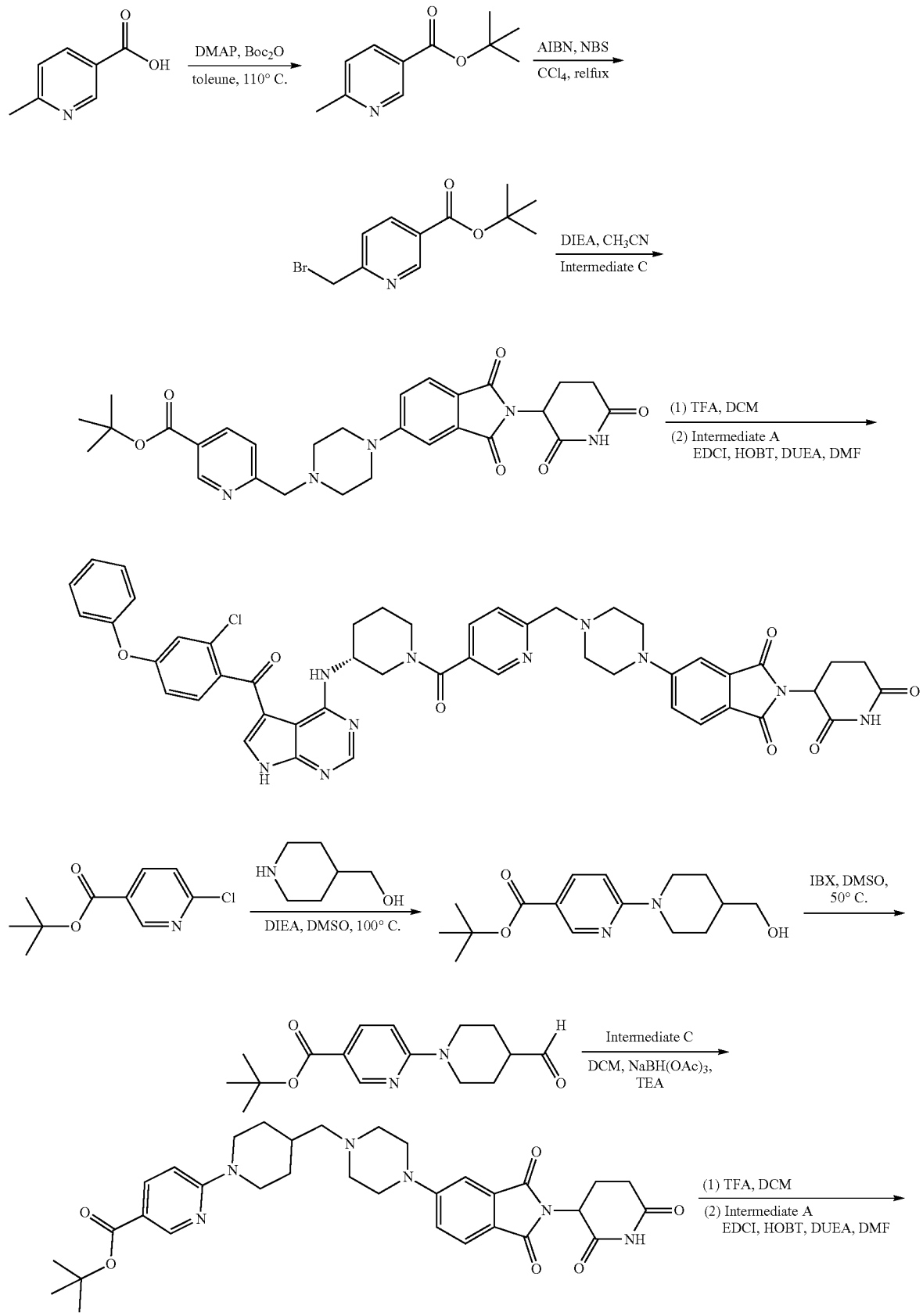

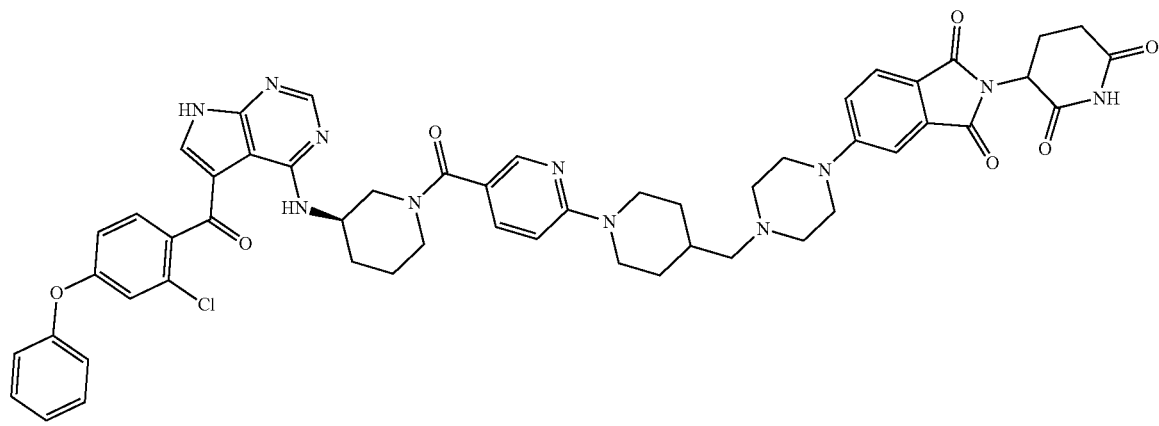 [SMILES: O=C1CCC(N2C(=O)c3ccc(N4CCN(CC5CCN(c6ccc(C(=O)N7CCC[C@@H](Nc8ncnc9[nH]cc(C(=O)c%10ccc(Oc%11ccccc%11)cc%10Cl)c89)C7)cn6)CC5)CC4)cc3C2=O)C(=O)N1]
Scheme 6: Method for the preparation of compounds 12 and 18
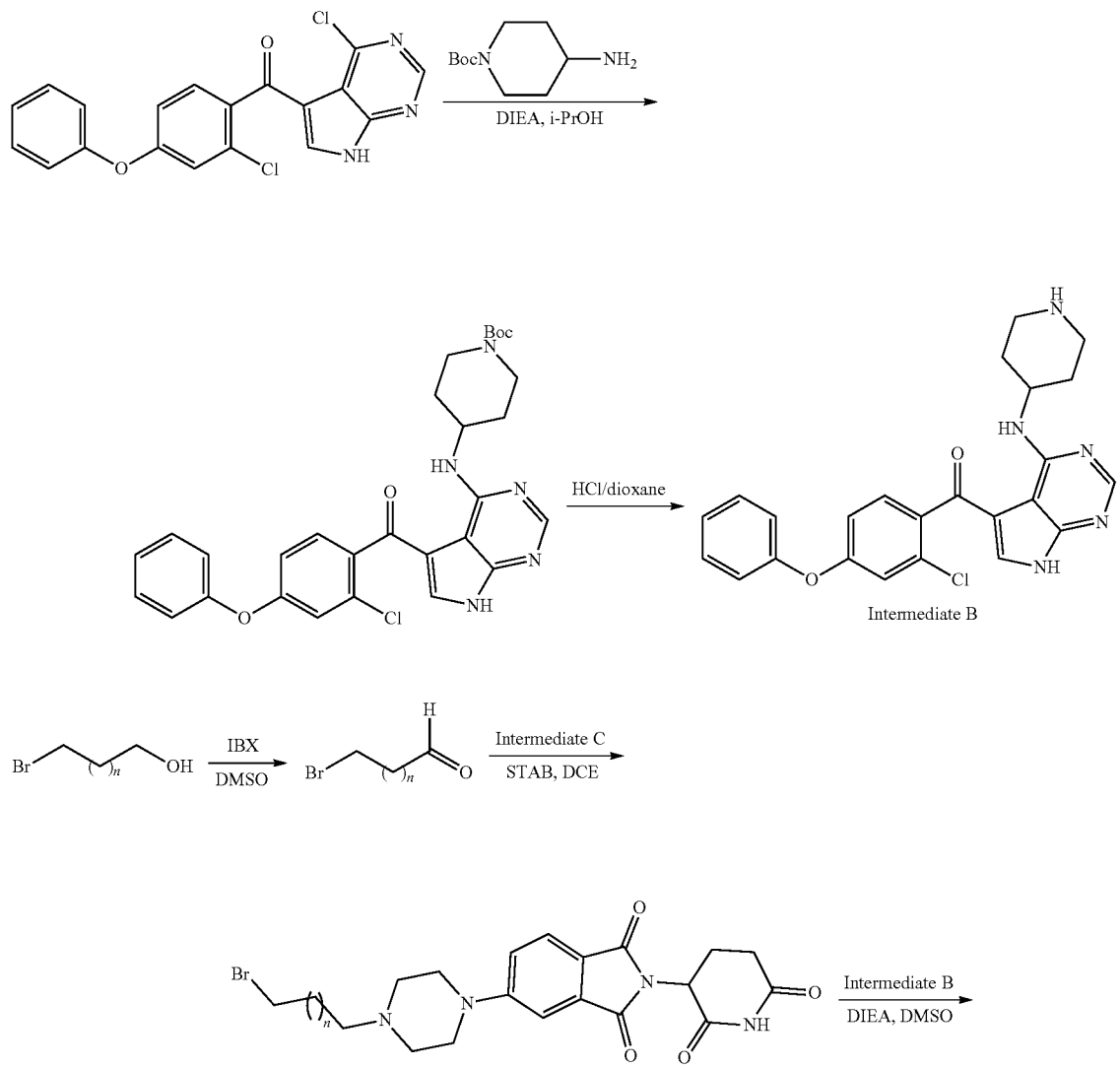

-continued

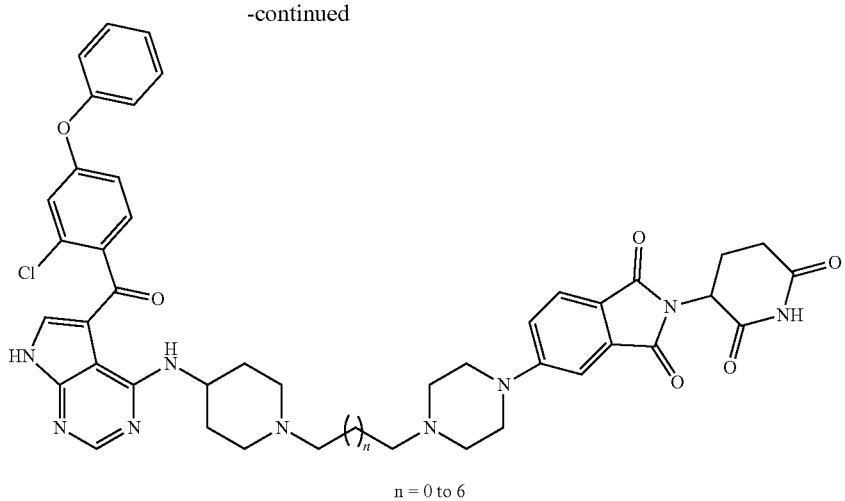

n = 0 to 6

The following compounds were prepared according to Scheme 3: compounds 22, 23, 28 and 31.

The following compounds were prepared according to Scheme 4: compounds 13, 21, 24, and 25.

The following compounds were prepared according to Scheme 6: compounds 15, 26, 27, 29, 30, and 34.

Scheme 7: Method for the preparation of compound 32

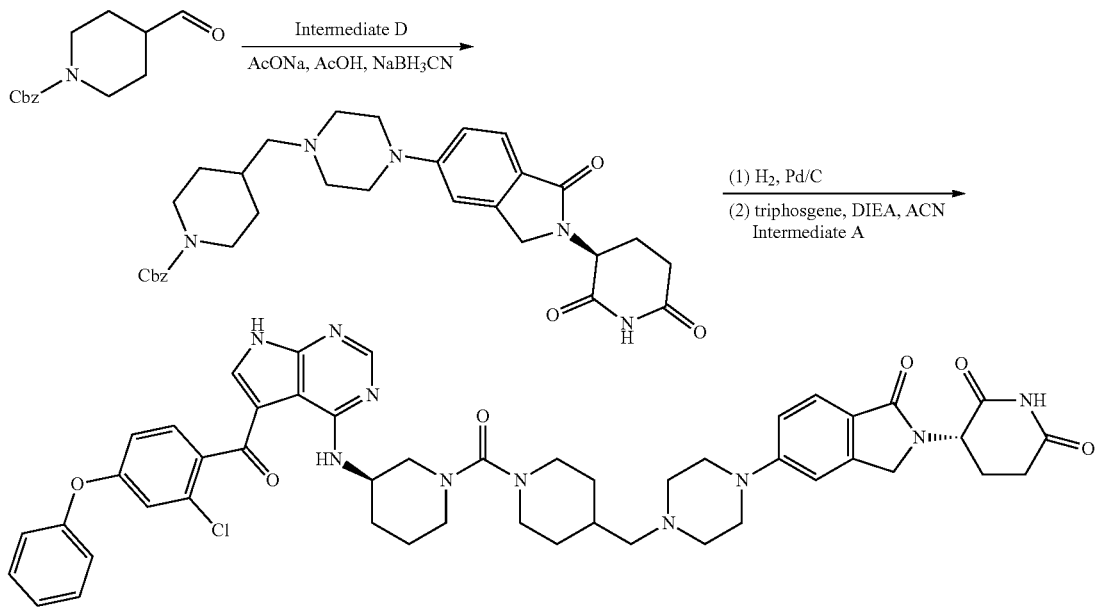

Compound 33 can be prepared using a similar method as described in the synthesis of compound 32.

Scheme 8: Method for preparation of compounds 35, 36, and 38

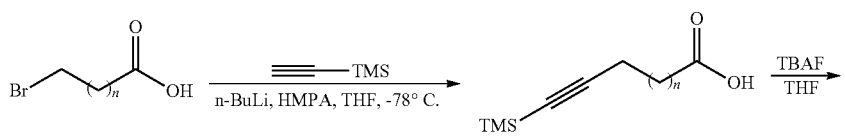

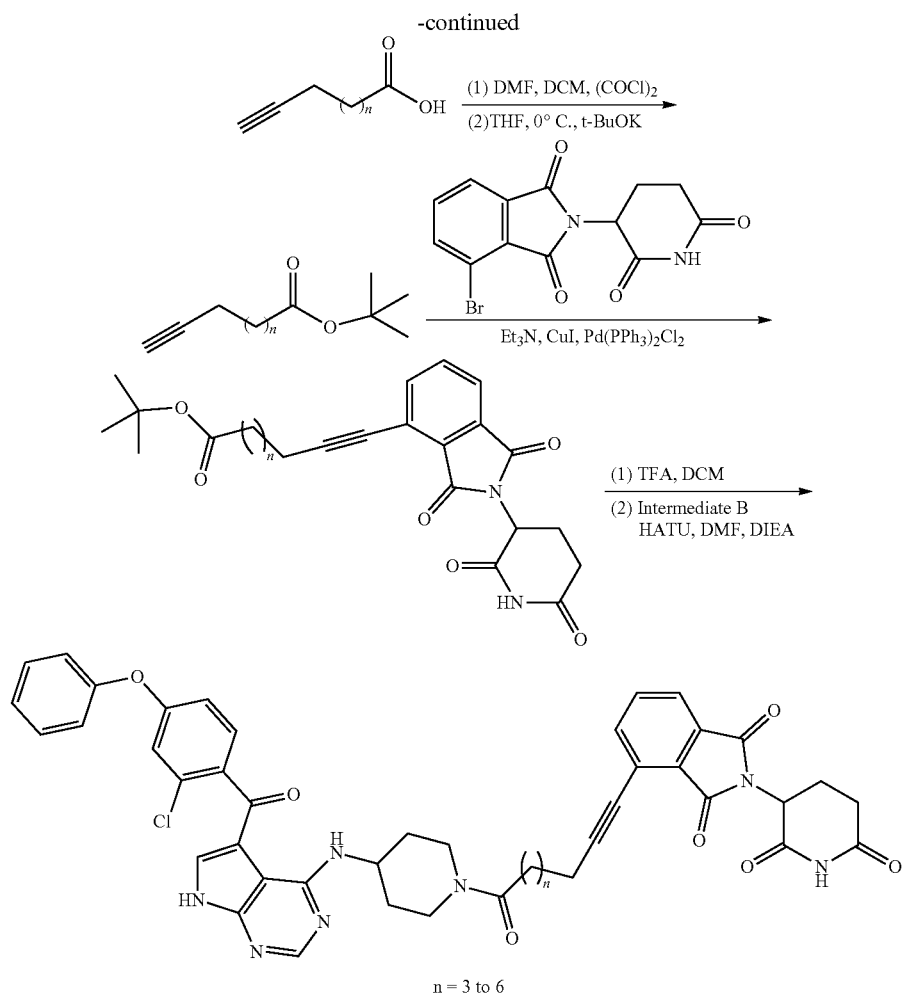
Compound 39, 40 and 41 can be prepared using methods as described in Scheme 8.
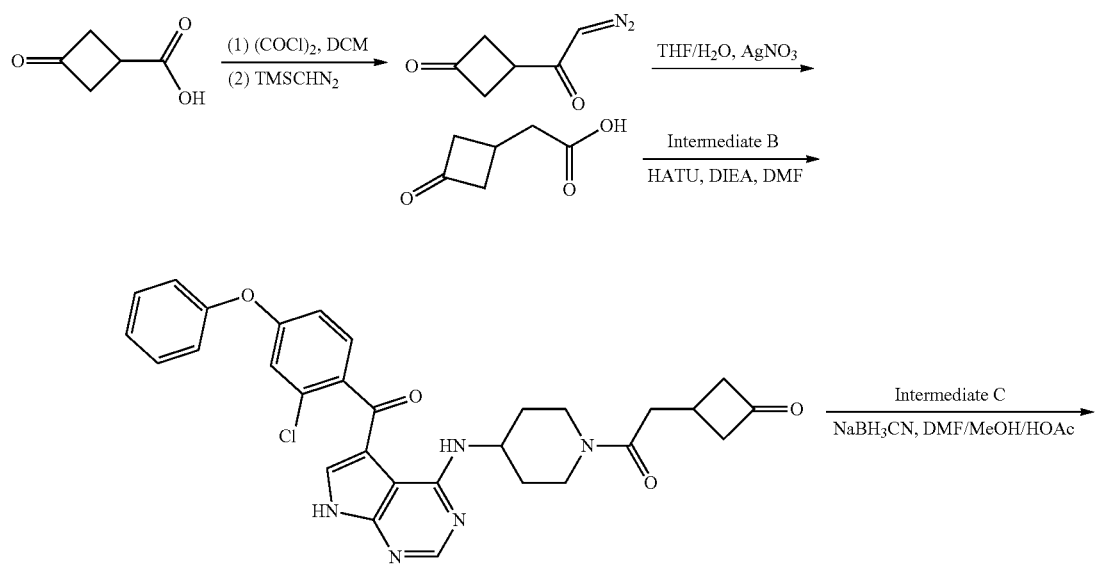

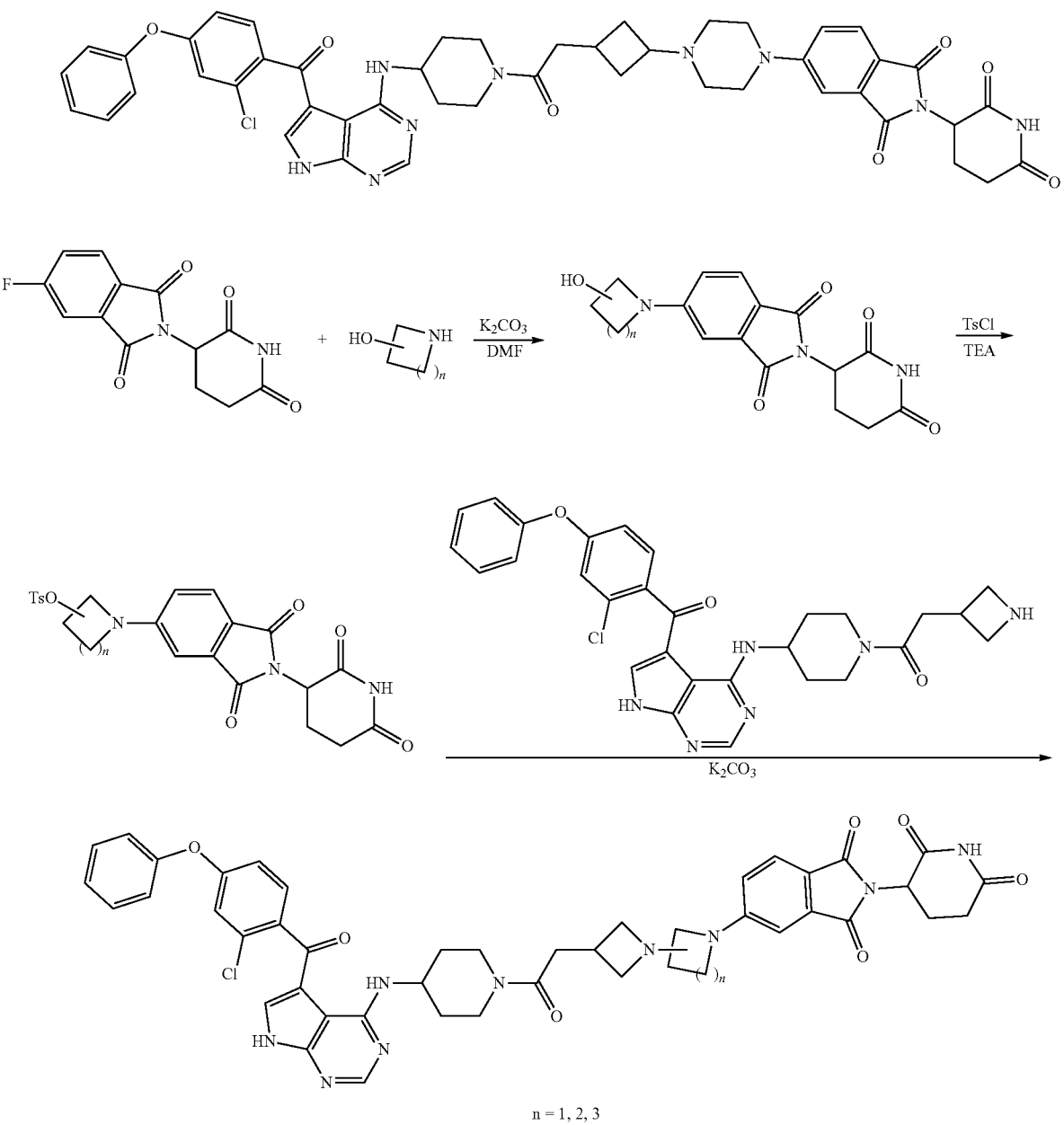
Compounds 42 and 43 can be synthesized using similar methods as described in Scheme 9.
Scheme 10: Method for the preparation of compound 44
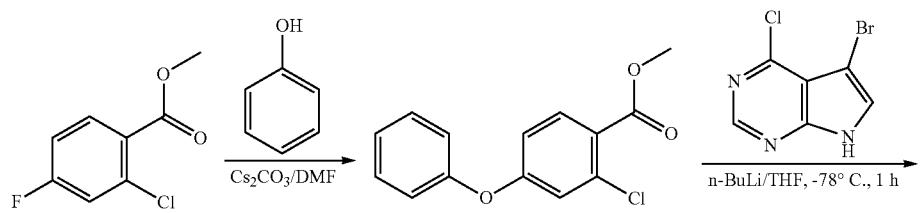

-continued
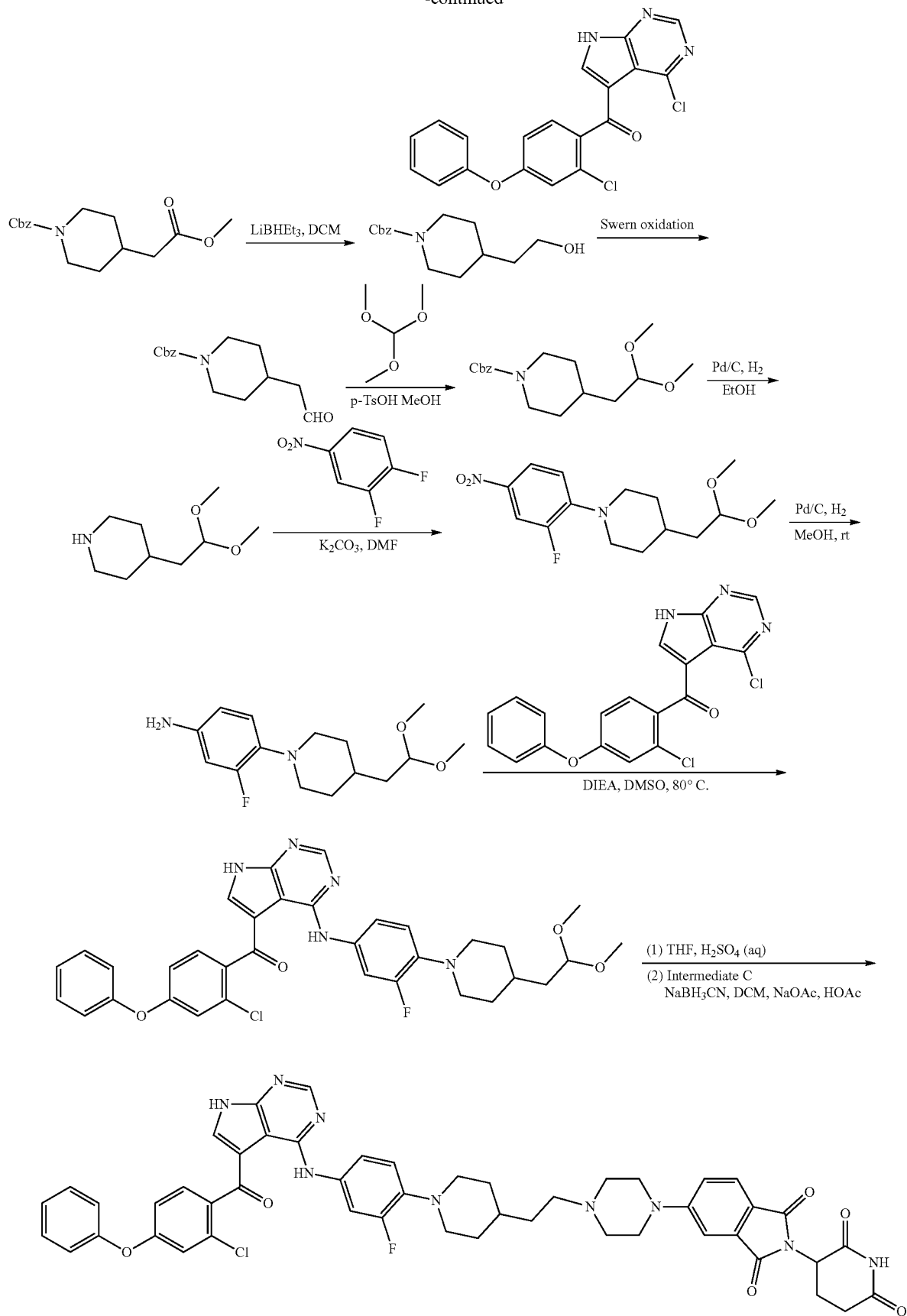

Compounds 45, 46 and 47 can be synthesized using similar methods as described in the preparation of compound 44.
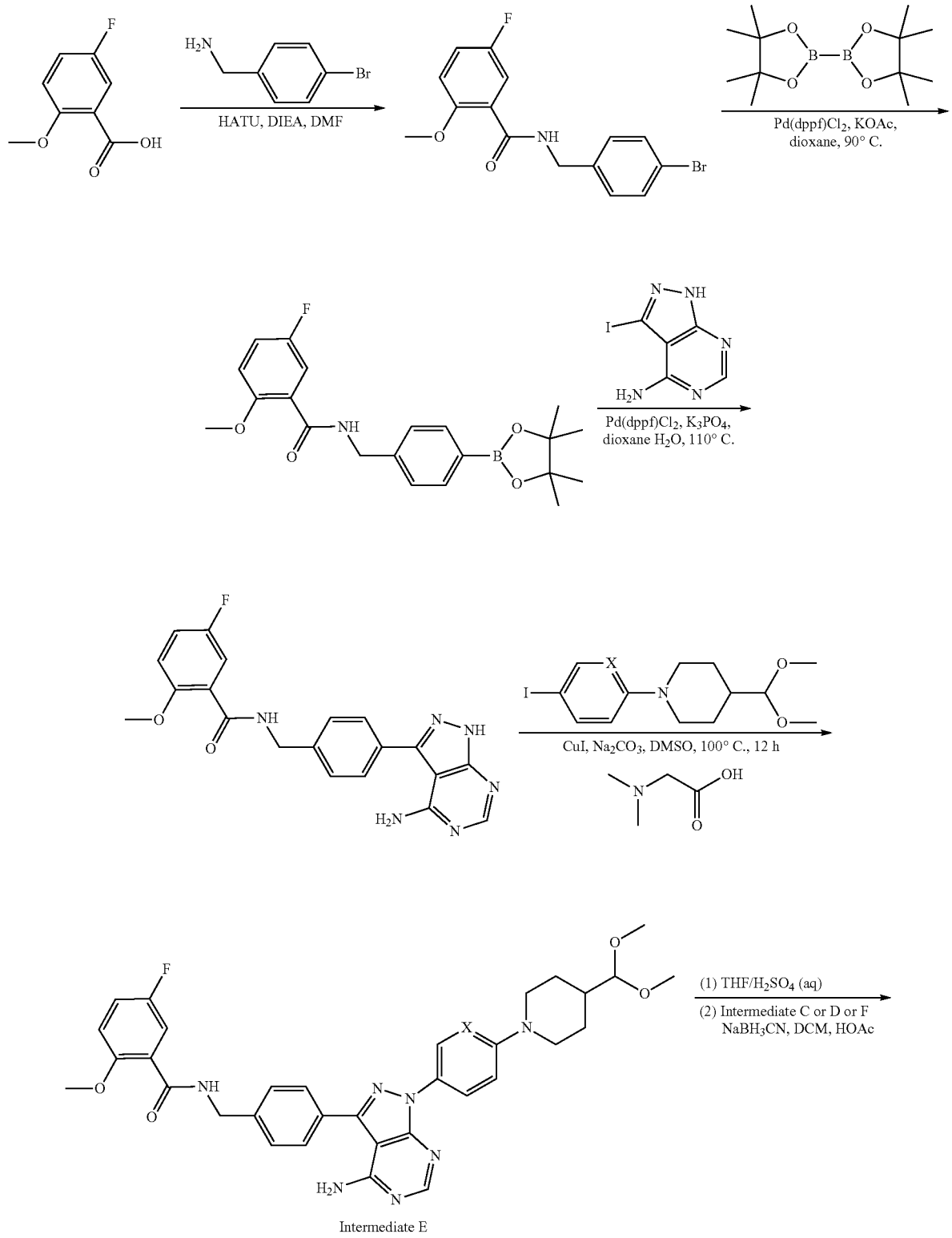
Scheme 11: Method for the preparation of compounds 49, 50, 51, 59, and 70
Intermediate E -continued
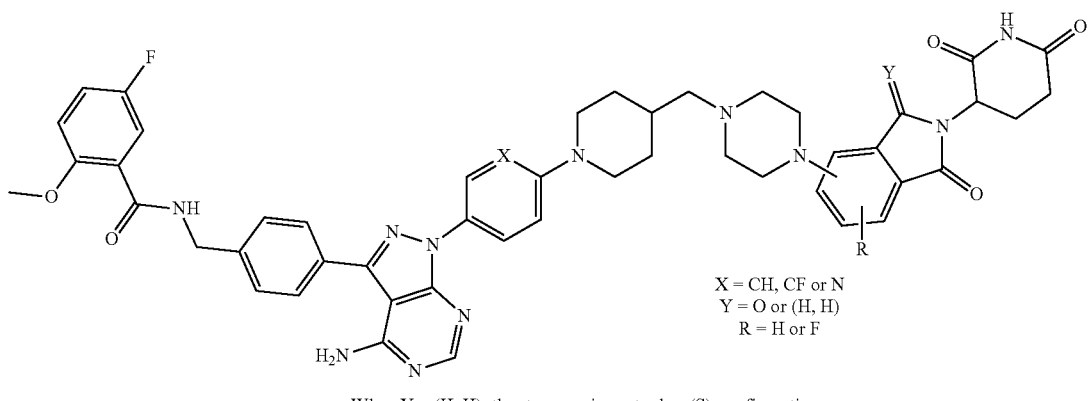
X = CH, CF or N
Y = O or (H, H)
R = H or F
When Y = (H, H), the stereogenic center has (S)-configuration
Compounds 65, 66, 67, 68, 81, 82 and 85 can be synthesized using similar methods as described in Scheme 11.
Scheme 12: Method for the preparation of compounds 52, 53, 54, 56, 57, 58, 60 and 61
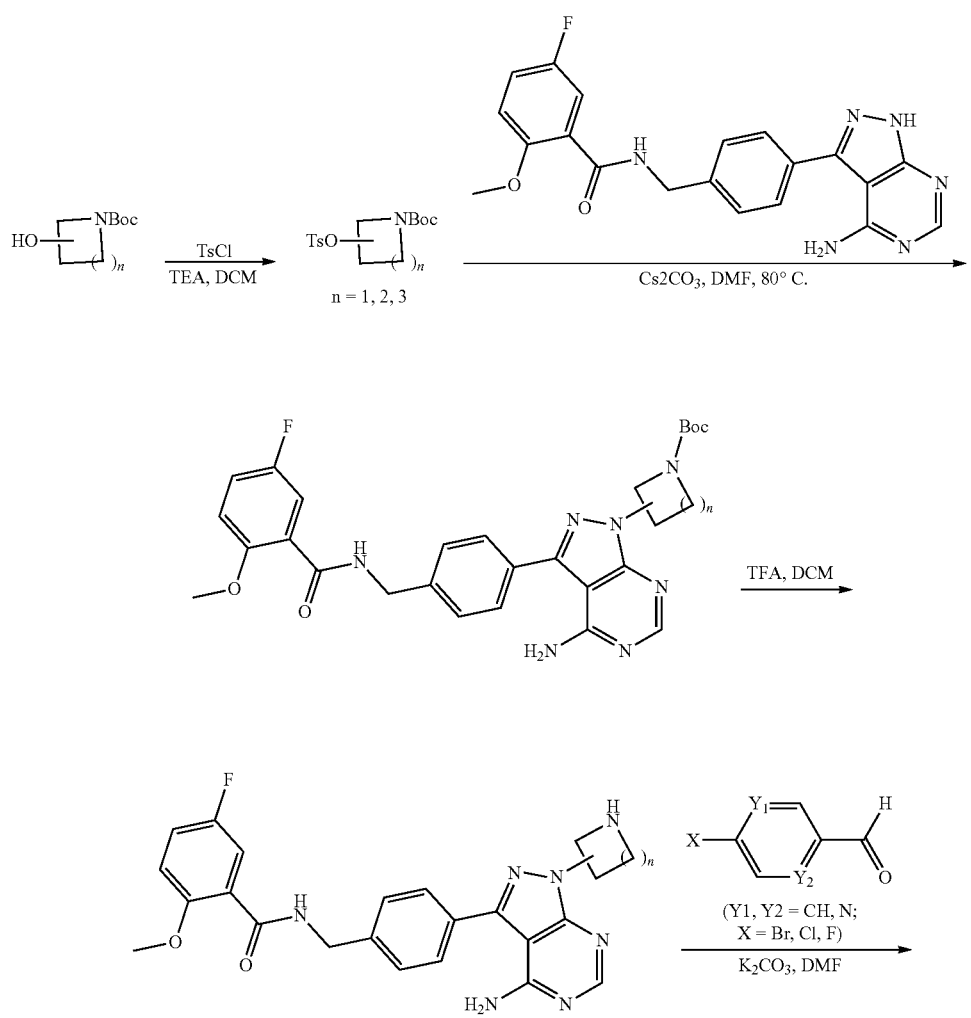

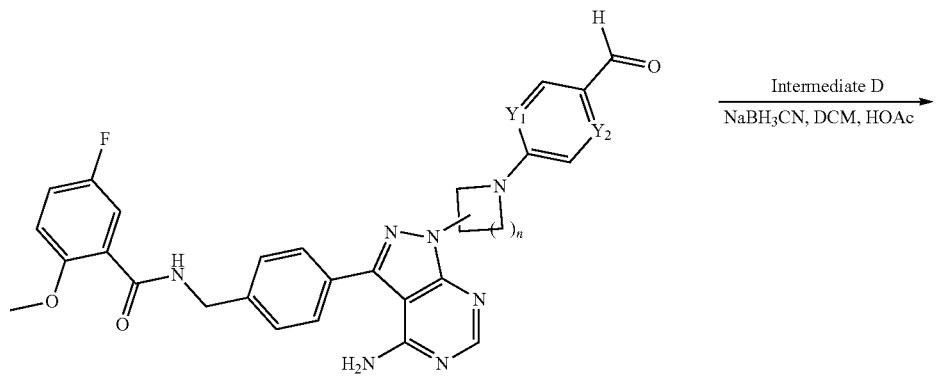
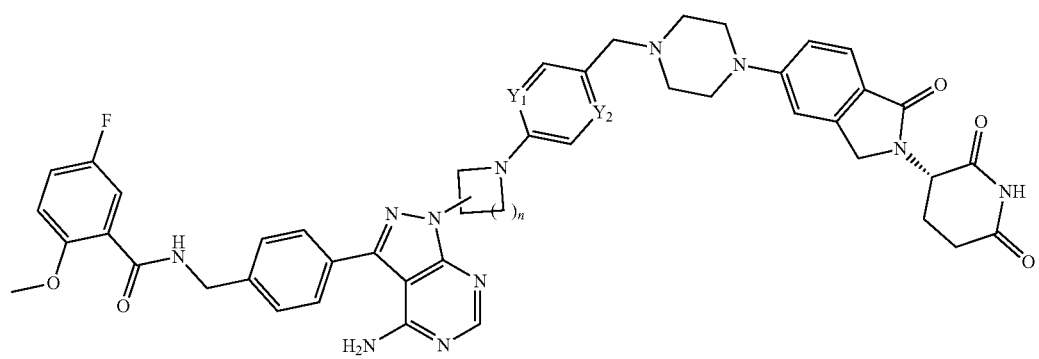
Scheme 13: Method for the preparation of compounds 71, 72, 78 and 80
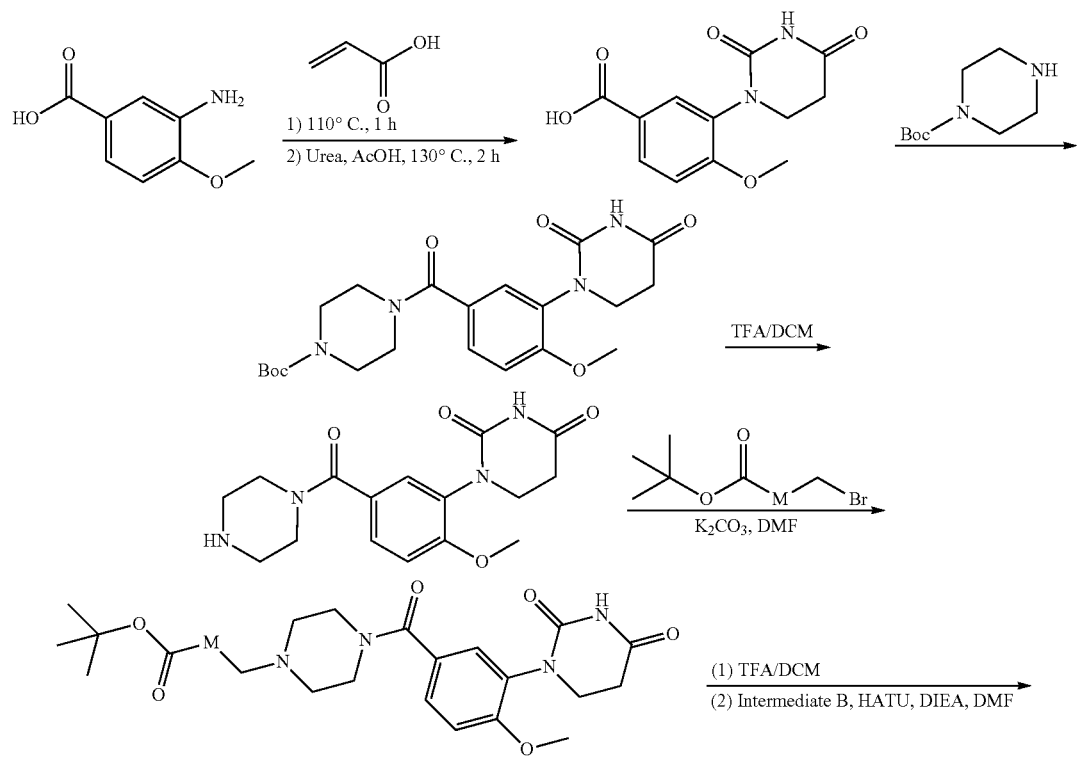

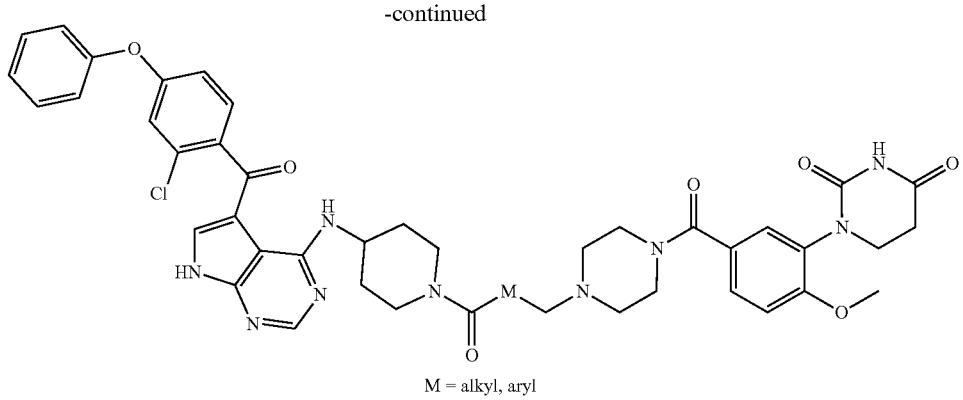
M = alkyl, aryl
Compound 79 can be synthesized with a similar method as described in Scheme 13.
Scheme 14: Method for the preparation of compounds 73 and 74
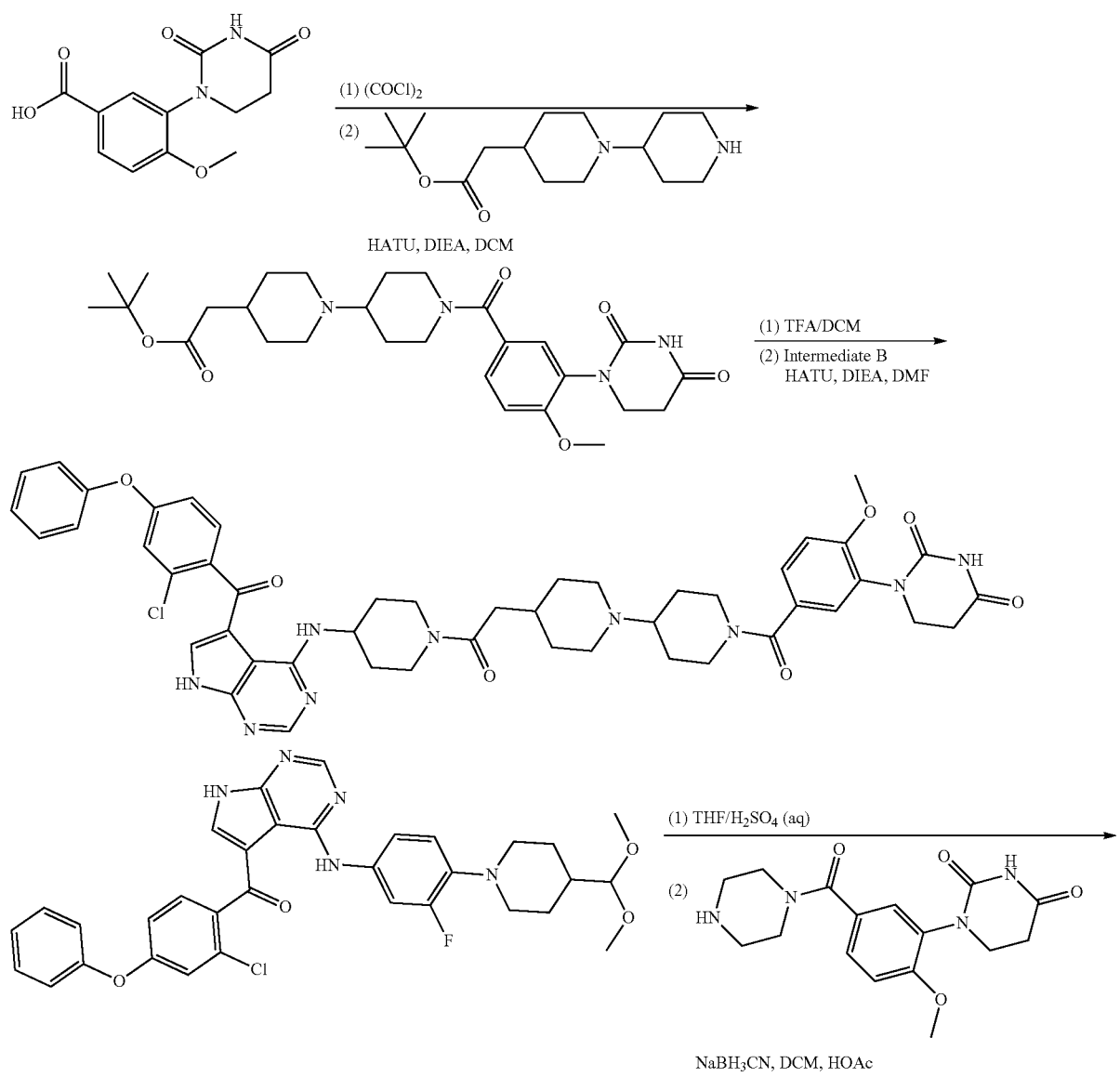

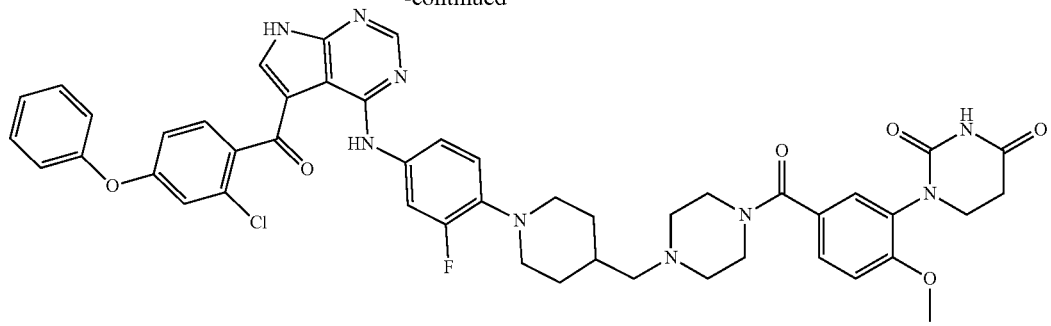
15
Compounds 75, 76 and 77 can be prepared using similar methods as described in Scheme 14.
Scheme 15: Method for the preparation of compounds 83 and 84
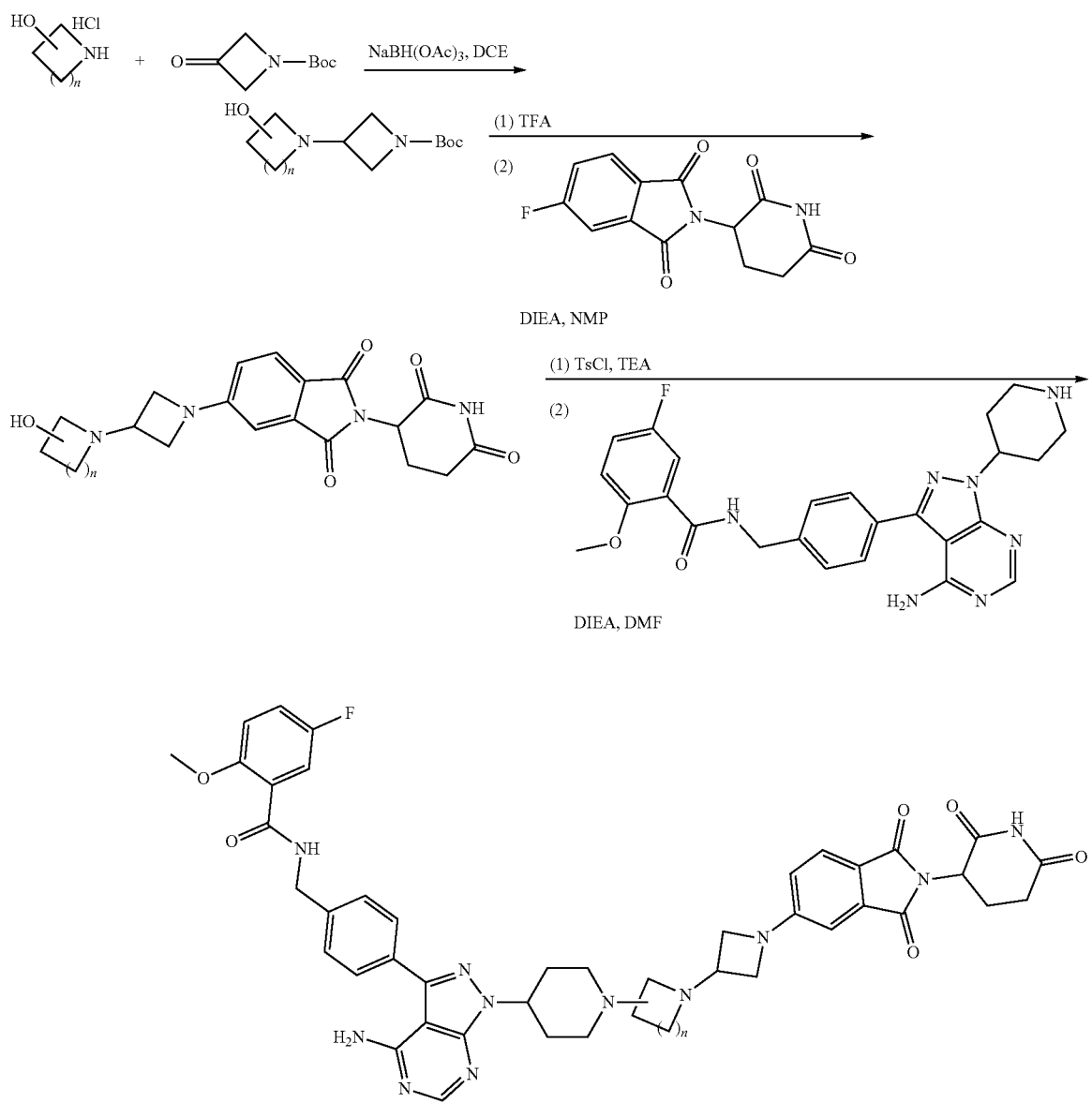
n = 1, 2, 3

-continued
Scheme 16: Method for the preparation of compounds 86 and 87
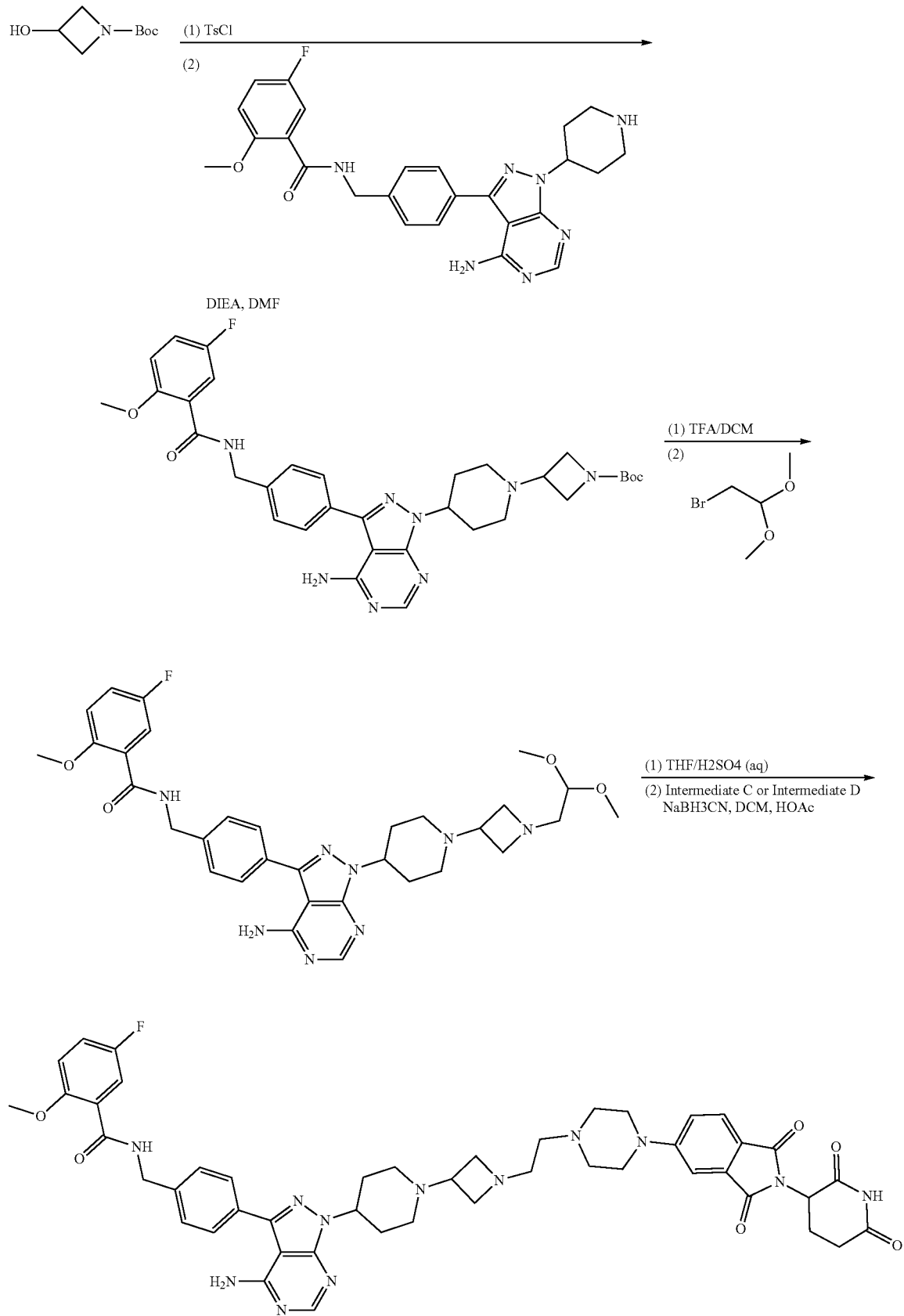

-continued
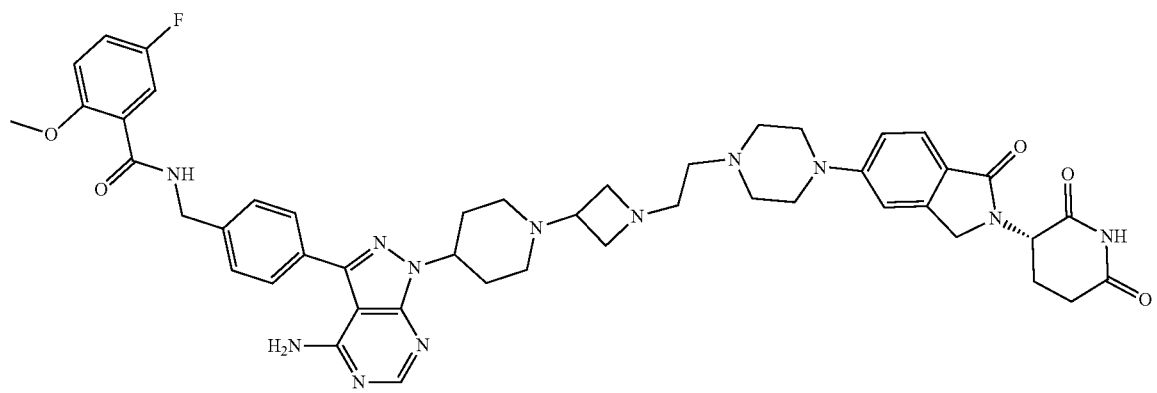 [SMILES: COc1ccc(F)cc1C(=O)NCc1ccc(-c2nn(C3CCN(C4CN(CCN5CCN(c6ccc7c(c6)CN([C@H]6CCC(=O)NC6=O)C7=O)CC5)C4)CC3)c3ncnc(N)c23)cc1]
Scheme 17: Method for the preparation of compounds 88-91 and 100-101
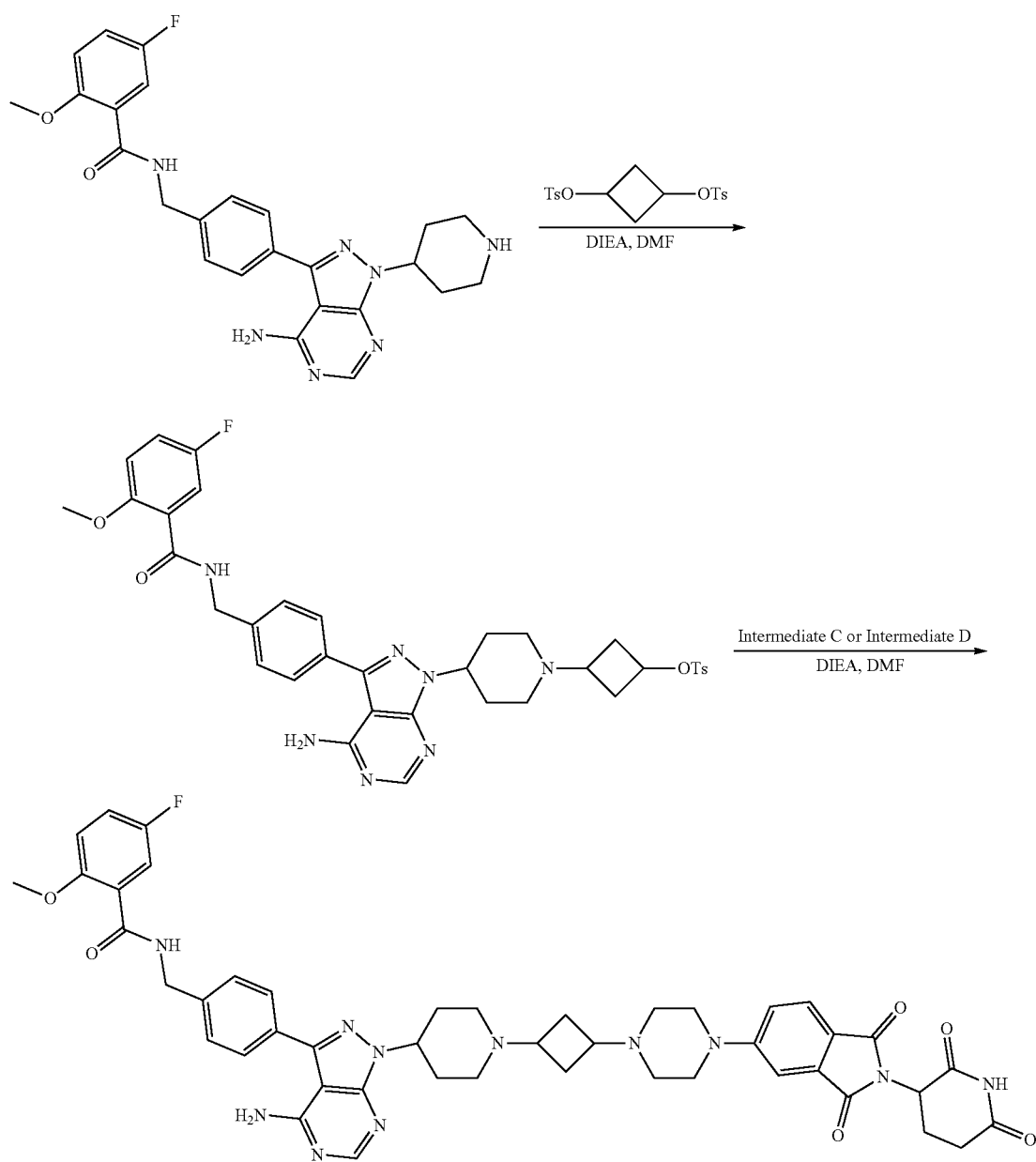

-continued
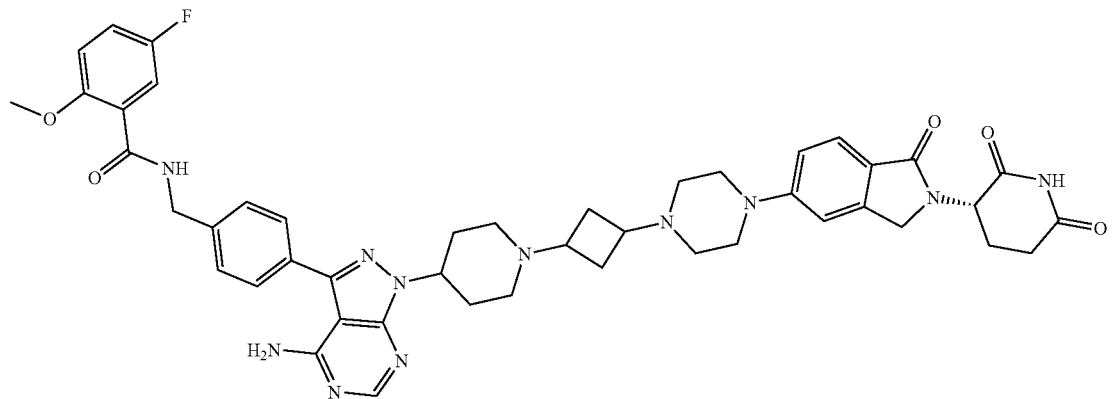
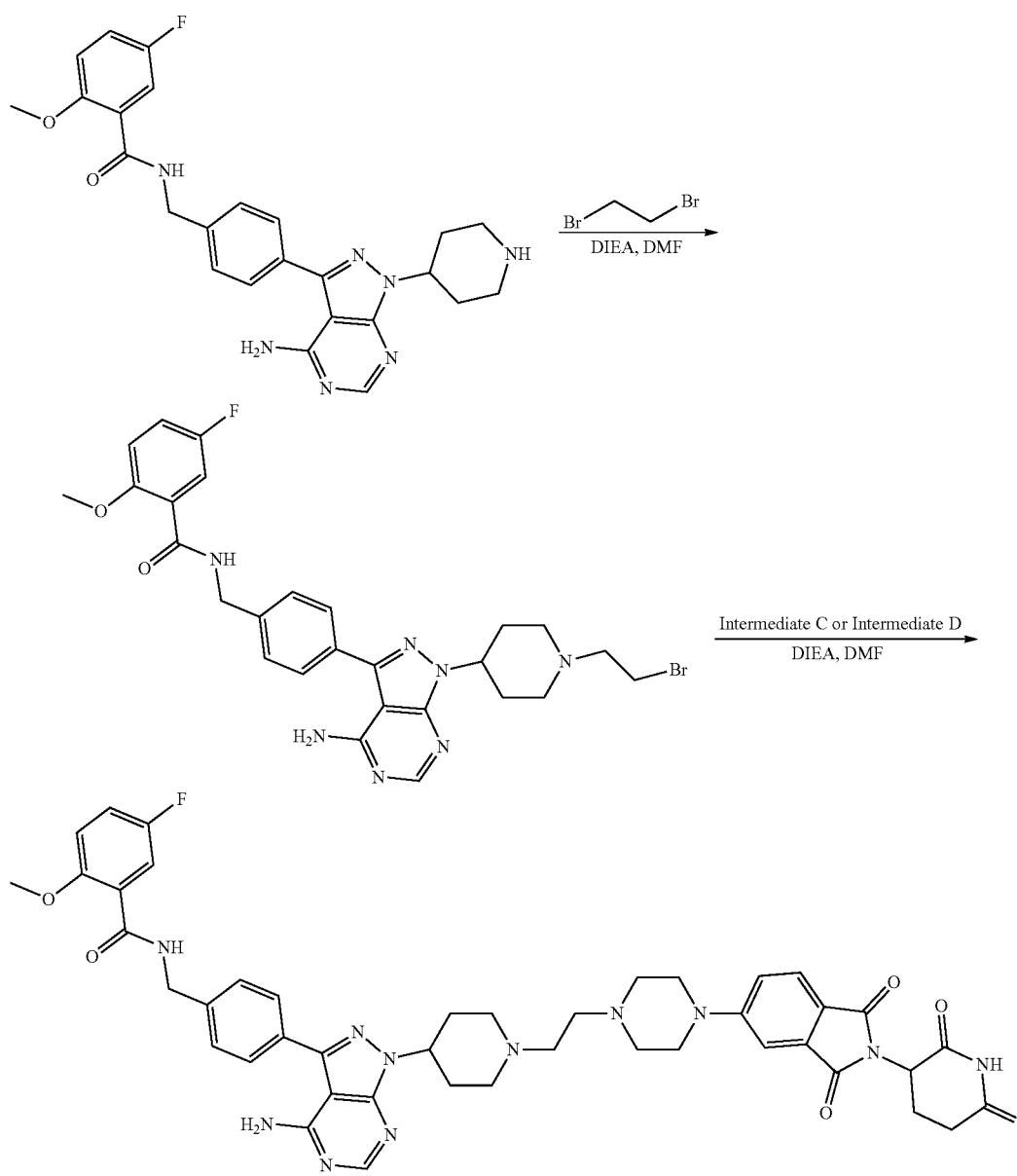

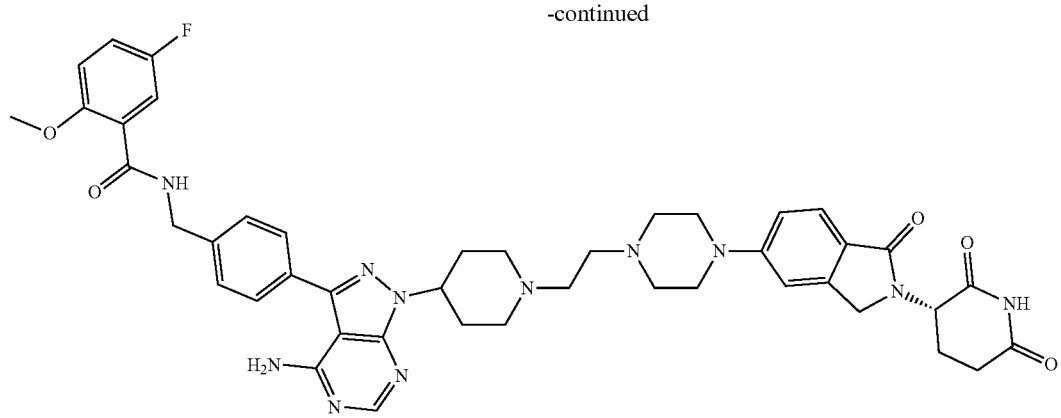
Compound 93, 94, 95, 96, 97, 98, 99, 102, 103 and 104 can be prepared using similar methods as described in Scheme 11.
Scheme 18: Method for the preparation of compounds 105-108
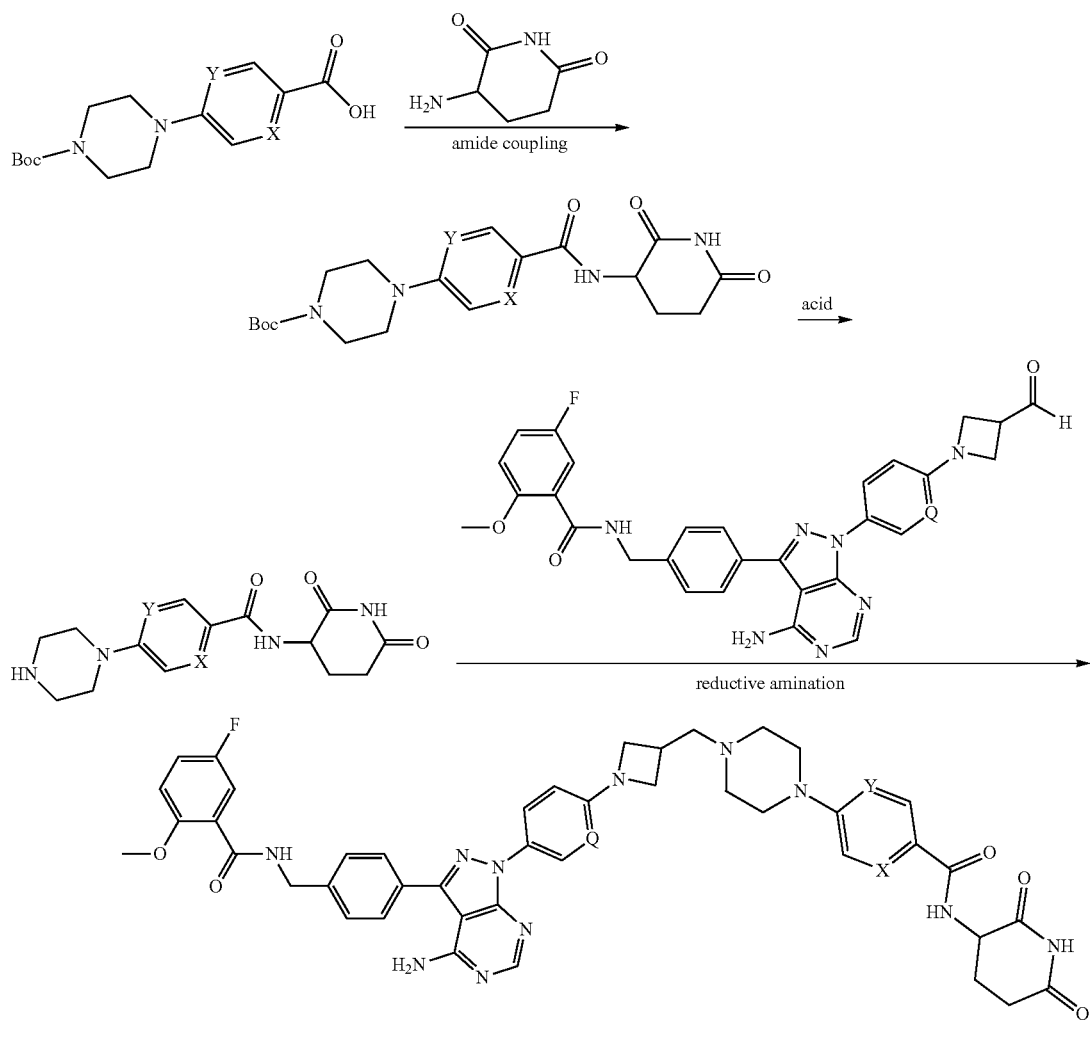
Q = CF, CH, N;
X and Y = CH, CF, N Compound 109 can be synthesized using a similar method as described in Scheme 18.

PREPARATION OF INTERMEDIATES

Preparation of (R)-(2-chloro-4-phenoxyphenyl)(4-(piperidin-3-ylamino)-7H-pyrrolo[2,3-d]pyrimidin-5-yl)methanone (Intermediate A)

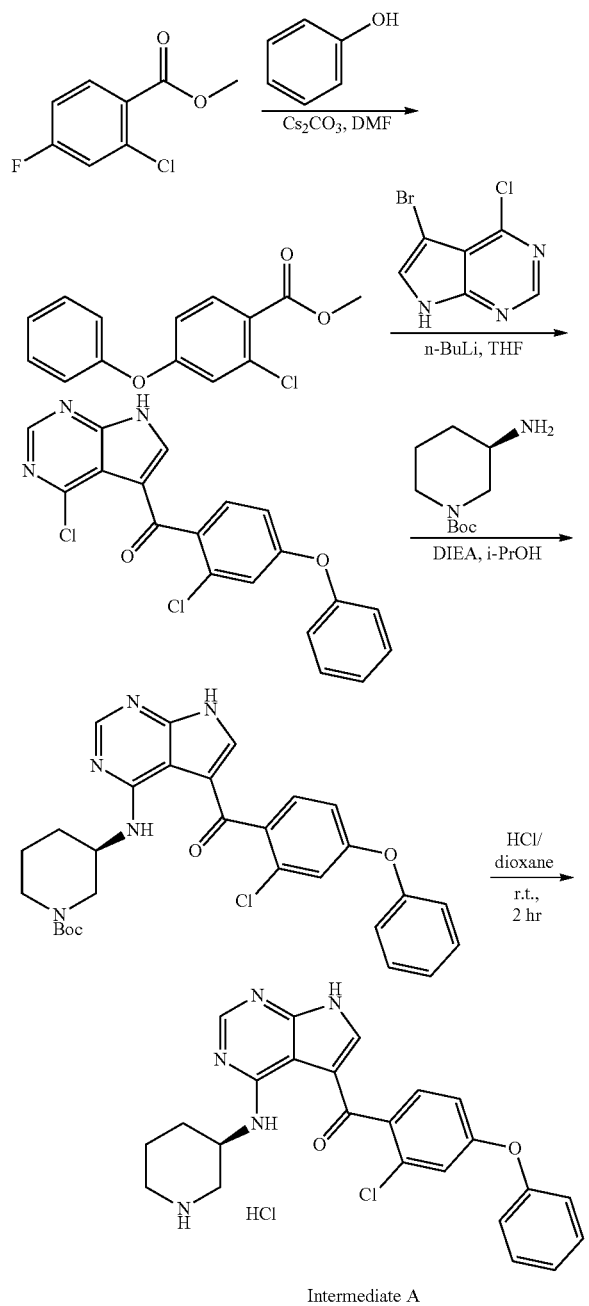

Intermediate A

Step 1: Preparation of methyl 2-chloro-4-phenoxybenzoate

The mixture of methyl 2-chloro-4-fluorobenzoate (20 g, 106.1 mmol), phenol (13 g, 137.9 mmol) and cesium carbonate (51.83 g, 156.1 mmol) in N,N-dimethylformamide (200 mL) was stirred for 16 h at 90° C. The mixture was extracted with EtOAc (200 mL×3). The organic layer was washed with a saturated NaCl solution, dried over sodium sulfate. After filtration, the filtrate was concentrated under reduced pressure. The residue was purified by silica gel column chromatography (hexane:ethyl acetate=50:1→5:1) to give methyl 2-chloro-4-phenoxybenzoate (18 g, 64.5%).

Step 2: Preparation of (2-chloro-4-phenoxyphenyl)(4-chloro-7H-pyrrolo[2,3-d]pyrimidin-5-yl)methanone 5-Bromo-4-chloro-7h-pyrrole [2,3-d] pyrimidine (1 g, 4.3 mmol) was dissolved in tetrahydrofuran (25 mL) and to this was added dropwise slowly n-BuLi (2.5 M in Hexane, 2 eq) at −78° C. under Ar. The mixture was stirred for 1 hour at −78° C. followed by addition of the solution of methyl 2-chloro-4-phenoxybenzoate (1.1 eq) dropwise. The mixture was stirred for 2 hr was at −78° C. The reaction was quenched with 1N HCl and extracted with EtOAc. The organic layer was washed with brine and dried over sodium sulfate. After filtration, the filtrate was concentrated under reduced pressure. The residue was purified by silica gel column chromatography (hexane:ethyl acetate=9:1 to 1:1) to give (2-chloro-4-phenoxyphenyl)(4-chloro-7H-pyrrolo[2,3-d]pyrimidin-5-yl)methanone (650 mg). LCMS: (ES+): m/z 383.02 [M]+.

Step 3: Preparation of tert-butyl (R)-3-((5-(2-chloro-4-phenoxybenzoyl)-7H-pyrrolo[2,3-d]pyrimidin-4-yl)amino)piperidine-1-carboxylate In a 20 mL microwave tube was charged with (2-chloro-4-phenoxyphenyl)(4-chloro-7H-pyrrolo[2,3-d]pyrimidin-5-yl)methanone (1 g, 2.6 mmol), DIEA (3 eq) and tert-butyl (R)-3-aminopiperidine-1-carboxylate (1.2 eq) and isopropanol (12 mL). The mixture was heated for 1.5 hr at 160° C. under microwave irradiation. After cooling to room temperature, the reaction was extracted with EtOAc (40 mL×4) and the organic layer was washed with brine and dried over sodium sulfate. After filtration, the filtrate was concentrated at reduced pressure. The residue was recrystallized with 25% EtOAc in petroleum ether to give tert-butyl (R)-3-((5-(2-chloro-4-phenoxybenzoyl)-7H-pyrrolo[2,3-d]pyrimidin-4-yl)amino)piperidine-1-carboxylate (1.1 g). LCMS: (ES+): m/z 547.2 [M]+.

Step 4: Preparation of (R)-(2-chloro-4-phenoxyphenyl)(4-(piperidin-3-ylamino)-7H-pyrrolo[2,3-d]pyrimidin-5-yl)methanone To a solution of tert-butyl (R)-3-((5-(2-chloro-4-phenoxybenzoyl)-7H-pyrrolo[2,3-d]pyrimidin-4-yl)amino)piperidine-1-carboxylate (11 g, 20.07 mmol) in 250 mL dioxane was added 4N HCl in dioxane (50 mL). The mixture reaction was stirred for 2.0 hr at room temperature. The mixture was concentrated to dry under vacuum. The residue was triturated with DCM to give crude product (9 g). The solid was purified further by reverse phase chromatography to give 7.8 g TFA salt.

1H NMR (400 MHz, DMSO-d6) δ 12.91 (br, 1H), 8.91-8.81 (m, 3H), 8.31 (s, 1H), 7.70 (s, 1H), 7.58 (d, J=8.4 Hz, 1H), 7.49 (t, J=7.6 Hz, 2H), 7.27 (t, J=7.6 Hz, 1H), 7.20-7.05 (m, 3H), 7.05 (d, J=6.7 Hz, 1H), 4.44 (s, 1H), 3.56 (br, 1H), 3.25 (br, 1H), 3.02-2.97 (m, 2H), 2.15 (br, 1H), 1.98 (br, 1H), 1.82-1.77 (m, 2H). LCMS: (ES+): m/z 448.2 [M]+.

Preparation of (2-chloro-4-phenoxyphenyl)(4-(piperidin-4-ylamino)-7H-pyrrolo[2,3-d]pyrimidin-5-yl)methanone hydrochloride (Intermediate B)

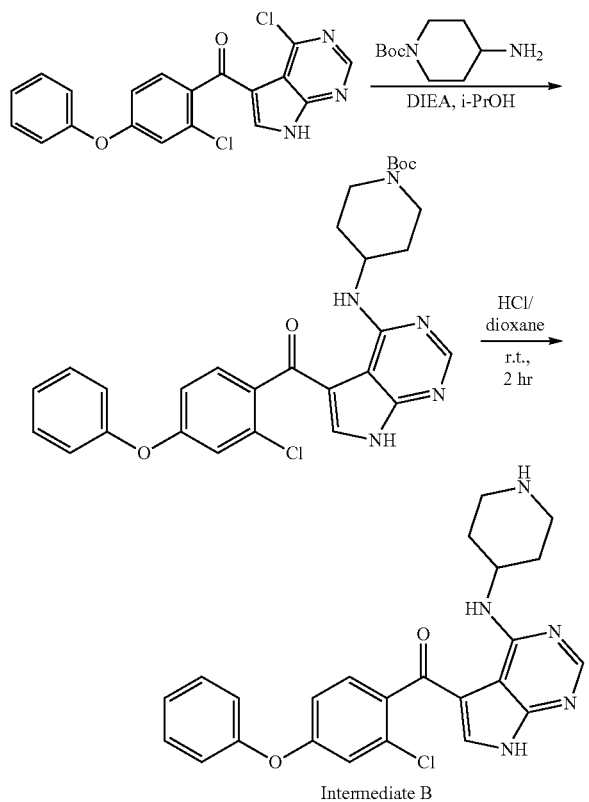

Step 1: Preparation of tert-butyl4-((5-(2-chloro-4-phenoxybenzoyl)-7H-pyrrolo[2,3-d]pyrimidin-4-yl)amino)piperidine-1-carboxylate A 20 mL microwave tube was charged with (2-chloro-4-phenoxyphenyl)(4-chloro-7H-pyrrolo[2,3-d]pyrimidin-5-yl)methanone (4.4 g, 11.45 mmol), DIEA (3 eq), 4-aminoperidine-1-tert-butyl carboxylate (1.2 eq) and isopropanol (12 ml). The mixture was heated for 1.5 hr at 160° C. under microwave irradiation. After cooling to room temperature, the reaction was extracted with EtOAc (40 mL×4) and the organic layer was washed with brine and dried over sodium sulfate. After filtration, the filtrate was concentrated at reduced pressure. The residue was recrystallized with 25% EtOAc in petroleum ether to give tert-butyl4-((5-(2-chloro-4-phenoxybenzoyl)-7H-pyrrolo[2,3-d]pyrimidin-4-yl)amino)piperidine-1-carboxylate (5 g). LCMS: (ES+): m/z 547.2 [M]+.

Step 2: Preparation of (2-chloro-4-phenoxyphenyl)(4-(piperidin-4-ylamino)-7H-pyrrolo[2,3-d]pyrimidin-5-yl)methanone hydrochloride To a solution of tert-butyl-4-((5-(2-chloro-4-phenoxybenzoyl)-7H-pyrrolo[2,3-d]pyrimidin-4-yl)amino)piperidine-1-carboxylate (10 g, 18.3 mmol) in 250 mL dioxane was added 4N HCl in dioxane (50 mL). The mixture reaction was stirred for 2.0 hr at room temperature. The mixture was concentrated to dryness under vacuum. The residue was triturated with DCM to give (2-chloro-4-phenoxyphenyl)(4-(piperidin-4-ylamino)-7H-pyrrolo[2,3-d]pyrimidin-5-yl)methanone hydrochloride (8 g).

$^1$H NMR (400 MHz, MeOD) δ 8.47 (s, 1H), 7.85 (s, 1H), 7.57 (d, J=7.9 Hz, 1H), 7.47 (t, J=7.8 Hz, 2H), 7.27 (t, J=7.4 Hz, 1H), 7.18-7.10 (m, 3H), 7.04 (d, J=6.7 Hz, 1H), 4.44 (s, 1H), 3.57 (br, 2H), 3.34 (br, 2H), 2.47 (br, 2H), 2.06 (br, 2H). LCMS: (ES+): m/z 448.2 [M]+.

Preparation of 2-(2,6-dioxopiperidin-3-yl)-5-(piperazin-1-yl)isoindoline-1,3-dione (Intermediate C)

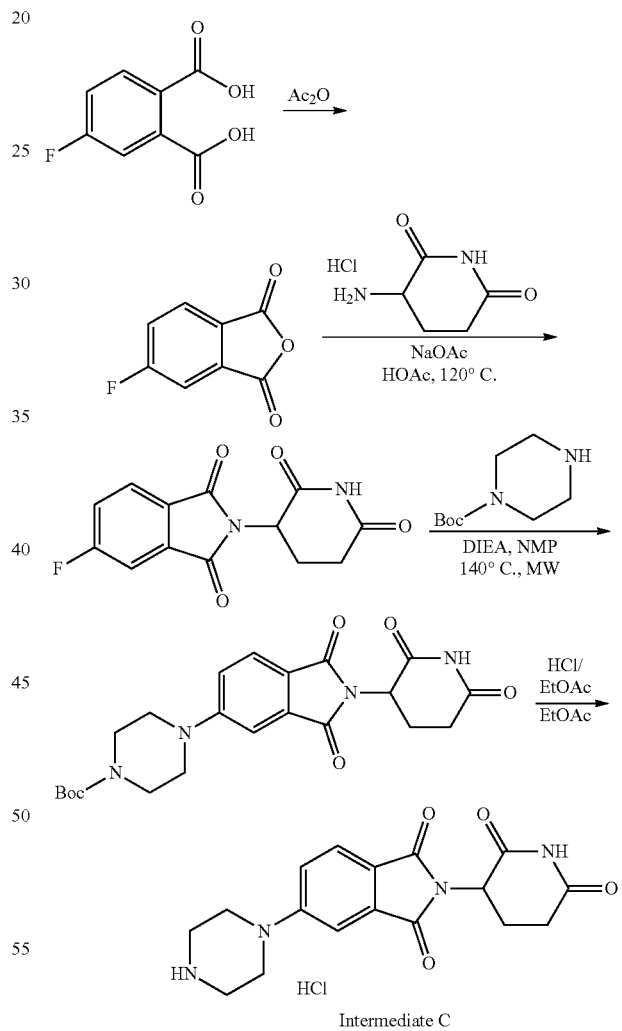

Intermediate 2-1 was prepared according to the above scheme as a hydrochloride salt using a similar method described in the literature. LC/MS 343.1 [M+H]+; $^1$H-NMR (400 MHz, CD$_3$OD) δ ppm 7.76 (d, J=8.36 Hz, 1H), 7.47 (s, 1H), 7.35 (dd, J=8.36, 1.54 Hz, 1H), 5.09 (br dd, J=12.8, 5.40 Hz, 1H), 3.67-3.74 (m, 4H), 3.37-3.42 (m, 4H), 2.63-2.94 (m, 3H), 2.07-2.17 (m, 1H).

Synthesis of (S)-3-(1-oxo-5-(piperazin-1-yl)isoindolin-2-yl)piperidine-2,6-dione benzenesulfonic acid (Intermediate D)

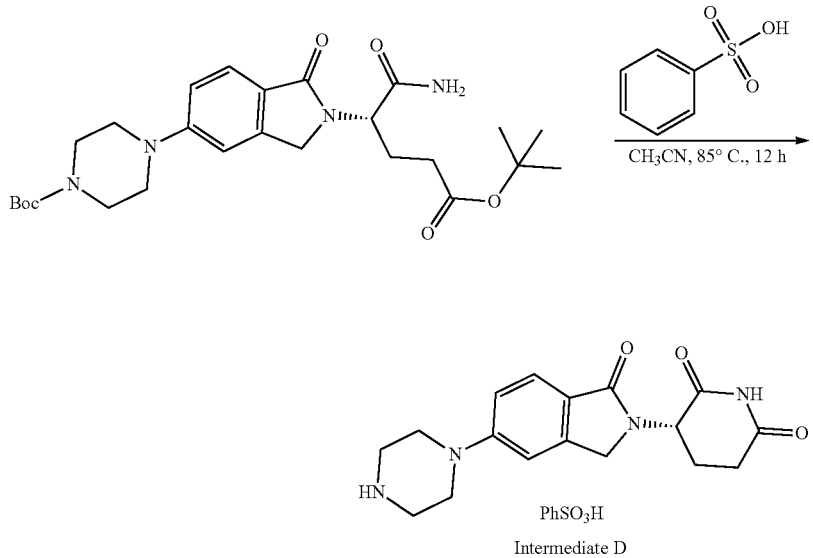

To a solution of (S)-tert-butyl 4-(2-(1-amino-5-tert-butoxy-1,5-dioxopentan-2-yl)-1-oxoisoindolin-5-yl)piperazine-1-carboxylate (5.8 g, 12 mol) in acetonitrile (90 mL) was added benzenesulfonic acid (3.64 g, 23 mol). The mixture was stirred at 85° C. for 12 h. LC/MS showed the reaction was complete. The mixture was concentrated in vacuum. The residue was triturated with ethyl acetate to afford (S)-3-(1-oxo-5-(piperazin-1-yl)isoindolin-2-yl)piperidine-2,6-dione benzenesulfonate (5.2 g, 93%) as off-white solid. LC/MS 329.1 [M+1]$^+$; $^1$H NMR (400 MHz, DMSO-d6) δ 1.95-1.99 (m, 1H), 2.36-2.41 (m, 1H), 2.58-2.62 (d, 1H), 2.88-2.91 (m, 1H), 3.26 (s, 4H), 3.49-3.52 (m, 4H), 4.21-4.38 (dd, 2H), 5.05-5.10 (dd, 1H), 7.12-7.16 (m, 2H), 7.30-7.358 (m, 3H), 7.58-7.62 (m, 3H), 8.72 (s, 2H).

Synthesis of N-(4-(4-amino-1-(4-(4-(dimethoxymethyl)piperidin-1-yl)-3-fluorophenyl)-1H-pyrazolo[3,4-d]pyrimidin-3-yl)benzyl)-5-fluoro-2-methoxybenzamide (Intermediate E)

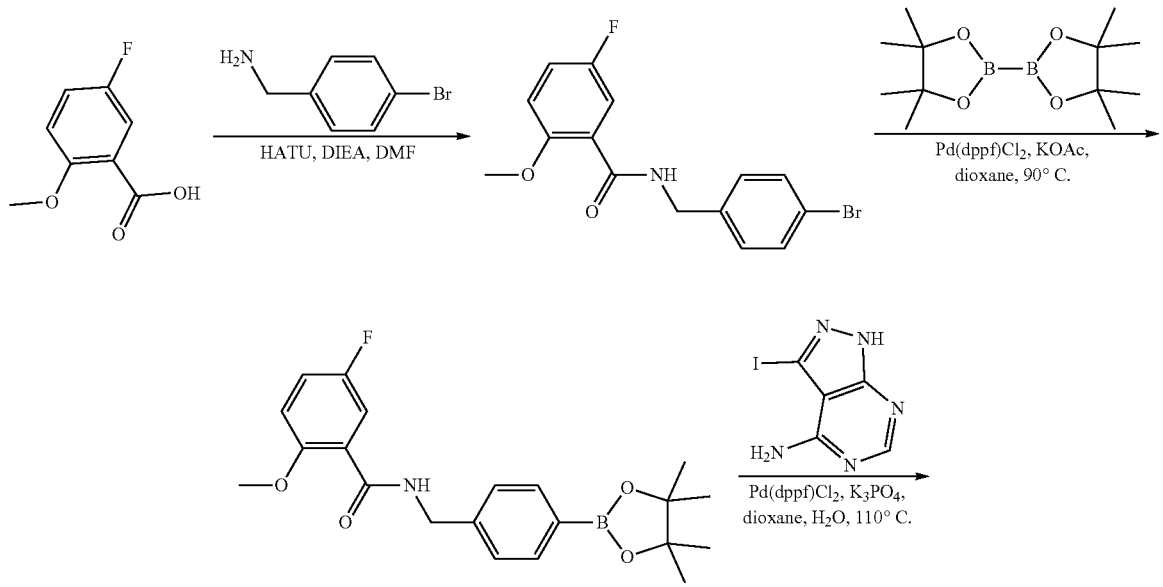

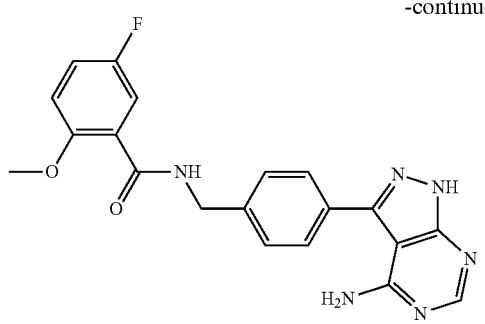
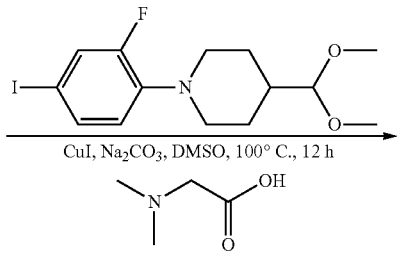
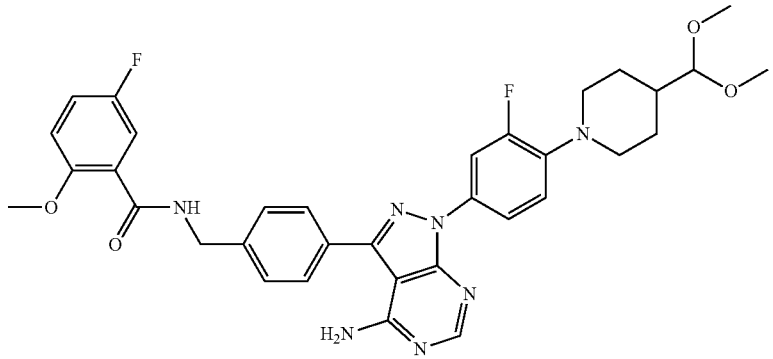

Intermediate E

Step 1: Preparation of N-(4-bromobenzyl)-5-fluoro-2-methoxybenzamide

A solution of 5-fluoro-2-methoxy-benzoic acid (30 g, 176 mmol, 1.0 eq), O-(7-azabenzotriazol-1-yl)-N,N,N',N'-tetramethyluronium hexafluorophosphate (80.5 g, 212 mmol, 1.2 eq) and N,N-diisopropylethylamine (45.6 g, 353 mmol, 2 eq) in N,N-dimethylformamide (300 mL) was stirred at 25° C. for 30 min. Then (4-bromophenyl)methanamine (32.8 g, 176 mmol, 1.0 eq) was added into the solution and the mixture was stirred at 25° C. for 12 h. The solution was poured into water (500 mL), extracted with ethyl acetate (500 mL×3). The combined organic phase was washed with brine (500 mL), dried with anhydrous sodium sulfate, filtered and concentrated. The residue was purified by silica gel chromatography with 20%-30% ethyl acetate in petroleum ether as eluent to afford desired compound (56 g, 94% yield) as a white solid.

$^1$HNMR (400 MHz, CDCl$_3$): δ 8.26 (br s, 1H), 7.94 (q, J=2.0 Hz, 1H), 7.45 (d, J=7.6 Hz, 2H), 7.22 (d, J=8.0 Hz, 2H), 7.16-7.12 (m, 1H), 6.94-6.91 (m, 1H), 4.61 (d, J=6.0 Hz, 2H), 3.91 (s, 3H).

Step 2: Preparation of 5-fluoro-2-methoxy-N-[[4-(4,4,5,5-tetramethyl-1,3,2-dioxaborolan-2-yl)phenyl]methyl]benzamide To a solution of N-[(4-bromophenyl)methyl]-5-fluoro-2-methoxy-benzamide (46 g, 136 mmol, 1.0 eq) and 4,4,5,5-tetramethyl-2-(4,4,5,5-tetramethyl-1,3,2-dioxaborolan-2-yl)-1,3,2-dioxaborolane (51.8 g, 204 mmol, 1.5 eq) in dioxane (500 mL) was added potassium acetate (26.7 g, 272 mmol, 2.0 eq) and 1,1-bis(diphenylphosphino)ferrocene]dichloropalladium(II) (9.95 g, 13.6 mmol, 0.1 eq). The suspension was degassed under vacuum and purged with nitrogen for three times. The mixture was stirred under nitrogen at 90° C. for 12 h. The solution was poured into water (2 L), extracted with ethyl acetate (1 L×3). The combined organic phase was washed with brine (2 L), dried with anhydrous sodium sulfate, filtered and concentrated. The combined crude product was purified by silica gel chromatography with 20%-30% ethyl acetate in petroleum ether as eluent. The crude product was triturated with petroleum ether (200 mL), filtered and the filter cake was dried under vacuum to afford the desired compound (50 g, 79% yield) as a white solid. LC/MS: 386.2 [M+H]$^+$.

Step 3: Preparation of N-(4-(4-amino-1H-pyrazolo[3,4-d]pyrimidin-3-yl)benzyl)-5-fluoro-2-methoxy-benzamide A mixture of 5-fluoro-2-methoxy-N-[[4-(4,4,5,5-tetramethyl-1,3,2-dioxaborolan-2-yl)phenyl]methyl]benzamide (10.0 g, 26.0 mmol, 1.0 eq), 3-iodo-1H-pyrazolo[3,4-d]pyrimidin-4-amine (6.78 g, 26.0 mmol, 1.0 eq), 1,1-bis(diphenylphosphino)ferrocene]dichloropalladium(II) (3.80 g, 5.19 mmol, 0.2 eq), potassium phosphate (16.5 g, 77.9 mmol, 3.0 eq) in dioxane (200 mL) and water (40 mL) was degassed and purged with nitrogen for three times, and then the mixture was stirred at 110° C. for 60 hr under nitrogen atmosphere. The reaction mixture was partitioned between ethyl acetate (1 L) and water (1 L). The organic phase was separated, washed with brine (1 L), dried over anhydrous sodium sulfate, filtered and concentrated. The residue was triturated with acetonitrile (50 mL) then ethyl acetate (50 mL), the solid was collected and dried under vacuum to afford the desired compound (6.0 g, 59% yield) as a light yellow solid. LC/MS: 393.1 [M+H]$^+$. $^1$H NMR (400 MHz, DMSO-d$_6$): δ 13.59 (s, 1H), 8.86 (t, J=6.0 Hz, 1H), 8.22 (s, 1H), 7.64 (d, J=8.0 Hz, 2H), 7.57-7.47 (m, 3H), 7.37-7.31 (m, 1H), 7.19 (dd, J=4.4, 9.2 Hz, 1H), 4.59 (d, J=6.0 Hz, 2H), 3.90 (s, 3H).

Step 4: Preparation of N-[[4-[4-amino-1-[4-[4-(dimethoxymethyl)-1-piperidyl]-3-fluoro-phenyl]pyrazolo[3,4-d]pyrimidin-3-yl]phenyl]methyl]-5-fluoro-2-methoxy-benzamide To a solution of N-[[4-(4-amino-1H-pyrazolo[3,4-d]pyrimidin-3-yl)phenyl]methyl]-5-fluoro-2-methoxy-benzamide (12.0 g, 30.6 mmol, 1.0 eq) and 4-(dimethoxymethyl)-1-(2-fluoro-4-iodo-phenyl)piperidine (11.6 g, 30.6 mmol, 1.0 eq) in dimethyl sulfoxide (150 mL) were added copper iodide (3.24 g, 17.0 mmol, 0.55 eq), 2-(dimethylamino)acetic acid (3.50 g, 33.98 mmol, 1.1 eq) and sodium carbonate (7.20 g, 68.0 mmol, 2.2 eq). The suspension was degassed under vacuum and purged with nitrogen for three times. The mixture was stirred under nitrogen at 110° C. for 12 h. The solution was partitioned between ethyl acetate (800 mL) and water (2.0 L). The separated aqueous layer was extracted with ethyl acetate (700 mL×3). The combined organic layers were washed with brine (500 mL), dried over anhydrous sodium sulfate, filtered and concentrated to give crude product (15 g). The crude product was dissolved in ethyl acetate (420 mL) with refluxing. Then the solution was cooled to ambient temperature along with little precipitate formed and the mixture was kept in refrigerator (~5° C.) for 48 h. The solution was filtered and the filter cake was washed with cold ethyl acetate (20 mL) to give the pure product (5.28 g). The mother liquid was concentrated and the residue was re-crystallized from ethyl acetate (100 mL) to give another crop of pure product (1.7 g) (total 6.98 g, 36% yield) as a gray solid. LC/MS: 644.2 [M+H]$^+$. $^1$HNMR (400 MHz, CDCl$_3$): δ 8.47 (s, 1H), 8.38 (t, J=5.2 Hz, 1H), 7.99 (dd, J=3.2, 9.2 Hz, 1H), 7.97-7.93 (m, 1H), 7.92 (s, 1H), 7.75 (d, J=8.0 Hz, 2H), 7.56 (d, J=8.0 Hz, 2H), 7.22-7.14 (m, 1H), 7.08 (t, J=8.8 Hz, 1H), 6.97 (dd, J=4.4, 8.8 Hz, 1H), 5.60 (br s, 2H), 4.78 (d, J=6.0 Hz, 2H), 4.12 (d, J=7.2 Hz, 1H), 3.97 (s, 3H), 3.53 (d, J=12.0 Hz, 2H), 3.39 (s, 6H), 2.69 (t, J=11.6 Hz, 2H), 1.88 (d, J=12.0 Hz, 2H), 1.82-1.73 (m, 1H), 1.64-1.48 (m, 2H).

Preparation of (S)-3-(6-fluoro-1-oxo-5-(piperazin-1-yl)isoindolin-2-yl)piperidine-2,6-dione benzenesulfonic acid (Intermediate F)

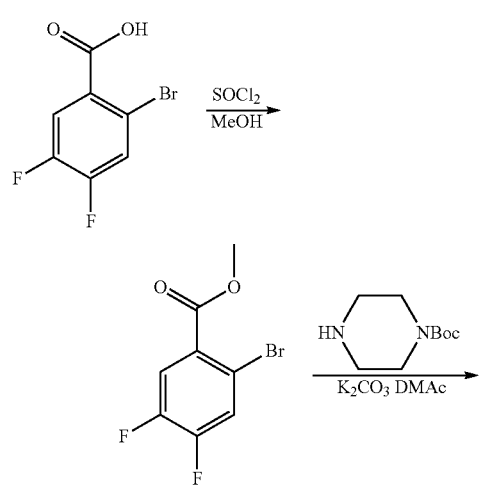

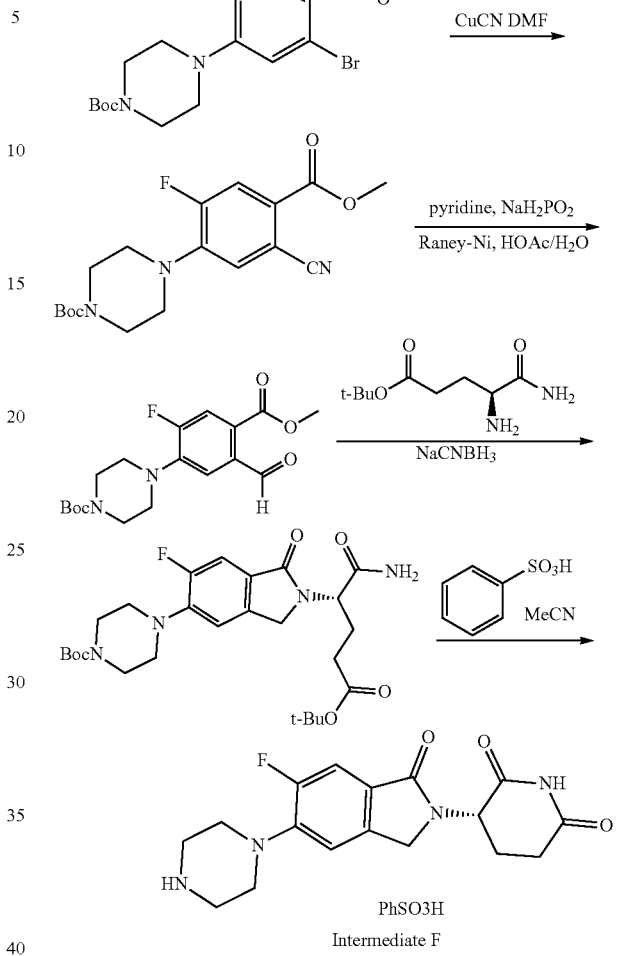

Step 1: Preparation of methyl 2-bromo-4,5-difluorobenzoate

Thionyl chloride (13 g, 0.11 mol) was added slowly to a mixture of 2-bromo-4,5-difluorobenzoic acid (20 g, 0.084 mol) in MeOH (60 mL) at 10° C., then stirred at 80° C. for 3 h. TLC showed the reaction was completed. The mixture was cooled to room temperature, concentrated then partitioned between ethyl acetate and water. The organic layer was washed with saturated Na$_2$CO$_3$ and brine twice, dried over Na$_2$SO$_4$ and concentrated to afford a crude desired product (21 g, yield: 100%) which was used for the next step without further purification.

Step 2: Preparation of tert-butyl 4-(5-bromo-2-fluoro-4-(methoxycarbonyl)phenyl) piperazine-1-carboxylate A mixture of methyl 2-bromo-4,5-difluorobenzoate (21 g, 0.084 mol), tert-butyl piperazine-1-carboxylate (23.4 g, 0.125 mol) and K$_2$CO$_3$ (17.3 g, 0.125 mol) in N,N-dimethylacetamide (60 mL) was stirred at 80° C. for 16 h. TLC showed the reaction was completed. The mixture was added to water (200 mL) and stirred for 10 min. EtOAc (200 mL)

was added. The mixture was partitioned between ethyl acetate and water. The organic layer was washed with water, brine, dried over Na₂SO₄ and concentrated to afford the title desired product (31.6 g, yield: 90%).

Step 3: Preparation of tert-butyl 4-(5-cyano-2-fluoro-4-(methoxycarbonyl)phenyl) piperazine-1-carboxylate A mixture of tert-butyl 4-(5-bromo-2-fluoro-4-(methoxycarbonyl)phenyl)piperazine-1-carboxylate (30.6 g, 0.073 mol) and CuCN (9.8 g, 0.11 mol) in DMF (120 mL) was stirred at 100° C. for 16 h. TLC showed the reaction was completed. The mixture was cooled to room temperature. Ethyl acetate (200 mL) and ammonium hydroxide (200 mL) was added and stirred for 30 min. The mixture was filtered. The organic layer was washed with water, dried over Na₂SO₄ and concentrated to afford a crude product (25.4 g). The crude material was taken into petrol ether (100 mL) at reflux. The mixture was filtered and dried in oven 50° C. to afford the title compound (21.5 g, yield: 81%).

Step 4: Preparation of tert-butyl 4-(2-fluoro-5-formyl-4-(methoxycarbonyl)phenyl) piperazine-1-carboxylate To a solution of pyridine (39.1 g, 495 mmol), water (20 mL), acetic acid (26.4 g, 440 mmol) was added tert-butyl 4-(5-cyano-2-fluoro-4-(methoxycarbonyl)phenyl)piperazine-1-carboxylate (20 g, 55 mmol) and Raney-nickel (85% in water, 10 g) at room temperature. The resulting mixture was heated to 60° C. Sodium hypophosphite (29.2 g in 50 mL water) was added dropwise into the mixture. The mixture was stirred for 16 h at 60° C. TLC showed the reaction not completed. The mixture was further stirred for 10 h. The mixture was cooled to room temperature. Ethyl acetate and water was added. The mixture was filtered. The organic layer was washed with water, 1N HCl and brine, dried over Na₂SO₄ and concentrated under reduced pressure to afford a crude product (20.8 g, crude). The resulting residue was purified by silica-gel pad to afford desired product (8.7 g, yield: 43%).

Step 5: Preparation of tert-butyl (S)-4-(2-(1-amino-5-(tert-butoxy)-1,5-dioxopentan-2-yl)-6-fluoro-1-oxoisoindolin-5-yl)piperazine-1-carboxylate To a solution of tert-butyl 4-(2-fluoro-5-formyl-4-(methoxycarbonyl)phenyl)piperazine-1-carboxylate (8.15 g, 22 mmol) in methanol (50 mL) was added tert-butyl (S)-4,5-diamino-5-oxopentanoate (5.4 g, 27 mmol) at room temperature. Acetic acid (1.98 g, 33 mmol) was added at 0° C. Sodium cyanoborohydride (2.76 g, 44 mmol) was added slowly. The mixture was stirred at room temperature for 16 hours. TLC showed the reaction was completed. The mixture was concentrated and partitioned between ethyl acetate and water. The organic layer was washed with saturated citric acid, brine, dried over Na₂SO₄ and concentrated under reduced pressure to afford a crude. The crude was purified by silica-gel pad to afford the desired product (8 g, yield: 69%).

Step 6: Preparation of (S)-3-(6-fluoro-1-oxo-5-(piperazin-1-yl)isoindolin-2-yl)piperidine-2,6-dione benzenesulfonic acid To a solution of tert-butyl (S)-4-(2-(1-amino-5-(tert-butoxy)-1,5-dioxopentan-2-yl)-6-fluoro-1-oxoisoindolin-5-yl)piperazine-1-carboxylate (6.7 g, 13 mmol) in acetonitrile (67 mL) was added benzenesulfonic acid (4.3 g, 26 mmol). The mixture was stirred at 80° C. for 16 h. LC/MS showed the reaction was complete. The mixture was cooled to room temperature. The mixture was filtered and dried to afford the desired product (5.6 g, 86%) as off-white solid. 1H NMR (400 MHz, DMSO-d6) δ 10.99 (s, 1H), 8.73 (br s, 2H), 7.60 (m, 2H), 7.49 (d, 1H), 7.32 (m, 4H), 5.08 (dd, J=13.2 and 5.2 Hz, 1H), 4.38 (d J=17.2 Hz, 1H), 4.27 (d, J=17.2 Hz, 1H), 3.30 (br s, 8H), 2.91 (m, 1H), 2.67 (m, 1H), 2.50 (m, 1H), 1.98 (m, 1H); LC/MS 347.3 [M+H]⁺

EXAMPLES

Example 1: Preparation of 5-((7-(4-(5-((R)-3-((5-(2-chloro-4-phenoxybenzoyl)-7H-pyrrolo [2,3-d]pyrimidin-4-yl)amino)piperidine-1-carbonyl)pyridin-2-yl)piperazin-1-yl)heptyl)oxy)-2-(2,6-dioxopiperidin-3-yl)isoindoline-1,3-dione (Compound 1)

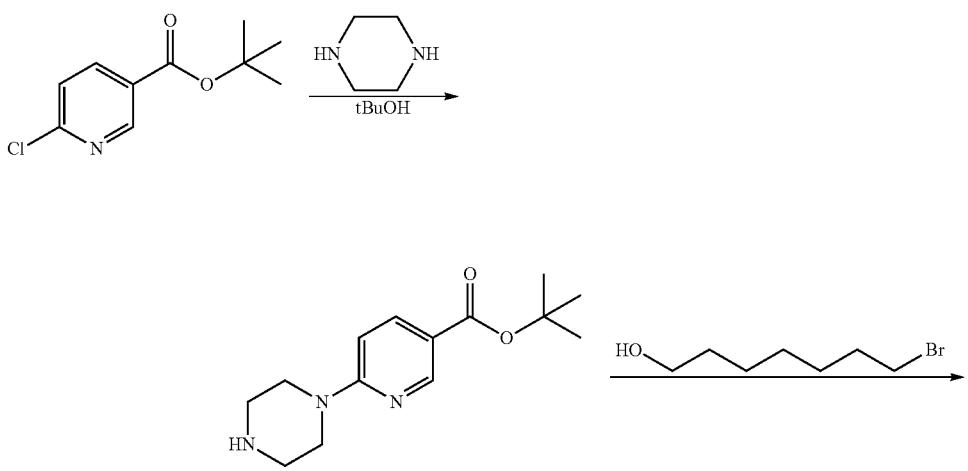

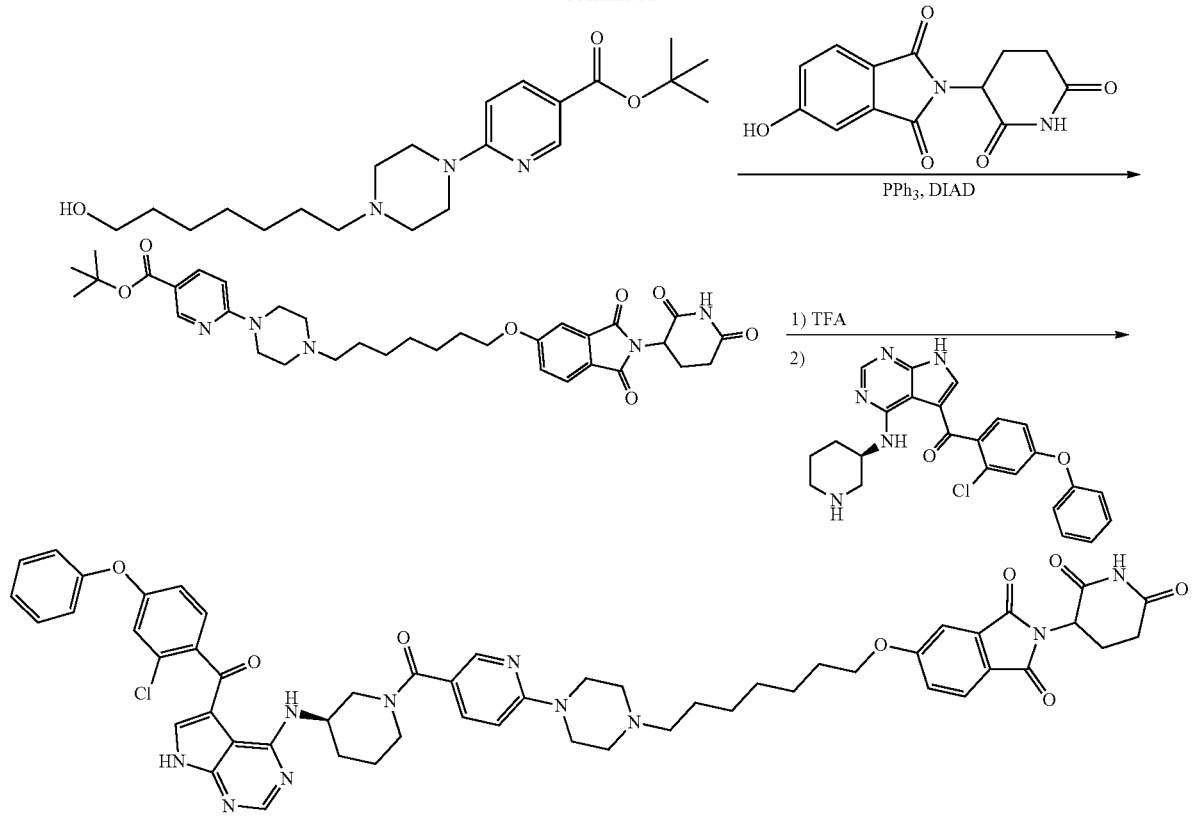

Step 1: Preparation of 2-(2,6-dioxopiperidin-3-yl)-5-hydroxyisoindoline-1,3-dione To a solution of 3-aminopiperidine-2,6-dione HCl salt (4.1 g, 24.7 mmol) in acetic acid (45 mL) was added sodium acetate (4.1 g, 49.4 mmol) and the mixture was stirred at 25° C. for 1 hr. 4-Hydroxyphthalic acid (3.0 g, 16.5 mmol) was added into the mixture and heated to 120° C. for 11 hr. The mixture was concentrated and then poured into water (20 mL). The suspension was filtered. The crude product was purified by column chromatography (dichloromethane: methanol=50:1 to 10:1) to afford 2-(2,6-dioxo-3-piperidyl)-5-hydroxy-isoindoline-1,3-dione (3.9 g, 14.3 mmol, 86% yield) as a colorless solid.

Step 2: Preparation of tert-butyl 6-(piperazin-1-yl)nicotinate

To a solution of tert-butyl 6-chloronicotinate (8.52 g, 40 mmol) in tert-butanol (100 mL) was added piperazine (17.2 g, 200 mmol) and the mixture was heated to 60° C. for 6 hr. The mixture was concentrated under vacuum and the crude product was purified by column chromatography to give the titled compound (10 g, 95%) as a colorless solid. LCMS: m/z=264.2 [M]+.

Step 3: Preparation of tert-butyl 6-(4-(7-hydroxyheptyl)piperazin-1-yl)nicotinate To a solution of tert-butyl 6-(piperazin-1-yl)nicotinate (526 mg, 2 mmol), 7-bromoheptan-1-ol (468 mg, 2.4 mmol) in CH$_3$CN (5 mL) was added K$_2$CO$_3$ at room temperature and the reaction mixture was stirred at 85° C. for 4 hr. The mixture was diluted with EtOAc and filtered through a celite pad. The filtrate was concentrated to afford tert-butyl 6-(4-(7-hydroxyheptyl)piperazin-1-yl)nicotinate (630 mg, 83%) as a light yellow solid. LCMS: m/z=378.3 [M]+.

Step 4: Preparation of tert-butyl 6-(4-(7-((2-(2,6-dioxopiperidin-3-yl)-1,3-dioxoisoindolin-5-yl)oxy)heptyl)piperazin-1-yl)nicotinate To a solution of tert-butyl 6-(4-(7-hydroxyheptyl)piperazin-1-yl)nicotinate (377 mg, 1 mmol) in dry THF (3 mL) was added 2-(2,6-dioxopiperidin-3-yl)-5-hydroxyisoindoline-1,3-dione (383.6 mg, 1.4 mmol), PPh$_3$ (524 mg, 2.0 mmol) at 25° C. under nitrogen. DIAD (404 mg, 2.0 mmol) was added to the mixture at room temperature. The resulting mixture was stirred at 45° C. for 2 hours. After cooling to r.t. the reaction was quenched with H$_2$O (10 mL) and extracted with EtOAc (10 mL×2). The combined organic layers were washed with brine (20 mL×5), dried over anhydrous sodium sulfate and concentrated. The residue was purified with prep-TLC to afford the desired product (80 mg, 12.6%) as a white solid. LCMS: m/z=634.3 [M+1]+.

Step 5: Preparation of 6-(4-(7-((2-(2,6-dioxopiperidin-3-yl)-1,3-dioxoisoindolin-5-yl)oxy)heptyl)piperazin-1-yl)nicotinic acid A solution of tert-butyl 6-(4-(7-((2-(2,6-dioxopiperidin-3-yl)-1,3-dioxoisoindolin-5-yl)oxy)heptyl)piperazin-1-yl) nicotinate (80 mg, 0.13 mmol) in TFA/DCM (6.0 mL, 1:5) was stirred at room temperature for 3 hr. The reaction mixture was concentrated by rotary evaporation to obtain the titled product (70 mg), which was used in the next step without further purification. LCMS: m/z=578.3 [M+1]+.

Step 6: Preparation of 5-((7-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)heptyl)oxy)-2-(2,6-dioxopiperidin-3-yl)isoindoline-1,3-dione To a solution of 6-(4-(7-((2-(2,6-dioxopiperidin-3-yl)-1,3-dioxoisoindolin-5-yl)oxy)heptyl)piperazin-1-yl)nicotinic acid (58 mg, 0.1 mmol), (R)-(2-chloro-4-phenoxyphenyl)(4-(piperidin-3-ylamino)-7H-pyrrolo[2,3-d]pyrimidin-5-yl)methanone (54 mg, 0.12 mmol) and DIEA (51.6 mg, 0.4 mmol) in DMF (3 mL) was added HATU (57 mg, 0.15 mmol) at room temperature. The reaction was stirred at room temperature until LCMS showed the reaction is complete. The mixture solution was quenched with ice water and extracted with DCM (10 mL×3). The organic layer was washed with water and brine, dried over Na2SO4, filtered and the solvent was removed by rotary evaporation. The residue was purified by Pre-TLC to obtain the titled product (21 mg, 20.8%) as a white solid. LCMS: m/z=1007.4 [M+H]+.

1HNMR (400 MHz, CDCl3-d): δ9.05 (s, 1H), 8.36-8.30 (m, 2H), 7.77-7.65 (m, 2H), 7.41-7.31 (m, 5H), 7.23-7.16 (m, 2H), 7.10-7.07 (m, 3H), 6.95-6.93 (m, 1H), 6.50-6.48 (m, 1H), 4.96-4.95 (m, 1H), 4.38 (s, 1H), 4.08 (s, 3H), 3.90 (s, 1H), 3.58-3.44 (m, 6H), 2.91-2.74 (m, 3H), 2.52 (m, 4H), 2.36 (s, 2H), 2.19-2.01 (m, 4H), 1.18-1.75 (m, 5H), 1.51-1.36 (m, 8H).

Example 2: Preparation of 5-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)-2-(2,6-dioxopiperidin-3-yl)isoindoline-1,3-dione (Compound 2)

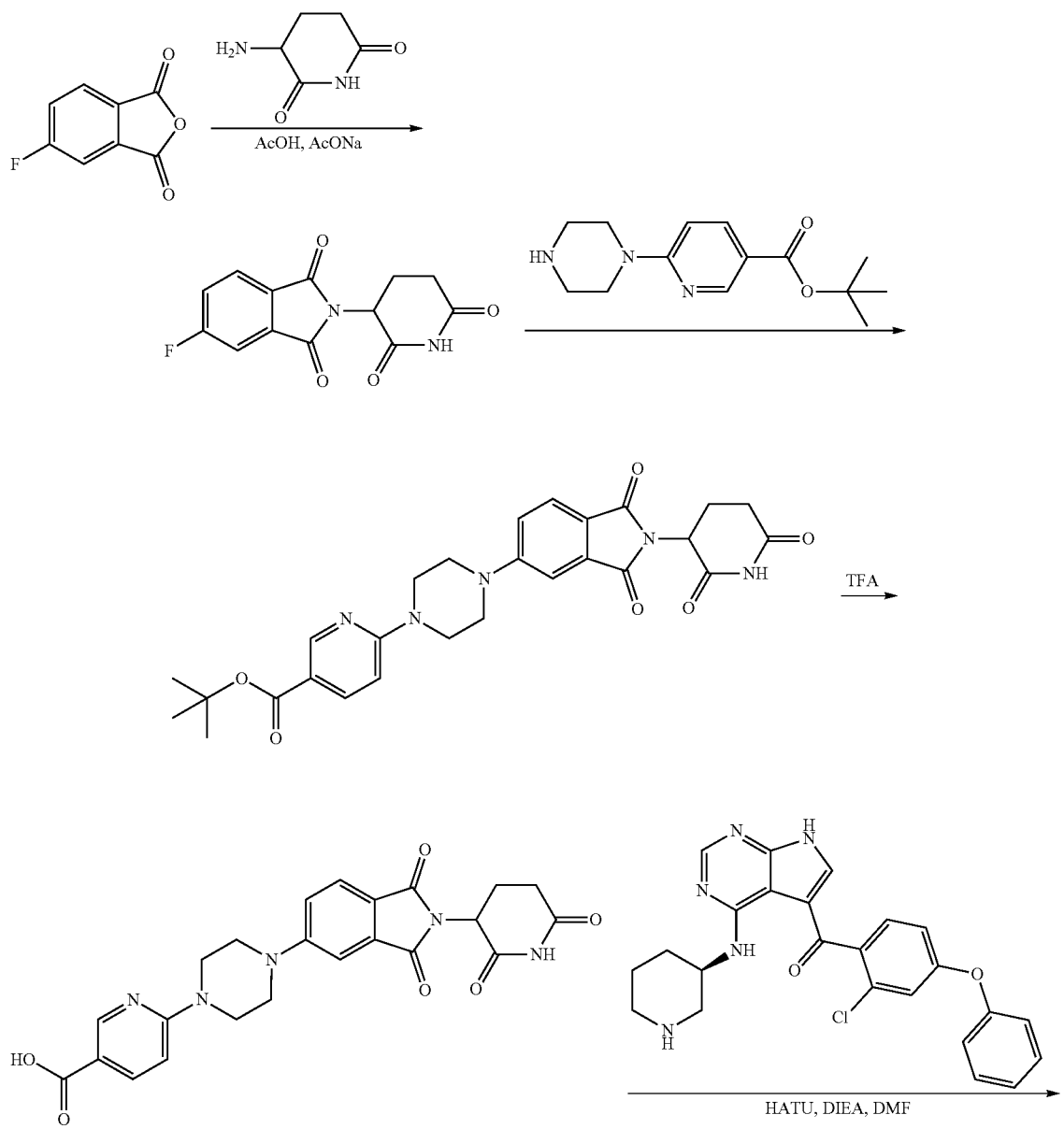

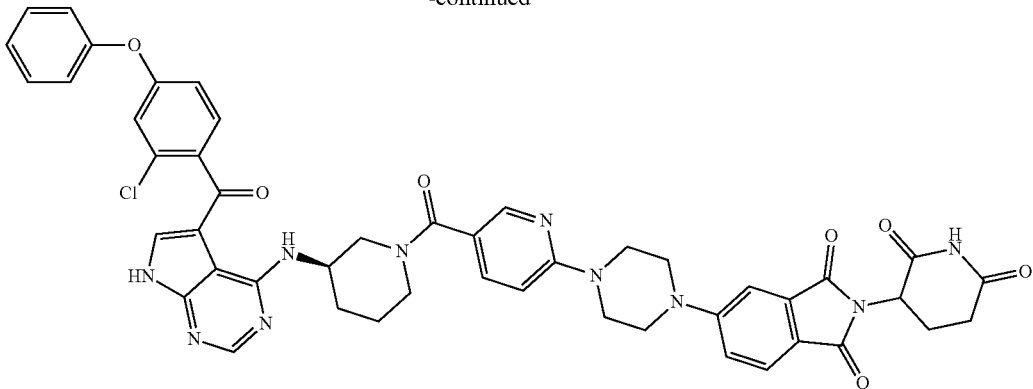

-continued

Step 1: Preparation of 2-(2,6-dioxopiperidin-3-yl)-5-fluoroisoindoline-1,3-dione To a solution of 5-fluoroisobenzofuran-1,3-dione (2 g, 12.05 mmol) in acetic acid (30 mL) was added sodium acetate (1.98 g, 24.08 mmol) and 3-aminopiperidine-2,6-dione hydrochloride (1.98 g, 12.05 mmol). The mixture was stirred at 120° C. for 18 hrs. The reaction mixture was concentrated under reduced pressure. The residue was poured into water (60 mL) and stirred for 10 mins. The solid was collected by filtration and washed with water (2×20 mL) and dried under vacuum to afford the titled compound (2.8 g, 94%) as a white solid.

Step 2: Preparation of tert-butyl 6-(4-(2-(2,6-dioxopiperidin-3-yl)-1,3-dioxoisoindolin-5-yl)piperazin-1-yl)nicotinate 2-(2,6-Dioxopiperidin-3-yl)-5-fluoroisoindoline-1,3-dione (200 mg, 0.724 mmol), tert-butyl 6-(piperazin-1-yl)nicotinate (158 mg, 0.603 mmol) and $K_2CO_3$ (167 mg, 1.207 mmol) was suspended in DMF in a 20 mL microwave tube. The mixture was irradiated with microwave at 120° C. for 1 hr. The mixture was extracted with EtOAc (30 mL×3) and washed with brine (20 mL×2). The combined organic phases was dried over $Na_2SO_4$ and concentrated under vacuum. The residue was purified by Prep-TLC to give tert-butyl 6-(4-(2-(2,6-dioxopiperidin-3-yl)-1,3-dioxoisoindolin-5-yl)piperazin-1-yl)nicotinate (200 mg)

Step 3: Preparation of 6-(4-(2-(2,6-dioxopiperidin-3-yl)-1,3-dioxoisoindolin-5-yl)piperazin-1-yl)nicotinic acid tert-Butyl 6-(4-(2-(2,6-dioxopiperidin-3-yl)-1,3-dioxoisoindolin-5-yl)piperazin-1-yl)nicotinate (180 mg, 0.346 mol) was dissolved in 4N HCl/dioxane and the mixture was stirred at room temperature for 1 hr. After concentration under vacuum, the titled compound (130 mg) was obtained as a yellow solid and used as is in the next step.

Step 4: Preparation of 5-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)-2-(2,6-dioxopiperidin-3-yl)isoindoline-1,3-dione To a solution of 6-(4-(2-(2,6-dioxopiperidin-3-yl)-1,3-dioxoisoindolin-5-yl)piperazin-1-yl)nicotinic acid (130 mg 0.281 mmol) in DMF (5 mL) was added (R)-(2-chloro-4-phenoxyphenyl)(4-(piperidin-3-ylamino)-7H-pyrrolo[2,3-d]pyrimidin-5-yl)methanone (163 mg, 0.337 mmol), HATU (128 mg 0.337 mmol) and DIEA (145 mg 1.12 mmol). The mixture was stirred at r.t. for 3 hrs and then extracted with ethyl acetate. The combined organic phases was washed with aqueous sodium chloride solution. After concentration under vacuum, the residue was purified by prep-HPLC to afford the titled compound (16.8 mg) as a yellow solid.

LCMS: (ES$^+$): m/z 893.3 [M+1]$^+$.

$^1$HNMR (400 MHz, CDCl$_3$): δ: 12.71 (s, 1H), 11.06 (s, 1H), 8.87 (s, 1H), 8.17 (m, 2H), 7.82 (d, J=13.6 Hz, 1H), 7.77-7.10 (m, 12H) 7.05 (br, 1H), 6.68 (br, 1H, 5.08-5.06 (m, 1H), 4.25 (br, 1H), 3.79-3.51 (m, 14H), 2.93-2.89 (m, 1H), 2.13-21.85 (m, 5H)

Example 3: Preparation of 5-((6-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)hexyl)oxy)-2-(2,6-dioxopiperidin-3-yl)isoindoline-1,3-dione (Compound 3)

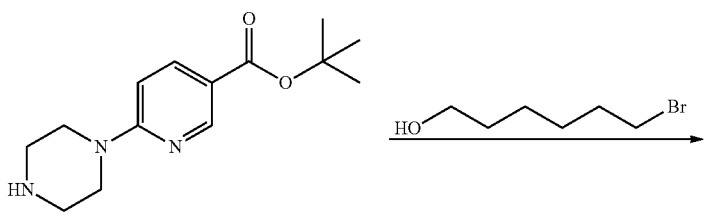

-continued
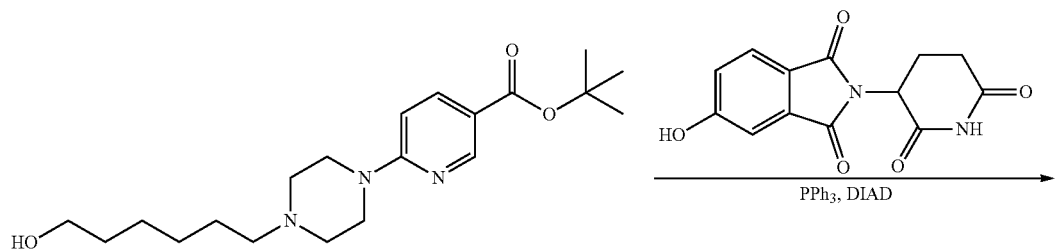
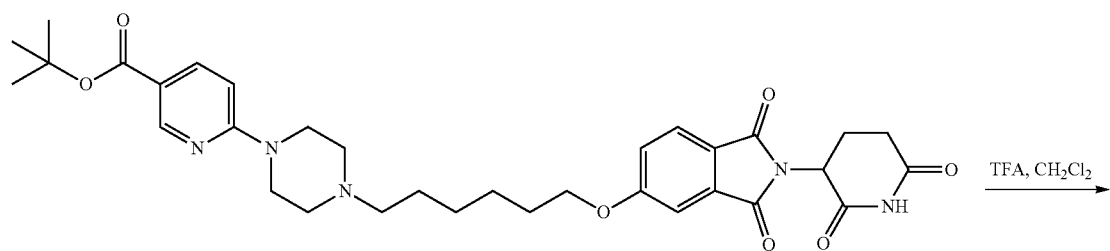
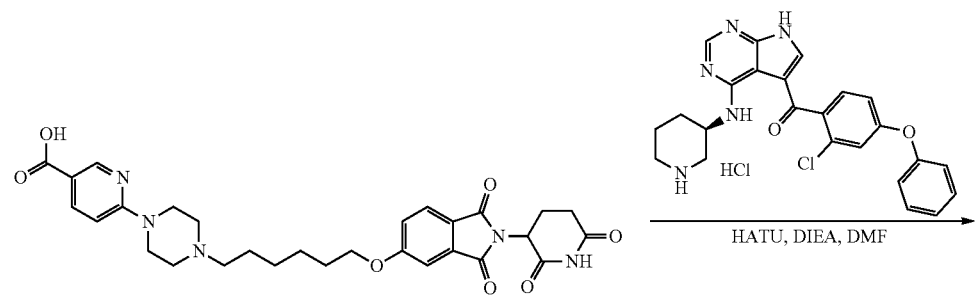
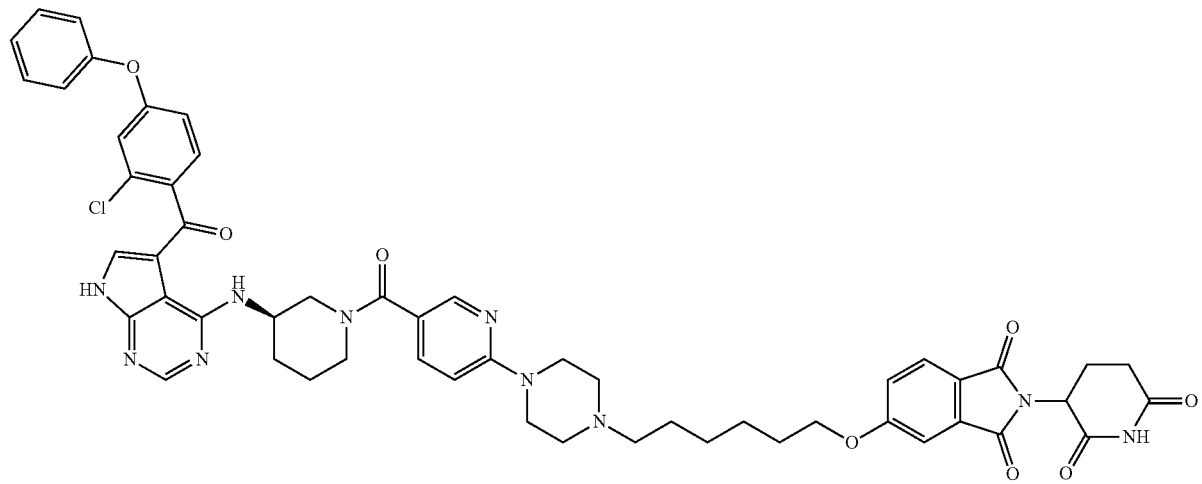

Compound 3 was prepared with the same procedure as described for compound 1 by replacing 7-bromoheptan-1-ol with 6-bromohexan-1-ol in step 3.

LCMS: m/z=993.4 [M]+.

$^1$HNMR (400 MHz, CDCl$_3$-d): δ9.04 (s, 1H), 8.36-8.30 (m, 2H), 7.77-7.65 (m, 2H), 7.41-7.32 (m, 5H), 7.22-7.18 (m, 2H), 7.10-7.07 (m, 3H), 6.95-6.93 (m, 1H), 6.54-6.50 (m, 1H), 4.96-4.95 (m, 1H), 4.37 (s, 1H), 4.10-4.06 (m, 4H), 3.57-3.42 (m, 6H), 2.90-2.78 (m, 3H), 2.49 (s, 4H), 2.35 (s, 2H), 2.18-2.15 (m, 2H), 2.00 (s, 3H), 1.83-1.51 (m, 10H).

Example 4: Preparation of 5-(3-(4-(5-((R)-3-((5-(2-chloro-4-phenoxybenzoyl)-7H-pyrrolo [2,3-d]pyrimidin-4-yl)amino)piperidine-1-carbonyl)pyridin-2-yl)piperazin-1-yl)propoxy)-2-(2,6-dioxopiperidin-3-yl)isoindoline-1,3-dione (Compound 4)

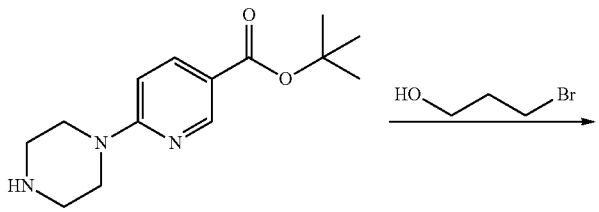

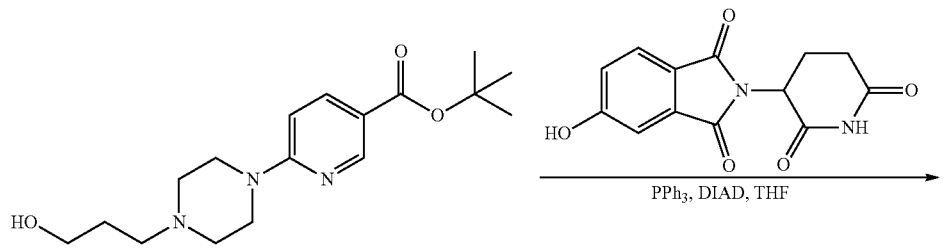

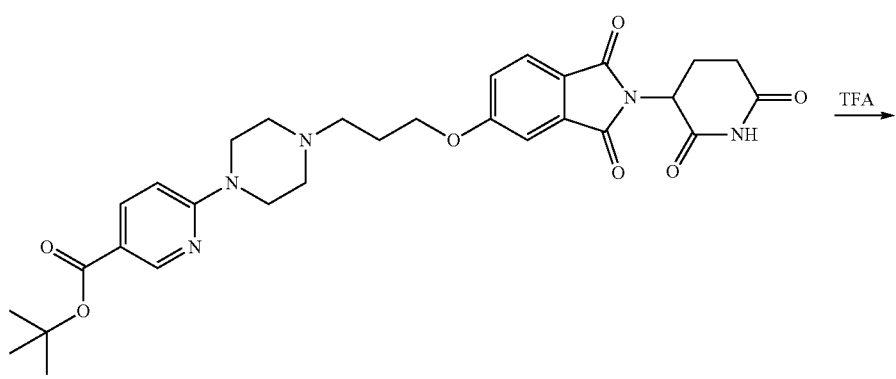

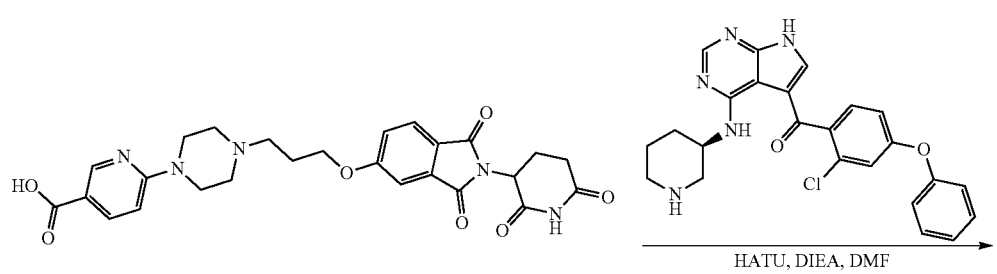

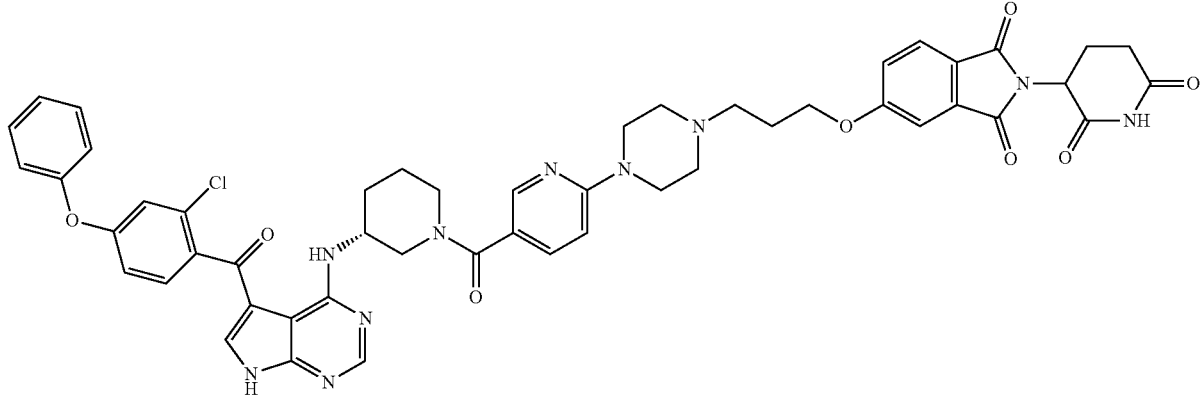

Compound 4 was prepared by the same procedure as described for Compound 1 by replacing 7-bromoheptan-1-ol with 3-bromopropan-1-ol in step 3.

LCMS: m/z=951.3 [M]+.

$^1$HNMR (400 MHz, CDCl$_3$-d): δ8.98-8.89 (m, 1H), 8.46-8.32 (m, 2H), 7.81-7.68 (m, 2H), 7.41-7.39 (m, 3H), 7.29-7.20 (m, 3H), 7.09-7.07 (m, 3H), 6.95-6.93 (m, 1H), 6.54-6.47 (m, 1H), 4.96-4.93 (m, 1H), 4.35-4.13 (m, 4H), 3.74-3.73 (m, 1H), 3.57 (s, 3H), 3.35-3.32 (m, 1H), 2.91-2.73 (m, 4H), 2.47 (s, 3H), 2.38-2.17 (m, 5H), 1.89-1.59 (m, 9H).

Example 5: Preparation of 5-(2-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)ethoxy)-2-(2,6-dioxopiperidin-3-yl)isoindoline-1,3-dione (Compound 5)

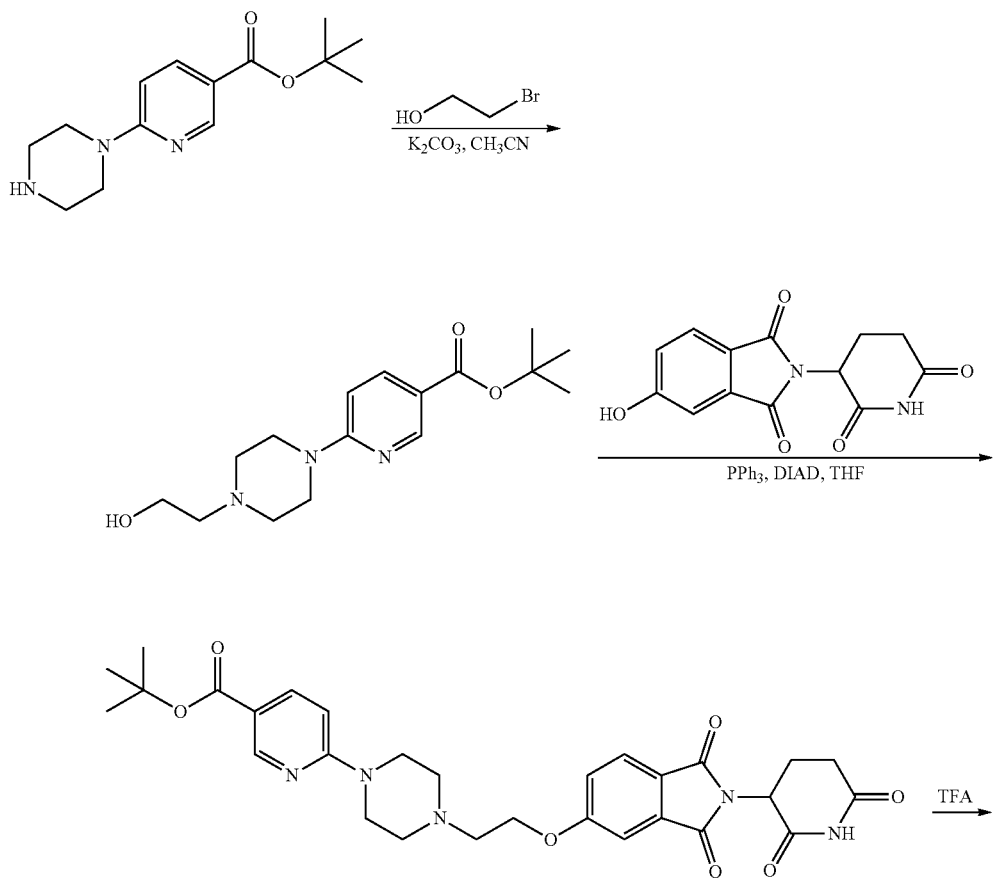

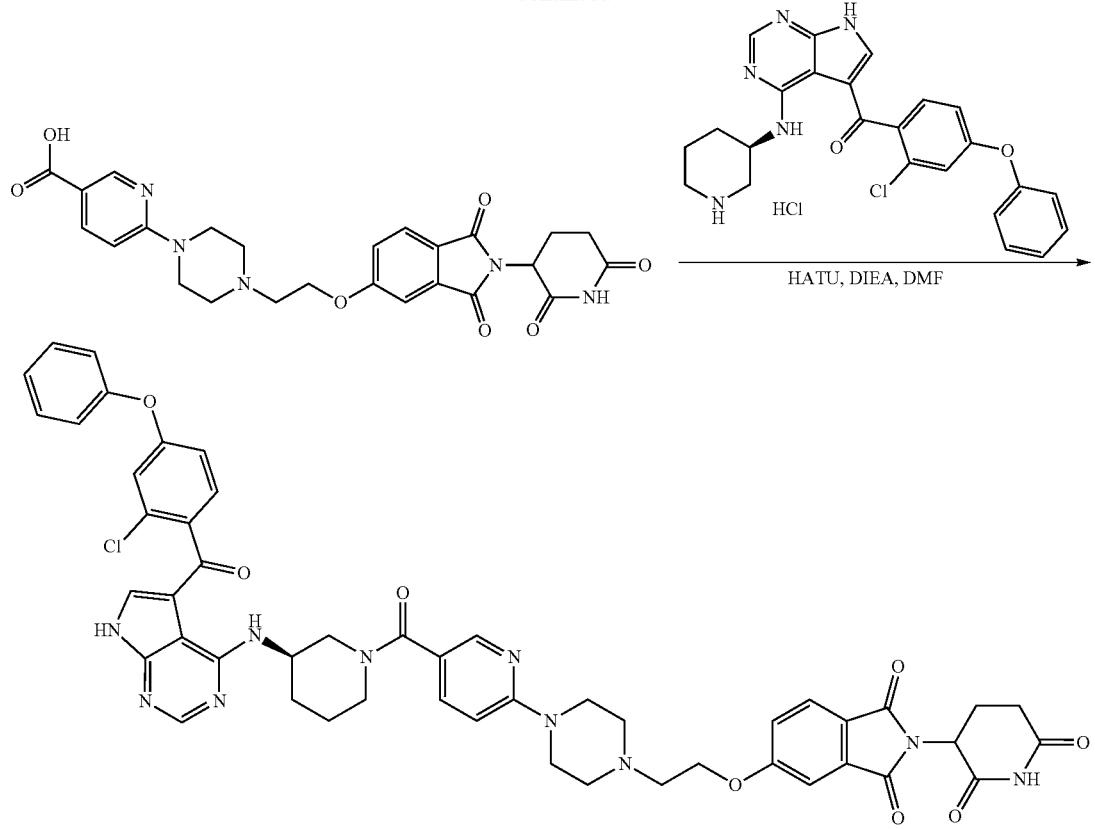

Step 1: Preparation of tert-butyl 6-(4-(2-hydroxyethyl)piperazin-1-yl)nicotinate To a solution of tert-butyl 6-(piperazin-1-yl) nicotinate (800 mg, 3.04 mmol) in 20 mL acetonitrile was added 2-bromoethanol (452 mg 3.65 mmol) and $K_2CO_3$ (839 mg 6.08 mmol). The mixture was stirred at 85° C. for 12 hrs. The mixture was diluted with ethyl acetate, and then filtered. The filtrated was concentrated to give tert-butyl 6-(4-(2-hydroxyethyl)piperazin-1-yl)nicotinate (760 mg, 78.9%) which was used as is in the next step.
LCMS: 308.2 [M+H]$^+$.

Step 2: Preparation of tert-butyl 6-(4-(2-((2-(2,6-dioxopiperidin-3-yl)-1,3-dioxoisoindolin-5-yl)oxy)ethyl)piperazin-1-yl)nicotinate To a solution of tert-butyl 6-(4-(2-hydroxyethyl)piperazin-1-yl)nicotinate (760 mg 2.47 mmol) in THF (10 mL) was added 2-(2,6-dioxopiperidin-3-yl)-5-hydroxyisoindoline-1,3-dione (813 mg, 2.97 mmol) and $PPh_3$ (1.01 g, 2.97 mmol) followed by DIAD (748 mg 3.70 mmol). The reaction was stirred at room temperature overnight. The reaction mixture was concentrated in vacuum. The residue was dissolved in ethyl acetate and wash with aqueous sodium chloride solution. The organics phase was concentrated to dryness and the residue was purified by silica gel column chromatography (DCM/MeOH=20/1) to give tert-butyl 6-(4-(2-((2-(2,6-dioxopiperidin-3-yl)-1,3-dioxoisoindolin-5-yl)oxy)ethyl)piperazin-1-yl)nicotinate (130 mg, 87.1%). LCMS: 564.3 [M+H]$^+$.

Step 3: Preparation of 6-(4-(2-((2-(2,6-dioxopiperidin-3-yl)-1,3-dioxoisoindolin-5-yl)oxy)ethyl)piperazin-1-yl)nicotinic acid The solution of tert-butyl 6-(4-(2-((2-(2,6-dioxopiperidin-3-yl)-1,3-dioxoisoindolin-5-yl)oxy)ethyl)piperazin-1-yl) nicotinate (130 mg, 0.23 mol) in DCM/TFA(3:1) was stirred at room temperature for 1 hr. After concentration under vacuum, 6-(4-(2-((2-(2,6-dioxopiperidin-3-yl)-1,3-dioxoisoindolin-5-yl)oxy)ethyl)piperazin-1-yl)nicotinic acid (120 mg) was obtained as a yellow oil and used as is in the next step. LCMS: 508.1 [M+H]$^+$.

Step 4: Preparation of 5-(2-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl) piperazin-1-yl)ethoxy)-2-(2,6-dioxopiperidin-3-yl) isoindoline-1,3-dione To a solution of 6-(4-(2-((2-(2,6-dioxopiperidin-3-yl)-1, 3-dioxoisoindolin-5-yl)oxy)ethyl)piperazin-1-yl)nicotinic acid (120 mg 0.236 mmol) in DMF (30 mL) was added (R)-(2-chloro-4-phenoxyphenyl)(4-(piperidin-3-ylamino)-7H-pyrrolo[2,3-d]pyrimidin-5-yl)methanone (137 mg, 0.283 mmol), HATU (90 mg 0.283 mmol) and DIEA (121 mg 0.944 mmol). The mixture was stirred at r.t. for 3 hrs and then extracted with ethyl acetate. The combined organic phases was washed with aqueous sodium chloride solution. After concentration under vacuum, the residue was purified by prep-HPLC to afford the titled compound (19 mg, 9%) as a yellow solid. LC-MS: (ES$^+$): m/z 940.3 [M+1]$^+$.
$^1$HNMR (400 MHz, CDCl$_3$): δ: 8.99 (s, 1H), 8.35 (s, 1H), 8.29 (s, 1H) 7.77 (d, J=8.4 Hz, 1H), 7.65 (s, 1H) 7.49-7.39

(m, 4H), 7.30 (s, 1H), 7.29-7.10 (s, 2H) 7.07-7.07 (m, 2H), 6.95 (d, J=1.6 Hz, 1H), 6.47 (s, 1H), 5.36-5.34 (m, 1H), 4.97-4.94 (m, 1H), 4.31 (s, 2H), 4.15-4.06 (m, 1H), 3.57 (s, 6H), 2.86 (s, 4H), 2.63 (s, 4H), 2.25-2.12 (m, 2H), 2.08-2.01 (m, 2H), 1.92 (s, 1H), 1.85 (s, 1H)
Example 6: Preparation of 5-((5-(4-(5-((R)-3-((5-(2-chloro-4-phenoxybenzoyl)-7H-pyrrolo [2,3-d]pyrimidin-4-yl)amino)piperidine-1-carbonyl)pyridin-2-yl)piperazin-1-yl)pentyl)oxy)-2-(2,6-dioxopiperidin-3-yl)isoindoline-1,3-dione (Compound 6)
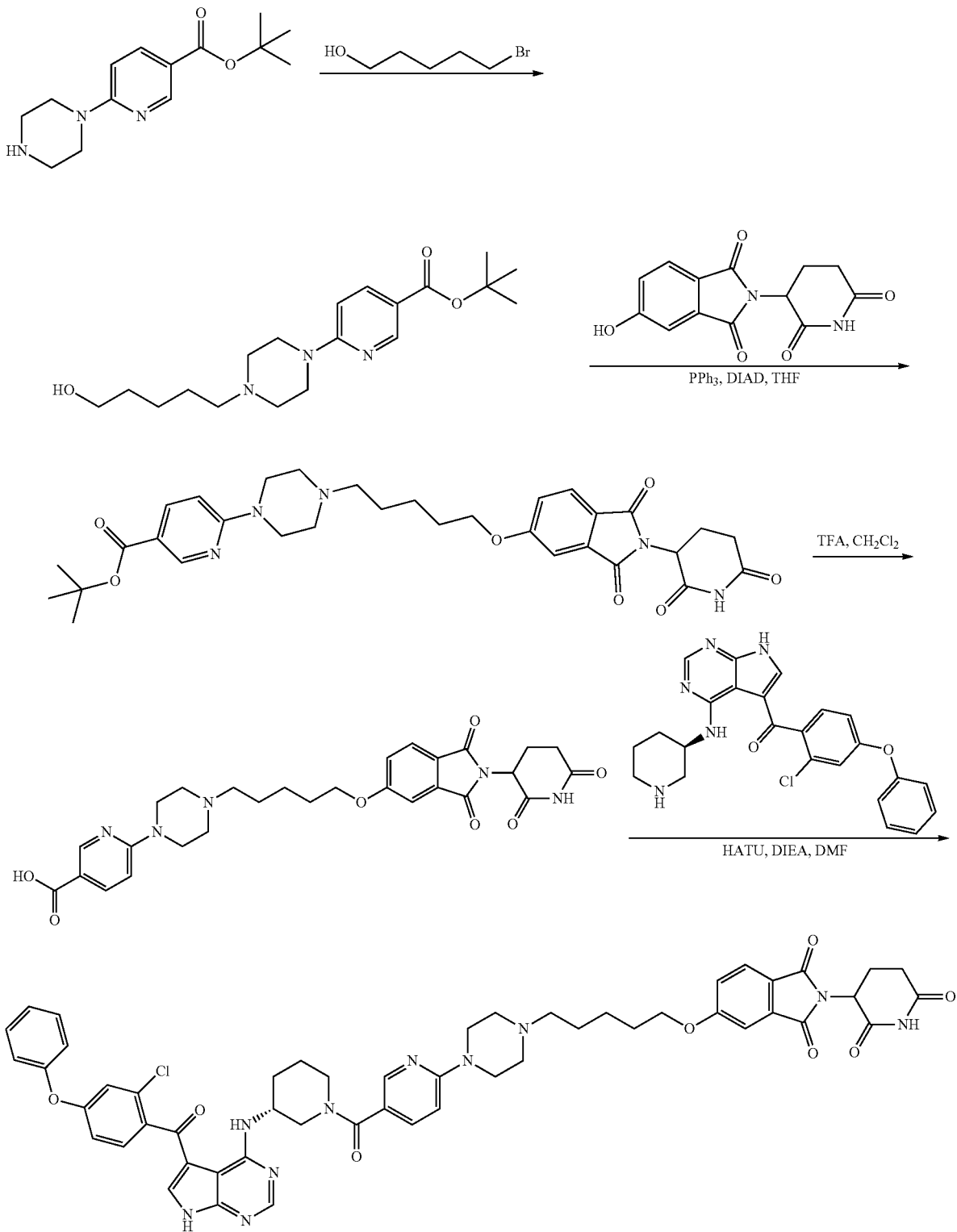

Compound 6 was prepared by the same procedure as described for compound 1 by replacing 7-bromoheptan-1-ol with 5-bromopentan-1-ol in step 3.

LCMS: m/z=979.4 [M]+.

¹HNMR (400 MHz, CDCl₃-d): δ9.06 (s, 1H), 8.36-8.30 (m, 2H), 7.77-7.64 (m, 2H), 7.43-7.38 (m, 3H), 7.33-7.31 (m, 2H), 7.23-7.15 (m, 2H), 7.10-7.06 (m, 3H), 6.95-6.93 (m, 1H), 6.51-6.48 (m, 1H), 4.97-4.93 (m, 1H), 4.38 (s, 1H), 4.12-4.07 (m, 3H), 3.56-3.47 (m, 6H), 2.90-2.73 (m, 3H), 2.49 (s, 4H), 2.36-2.35 (m, 2H), 2.19-2.01 (m, 4H), 1.88-1.50 (m, 10H).

Example 7: Preparation of 5-(4-(6-((R)-3-((5-(2-chloro-4-phenoxybenzoyl)-7H-pyrrolo[2,3-d]pyrimidin-4-yl)amino)piperidin-1-yl)-6-oxohexyl)piperazin-1-yl)-2-(2,6-dioxopiperidin-3-yl)isoindoline-1,3-dione (Compound 7)

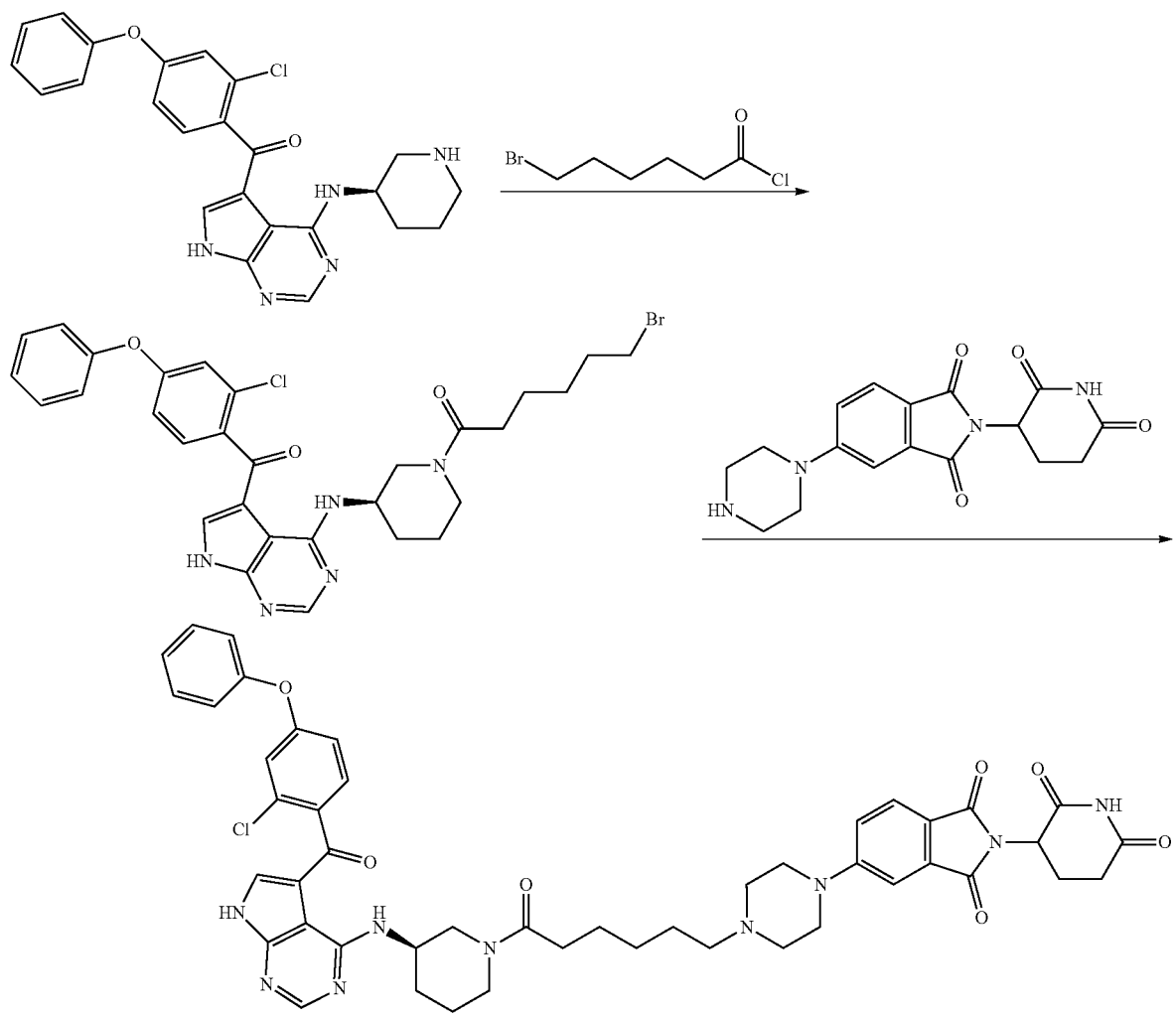

Step 1: Preparation of (R)-6-bromo-1-(3-((5-(2-chloro-4-phenoxybenzoyl)-7H-pyrrolo[2,3-d]pyrimidin-4-yl)amino)piperidin-1-yl)hexan-1-one The mixture of 6-bromohexanoyl chloride (45 mg, 0.21 mmol), (R)-(2-chloro-4-phenoxyphenyl)(4-(piperidin-3-ylamino)-7H-pyrrolo[2,3-d]pyrimidin-5-yl)methanone (94 mg, 0.21 mmol) and DIEA (136 mg, 1 mmol) in DCM (5 mL) was stirred for 1 hour at room temperature. The reaction mixture was quenched by adding water (5 mL). The organic phase was collected and concentrated in vacuum to give a crude product. The crude product was purified by Prep-TLC (DCM/MeOH=10:1) to give the desired product as a white solid (150 mg, 98%) LC/MS: 624.5 [M+H]+.

Step 2: Preparation of 5-(4-(6-((R)-3-((5-(2-chloro-4-phenoxybenzoyl)-7H-pyrrolo[2,3-d]pyrimidin-4-yl)amino)piperidin-1-yl)-6-oxohexyl)piperazin-1-yl)-2-(2,6-dioxopiperidin-3-yl)isoindoline-1,3-dione The mixture of (R)-6-bromo-1-(3-((5-(2-chloro-4-phenoxybenzoyl)-7H-pyrrolo[2,3-d]pyrimidin-4-yl)amino)piperidin-1-yl)hexan-1-one (150 mg, 0.20 mmol), 2-(2,6-dioxopiperidin-3-yl)-5-(piperazin-1-yl)isoindoline-1,3-dione (90.9 mg, 0.24 mmol), K₂CO₃ (165.9 mg, 1.2 mmol) and KI (7.9 mg, 0.05 mmol) in DMF (3 mL) was stirred at 60° C. for 16 hours. The reaction mixture was filtered, and the solution was concentrated in vacuum. The residue was purified by Prep-TLC (DCM/MeOH=10:1) to give the desired product as a white solid (37 mg, 19.8%) LC/MS: 885.5 [M+H]+.

¹H NMR (400 MHz, DMSO) δ 12.78 (br, 1H), 11.11 (s, 1H), 8.92-8.89 (m, 1H), 8.30-8.25 (m, 1H), 7.71-7.61 (m, 2H), 7.59-7.52 (m, 1H), 7.51-7.39 (m, 2H), 7.37 (s, 1H), 7.32-7.23 (m, 2H), 7.22-7.12 (m, 3H), 7.07-6.96 (m, 1H), 5.09 (dd, J=12.9, 5.3 Hz, 1H), 4.31-4.13 (m, 1H), 3.89-3.71 (m, 1H), 3.67-3.37 (m, 6H), 2.96-2.81 (m, 1H), 2.70-2.54 (m, 2H), 2.49-2.17 (m, 5H), 2.03 (d, J=4.9 Hz, 2H), 1.95-1.67 (m, 3H), 1.65-1.41 (m, 4H), 1.39-1.02 (m, 5H), 1.00-0.70 (m, 1H).

Example 8: Preparation of 5-(4-(5-((R)-3-((5-(2-chloro-4-phenoxybenzoyl)-7H-pyrrolo[2,3-d]pyrimidin-4-yl)amino)piperidin-1-yl)pentyl)piperazin-1-yl)-2-(2,6-dioxopiperidin-3-yl)isoindoline-1,3-dione (Compound 8)

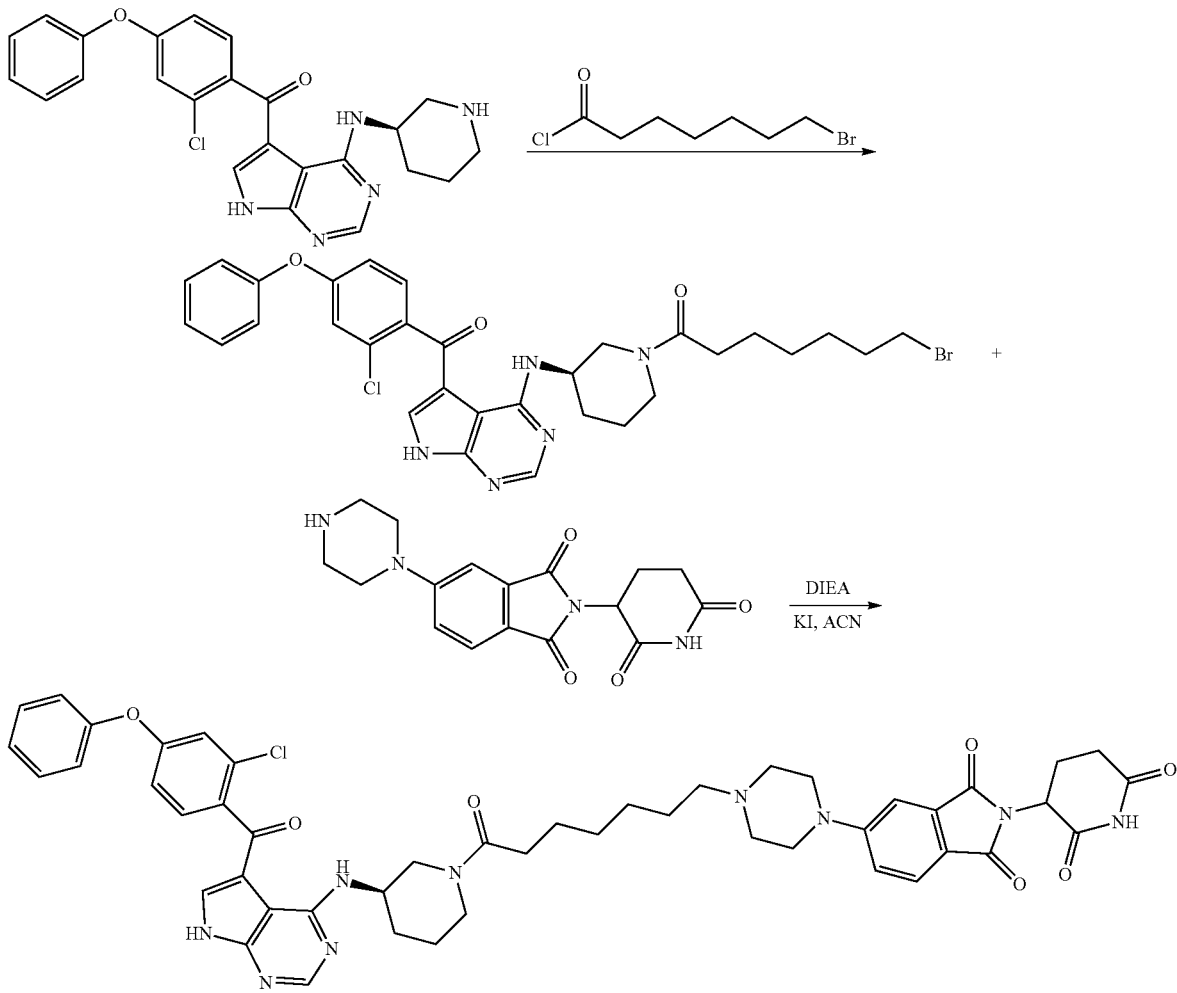

Step 1: Preparation of (R)-7-bromo-1-(3-((5-(2-chloro-4-phenoxybenzoyl)-7H-pyrrolo[2,3-d]pyrimidin-4-yl)amino)piperidin-1-yl)heptan-1-one To a solution of 7-bromoheptanoyl chloride (60 mg, 0.26 mmol) in DCM (5 mL) was added (R)-(2-chloro-4-phenoxyphenyl)(4-(piperidin-3-ylamino)-7H-pyrrolo[2,3-d]pyrimidin-5-yl)methanone (145.8 mg, 0.26 mmol) and N,N-diisopropylethylamine (335.4 mg, 2.6 mmol). The reaction mixture was stirred at room temperature overnight. The mixture was evaporated under vacuum and purified by Prep-TLC with MeOH:DCM=1:10 to give the titled compound (45 mg, 27%) as a white oil. LC/MS: 639.6 [M+H]⁺.

Step 2: Preparation of 5-(4-(5-((R)-3-((5-(2-chloro-4-phenoxybenzoyl)-7H-pyrrolo[2,3-d]pyrimidin-4-yl)amino)piperidin-1-yl)pentyl)piperazin-1-yl)-2-(2,6-dioxopiperidin-3-yl)isoindoline-1,3-dione To a solution of (R)-7-bromo-1-(3-((5-(2-chloro-4-phenoxybenzoyl)-7H-pyrrolo[2,3-d]pyrimidin-4-yl)amino)piperidin-1-yl)heptan-1-one (45 mg, 0.07 mmol) and 2-(2,6-dioxopiperidin-3-yl)-5-(piperazin-1-yl)isoindoline-1,3-dione (23 mg, 0.06 mmol) in acetonitrile stirred at room temperature was added N,N-Diisopropylethylamine (27.09 mg, 0.21 mmol) and KI (1.2 mg, 0.007 mmol). The reaction mixture was stirred at room temperature overnight. The mixture was evaporated in vacuum and purified by Prep-TLC with MeOH:DCM=1:10 to give the title compound (32 mg, 50.8%). LC/MS: 899.3 [M+H]⁺.

¹H NMR (400 MHz, DMSO) δ 12.81 (br, 1H), 11.10 (s, 1H), 8.95-8.85 (m, 1H), 8.32-8.25 (m, 1H), 7.70-7.61 (m, 2H), 7.59-7.53 (m, 1H), 7.51-7.49 (m, 2H), 7.40-7.25 (m, 3H), 7.24-7.15 (m, 3H), 7.12-7.03 (m, 1H), 5.14-5.07 (m, 1H), 4.27-4.16 (m, 1H), 3.82-3.74 (m, 1H), 3.62-3.41 (m, 4H), 3.29-3.27 (m, 2H), 2.95-2.85 (m, 1H), 2.70-2.62 (m, 2H), 2.45-2.12 (m, 5H), 2.08-1.98 (m, 2H), 1.90-1.70 (m, 3H), 1.65-1.40 (m, 4H), 1.31-1.10 (m, 7H), 0.95-0.82 (m, 1H).

Example 9: 5-(4-((5-((R)-3-((5-(2-chloro-4-phenoxybenzoyl)-7H-pyrrolo[2,3-d]pyrimidin-4-yl)amino)piperidine-1-carbonyl)pyridin-2-yl)methyl)piperazin-1-yl)-2-(2,6-dioxopiperidin-3-yl)isoindoline-1,3-dione (Compound 9)

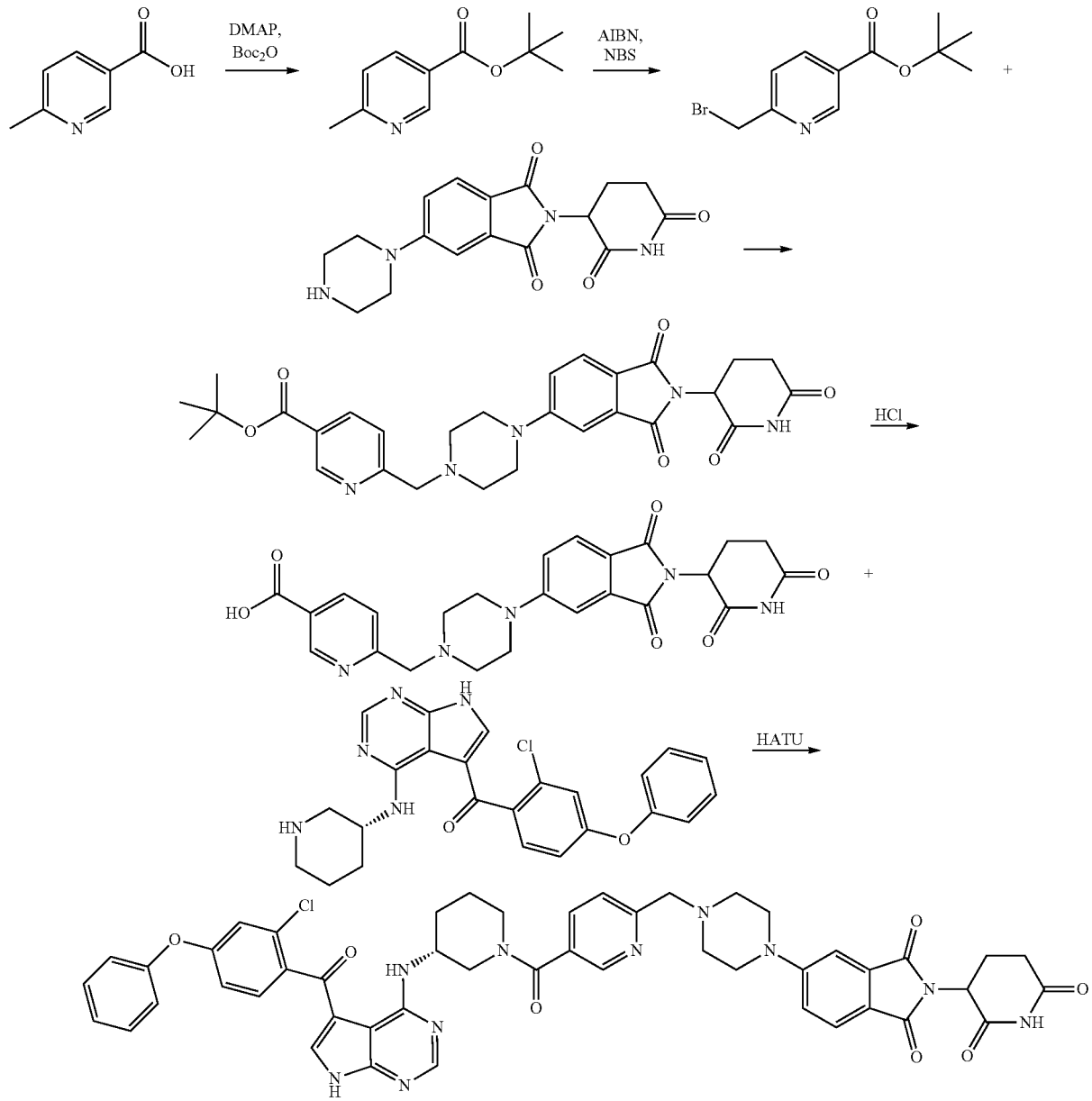

Step 1: Preparation of tert-butyl 6-methylnicotinate

To a solution of 6-methylnicotinic acid (5.2 g, 37.9 mmol) in toluene (150 mL) was added DMAP (520 mg, 3.79 mmol) and Boc₂O (12.37 g, 56.9 mmol). The mixture was stirred at 110° C. for 12 hours. After cooling to room temperature, the mixture was diluted with ethyl acetate and extracted with aqueous sodium chloride solution. The combined organic phase was concentrated under vacuum and the residue was purified by silica gel column chromatography (eluting with 3% EtOAc in petroleum ether) to give the titled product (5.09 g, 69%). LCMS: m/z 194.2 [M+1]⁺.

Step 2: Preparation of tert-butyl 6-(bromomethyl)nicotinate

To a solution of tert-butyl 6-methylnicotinate (590 mg, 3.05 mmol) in carbon tetrachloride (10 mL) was added NBS (440 mg, 2.48 mmol) and AIBN (59 mg 0.3 mmol). The mixture was stirred at 70° C. for 12 hr and then diluted with ethyl acetate. After extraction with aqueous sodium chloride solution, the combined organic phase was concentrated under vacuum. The residue was purified by silica gel column chromatography (eluting with 3% EtOAc in petroleum ether) to give the titled product (320 mg, 38.5%)

Step 3: Preparation of tert-butyl 6-((4-(2-(2,6-dioxopiperidin-3-yl)-1,3-dioxoisoindolin-5-yl)piperazin-1-yl)methyl)nicotinate To a solution of 2-(2,6-dioxopiperidin-3-yl)-5-(piperazin-1-yl)isoindoline-1,3-dione (520 mg, 1.52 mmol) in CH$_3$CN (10 mL) was added DIEA (770 mg 5.96 mmol) and the mixture was stirred at room temperature for 20 min. tert-Butyl 6-(bromomethyl)nicotinate (316 mg, 1.16 mmol) was added to the reaction mixture and stirred at room temperature for 12 hrs. The reaction was quenched with water and extracted with EtOAc (100 mL×3). The combined organic phase was washed with brine and dried over Na$_2$SO$_4$. After filtration, the organic solvent was removed under vacuum. The residue was purified by column chromatography (DCM/MeOH=50/1) to afford tert-butyl 6-((4-(2-(2,6-dioxopiperidin-3-yl)-1,3-dioxoisoindolin-5-yl) piperazin-1-yl)methyl) nicotinate (480 mg, 59%). LCMS: m/z 534.3 [M+1]$^+$.

Step 4: Preparation of 6-((4-(2-(2,6-dioxopiperidin-3-yl)-1,3-dioxoisoindolin-5-yl)piperazin-1-yl) methyl)nicotinic acid tert-Butyl 6-((4-(2-(2,6-dioxopiperidin-3-yl)-1,3-dioxoisoindolin-5-yl) piperazin-1-yl)methyl) nicotinate (480 mg, 0.9 mmol) was dissolved in 4N HCl/dioxane (30 mL) and stirred at room temperature for 5 hours. The mixture was concentrated under vacuum to afford the titled product (470 mg) which was used in the next step without further purification.
LCMS: (ES$^+$): m/z 478.2 [M+1]$^+$.

Step 5: Preparation of 5-(4-((5-((R)-3-((5-(2-chloro-4-phenoxybenzoyl)-7H-pyrrolo[2,3-d]pyrimidin-4-yl)amino)piperidine-1-carbonyl)pyridin-2-yl)methyl) piperazin-1-yl)-2-(2,6-dioxopiperidin-3-yl) isoindoline-1,3-dione To a solution of 6-((4-(2-(2,6-dioxopiperidin-3-yl)-1,3-dioxoisoindolin-5-yl)piperazin-1-yl)methyl)nicotinic acid (220 mg, 0.46 mmol) in DMF (5 mL) was added (R)-(2-chloro-4-phenoxyphenyl)(4-(piperidin-3-ylamino)-7H-pyrrolo[2,3-d]pyrimidin-5-yl)methanone (240 mg, 536 mmol), HOBT (120 mg 0.88 mmol), EDCI (170 mg 0.89 mmol) and DIEA (350 mg, 2.713 mmol). The mixture was stirred at room temperature for 12 hrs. The mixture was diluted with water and extracted with EtOAc (100 mL×3). The combined organic phase was washed with brine and dried over Na$_2$SO$_4$. After filtration, the solvent was removed by rotary evaporation and the residue was purified by prep-HPLC to afford the titled product (27 mg, 6%) as a yellow solid. LCMS: m/z 454.2 [M+1]$^+$.
$^1$HNMR (400 MHz, CDCl$_3$): δ: 8.91 (s, 1H), 8.34 (s, 1H) 8.68 (d, J=8.4 Hz, 1H) 8.20 (d, J=8 Hz, 1H) 7.85-7.61 (m, 2H) 7.45-7.35 (m, 5H) 7.31 (s, 2H) 7.29-7.11 (m, 2H) 7.10 (s, 1H) 7.09-7.01 (m, 3H) 6.96 (d, J=8.0 Hz, 1H) 5.98-5.91 (m, 1H) 4.21 (s, 1H) 4.11 (s, 1H) 4.12-3.89 (m, 1H) 3.72 (s, 3H) 3.35 (s, 6H) 2.92-2.71 (m, 4H) 2.55 (s, 3H) 2.27-2.15 (m, 1H) 2.14-2.09 (m, 3H)

Example 10: Preparation of 5-(4-((1-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperidin-4-yl)methyl)piperazin-1-yl)-2-(2,6-dioxopiperidin-3-yl)isoindoline-1,3-dione
(Compound 10)

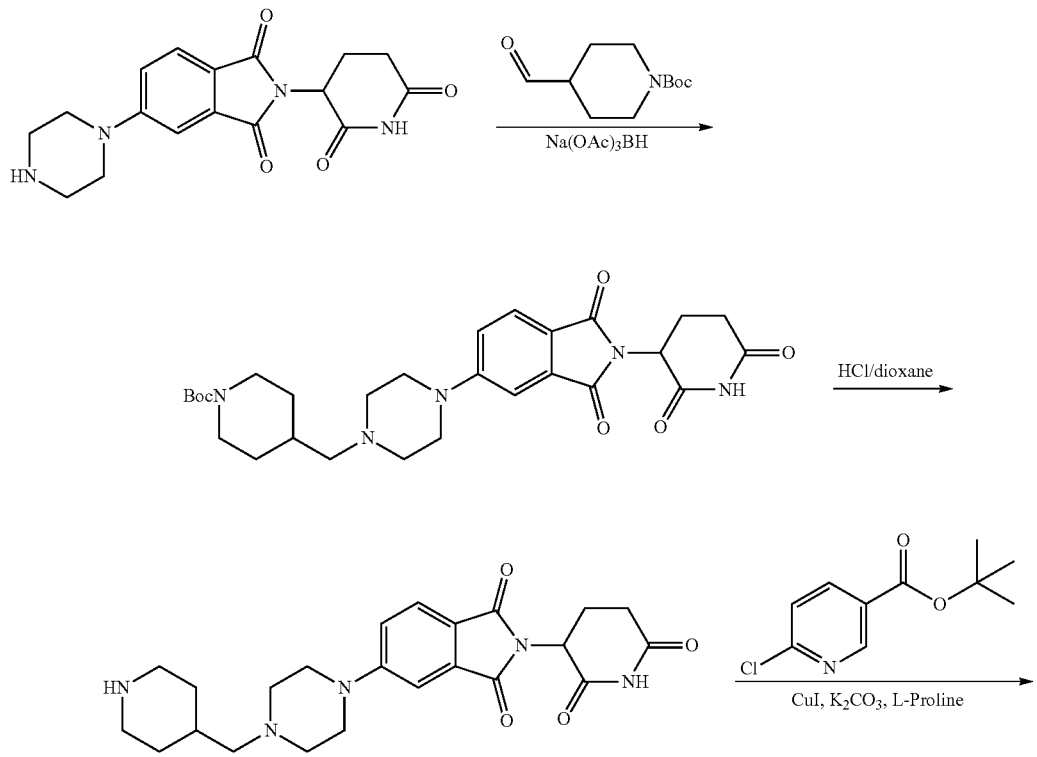

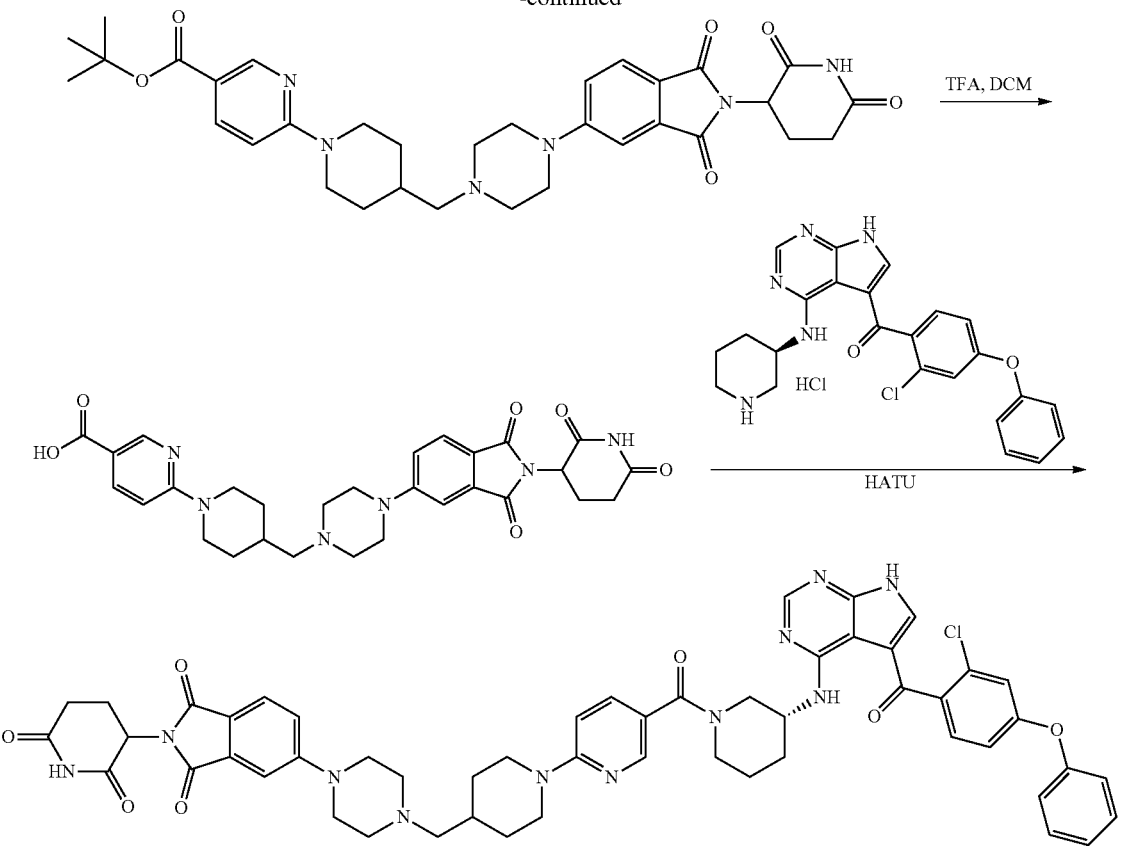

Step 1: Preparation of tert-butyl 4-((4-(2-(2,6-di-oxopiperidin-3-yl)-1,3-dioxoisoindolin-5-yl) piper-azin-1-yl)methyl)piperidine-1-carboxylate To a solution of 2-(2,6-dioxopiperidin-3-yl)-5-(piperazin-1-yl)isoindoline-1,3-dione (540 mg, 1.578 mmol) in DCM (20 mL) was added tert-butyl 4-formylpiperidine-1-carboxylate (350 mg, 1.643 mmol) and sodium triacetoxyboronhydride (990 mg, 4.691 mmol). The mixture was stirred at room temperature overnight. The reaction mixture was extracted with ethyl acetate (40 mL×4) and washed with aqueous sodium chloride solution. The organic phase was concentrated under vacuum and the residue was purified by column chromatography with DCM/MeOH 100:1 to 50:1 to give the titled compound (469 mg, 55.1%) LCMS: (ES$^+$): m/z 440 [M+1-Boc]$^+$.

Step 2: Preparation of 2-(2,6-dioxopiperidin-3-yl)-5-(4-(piperidin-4-ylmethyl)piperazin-1-yl)isoindo-line-1,3-dione tert-Butyl 4-((4-(2-(2,6-dioxopiperidin-3-yl)-1,3-dioxoi-soindolin-5-yl)piperazin-1-yl) methyl)piperidine-1-car-boxylate (400 mg, 0.74 mmol) was dissolved in HCl/dioxane (10 mL) and the mixture was stirred at room temperature for 1.5 hr. The solid was collected by filtration to give the titled compound (450 mg) as a HCl salt. LCMS: 440.2 [M+H]$^+$.

Step 3: Preparation of tert-butyl 6-(4-((4-(2-(2,6-dioxopiperidin-3-yl)-1,3-dioxoisoindolin-5-yl) piper-azin-1-yl)methyl)piperidin-1-yl)nicotinate To a solution of 2-(2,6-dioxopiperidin-3-yl)-5-(4-(piperidin-4-ylmethyl) piperazin-1-yl)isoindoline-1,3-dione (350 mg, 0.797 mmol) in DMSO (20 mL) was added tert-butyl 6-chloronicotinate (169 mg, 0.793 mmol), L-Proline (70 mg, 10%, K$_2$CO$_3$ (220 mg, 1.59 mmol) and CuI (35 mg, 10%). The mixture was stirred at 90° C. for 12 hr. The mixture was extracted with EtOAc (50 mL×4) and the organic phase was washed with aqueous sodium chloride (40 mL×3). The organic phase was concentrated under vacuum and the residue was purified by column chromatography (DCM/MeOH 20:1) to give the titled compound (280 mg, 71.4%) as a yellow oil. LCMS: (ES$^+$): m/z 617.3 [M+H]$^+$.

Step 4: Preparation of 6-(4-((4-(2-(2,6-dioxopiperi-din-3-yl)-1,3-dioxoisoindolin-5-yl)piperazin-1-yl) methyl)piperidin-1-yl)nicotinic acid tert-Butyl 6-(4-((4-(2-(2,6-dioxopiperidin-3-yl)-1,3-di-oxoisoindolin-5-yl)piperazin-1-yl) methyl)piperidin-1-yl) nicotinate (280 mg, 0.133 mmol) was dissolved in DCM (6 mL) and TFA (2 mL). The mixture was stirred at room temperature for 2 hrs. After evaporation of the solvent under vacuum, the residue was dissolved in DCE and then concentrated to dry under vacuum. The residue was azeotroped with DCE three times to give the titled compound (340 mg) as a light yellow oil. LCMS: (ES$^+$): m/z 562.2 [M+1]$^+$.

Step 5: Preparation of 5-(4-((1-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperidin-4-yl)methyl)piperazin-1-yl)-2-(2,6-dioxopiperidin-3-yl)isoindoline-1,3-dione To a solution of 6-(4-((4-(2-(2,6-dioxopiperidin-3-yl)-1,3-dioxoisoindolin-5-yl) piperazin-1-yl)methyl)piperidin-1-yl)nicotinic acid (110 mg, 0.196 mmol) in DMF (20 mL) was added (R)-(2-chloro-4-phenoxyphenyl)(4-(piperidin-3-ylamino)-7H-pyrrolo[2,3-d]pyrimidin-5-yl)methanone (70 mg, 0.156 mmol) and DIEA (300 mg, 2.34 mmol) followed by the addition of HATU (89 mg, 0.234 mmol) at room temperature. The mixture was stirred at room temperature for 2 hr. After extraction with EtOAc (30 mL×4) and washed with brine (20 mL×3), the organic phase was concentrated under vacuum. The residue was purified by pre-HPLC to give the titled product (18.8 mg) as a yellow solid. LCMS: (ES+): m/z 992.3[M+1]+, ¹HNMR (400 MHz, CDCl₃): δ: 10.20 (s, 1H), 8.34 (s, 1H), 8.18 (s, 1H), 8.06 (s, 1H), 7.77 (d, J=8.4 Hz, 1H), 7.22-7.12 (m, 5H), 7.11-6.19 (m, 2H), 5.35-5.33 (m, 1H), 4.97-4.93 (m, 1H), 4.51-4.21 (m, 3H), 3.91-3.85 (m, 3H), 3.76 (s, 5H), 3.41-3.03 (m, 8H), 2.91-2.71 (m, 4H), 1.71-1.59 (m, 1H), 1.54 (d, J=6.8 Hz, 4H), 1.45 (s, 2H).

Example 11: Preparation of 5-(4-(5-((R)-3-((5-(2-chloro-4-phenoxybenzoyl)-7H-pyrrolo[2,3-d]pyrimidin-4-yl)amino)piperidin-1-yl)-5-oxopentyl)piperazin-1-yl)-2-(2,6-dioxopiperidin-3-yl)isoindoline-1,3-dione (Compound 11)

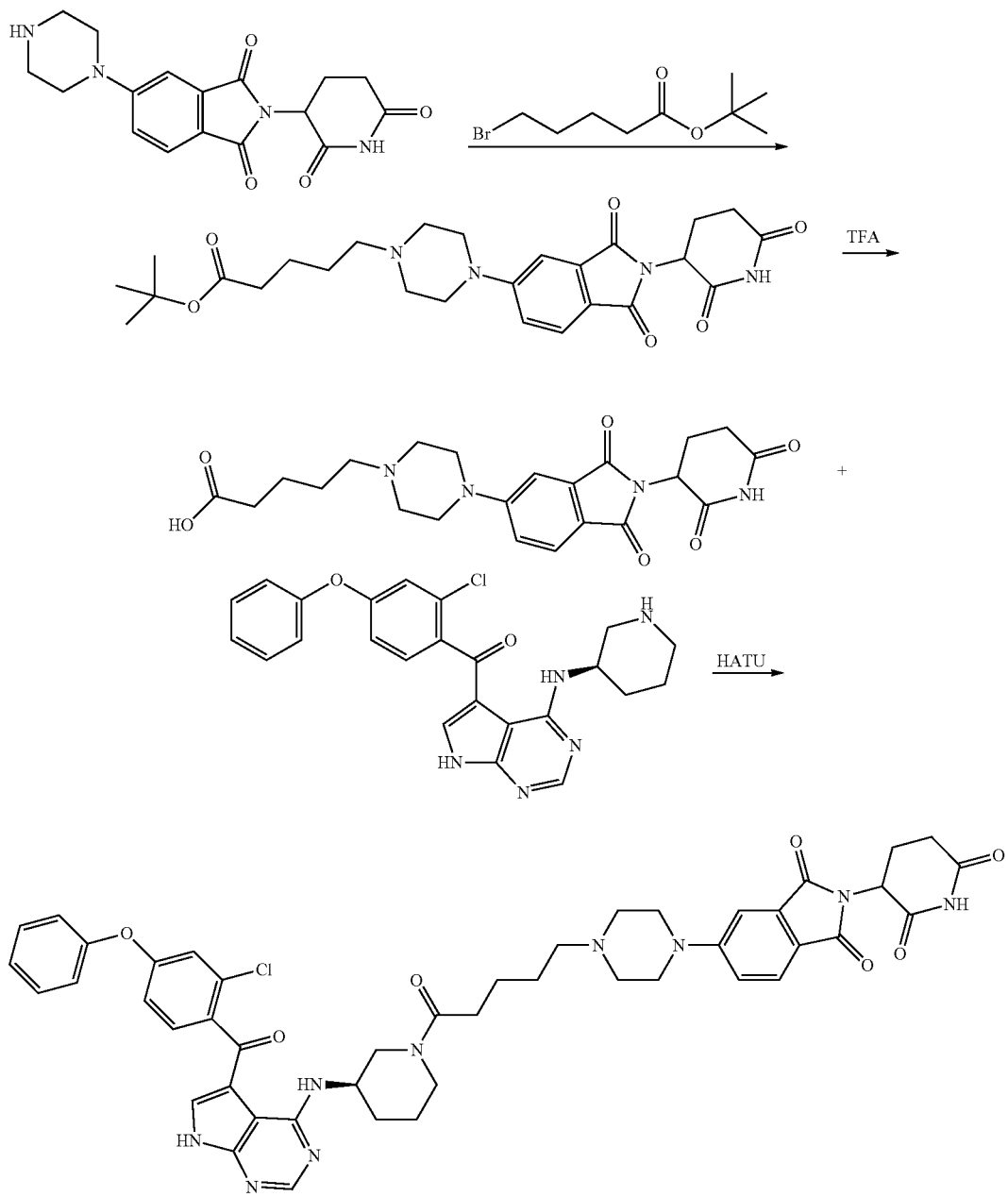

Step 1: Preparation of tert-butyl 5-(4-(2-(2,6-dioxopiperidin-3-yl)-1,3-dioxoisoindolin-5-yl)piperazin-1-yl)pentanoate To a solution of tert-butyl 5-bromopentanoate (47 mg, 0.2 mmol) in ACN (10 mL) was added 2-(2,6-dioxopiperidin-3-yl)-5-(piperazin-1-yl)isoindoline-1,3-dione (75.7 mg, 0.2 mmol) and N, N-diisopropylethylamine (38.7 mg, 0.3 mmol). The reaction mixture was stirred at 60° C. overnight. The mixture was evaporated under vacuum and purified by Prep-TLC with MeOH:DCM=1:10 to give the titled compound (60 mg, 60.1%) as a yellow solid.
LC/MS: 498.8 [M+H]$^+$.

Step 2: Preparation of 5-(4-(2-(2,6-dioxopiperidin-3-yl)-1,3-dioxoisoindolin-5-yl)piperazin-1-yl)pentanoic acid To a solution of tert-butyl 5-(4-(2-(2,6-dioxopiperidin-3-yl)-1,3-dioxoisoindolin-5-yl)piperazin-1-yl)pentanoate (40 mg, 0.08 mmol) in DCM (10 mL) was added TFA (2 mL). The reaction was stirred at room temperature for 4 hours. The solution was concentrated in vacuum to give a crude product (35 mg, yield: 100%) as a yellow solid. LC/MS: 442.7 [M+H]$^+$.

Step 3: Preparation of 5-(4-(5-((R)-3-((5-(2-chloro-4-phenoxybenzoyl)-7H-pyrrolo[2,3-d]pyrimidin-4-yl)amino)piperidin-1-yl)-5-oxopentyl)piperazin-1-yl)-2-(2,6-dioxopiperidin-3-yl)isoindoline-1,3-dione To a solution of 5-(4-(2-(2,6-dioxopiperidin-3-yl)-1,3-dioxoisoindolin-5-yl)piperazin-1-yl)pentanoic acid (35 mg, 0.08 mmol) and (R)-(2-chloro-4-phenoxyphenyl)(4-(piperidin-3-ylamino)-7H-pyrrolo[2,3-d]pyrimidin-5-yl)methanone (44.88 mg, 0.08 mmol) in DMF (10 mL) stirred under nitrogen at room temperature was added HATU (36.48 mg, 0.096 mmol) and DIEA (15.48 mg, 0.12 mmol). The reaction mixture was stirred at room temperature overnight. The solvent was removed under vacuum to give a crude product. The crude product was purified by Prep-TLC with MeOH:DCM=1:10 to give the title compound (40 mg, 57.4%). LC/MS: 871.3 [M+H]$^+$.

$^1$H NMR (400 MHz, DMSO) δ 12.84 (br, 1H), 11.12 (s, 1H), 9.57-9.51 (m, 1H), 8.96-8.90 (m, 1H), 8.38-8.35 (m, 1H), 7.77 (d, J=8.5 Hz, 1H), 7.68 (d, J=9.7 Hz, 1H), 7.57 (dd, J=8.5, 3.0 Hz, 1H), 7.51-7.46 (m, 2H), 7.38-7.15 (m, 5H), 7.08-7.01 (m, 1H), 5.14-5.06 (m, 1H), 4.26-4.16 (m, 3H), 3.99-3.85 (m, 2H), 3.56-3.52 (m, 2H), 3.27-3.03 (m, 5H), 2.94-2.84 (m, 1H), 2.69-2.54 (m, 3H), 2.45-2.41 (m, 1H), 2.37-2.31 (m, 1H), 2.10-1.99 (m, 2H), 1.80-1.50 (m, 6H), 1.30-1.23 (m, 2H), 0.90-0.80 (m, 1H).

Example 12: Preparation of 5-(4-(7-(4-((5-(2-chloro-4-phenoxybenzoyl)-7H-pyrrolo[2,3-d]pyrimidin-4-yl)amino)piperidin-1-yl)heptyl)piperazin-1-yl)-2-(2,6-dioxopiperidin-3-yl)isoindoline-1,3-dione (Compound 12)

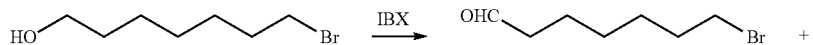

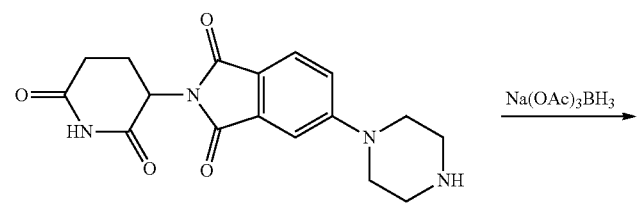

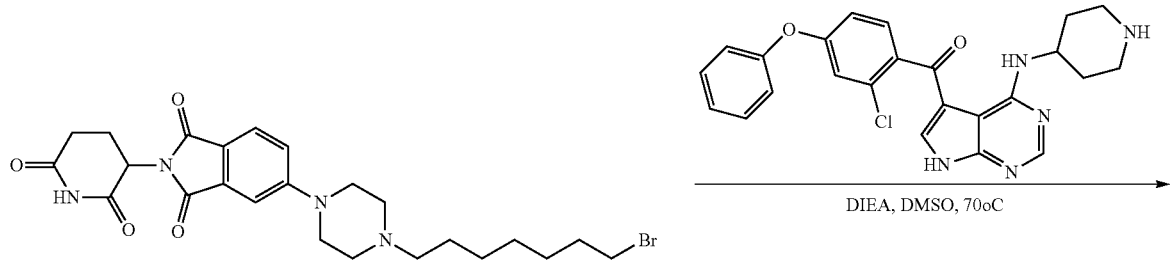

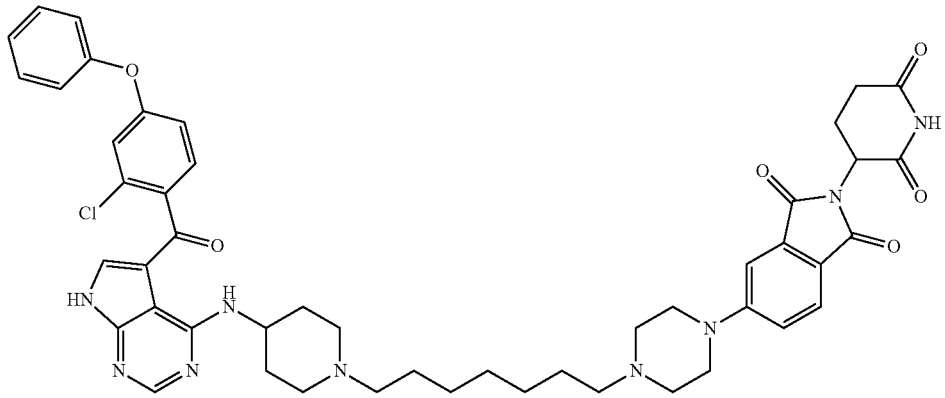

Step 1: Preparation of 7-bromoheptanal

To a solution of 7-bromoheptan-1-ol (1 g, 5.52 mmol) in DMSO (30 mL) was added IBX (1.8 g, 6.62 mmol) and the mixture was stirred at room temperature for 12 hrs. The mixture was diluted with water (30 mL) and filtered. The filtrate was extracted with EtOAc. The combined organic phase was washed with aqueous sodium bicarbonate solution and brine. After drying over $Na_2SO_4$, the solvent was concentrated under vacuum to give 7-bromoheptanal (780 mg, 4.062 mmol) as a yellow oil

Step 2: Preparation of 5-(4-(7-bromoheptyl)piperazin-1-yl)-2-(2,6-dioxopiperidin-3-yl) isoindoline-1,3-dione To a solution of 2-(2,6-dioxopiperidin-3-yl)-5-(piperazin-1-yl)isoindoline-1,3-dione (260 mg, 0.76 mmol) in DCM (20 mL) was added 7-bromoheptanal (161 mg, 0.83 mmol) at 0° C. and the mixture was stirred for 30 min followed by addition of $Na(OAc)_3BH$ (483 mg, 2.28 mmol). After stirring at room temperature for 12 hrs, the mixture was extracted with ethyl acetate and washed with sodium chloride solution. The combined organic phase was dried over $Na_2SO_4$ and concentrated under vacuum to give 5-(4-(7-bromoheptyl)piperazin-1-yl)-2-(2,6-dioxopiperidin-3-yl) isoindoline-1,3-dione (410 mg, 89%) as a yellow solid. LCMS: m/z 519 [M+1]$^+$.

Step 3: Preparation of 5-(4-(7-(4-((5-(2-chloro-4-phenoxybenzoyl)-7H-pyrrolo[2,3-d] pyrimidin-4-yl) amino)piperidin-1-yl)heptyl)piperazin-1-yl)-2-(2,6-dioxopiperidin-3-yl)isoindoline-1,3-dione To a solution of 5-(4-(7-bromoheptyl) piperazin-1-yl)-2-(2,6-dioxopiperidin-3-yl) isoindoline-1,3-dione (410 mg, 0.75 mmol) in DMSO (10 mL) was added (2-chloro-4-phenoxyphenyl)(4-(piperidin-4-ylamino)-7H-pyrrolo[2,3-d] pyrimidin-5-yl)methanone (472 mg 0.97 mmol) and DIEA (483 mg, 3.75 mmol). The mixture was stirred at 70° C. for 12 hr and filtered. The filtrate was extracted with ethyl acetate and washed with brine. The organic phase was dried over $Na_2SO_4$ and concentrated under vacuum. The residue was purified by pre-HPLC to afford desired product (42.8 mg, 6%) as a yellow solid. LCMS: m/z 443[M+1]$^{2+}$.

$^1$HNMR (400 MHz, DMSO): δ: 12.85 (s, 1H), 11.09 (s, 1H), 8.81 (d, J=7.2 Hz, 1H) 8.29 (s, 1H), 7.77 (d, J=8.4 Hz, 1H) 7.68 (s, 1H), 7.58 (d, J=8.4 Hz, 1H), 7.53-7.45 (m, 3H), 7.39 (s, 1H), 7.29-7.21 (m, 1H) 7.18 (d, J=8.8 Hz, 3H), 7.05 (d, J=2.4 Hz, 1H), 5.12-5.10 (m, 2H), 4.32 (s, 1H), 4.22 (s, 2H), 3.59-3.48 (m, 4H), 3.21-3.09 (m, 8H), 2.95-2.81 (m, 1H), 2.69-2.52 (m, 2H), 2.36 (d, J=14.0 Hz, 1H), 2.15 (s, 2H), 2.05-2.01 (m, 1H), 2.71 (s, 4H), 1.34 (s, 6H), 1.23 (s, 2H)

Example 13: (S)-3-(5-(4-(6-(4-((5-(2-chloro-4-phenoxybenzoyl)-7H-pyrrolo[2,3-d]pyrimidin-4-yl) amino)piperidin-1-yl)-6-oxohexyl)piperazin-1-yl)-1-oxoisoindolin-2-yl)piperidine-2,6-dione (Compound 13)

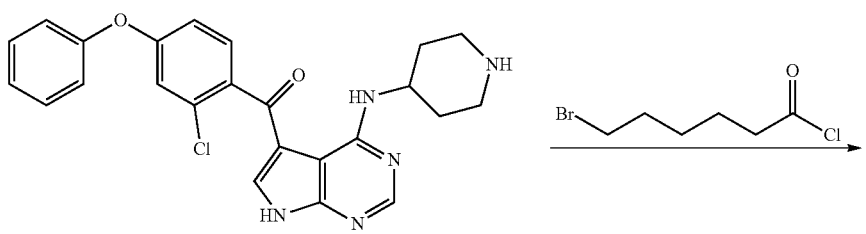

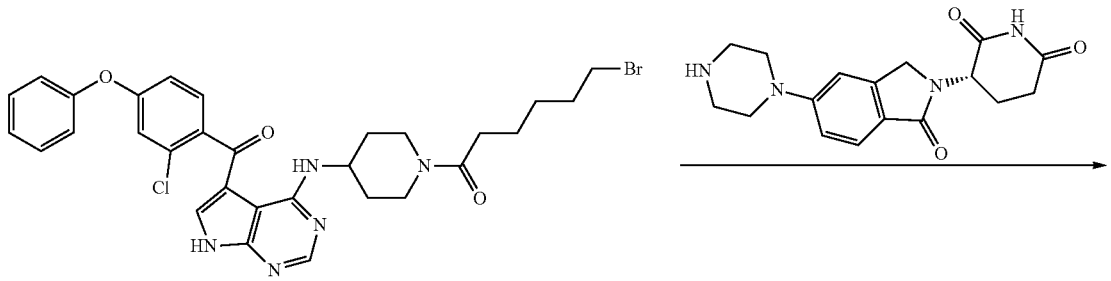

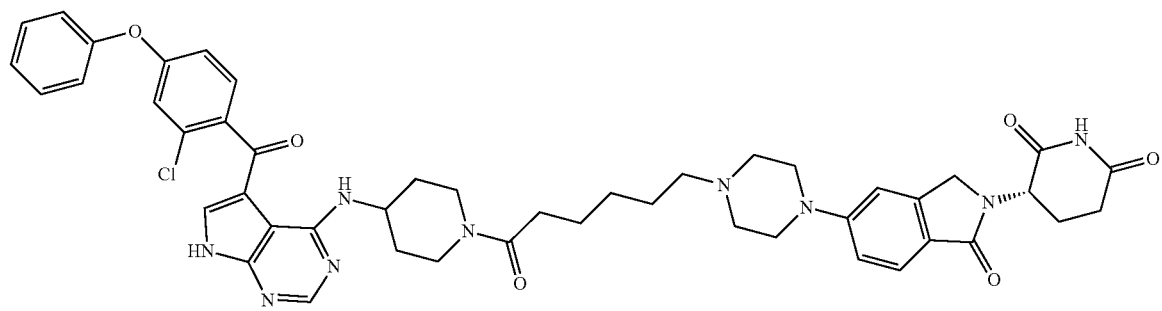

Step 1: Preparation of 6-bromo-1-(4-((5-(2-chloro-4-phenoxybenzoyl)-7H-pyrrolo[2,3-d]pyrimidin-4-yl)amino)piperidin-1-yl)hexan-1-one To a solution of (2-chloro-4-phenoxyphenyl)(4-(piperidin-4-ylamino)-7H-pyrrolo[2,3-d]pyrimidin-5-yl)methanone (90 mg, 0.2 mmol) in DCM (5 mL) stirred under argon was added 6-bromohexanoyl chloride (43 mg, 0.2 mmol) and DIEA (130 mg, 1.0 mmol) at room temperature. The reaction mixture was stirred at room temperature for 16 hours. The mixture was concentrated under vacuum and purified by Prep-TLC (DCM/MeOH=10:1) to give the titled compound (120 mg, 96%) as a white solid. LC/MS: 623.6 [M+H]⁺.

Step 2: Preparation of (S)-3-(5-(4-(6-(4-((5-(2-chloro-4-phenoxybenzoyl)-7H-pyrrolo[2,3-d]pyrimidin-4-yl)amino)piperidin-1-yl)-6-oxohexyl)piperazin-1-yl)-1-oxoisoindolin-2-yl)piperidine-2,6-dione To a solution of 6-bromo-1-(4-((5-(2-chloro-4-phenoxybenzoyl)-7H-pyrrolo[2,3-d]pyrimidin-4-yl)amino)piperidin-1-yl)hexan-1-one (110 mg, 0.18 mmol) in ACN (2 mL) stirred under argon at room temperature was added (S)-3-(1-oxo-5-(piperazin-1-yl)isoindolin-2-yl)piperidine-2,6-dione (88 mg, 0.18 mmol), DIEA (116 mg, 0.9 mmol) and potassium iodide (6.0 mg, 0.04 mmol). The reaction mixture was stirred at 25° C. for 16 hours. The crude product was concentrated under vacuum and purified by Prep-TLC (DCM/MeOH=10:1) to give the titled compound (13 mg, 8.3%). LC/MS: 872.5 [M+H]⁺.

¹H NMR (400 MHz, DMSO) δ 12.80 (s, 1H), 10.97 (s, 1H), 10.49 (br, 1H), 8.84 (d, J=7.4 Hz, 1H), 8.27 (s, 1H), 7.65 (s, 1H), 7.59 (d, J=8.5 Hz, 2H), 7.49 (t, J=7.9 Hz, 2H), 7.26 (t, J=7.4 Hz, 1H), 7.22-7.19 (m, 2H), 7.18-7.15 (m, 1H), 7.07-7.00 (m, 1H), 5.07 (dd, J=13.2, 5.0 Hz, 1H), 4.42-4.30 (m, 2H), 4.27-4.13 (m, 2H), 4.05-3.96 (m, 1H), 3.90-3.82 (m, 1H), 3.62-3.54 (m, 1H), 3.30-3.20 (m, 2H), 3.19-2.97 (m, 4H), 2.95-2.86 (m, 1H), 2.69-2.56 (m, 1H), 2.47-2.31 (m, 4H), 2.13-2.01 (m, 2H), 2.00-1.92 (m, 1H), 1.82-1.65 (m, 2H), 1.64-1.45 (m, 4H), 1.43-1.32 (m, 3H), 1.30-1.17 (m, 3H).

Example 14: (S)-3-(5-(4-(5-((R)-3-((5-(2-chloro-4-phenoxybenzoyl)-7H-pyrrolo[2,3-d]pyrimidin-4-yl)amino)piperidin-1-yl)-5-oxopentyl)piperazin-1-yl)-1-oxoisoindolin-2-yl)piperidine-2,6-dione
(Compound 14)

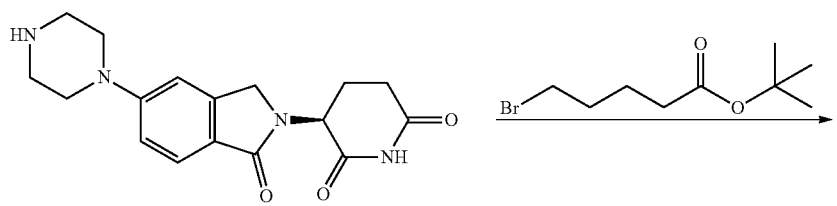

-continued

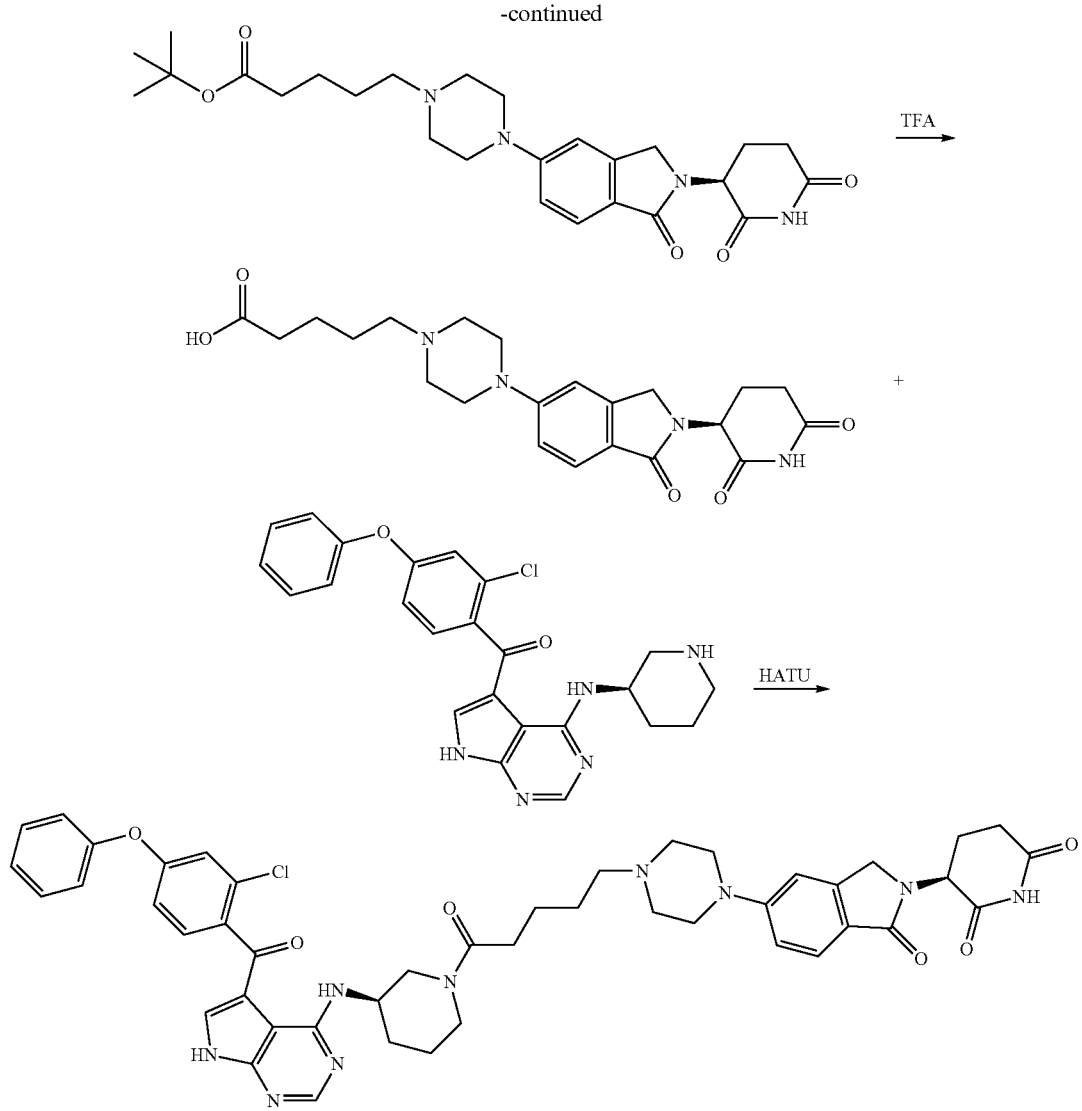

Step 1: Preparation of tert-butyl (S)-5-(4-(2-(2,6-dioxopiperidin-3-yl)-1-oxoisoindolin-5-yl)piperazin-1-yl)pentanoate To a solution of tert-butyl 5-bromopentanoate (50 mg, 0.21 mmol) in MeCN (5 mL) stirred at room temperature was added (S)-3-(1-oxo-5-(piperazin-1-yl)isoindolin-2-yl)piperidine-2,6-dione (103 mg, 0.21 mmol), KI (35 mg, 0.21 mmol) and DIEA (109 mg, 0.84 mmol). The reaction mixture was stirred at 60° C. for 12 hours. The mixture was cooled to room temperature, poured into water (45 mL), and extracted with EtOAc (50 mL×2). The combined organic layer was washed with brine, dried over Na$_2$SO$_4$, and concentrated in vacuum to give a crude product. The crude product was purified by flash chromatography (MeOH/DCM=1:10) to give the desired product (100 mg, yield=98.4%) as a yellow solid. LC/MS: 484.9 [M+H]$^+$.

Step 2: Preparation of (S)-5-(4-(2-(2,6-dioxopiperidin-3-yl)-1-oxoisoindolin-5-yl)piperazin-1-yl)pentanoic acid A solution of tert-butyl (S)-5-(4-(2-(2,6-dioxopiperidin-3-yl)-1-oxoisoindolin-5-yl)piperazin-1-yl)pentanoate (100 mg, 0.20 mmol) in TFA/DCM (1:5, 12 mL) was stirred at room temperature for 2 hours. The mixture was concentrated in vacuum to give a crude product (100 mg, crude). LC/MS: 428.8 [M+H]$^+$.

Step 3: Preparation of (S)-3-(5-(4-(5-((R)-3-((5-(2-chloro-4-phenoxybenzoyl)-7H-pyrrolo[2,3-d]pyrimidin-4-yl)amino)piperidin-1-yl)-5-oxopentyl)piperazin-1-yl)-1-oxoisoindolin-2-yl)piperidine-2,6-dione To a solution of (S)-5-(4-(2-(2,6-dioxopiperidin-3-yl)-1-oxoisoindolin-5-yl)piperazin-1-yl)pentanoic acid (100 mg, 0.20 mmol) in DMF (5 mL) was added HATU (94 mg, 0.25 mmol), DIEA (107 mg, 0.828 mmol) and (R)-(2-chloro-4-phenoxyphenyl)(4-(piperidin-3-ylamino)-7H-pyrrolo[2,3-d]pyrimidin-5-yl)methanone (116 mg, 0.187 mmol) at room temperature. The reaction mixture was stirred at room temperature for 2 hours. The mixture was poured into water (45 mL) and extracted with EtOAc (50 mL×2). The combined organic layer was washed with brine, dried over Na$_2$SO$_4$, and concentrated in vacuum to give a crude product. The crude product was purified by Prep-TLC (MeOH/

DCM=1:10) to give the desired product (25 mg, yield=14.5% with two steps). LC/MS: 857.6 [M+H]$^+$.

$^1$H NMR (400 MHz, DMSO) δ 12.83 (br, 1H), 10.97 (s, 1H), 8.95-8.85 (m, 1H), 8.37-8.25 (m, 1H), 7.71-7.63 (m, 1H), 7.60-7.53 (m, 3H), 7.48 (t, J=7.6 Hz, 2H), 7.25 (t, J=7.6 Hz, 1H), 7.24-7.16 (m, 3H), 7.15-7.06 (m, 2H), 7.04 (dd, J=8.4, 2.4 Hz, 1H), 5.09-5.04 (m, 1H), 4.40-4.30 (m, 1H), 4.28-4.15 (m, 2H), 3.95-3.75 (m, 1H), 3.65-3.41 (m, 5H), 3.22-3.10 (m, 2H), 2.98-2.85 (m, 2H), 2.60-2.52 (m, 2H), 2.47-2.28 (m, 3H), 2.28-2.15 (m, 1H), 2.09-1.94 (m, 2H), 1.88-1.70 (m, 2H), 1.65-1.40 (m, 4H), 1.31 (t, J=7.2 Hz, 2H), 1.26-1.21 (m, 1H).

Example 15: 5-(4-(6-((R)-3-((5-(2-chloro-4-phenoxybenzoyl)-7H-pyrrolo[2,3-d]pyrimidin-4-yl)amino)piperidin-1-yl)hexyl)piperazin-1-yl)-2-(2,6-dioxopiperidin-3-yl)isoindoline-1,3-dione (Compound 15)

Step 1: Preparation of (R)-(2-chloro-4-phenoxyphenyl)(4-((1-(6,6-dimethoxyhexyl)piperidin-3-yl)amino)-7H-pyrrolo[2,3-d]pyrimidin-5-yl)methanone A suspension of 6-bromo-1,1-dimethoxyhexane (21 mg, 0.09 mmol), (R)-(2-chloro-4-phenoxyphenyl)(4-(piperidin-3-ylamino)-7H-pyrrolo[2,3-d]pyrimidin-5-yl)methanone (50 mg, 0.09 mmol), KI (15 mg, 0.09 mmol) and DIEA (24 mg, 0.18 mmol) in DMF (2 mL) was stirred at 25° C. for 16 hours. The solvent was removed in vacuum. The residue was purified by chromatography eluted with DCM/MeOH=20:1 to afford the product (50 mg, 94%) as a yellow solid. LC/MS: 592.3 [M+H]$^+$.

Step 2: Preparation of (R)-6-(3-((5-(2-chloro-4-phenoxybenzoyl)-7H-pyrrolo[2,3-d]pyrimidin-4-yl)amino)piperidin-1-yl)hexanal A solution of (R)-(2-chloro-4-phenoxyphenyl)(4-((1-(6,6-dimethoxypentyl)piperidin-3-yl)amino)-7H-pyrrolo[2,3-d]

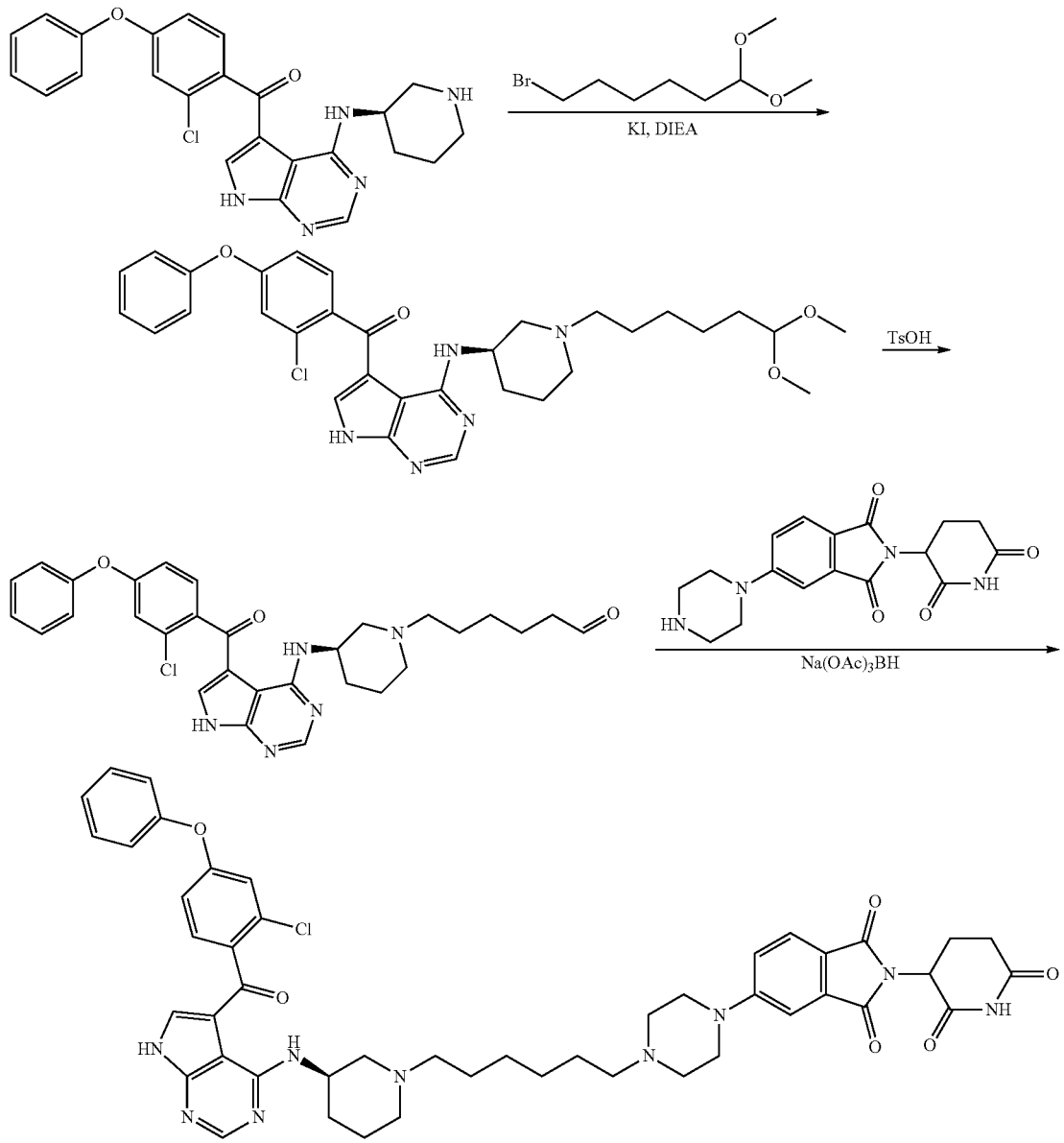

pyrimidin-5-yl)methanone (50 mg, 0.08 mmol) in ACN (2 mL) was added TsOH (14 mg, 0.08 mmol) and HOAc (14 mg, 0.08 mmol). The reaction mixture was stirred at 25° C. for 5 hours. The mixture was concentrated under vacuum. The residue was dissolved with EtOAc (10 mL) and washed with saturated NaHCO$_3$ solution. The organic phase was dried over Na$_2$SO$_4$ and concentrated in vacuum to afford the titled product (35 mg, 80%) as a yellow solid. LC/MS: 546.2 [M+H]$^+$.

Step 3: Preparation of 5-(4-(6-((R)-3-((5-(2-chloro-4-phenoxybenzoyl)-7H-pyrrolo[2,3-d]pyrimidin-4-yl)amino)piperidin-1-yl)hexyl)piperazin-1-yl)-2-(2,6-dioxopiperidin-3-yl)isoindoline-1,3-dione A solution of (R)-6-(3-((5-(2-chloro-4-phenoxybenzoyl)-7H-pyrrolo[2,3-d]pyrimidin-4-yl)amino) piperidin-1-yl) hexanal (35 mg, 0.07 mmol), Et$_3$N (14 mg, 0.14 mmol) and 2-(2,6-dioxopiperidin-3-yl)-5-(piperazin-1-yl)isoindoline-1,3-dione (27 mg, 0.07 mmol) in DCM (5 mL) was stirred at 25° C. for 10 minutes. The mixture was cooled to 0° C. and NaBH(OAc)$_3$ (22 mg, 0.11 mmol) was added portion wise. The mixture was stirred at 25° C. for 16 hours. The solvent was removed under vacuum and the residue was purified by chromatography eluted with DCM/MeOH=20:1 to afford the titled product (15 mg, 24%) as a yellow solid. LC/MS: 872.3 [M+H]$^+$.

$^1$H NMR (400 MHz, DMSO) δ 12.79 (br, 1H), 10.97 (s, 1H), 10.60 (br, 1H), 8.83 (d, J=7.5 Hz, 1H), 8.27 (s, 1H), 7.64 (s, 1H), 7.60-7.46 (m, 3H), 7.26 (t, J=7.4 Hz, 1H), 7.23-7.06 (m, 4H), 7.04-7.01 (m, 1H), 5.09-5.04 (m, 1H), 4.42-4.13 (m, 4H), 4.09-3.93 (m, 1H), 3.92-3.78 (m, 1H), 3.72-3.41 (m, 2H), 3.29-3.17 (m, 3H), 3.14-2.85 (m, 4H), 2.77-2.52 (m, 4H), 2.42-2.30 (m, 3H), 2.13-1.60 (m, 3H), 1.77-1.65 (m, 1H), 1.58-1.45 (m, 3H), 1.41-1.19 (m, 5H).

Example 16: Preparation of (S)-3-(5-(4-(6-((R)-3-((5-(2-chloro-4-phenoxybenzoyl)-7H-pyrrolo[2,3-d]pyrimidin-4-yl)amino)piperidin-1-yl)-6-oxohexyl)piperazin-1-yl)-1-oxoisoindolin-2-yl)piperidine-2,6-dione (Compound 16)

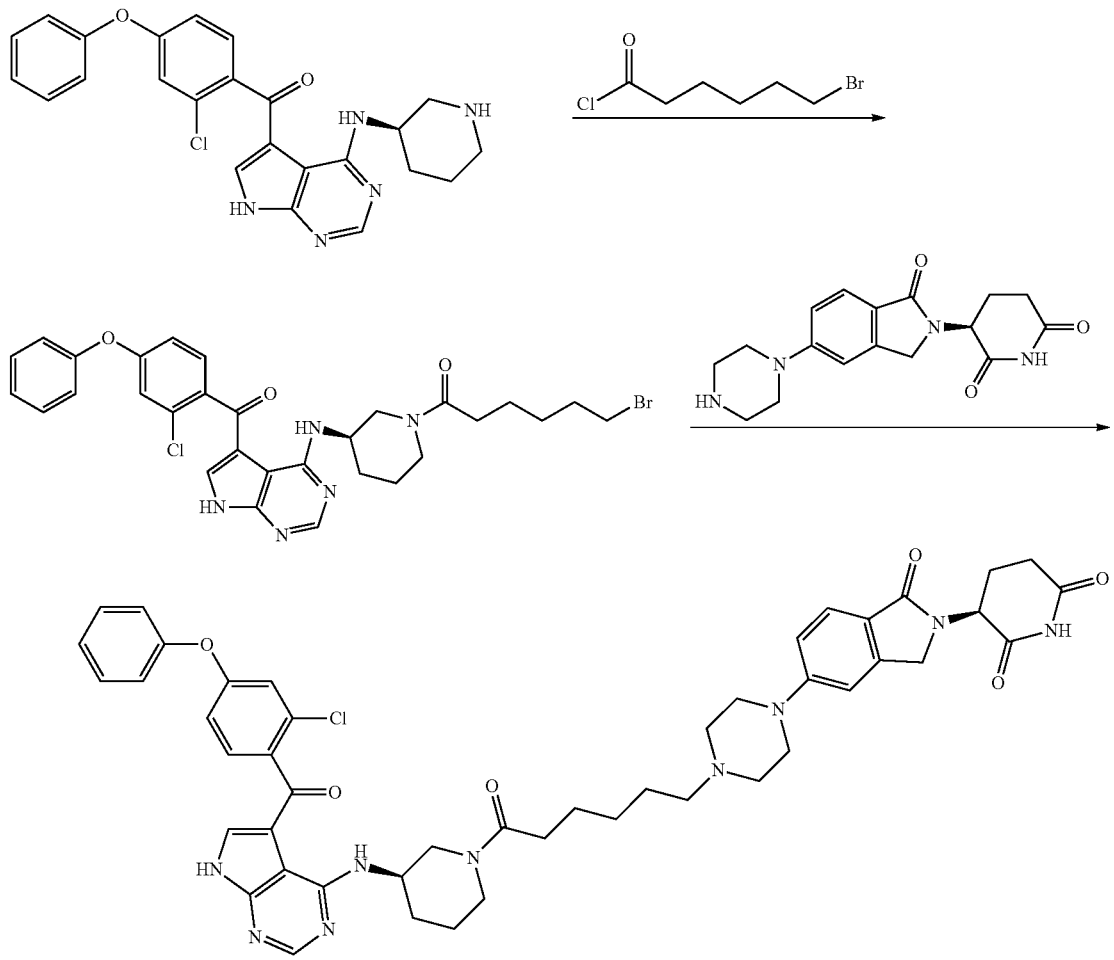

Step 1: Preparation of (R)-6-bromo-1-(3-((5-(2-chloro-4-phenoxybenzoyl)-7H-pyrrolo[2,3-d]pyrimidin-4-yl)amino)piperidin-1-yl)hexan-1-one To a mixture of (R)-(2-chloro-4-phenoxyphenyl)(4-(piperidin-3-ylamino)-7H-pyrrolo[2,3-d]pyrimidin-5-yl)methanone (113 mg, 0.20 mmol) and DIEA (77.8 mg, 0.60 mmol) in DCM (10 mL) was added 6-bromohexanoyl chloride (42.8 mg, 0.20 mmol) at 0° C. The mixture was stirred at room temperature for 5 hours. The mixture was concentrated in vacuum. The crude product was purified by silica gel chromatography with 4-8% MeOH in DCM to afford the desired compound (80 mg, 64%). LC/MS: 623.5[M+H]+.

Step 2: Preparation of (S)-3-(5-(4-(6-((R)-3-((5-(2-chloro-4-phenoxybenzoyl)-7H-pyrrolo[2,3-d]pyrimidin-4-yl)amino)piperidin-1-yl)-6-oxohexyl)piperazin-1-yl)-1-oxoisoindolin-2-yl)piperidine-2,6-dione A mixture of (R)-6-bromo-1-(3-((5-(2-chloro-4-phenoxybenzoyl)-7H-pyrrolo[2,3-d]pyrimidin-4-yl)amino)piperidin-1-yl)hexan-1-one (50 mg, 0.08 mmol), (S)-3-(1-oxo-5-(piperazin-1-yl)isoindolin-2-yl)piperidine-2,6-dione (38.8 mg, 0.08 mmol), DIEA (20 mg, 0.16 mmol) and NaI (1.2 mg, 0.008 mmol) in ACN (9 mL) was stirred at 90° C. for 18 hours under N₂ atmosphere. The mixture was concentrated in vacuum. The residue was purified by silica gel chromatography with 5-10% MeOH in DCM to afford the desired compound (38 mg, 70%). LC/MS: 871.4[M+H]+.

¹H NMR (400 MHz, DMSO) δ 12.75 (br, 1H), 10.96 (s, 1H), 8.91 (d, J=6.8 Hz, 1H), 8.30-8.26 (m, 1H), 7.68-7.59 (m, 1H), 7.56-7.46 (m, 4H), 7.32-7.24 (m, 1H), 7.21-7.13 (m, 3H), 7.10-7.02 (m, 3H), 5.08-5.03 (m, 1H), 4.37-4.29 (m, 1H), 4.25-4.16 (m, 2H), 3.82-3.70 (m, 1H), 3.65-3.39 (m, 3H), 3.28-3.15 (m, 2H), 2.95-2.83 (m, 2H), 2.72-2.65 (m, 1H), 2.63-2.59 (m, 1H), 2.57-2.55 (m, 1H), 2.49-2.40 (m, 2H), 2.37-2.31 (m, 1H), 2.28-2.15 (m, 2H), 2.03-1.95 (m, 2H), 1.81-1.71 (m, 2H), 1.63-1.32 (m, 4H), 1.30-1.18 (m, 3H), 1.15-1.08 (s, 2H), 0.90-0.84 (m, 1H).

Example 17: 3-(5-(4-(7-((R)-3-((5-(2-chloro-4-phenoxybenzoyl)-7H-pyrrolo[2,3-d]pyrimidin-4-yl)amino)piperidin-1-yl)-7-oxoheptyl)piperazin-1-yl)-1-oxoisoindolin-2-yl)piperidine-2,6-dione
(Compound 17)

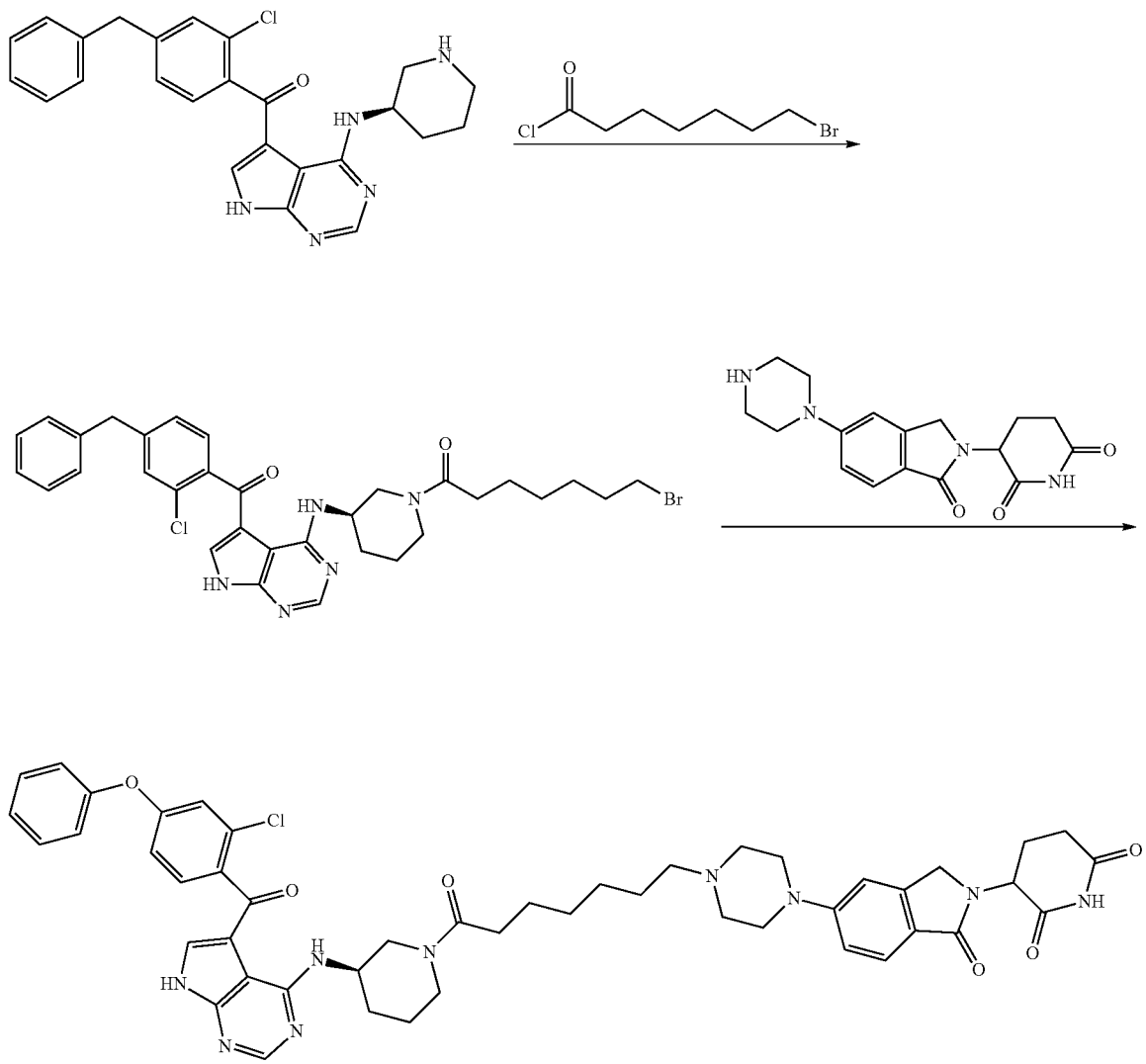

Step 1: Preparation of (R)-7-bromo-1-(3-((5-(2-chloro-4-phenoxybenzoyl)-7H-pyrrolo[2,3-d]pyrimidin-4-yl)amino)piperidin-1-yl)heptan-1-one To a mixture of (R)-(2-chloro-4-phenoxyphenyl)(4-(piperidin-3-ylamino)-7H-pyrrolo[2,3-d]pyrimidin-5-yl)methanone (113 mg, 0.20 mmol) and DIEA (77.8 mg, 0.60 mmol) in DCM (10 mL) was added 7-bromoheptanoyl chloride (45.7 mg, 0.20 mmol) at 0° C. The mixture was stirred at room temperature for 5 hours. The mixture was concentrated in vacuum. The crude product was purified by silica gel chromatography with 4-8% MeOH in DCM to afford the desired compound (80 mg, 63%). LC/MS: 637.4[M+H]$^+$.

Step 2: Preparation of 3-(5-(4-(7-((R)-3-((5-(2-chloro-4-phenoxybenzoyl)-7H-pyrrolo[2,3-d]pyrimidin-4-yl)amino)piperidin-1-yl)-7-oxoheptyl)piperazin-1-yl)-1-oxoisoindolin-2-yl)piperidine-2,6-dione A mixture of (R)-7-bromo-1-(3-((5-(2-chloro-4-phenoxybenzoyl)-7H-pyrrolo[2,3-d]pyrimidin-4-yl)amino)piperidin-1-yl)heptan-1-one (50 mg, 0.08 mmol), (S)-3-(1-oxo-5-(piperazin-1-yl)isoindolin-2-yl)piperidine-2,6-dione (38.8 mg, 0.08 mmol), DIEA (20 mg, 0.16 mmol) and NaI (1.2 mg, 0.008 mmol) in ACN (9 mL) was stirred at 90° C. for 18 hours under $N_2$ atmosphere. The mixture was concentrated in vacuum. The residue was purified by silica gel chromatography with 5-10% MeOH in DCM to afford the desired compound (22 mg, 98% purity, 30% yield). Chiral chromatography analysis indicated partial racemization.

LC/MS: 885.5[M+H]$^+$.

$^1$H NMR (400 MHz, DMSO) δ 12.75 (br, 1H), 10.96 (s, 1H), 8.92-8.86 (m, 1H), 8.32-8.25 (m, 1H), 7.72-7.60 (m, 1H), 7.57-7.46 (m, 4H), 7.32-7.20 (m, 1H), 7.21-7.15 (m, 3H), 7.08-7.02 (m, 3H), 5.06 (dd, J=13.3, 5.1 Hz, 1H), 4.37-4.30 (m, 1H), 4.28-4.15 (m, 2H), 3.77 (d, J=13.2 Hz, 1H), 3.61-3.45 (m, 3H), 3.29-3.21 (m, 2H), 3.02-2.79 (m, 2H), 2.69-2.55 (m, 2H), 2.40-2.29 (m, 3H), 2.25-2.12 (m, 2H), 2.07-1.91 (m, 3H), 1.88-1.73 (m, 2H), 1.63-1.55 (m, 1H), 1.50-1.32 (m, 4H), 1.28-1.23 (m, 3H), 1.17-1.08 (m, 3H), 0.89-0.78 (m, 1H).

Example 18: Preparation of 5-(4-(6-(4-((5-(2-chloro-4-phenoxybenzoyl)-7H-pyrrolo[2,3-d]pyrimidin-4-yl)amino)piperidin-1-yl)hexyl)piperazin-1-yl)-2-(2,6-dioxopiperidin-3-yl)isoindoline-1,3-dione (Compound 18)

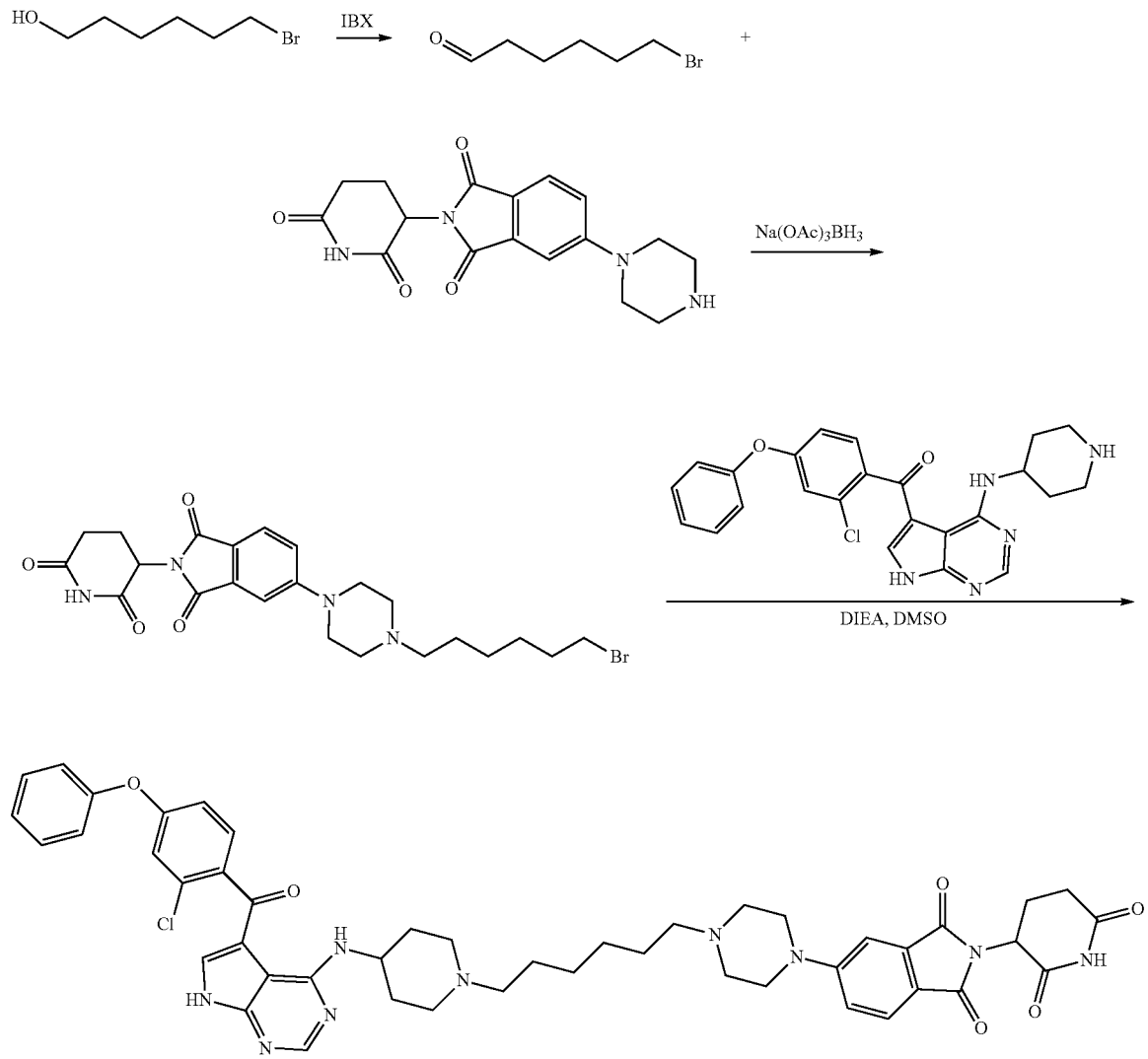

Compound 18 was prepared analogously with the procedure described for Compound 12.
LCMS: m/z 436.8 [M+1]$^{2+}$.
$^1$HNMR (400 MHz, DMSO): δ: 12.91 (s, 1H), 11.12 (s, 1H), 8.81 (d, J=6.8 Hz, 1H), 8.31 (s, 1H), 7.77 (d, J=8.8 Hz, 1H) 7.72 (s, 1H), 7.61 (s, 1H), 7.51-7.48 (m, 3H), 7.31 (s, 1H), 7.15 (s, 1H), 7.13 (s, 3H), 7.05 (d, J=2 Hz, 1H), 5.19-5.15 (m, 1H), 4.35 (s, 1H), 4.21 (s, 2H), 3.61 (s, 6H), 3.19 (s, 7H), 2.91-2.87 (m, 1H), 2.71-2.69 (m, 1H), 2.50 (d, J=1.6 Hz, 2H), 2.12-2.08 (m, 2H), 1.71 (s, 4H), 1.35 (s, 4H), 1.22 (s, 3H)
Example 19: 5-(4-(4-((R)-3-((5-(2-chloro-4-phenoxybenzoyl)-7H-pyrrolo[2,3-d]pyrimidin-4-yl)amino)piperidin-1-yl)-4-oxobutyl)piperazin-1-yl)-2-(2,6-dioxopiperidin-3-yl)isoindoline-1,3-dione
(Compound 19)
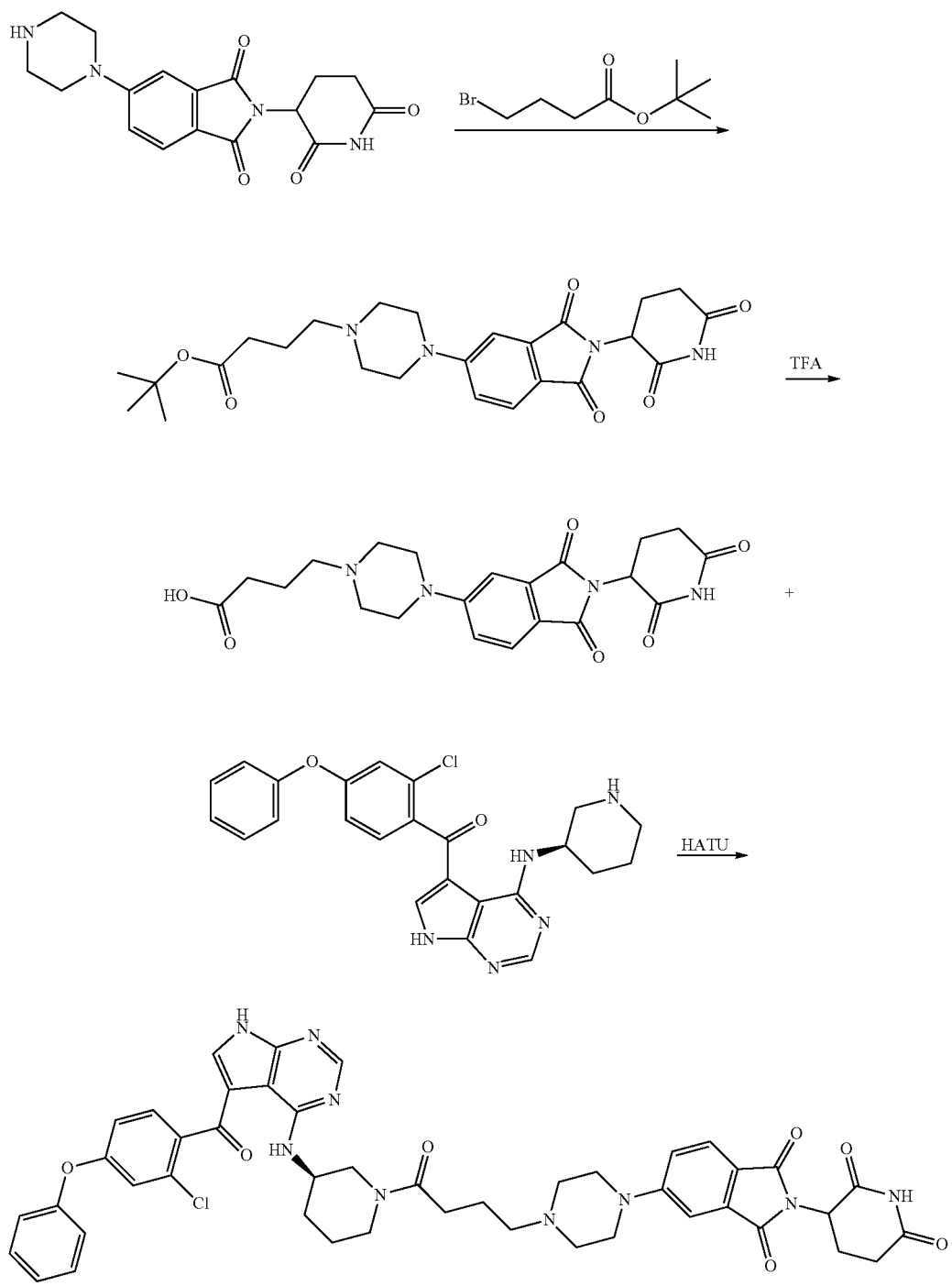

Compound 19 was prepared analogously with the procedure described for Compound 14.
LC/MS: 857.5 [M+H]+.
¹H NMR (400 MHz, DMSO) δ 12.81 (br, 1H), 11.10 (s, 1H), 8.92-8.83 (m, 1H), 8.32-8.19 (m, 1H), 7.84-7.55 (m, 3H), 7.54-7.40 (m, 2H), 7.39-6.97 (m, 6H), 5.17-5.02 (m, 1H), 4.37-4.05 (m, 2H), 3.97-3.75 (m, 1H), 3.72-3.33 (m, 6H), 3.27-2.81 (m, 4H), 2.73-2.54 (m, 2H), 2.47-2.09 (m, 5H), 2.06-1.97 (m, 2H), 1.93-1.45 (m, 5H), 1.35-1.15 (m, 1H).
Example 20: (S)-3-(5-(4-(4-((R)-3-((5-(2-chloro-4-phenoxybenzoyl)-7H-pyrrolo[2,3-d]pyrimidin-4-yl)amino)piperidin-1-yl)-4-oxobutyl)piperazin-1-yl)-1-oxoisoindolin-2-yl)piperidine-2,6-dione (Compound 20)
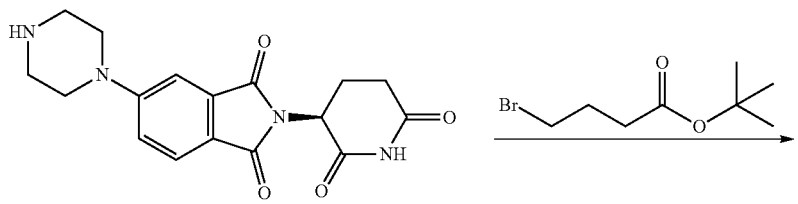
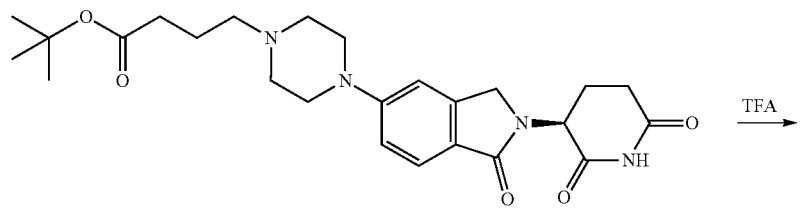
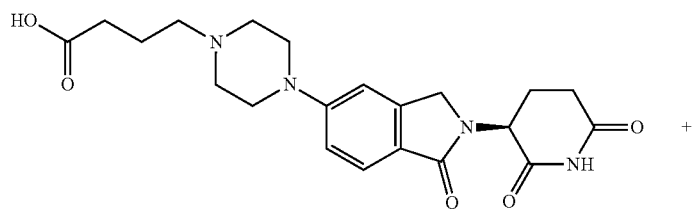
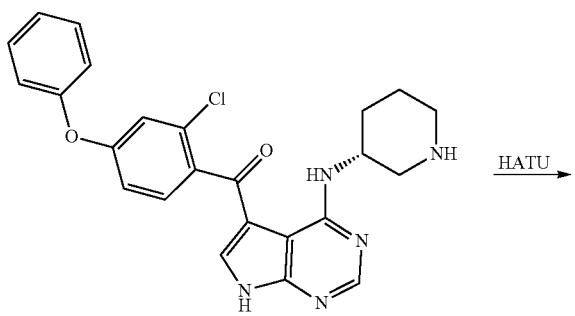
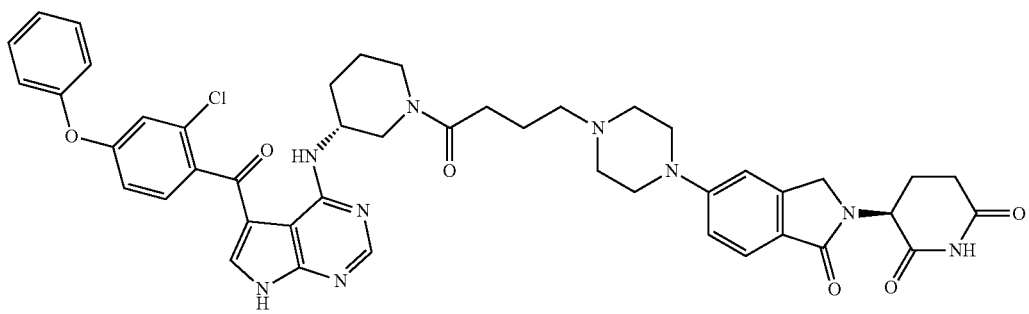

Compound 20 was prepared analogously with the procedure described for Compound 14.

LC/MS: 843.6 [M+H]+.

$^1$H NMR (400 MHz, DMSO) δ 12.90-12.75 (m, 1H), 10.97 (s, 1H), 10.47 (br, 1H), 8.93-8.81 (m, 1H), 8.35-8.24 (m, 1H), 7.73-7.43 (m, 5H), 7.29-7.08 (m, 5H), 7.07-7.00 (m, 1H), 5.13-5.03 (m, 1H), 4.42-4.15 (m, 3H), 4.03-3.85 (m, 2H), 3.78-3.38 (m, 5H), 3.29-3.01 (m, 5H), 2.96-2.86 (m, 1H), 2.64-2.56 (m, 1H), 2.47-2.32 (m, 3H), 2.06-1.91 (m, 3H), 1.83-1.46 (m, 4H), 1.28-1.18 (m, 1H), 0.96-0.75 (m, 1H).

Example 21: Preparation of (S)-3-(5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazin-1-yl)-1-oxoisoindolin-2-yl)piperidine-2,6-dione (Compound 21)

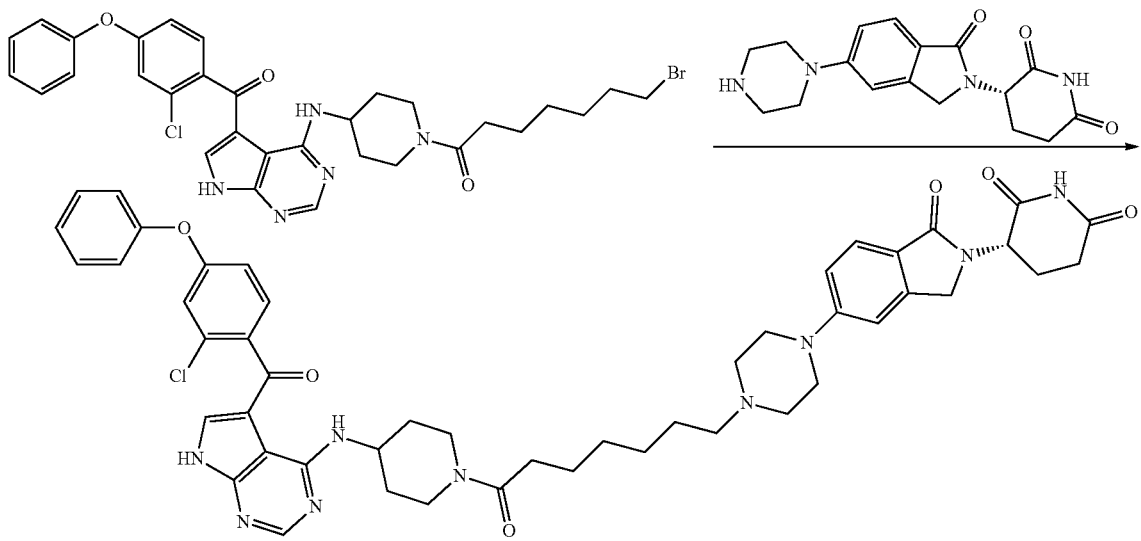

Step 1: Preparation of (S)-3-(5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazin-1-yl)-1-oxoisoindolin-2-yl)piperidine-2,6-dione To a solution of 7-bromo-1-(4-((5-(2-chloro-4-phenoxybenzoyl)-7H-pyrrolo[2,3-d]pyrimidin-4-yl) amino)piperidin-1-yl)heptan-1-one (80 mg, 0.13 mmol) in DMF (5 mL) stirred under argon was added (S)-3-(1-oxo-5-(piperazin-1-yl)isoindolin-2-yl)piperidine-2,6-dione (63 mg, 0.13 mmol), DIEA (50 mg, 0.39 mmol) and potassium iodide (20 mg, 0.13 mmol) at room temperature. The reaction mixture was stirred at 70° C. for 15 hours. The crude product was concentrated under vacuum and purified by Prep-TLC (DCM/MeOH=10:1) to give the titled compound (30 mg, 26.0%). LC/MS: 886.3 [M+H]+.

$^1$H NMR (400 MHz, DMSO) δ 12.79 (s, 1H), 10.97 (s, 1H), 10.25 (br, 1H), 8.83 (d, J=7.3 Hz, 1H), 8.27 (s, 1H), 7.64 (s, 1H), 7.60-7.46 (m, 3H), 7.26 (t, J=7.4 Hz, 1H), 7.22-7.01 (m, 5H), 5.06 (dd, J=13.4, 5.1 Hz, 1H), 4.38-4.15 (m, 4H), 4.08-3.92 (m, 1H), 3.90-3.77 (m, 1H), 3.75-3.50 (m, 2H), 3.45-3.35 (m, 1H), 3.32-3.18 (m, 3H), 3.14-2.85 (m, 4H), 2.75-2.53 (m, 5H), 2.42-2.31 (m, 3H), 2.15-1.95 (m, 3H), 1.77-1.62 (m, 1H), 1.57-1.47 (m, 3H), 1.45-1.27 (m, 5H).

Example 22: Preparation of 5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazin-1-yl)-2-(2,6-dioxopiperidin-3-yl)isoindoline-1,3-dione (Compound 22)

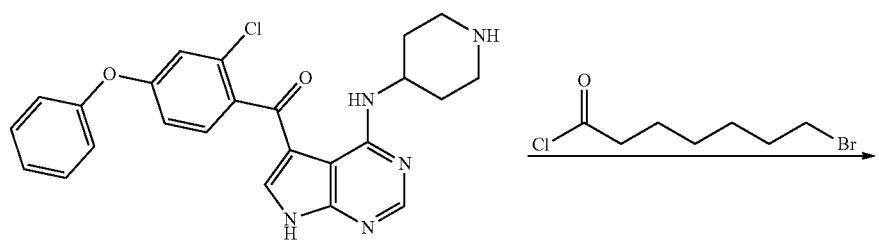

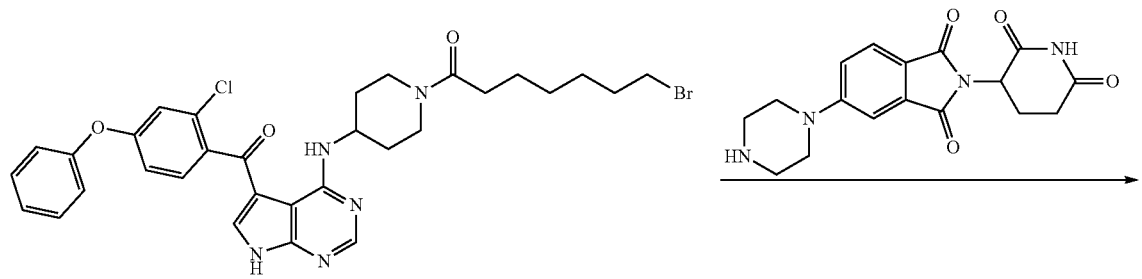
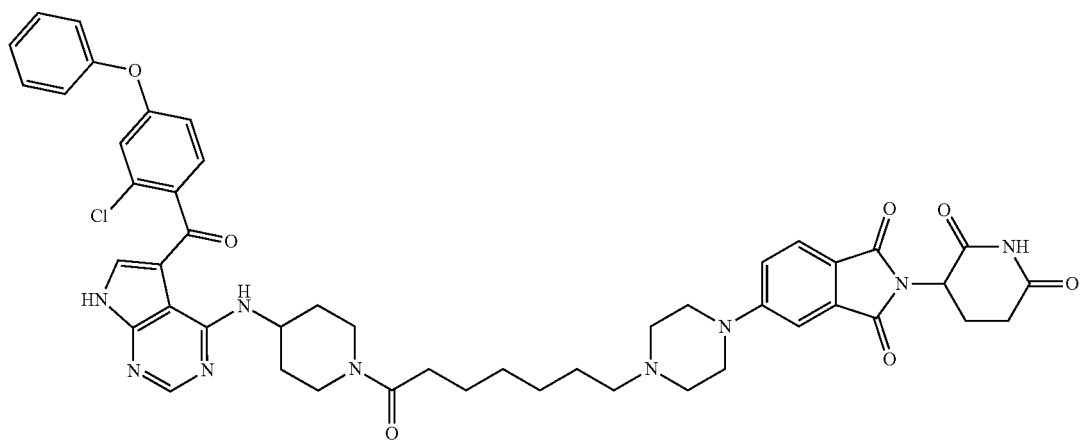
Compound 22 was prepared analogously with the procedure described for Compound 13.
LC/MS: 901.2 [M+H]+.
1H NMR (400 MHz, DMSO) δ=12.87 (br, 1H), 11.10 (s, 1H), 8.83 (d, J=7.4, 1H), 8.26 (s, 1H), 7.78-7.67 (m, 1H), 7.65-7.56 (m, 2H), 7.50-7.45 (m, 2H), 7.35-7.23 (m, 2H), 7.22-7.14 (m, 3H), 7.06-7.01 (m, 1H), 5.15-5.05 (m, 1H), 4.38-4.30 (m, 1H), 4.28-4.12 (m, 2H), 3.89-3.80 (m, 1H), 3.65-3.40 (m, 3H), 3.29-3.23 (m, 2H), 3.17-2.82 (m, 5H), 2.65-2.54 (m, 2H), 2.39-2.32 (m, 2H), 2.12-1.99 (m, 3H), 1.80-1.68 (m, 1H), 1.60-1.44 (m, 4H), 1.40-1.20 (m, 7H), 0.94-0.73 (m, 1H).
Example 23: Preparation of 5-(4-(4-(4-((5-(2-chloro-4-phenoxybenzoyl)-7H-pyrrolo[2,3-d]pyrimidin-4-yl)amino)piperidin-1-yl)-4-oxobutyl)piperazin-1-yl)-2-(2,6-dioxopiperidin-3-yl)isoindoline-1,3-dione (Compound 23)
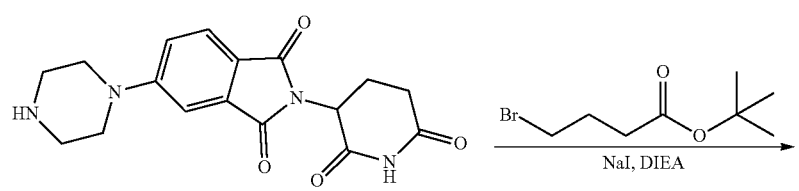
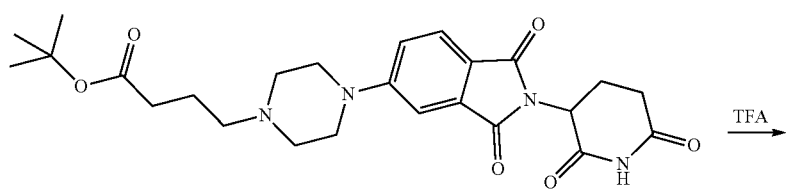

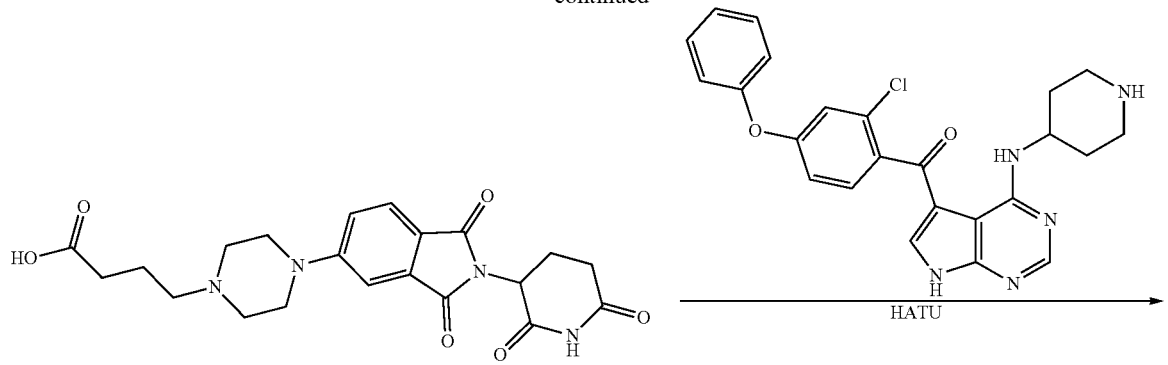
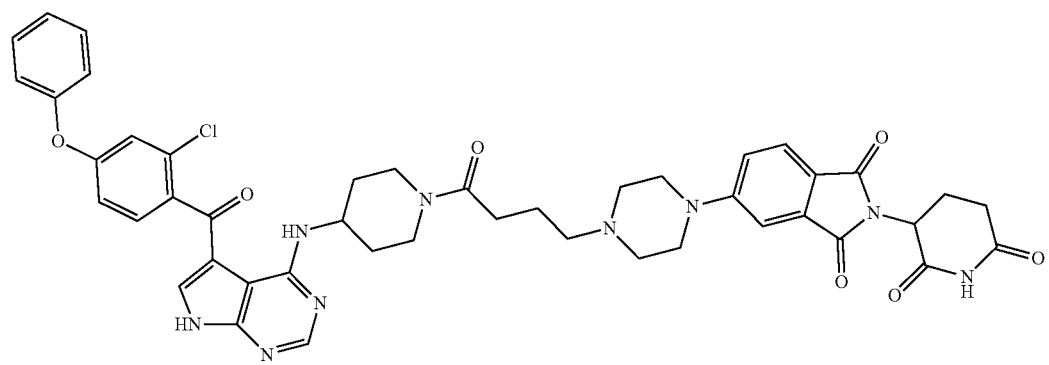
Compound 23 was prepared analogously with the procedure described for Compound 11.
LC/MS: 857.3 [M+H]$^+$.
$^1$H NMR (400 MHz, DMSO) δ 12.79 (br, 1H), 11.10 (s, 1H), 8.84 (d, J=7.2 Hz, 1H), 8.27 (s, 1H), 7.72 (brs, 1H), 7.64 (s, 1H), 7.58 (d, J=8.5 Hz, 1H), 7.49 (t, J=7.9 Hz, 2H), 7.46-7.35 (m, 1H), 7.34-7.23 (m, 2H), 7.23-7.15 (m, 3H), 7.08-7.00 (m, 1H), 5.14-5.03 (m, 1H), 4.40-4.31 (m, 1H), 4.28-4.07 (m, 2H), 3.93-3.81 (m, 1H), 3.70-3.39 (m, 3H), 3.10-2.85 (m, 3H), 2.71-2.56 (m, 2H), 2.36-2.32 (m, 1H), 2.14-1.97 (m, 4H), 1.94-1.75 (m, 2H), 1.68-1.48 (m, 2H), 1.48-1.15 (m, 4H), 1.06-0.74 (m, 2H).
Example 24: Preparation of (S)-3-(5-(4-(4-(4-((5-(2-chloro-4-phenoxybenzoyl)-7H-pyrrolo[2,3-d]pyrimidin-4-yl)amino)piperidin-1-yl)-4-oxobutyl)piperazin-1-yl)-1-oxoisoindolin-2-yl)piperidine-2,6-dione (Compound 24)
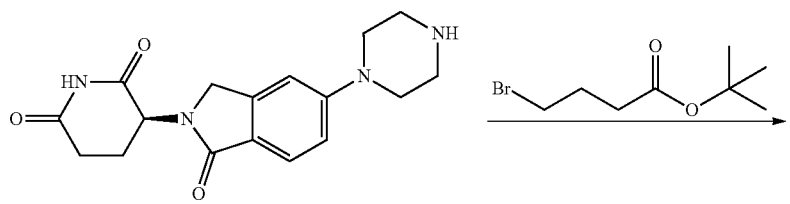
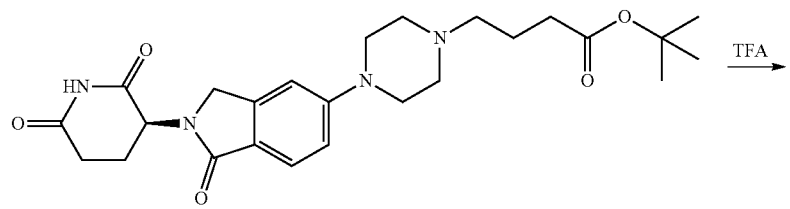

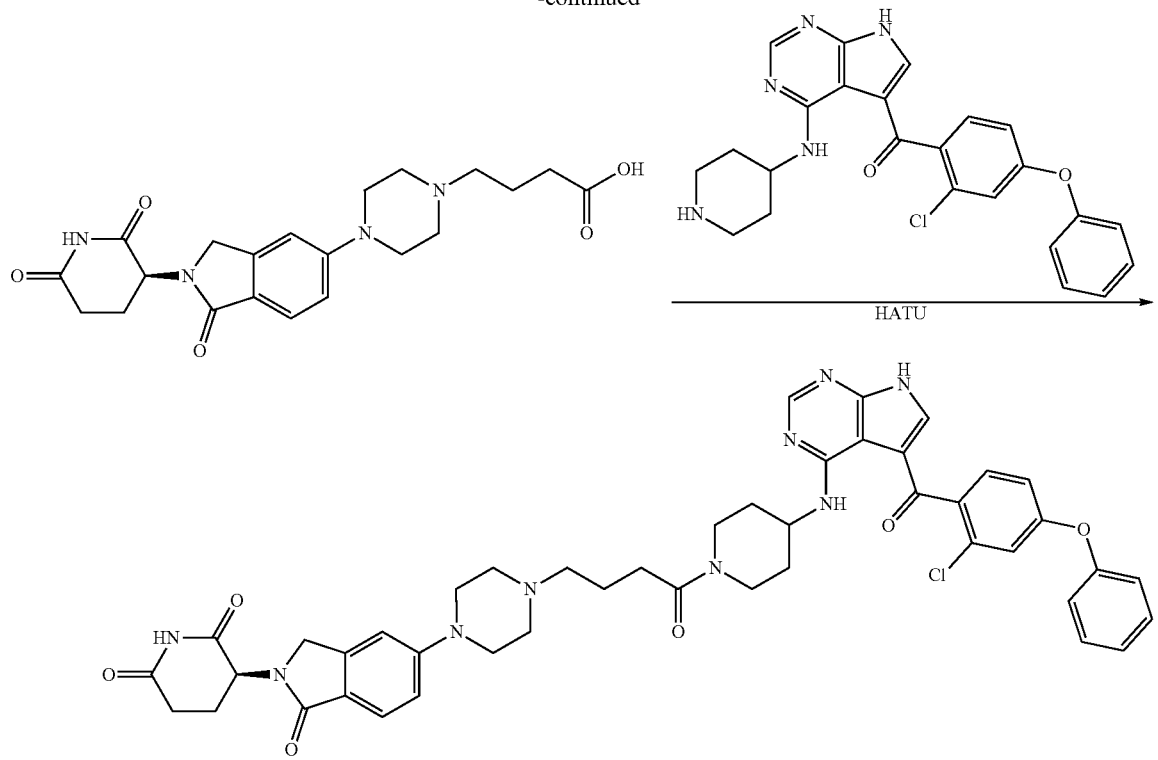

Compound 24 was prepared analogously with the procedure described for Compound 14.

LC/MS: 843.4 [M+H]$^+$.

$^1$H NMR (400 MHz, DMSO) δ 12.81 (br, 1H), 10.96 (s, 1H), 8.84 (d, J=7.3 Hz, 1H), 8.73 (s, 0.5H), 8.51 (d, J=8.4 Hz, 0.5H), 8.27 (s, 1H), 7.64 (s, 1H), 7.59 (d, J=8.5 Hz, 1H), 7.54 (d, J=8.4 Hz, 1H), 7.50-7.46 (m, 2H), 7.26 (t, J=7.4 Hz, 1H), 7.23-7.15 (m, 3H), 7.14-7.06 (m, 2H), 7.03 (dd, J=8.5, 2.3 Hz, 1H), 5.10-5.05 (m, 1H), 4.39-4.30 (m, 2H), 4.25-4.17 (m, 2H), 3.89-3.82 (m, 1H), 3.50-3.32 (m, 4H), 3.06-3.00 (m, 1H), 2.94-2.88 (m, 3H), 2.76-2.66 (m, 2H), 2.62-2.56 (m, 1H), 2.47-2.33 (m, 3H), 2.18-1.92 (m, 4H), 1.89-1.80 (m, 2H), 1.59-1.52 (m, 1H), 1.47-1.34 (m, 2H).

Example 25: Preparation of (S)-3-(5-(4-(5-(4-((5-(2-chloro-4-phenoxybenzoyl)-7H-pyrrolo[2,3-d]pyrimidin-4-yl)amino)piperidin-1-yl)-5-oxopentyl)piperazin-1-yl)-1-oxoisoindolin-2-yl)piperidine-2,6-dione (Compound 25)

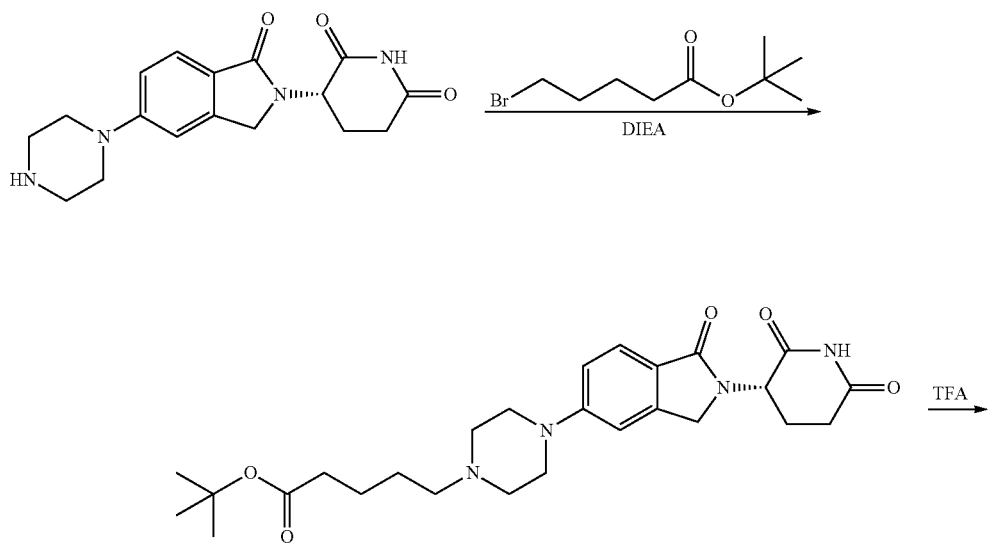

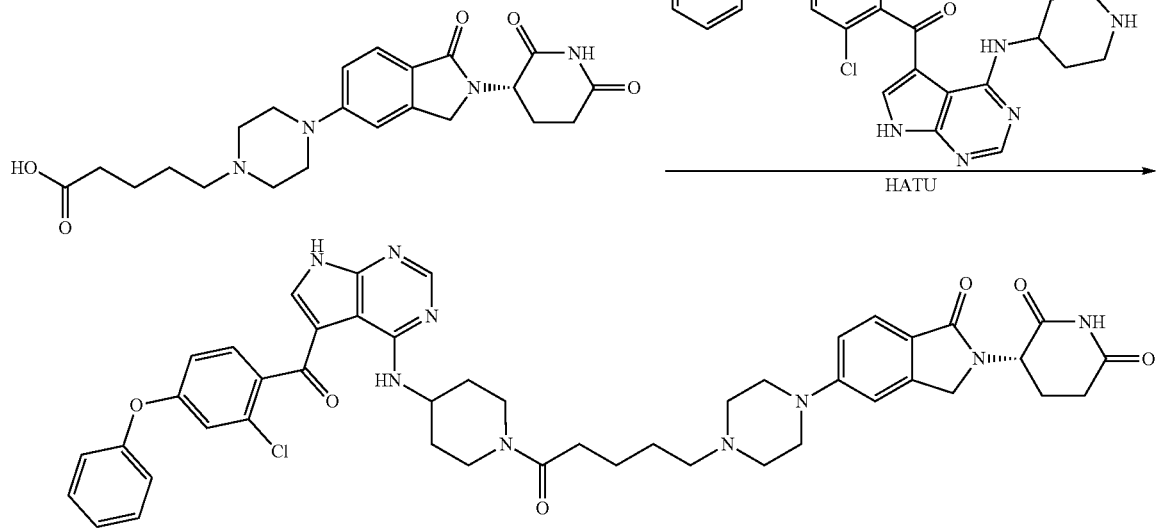

Step 1: Preparation of tert-butyl (S)-5-(4-(2-(2,6-dioxopiperidin-3-yl)-1-oxoisoindolin-5-yl)piperazin-1-yl)pentanoate To a solution of tert-butyl 5-bromopentanoate (200 mg, 0.84 mmol), (S)-3-(1-oxo-5-(piperazin-1-yl)isoindolin-2-yl)piperidine-2,6-dione (410.37 mg, 0.84 mmol) and DIEA (326.87 mg, 2.53 mmol) in MeCN (20 mL) was added KI (14.00 mg, 0.084 mmol) at room temperature. The reaction mixture was stirred at 60° C. for 12 hours. The reaction mixture was evaporated in vacuum to give a crude product. The crude was purified by silica-gel column with DCM/MeOH (50/1-10/1) to afford the product (250 mg, 61%) as a yellow solid. LC/MS: 484.7 [M+H]+.

Step 2: Preparation of (S)-5-(4-(2-(2,6-dioxopiperidin-3-yl)-1-oxoisoindolin-5-yl)piperazin-1-yl)pentanoic acid tert-Butyl (S)-5-(4-(2-(2,6-dioxopiperidin-3-yl)-1-oxoisoindolin-5-yl)piperazin-1-yl)pentanoate (250 mg, 0.52 mmol) was dissolved in DCM (10 mL) and TFA (2 mL). The reaction mixture was stirred at 25° C. for 5 hours. The mixture was concentrated to afford the product (200 mg, 78%) as a brown solid. LC/MS: 428.8 [M+H]+.

Step 3: Preparation of (S)-3-(5-(4-(5-(4-((5-(2-chloro-4-phenoxybenzoyl)-7H-pyrrolo[2,3-d]pyrimidin-4-yl)amino)piperidin-1-yl)-5-oxopentyl)piperazin-1-yl)-1-oxoisoindolin-2-yl)piperidine-2,6-dione To a solution of (S)-5-(4-(2-(2,6-dioxopiperidin-3-yl)-1-oxoisoindolin-5-yl)piperazin-1-yl)pentanoic acid (50 mg, 0.10 mmol), HATU (53.24 mg, 0.14 mmol) and DIEA (45.23 mg, 0.35 mmol) in DCM (15 mL) was stirred for 10 minutes. (2-chloro-4-phenoxyphenyl)(4-(piperidin-4-ylamino)-7H-pyrrolo[2,3-d]pyrimidin-5-yl)methanone (53.24 mg, 0.14 mmol) was added. The mixture was stirred at 25° C. for 2 hours. The solvent was removed and the residue was purified by silica-gel column (DCM/MeOH=20/1) to afford the product (35 mg, 0.04 mmol, 40%) as a yellow solid. LC/MS: 858.3 [M+H]+.
1H NMR (400 MHz, DMSO) δ 12.78 (s, 1H), 10.96 (s, 1H), 10.13 (br, 1H), 8.84 (d, J=7.4 Hz, 1H), 8.27 (s, 1H), 7.64 (s, 1H), 7.60-7.46 (m, 3H), 7.26 (t, J=7.4 Hz, 1H), 7.23-6.97 (m, 5H), 5.06-5.01 (m, 1H), 4.48-4.12 (m, 4H), 4.061-3.81 (m, 2H), 3.66-3.49 (m, 1H), 3.34-3.11 (m, 5H), 3.10-2.76 (m, 3H), 2.67-2.52 (m, 3H), 2.50-2.24 (m, 6H), 2.17-2.08 (m, 2H), 2.01-1.87 (m, 1H), 1.74-1.46 (m, 4H), 1.43-1.31 (m, 1H).

Example 26: Preparation of 5-(4-(3-(4-((5-(2-chloro-4-phenoxybenzoyl)-7H-pyrrolo[2,3-d]pyrimidin-4-yl)amino)piperidin-1-yl)propyl)piperazin-1-yl)-2-(2,6-dioxopiperidin-3-yl)isoindoline-1,3-dione (Compound 26)

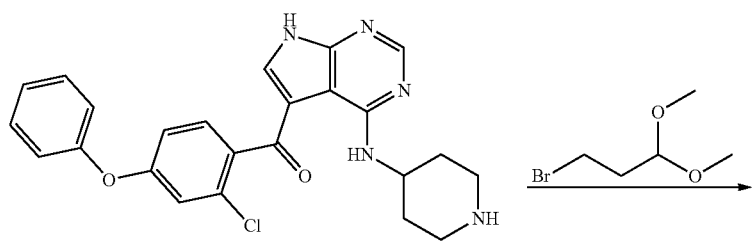

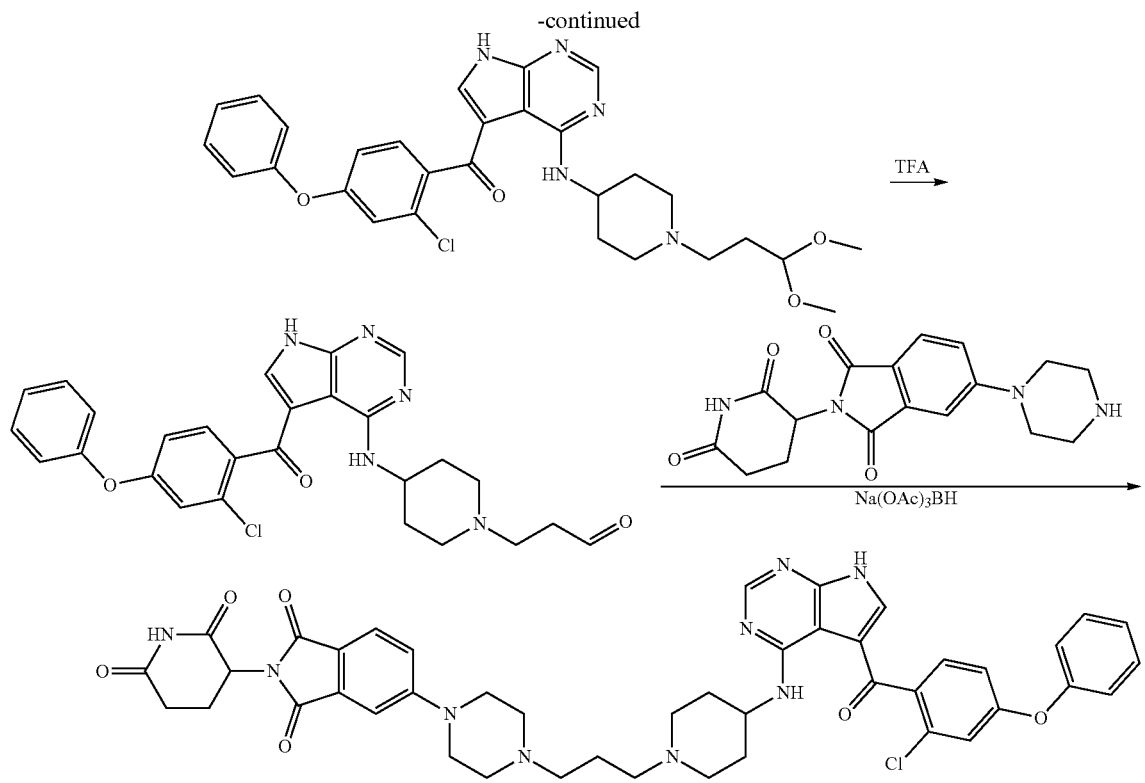
Compound 26 was prepared analogously with the procedure described for Compound 15.
LC/MS: 830.5 [M+H]⁺.
$^1$H NMR (400 MHz, DMSO) δ 12.87 (s, 1H), 11.11 (s, 1H), 8.81 (s, 1H), 8.29 (s, 1H), 7.70 (s, 1H), 7.64-7.56 (m, 1H), 7.53-7.45 (m, 2H), 7.40-7.35 (m, 1H), 7.30-7.23 (m, 2H), 7.22-7.17 (m, 2H), 7.15-7.10 (m, 1H), 7.07-7.00 (m, 1H), 5.17-5.05 (m, 1H), 4.42-4.16 (m, 2H), 3.72-3.41 (m, 7H), 3.27-3.07 (m, 6H), 2.97-2.82 (m, 1H), 2.73-2.53 (m, 3H), 2.37-2.21 (m, 3H), 2.12-1.85 (m, 4H), 1.04-0.72 (m, 2H).
Example 27: Preparation of 5-(4-(4-(4-((5-(2-chloro-4-phenoxybenzoyl)-7H-pyrrolo[2,3-d]pyrimidin-4-yl)amino)piperidin-1-yl)butyl)piperazin-1-yl)-2-(2,6-dioxopiperidin-3-yl)isoindoline-1,3-dione (Compound 27)
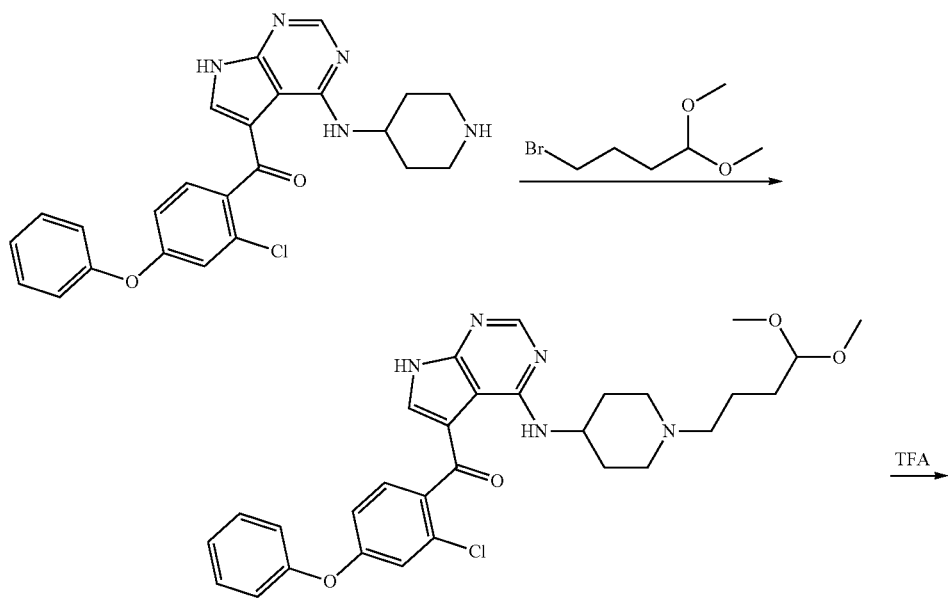

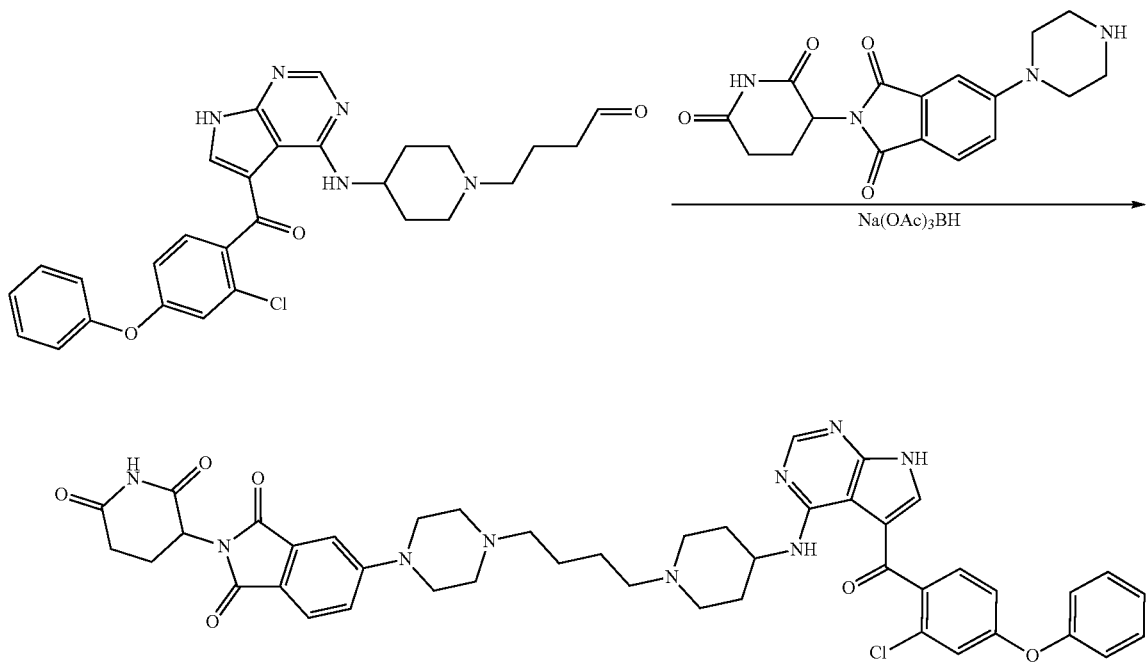
Compound 27 was prepared analogously with the procedure described for Compound 15.
LC/MS: 844.4 [M+H]+.
¹H NMR (400 MHz, DMSO) δ 12.97 (s, 1H), 11.11 (s, 1H), 8.86 (s, 1H), 8.30 (s, 1H), 7.80-7.59 (m, 2H), 7.54-7.43 (m, 3H), 7.39-7.29 (m, 3H), 7.26-7.16 (m, 3H), 5.21-4.98 (m, 1H), 4.35-4.13 (m, 2H), 3.72-3.35 (m, 9H), 3.27-3.18 (m, 4H), 3.01-2.93 (m, 1H), 2.80-2.51 (m, 4H), 2.41-2.19 (m, 4H), 2.08-1.79 (m, 4H), 0.96-0.69 (m, 2H).
Example 28: Preparation of 5-(4-(6-(4-((5-(2-chloro-4-phenoxybenzoyl)-7H-pyrrolo[2,3-d]pyrimidin-4-yl)amino)piperidin-1-yl)-6-oxohexyl)piperazin-1-yl)-2-(2,6-dioxopiperidin-3-yl)isoindoline-1,3-dione (Compound 28)
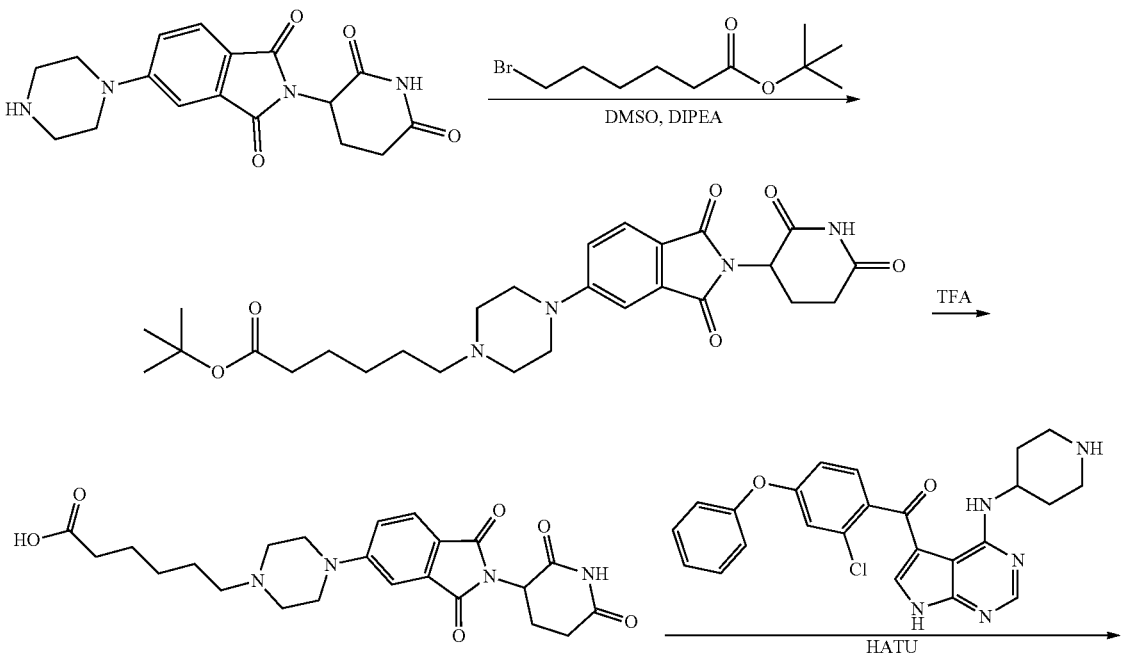

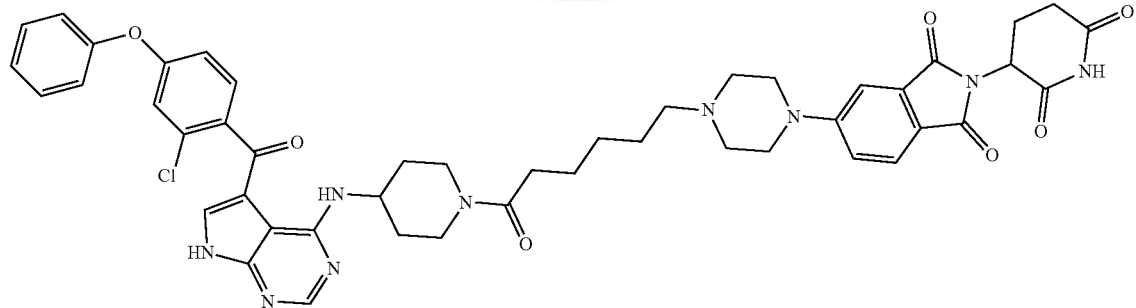
Compound 28 was prepared analogously with the procedure described for Compound 11.
LCMS: m/z=886.3 [M+1]+.
1HNMR (400 MHz, CDCl3): δ 11.06 (s, 1H), 8.85 (s, 1H), 8.229 (s, 1H), 7.69-7.67 (m, 1H), 7.58-7.56 (m, 1H), 7.51-7.49 (m, 2H), 7.32 (s, 1H), 7.28-7.21 (s, 2H), 7.19-7.15 (m, 3H), 7.01-6.99 (s, 1H), 6.65 (s, 1H), 5.32 (s, 2H), 5.11-5.08 (m, 1H), 4.35 (s, 1H), 4.19 (s, 1H), 3.91-3.88 (m, 2H), 2.68 (s, 1H), 2.39-2.31 (m, 5H), 2.09-1.99 (m, 8H), 1.60-1.42 (m, 8H), 0.85 (s, 4H).
Example 29: 5-(4-(7-((R)-3-((5-(2-chloro-4-phenoxybenzoyl)-7H-pyrrolo[2,3-d]pyrimidin-4-yl)amino)piperidin-1-yl)heptyl)piperazin-1-yl)-2-(2,6-dioxopiperidin-3-yl)isoindoline-1,3-dione (Compound 29)
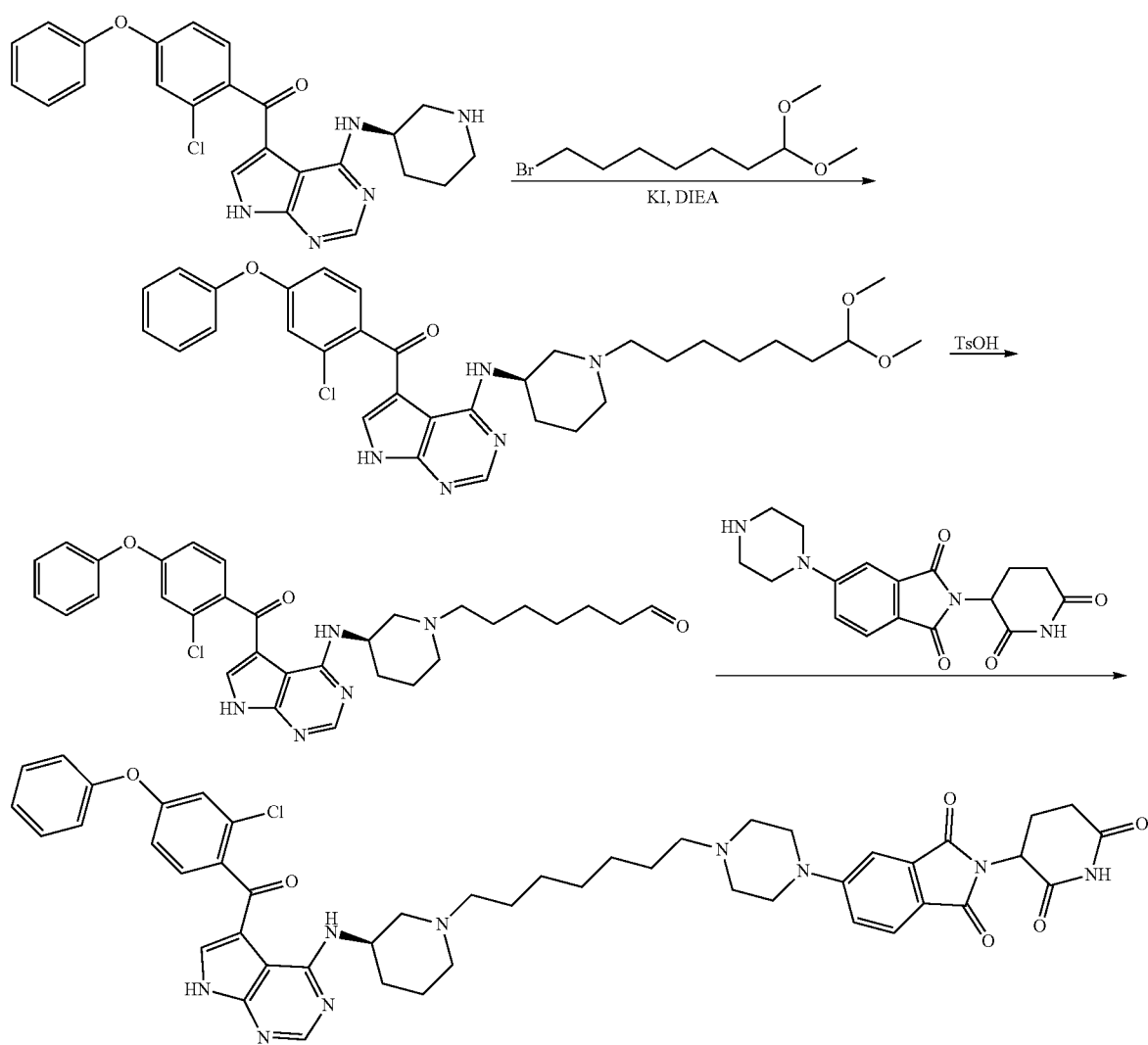

Compound 29 was prepared analogously with the procedure described for Compound 15.
LC/MS: 886.3 [M+H]⁺.
¹H NMR (400 MHz, DMSO) δ 12.89 (br, 1H), 11.10 (s, 1H), 8.79 (s, 1H), 8.31 (s, 1H), 7.77-7.65 (m, 2H), 7.58 (d, J=8.5 Hz, 1H), 7.54-7.45 (m, 2H), 7.44-7.32 (m, 1H), 7.30-7.17 (m, 4H), 7.04 (dd, J=8.5, 2.4 Hz, 1H), 5.09 (dd, J=12.8, 5.3 Hz, 1H), 4.64-4.46 (m, 1H), 4.30-4.12 (m, 1H), 3.81-3.65 (m, 1H), 3.57-3.38 (m, 4H), 3.17-3.02 (m, 3H), 2.98-2.79 (m, 3H), 2.71-2.53 (m, 3H), 2.46-2.21 (m, 3H), 2.20-1.86 (m, 5H), 1.81-1.42 (m, 6H), 1.40-1.27 (m, 6H).
Example 30: Preparation of 5-(4-(5-((R)-3-((5-(2-chloro-4-phenoxybenzoyl)-7H-pyrrolo[2,3-d]pyrimidin-4-yl)amino)piperidin-1-yl)pentyl)piperazin-1-yl)-2-(2,6-dioxopiperidin-3-yl)isoindoline-1,3-dione (Compound 30)
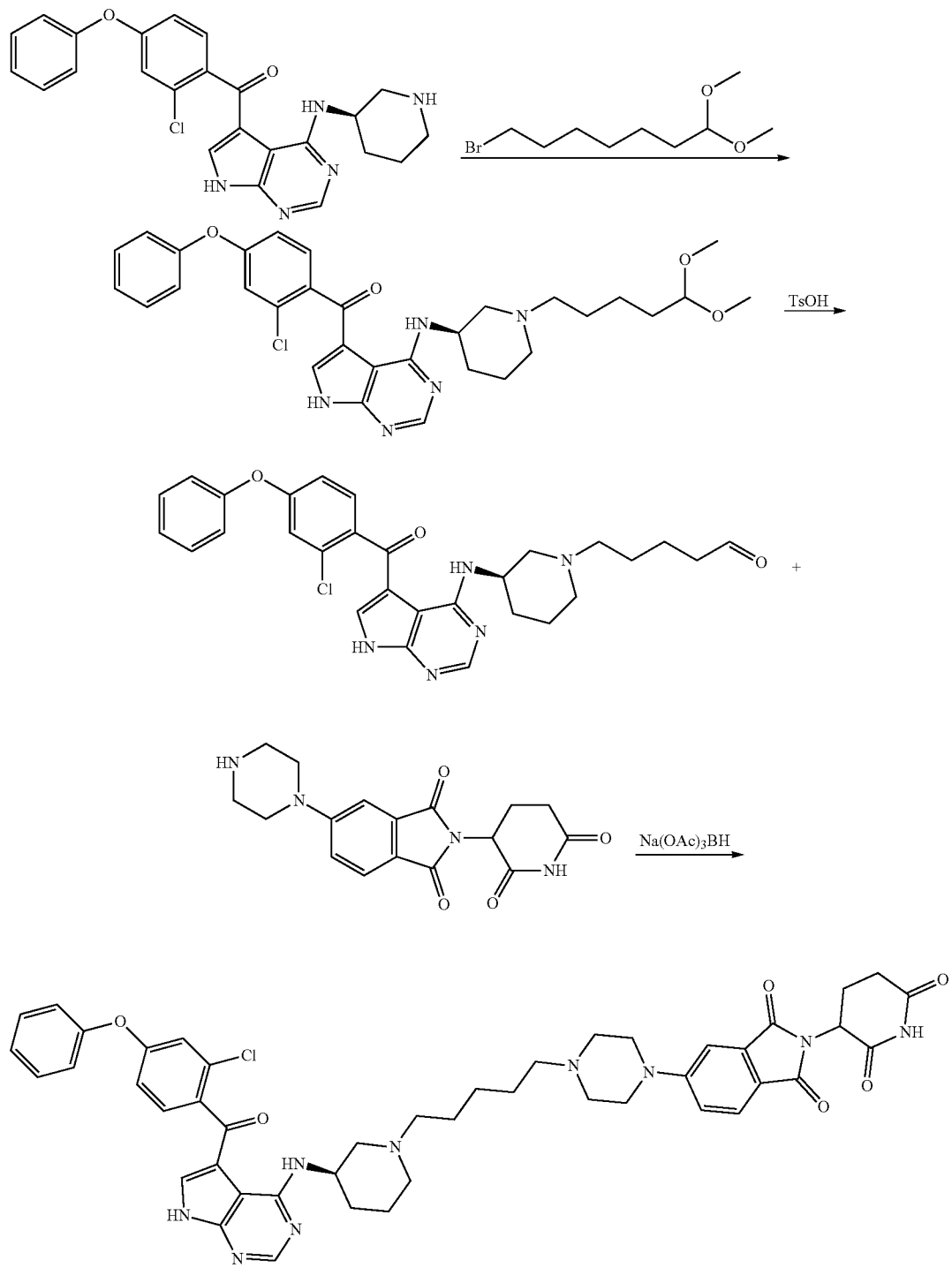

Compound 30 was prepared analogously with the procedure described for Compound 15.
LC/MS: 857.4 [M+H]+.
1H NMR (400 MHz, DMSO) δ 12.87 (br, 1H), 11.10 (s, 1H), 8.82 (br, 1H), 8.30 (s, 1H), 7.75-7.65 (m, 2H), 7.58 (d, J=8.5 Hz, 1H), 7.52-7.46 (m, 2H), 7.41-7.31 (m, 1H), 7.29-7.16 (m, 4H), 7.07-7.01 (m, 1H), 5.13-5.06 (m, 1H), 4.59-4.45 (m, 1H), 3.61-3.43 (m, 5H), 3.07-2.77 (m, 5H), 2.72-2.55 (m, 4H), 2.45-2.25 (m, 3H), 2.15-1.87 (m, 4H), 1.80-1.46 (m, 6H), 1.42-1.17 (m, 4H).
Example 31: Preparation of 5-(4-(5-(4-((5-(2-chloro-4-phenoxybenzoyl)-7H-pyrrolo[2,3-d]pyrimidin-4-yl)amino)piperidin-1-yl)-5-oxopentyl)piperazin-1-yl)-2-(2,6-dioxopiperidin-3-yl)isoindoline-1,3-dione (Compound 31)
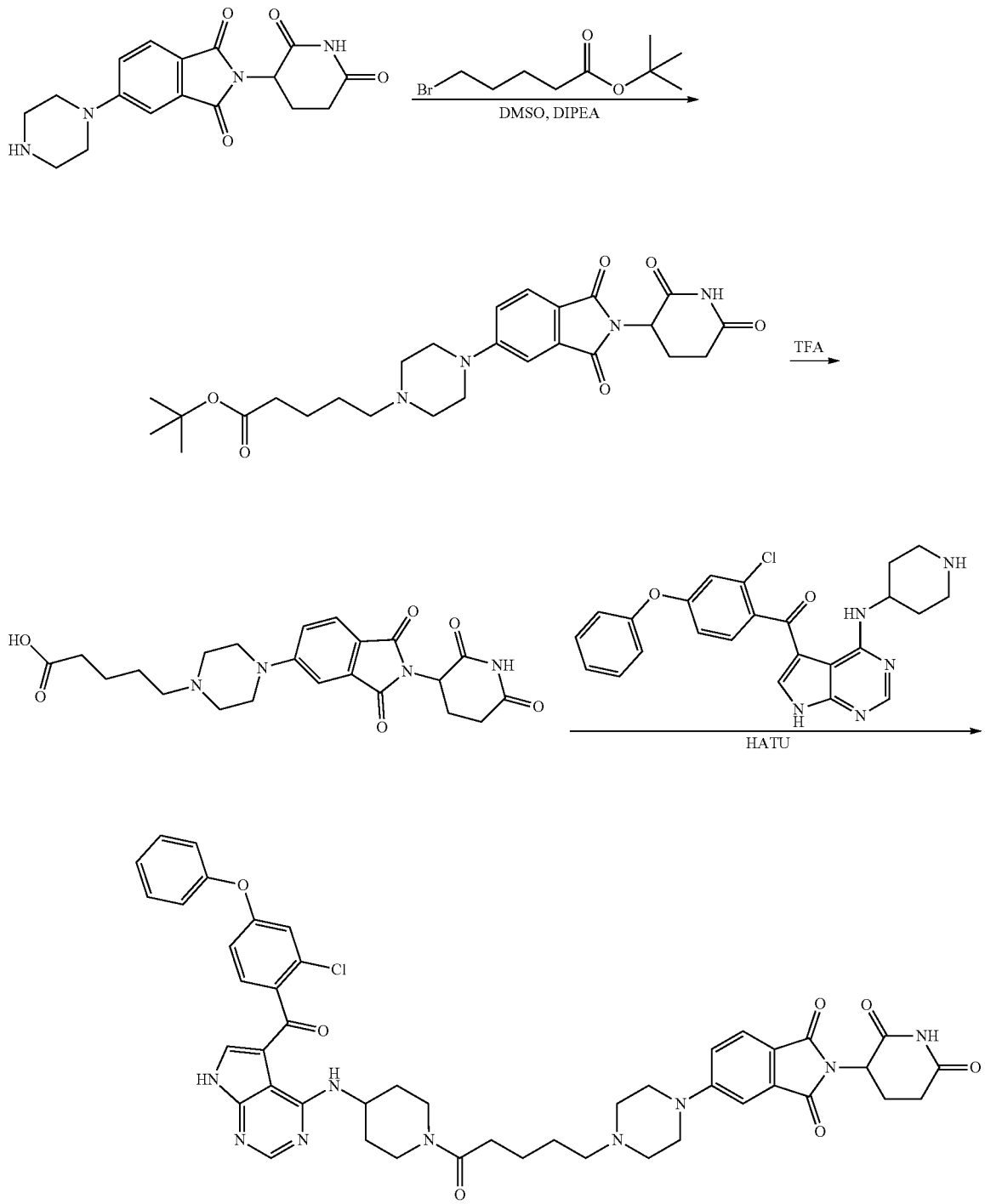

Compound 31 was prepared analogously with the procedure described for Compound 14.

LCMS: m/z=872.3 [M+1]+.

1HNMR (400 MHz, DMSO): δ: 12.91 (s, 1H), 11.09 (s, 1H), 9.71 (s, 1H), 9.01-8.98 (m, 1H), 8.31 (s, 1H), 7.81-7.79 (m, 1H), 7.70 (s, 1H), 7.60 (s, 1H), 7.59-7.49 (m, 3H), 7.45-7.35 (m, 1H), 7.21 (s, 1H), 7.19-7.16 (m, 2H), 7.02 (s, 1H), 5.19-5.09 (m, 1H), 4.31 (s, 2H), 3.89 (s, 2H), 3.61 (s, 1H), 3.39-2.91 (m, 8H), 2.92-2.85 (m, 1H), 2.69-2.59 (m, 1H), 2.45-2.35 (s, 1H), 2.21-2.01 (s, 3H), 1.75 (s, 2H), 1.62-1.52 (m, 3H), 1.49-1.32 (m, 1H), 1.25 (s, 1H).

Example 32: Preparation of (S)-3-(5-(4-((1-((R)-3-((5-(2-chloro-4-phenoxybenzoyl)-7H-pyrrolo[2,3-d]pyrimidin-4-yl)amino)piperidine-1-carbonyl)piperidin-4-yl)methyl)piperazin-1-yl)-1-oxoisoindolin-2-yl)piperidine-2,6-dione (Compound 32)

room temperature was added (S)-3-(1-oxo-5-(piperazin-1-yl)isoindolin-2-yl)piperidine-2,6-dione (117 mg, 0.24 mmol), MgSO4 (288 mg, 2.4 mmol) and TEA (49 mg, 0.48 mmol). The reaction mixture was stirred at room temperature for 30 minutes followed by addition of sodium triacetoxyborohydride (127 mg, 0.6 mmol). The reaction mixture was stirred at room temperature for 1 hour. The solid was filtered off and washed with DCM (5 mL×3). The combined solution was concentrated in vacuum to give a crude product. The crude product was purified by Prep-TLC with PE:EA=1:1 to give the titled product (100 mg, 74%) as a white solid. LC/MS: 560.8 [M+H]+.

Step 2: Preparation of (S)-3-(1-oxo-5-(4-(piperidin-4-ylmethyl)piperazin-1-yl)isoindolin-2-yl)piperidine-2,6-dione A solution of benzyl (S)-4-((4-(2-(2,6-dioxopiperidin-3-yl)-1-oxoisoindolin-5-yl)piperazin-1-yl)methyl)piperidine-

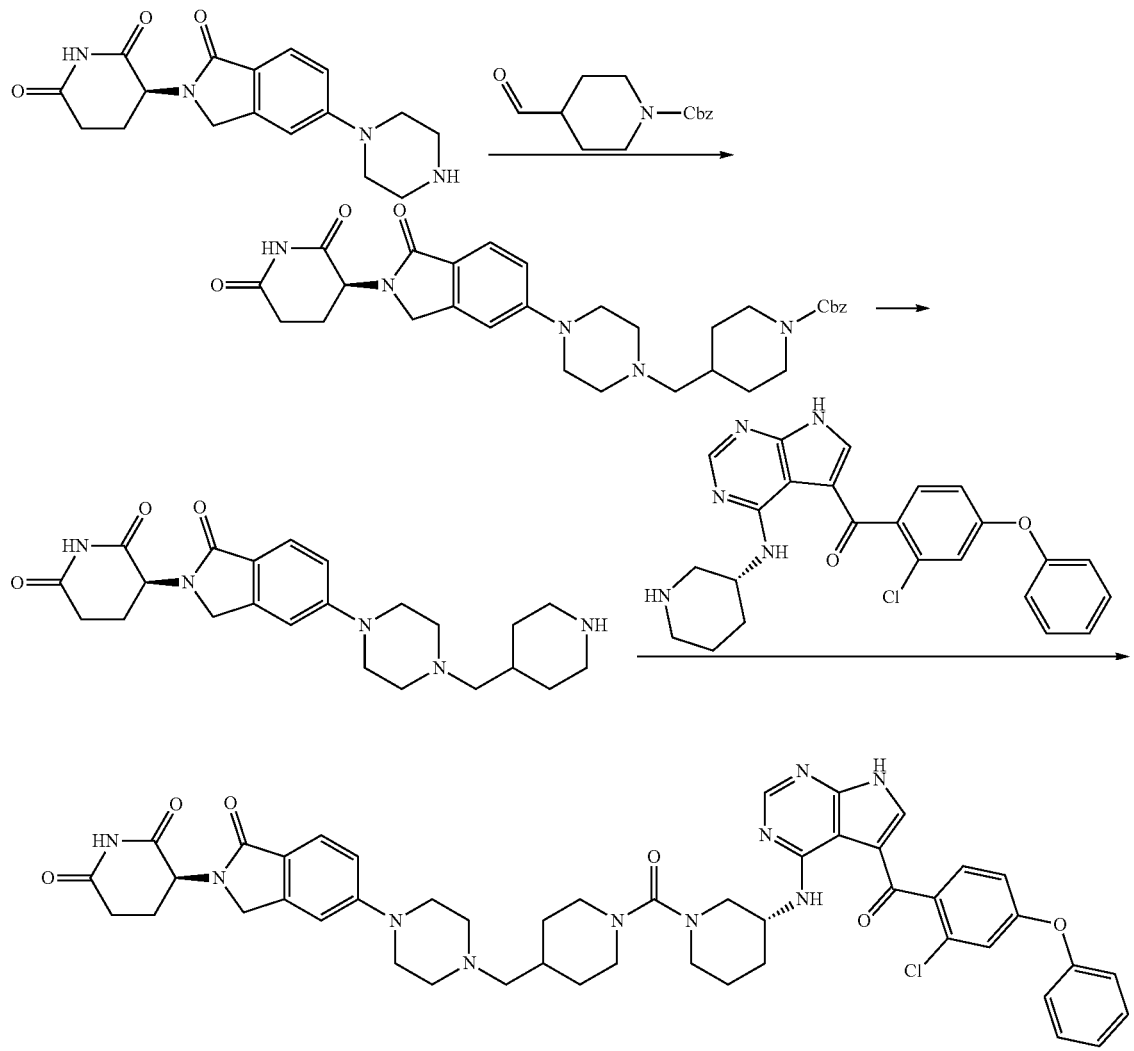

Step 1: Preparation of benzyl (S)-4-((4-(2-(2,6-dioxopiperidin-3-yl)-1-oxoisoindolin-5-yl)piperazin-1-yl)methyl)piperidine-1-carboxylate To a solution benzyl 4-formylpiperidine-1-carboxylate (60 mg, 0.24 mmol) in DCM (10 mL) stirred under argon at 1-carboxylate (100 mg, 0.18 mmol) in TFA (4 mL) was stirred at 70° C. overnight. The mixture was concentrated in vacuum to give a crude product (136 mg) as a yellow solid which was used in the next step without further purification. LC/MS: 426.8[M+H]+.

Step 3: Preparation of (S)-3-(5-(4-((1-((R)-3-((5-(2-chloro-4-phenoxybenzoyl)-7H-pyrrolo[2,3-d]pyrimidin-4-yl)amino)piperidine-1-carbonyl)piperidin-4-yl)methyl)piperazin-1-yl)-1-oxoisoindolin-2-yl)piperidine-2,6-dione To a solution of (R)-(2-chloro-4-phenoxyphenyl)(4-(piperidin-3-ylamino)-7H-pyrrolo[2,3-d]pyrimidin-5-yl)methanone (90 mg, 0.16 mmol) in DCM (5 mL) stirred under argon was added triphosgene (14 mg, 0.05 mmol) and DIEA (124 mg, 0.96 mmol) at room temperature. The reaction mixture was stirred at room temperature for 1 hour. The solution was concentrated in vacuum. The residue was dissolved with DCM (5 mL). (S)-3-(1-oxo-5-(4-(piperidin-4-ylmethyl)piperazin-1-yl)isoindolin-2-yl)piperidine-2,6-dione (136 mg) and DIEA (124 mg, 0.96 mmol) was added. The reaction mixture was stirred at room temperature for 2 hours. The reaction was quenched by adding water (2 mL) and the organic phase was separated. The organic phase was dried over Na$_2$SO$_4$ and concentrated in vacuum to give a crude product. The crude product was purified by Prep-TLC with DCM/MeOH=10:1 to give the product (30 mg, 20%) as a white solid. LC/MS: 898.4 [M+H]$^+$.

$^1$H NMR (400 MHz, DMSO) δ 12.81 (br, 1H), 10.97 (s, 1H), 8.90 (br, 1H), 8.29 (s, 1H), 7.64 (s, 1H), 7.62-7.44 (m, 4H), 7.29-7.15 (m, 4H), 7.13-7.01 (m, 2H), 5.07 (dd, J=13.3, 5.1 Hz, 1H), 4.38-4.18 (m, 3H), 4.00-3.87 (m, 1H), 3.75-3.50 (m, 4H), 3.30-3.20 (m, 2H), 3.17-3.05 (m, 3H), 2.95-2.88 (m, 1H), 2.73-2.53 (m, 4H), 2.46-2.34 (m, 2H), 2.06-1.85 (m, 4H), 1.79-1.45 (m, 5H), 1.37-1.17 (m, 3H), 1.10-0.80 (m, 3H).

Example 33: Preparation of 5-(4-((1-((R)-3-((5-(2-chloro-4-phenoxybenzoyl)-7H-pyrrolo[2,3-d]pyrimidin-4-yl)amino)piperidine-1-carbonyl)piperidin-4-yl)methyl)piperazin-1-yl)-2-((S)-2,6-dioxopiperidin-3-yl)isoindoline-1,3-dione (Compound 33)

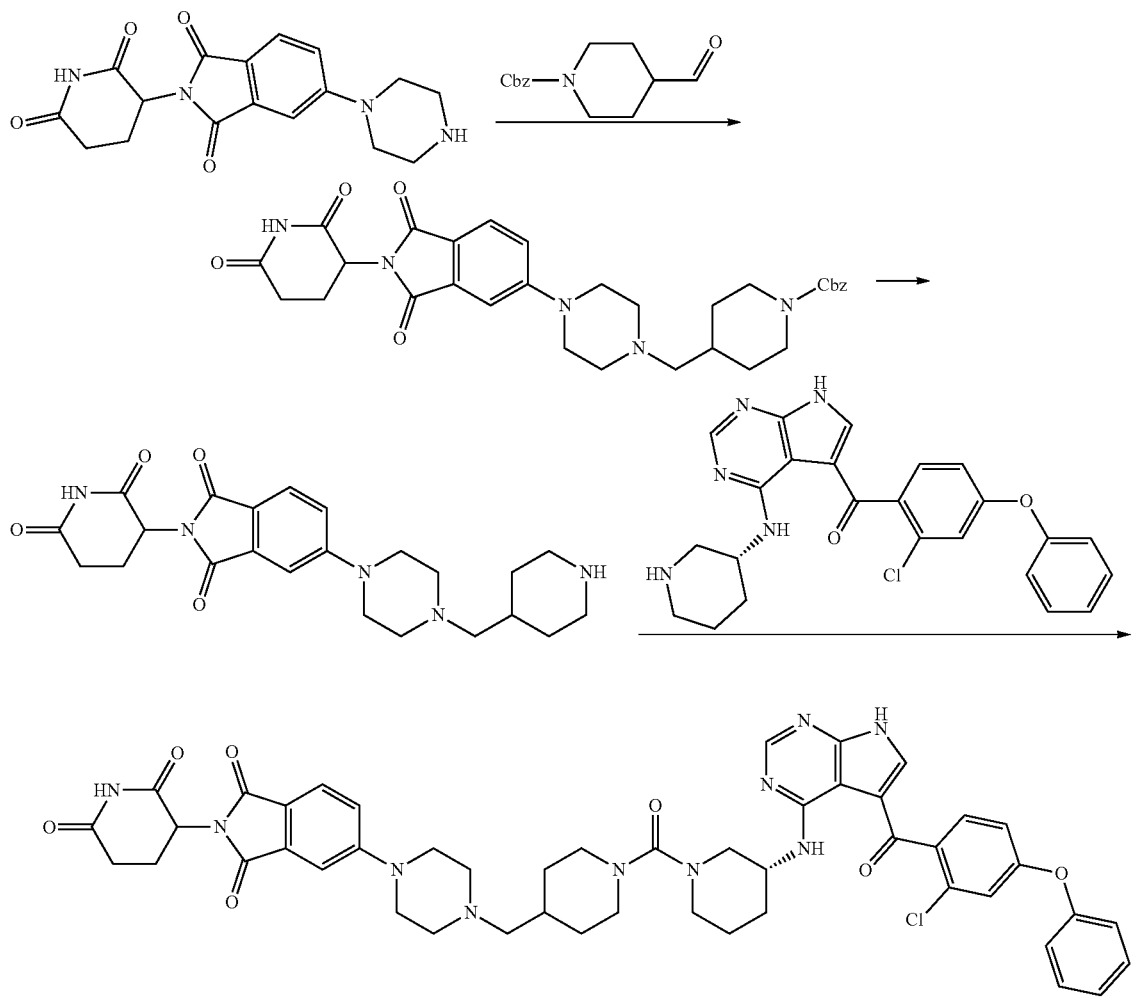

Compound 33 was prepared analogously with the procedure described for Compound 32.

LC/MS: 913.2[M+H]$^+$.

$^1$H NMR (400 MHz, DMSO) δ 12.79 (s, 1H), 11.11 (s, 1H), 8.90 (s, 1H), 8.28 (s, 1H), 7.76-7.62 (m, 2H), 7.57 (d, J=8.5 Hz, 1H), 7.51-7.44 (m, 2H), 7.40-7.31 (m, 1H), 7.30-7.15 (m, 4H), 7.12-7.00 (m, 1H), 5.14-5.05 (m, 1H), 4.35-4.12 (m, 2H), 3.68-3.40 (m, 6H), 3.02-2.84 (m, 5H), 2.70-2.61 (m, 2H), 2.59-2.54 (m, 1H), 2.46-2.33 (m, 2H), 2.19-1.84 (m, 5H), 1.72-1.48 (m, 4H), 1.33-1.14 (m, 3H), 0.99-0.72 (m, 3H).

Example 34: Preparation of 5-(4-(5-(4-((5-(2-chloro-4-phenoxybenzoyl)-7H-pyrrolo[2,3-d]pyrimidin-4-yl)amino)piperidin-1-yl)pentyl)piperazin-1-yl)-2-(2,6-dioxopiperidin-3-yl)isoindoline-1,3-dione (Compound 34)

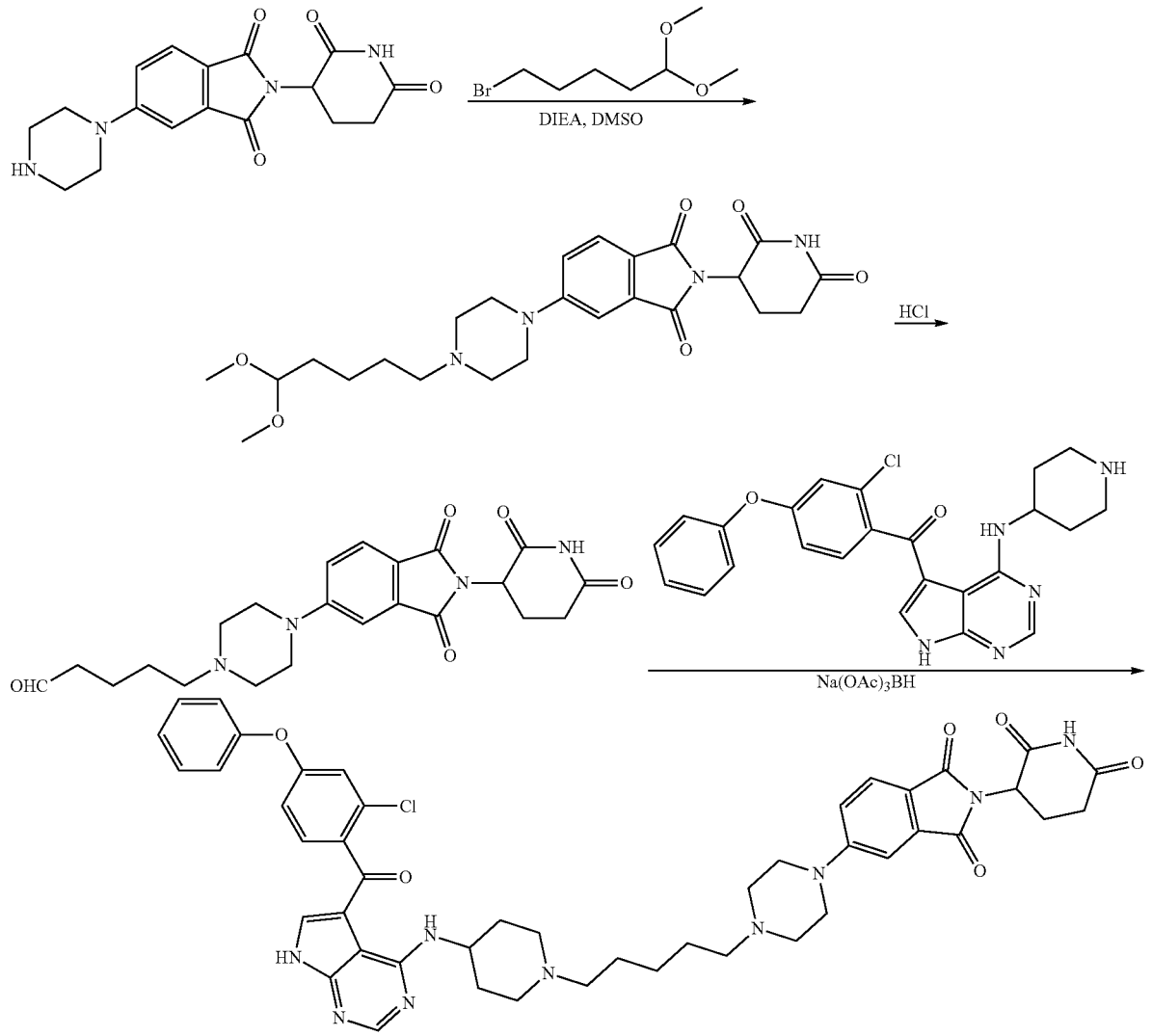

Step 1: Preparation of 5-(4-(5,5-dimethoxypentyl)piperazin-1-yl)-2-(2,6-dioxopiperidin-3-yl)isoindoline-1,3-dione To the solution of 5-bromo-1,1-dimethoxypentane (250 mg, 1.19 mmol) in DMSO (10 mL) was added 2-(2,6-dioxopiperidin-3-yl)-5-(piperazin-1-yl)isoindoline-1,3-dione (340 mg, 0.994 mmol) and DIEA (350 mg 2.71 mmol). The mixture was stirred at 70° C. for 12 hrs and extracted with ethyl acetate. The combined organic phase was washed with aqueous sodium chloride solution and then dried over $Na_2SO_4$. The solvent was removed under vacuum and the residue was purified by Prep-TLC (DCM/MeOH=10/1) to give the desired product (135 mg, 24%) as a yellow solid.

Step 2: Preparation of 5-(4-(2-(2,6-dioxopiperidin-3-yl)-1,3-dioxoisoindolin-5-yl)piperazin-1-yl)pentanal 5-(4-(5,5-dimethoxypentyl)piperazin-1-yl)-2-(2,6-dioxopiperidin-3-yl)isoindoline-1,3-dione (360 mg, 0.762 mmol) was dissolved in 2N HCl/dioxane (10 mL) and the reaction mixture was stirred at room temperature for 3 hrs. The mixture was adjusted to pH 8-9 with aqueous $NaHCO_3$ solution and then extracted with EtOAc (40 mL×3). The organic layer was washed with water and brine and dried over $Na_2SO_4$. The solvent was removed by rotary evaporation and the residue was purified by Prep-TLC (DCM/MeOH=20/1) to afford 5-(4-(2-(2,6-dioxopiperidin-3-yl)-1,3-dioxoisoindolin-5-yl)piperazin-1-yl)pentanal (240 mg, 70%).

Step 3: Preparation of 5-(4-(5-(4-((5-(2-chloro-4-phenoxybenzoyl)-7H-pyrrolo[2,3-d]pyrimidin-4-yl)amino)piperidin-1-yl)pentyl)piperazin-1-yl)-2-(2,6-dioxopiperidin-3-yl)isoindoline-1,3-dione To a solution of (2-chloro-4-phenoxyphenyl)(4-(piperidin-4-ylamino)-7H-pyrrolo[2,3-d]pyrimidin-5-yl)methanone (220 mg 0.492 mmol) in DCM (3 mL) was added potassium acetate (72.3 mg 0.738 mmol). The mixture was stirred for 30 min. A solution of 5-(4-(2-(2,6-dioxopiperidin-3-yl)-1,3-dioxoisoindolin-5-yl)piperazin-1-yl)pentanal (210 mg, 0.492 mmol) and AcOH (44.28 mg, 0.738 mmol) in DCM (5 mL) was added. After stirring for 30 min, sodium triacetoxyborohydride (312 mg 1.476 mmol) was added and the mixture was stirred at room temperature overnight. The mixture was extracted with EtOAc (30 mL×3). The organic layer was washed with water and brine and dried over Na$_2$SO$_4$. The solvent was removed by rotary evaporation and the residue was purified by prep-HPLC to give 5-(4-(5-(4-((5-(2-chloro-4-phenoxybenzoyl)-7H-pyrrolo[2,3-d]pyrimidin-4-yl)amino)piperidin-1-yl)pentyl)piperazin-1-yl)-2-(2,6-dioxopiperidin-3-yl)isoindoline-1,3-dione (43.1 mg, 9.7%) as a white solid. LCMS: m/z=860.3 [M+H]$^+$.

1H NMR (400 MHz, DMSO) δ 12.87 (s, 1H), 11.09 (s, 1H), 10.11 (s, 1H), 9.52 (s, 1H), 8.82 (d, J=6.4 Hz, 1H), 8.29 (s, 1H), 7.69-7.59 (m, 1H) 7.58 (s, 1H), 7.56 (s, 1H), 7.50-7.48 (m, 2H), 7.45-7.44 (m, 1H), 7.42-7.40 (m, 1H), 7.25-7.23 (m, 2H), 7.09-7.01 (s, 1H), 5.12-5.07 (m, 2H), 4.26-4.23 (m, 4H), 3.61 (s, 4H), 3.61-3.58 (m, 2H), 3.21-3.12 (s, 9H), 2.99-2.81 (m, 2H), 2.69-2.52 (m, 2H), 2.40 (d, J=2.4 Hz, 2H), 2.15 (s, 1H), 2.09-1.98 (m, 2H), 1.35 (s, 2H).

Example 35: Preparation of 4-(9-(4-((5-(2-chloro-4-phenoxybenzoyl)-7H-pyrrolo[2,3-d]pyrimidin-4-yl)amino)piperidin-1-yl)-9-oxonon-1-yn-1-yl)-2-(2,6-dioxopiperidin-3-yl)isoindoline-1,3-dione
(Compound 35)

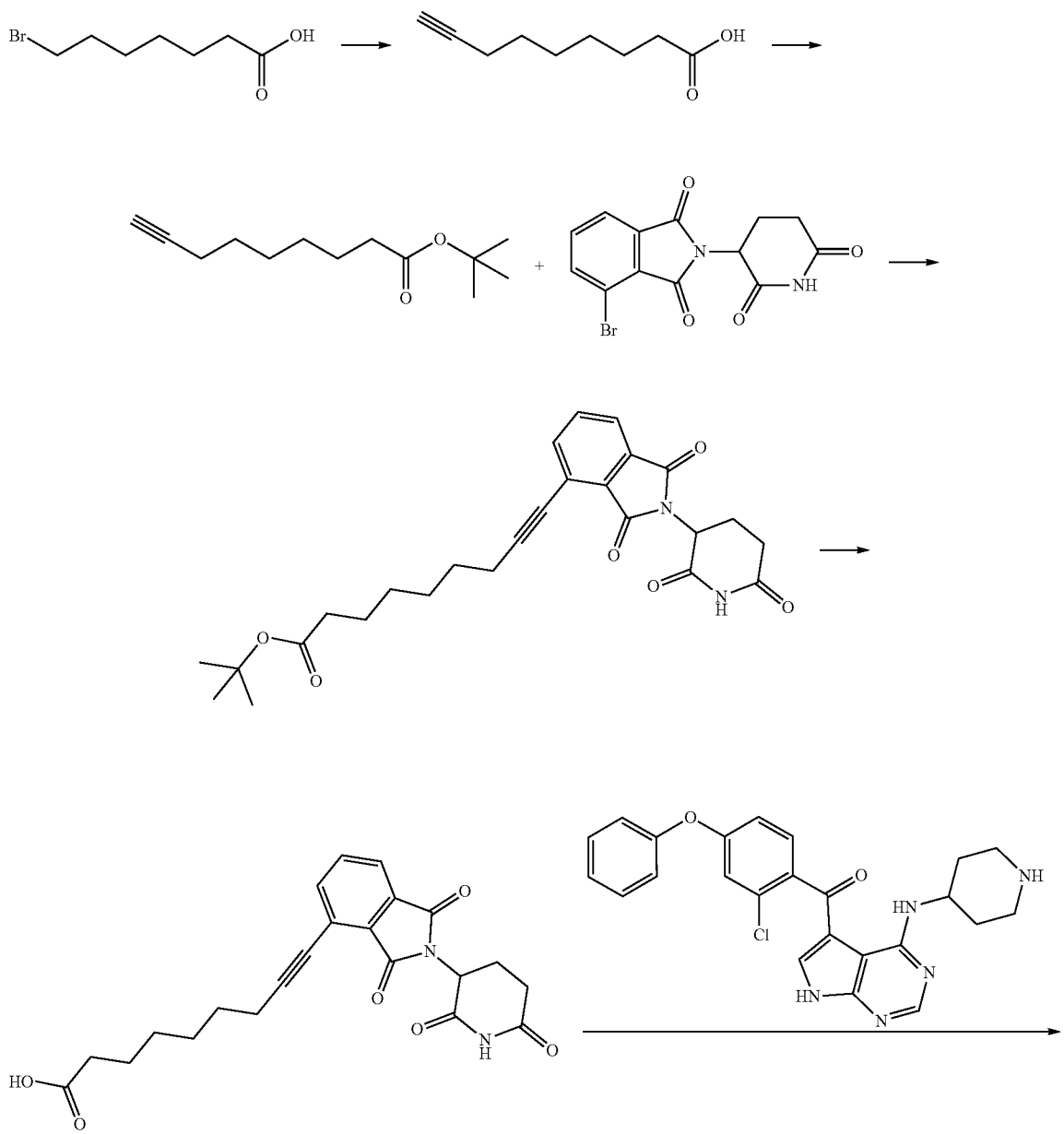

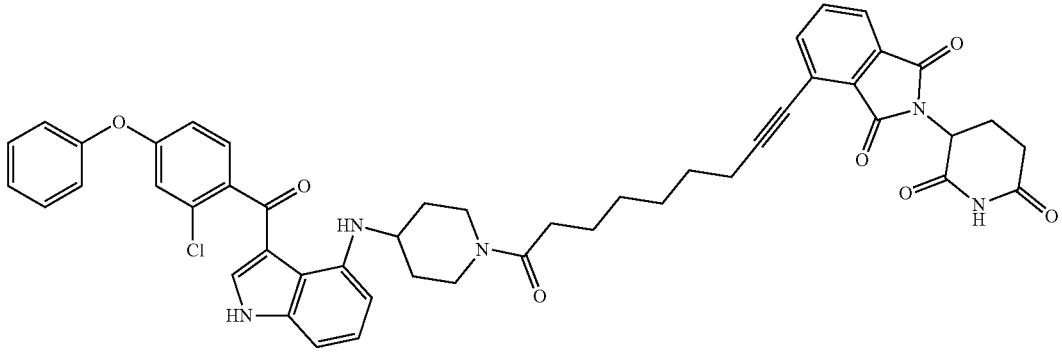

Step 1: Preparation of non-8-ynoic acid

To a solution of lithium acetylide-ethylenediamine complex (2.20 g, 21.5 mmol, 90%) in DMSO (5 mL) was added 7-bromoheptanoic acid (1.50 g, 7.17 mmol) in DMSO (7 mL) dropwise at 0° C. The solution was stirred at room temperature for 2 hours. The reaction mixture was poured into ice/water, acidified with 1N HCl and extracted with DCM. The organic layer was dried over $Na_2SO_4$ and concentrated in vacuum. The residue was purified by flash column chromatography (10~30% of EA in PE) to yield the titled compound (713 mg, 64%) as a clear oil. LC/MS: 155.1 $[M+H]^+$.

$^1$H NMR (400 MHz, $CDCl_3$) δ 2.38 (t, J=7.5 Hz, 2H), 2.21 (td, J=7.0, 2.6 Hz, 2H), 1.96 (t, J=2.6 Hz, 1H), 1.71-1.63 (m, 2H), 1.60-1.52 (m, 2H), 1.49-1.38 (m, 4H).

Step 2: Preparation of tert-butyl non-8-ynoate

To a solution of non-8-ynoic acid (900 mg, 5.84 mmol), anhydrous N, N-dimethylformamide (85 mg, 1.17 mmol) in anhydrous DCM (20 mL) stirred under Ar at room temperature was added oxalyl chloride (1.5 g, 11.68 mmol) dropwise. The reaction mixture was stirred at room temperature for 1 hour. The mixture was evaporated under vacuum and the residue was dissolved in anhydrous THF (20 mL). The solution was cooled to 0° C. and t-BuOK (1.3 g, 11.68 mmol) was added portion wise. The mixture was stirred at room temperature for 1 hour. The reaction was quenched by adding ice-water and extracted with $Et_2O$. The organic layer was dried over $Na_2SO_4$ and evaporated in vacuum. The residue was purified by flash chromatography with PE/EA=10:1 to yield the titled compound (657 mg, 53%) as a clear oil.

LC/MS: 232.9 $[M+Na]^+$.

$^1$H NMR (400 MHz, $CDCl_3$) δ 2.26-2.17 (m, 4H), 1.96 (t, J=2.6 Hz, 1H), 1.65-1.52 (m, 4H), 1.46 (s, 9H), 1.45-1.30 (m, 4H).

Step 3: Preparation of tert-butyl 9-(2-(2,6-dioxopiperidin-3-yl)-1,3-dioxoisoindolin-4-yl) non-8-ynoate A suspension of tert-butyl non-8-ynoate (63 mg, 0.3 mmol), 4-bromo-2-(2,6-dioxopiperidin-3-yl)isoindole-1,3-dione (50 mg, 0.15 mmol), Copper(I) iodide (6.3 mg, 0.033 mmol), bis(triphenyl phosphine)palladium(II) chloride (11 mg, 0.017 mmol) and $Et_3N$ (2 mL) in THF (5 mL) was stirred at 70° C. under Ar atmosphere for 10 hours. The mixture was cooled to room temperature and filtered. The filtrate was evaporated under vacuum. The residue was purified by prep-TLC with PE/EA=1:1 to give the titled compound (48 mg, 68%) as white solid.

LC/MS: 488.7 $[M+Na]^+$.

Step 4: Preparation of 9-(2-(2,6-dioxopiperidin-3-yl)-1,3-dioxoisoindolin-4-yl) non-8-ynoic acid A solution of tert-butyl 9-(2-(2,6-dioxopiperidin-3-yl)-1,3-dioxoisoindolin-4-yl) non-8-ynoate (30 mg, 0.06 mmol) in TFA (1 mL) and DCM (3 mL) was stirred at room temperature for 2 hours. The mixture was evaporated under vacuum to give crude product (33 mg) which was used in the next step without further purification. LC/MS: 432.7 $[M+Na]^+$.

Step 5: Preparation of 4-(9-(4-((5-(2-chloro-4-phenoxybenzoyl)-7H-pyrrolo[2,3-d] pyrimidin-4-yl)amino)piperidin-1-yl)-9-oxonon-1-yn-1-yl)-2-(2,6-dioxopiperidin-3-yl)isoindoline-1,3-dione A mixture of 9-(2-(2,6-dioxopiperidin-3-yl)-1,3-dioxoisoindolin-4-yl) non-8-ynoic acid (33 mg, 80% purity, 0.06 mmol), (2-chloro-4-phenoxyphenyl)(4-(piperidin-4-ylamino)-7H-pyrrolo[2,3-d]pyrimidin-5-yl)methanone (31 mg, 0.070 mmol), HATU (40 mg, 0.11 mmol), N, N-diisopropylethylamine (27 mg, 0.21 mmol) and DMF (5 mL) was stirred at room temperature for 2 hours. The mixture was concentrated under vacuum and purified by prep-TLC with DCM/MeOH=10:1 to give the titled compound (16.1 mg, 29%) as white solid.

LC/MS: 839.5 $[M+H]^+$.

$^1$H NMR (400 MHz, DMSO) δ 12.78 (br, 1H), 11.15 (br, 1H), 8.83 (s, 1H), 8.26 (s, 1H), 7.88-7.80 (m, 3H), 7.65-7/62 (m, 1H), 7.59 (d, J=8.0 Hz, 1H), 7.49 (t, J=7.7 Hz, 2H), 7.29-7.17 (m, 4H), 7.03 (d, J=7.6 Hz, 1H), 5.18-5.12 (m, 1H), 4.35-4.06 (m, 2H), 3.91-3.76 (m, 1H), 3.05-2.85 (m, 2H), 2.70-2.57 (m, 2H), 2.37-2.35 (m, 2H), 2.30-2.20 (m, 3H), 1.63-1.48 (m, 8H), 1.36-1.25 (m, 5H).

Example 36: Preparation of 4-(7-(4-((5-(2-chloro-4-phenoxybenzoyl)-7H-pyrrolo[2,3-d]pyrimidin-4-yl)amino)piperidin-1-yl)-7-oxohept-1-yn-1-yl)-2-(2,6-dioxopiperidin-3-yl)isoindoline-1,3-dione (Compound 36)
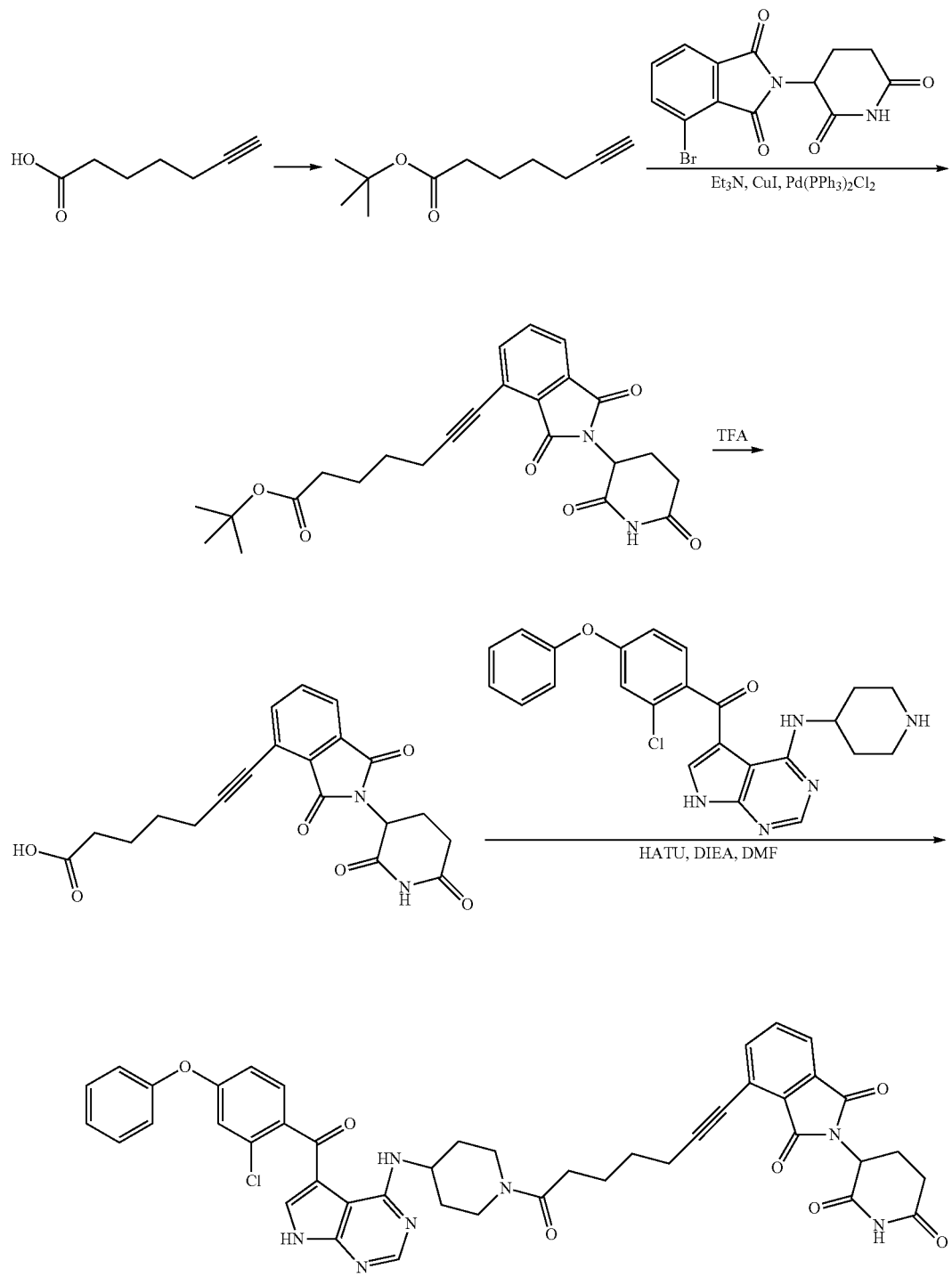

Compound 36 was prepared analogously with the procedure described for compound 35.

LC/MS: 811.4 [M+H]$^+$.

$^1$H NMR (400 MHz, DMSO) δ 12.78 (br, 1H), 11.16 (s, 1H), 8.82 (d, J=6.5 Hz, 1H), 8.26 (s, 1H), 7.91-7.87 (m, 3H), 7.64 (s, 1H), 7.58 (d, J=8.3 Hz, 1H), 7.49 (t, J=7.3 Hz, 2H), 7.30-7.25 (m, 1H), 7.28-7.22 (m, 3H), 7.07-7.02 (m, 1H), 5.18-5.11 (m, 1H), 4.39-4.14 (m, 2H), 3.90-3.80 (m, 1H), 3.07-2.81 (m, 2H), 2.70-2.58 (m, 2H), 2.43-2.31 (m, 2H), 2.15-2.02 (m, 3H), 1.78-1.61 (m, 4H), 1.60-1.30 (m, 3H), 1.30-1.03 (m, 2H).

Example 37: Preparation of 5-(4-(3-(2-(4-((5-(2-chloro-4-phenoxybenzoyl)-7H-pyrrolo[2,3-d]pyrimidin-4-yl)amino)piperidin-1-yl)-2-oxoethyl)cyclobutyl)piperazin-1-yl)-2-(2,6-dioxopiperidin-3-yl)isoindoline-1,3-dione (Compound 37)

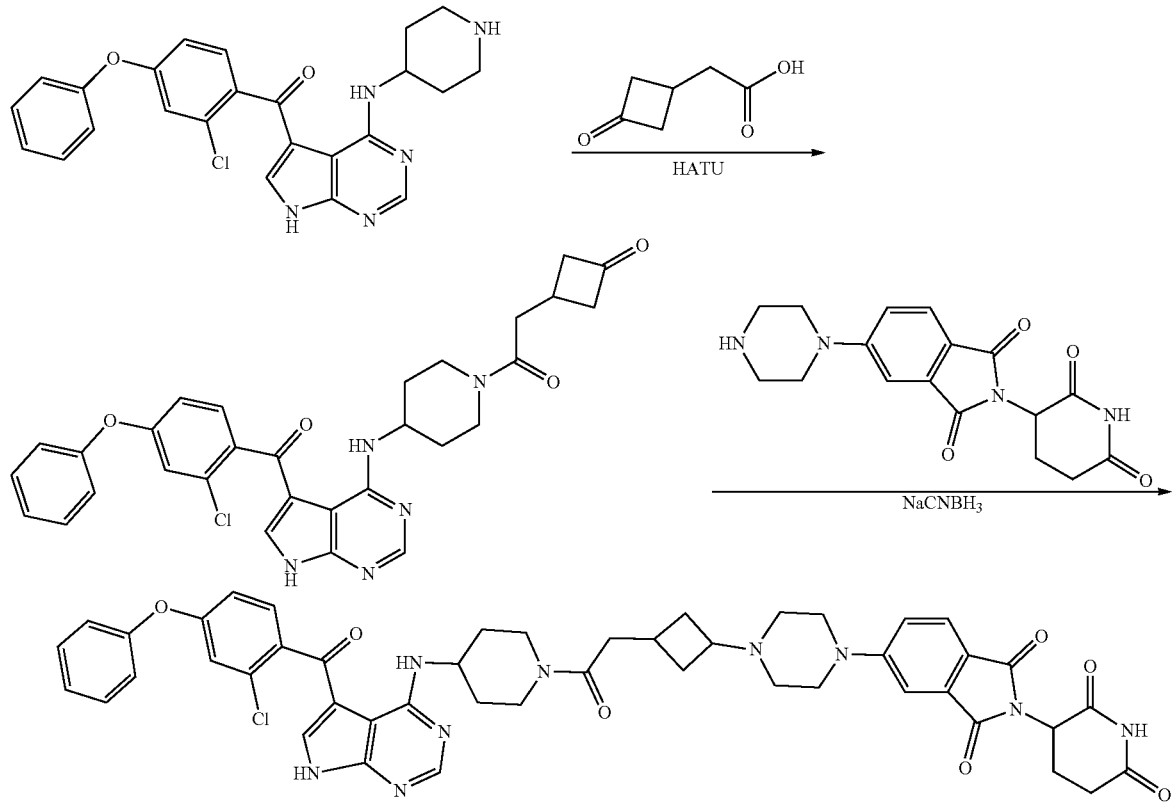

Step 1: Preparation of 3-(2-(4-((5-(2-chloro-4-phenoxybenzoyl)-7H-pyrrolo[2,3-d]pyrimidin-4-yl)amino)piperidin-1-yl)-2-oxoethyl)cyclobutan-1-one To a solution of (3-oxocyclobutyl) acetic acid (250 mg, 1.95 mmol) in DMF (10 ml) stirred at room temperature was added HATU (890 mg, 2.34 mmol), DIEA (756 mg, 5.85 mmol) and (2-chloro-4-phenoxyphenyl)(4-(piperidin-4-ylamino)-7H-pyrrolo[2,3-d]pyrimidin-5-yl)methanone (944 mg, 1.95 mmol). The reaction mixture was stirred at room temperature for 12 hours. The mixture was poured into water (40 mL) and extracted with EtOAc (50 mL×2). The combined organic layer was washed with brine, dried over Na$_2$SO$_4$ and concentrated in vacuum to give a crude product. The crude product was purified by flash chromatography (DCM/MeOH=10:1) to give the desired product (1 g, 91.79%) as a yellow solid. LC/MS: 558.0 [M+H]$^+$.

Step 2: Preparation of 5-(4-(3-(2-(4-((5-(2-chloro-4-phenoxybenzoyl)-7H-pyrrolo[2,3-d]pyrimidin-4-yl)amino)piperidin-1-yl)-2-oxoethyl)cyclobutyl)piperazin-1-yl)-2-(2,6-dioxopiperidin-3-yl)isoindoline-1,3-dione To a solution of 3-{2-[4-({5-[(2-chloro-4-phenoxyphenyl)carbonyl]-7H-pyrrolo[2,3-d]pyrimidin-4-yl}amino)piperidin-1-yl]-2-oxoethyl}cyclobutan-1-one (1 g, 1.79 mmol) in MeOH/DMF/AcOH (8 mL, 4 mL, 0.5 mL) stirred at room temperature was added 2-(2,6-dioxopiperidin-3-yl)-5-(piperazin-1-yl)isoindoline-1,3-dione (678 mg, 1.79 mmol) and NaBH$_3$CN (169 mg, 2.685 mmol). The reaction mixture was stirred at 60° C. for 1 hour. The mixture was concentrated in vacuum to give a crude product. The crude product was purified by flash chromatography (DCM/MeOH=10:1) to give the desired product (290 mg, 18.44%) as a yellow solid. LC/MS: 884.1 [M+H]$^+$.

$^1$H NMR (400 MHz, DMSO) δ 12.76 (s, 1H), 11.09 (s, 1H), 10.1 (br, 1H), 8.83 (d, J=7.2 Hz, 1H), 8.26 (s, 1H), 7.85-7.72 (m, 1H), 7.64 (s, 1H), 7.58 (d, J=8.4 Hz, 1H), 7.48 (t, J=8.4 Hz, 2H), 7.35-7.30 (m, 1H), 7.26 (t, J=7.6 Hz, 2H), 7.2-7.16 (m, 3H), 7.03 (dd, J=8.4, 2.4 Hz, 1H), 5.18-5.05 (m, 1H), 4.40-4.30 (m, 1H), 4.19-4.13 (m, 1H), 3.86-3.82 (m, 1H), 3.48-3.39 (m, 3H), 3.29-3.25 (m, 2H), 3.05-2.80 (m, 4H), 2.64-2.53 (m, 3H), 2.43-2.30 (m, 4H), 2.27-2.21 (m, 2H), 2.18-1.95 (m, 4H), 1.61-1.48 (m, 2H), 1.40-1.35 (m, 1H).

Example 38: Preparation of 4-(8-(4-((5-(2-chloro-4-phenoxybenzoyl)-7H-pyrrolo[2,3-d]pyrimidin-4-yl)amino)piperidin-1-yl)-8-oxooct-1-yn-1-yl)-2-(2,6-dioxopiperidin-3-yl)isoindoline-1,3-dione
(Compound 38)
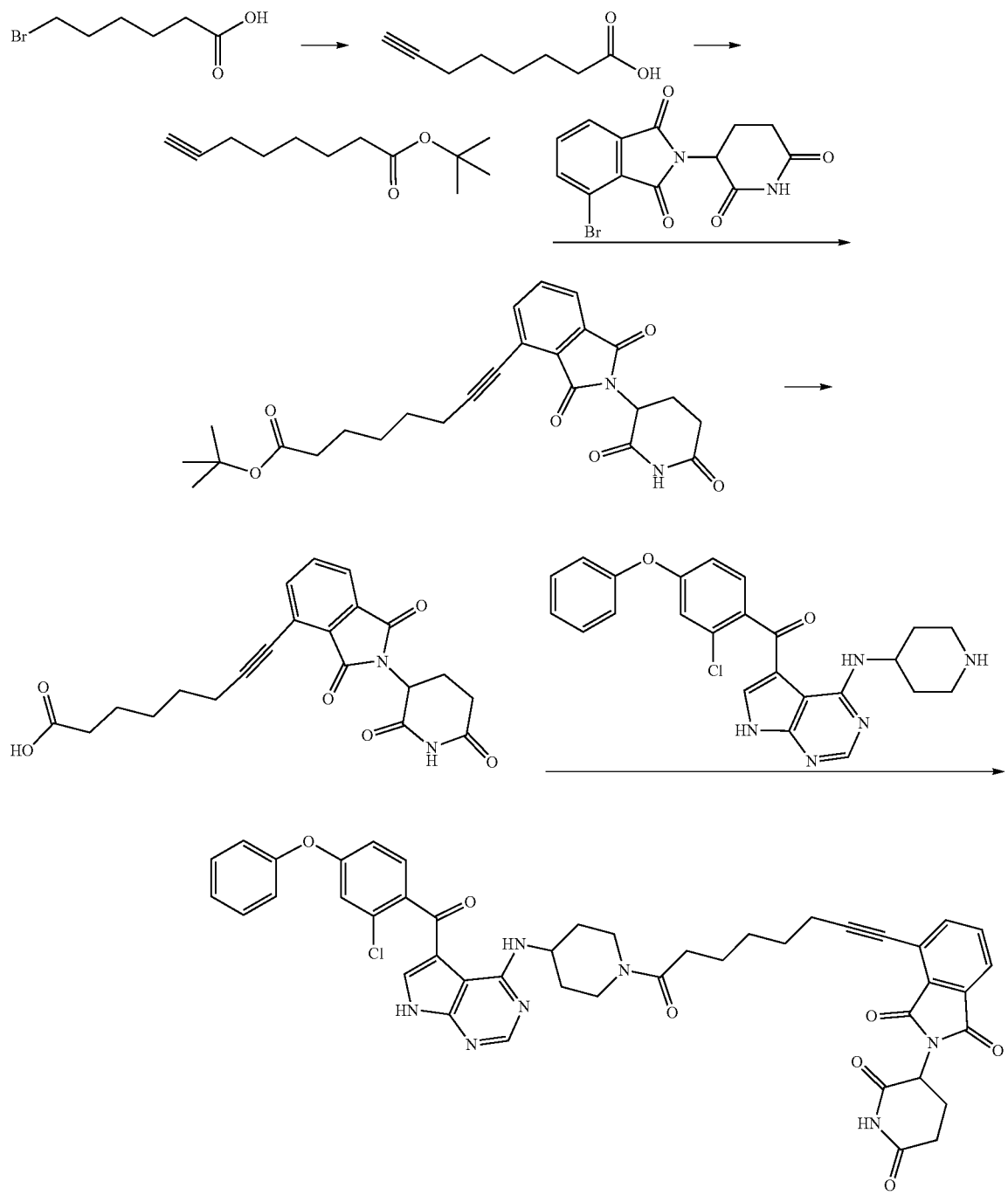
Compound 38 was prepared analogously with the procedure described for compound 35.
LC/MS: 825.5 [M+H]+.
1H NMR (400 MHz, DMSO) δ 12.77 (br, 1H), 11.15 (s, 1H), 8.83 (d, J=7.3 Hz, 1H), 8.26 (s, 1H), 7.87-7.81 (m, 3H), 7.63 (s, 1H), 7.58 (d, J=8.5 Hz, 1H), 7.52-7.46 (m, 2H), 7.26 (t, J=7.4 Hz, 1H), 7.22-7.17 (m, 3H), 7.02 (dd, J=8.5, 2.3 Hz, 1H), 5.15 (dd, J=12.9, 5.3 Hz, 1H), 4.35-4.20 (m, 1H), 4.18-4.13 (m, 1H), 3.85 (d, J=14.3 Hz, 1H), 3.32-3.26 (m, 1H), 3.05-2.98 (m, 1H), 2.92-2.84 (m, 1H), 2.63-2.53 (m, 3H), 2.42-2.32 (m, 3H), 2.09-2.01 (m, 3H), 1.64-1.51 (m, 6H), 1.44-1.29 (m, 2H).

Example 39: Preparation of 3-(4-(9-(4-((5-(2-chloro-4-phenoxybenzoyl)-7H-pyrrolo[2,3-d]pyrimidin-4-yl)amino)piperidin-1-yl)-9-oxonon-1-yn-1-yl)-1-oxoisoindolin-2-yl)piperidine-2,6-dione
(Compound 39)

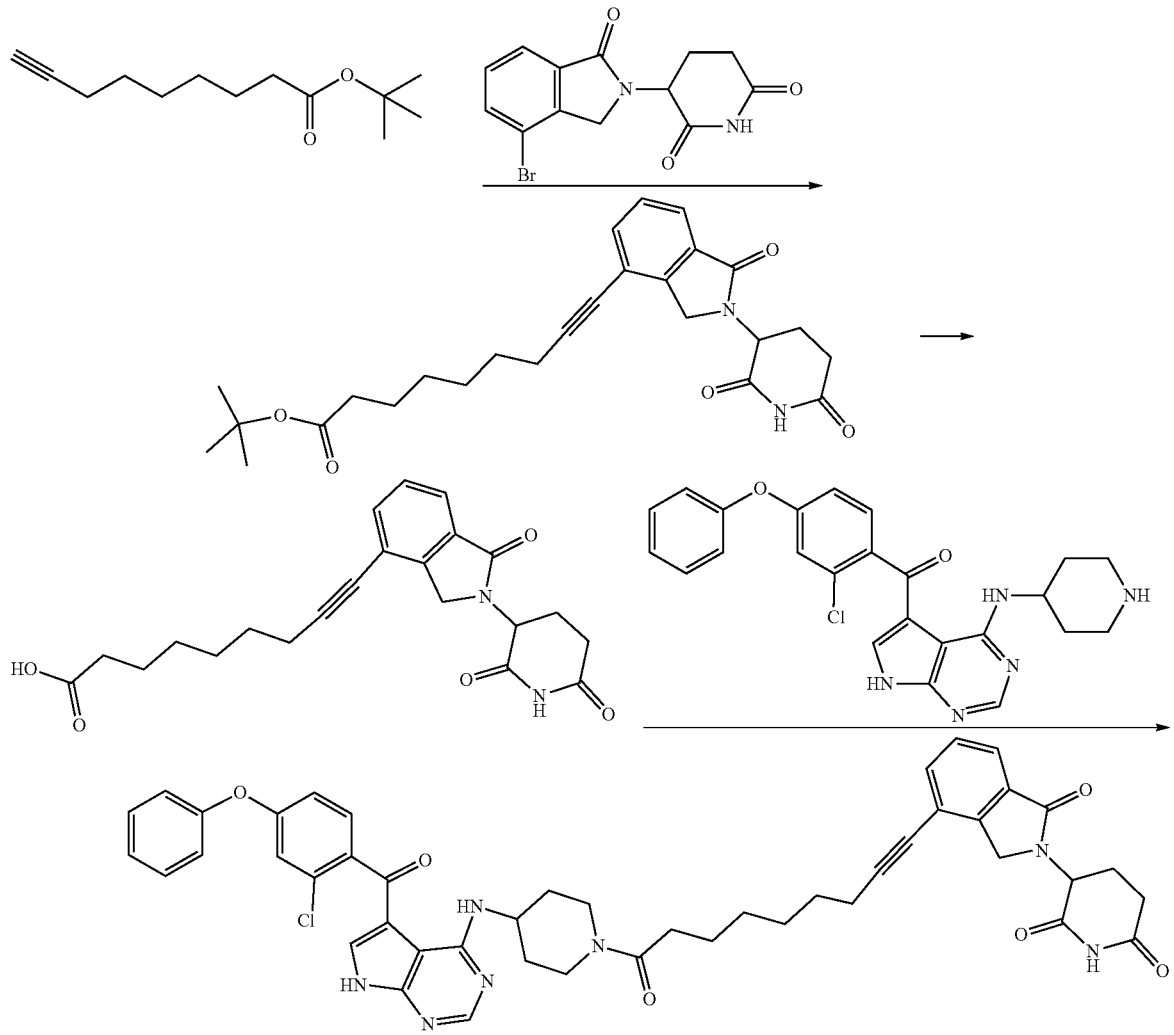

Compound 39 was prepared analogously with the procedure described for compound 35.

LC/MS: 825.5 [M+H]⁺.

¹H NMR (400 MHz, DMSO) δ 12.76 (br, 1H), 11.00 (br, 1H), 9.00-8.75 (m, 1H), 8.26 (br, 1H), 7.72-7.46 (m, 7H), 7.35-7.16 (m, 4H), 7.12-7.04 (m, 1H), 5.23-5.10 (m, 1H), 4.51-4.42 (m, 1H), 4.39-4.27 (m, 2H), 4.22-4.12 (m, 1H), 3.89-3.77 (m, 1H), 3.01-2.88 (m, 2H), 2.76-2.65 (m, 2H), 2.38-2.33 (m, 2H), 2.04 (s, 3H), 1.70-1.30 (m, 13H).

Example 40: Preparation of 3-(4-(8-(4-((5-(2-chloro-4-phenoxybenzoyl)-7H-pyrrolo[2,3-d]pyrimidin-4-yl)amino) piperidin-1-yl)-8-oxooct-1-yn-1-yl)-1-oxoisoindolin-2-yl)piperidine-2,6-dione
(Compound 40)

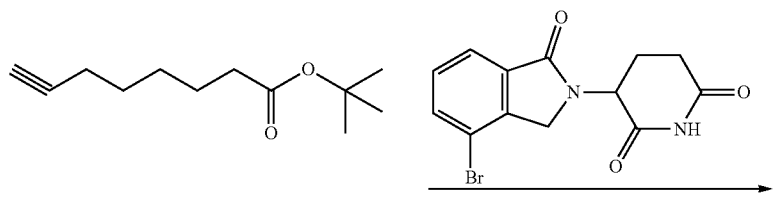

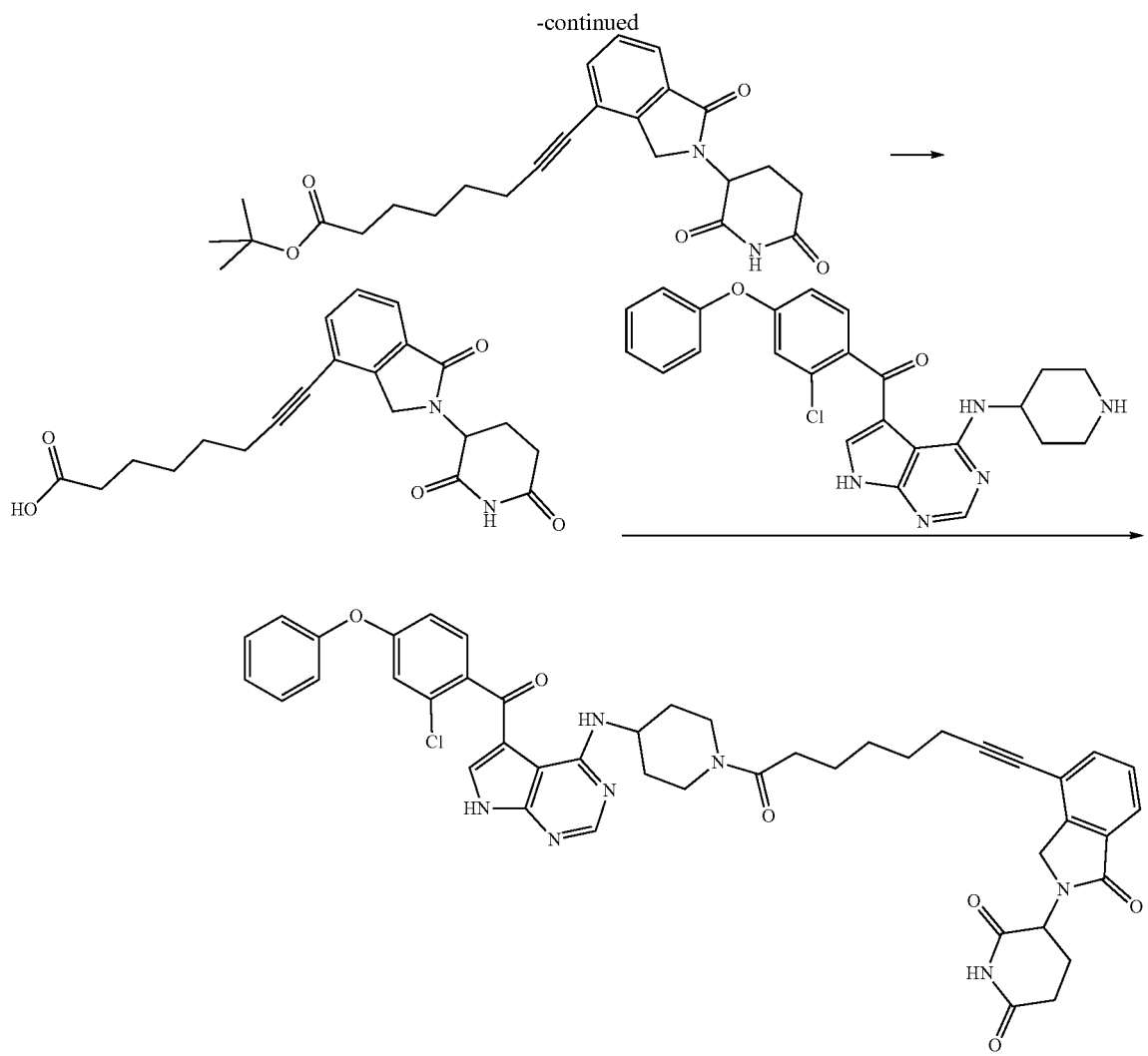
Compound 40 was prepared analogously with the procedure described for compound 35.
LC/MS: 811.5 [M+H]+.
¹H NMR (400 MHz, DMSO) δ 12.76 (br, 1H), 11.00 (s, 1H), 8.82 (d, J=7.4 Hz, 1H), 8.26 (s, 1H), 7.70 (d, J=7.0 Hz, 1H), 7.64 (t, J=3.4 Hz, 2H), 7.58 (d, J=8.5 Hz, 1H), 7.54-7.43 (m, 3H), 7.28-7.24 (m, 1H), 7.20-7.18 (m, 2H), 7.02 (dd, J=8.5, 2.4 Hz, 1H), 5.19-5.10 (m, 1H), 4.53-4.45 (m, 1H), 4.39-4.25 (m, 2H), 4.20-4.15 (m, 1H), 3.90-3.81 (m, 1H), 3.29-3.25 (m, 1H), 3.04-2.85 (m, 3H), 2.70-2.66 (m, 1H), 2.62-2.54 (m, 2H), 2.40-2.33 (m, 2H), 2.10-1.98 (m, 3H), 1.63-1.36 (m, 8H), 1.29-1.21 (m, 1H).
Example 41: Preparation of 3-(4-(7-(4-((5-(2-chloro-4-phenoxybenzoyl)-7H-pyrrolo[2,3-d]pyrimidin-4-yl)amino)piperidin-1-yl)-7-oxohept-1-yn-1-yl)-1-oxoisoindolin-2-yl)piperidine-2,6-dione (Compound 41)
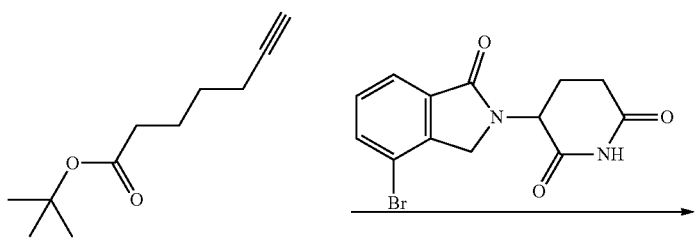

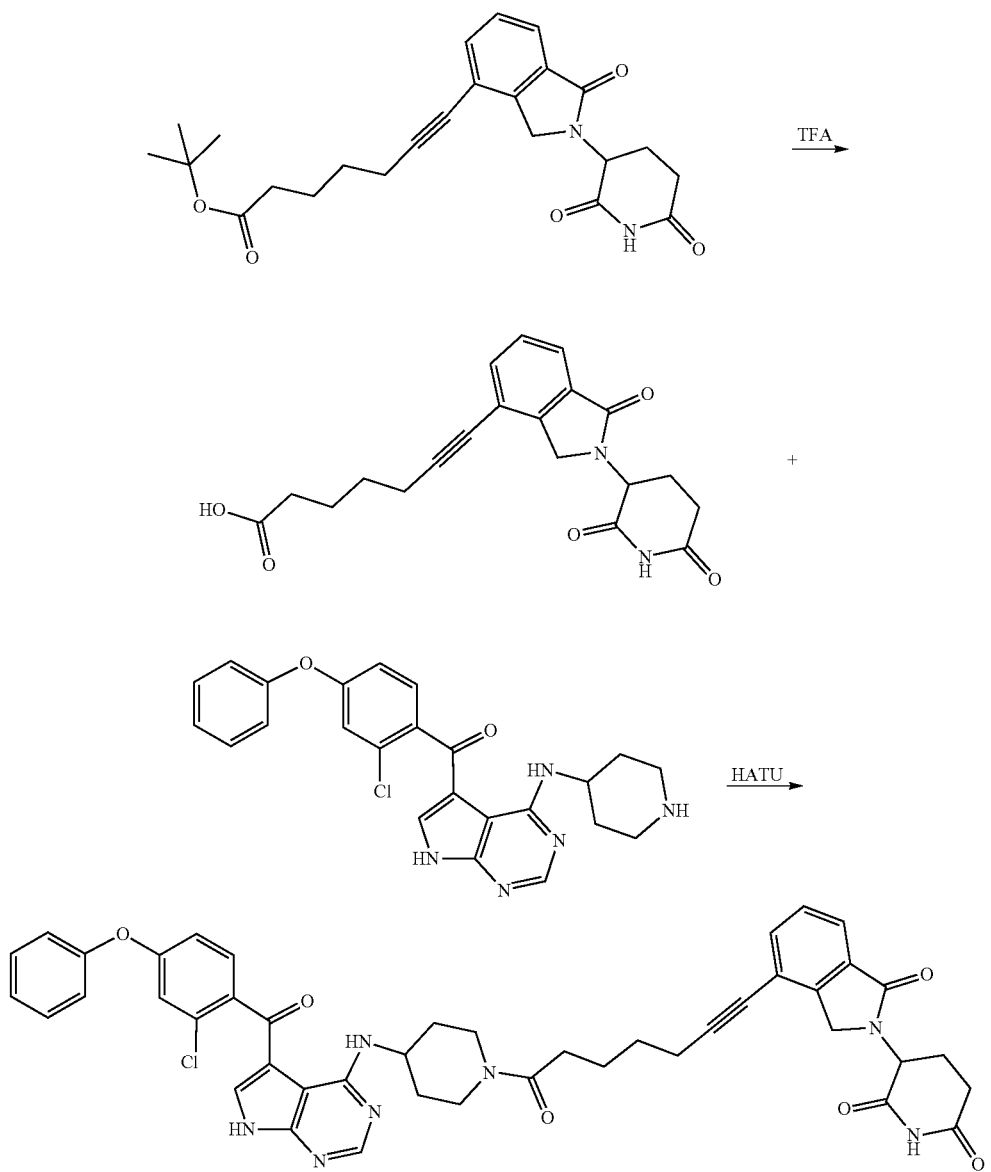

Compound 41 was prepared analogously with the procedure described for compound 35.

LC/MS: 798.3[M+H]⁺.

¹H NMR (400 MHz, DMSO) δ 12.79 (s, 1H), 11.1-10.9 (m, 1H), 8.82 (d, J=7.6 Hz, 1H), 8.26 (s, 1H), 7.70 (d, J=6.8 Hz, 1H), 7.63 (t, J=3.6 Hz, 2H), 7.58 (d, J=8.4 Hz, 1H), 7.54-7.43 (m, 3H), 7.30-7.23 (m, 1H), 7.23-7.14 (m, 3H), 7.02 (dd, J=8.4, 2.4 Hz, 1H), 5.15 (dd, J=13.2, 4.6 Hz, 1H), 4.50-4.45 (m, 1H), 4.35-4.28 (m, 2H), 4.20-4.10 (m, 1H), 3.89-3.80 (m, 1H), 3.65-3.57 (m, 1H), 3.33-3.25 (m, 1H), 3.15-3.08 (m, 1H), 3.02-2.87 (m, 2H), 2.62-2.53 (m, 2H), 2.42 (t, J=7.2 Hz, 2H), 2.09-1.97 (m, 3H), 1.72-1.60 (m, 3H), 1.55-1.46 (m, 1H), 1.41-1.31 (m, 2H).

Example 42: Preparation of (S)-3-(5-(4-(3-(2-(4-((5-(2-chloro-4-phenoxybenzoyl)-7H-pyrrolo[2,3-d]pyrimidin-4-yl)amino)piperidin-1-yl)-2-oxoethyl)cyclobutyl)piperazin-1-yl)-1-oxoisoindolin-2-yl)piperidine-2,6-dione (Compound 42)

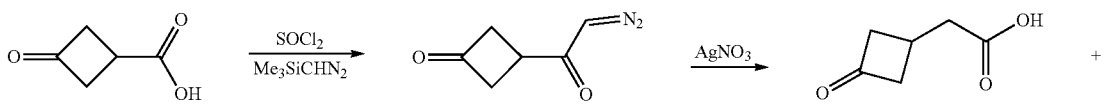

-continued

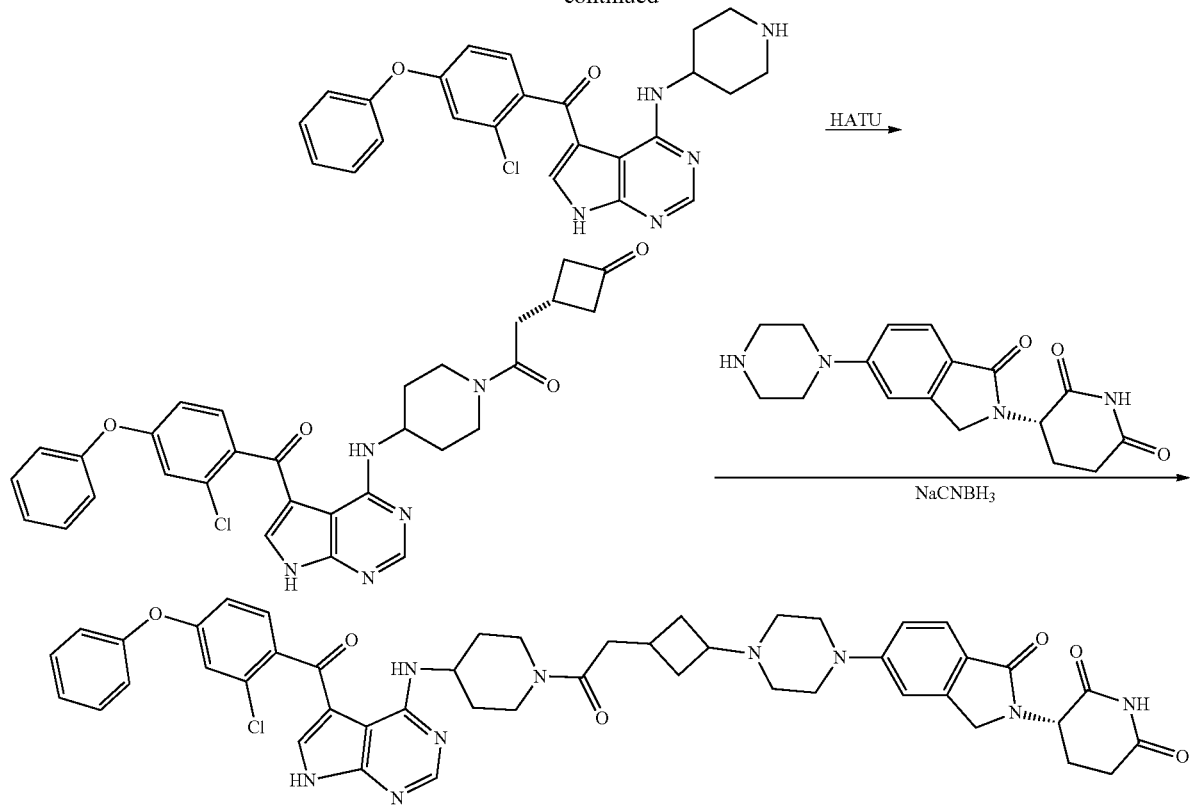

Step 1: Preparation of 3-(2-diazoacetyl)cyclobutan-1-one

To a solution of 3-oxocyclobutane-1-carboxylic acid (2 g, 17.54 mmol) in DCM (10 mL) was added SOCl₂ (3.84 mL). The reaction mixture was stirred at 20° C. for 2 hours. The mixture was evaporated to dryness under reduced pressure. To a solution of the residue in THF (5 mL) and acetonitrile (5 mL) was added (diazomethyl)trimethylsilane (2 M in hexane, 17.5 mL). The reaction mixture was stirred at 20° C. for overnight and then evaporated under vacuum to give a crude product. The crude product was purified by column chromatography (silica gel, PE/EA=2:1) to afford the title compound (1.6 g, 52.8% yield) as a yellow oil. LC/MS: 139.1 [M+H]⁺.

Step 2: Preparation of 2-(3-oxocyclobutyl)acetic acid

To a solution of 3-(2-diazoacetyl)cyclobutan-1-one (1.6 g, 9.27 mmol) in THF (30 mL) and water (15 mL) was added AgNO₃ (1.87 g, 11.12 mmol). The reaction mixture was stirred at room temperature for overnight then evaporated in vacuum to remove THF. The aqueous phase was extracted with EA (20 mL×3). The combined organic layer was dried over Na₂SO₄ and evaporated under vacuum to afford the title compound (1.0 g, 76.4% yield) as a yellow oil. LC/MS: 127.1 [M−H]⁻.

Step 3: Preparation of 3-(2-(4-((5-(2-chloro-4-phenoxybenzoyl)-7H-pyrrolo[2,3-d]pyrimidin-4-yl)amino)piperidin-1-yl)-2-oxoethyl)cyclobutan-1-one A solution of 2-(3-oxocyclobutyl)acetic acid (50 mg, 90% purity, 0.35 mmol), (2-chloro-4-phenoxyphenyl)(4-(piperidin-4-ylamino)-7H-pyrrolo[2,3-d]pyrimidin-5-yl)methanone (207.8 mg, 0.43 mmol), HATU (177.9 mg, 0.47 mmol), N,N-diisopropylethylamine (75.6 mg, 0.59 mmol) and DMF (10 mL) was stirred at room temperature for 4 hours. The mixture was evaporated in vacuum and purified by prep-TLC with MeOH:DCM (1:10) to give the title compound (100 mg, 51%). LC/MS: 557.6 [M+H]⁺.

Step 4: Preparation of (S)-3-(5-(4-(3-(2-(4-((5-(2-chloro-4-phenoxybenzoyl)-7H-pyrrolo[2,3-d]pyrimidin-4-yl)amino)piperidin-1-yl)-2-oxoethyl)cyclobutyl)piperazin-1-yl)-1-oxoisoindolin-2-yl)piperidine-2,6-dione A solution of 3-(2-(4-((5-(2-chloro-4-phenoxybenzoyl)-7H-pyrrolo[2,3-d]pyrimidin-4-yl) amino)piperidin-1-yl)-2-oxoethyl)cyclobutan-1-one (100 mg, 0.18 mmol), (S)-3-(1-oxo-5-(piperazin-1-yl)isoindolin-2-yl)piperidine-2,6-dione (87.5 mg, 0.18 mmol) and sodium cyanoborohydride (21.6 mg, 0.36 mmol) in DMF/MeOH/HOAc (16 mL, 5:10:1) was stirred at room temperature for overnight. The mixture was evaporated in vacuum and purified by prep-TLC with MeOH:DCM=1:10 to give the title compound (40 mg, 25.6%). LC/MS: 869.5 [M+H]⁺.

¹H NMR (400 MHz, DMSO) δ 12.77 (s, 1H), 10.96 (s, 1H), 8.83 (d, J=7.5 Hz, 1H), 8.26 (s, 1H), 7.64 (s, 1H), 7.58 (d, J=8.5 Hz, 1H), 7.51-7.46 (m, 2H), 7.26 (t, J=7.4 Hz, 1H), 7.21-7.16 (m, 3H), 7.08-7.01 (m, 2H), 5.06 (d, J=12.7 Hz, 1H), 4.37-4.13 (m, 4H), 4.00 (s, 1H), 3.87-3.79 (m, 1H), 3.71-3.34 (m, 2H), 3.31-3.13 (m, 4H), 3.06-2.85 (m, 3H), 2.80-2.52 (m, 2H), 2.49-2.46 (m, 1H), 2.37 (s, 4H), 2.23 (s, 2H), 2.13-1.89 (m, 5H), 1.51 (br, 2H), 1.41-1.34 (m, 1H), 1.24 (s, 1H).

Example 43: Preparation of 5-(4-(3-(2-((R)-3-((5-(2-chloro-4-phenoxybenzoyl)-7H-pyrrolo[2,3-d]pyrimidin-4-yl)amino)piperidin-1-yl)-2-oxoethyl)cyclobutyl)piperazin-1-yl)-2-(2,6-dioxopiperidin-3-yl)isoindoline-1,3-dione (Compound 43)

Compound 43 was prepared using the same method as described in the preparation of compound 42. LC/MS: 884.4 [M+H]+1H NMR (400 MHz, DMSO) δ 12.81-12.75 (m, 1H), 11.09 (s, 1H), 8.92-8.86 (m, 1H), 8.33-8.25 (m, 1H), 7.67-7.63 (m, 2H), 7.59-7.42 (m, 3H), 7.35-7.30 (m, 1H), 7.29-7.11 (m, 5H), 7.07-7.01 (m, 1H), 5.10-5.06 (m, 1H), 4.28-4.20 (m, 1H), 3.79-3.35 (m, 8H), 2.94-2.84 (m, 1H), 2.68-2.55 (m, 3H), 2.46-2.08 (m, 9H), 2.05-1.80 (m, 3H), 1.78-1.72 (m, 3H), 1.27-1.20 (M, 1H).

Example 44: Preparation of 5-(4-(2-(1-(4-((5-(2-chloro-4-phenoxybenzoyl)-7H-pyrrolo[2,3-d]pyrimidin-4-yl)amino)-2-fluorophenyl)piperidin-4-yl)ethyl)piperazin-1-yl)-2-(2,6-dioxopiperidin-3-yl)isoindoline-1,3-dione (Compound 44)

was dried over sodium sulfate and concentrated in vacuum to give the desired product (200 mg, 82%) as a yellow solid. LC/MS: 583. [M+1]+.

Step 2: Preparation of 5-(4-(2-(1-(4-((5-(2-chloro-4-phenoxybenzoyl)-7H-pyrrolo[2,3-d]pyrimidin-4-yl)amino)-2-fluorophenyl)piperidin-4-yl)ethyl)piperazin-1-yl)-2-(2,6-dioxopiperidin-3-yl)isoindoline-1,3-dione A solution of 2-(1-(4-((5-(2-chloro-4-phenoxybenzoyl)-7H-pyrrolo[2,3-d]pyrimidin-4-yl)amino)-2-fluorophenyl)piperidin-4-yl)acetaldehyde (100 mg, 0.17 mmol), 2-(2,6-dioxopiperidin-3-yl)-5-(piperazin-1-yl)isoindoline-1,3-dione (64 mg, 0.17 mmol), TEA (52 mg, 0.51 mmol) and MgSO4 (408 mg, 3.4 mmol) in DCM (20 mL) was stirred under nitrogen at room temperature for 30 minutes. Sodium triacetoxyborohydride (72 mg, 0.34 mmol) was added at 0° C. portion wise. The reaction mixture was stirred at room temperature for 2 hours. The reaction mixture was filtered and extracted with water. The organic phase was concentrated under vacuum to give a crude product. The crude

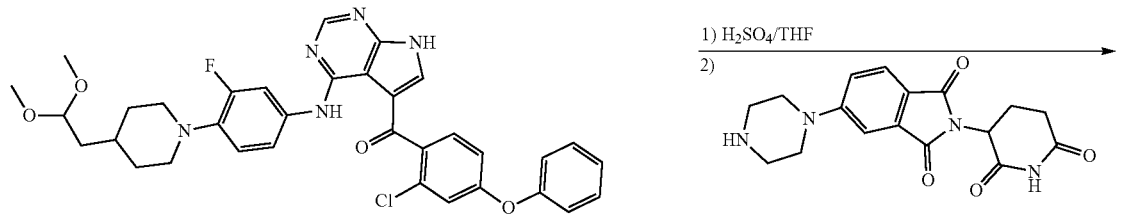

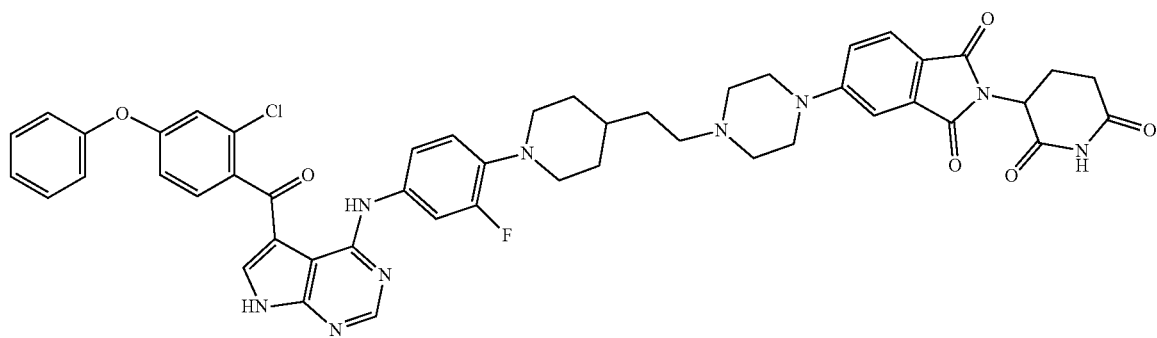

Step 1: Preparation of 2-(1-(4-((5-(2-chloro-4-phenoxybenzoyl)-7H-pyrrolo[2,3-d]pyrimidin-4-yl)amino)-2-fluorophenyl)piperidin-4-yl)acetaldehyde A solution of (2-chloro-4-phenoxyphenyl)(4-((4-(4-(2,2-dimethoxyethyl)piperidin-1-yl)-3-fluorophenyl)amino)-7H-pyrrolo[2,3-d]pyrimidin-5-yl)methanone (250 mg, 0.4 mmol) in THF/H2SO4 (10% aq) (30 mL, THF/H2SO4=1/1) was stirred at 70° C. for 1 hour. The reaction mixture was adjusted to pH=10 with sodium hydroxide solution (2 M) and extracted with EtOAc (15 mL×3). The organic phase product was purified by Prep-TLC (MeOH:DCM=1:10) to give the desired product (50 mg, 32%) as a yellow solid. LC/MS: 910.4[M+1]+.

1H NMR (400 MHz, DMSO) δ 13.06 (br, 1H), 11.12 (d, J=18.0 Hz, 2H), 8.46 (s, 1H), 8.11-8.02 (m, 1H), 7.84 (s, 1H), 7.74-7.61 (m, 2H), 7.54-7.45 (m, 2H), 7.38-7.18 (m, 6H), 7.14-7.02 (m, 2H), 5.08 (dd, J=12.8, 5.3 Hz, 1H), 3.52-3.37 (m, 2H), 3.36-3.28 (m, 7H), 2.95-2.82 (m, 1H), 2.71-2.53 (m, 4H), 2.45-2.27 (m, 3H), 2.04-1.97 (m, 1H), 1.85-1.73 (m, 2H), 1.55-1.3.0 (m, 5H), 1.28-1.20 (m, 1H).

Example 45: Preparation of (S)-3-(5-(4-(2-(1-(4-((5-(2-chloro-4-phenoxybenzoyl)-7H-pyrrolo[2,3-d]pyrimidin-4-yl)amino)-2-fluorophenyl)piperidin-4-yl)ethyl)piperazin-1-yl)-1-oxoisoindolin-2-yl)piperidine-2,6-dione (Compound 45)

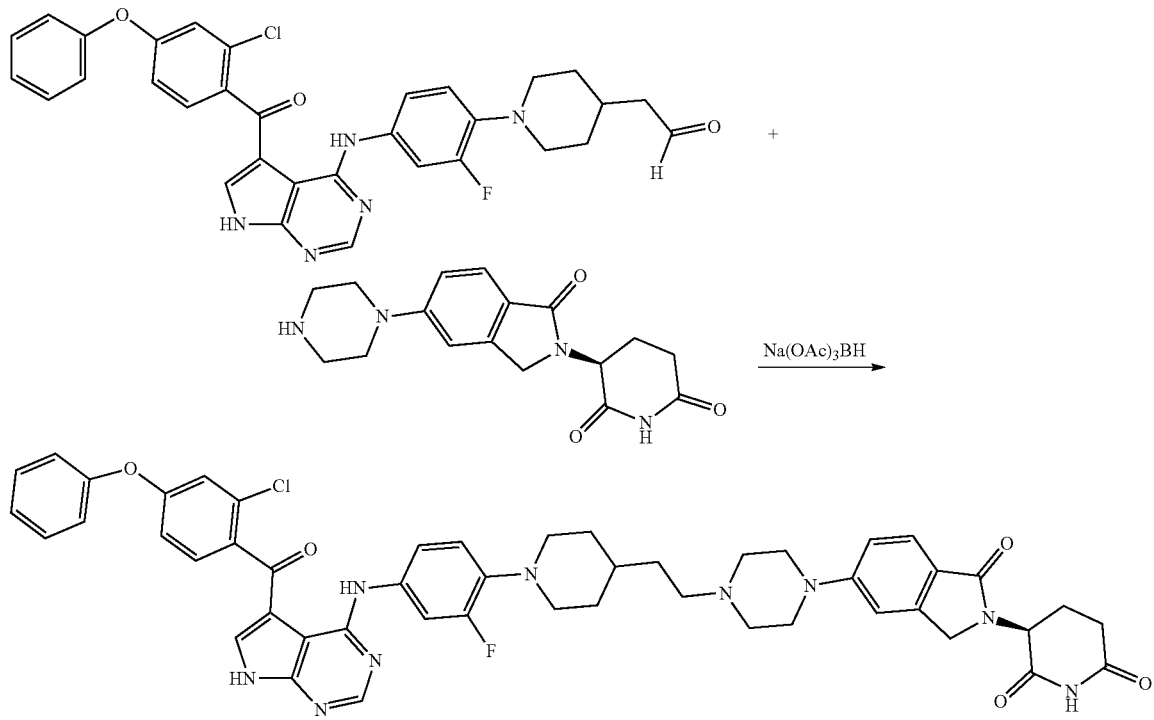

A solution of 2-(1-(4-((5-(2-chloro-4-phenoxybenzoyl)-7H-pyrrolo[2,3-d]pyrimidin-4-yl)amino)-2-fluorophenyl)piperidin-4-yl)acetaldehyde (100 mg, 0.17 mmol), (S)-3-(1-oxo-5-(piperazin-1-yl)isoindolin-2-yl)piperidine-2,6-dione (83 mg, 0.17 mmol), TEA (52 mg, 0.51 mmol) and MgSO$_4$ (408 mg, 3.4 mmol) in DCM (20 mL) was stirred under nitrogen at room temperature for 30 minutes. Sodium triacetoxy borohydride (72 mg, 0.34 mmol) was added at 0° C. portion wise. The reaction mixture was stirred at room temperature for 2 hours. The reaction mixture was filtered. The organic layer was washed with water and concentrated under vacuum to give a crude product. The crude product was purified by Prep-TLC (MeOH:DCM=1:10) to give the desired product (30 mg, 17.6%) as a yellow solid. LC/MS: 896.4[M+1]$^+$.

$^1$H NMR (400 MHz, DMSO) δ 13.06 (br, 1H), 11.14 (s, 1H), 10.96 (s, 1H), 8.46 (s, 1H), 8.05 (dd, J=15.0, 2.1 Hz, 1H), 7.84 (s, 1H), 7.64 (d, J=8.5 Hz, 1H), 7.65-7.39 (m, 3H), 7.35-7.18 (m, 5H), 7.12-7.02 (m, 4H), 5.06 (dd, J=13.2, 5.0 Hz, 1H), 4.39-4.19 (m, 2H), 3.35-3.25 (m, 7H), 2.94-2.85 (m, 1H), 2.70-2.53 (m, 4H), 2.49-2.25 (m, 4H), 1.95-1.85 (m, 1H), 1.80-1.75 (m, 2H), 1.62-1.30 (m, 5H), 1.25-1.15 (m, 1H).

Example 46: Preparation of (S)-3-(5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)piperazin-1-yl)-1-oxoisoindolin-2-yl)piperidine-2,6-dione (Compound 46)

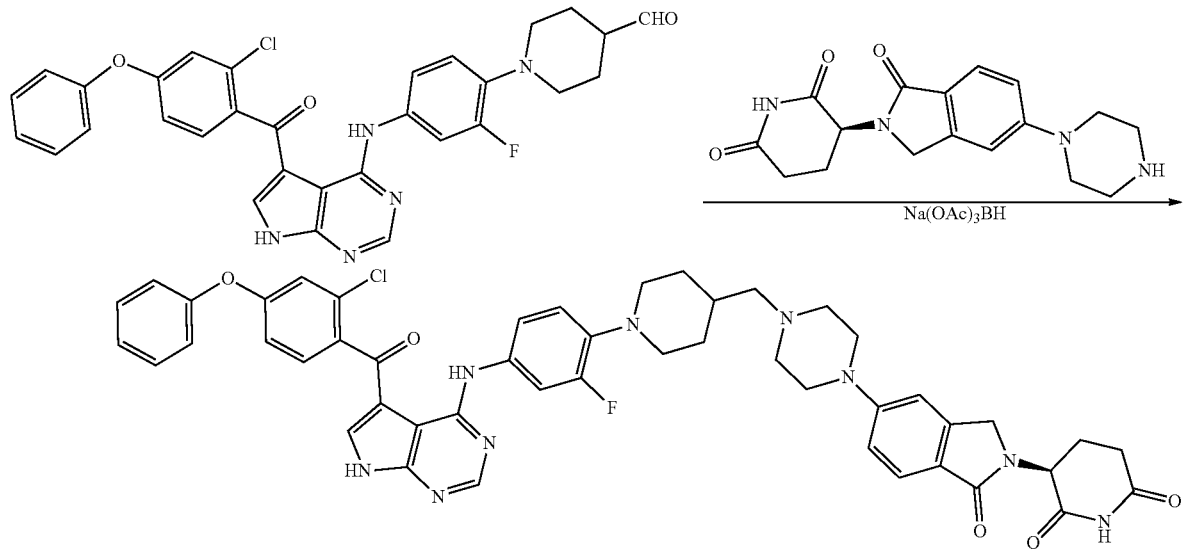

Step 1: Preparation of 1-(4-((5-(2-chloro-4-phenoxybenzoyl)-7H-pyrrolo[2,3-d]pyrimidin-4-yl)amino)-2-fluorophenyl)piperidine-4-carbaldehyde A solution of (2-chloro-4-phenoxyphenyl)(4-((4-(4-(dimethoxymethyl)piperidin-1-yl)-3-fluorophenyl)amino)-7H-pyrrolo[2,3-d]pyrimidin-5-yl)methanone (200 mg, 0.32 mmol) in THF/H$_2$SO$_4$ (10% aq) (20 mL, 1:1) was stirred at 70° C. for 1 hour. The reaction mixture was adjusted to pH=10 with sodium hydroxide solution (2 M), extracted with EtOAc (100 mL). The organic phase was dried over sodium sulfate and evaporated in vacuo to give the desired product (150 mg, 82% yield) as a yellow solid. LC/MS: 570.1 [M+1]$^+$.

Step 2: Preparation of (S)-3-(5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)piperazin-1-yl)-1-oxoisoindolin-2-yl)piperidine-2,6-dione A solution of 1-(4-((5-(2-chloro-4-phenoxybenzoyl)-7H-pyrrolo[2,3-d]pyrimidin-4-yl)amino)-2-fluorophenyl)piperidine-4-carbaldehyde (70 mg, 0.12 mmol), (S)-3-(1-oxo-5-(piperazin-1-yl)isoindolin-2-yl)piperidine-2,6-dione (60 mg, 0.12 mmol), TEA (24 mg, 0.24 mmol) and MgSO$_4$ (289 mg, 2.4 mmol) in DCM (10 mL) was stirred under nitrogen at room temperature for 30 minutes. To the solution was added sodium triacetoxyborohydride (64 mg, 0.3 mmol) at 0° C. portion-wise. The reaction mixture was stirred at room temperature for 2 hours. The reaction mixture was filtered. The organic layer was washed with water, extracted with DCM (50 mL) to give the crude product which was purified by Prep-TLC (PE:EA=5:1) to give the desired product (20 mg, 19% yield) as a yellow solid. LC/MS: 882.0[M+1]$^+$ $^1$H NMR (400 MHz, DMSO) δ 13.05 (br, 1H), 11.14 (s, 1H), 10.96 (s, 1H), 8.46 (s, 1H), 8.04 (d, J=16.6 Hz, 1H), 7.84 (s, 1H), 7.65 (d, J=8.5 Hz, 1H), 7.59-7.46 (m, 3H), 7.39-7.14 (m, 5H), 7.11-7.03 (m, 3H), 5.05 (dd, J=13.4, 5.1 Hz, 1H), 4.34 (d, J=17.0 Hz, 1H), 4.21 (d, J=16.9 Hz, 1H), 3.30-3.27 (m, 6H), 2.96-2.86 (m, 1H), 2.71-2.53 (m, 4H), 2.46-2.31 (m, 3H), 2.26 (d, J=6.5 Hz, 2H), 2.02-1.92 (m, 1H), 1.88-1.78 (m, 2H), 1.76-1.62 (m, 2H), 1.38-1.19 (m, 3H).

Example 47: Preparation of 5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)piperazin-1-yl)-2-(2,6-dioxopiperidin-3-yl)isoindoline-1,3-dione (Compound 47)

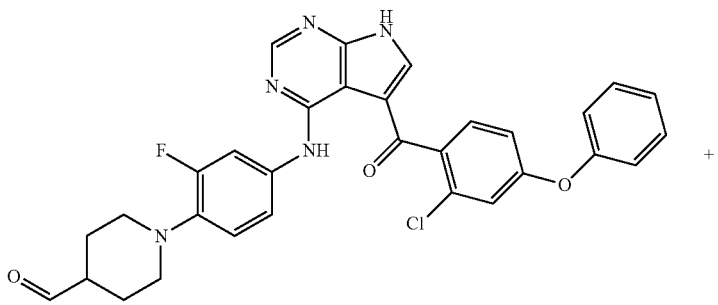

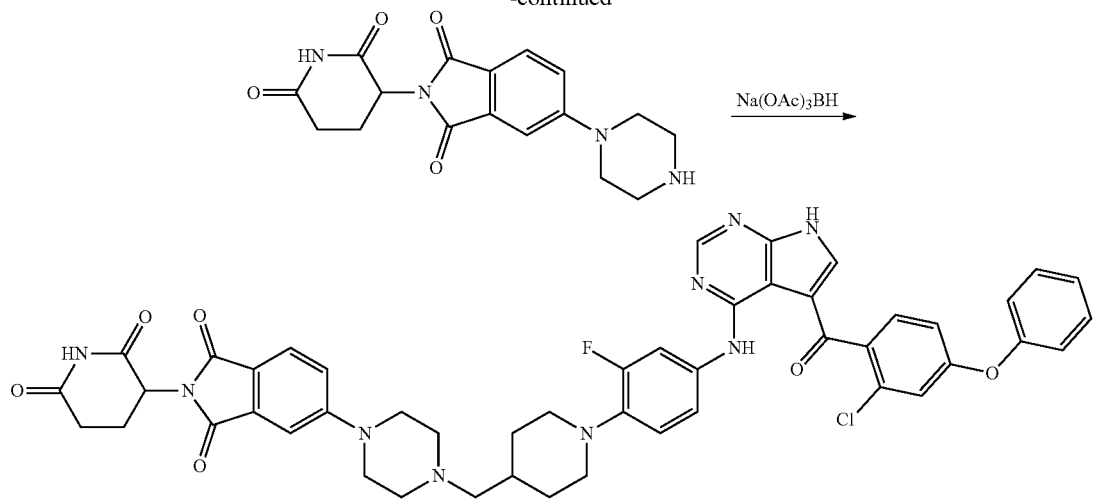

A solution of 1-(4-((5-(2-chloro-4-phenoxybenzoyl)-7H-pyrrolo[2,3-d]pyrimidin-4-yl)amino)-2-fluorophenyl)piperidine-4-carbaldehyde (70 mg, 0.12 mmol), 2-(2,6-dioxopiperidin-3-yl)-5-(piperazin-1-yl)isoindoline-1,3-dione (45 mg, 0.12 mmol), TEA (24 mg, 0.24 mmol) and MgSO₄ (289 mg, 2.4 mmol) in DCM (10 mL) was stirred under nitrogen at room temperature for 30 minutes. Sodium triacetoxyborohydride (64 mg, 0.3 mmol) was added at 0° C. portion wise. The reaction mixture was stirred at room temperature for 2 hours. The reaction mixture was filtered. The organic layer was washed with water and concentrated in vacuum to give a crude product. The crude product was purified by Prep-TLC (MeOH:DCM=1:10) to give the desired product (20 mg, 18%) as a yellow solid. LC/MS: 898.1[M+1]⁺.

¹H NMR (400 MHz, DMSO) δ 13.05 (s, 1H), 11.14 (s, 1H), 11.09 (s, 1H), 8.46 (s, 1H), 8.08-8.01 (m, 1H), 7.84 (s, 1H), 7.72-7.61 (m, 2H), 7.54-7.45 (m, 2H), 7.37-7.18 (m, 6H), 7.13-7.02 (m, 2H), 5.08 (dd, J=13.0, 5.4 Hz, 1H), 3.50-3.41 (m, 3H), 3.33-3.29 (m, 2H), 2.93-2.84 (m, 1H), 2.75-2.58 (m, 3H), 2.57-2.52 (m, 2H), 2.47-2.30 (m, 2H), 2.29-2.20 (m, 2H), 2.10-1.92 (m, 2H), 1.90-1.64 (m, 4H), 1.39-1.22 (m, 3H).

Example 48: Preparation of 5-(4-(3-(2-(4-((5-(2-chloro-4-phenoxybenzoyl)-7H-pyrrolo[2,3-d]pyrimidin-4-yl)amino)piperidin-1-yl)-2-oxoethyl)azetidin-1-yl)piperidin-1-yl)-2-(2,6-dioxopiperidin-3-yl)isoindoline-1,3-dione (Compound 48)

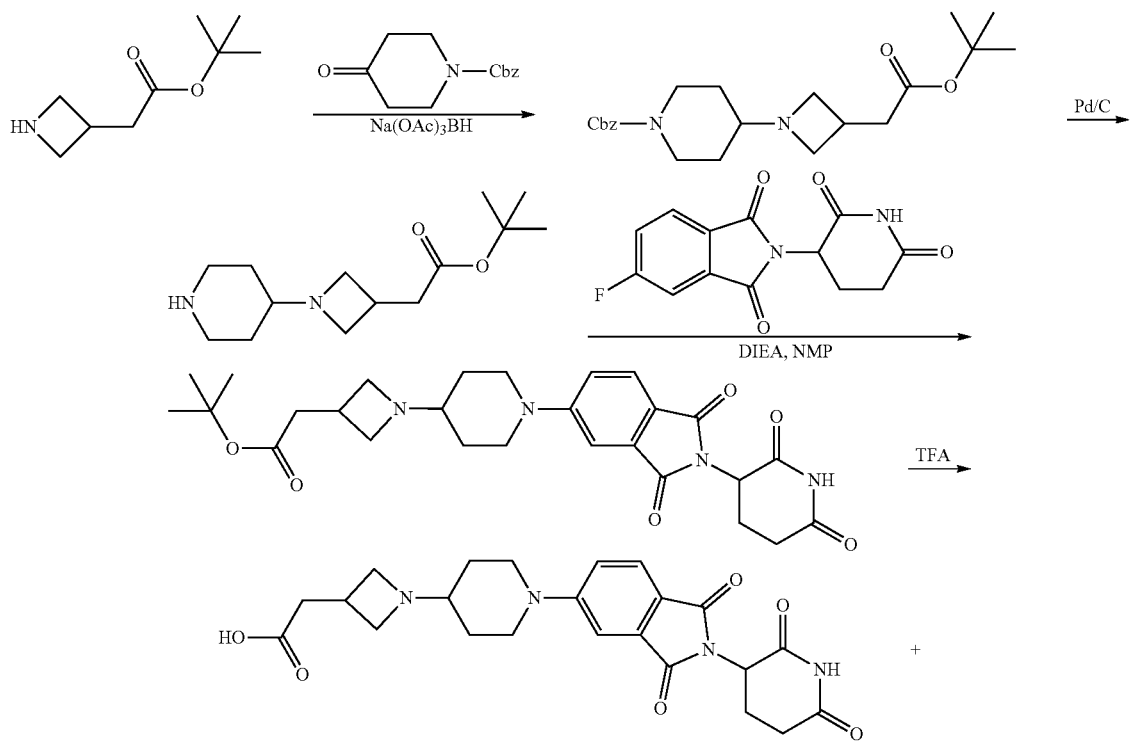

-continued

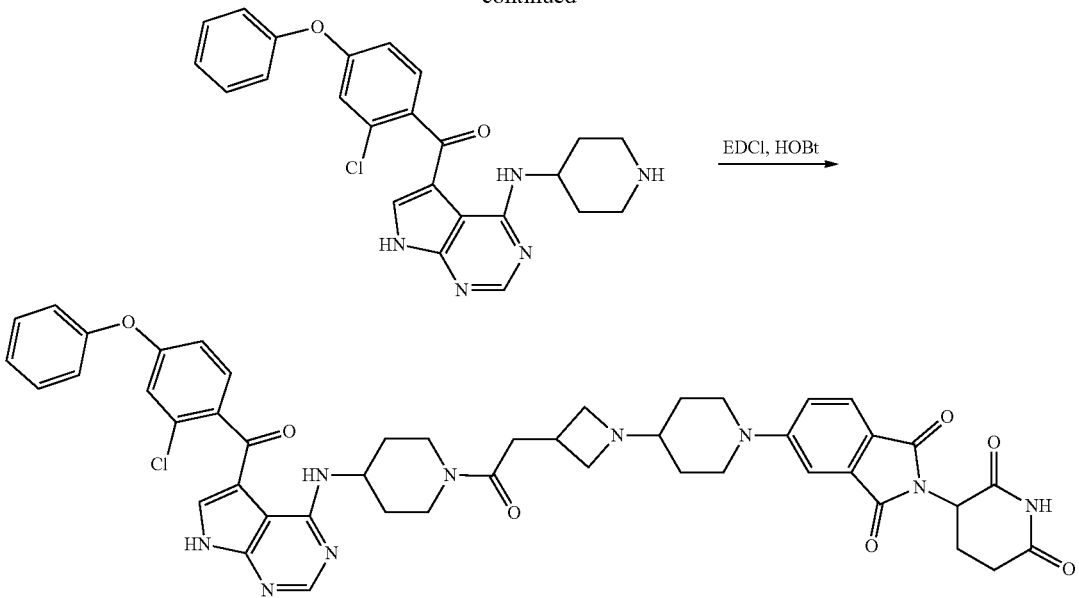

Step 1: Preparation of benzyl 4-(3-(2-(tert-butoxy)-2-oxoethyl)azetidin-1-yl)piperidine-1-carboxylate To a solution of tert-butyl 2-(azetidin-3-yl)acetate (200 mg, 0.96 mmol) in DCM (5 mL) stirred at room temperature was added Et$_3$N (194 mg, 1.92 mmol), MgSO$_4$ (300 mg) and [3-(4-oxopiperidin-1-yl)phenyl]methyl formate (224 mg, 0.96 mmol). The mixture was stirred at room temperature for 30 minutes before NaBH(OAc)$_3$ (406 mg, 1.92 mmol) was added slowly (0.5 eq per 30 minutes). The reaction mixture was stirred at room temperature for 1 hour. The mixture was filtered and the filtrate was concentrated under pressure. The residue was purified by flash chromatography (MeOH/DCM=1:10) to give the desired product (255 mg, 68.37%) as a colorless oil. LC/MS: 388.8 [M+H]$^+$.

Step 2: Preparation of tert-butyl 2-(1-(piperidin-4-yl)azetidin-3-yl)acetate To a solution of tert-butyl 2-[1-(1-{3-[(formyloxy)methyl]phenyl}piperidin-4-yl)azetidin-3-yl] acetate (255 mg, 0.66 mmol) in MeOH (5 mL) stirred at room temperature was added Pd/C (70 mg, 0.66 mmol). The reaction mixture was stirred at room temperature under H$_2$ for 3 hours. The mixture was filtered and the filtrate was concentrated under pressure to give the desired product (160 mg, yield=95.3%) as a white solid. LC/MS: 251.1 [M+H]$^+$.

Step 3: Preparation of tert-butyl 2-(1-(1-(2-(2,6-dioxopiperidin-3-yl)-1,3-dioxoisoindolin-5-yl) piperidin-4-yl)azetidin-3-yl)acetate To a solution of 2-(2,6-dioxopiperidin-3-yl)-5-fluoroisoindole-1,3-dione (140 mg, 0.55 mmol) in NMP (5 mL) stirred at room temperature was added tert-butyl 2-[1-(piperidin-4-yl)azetidin-3-yl]acetate (140 mg, 0.55 mmol) and DIEA (142 mg, 1.1 mmol). The reaction mixture was stirred at 90° C. for 12 hours. The mixture was poured into water (25 mL) and extracted with EtOAc (30 mL×2). The combined organic layer was washed with brine, dried over Na$_2$SO$_4$ and concentrated in vacuum to give a crude product. The crude product was purified by flash chromatography (MeOH/DCM=1:10) to give the desired product (70 mg, yield=25.4%) as a yellow solid. LC/MS: 510.8 [M+H]$^+$.

Step 4: Preparation of 2-(1-(1-(2-(2,6-dioxopiperidin-3-yl)-1,3-dioxoisoindolin-5-yl)piperidin-4-yl)azetidin-3-yl)acetic acid A solution of tert-butyl 2-(1-{1-[2-(2,6-dioxopiperidin-3-yl)-1,3-dioxoisoindol-5-yl]piperidin-4-yl}azetidin-3-yl)acetate (70 mg, 0.14 mmol) in TFA/DCM (1:5, 6 mL) was stirred at room temperature for 2 hour. The solution was concentrated in vacuum to give the crude product (80 mg, crude). LC/MS: 455.1 [M+H]$^+$.

Step 5: Preparation of 5-(4-(3-(2-(4-((5-(2-chloro-4-phenoxybenzoyl)-7H-pyrrolo[2,3-d]pyrimidin-4-yl)amino)piperidin-1-yl)-2-oxoethyl)azetidin-1-yl)piperidin-1-yl)-2-(2,6-dioxopiperidin-3-yl)isoindoline-1,3-dione To a solution of (1-{1-[2-(2,6-dioxopiperidin-3-yl)-1,3-dioxoisoindol-5-yl]piperidin-4-yl}azetidine-3-yl)acetic acid (70 mg, crude, 0.14 mmol) in DMF (5 ml) stirred at room temperature was added HOBt (22 mg, 0.156 mmol), EDCI (30 mg, 0.156 mmol), NMM (53 mg, 0.52 mmol) and N-{5-[(2-chloro-4-phenoxyphenyl)carbonyl]-7H-pyrrolo[2,3-d]pyrimidin-4-yl}piperidin-4-amine hydrochloride (63 mg, 0.14 mmol). The reaction mixture was stirred at room temperature for 12 hours. The mixture was poured into water (25 mL) and extracted with EtOAc (30 mL×2). The combined organic layer was washed with brine, dried over Na$_2$SO$_4$ and concentrated in vacuum to give a crude product. The crude product was purified by Prep-TLC (MeOH/DCM=1:10) to get the desired product (30 mg, yield=24.2%) as a yellow solid. LC/MS: 884.1 [M+H]$^+$.
$^1$H NMR (400 MHz, DMSO) δ 12.75 (br, 1H), 11.09 (s, 1H), 8.83 (d, J=7.2 Hz, 1H), 8.26 (s, 1H), 7.66-7.61 (m, 2H), 7.58 (d, J=8.8 Hz, 1H), 7.47 (t, J=8.0 Hz, 2H), 7.30 (s, 1H), 7.28-7.14 (m, 5H), 7.02 (dd, J=8.8, 2.4 Hz, 1H), 5.09-5.04 (m, 1H), 4.40-4.30 (m, 1H), 4.18-4.13 (m, 1H), 3.95-3.73 (m, 3H), 3.13-3.05 (m, 2H), 3.03-2.95 (m, 1H), 2.94-2.86 (m, 1H), 2.84-2.73 (m, 2H), 2.70-2.65 (m, 2H), 2.62-2.54 (m, 2H), 2.34-2.21 (m, 2H), 2.10-1.95 (m, 4H), 1.74-1.64 (m, 2H), 1.58-1.45 (m, 2H), 1.43-1.30 (m, 2H), 1.22-1.15 (m, 2H).

Example 49: Preparation of (S)—N-(4-(4-amino-1-(4-(4-((4-(2-(2,6-dioxopiperidin-3-yl)-1-oxoisoindolin-5-yl)piperazin-1-yl)methyl)piperidin-1-yl)-3-fluorophenyl)-1H-pyrazolo[3,4-d]pyrimidin-3-yl)benzyl)-5-fluoro-2-methoxybenzamide (Compound 49)
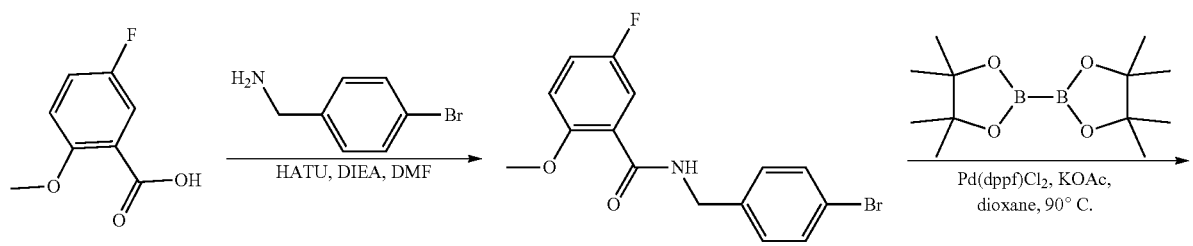
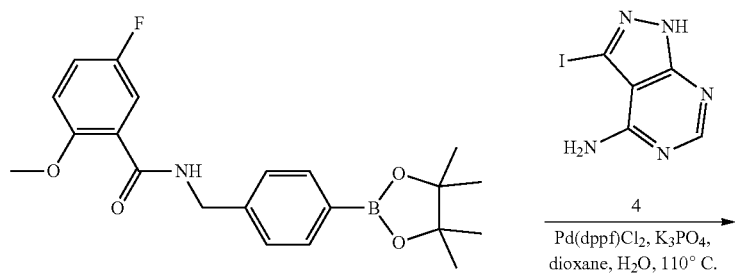
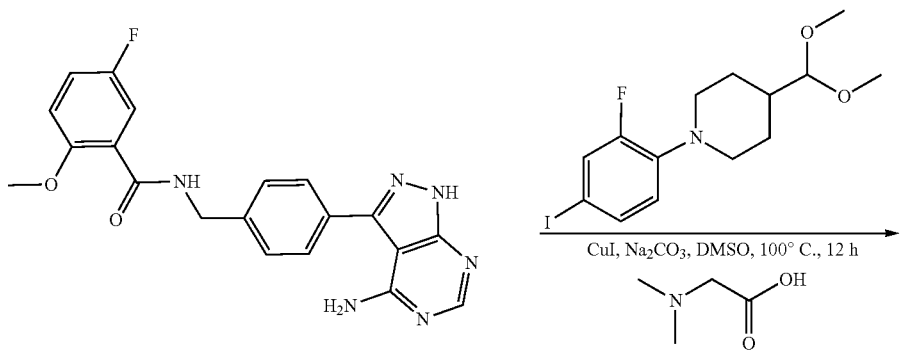
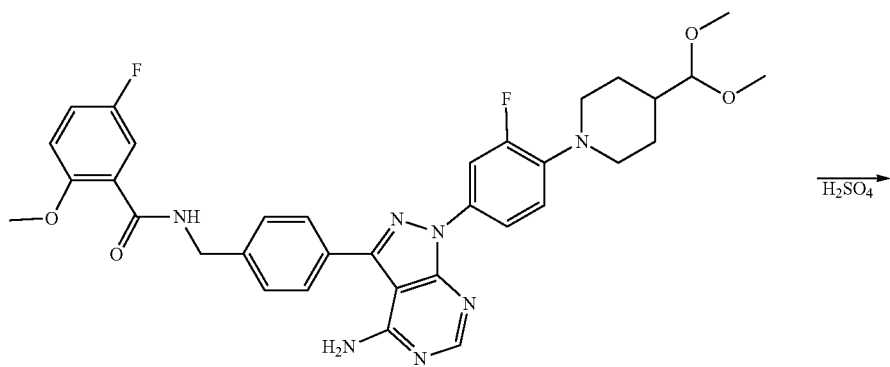

-continued

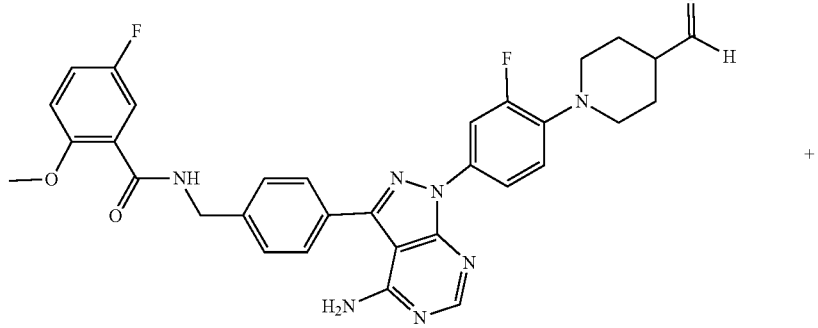

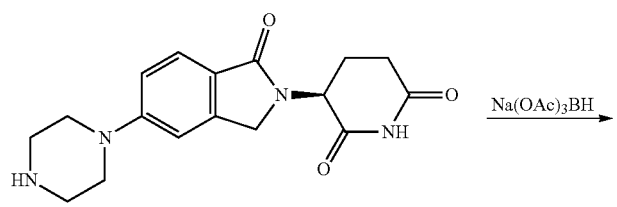

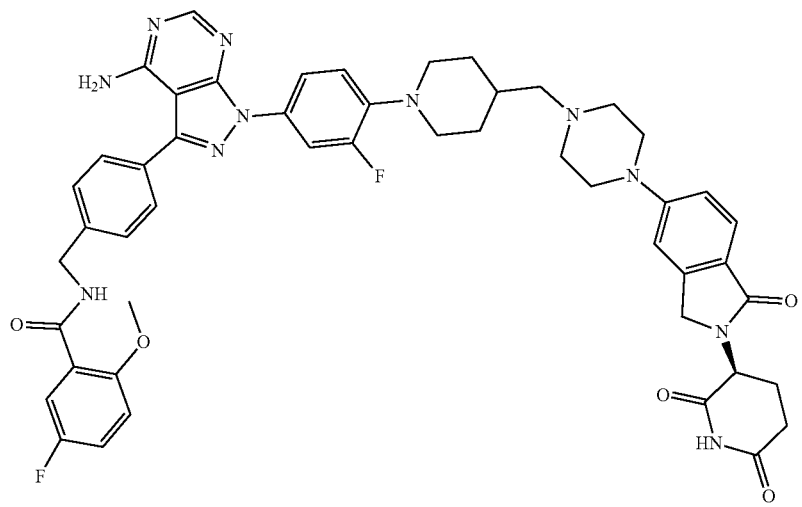

Step 1: Preparation of N-(4-bromobenzyl)-5-fluoro-2-methoxybenzamide

A solution of 5-fluoro-2-methoxy-benzoic acid (30 g, 176 mmol, 1.0 eq), O-(7-azabenzotriazol-1-yl)-N,N,N',N'-tetramethyluronium hexafluorophosphate (80.5 g, 212 mmol, 1.2 eq) and N,N-diisopropylethylamine (45.6 g, 353 mmol, 2 eq) in N,N-dimethylformamide (300 mL) was stirred at 25° C. for 30 min. (4-Bromophenyl)methanamine (32.8 g, 176 mmol, 1.0 eq) was added into the solution and the mixture was stirred at 25° C. for 12 h. The solution was poured into water (500 mL), extracted with ethyl acetate (500 mL×3). The combined organic phase was washed with brine (500 mL), dried over anhydrous sodium sulfate, filtered and concentrated. The residue was purified by silica gel chromatography with 20%-30% ethyl acetate in petroleum ether as eluent to afford desired compound (56 g, 94% yield) as a white solid.

$^1$HNMR (400 MHz, CDCl$_3$): δ 8.26 (br s, 1H), 7.94 (q, J=2.0 Hz, 1H), 7.45 (d, J=7.6 Hz, 2H), 7.22 (d, J=8.0 Hz, 2H), 7.16-7.12 (m, 1H), 6.94-6.91 (m, 1H), 4.61 (d, J=6.0 Hz, 2H), 3.91 (s, 3H).

Step 2: Preparation of 5-fluoro-2-methoxy-N-[[4-(4,4,5,5-tetramethyl-1,3,2-dioxaborolan-2-yl)phenyl]methyl]benzamide To a solution of N-[(4-bromophenyl)methyl]-5-fluoro-2-methoxy-benzamide (46 g, 136 mmol, 1.0 eq) and 4,4,5,5-tetramethyl-2-(4,4,5,5-tetramethyl-1,3,2-dioxaborolan-2-yl)-1,3,2-dioxaborolane (51.8 g, 204 mmol, 1.5 eq) in dioxane (500 mL) was added potassium acetate (26.7 g, 272 mmol, 2.0 eq) and 1,1-bis(diphenylphosphino) ferrocene] dichloropalladium(II) (9.95 g, 13.6 mmol, 0.1 eq). The suspension was degassed under vacuum and purged with nitrogen for three times. The mixture was stirred under nitrogen at 90° C. for 12 h. The solution was poured into water (2 L), extracted with ethyl acetate (1 L×3). The combined organic phase was washed with brine (2 L), dried with anhydrous sodium sulfate, filtered and concentrated. The combined crude product was purified by silica gel chromatography with 20%-30% ethyl acetate in petroleum ether as eluent. The crude product was triturated with petroleum ether (200 mL), filtered and the filter cake was dried under vacuum to afford the desired compound (50 g, 79% yield) as a white solid. LC/MS: 386.2 [M+H]$^+$.

Step 3: Preparation of N-(4-(4-amino-1H-pyrazolo[3,4-d]pyrimidin-3-yl)benzyl)-5-fluoro-2-methoxy-benzamide A mixture of 5-fluoro-2-methoxy-N-[[4-(4,4,5,5-tetramethyl-1,3,2-dioxaborolan-2-yl)phenyl]methyl]benzamide (10.0 g, 26.0 mmol, 1.0 eq), 3-iodo-1H-pyrazolo[3,4-d]pyrimidin-4-amine (6.78 g, 26.0 mmol, 1.0 eq), 1,1-bis(diphenylphosphino)ferrocene]dichloropalladium(II) (3.80 g, 5.19 mmol, 0.2 eq), potassium phosphate (16.5 g, 77.9 mmol, 3.0 eq) in dioxane (200 mL) and water (40 mL) was degassed and purged with nitrogen for three times, and the mixture was stirred at 110° C. for 60 hr under nitrogen atmosphere. The reaction mixture was partitioned between ethyl acetate (1 L) and water (1 L). The organic phase was separated, washed with brine (1 L), dried over anhydrous sodium sulfate, filtered and concentrated. The residue was triturated with acetonitrile (50 mL) and ethyl acetate (50 mL) sequentially. The solid was collected and dried under vacuum to afford the desired compound (6.0 g, 59% yield) as a light yellow solid. LC/MS: 393.1 [M+H]$^+$. $^1$H NMR (400 MHz, DMSO-d$_6$): δ 13.59 (s, 1H), 8.86 (t, J=6.0 Hz, 1H), 8.22 (s, 1H), 7.64 (d, J=8.0 Hz, 2H), 7.57-7.47 (m, 3H), 7.37-7.31 (m, 1H), 7.19 (dd, J=4.4, 9.2 Hz, 1H), 4.59 (d, J=6.0 Hz, 2H), 3.90 (s, 3H).

Step 4: Preparation of N-[[4-[4-amino-1-[4-[4-(dimethoxymethyl)-1-piperidyl]-3-fluoro-phenyl]pyrazolo[3,4-d]pyrimidin-3-yl]phenyl]methyl]-5-fluoro-2-methoxy-benzamide To a solution of N-[[4-(4-amino-1H-pyrazolo[3,4-d]pyrimidin-3-yl)phenyl]methyl]-5-fluoro-2-methoxy-benzamide (12.0 g, 30.6 mmol, 1.0 eq) and 4-(dimethoxymethyl)-1-(2-fluoro-4-iodo-phenyl)piperidine (11.6 g, 30.6 mmol, 1.0 eq) in dimethyl sulfoxide (150 mL) were added copper iodide (3.24 g, 17.0 mmol, 0.55 eq), 2-(dimethylamino)acetic acid (3.50 g, 33.98 mmol, 1.1 eq) and sodium carbonate (7.20 g, 68.0 mmol, 2.2 eq). The suspension was degassed under vacuum and purged with nitrogen for three times. The mixture was stirred under nitrogen at 110° C. for 12 h. The reaction mixture was partitioned between ethyl acetate (800 mL) and water (2.0 L). The aqueous layer was extracted with ethyl acetate (700 mL×3). The combined organic layers were washed with brine (500 mL), dried over anhydrous sodium sulfate, filtered and concentrated to give crude product (15 g). The crude product was dissolved in ethyl acetate (420 mL) with refluxing and the solution was cooled to ambient temperature and then kept in refrigerator (~5° C.) for 48 h. The suspension was filtered and the wet cake was washed with cold ethyl acetate (20 mL) to give pure product (5.28 g). The mother liquid was concentrated and the residue was re-crystallized from ethyl acetate (100 mL) to give another crop of pure product (1.7 g) (total 6.98 g, 36% yield) as a gray solid.

LC/MS: 644.2 [M+H]$^+$. $^1$HNMR (400 MHz, CDCl$_3$): δ 8.47 (s, 1H), 8.38 (t, J=5.2 Hz, 1H), 7.99 (dd, J=3.2, 9.2 Hz, 1H), 7.97-7.93 (m, 1H), 7.92 (s, 1H), 7.75 (d, J=8.0 Hz, 2H), 7.56 (d, J=8.0 Hz, 2H), 7.22-7.14 (m, 1H), 7.08 (t, J=8.8 Hz, 1H), 6.97 (dd, J=4.4, 8.8 Hz, 1H), 5.60 (br s, 2H), 4.78 (d, J=6.0 Hz, 2H), 4.12 (d, J=7.2 Hz, 1H), 3.97 (s, 3H), 3.53 (d, J=12.0 Hz, 2H), 3.39 (s, 6H), 2.69 (t, J=11.6 Hz, 2H), 1.88 (d, J=12.0 Hz, 2H), 1.82-1.73 (m, 1H), 1.64-1.48 (m, 2H).

Step 5: Preparation of N-(4-(4-amino-1-(3-fluoro-4-(4-formylpiperidin-1-yl)phenyl)-1H-pyrazolo [3,4-d]pyrimidin-3-yl)benzyl)-5-fluoro-2-methoxybenzamide A solution of N-(4-(4-amino-1-(4-(4-(dimethoxymethyl)piperidin-1-yl)-3-fluorophenyl)-1H-pyrazolo[3,4-d]pyrimidin-3-yl)benzyl)-5-fluoro-2-methoxybenzamide (1.03 g, 1.60 mmol) in THF (20 mL) and H$_2$SO$_4$ (2 M, 20 ml) was stirred at 70° C. for 1 hour. The reaction mixture was diluted with DCM (50 mL), adjusted pH to 8 with aqueous sodium hydroxide dropwise (2 M). The organic layer was evaporated in vacuo to give the desired product as yellow solid (900 mg, 96% yield). LC/MS: 598.1 [M+1]$^+$.

Step 6: Preparation of (S)—N-(4-(4-amino-1-(4-((4-(2-(2,6-dioxopiperidin-3-yl)-1-oxoisoindolin-5-yl)piperazin-1-yl)methyl)piperidin-1-yl)-3-fluoro-phenyl)-1H-pyrazolo[3,4-d]pyrimidin-3-yl)benzyl)-5-fluoro-2-methoxybenzamide A solution of N-(4-(4-amino-1-(3-fluoro-4-(4-formylpiperidin-1-yl)phenyl)-1H-pyrazolo [3,4-d]pyrimidin-3-yl)benzyl)-5-fluoro-2-methoxybenzamide (900 mg 1.51 mmol), (S)-3-(1-oxo-5-(piperazin-1-yl)isoindolin-2-yl)piperidine-2,6-dione (1.46 g, 3.02 mmol) and triethylamine (325 mg, 3.21 mmol) in DCM (60 mL) was stirred in air at room temperature for 1 hour. Sodium triacetoxyborohydride (956 mg, 4.53 mmol) was added to the solution at 0° C. portion-wise. The reaction mixture was stirred at room temperature overnight and then partitioned between water (50 mL) and DCM (60 mL). The organic phase was dried over sodium sulfate and evaporated in vacuo. The crude product was triturated with MeOH to give the product as a white solid (1.0 g, 1.10 mmol, 73% yield). LC/MS: 910.4 [M+1]$^+$.

$^1$H NMR (400 MHz, DMSO) δ 10.96 (s, 1H), 8.90 (t, J=6.0 Hz, 1H), 8.38 (s, 1H), 8.05-7.99 (m, 2H), 7.74 (d, J=8.1 Hz, 2H), 7.57-7.50 (m, 4H), 7.37-7.32 (m, 1H), 7.25-7.18 (m, 2H), 7.07 (d, J=8.5 Hz, 2H), 5.05 (dd, J=13.1, 4.9 Hz, 1H), 4.61 (d, J=6.0 Hz, 2H), 4.33 (d, J=17.2 Hz, 1H), 4.20 (d, J=17.2 Hz, 1H), 3.91 (s, 3H), 3.42 (d, J=10.4 Hz, 2H), 3.30 (br s, 4H), 2.96-2.85 (m, 1H), 2.77-2.67 (m, 2H), 2.64-2.52 (m, 5H), 2.43-2.30 (m, 1H), 2.24 (br d, J=6.4 Hz, 2H), 2.01-1.66 (m, 4H), 1.38-1.25 (m, 2H).

Example 50: Preparation of N-(4-(4-amino-1-(4-(4-((4-(2-(2,6-dioxopiperidin-3-yl)-1,3-dioxoisoindolin-5-yl)piperazin-1-yl)methyl)piperidin-1-yl)-3-fluorophenyl)-1H-pyrazolo[3,4-d]pyrimidin-3-yl)benzyl)-5-fluoro-2-methoxybenzamide (Compound 50)

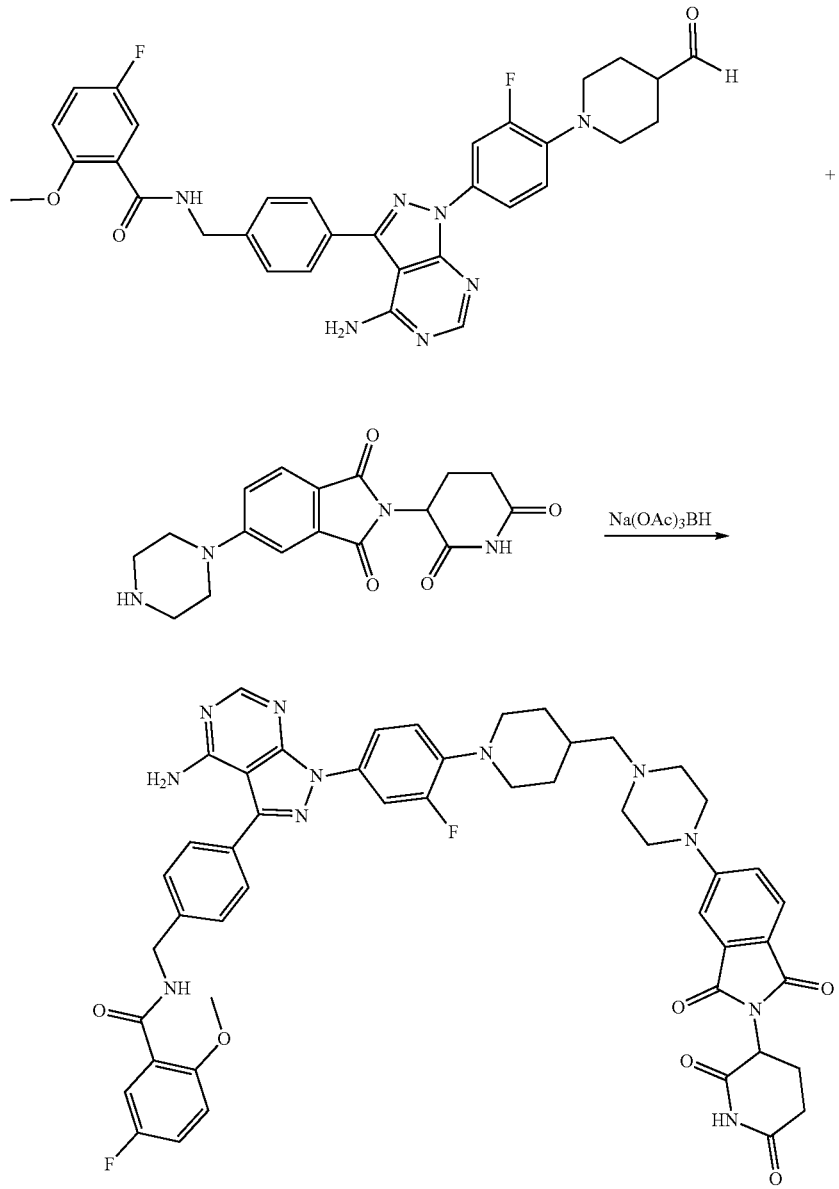 [SMILES: COc1ccc(F)cc1C(=O)NCc1ccc(-c2nn(-c3ccc(N4CCC(C=O)CC4)c(F)c3)c3ncnc(N)c23)cc1 ; O=C1CCC(N2C(=O)c3ccc(N4CCNCC4)cc3C2=O)C(=O)N1 ; COc1ccc(F)cc1C(=O)NCc1ccc(-c2nn(-c3ccc(N4CCC(CN5CCN(c6ccc7c(c6)C(=O)N(C6CCC(=O)NC6=O)C7=O)CC5)CC4)c(F)c3)c3ncnc(N)c23)cc1 ; "Na(OAc)3BH"]

A solution of N-[(4-{4-amino-1-[3-fluoro-4-(4-formylpiperidin-1-yl)phenyl]pyrazolo[3,4-d]pyrimidin-3-yl}phenyl)methyl]-5-fluoro-2-methoxybenzamide (60 mg, 0.1 mmol), 2-(2,6-dioxopiperidin-3-yl)-5-(piperazin-1-yl)isoindoline-1,3-dione hydrochloride (57 mg, 0.15 mmol) and triethylamine (30 mg, 0.3 mmol) in DCM (5.0 mL) was stirred in air at room temperature. The reaction mixture was stirred at room temperature for 2 hours. Then sodium triacetoxyborohydride (53 mg, 0.25 mmol) was added at 0° C. portionwise. The reaction mixture was stirred at room temperature for 2 hours. The reaction mixture was evaporated in vacuo to give the crude product. The crude product was purified by Prep-TLC (DCM:MeOH=10:1) to obtain the desired product as white solid (31.8 mg, 0.034 mmol, 34% yield). LC/MS: 924 [M+1]$^+$.

$^1$H NMR (400 MHz, DMSO) δ=11.12 (s, 1H), 9.41 (s, 1H), 8.92 (t, J=6.2, 1H), 8.39 (s, 1H), 8.04 (dd, J=14.0, 2.4, 1H), 7.98 (d, J=8.9 Hz, 1H), 7.76 (dd, J=19.5, 8.3 Hz, 3H), 7.53 (dd, J=9.2, 3.4 Hz, 3H), 7.39-7.33 (m, 2H), 7.20 (dd, J=9.2, 4.3 Hz, 2H), 5.11 (dd, J=13.1, 5.1 Hz, 1H), 4.60 (s, 2H), 4.23 (m, 2H), 3.92 (m, 8H), 3.64 (s, 2H), 3.45 (d, J=10.4, 2H), 3.14-3.22 (m, 3H), 2.84-2.95 (m, 2H), 2.78 (t, J=11.6 Hz, 2H), 1.85-2.06 (m, 3H), 1.33-1.47 (m, 2H).

Example 51: Preparation of (S)—N-(4-(4-amino-1-(4-(4-((4-(2-(2,6-dioxopiperidin-3-yl)-6-fluoro-1-oxoisoindolin-5-yl)piperazin-1-yl)methyl)piperidin-1-yl)-3-fluorophenyl)-1H-pyrazolo[3,4-d]pyrimidin-3-yl)benzyl)-5-fluoro-2-methoxybenzamide (Compound 51)

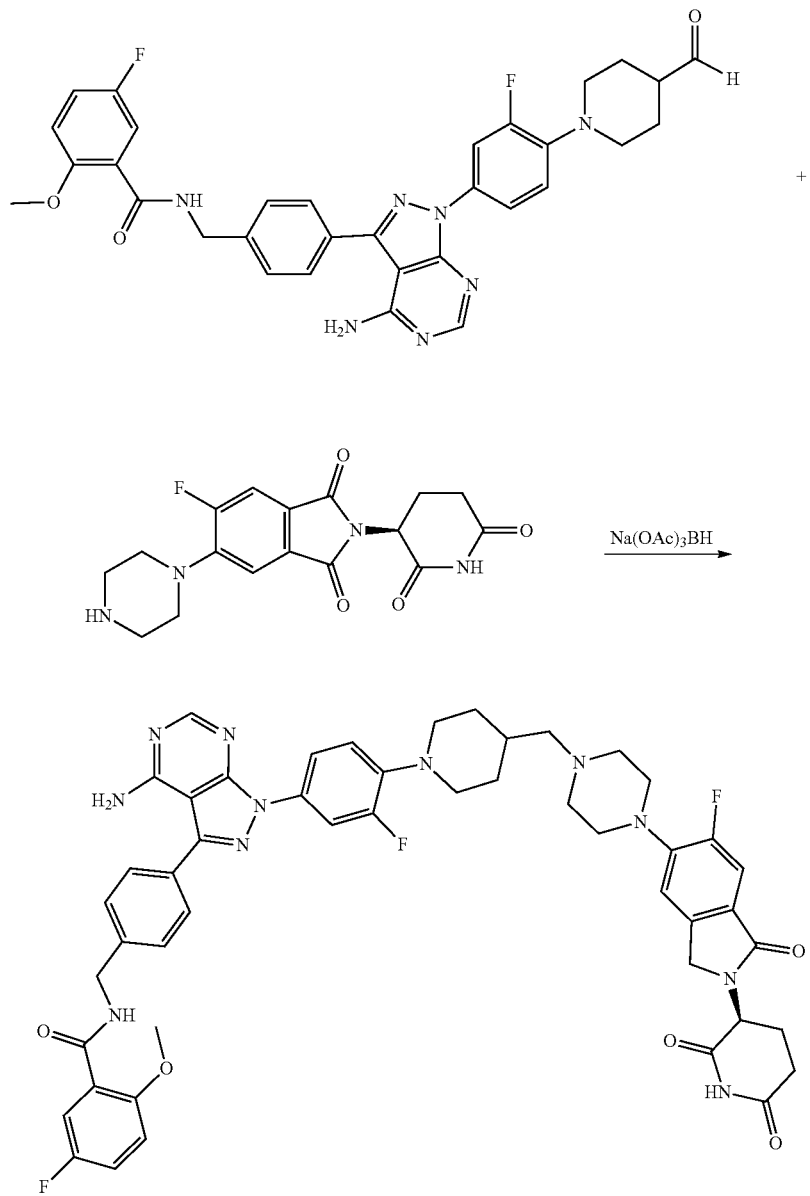

A solution of N-[(4-{4-amino-1-[3-fluoro-4-(4-formylpiperidin-1-yl)phenyl]pyrazolo[3,4-d]pyrimidin-3-yl}phenyl)methyl]-5-fluoro-2-methoxybenzamide (60 mg, 0.1 mmol), (S)-2-(2,6-dioxopiperidin-3-yl)-5-fluoro-6-(piperazin-1-yl)isoindoline-1,3-dione benzenesulfonic acid (76 mg, 0.15 mmol) and triethylamine (30 mg, 0.3 mmol) in DCM (5.0 mL) was stirred in air at room temperature. The reaction mixture was stirred at room temperature for 2 hours. Then sodium triacetoxyborohydride (53 mg, 0.25 mmol) was added at 0° C. portion-wise. The reaction mixture was stirred at room temperature for 2 hours. The reaction mixture was evaporated in vacuo to give the crude product. The crude product was purified by Prep-TLC (DCM:MeOH=10:1) to obtain the desired product as a white solid (29.7 mg, 0.032 mmol, 32% yield). LC/MS: 927 [M+1]$^+$.

$^1$H NMR (400 MHz, DMSO) δ=11.01 (s, 1H), 9.45 (s, 1H), 8.92 (s, 1H), 8.40 (s, 1H), 7.95-8.20 (m, 2H), 7.74 (d, J=7.2 Hz, 2H), 7.53 (m, 3H), 7.46-7.04 (m, 4H), 5.10 (br d, J=9.0 Hz, 1H), 4.61 (d, J=4.9 Hz, 2H), 4.34 (m, 3H), 3.92 (m, 5H), 3.46 (m, 3H), 3.15-3.35 (m, 6H), 2.85-2.96 (m, 2H), 2.70-2.79 (m, 3H), 2.11-1.69 (m, 6H).

Example 52: Preparation of (S)—N-(4-(4-amino-1-(1-(5-((4-(2-(2,6-dioxopiperidin-3-yl)-1-oxoisoindolin-5-yl)piperazin-1-yl)methyl)pyridin-2-yl)piperidin-4-yl)-1H-pyrazolo[3,4-d]pyrimidin-3-yl)benzyl)-5-fluoro-2-methoxybenzamide (Compound 52)

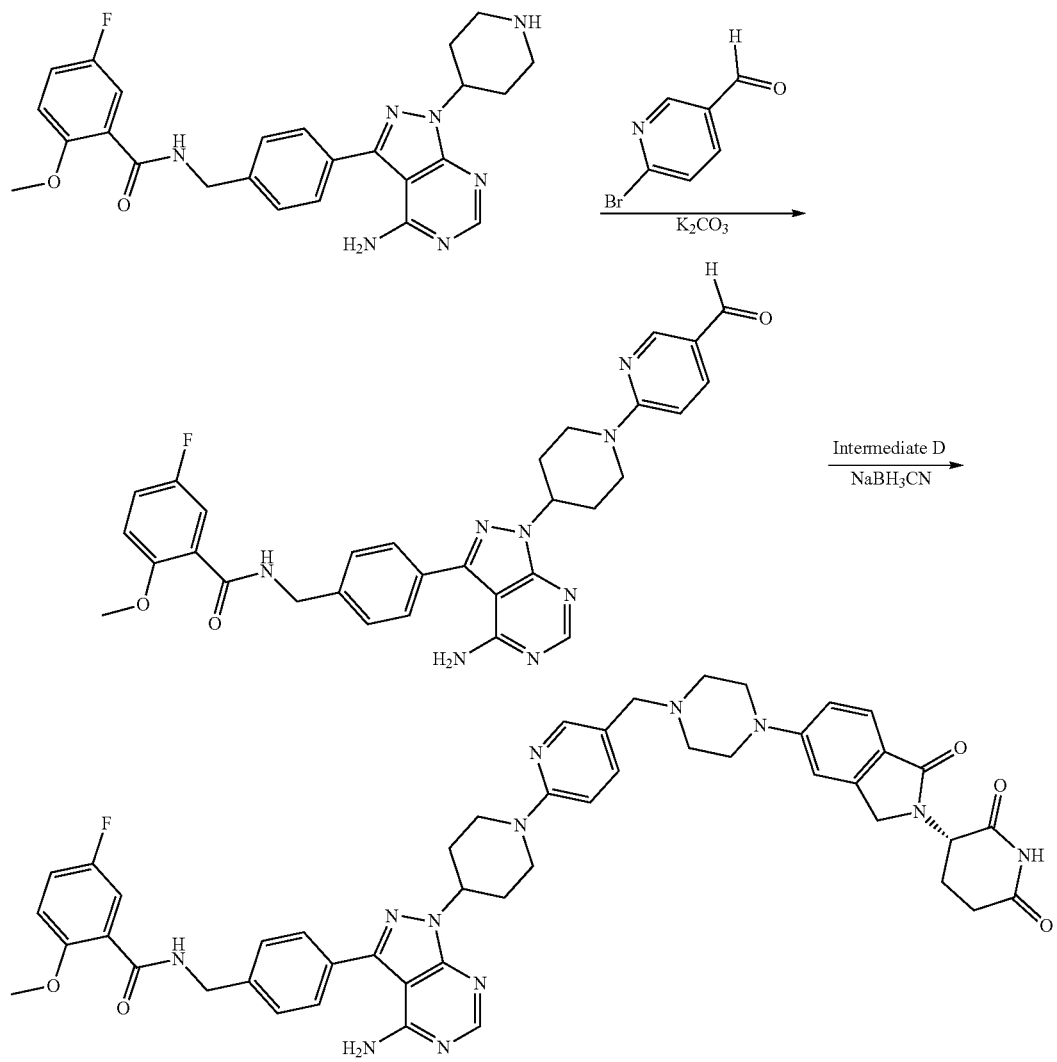

Step 1: Preparation of N-(4-(4-amino-1-(1-(5-formylpyridin-2-yl)piperidin-4-yl)-1H-pyrazolo[3,4-d]pyrimidin-3-yl)benzyl)-5-fluoro-2-methoxybenzamide To a solution of N-(4-(4-amino-1-(1-(5-formylpyridin-2-yl)piperidin-4-yl)-1H-pyrazolo[3,4-d]pyrimidin-3-yl)benzyl)-5-fluoro-2-methoxybenzamide (200 mg, 0.42 mmol) in DMF (10 mL) stirred at room temperature was added 6-bromonicotinaldehyde (156 mg, 0.84 mmol) and $K_2CO_3$ (116 mg, 0.84 mmol). The reaction mixture was stirred at 100° C. for 3 hours. The mixture was cooled to room temperature, poured into water (40 mL) and extracted with EA (50 mL×2). The combined organic layer was washed with brine, dried over $Na_2SO_4$ and concentrated in vacuum to give a crude product. The crude product was purified by flash chromatography (DCM/MeOH=10:1) to give the desired product (100 mg, 41.0%). LC/MS: 581.0 [M+H]$^+$.

Step 2: Preparation of (S)—N-(4-(4-amino-1-(1-(5-((4-(2-(2,6-dioxopiperidin-3-yl)-1-oxoisoindolin-5-yl)piperazin-1-yl)methyl)pyridin-2-yl)piperidin-4-yl)-1H-pyrazolo[3,4-d]pyrimidin-3-yl) benzyl)-5-fluoro-2-methoxybenzamide (S)-2-(2,6-dioxopiperidin-3-yl)-5-fluoro-6-(piperazin-1-yl)isoindoline-1,3-dione benzenesulfonic acid (63 mg, 0.13 mmol) and $Et_3N$ (13 mg, 0.13 mmol) was added to MeOH (4 mL). The mixture was stirred at room temperature for 10 minutes. Then N-(4-(4-amino-1-(1-(5-formylpyridin-2-yl) piperidin-4-yl)-1H-pyrazolo[3,4-d]pyrimidin-3-yl)benzyl)-5-fluoro-2-methoxybenzamide (75 mg, 0.13 mmol) in DCM (4 mL), HOAc (155 mg, 2.58 mmol) and $NaBH_3CN$ (32 mg, 0.52 mmol) were added. The mixture was stirred at room temperature for 2 days. The reaction was quenched by adding water (10 mL) and extracted with EA (15 mL×3). The organic layer was concentrated in vacuum. The residue was purified by Prep-HPLC (ACN (15-30%) in water (0.1% FA)) to afford the desired product as a white solid. (16 mg, 13%).

LC/MS: 893 [M+H]⁺.

¹H NMR (400 MHz, DMSO) δ 10.98-10.91 (m, 1H), 8.89-8.82 (m, 1H), 8.26-8.25 (m, 1H), 8.07-8.02 (m, 1H), 7.62 (d, J=8.2 Hz, 2H), 7.55-7.45 (m, 5H), 7.36-7.31 (m, 1H), 7.18 (dd, J=9.1, 4.3 Hz, 1H), 7.05 (d, J=8.1 Hz, 2H), 6.92 (d, J=8.9 Hz, 1H), 5.08-4.96 (m, 2H), 4.57 (d, J=6.1 Hz, 2H), 4.49-4.46 (m, 2H), 4.33-4.28 (m, 1H), 4.22-4.18 (m, 1H), 3.89 (s, 3H), 3.41-3.39 (m, 2H), 3.29-3.25 (m, 5H), 3.08 (t, J=12.4 Hz, 2H), 2.94-2.85 (m, 1H), 2.62-2.52 (m, 4H), 2.40-2.30 (m, 1H), 2.18-2.06 (m, 2H), 2.10-1.92 (m, 3H).

Example 53: Preparation of (S)—N-(4-(4-amino-1-(1-(4-((4-(2-(2,6-dioxopiperidin-3-yl)-1-oxoisoindolin-5-yl)piperazin-1-yl)methyl)phenyl)piperidin-4-yl)-1H-pyrazolo[3,4-d]pyrimidin-3-yl)benzyl)-5-fluoro-2-methoxybenzamide (Compound 53)

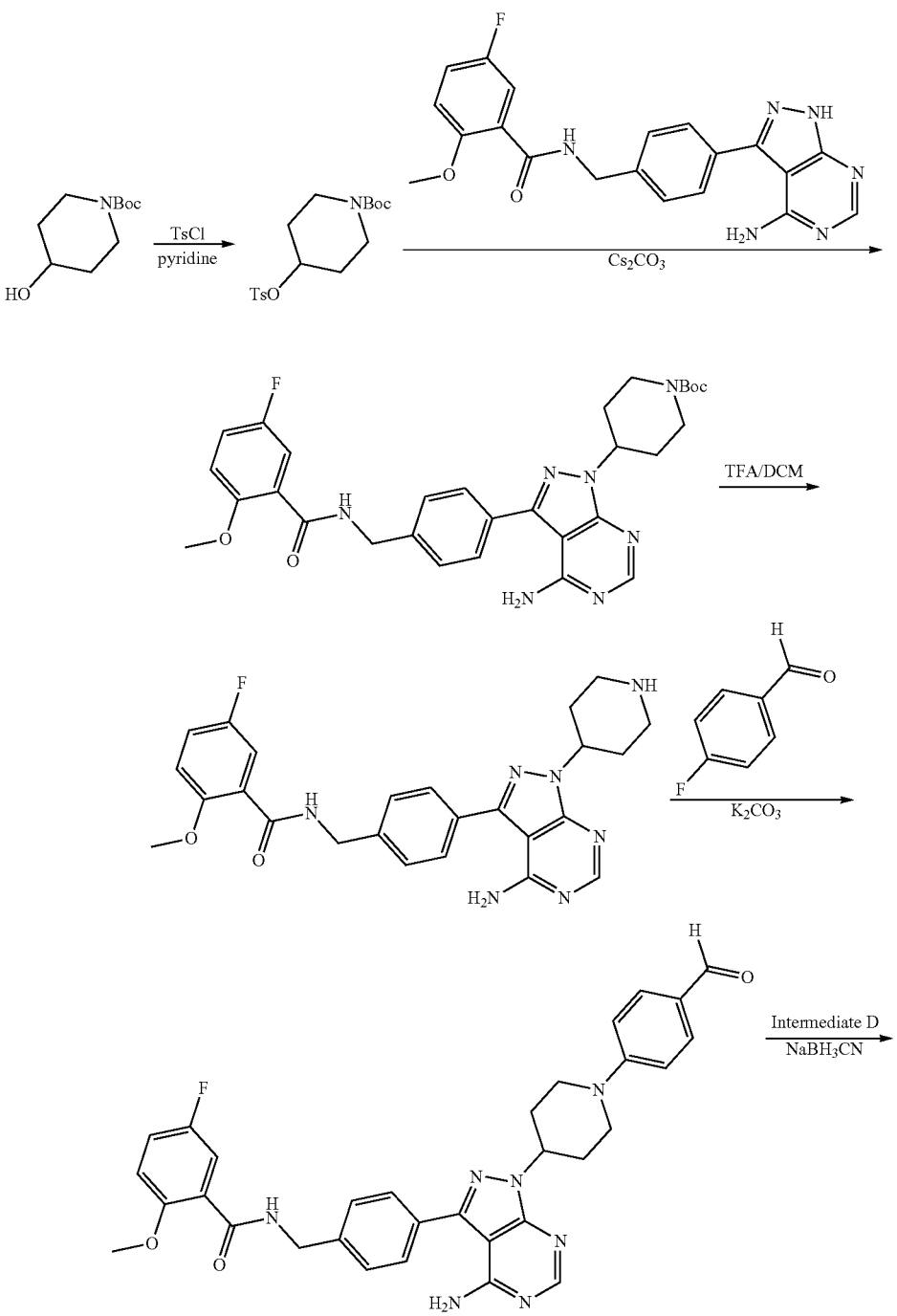

-continued

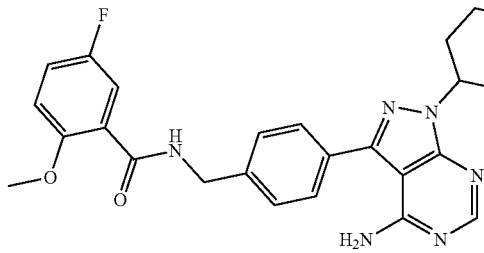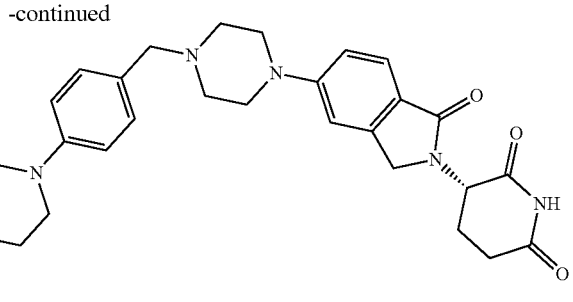

Step 1: Preparation of tert-butyl 4-(tosyloxy)piperidine-1-carboxylate

To a solution of tert-butyl 4-hydroxypiperidine-1-carboxylate (2 g, 9.94 mmol) in pyridine (20 mL) stirred at room temperature was added TsCl (2.27 g, 11.93 mmol). The reaction mixture was stirred at room temperature for 12 hours. The mixture was poured in water (80 mL) and extracted with EA (100 mL×2). The combined organic layer was washed with brine, dried over $Na_2SO_4$ and concentrated in vacuum to give a crude product. The crude product was purified by flash chromatography (PE/EtOAc=3:1) to give the desired product (2.2 g, 62%). LC/MS: 377.8 $[M+Na]^+$.

Step 2: Preparation of tert-butyl 4-(4-amino-3-(4-((5-fluoro-2-methoxybenzamido)methyl)phenyl)-1H-pyrazolo[3,4-d]pyrimidin-1-yl)piperidine-1-carboxylate To a solution of tert-butyl 4-(tosyloxy)piperidine-1-carboxylate (2.2 g, 6.19 mmol) in DMF (2 mL) stirred at room temperature was added $Cs_2CO_3$ (4.03 g, 12.38 mmol) and N-(4-(4-amino-1H-pyrazolo[3,4-d]pyrimidin-3-yl)benzyl)-5-fluoro-2-methoxybenzamide (2.43 g, 6.19 mmol). The reaction mixture was stirred at 60° C. for 12 hours. The mixture was cooled to room temperature, poured into water (75 mL) and extracted with EA (100 mL×2). The combined organic layer was washed with brine, dried over $Na_2SO_4$ and concentrated in vacuum to give a crude product. The crude product was purified by flash chromatography (DCM/MeOH=10:1) to give the desired product (2.5 g, 70%). LC/MS: 575.8 $[M+H]^+$.

Step 3: Preparation of N-(4-(4-amino-1-(piperidin-4-yl)-1H-pyrazolo[3,4-d]pyrimidin-3-yl)benzyl)-5-fluoro-2-methoxybenzamide A solution of tert-butyl 4-(4-amino-3-(4-((5-fluoro-2-methoxybenzamido)methyl)phenyl)-1H-pyrazolo[3,4-d]pyrimidin-1-yl)piperidine-1-carboxylate (2.5 g, 4.34 mmol) in TFA/DCM (1:5, 30 mL) was stirred at room temperature for 2 hours. The solution was concentrated in vacuum. The residue was dissolved with DCM (100 mL) and washed with saturated sodium bicarbonate solution (100 mL×2). The organic layer was dried over $Na_2SO_4$ and concentrated in vacuum to give the desired product (1.5 g, 72%). LC/MS: 476.0 $[M+H]^+$.

Step 4: Preparation of N-(4-(4-amino-1-(1-(4-formylphenyl)piperidin-4-yl)-1H-pyrazolo[3,4-d]pyrimidin-3-yl)benzyl)-5-fluoro-2-methoxybenzamide To a solution of N-({4-[4-amino-1-(piperidin-4-yl)pyrazolo[3,4-d]pyrimidin-3-yl]phenyl}methyl)-5-fluoro-2-methoxybenzamide (700 mg, 1.47 mmol) in DMF (10 mL) stirred at room temperature was added 4-fluorobenzaldehyde (365 mg, 2.94 mmol) and $K_2CO_3$ (406 mg, 2.94 mmol). The reaction mixture was stirred at 100° C. for 3 hours. The mixture was cooled to room temperature, poured in water (40 mL) and extracted with EA (50 mL×2). The combined organic layer was washed with brine, dried over $Na_2SO_4$ and concentrated in vacuum to give a crude product. The crude product was purified by flash chromatography (DCM/MeOH=10:1) to give the desired product (300 mg, 35%). LC/MS: 580.0 $[M+H]^+$.

Step 5: Preparation of (S)—N-(4-(4-amino-1-(1-(4-((4-(2-(2,6-dioxopiperidin-3-yl)-1-oxoisoindolin-5-yl)piperazin-1-yl)methyl)phenyl)piperidin-4-yl)-1H-pyrazolo[3,4-d]pyrimidin-3-yl)benzyl)-5-fluoro-2-methoxybenzamide (S)-2-(2,6-dioxopiperidin-3-yl)-5-fluoro-6-(piperazin-1-yl)isoindoline-1,3-dione benzenesulfonic acid (71 mg, 0.15 mmol) and $Et_3N$ (15 mg, 0.15 mmol) was added into MeOH (4 mL). The mixture was stirred at room temperature for 10 minutes. Then N-(4-(4-amino-1-(1-(4-formylphenyl)piperidin-4-yl)-1H-pyrazolo[3,4-d]pyrimidin-3-yl)benzyl)-5-fluoro-2-methoxybenzamide (85 mg, 0.15 mmol) in DCM (4 mL), HOAc (176 mg, 2.93 mmol) and $NaBH_3CN$ (37 mg, 0.59 mmol) was added. The solution was stirred at room temperature for 2 days. The reaction was quenched by adding water (10 mL) and extracted with EA (3×15 mL). The organic layer was combined and concentrated in vacuum. The residue was purified by preparative HPLC [ACN (20-40%) in water (0.1% FA)] to afford the desired product as a white solid (26 mg, 19%). LC/MS: 892 $[M+H]^+$.

$^1$H NMR (400 MHz, DMSO) δ 10.95 (s, 1H), 8.87 (t, J=6.3 Hz, 1H), 8.26 (s, 1H), 7.64 (d, J=8.1 Hz, 2H), 7.55-7.47 (m, 4H), 7.37-7.31 (m, 1H), 7.18 (dd, J=9.1, 4.3 Hz, 3H), 7.10-6.94 (m, 4H), 5.09-5.03 (m, 1H), 4.93-4.89 (m, 1H), 4.58 (d, J=6.1 Hz, 2H), 4.35-4.10 (m, 2H), 3.95-3.80 (m, 5H), 3.48-3.35 (m, 2H), 3.31-3.19 (m, 3H), 3.15-2.85 (m, 4H), 2.63-2.53 (m, 4H), 2.44-2.34 (m, 2H), 2.47-2.25 (m, 2H), 2.09-1.95 (m, 3H).

Example 54: Preparation of (S)—N-(4-(4-amino-1-(1-(5-((4-(2-(2,6-dioxopiperidin-3-yl)-1-oxoisoindolin-5-yl)piperazin-1-yl)methyl)pyridin-2-yl)azetidin-3-yl)-1H-pyrazolo[3,4-d]pyrimidin-3-yl)benzyl)-5-fluoro-2-methoxybenzamide (Compound 54)
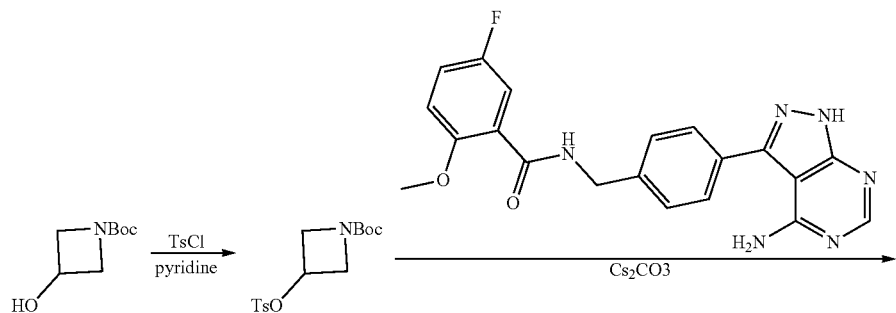
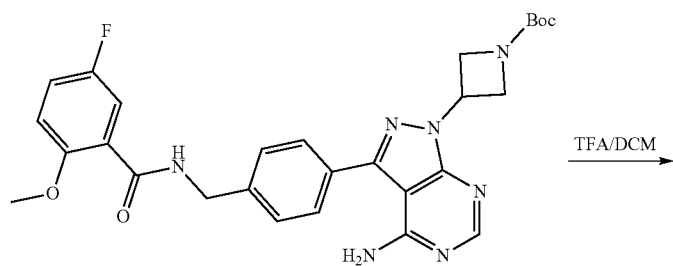
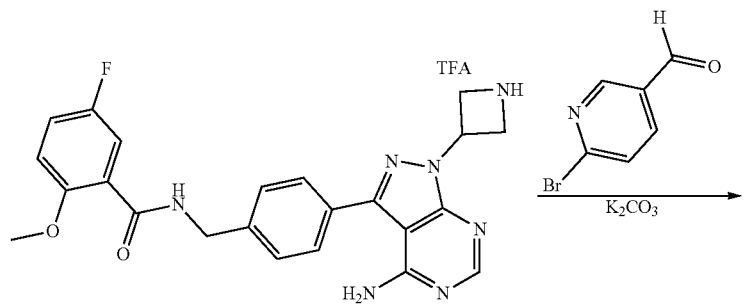
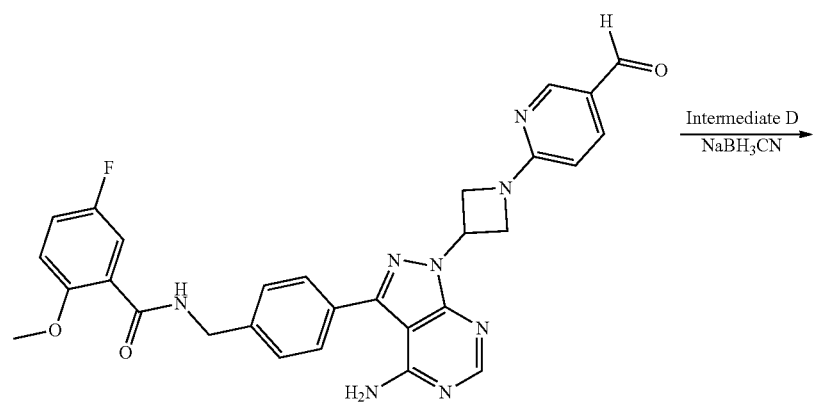

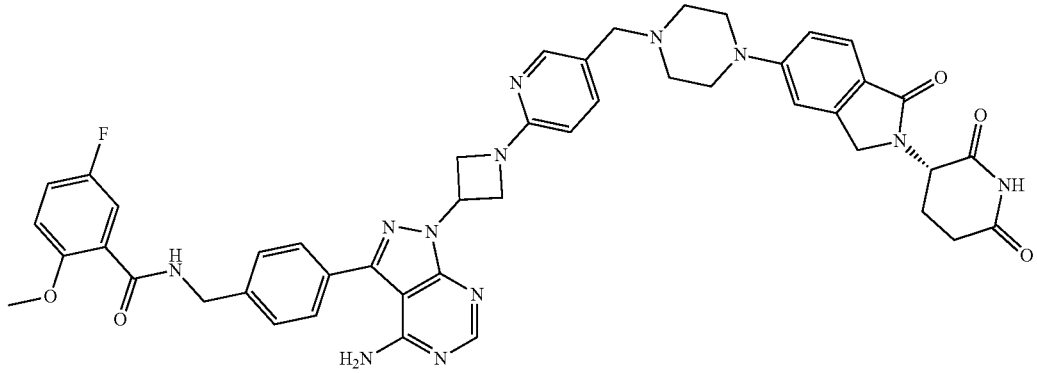

Step 1: Preparation of tert-butyl 3-(tosyloxy)azetidine-1-carboxylate

A solution of tert-butyl 3-hydroxyazetidine-1-carboxylate (1270 mg, 7.33 mmol), $Et_3N$ (1113 mg, 11.00 mmol) and TsCl (1677 mg, 8.80 mmol) in DCM (20 mL) was stirred at room temperature under $N_2$ overnight. The reaction was quenched by adding water (20 mL) and extracted with DCM (20 mL×3). The organic phase was washed with brine and concentrated in vacuum. The residue was purified by flash chromatography (PE/EA=9/1) to afford the desired product as a colorless oil (2.4 g, 100%). LC/MS: 328 [M+H]$^+$.

Step 2: Preparation of tert-butyl 3-(4-amino-3-(4-((5-fluoro-2-methoxybenzamido)methyl)phenyl)-1H-pyrazolo[3,4-d]pyrimidin-1-yl)azetidine-1-carboxylate A suspension of tert-butyl 3-(tosyloxy)azetidine-1-carboxylate (667 mg, 2.04 mmol), N-(4-(4-amino-1H-pyrazolo[3,4-d]pyrimidin-3-yl)benzyl)-5-fluoro-2-methoxybenzamide (800 mg, 2.04 mmol) and $Cs_2CO_3$ (1993 mg, 6.12 mmol) in DMF (10 mL) was stirred at 80° C. overnight. The reaction was quenched by adding water (20 mL) and extracted with EA (20 mL×3). The organic layer was washed with brine and concentrated in vacuum. The residue was purified by flash chromatography (DCM/MeOH=97/3) to afford the desired product as a light brown solid (200 mg, 17.9%). LC/MS: 548 [M+H]$^+$.

Step 3: Preparation of N-(4-(4-amino-1-(azetidin-3-yl)-1H-pyrazolo[3,4-d]pyrimidin-3-yl)benzyl)-5-fluoro-2-methoxybenzamide A solution of tert-butyl 3-(4-amino-3-(4-((5-fluoro-2-methoxybenzamido)methyl)phenyl)-1H-pyrazolo[3,4-d]pyrimidin-1-yl)azetidine-1-carboxylate (200 mg, 0.36 mmol) in DCM/TFA (8 mL, 3:1) was stirred at room temperature for 1 hour. The solution was concentrated in vacuum to afford the desired product as a white solid. (198 mg of TFA salt, 100%). LC/MS: 448 [M+H]$^+$.

Step 4: Preparation of N-(4-(4-amino-1-(1-(5-formylpyridin-2-yl)azetidin-3-yl)-1H-pyrazolo[3,4-d]pyrimidin-3-yl)benzyl)-5-fluoro-2-methoxybenzamide To a solution of N-(4-(4-amino-1-(azetidin-3-yl)-1H-pyrazolo[3,4-d]pyrimidin-3-yl)benzyl)-5-fluoro-2-methoxybenzamide (TFA salt, 198 mg, 0.36 mmol) and 6-bromonicotinaldehyde (136 mg, 0.73 mmol) in DMF (4 mL) was added $K_2CO_3$ (151 mg, 1.11 mmol). The mixture was stirred at 80° C. overnight. The reaction was quenched by adding water (10 mL) and extracted with EA (20 mL×3). The organic layer was washed with brine and concentrated in vacuum. The residue was purified by flash chromatography (DCM/MeOH=75/15) to afford the desired product as a yellow solid (100 mg, 50%). LC/MS: 553 [M+H]$^+$.

Step 5: Preparation of (S)—N-(4-(4-amino-1-(1-(5-((4-(2-(2,6-dioxopiperidin-3-yl)-1-oxoisoindolin-5-yl)piperazin-1-yl)methyl)pyridin-2-yl)azetidin-3-yl)-1H-pyrazolo[3,4-d]pyrimidin-3-yl)benzyl)-5-fluoro-2-methoxybenzamide (S)-2-(2,6-dioxopiperidin-3-yl)-5-fluoro-6-(piperazin-1-yl)isoindoline-1,3-dione benzenesulfonic acid (84 mg, 0.17 mmol) and $Et_3N$ (17 mg, 0.17 mmol) was added into MeOH (4 mL). The mixture was stirred at room temperature for 10 minutes. Then N-(4-(4-amino-1-(1-(5-formylpyridin-2-yl)azetidin-3-yl)-1H-pyrazolo[3,4-d]pyrimidin-3-yl)benzyl)-5-fluoro-2-methoxybenzamide (95 mg, 0.17 mmol) in DCM (4 mL), HOAc (206 mg, 3.44 mmol) and $NaBH_3CN$ (65 mg, 1.03 mmol) were added. The mixture was stirred at room temperature for 2 days. The reaction was quenched by adding water (10 mL) and extracted with EA (15 mL×3). The organic phase was concentrated in vacuum. The residue was purified by preparative HPLC [ACN (15-25%) in water (0.1% FA)] to afford the desired product as a white solid. (13.8 mg, 9.3%). LC/MS: 865 [M+H]$^+$.

$^1$H NMR (400 MHz, DMSO) δ 10.95 (s, 1H), 8.87 (t, J=6.1 Hz, 1H), 8.28 (s, 1H), 8.03 (s, 1H), 7.66 (d, J=8.1 Hz, 2H), 7.56-7.47 (m, 5H), 7.37-7.30 (m, 1H), 7.18 (dd, J=9.2, 4.3 Hz, 1H), 7.04 (d, J=8.3 Hz, 2H), 6.50 (d, J=8.4 Hz, 1H), 5.87 (t, J=7.5 Hz, 1H), 5.06-5.02 (m, 1H), 4.57 (d, J=6.1 Hz, 2H), 4.55-4.37 (m, 4H), 4.35-4.17 (m, 2H), 3.89 (s, 3H), 3.42 (s, 2H), 3.29-3.05 (m, 5H), 2.98-2.89 (m, 1H), 2.65-2.55 (m, 4H), 2.37-2.33 (m, 1H), 1.97-1.95 (m, 1H).

Example 55: Preparation of N-(4-(4-amino-1-(1-(5-(4-(2-((S)-2,6-dioxopiperidin-3-yl)-1-oxoisoindolin-5-yl)piperazin-1-yl)pentanoyl)pyrrolidin-3-yl)-1H-pyrazolo[3,4-d]pyrimidin-3-yl)benzyl)-5-fluoro-2-methoxybenzamide (Compound 55)

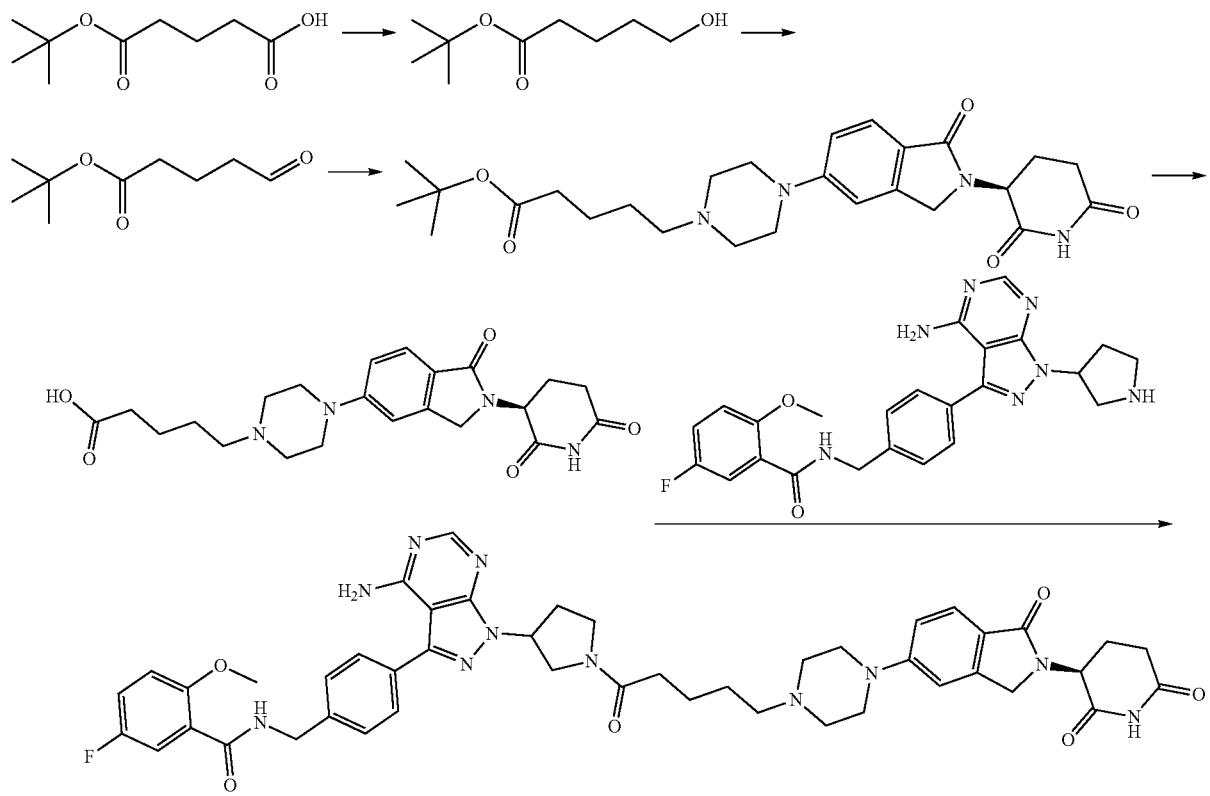

Step 1: Preparation of tert-butyl 5-hydroxypentanoate

To a solution of 5-(tert-butoxy)-5-oxopentanoic acid (3.00 g, 6.96 mmol) in dry THF (60 mL) cooled to 0° C. was added NaBH$_4$ (630 mg, 16.74 mmol). The solution was stirred until evolution of H$_2$ stopped then BF$_3$.OEt$_2$ (2.71 g, 19.13 mmol) was added dropwise. The reaction was stirred at room temperature for 4 hours. The reaction was quenched by adding H$_2$O (50 mL) at 0° C. The mixture was extracted with EA (50 mL×3). The combined organic layers were washed with sat. Na$_2$CO$_3$ solution and brine then concentrated in vacuum to give a crude product (2.50 g, 90.0%) as a colorless oil. LC/MS: 197.2 [M+Na]$^+$.

Step 2: Preparation of tert-butyl 5-oxopentanoate

To a solution of tert-butyl 5-hydroxypentanoate (500 mg, 2.87 mmol) in DCM (20 mL) stirred under argon at room temperature was added PDC (1.62 g, 4.30 mmol). The mixture was stirred at room temperature for 4 hours. The mixture was filtered and the filtration was collected. The filtrate cake was washed with DCM (20 mL). The combined solution was concentrated in vacuum. The residue was purified by flash chromatography (0~65% EA in PE) to give the desired product (200 mg, 40.5%) as a colorless oil. LC/MS: 195.0 [M+Na]$^+$.

Step 3: Preparation of tert-butyl (S)-5-(4-(2-(2,6-dioxopiperidin-3-yl)-1-oxoisoindolin-5-yl)piperazin-1-yl)pentanoate To a solution of tert-butyl 5-oxopentanoate (90 mg, 0.52 mmol), (S)-3-(1-oxo-5-(piperazin-1-yl)isoindolin-2-yl)piperidine-2,6-dione (254 mg, 0.52 mmol) and NaOAc (51 mg, 0.63 mmol) in MeOH (10 mL) was added NaBH$_3$CN (66 mg, 1.05 mmol). The reaction mixture was stirred at room temperature for overnight. The reaction mixture was partitioned between DCM (50 mL) and Water (30 mL). The organic layer was evaporated to give a crude product. The crude product was purified by flash chromatography (0~10% MeOH in DCM) to give the desired product (200 mg, 79.0% yield). LC/MS: 484.9 [M+H]$^+$.

Step 4: Preparation of (S)-5-(4-(2-(2,6-dioxopiperidin-3-yl)-1-oxoisoindolin-5-yl)piperazin-1-yl)pentanoic acid To a solution of tert-butyl (S)-5-(4-(2-(2,6-dioxopiperidin-3-yl)-1-oxoisoindolin-5-yl)piperazin-1-yl)pentanoate (200 mg, 0.41 mmol) in DCM (3 mL) was added TFA (1 mL). The mixture was stirred at room temperature for 3 hours. The reaction mixture was concentrated under vacuum to give the desired product (170 mg, 96.1% yield) as a light yellow solid. LC/MS: 428.9 [M+H]$^+$.

Step 5: Preparation of N-(4-(4-amino-1-(1-(5-(4-(2-((S)-2,6-dioxopiperidin-3-yl)-1-oxoisoindolin-5-yl)piperazin-1-yl)pentanoyl)pyrrolidin-3-yl)-1H-pyrazolo[3,4-d]pyrimidin-3-yl)benzyl)-5-fluoro-2-methoxybenzamide To a solution of (S)-5-(4-(2-(2,6-dioxopiperidin-3-yl)-1-oxoisoindolin-5-yl)piperazin-1-yl)pentanoic acid (177 mg, 0.41 mmol), N-(4-(4-amino-1-(pyrrolidin-3-yl)-1H-pyrazolo[3,4-d]pyrimidin-3-yl)benzyl)-5-fluoro-2-methoxybenzamide (191 mg, 0.41 mmol) and DIEA (160 mg, 1.24 mmol) in DMF (10 mL) was added HOBT (61 mg, 0.45 mmol) and EDCI (87 mg, 0.45 mmol). The reaction mixture was stirred at room temperature for overnight. The reaction mixture was partitioned between DCM (50 mL) and Water (30 mL). The organic layer was evaporated to give a crude product. The crude product was purified by Prep-HPLC (20~22% ACN in H$_2$O (0.1% of FA)) to give the desired product (25 mg, 6.64% yield) as a white solid. LC/MS: 872.6 [M+H]$^+$.

$^1$H NMR (400 MHz, DMSO) δ 10.95 (s, 1H), 8.87 (t, J=5.9 Hz, 1H), 8.87-8.26 (m, 1H), 7.63 (dd, J=7.3, 5.3 Hz, 2H), 7.55-7.48 (m, 4H), 7.34 (td, J=8.7, 3.5 Hz, 1H), 7.18 (dd, J=9.1, 4.3 Hz, 1H), 7.02 (dd, J=10.7, 7.8 Hz, 2H), 5.55-5.39 (m, 1H), 5.10-4.95 (m, 1H), 4.58 (d, J=6.0 Hz, 2H), 4.32 (d, J=15.9 Hz, 1H), 4.19 (d, J=16.9 Hz, 1H), 4.07-3.87 (m, 4H), 3.87-3.56 (m, 3H), 3.54-3.41 (m, 1H), 3.26-3.18 (m, 4H), 2.95-2.85 (m, 1H), 2.60-2.52 (m, 1H), 2.48-2.41 (m, 4H), 2.39-2.23 (m, 6H), 2.00-1.91 (m, 1H), 1.59-1.42 (m, 4H).

Example 56: Preparation of N-(4-(4-amino-1-(1-(6-((4-(2-((S)-2,6-dioxopiperidin-3-yl)-1-oxoisoindolin-5-yl)piperazin-1-yl)methyl)pyridin-3-yl)pyrrolidin-3-yl)-1H-pyrazolo[3,4-d]pyrimidin-3-yl)benzyl)-5-fluoro-2-methoxybenzamide (Compound 58)

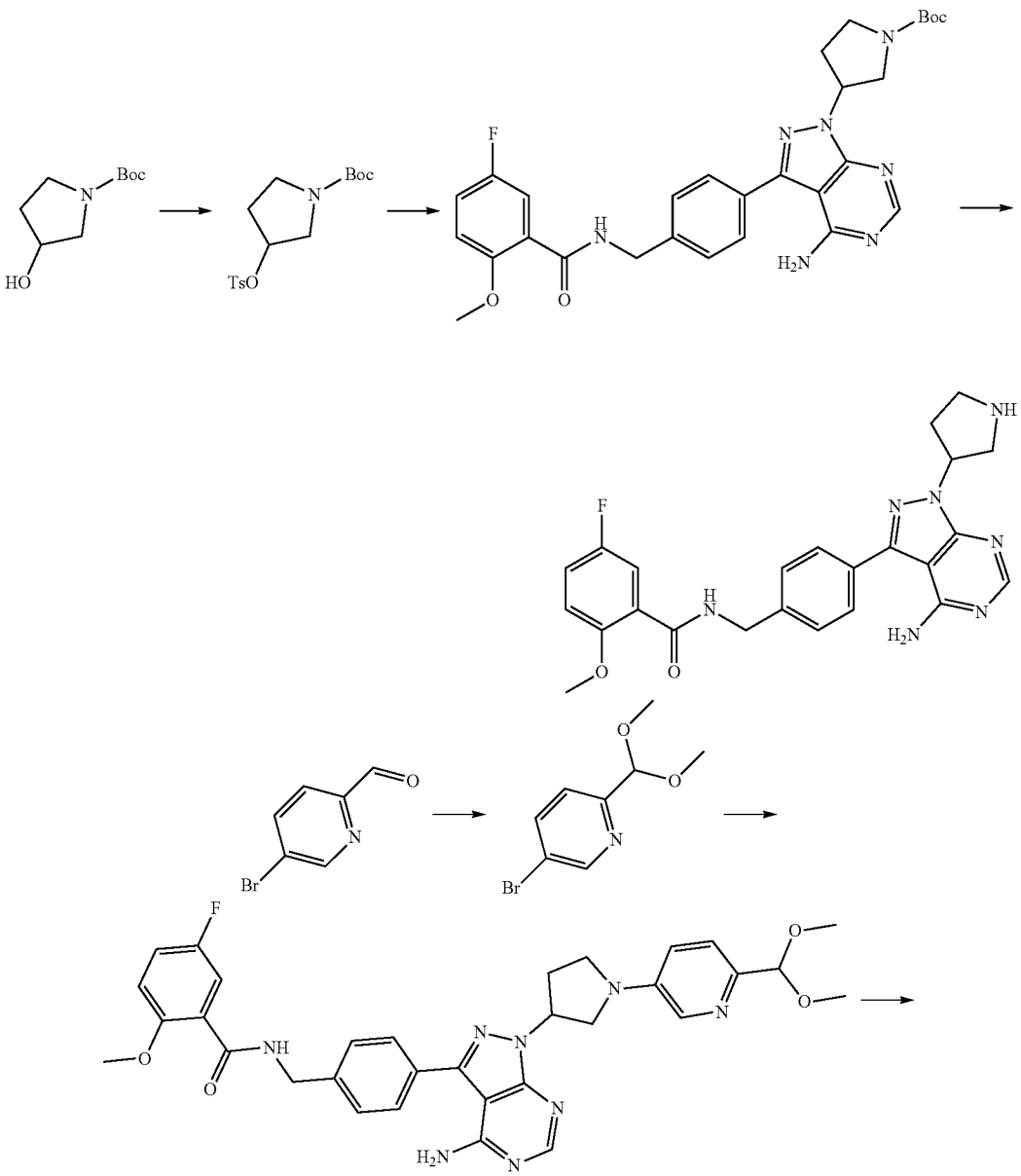

-continued

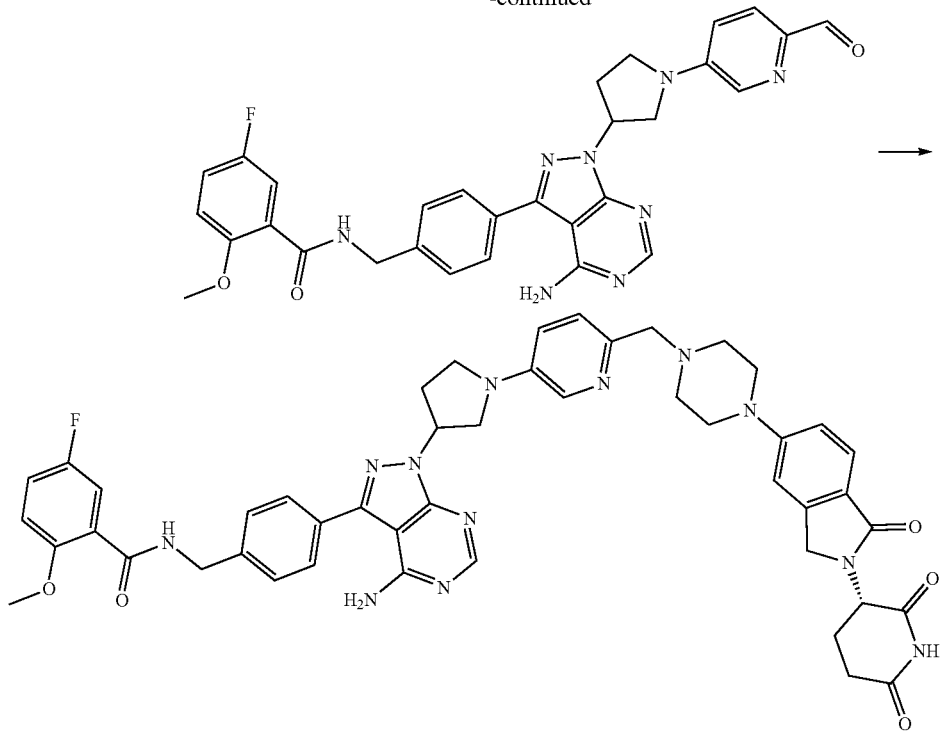

Step 1: Preparation of tert-butyl 3-(tosyloxy)pyrrolidine-1-carboxylate

To a solution of tert-butyl (3-hydroxypyrrolidin-1-yl) formate (5 g, 26.6 mmol) in pyridine (50 mL) was added TsCl (6.1 g, 31.9 mmol) at room temperature. The reaction mixture was stirred at room temperature for 12 hours. The reaction mixture was diluted with DCM (100 mL) then washed with water and brine. The organic phase was dried over $Na_2SO_4$ and concentrated under vacuum to give a crude product. The crude product was purified by flash chromatography (PE/EA=3:1) to give the desired product (8 g, 87.9%) as a white solid.

LC/MS: 364.0 [M+Na]$^+$.

Step 2: Preparation of tert-butyl 3-(4-amino-3-(4-((5-fluoro-2-methoxybenzamido)methyl)phenyl)-1H-pyrazolo[3,4-d]pyrimidin-1-yl)pyrrolidine-1-carboxylate To a solution of tert-butyl (3-{[(4-methylbenzene)sulfonyl]oxy}pyrrolidin-1-yl) formate (2 g, 5.84 mmol) in DMF (20 mL) stirred at room temperature was added N-[(4-{4-amino-1H-pyrazolo[3,4-d]pyrimidin-3-yl}phenyl)methyl]-5-fluoro-2-methoxybenzamide (2.3 g, 5.84 mmol) and $Cs_2CO_3$ (3.8 g, 11.68 mmol). The reaction mixture was stirred at 80° C. for 12 hours. The reaction mixture was poured into water (80 mL) then extracted with EA (100 mL×2). The combined organic layers were washed with brine (200 mL), dried over $Na_2SO_4$ and concentrated under vacuum to give a crude product. The crude product was purified by flash chromatography (10% MeOH in DCM) to give the desired product (2.3 g, 70.0%) as a yellow solid. LC/MS: 562.0[M+H]$^+$.

Step 3: Preparation of N-(4-(4-amino-1-(pyrrolidin-3-yl)-1H-pyrazolo[3,4-d]pyrimidin-3-yl)benzyl)-5-fluoro-2-methoxybenzamide A solution of tert-butyl-3-(4-amino-3-(4-((5-fluoro-2-methoxybenzamido)methyl)phenyl)-1H-pyrazolo[3,4-d]pyrimidin-1-yl)pyrrolidine-1-carboxylate (2.3 g, 4.09 mmol) in TFA/DCM (24 mL, 5:1) was stirred at room temperature for 2 hours. The mixture was concentrated under vacuum. The residue was dissolved with saturated sodium bicarbonate solution (100 mL) then extracted with DCM (100 mL×2). The combined organic layers were washed with brine (200 mL), dried over $Na_2SO_4$ and concentrated under vacuum to give the desired product (1.2 g, 63.6%) as a brown solid. LC/MS: 462.0[M+H]$^+$.

Step 4: Preparation of 5-bromo-2-(dimethoxymethyl)pyridine

To a solution of 5-bromopyridine-2-carbaldehyde (1 g, 5.37 mmol) in MeOH (10 mL) stirred at room temperature was added trimethoxymethane (1.71 g, 16.13 mmol) and TsOH (278 mg, 1.61 mmol). The reaction mixture was stirred at 70° C. for 2 hours. The mixture was concentrated under vacuum to get a crude product. The crude product was purified by Flash Chromatography (PE/EA=10:1) to give the desired product (600 mg, 48.1%). LC/MS: 232.0 [M+H]$^+$.

Step 5: Preparation of N-(4-(4-amino-1-(1-(6-(dimethoxymethyl)pyridin-3-yl)pyrrolidin-3-yl)-1H-pyrazolo[3,4-d]pyrimidin-3-yl)benzyl)-5-fluoro-2-methoxybenzamide To a solution of N-({4-[4-amino-1-(pyrrolidin-3-yl)pyrazolo[3,4-d]pyrimidin-3-yl]phenyl} methyl)-5-fluoro-2-methoxybenzamide (160 mg, 0.35 mmol) in toluene (10 mL)

stirred at room temperature was added 5-bromo-2-(dimethoxymethyl)pyridine (123 mg, 0.53 mmol), BINAP (130 mg, 0.21 mmol), t-BuONa (67 mg, 0.7 mmol) and Pd$_2$(dba)$_3$ (96 mg, 0.105 mmol) under Ar. The reaction mixture was stirred at 80° C. for 12 hours. The mixture was concentrated under vacuum to give a crude product. The crude product was purified by Flash Chromatography (DCM/MeOH=10:1) to give the desired product (60 mg, 28.2%). LC/MS: 635.0 [M+H]$^+$.

Step 6: Preparation of N-(4-(4-amino-1-(1-(6-formylpyridin-3-yl)pyrrolidin-3-yl)-1H-pyrazolo [3,4-d]pyrimidin-3-yl)benzyl)-5-fluoro-2-methoxybenzamide To a solution of N-{[4-(4-amino-1-{1-[5-(dimethoxymethyl)pyridin-2-yl]piperidin-4-yl}pyrazolo[3,4-d]pyrimidin-3-yl)phenyl]methyl}-5-fluoro-2-methoxybenzamide (55 mg, 0.09 mmol) in THF (5 mL) stirred at room temperature was added HCl (0.2 mL). The reaction mixture was stirred at 50° C. for 12 hours. The mixture was poured into H$_2$O (20 mL), adjusted pH to 7-8 with saturated sodium bicarbonate solution, then extracted with EA (20 mL×3). The combined organic layers were washed with brine (50 mL), dried over Na$_2$SO$_4$ and concentrated under vacuum to give a crude product. The crude product was purified by Flash Chromatography (DCM/MeOH=10:1) to give the desired product (21 mg, 41.1%). LC/MS: 566.9 [M+H]$^+$.

Step 7: Preparation of N-(4-(4-amino-1-(1-(6-((4-(2-((S)-2,6-dioxopiperidin-3-yl)-1-oxoisoindolin-5-yl)piperazin-1-yl)methyl)pyridin-3-yl)pyrrolidin-3-yl)-1H-pyrazolo[3,4-d]pyrimidin-3-yl)benzyl)-5-fluoro-2-methoxybenzamide To a solution of N-(4-(4-amino-1-(1-(6-formylpyridin-3-yl)pyrrolidin-3-yl)-1H-pyrazolo[3,4-d]pyrimidin-3-yl)benzyl)-5-fluoro-2-methoxybenzamide (21 mg, 0.03 mmol) in MeOH/DMF/HOAc (5 mL, 2:1:0.02) was added TEA (7.5 mg, 0.04 mmol), (S)-3-(1-oxo-5-(piperazin-1-yl)isoindolin-2-yl)piperidine-2,6-dione (21.66 mg, 0.04 mmol) and NaBH$_3$CN (6.99 mg, 0.11 mmol). The mixture was stirred at 60° C. for 1 hour. The reaction was quenched by adding water (5 mL) and extracted with DCM (10 mL×2). The organic phase was washed with brine and dried over Na$_2$SO$_4$. The solvent was removed in vacuum and the residue was purified by Prep-HPLC (ACN/H$_2$O (0.1% FA), 10-40%) to afford the desired compound (3 mg, 9.2%).

LC/MS: 879.6 [M+H]$^+$.

$^1$H NMR (400 MHz, DMSO) δ 10.96 (s, 1H), 8.87 (t, J=6.3 Hz, 1H), 8.39-8.27 (m, 2H), 7.91 (s, 1H), 7.62 (d, J=8.0 Hz, 2H), 7.49 (t, J=9.8 Hz, 3H), 7.37-7.31 (m, 1H), 7.27-7.14 (m, 2H), 7.11-6.93 (m, 3H), 5.68-5.60 (m, 1H), 5.04 (dd, J=13.1, 5.1 Hz, 1H), 4.57 (d, J=6.2 Hz, 2H), 4.32 (d, J=17.4 Hz, 1H), 4.19 (d, J=17.2 Hz, 1H), 3.94-3.82 (m, 4H), 3.69-3.64 (m, 2H), 3.53-3.50 (m, 4H), 3.29-3.25 (m, 3H), 2.94-2.86 (m, 1H), 2.68-2.52 (m, 6H), 2.42-2.28 (m, 2H), 1.99-1.90 (m, 1H).

Example 57: Preparation of (S)—N-(4-(4-amino-1-(6-(4-((4-(2-(2,6-dioxopiperidin-3-yl)-1-oxoisoindolin-5-yl)piperazin-1-yl)methyl)piperidin-1-yl)pyridin-3-yl)-1H-pyrazolo[3,4-d]pyrimidin-3-yl)benzyl)-5-fluoro-2-methoxybenzamide (Compound 59)

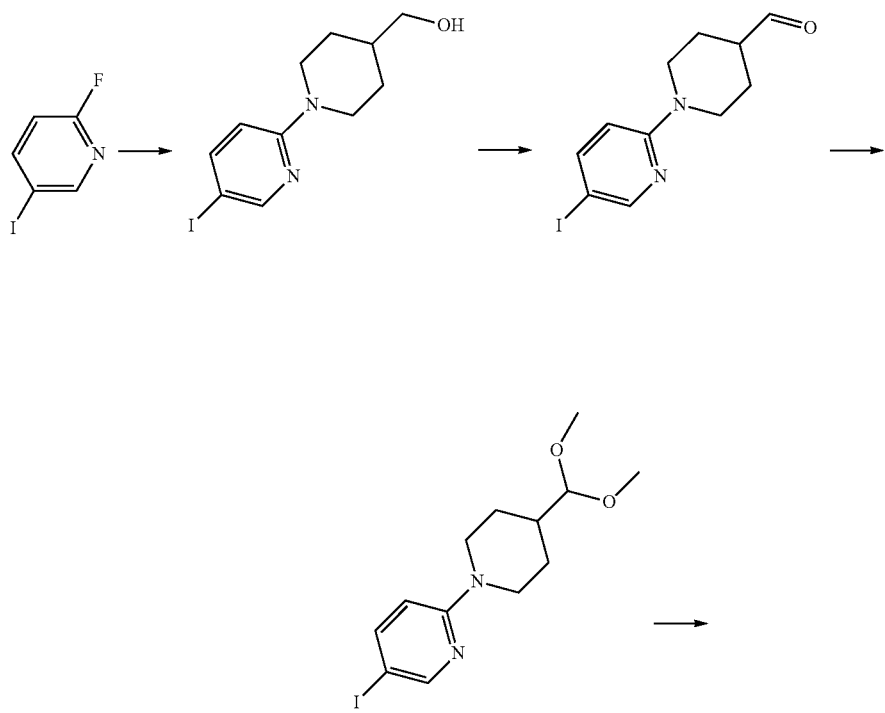

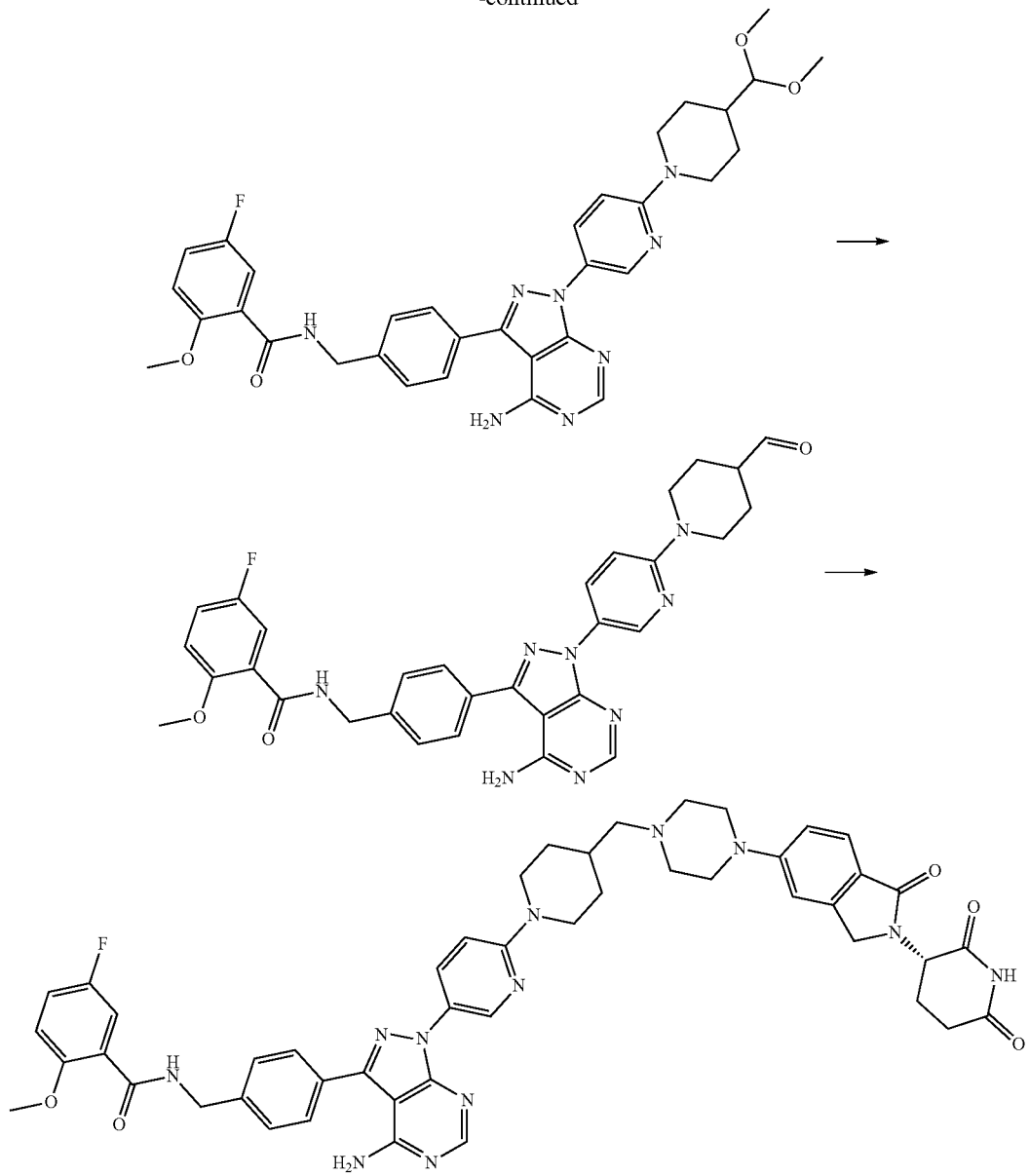

Step 1: Preparation of (1-(5-iodopyridin-2-yl)piperidin-4-yl)methanol

To a solution of 2-fluoro-5-iodopyridine (2 g, 9.0 mmol) and piperidin-4-ylmethanol (1.2 g, 10.8 mmol) in DMF (50 mL) stirred under nitrogen at 25° C. was added potassium carbonate (3.7 g, 27.0 mmol). The reaction mixture was stirred at 100° C. for 2 hours. The reaction mixture was evaporated in vacuum to give a crude product which was purified by silica-gel column (PE:EA=10:1-1:1) to give desired product (2 g, 69.8%) as a white solid.

LC/MS: 319.0[M+1]$^+$.

Step 2: Preparation of 1-(5-iodopyridin-2-yl)piperidine-4-carbaldehyde

To a solution of [1-(5-iodopyridin-2-yl)piperidin-4-yl]methanol (1 g, 3.1 mmol) in DCM (50 mL) stirred under nitrogen at 25° C. was added Dess-Martin periodinane (2.0 g, 4.6 mmol) in portions. The reaction mixture was stirred at 25° C. for 1 hour. The reaction mixture was quenched with $Na_2S_2O_3$ (2 M), extracted with DCM (200 mL), dried over sodium sulfate and evaporated in vacuum to give a crude product. The crude product was purified by silica-gel column (PE:EA=10:1-1:1) to give desired product (0.7 g, 70.9%) as a white solid.

LC/MS: 317.0 [M+1]$^+$.

Step 3: Preparation of 2-(4-(dimethoxymethyl)piperidin-1-yl)-5-iodopyridine

To a solution of 1-(5-iodopyridin-2-yl)piperidine-4-carbaldehyde (700 mg, 2.2 mmol) in Trimeth-oxymethane (15 mL) stirred under nitrogen at 25° C. was added TsOH (40 mg, 0.2 mmol). The reaction mixture was stirred at 100° C. for 2 hours. The reaction mixture was evaporated in vacuum to give a crude product. The crude product was purified by silica-gel column (PE:EA=10:1-1:1) to give desired product (0.6 g, 75.2%) as a white solid. LC/MS: 362.9 [M+1]+.

Step 4: Preparation of N-(4-(4-amino-1-(6-(4-(dimethoxymethyl)piperidin-1-yl)pyridin-3-yl)-1H-pyrazolo[3,4-d]pyrimidin-3-yl)benzyl)-5-fluoro-2-methoxybenzamide To a solution of 2-[4-(dimethoxymethyl)piperidin-1-yl]-5-iodopyridine (100 mg, 0.3 mmol), N-[(4-{4-amino-1H-pyrazolo[3,4-d]pyrimidin-3-yl}phenyl)methyl]-5-fluoro-2-methoxybenzamide (108.3 mg, 0.3 mmol) and $N^1,N^1$-dimethylcyclohexane-1,2-diamine (39.3 mg, 0.3 mmol) in DMF (10 mL) stirred under nitrogen at 25° C. was added Copper(I) iodide (52.6 mg, 0.3 mmol) and cesium carbonate (269.8 mg, 0.8 mmol). The reaction mixture was stirred at 110° C. for 12 hours. The reaction mixture was filtered and evaporated in vacuum to give a crude product. The crude product was purified by silica-gel column (DCM: MeOH=100:1-10:1) to give desired product (20 mg, 11.5%) as a yellow solid. LC/MS: 627.0 [M+1]+.

Step 5: Preparation of N-(4-(4-amino-1-(6-(4-formylpiperidin-1-yl)pyridin-3-yl)-1H-pyrazolo [3,4-d]pyrimidin-3-yl)benzyl)-5-fluoro-2-methoxybenzamide A solution of N-{[4-(4-amino-1-{6-[4-(dimethoxymethyl)piperidin-1-yl]pyridin-3-yl}pyrazolo [3,4-d]pyrimidin-3-yl)phenyl]methyl}-5-fluoro-2-methoxybenzamide (15 mg, 0.023 mmol) in THF/$H_2SO_4$ (2N) (5 mL, 1:1) was stirred at 70° C. for 1 hour. The mixture was diluted with EA (100 mL), neutralized with NaOH (2 M), dried over sodium sulfate and evaporated in vacuum to give desired product (10 mg, 71.9%) as a yellow solid. LC/MS: 581.0 [M+1]+.

Step 6: Preparation of (S)—N-(4-(4-amino-1-(6-(4-((4-(2-(2,6-dioxopiperidin-3-yl)-1-oxoisoindolin-5-yl)piperazin-1-yl)methyl)piperidin-1-yl)pyridin-3-yl)-1H-pyrazolo[3,4-d]pyrimidin-3-yl) benzyl)-5-fluoro-2-methoxybenzamide To a solution of N-[(4-{4-amino-1-[6-(4-formylpiperidin-1-yl)pyridin-3-yl]pyrazolo[3,4-d]pyrimidin-3-yl}phenyl)methyl]-5-fluoro-2-methoxybenzamide (15 mg, 0.025 mmol), (3S)-3-[1-oxo-5-(piperazin-1-yl)-3H-isoindol-2-yl]piperidine-2,6-dione (8.47 mg, 0.025 mmol) and acetic acid (62 mg, 0.52 mmol) in $CH_3OH$/DMF (2 mL, 1:1) stirred under nitrogen at 60° C. was added triethylamine (13.05 mg, 0.13 mmol) and $NaBH_3CN$ (8.11 mg, 0.13 mmol). The reaction mixture was stirred at 60° C. for 1 hour. The reaction mixture was concentrated in vacuum. The residue was dissolved with EA (50 mL) and washed with water (10 mL×2). The organic phase was dried over sodium sulphate and evaporated in vacuum to give a crude product. The crude product was purified by Prep-HPLC to give desired product (5 mg, 21.7%) as a white solid. LC/MS: 893.0 [M+1]+.

$^1$H NMR (400 MHz, DMSO) δ 10.96 (s, 1H), 8.90 (t, J=6.1 Hz, 1H), 8.72 (d, J=2.5 Hz, 1H), 8.32 (s, 1H), 8.24 (s, 1H), 8.12 (d, J=9.2 Hz, 1H), 7.73 (d, J=8.1 Hz, 2H), 7.58-7.48 (m, 3H), 7.40-7.32 (m, 1H), 7.23-7.17 (m, 1H), 7.08-6.96 (m, 3H), 6.61-6.49 (m, 3H), 5.15-5.01 (m, 1H), 4.60 (d, J=6.1 Hz, 2H), 4.44-4.28 (m, 3H), 3.91 (s, 3H), 3.29-3.24 (m, 7H), 3.00-2.82 (m, 3H), 2.74-2.59 (m, 2H), 2.44-2.31 (m, 2H), 2.29-2.17 (d, J=6.6 Hz, 2H), 2.02-1.73 (m, 4H), 1.34-1.05 (m, 2H).

Example 58: Preparation of N-(4-(4-amino-1-(1-(4-((4-(2-((S)-2,6-dioxopiperidin-3-yl)-1-oxoisoindolin-5-yl)piperazin-1-yl)methyl)phenyl)pyrrolidin-3-yl)-1H-pyrazolo[3,4-d]pyrimidin-3-yl)benzyl)-5-fluoro-2-methoxybenzamide (Compound 60)

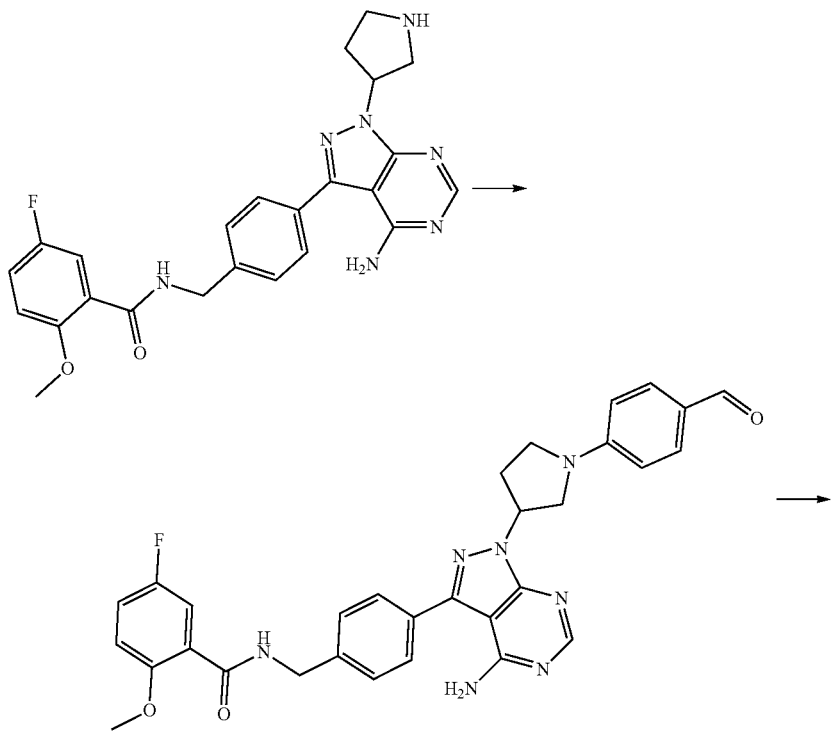

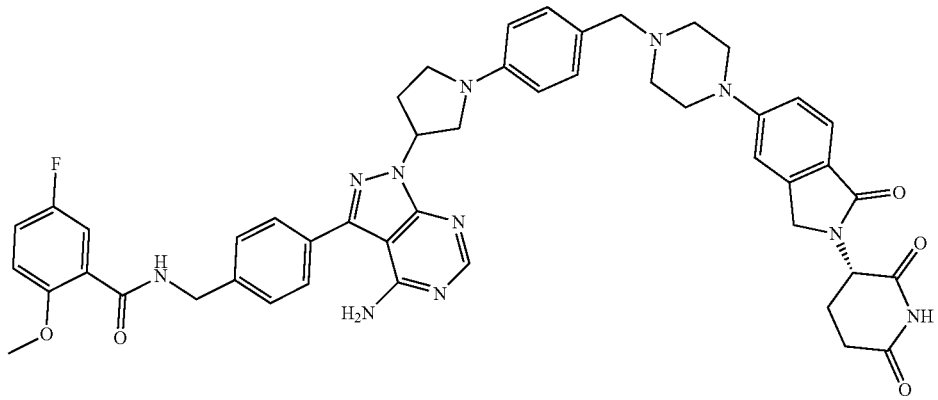

Step 1: Preparation of N-(4-(4-amino-1-(1-(4-formylphenyl)pyrrolidin-3-yl)-1H-pyrazolo[3,4-d]pyrimidin-3-yl)benzyl)-5-fluoro-2-methoxybenzamide To a solution of N-({4-[4-amino-1-(pyrrolidin-3-yl)pyrazolo[3,4-d]pyrimidin-3-yl]phenyl}methyl)-5-fluoro-2-methoxybenzamide (300 mg, 0.65 mmol) in DMSO (5 mL) stirred at room temperature was added 4-fluorobenzaldehyde (121 mg, 0.98 mmol) and $K_2CO_3$ (180 mg, 1.3 mmol). The reaction mixture was stirred at 80° C. for 12 hours. The reaction mixture was poured into water (100 mL) and extracted with EA (100 mL×2). The combined organic layers were washed with water, brine, dried over $Na_2SO_4$ then concentrated under vacuum to give a crude product. The crude product was purified by Flash Chromatography (DCM/MeOH=10:1) to give the desired product (100 mg, 27.2%). LC/MS: 566.0 [M+H]$^+$.

Step 2: Preparation of N-(4-(4-amino-1-(1-(4-((4-(2-((S)-2,6-dioxopiperidin-3-yl)-1-oxoisoindolin-5-yl)piperazin-1-yl)methyl)phenyl)pyrrolidin-3-yl)-1H-pyrazolo[3,4-d]pyrimidin-3-yl)benzyl)-5-fluoro-2-methoxybenzamide To a solution of N-[(4-{4-amino-1-[1-(4-formylphenyl)pyrrolidin-3-yl]pyrazolo[3,4-d]pyrimidin-3-yl}phenyl)methyl]-5-fluoro-2-methoxybenzamide (100 mg, 0.18 mmol) in MeOH/DMF/HOAc (12 mL, 2:1:0.06) stirred at room temperature was added (S)-3-(1-oxo-5-(piperazin-1-yl)isoindolin-2-yl)piperidine-2,6-dione (86 mg, 0.18 mmol), $Et_3N$ (36 mg, 0.36 mmol) and $NaBH_3CN$ (45 mg, 0.72 mmol). The reaction mixture was stirred at 60° C. for 1 hour. The mixture was concentrated in vacuum, poured into water (50 mL) and extracted with EA (100 mL×2). The combined organic layers were washed with brine (200 mL), dried over $Na_2SO_4$ and concentrated under vacuum to give a crude product. The crude product was purified by Prep-HPLC to give the desired product (19 mg, 12.2%). LC/MS: 900.0 [M+Na]$^+$.

$^1$H NMR (400 MHz, DMSO) δ=10.95 (s, 1H), 8.86 (t, J=6.0 Hz 1H), 8.30 (s, 1H), 8.28 (s, 1H), 7.63 (d, J=8.0 Hz, 2H), 7.52-7.47 (m, 5H), 7.36-7.31 (m, 1H), 7.18 (dd, J=9.2, 4.4 Hz, 1H), 7.12 (d, J=8.4 Hz, 2H), 7.06-7.01 (m, 2H), 6.56 (d, J=8.4 Hz, 2H), 5.65-5.60 (m, 1H), 5.04 (dd, J=13.2, 5.2 Hz, 1H), 4.57 (d, J=6.0 Hz, 2H), 4.32 (d, J=16.8 Hz, 1H), 4.19 (d, J=16.8 Hz, 1H), 3.89 (s, 3H), 3.84-3.79 (m, 1H), 3.66-3.60 (m, 2H), 3.48-3.39 (m, 2H), 3.30-3.20 (m, 5H), 2.95-2.83 (m, 2H), 2.64-2.59 (m, 2H), 2.57-2.54 (m, 2H), 2.47 (s, 3H), 1.96-1.90 (m, 1H).

Example 59: Preparation of (S)—N-(4-(4-amino-1-(1-(4-((4-(2-(2,6-dioxopiperidin-3-yl)-1-oxoisoindolin-5-yl)piperazin-1-yl)methyl)phenyl)azetidin-3-yl)-1H-pyrazolo[3,4-d]pyrimidin-3-yl)benzyl)-5-fluoro-2-methoxybenzamide (Compound 61)

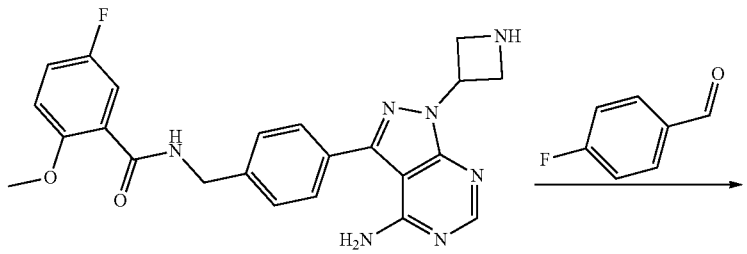

-continued

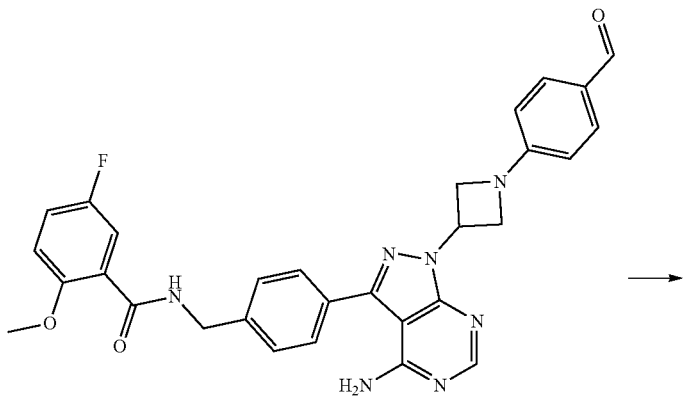

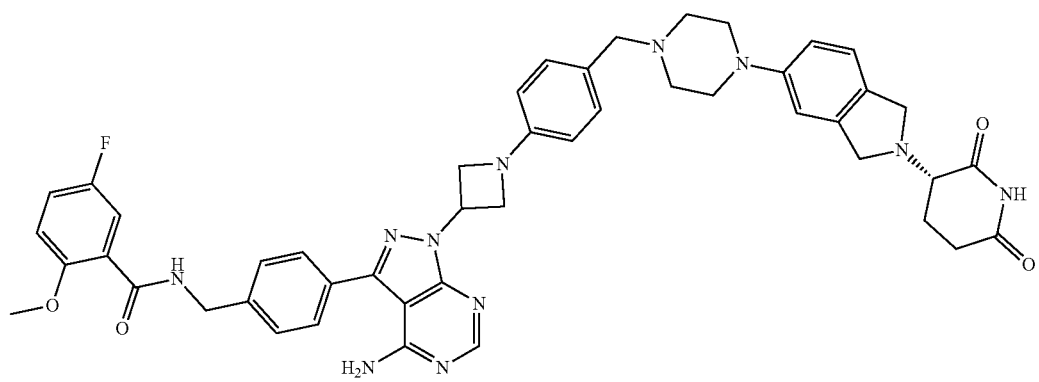

Step 1: Preparation of N-(4-(4-amino-1-(1-(4-formylphenyl)azetidin-3-yl)-1H-pyrazolo[3,4-d]pyrimidin-3-yl)benzyl)-5-fluoro-2-methoxybenzamide The mixture of N-(4-(4-amino-1-(azetidin-3-yl)-1H-pyrazolo[3,4-d]pyrimidin-3-yl)benzyl)-5-fluoro-2-methoxybenzamide (60 mg, 0.13 mmol), 4-fluorobenzaldehyde (25 mg, 0.20 mmol) and K$_2$CO$_3$ (56 mg, 0.41 mmol) in DMSO (5 mL) was stirred at 80° C. for overnight. The reaction mixture was poured into water (5 mL) and extracted with EA (10 mL×3). The combined organic layers were washed with water, dried over Na$_2$SO$_4$ and concentrated in vacuum to give a crude product. The crude product was purified by Pre-TLC with DCM/MeOH=10:1 to give the desired product (20 mg, 80% purity, 21.6% yield). LC/MS: 552.7 [M+H]$^+$.

Step 2: Preparation of (S)—N-(4-(4-amino-1-(1-(4-((4-(2-(2,6-dioxopiperidin-3-yl)-1-oxoisoindolin-5-yl)piperazin-1-yl)methyl)phenyl)azetidin-3-yl)-1H-pyrazolo[3,4-d]pyrimidin-3-yl)benzyl)-5-fluoro-2-methoxybenzamide To a solution of N-(4-(4-amino-1-(1-(4-formylphenyl)azetidin-3-yl)-1H-pyrazolo[3,4-d]pyrimidin-3-yl)benzyl)-5-fluoro-2-methoxybenzamide (20 mg, 80% purity, 0.029 mmol) in MeOH/DMF (2:1, 3 mL) stirred at room temperature was added (S)-3-(1-oxo-5-(piperazin-1-yl)isoindolin-2-yl)piperidine-2,6-dione (22 mg, 0.045 mmol) and Et$_3$N (7 mg, 0.069 mmol). The mixture was stirred at room temperature for 30 minutes then AcOH (0.1 mL) and NaBH$_3$CN (4 mg, 0.064 mmol) was added. The reaction mixture was stirred at 60° C. for 1 hour. The mixture was concentrated in vacuum. The residue was poured into water (4 ml) and extracted with EA (8 mL×3). The combined organic layers were washed with brine (10 mL), dried over Na$_2$SO$_4$ and concentrated in vacuum to give a crude product. The crude product was purified by Prep-HPLC to give the desired product (8 mg, 31.9%). LC/MS: 864 [M+H]$^+$.

1H NMR (400 MHz, DMSO) δ 10.95 (s, 1H), 8.86 (t, J=6.1 Hz, 1H), 8.33-8.20 (m, 2H), 7.65 (d, J=8.1 Hz, 2H), 7.53-7.48 (m, 3H), 7.37-7.31 (m, 1H), 7.24-7.11 (m, 3H), 7.08-6.98 (m, 2H), 6.52 (d, J=8.5 Hz, 2H), 5.88-5.81 (m, 1H), 5.05-5.02 (m, 1H), 4.57 (d, J=6.0 Hz, 2H), 4.42-4.16 (m, 6H), 3.89 (s, 3H), 3.42-3.36 (m, 4H), 3.28-3.25 (m, 5H), 2.97-2.83 (m, 2H), 2.69-2.54 (m, 2H), 2.41-2.31 (m, 2H), 1.98-1.92 (m, 1H).

Example 60: Preparation of (S)—N-(4-(4-amino-1-(1-(4-((4-(2-(2,6-dioxopiperidin-3-yl)-1-oxoisoindolin-5-yl)piperazin-1-yl)methyl)benzoyl)azetidin-3-yl)-1H-pyrazolo[3,4-d]pyrimidin-3-yl)benzyl)-5-fluoro-2-methoxybenzamide (Compound 62)

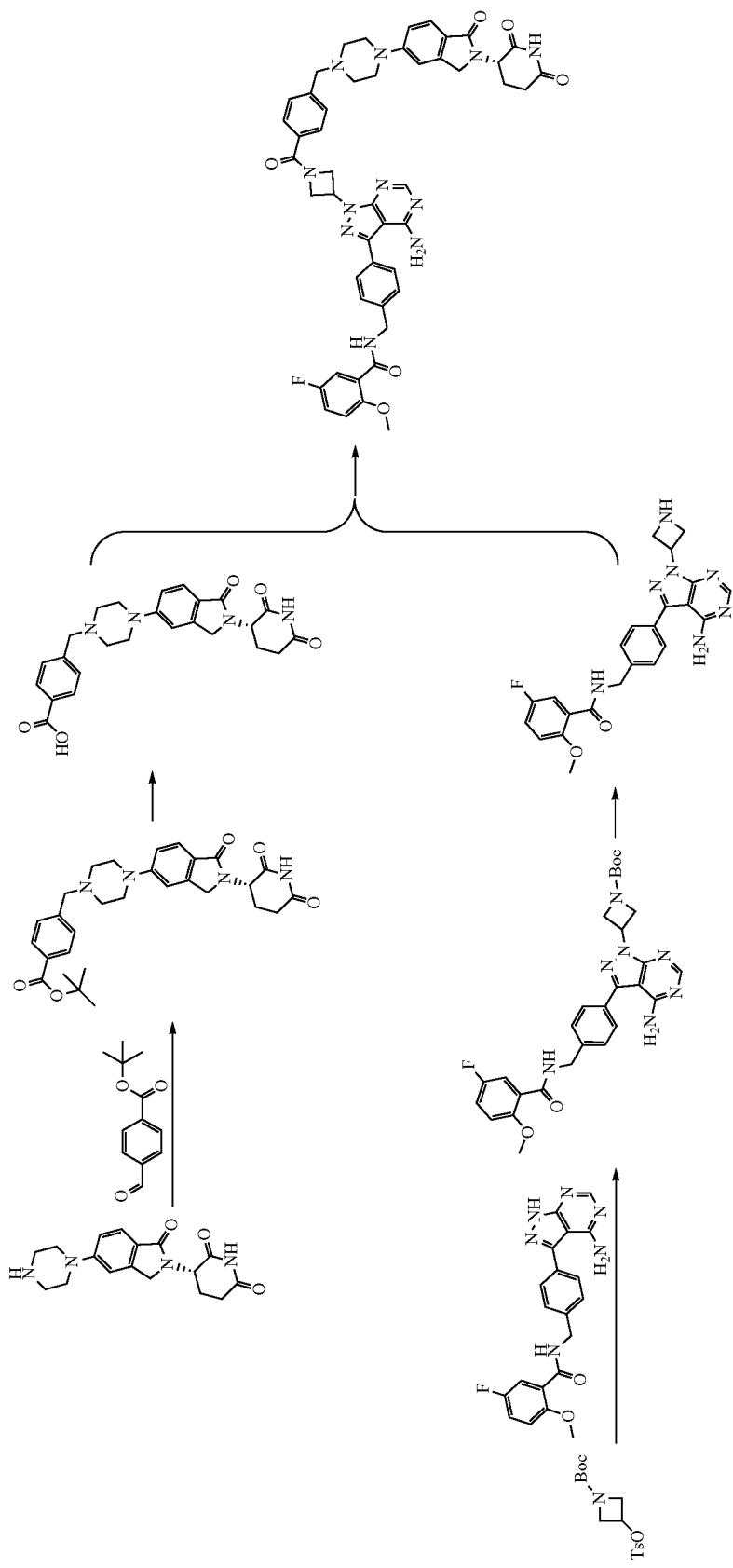

Step 1: Preparation of tert-butyl (S)-4-((4-(2-(2,6-dioxopiperidin-3-yl)-1-oxoisoindolin-5-yl)piperazin-1-yl)methyl)benzoate To a solution of (S)-3-(1-oxo-5-(piperazin-1-yl)isoindolin-2-yl)piperidine-2,6-dione (100 mg, 0.2 mmol) in DMF (10 mL) was added TEA (41.51 mg, 0.4 mmol). The mixture was stirred under nitrogen at room temperature for 5 minutes. Then tert-butyl-4-formyl benzoate (42.38 mg, 0.2 mmol) and NaBH$_3$CN (38.74 mg, 0.61 mmol) was added. The reaction mixture was stirred at 60° C. for 1 hour. The reaction was quenched by adding water (20 mL) and extracted with EA (20 mL×3). The organic phase was washed with brine and dried over Na$_2$SO$_4$. The solution was concentrated in vacuum and the residue was purified by flash column chromatography with DCM:MeOH=10:1 to afford the desired product (100 mg, 90% purity, 86.7% yield) as a yellow solid. LC/MS: 519.1 [M+H]$^+$.

Step 2: Preparation of (S)-4-((4-(2-(2,6-dioxopiperidin-3-yl)-1-oxoisoindolin-5-yl)piperazin-1-yl)methyl)benzoic acid A solution of tert-butyl (S)-4-((4-(2-(2,6-dioxopiperidin-3-yl)-1-oxoisoindolin-5-yl)piperazin-1-yl)methyl)benzoate (100 mg, 90% purity, 0.17 mmol) in DCM (3 mL) and TFA (1 mL) was stirred at room temperature for 2 hours. The mixture was concentrated to give the title compound (70 mg, 80% purity, 69.5% yield) as a yellow oil. LC/MS: 462.8 [M+H]$^+$.

Step 3: Preparation of tert-butyl 3-(4-amino-3-(4-((5-fluoro-2-methoxybenzamido)methyl) phenyl)-1H-pyrazolo[3,4-d]pyrimidin-1-yl)azetidine-1-carboxylate To a solution of N-(4-(4-amino-1H-pyrazolo[3,4-d]pyrimidin-3-yl)benzyl)-5-fluoro-2-methoxy benzamide (500 mg, 1.27 mmol) in DMF (10 ml) was added tert-butyl-3-(tosyloxy)azetidine-1-carboxylate (502 mg, 1.52 mmol) and Cs$_2$CO$_3$ (1.24 g, 3.82 mmol). The reaction mixture was stirred at 80° C. for 16 hours. The reaction was quenched by adding water (20 mL) and extracted with DCM (20 mL×2). The organic phase was washed with brine and dried over Na$_2$SO$_4$. The solution was concentrated in vacuum and the residue was purified by flash column chromatography with DCM:MeOH=10:1 to afford the desired product (230 mg, 90% purity, 29.7%) as a yellow oil. LC/MS: 547.8 [M+H]$^+$.

Step 4: Preparation of N-(4-(4-amino-1-(azetidin-3-yl)-1H-pyrazolo[3,4-d]pyrimidin-3-yl)benzyl)-5-fluoro-2-methoxybenzamide A solution of tert-butyl 3-(4-amino-3-(4-((5-fluoro-2-methoxybenzamido)methyl) phenyl)-1H-pyrazolo[3,4-d]pyrimidin-1-yl)azetidine-1-carboxylate (230 mg, 90% purity, 0.4 mmol) in DCM (8 mL) and TFA (2 mL) was stirred at room temperature for 2 hours. The solvent was removed in vacuum then dissolved with DCM (20 mL). The mixture was adjusted to pH around 10 with saturated Na$_2$CO$_3$ solution. The organic phase was concentrated in vacuum to give the title compound (100 mg, 60.3%) as a yellow solid.

LC/MS: 448.1 [M+H]$^+$.

Step 5: Preparation of (S)—N-(4-(4-amino-1-(1-(4-((4-(2-(2,6-dioxopiperidin-3-yl)-1-oxoisoindolin-5-yl)piperazin-1-yl)methyl)benzoyl)azetidin-3-yl)-1H-pyrazolo[3,4-d]pyrimidin-3-yl)benzyl)-5-fluoro-2-methoxybenzamide To a solution of 4-[(4-{2-[(3S)-2,6-dioxopiperidin-3-yl]-1-oxo-3H-isoindol-5-yl}piperazin-1-yl)methyl]benzoic acid (44 mg, 80% purity, 0.07 mmol) in THF (5 mL) was added N-({4-[4-amino-1-(azetidin-3-yl)pyrazolo[3,4-d]pyrimidin-3-yl]phenyl}methyl)-5-fluoro-2-methoxybenzamide (33.9 mg, 0.07 mmol), 1-Hydroxybenzotrizole (15.3 mg, 0.11 mmol), EDCI (21.8 mg, 0.11 mmol) and TEA (22.9 mg, 0.22 mmol). The mixture was stirred at room temperature for 2 hours. The reaction was quenched by adding water (15 mL) and extracted with DCM (10 mL×3). The organic phase was washed with brine and dried over Na$_2$SO$_4$. The solution was concentrated in vacuum and the residue was purified by Prep-HPLC (ACN/H$_2$O (0.1% FA), 10-40%) to afford the desired compound (10 mg, 14.3%) as a white solid. LC/MS: 892.6 [M+H]$^+$.

$^1$H NMR (400 MHz,) δ 10.95 (s, 1H), 8.88 (t, J=6.0 Hz, 1H), 8.27 (s, 1H), 7.68-7.64 (m, 4H), 7.51-7.47 (m, 4H), 7.45-7.40 (m, 2H), 7.34 (td, J=8.5, 3.3 Hz, 1H), 7.19 (dd, J=9.1, 4.3 Hz, 1H), 7.05 (d, J=8.1 Hz, 2H), 5.80-5.71 (m, 1H), 5.05 (dd, J=13.2, 5.0 Hz, 1H), 4.93-4.72 (m, 2H), 4.66-4.49 (m, 4H), 4.32 (d, J=16.9 Hz, 1H), 4.20 (d, J=16.9 Hz, 1H), 3.90 (s, 3H), 3.59 (s, 2H), 3.32-3.25 (m, 4H), 2.96-2.84 (m, 1H), 2.68-2.56 (m, 4H), 2.44-2.29 (m, 2H), 1.99-1.91 (m, 1H).

Example 61: Preparation of (N-(4-(4-amino-1-(1-(4-((4-(2-((S)-2,6-dioxopiperidin-3-yl)-1-oxoisoindolin-5-yl)piperazin-1-yl)methyl)benzoyl)pyrrolidin-3-yl)-1H-pyrazolo[3,4-d]pyrimidin-3-yl)benzyl)-5-fluoro-2-methoxybenzamide (Compound 63)

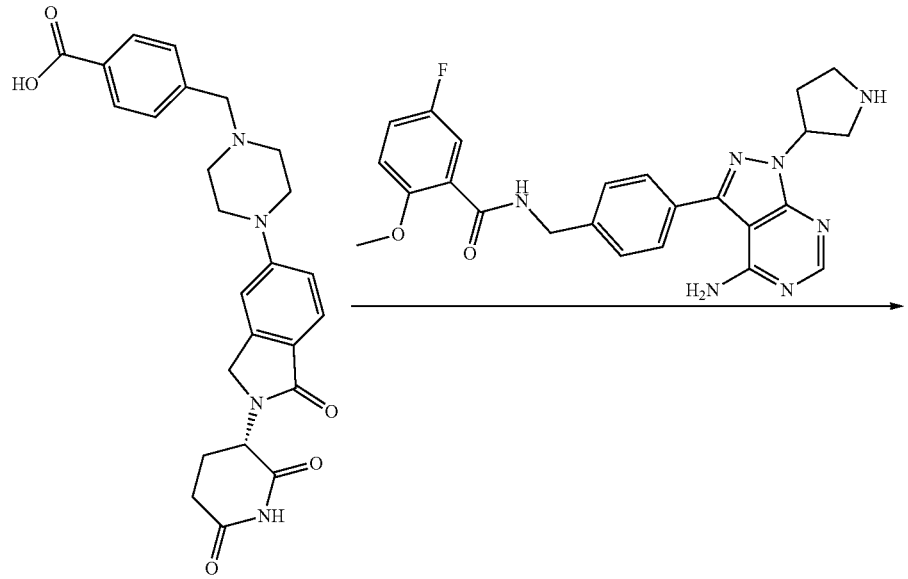

-continued

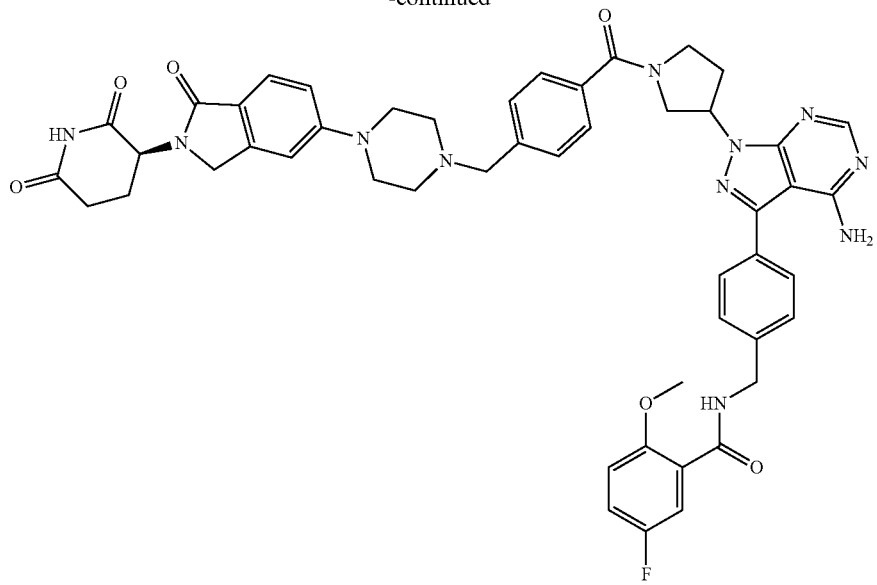

Step 1: Preparation of (N-(4-(4-amino-1-(1-(4-((4-(2-((S)-2,6-dioxopiperidin-3-yl)-1-oxoisoindolin-5-yl)piperazin-1-yl)methyl)benzoyl)pyrrolidin-3-yl)-1H-pyrazolo[3,4-d]pyrimidin-3-yl)benzyl)-5-fluoro-2-methoxybenzamide To a solution of (S)-4-((4-(2-(2,6-dioxopiperidin-3-yl)-1-oxoisoindolin-5-yl)piperazin-1-yl)methyl)benzoic acid (44 mg, 80% purity, 0.07 mmol) in THF (5 mL) was added N-(4-(4-amino-1-(pyrrolidin-3-yl)-1H-pyrazolo[3,4-d]pyrimidin-3-yl)benzyl)-5-fluoro-2-methoxy benzamide (34.9 mg, 0.07 mmol), 1-Hydroxybenzotrizole (15.3 mg, 0.11 mmol), EDCI (21.8 mg, 0.11 mmol) and TEA (22.9 mg, 0.22 mmol). The reaction mixture was stirred at room temperature for 2 hours. The reaction was quenched by adding water (10 mL) and extracted with DCM (10 mL×2). The organic phase was washed with brine dried over $Na_2SO_4$. The solution was concentrated in vacuum and the residue was purified by Prep-HPLC (ACN/$H_2O$ (0.1% FA), 10-40%) to afford the desired compound (4 mg, 6.3%). LC/MS: 906.5 [M+H]$^+$.

$^1$H NMR (400 MHz, DMSO) δ 10.96 (s, 1H), 8.94-8.86 (m, 1H), 8.25-8.12 (m, 1H), 7.75-7.28 (m, 11H), 7.25-7.15 (m, 1H), 7.10-6.97 (m, 2H), 5.62-5.35 (m, 1H), 5.05 (d, J=8.7 Hz, 1H), 4.59 (d, J=5.6 Hz, 2H), 4.32 (d, J=16.2 Hz, 1H), 4.19 (d, J=15.3 Hz, 1H), 4.06-3.72 (m, 6H), 3.67 (d, J=6.4 Hz, 1H), 3.55 (d, J=16.0 Hz, 2H), 3.32-3.18 (m, 4H), 2.90 (t, J=12.8 Hz, 1H), 2.69-2.53 (m, 4H), 2.48-2.43 (m, 2H), 2.41-2.28 (m, 2H), 2.02-1.86 (m, 1H).

Example 62: Preparation of N-(4-(4-amino-1-(1-(6-(4-(2-((S)-2,6-dioxopiperidin-3-yl)-1-oxoisoindolin-5-yl)piperazin-1-yl)hexanoyl)pyrrolidin-3-yl)-1H-pyrazolo[3,4-d]pyrimidin-3-yl)benzyl)-5-fluoro-2-methoxybenzamide (Compound 64)

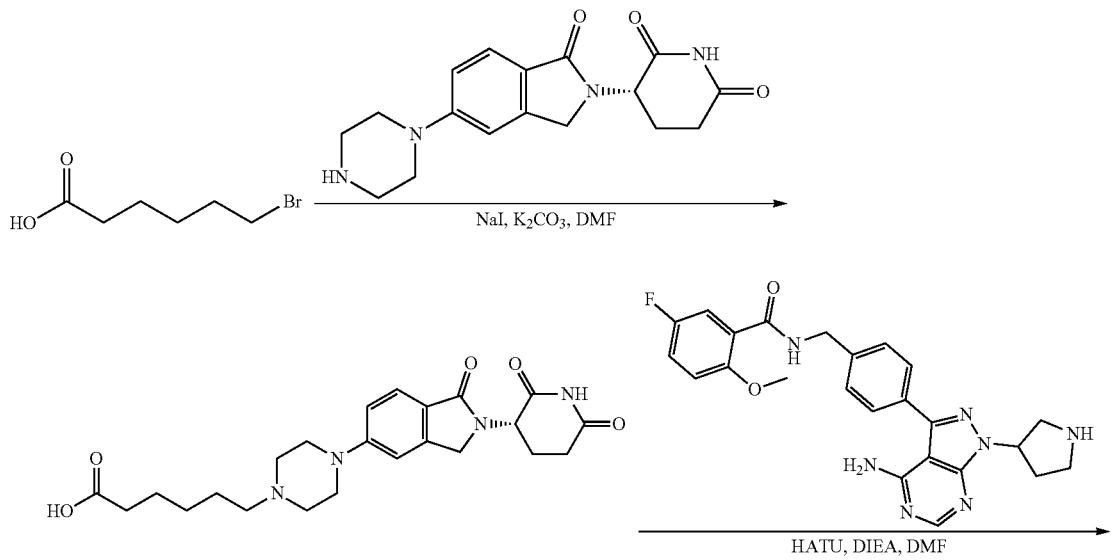

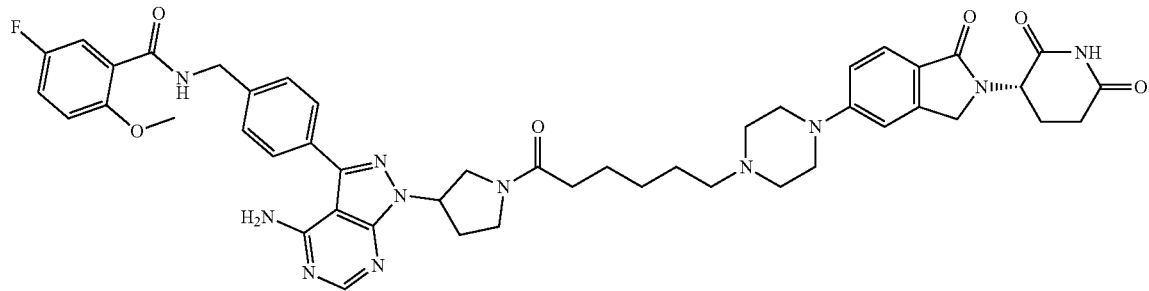

Step 1: Preparation of (S)-6-(4-(2-(2,6-dioxopiperidin-3-yl)-1-oxoisoindolin-5-yl)piperazin-1-yl)hexanoic acid A suspension of 6-bromohexanoic acid (100 mg, 0.51 mmol), (S)-3-(1-oxo-5-(piperazin-1-yl)isoindolin-2-yl)piperidine-2,6-dione (168.3 mg, 0.51 mmol), $K_2CO_3$ (212.3 mg, 1.54 mmol) and KI (85.1 mg, 0.51 mmol) in DMF (3 mL) was stirred at room temperature for overnight. The reaction mixture was concentrated in vacuum. The residue was dissolved with EA (50 mL), washed with water (10 mL), dried over $Na_2SO_4$ and evaporated in vacuum to give a crude product. The crude product was purified by flash column chromatography (DCM/MeOH=10:1) to give the desired product (50 mg, purity=90%, yield=19.8%) as a white solid. LC/MS: 442.9 [M+H]$^+$.

Step 2: Preparation of N-(4-(4-amino-1-(1-(6-(4-(2-((S)-2,6-dioxopiperidin-3-yl)-1-oxoisoindolin-5-yl)piperazin-1-yl)hexanoyl)pyrrolidin-3-yl)-1H-pyrazolo[3,4-d]pyrimidin-3-yl)benzyl)-5-fluoro-2-methoxybenzamide A solution of (S)-6-(4-(2-(2,6-dioxopiperidin-3-yl)-1-oxoisoindolin-5-yl)piperazin-1-yl)hexanoic acid 50 mg, purity=90%), N-(4-(4-amino-1-(pyrrolidin-3-yl)-1H-pyrazolo[3,4-d]pyrimidin-3-yl)benzyl)-5-fluoro-2-methoxybenzamide (69.9 mg, 0.15 mmol), HATU (86.4 mg, 0.23 mmol) and DIEA (58.7 mg, 0.45 mmol) in DMF (5 mL) was stirred at room temperature for 4 hours. The reaction mixture was concentrated in vacuum. The residue was dissolved with EA (50 mL), washed with water (10 mL), dried over $Na_2SO_4$ and evaporated in vacuum to give a crude product. The crude product was purified by Prep-TLC (DCM/MeOH=10:1) to give the desired product (8 mg, 12.5%) as a white solid. LC/MS: 886.1 [M+H]$^+$.

1H NMR (400 MHz, DMSO) δ 10.92 (s, 1H), 8.84 (t, J=6.0 Hz, 1H), 8.24 (d, J=3.8 Hz, 1H), 7.60 (d, J=8.1 Hz, 2H), 7.52-7.45 (m, 4H), 7.33-7.28 (m, 1H), 7.17-7.14 (m, 1H), 7.10-7.02 (m, 2H), 5.51-5.34 (m, 1H), 5.06-4.97 (m, 1H), 4.54 (d, J=6.1 Hz, 2H), 4.33-4.15 (m, 2H), 4.05-3.57 (m, 8H), 3.50-3.41 (m, 1H), 3.24-3.05 (m, 2H), 2.93-2.78 (m, 2H), 2.60-2.48 (m, 3H), 2.45-2.14 (m, 9H), 1.96-1.88 (m, 1H), 1.56-1.44 (m, 4H), 1.33-1.17 (m, 3H).

Example 63: Preparation of N-(4-(4-amino-1-(4-(3-((4-(2-((S)-2,6-dioxopiperidin-3-yl)-1-oxoisoindolin-5-yl)piperazin-1-yl)methyl)pyrrolidin-1-yl)-3-fluorophenyl)-1H-pyrazolo[3,4-d]pyrimidin-3-yl)benzyl)-5-fluoro-2-methoxybenzamide (Compound 65)

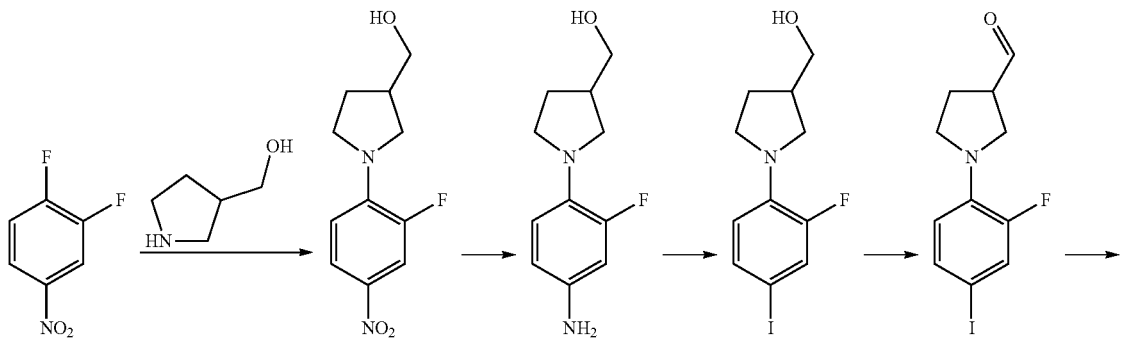

289 290
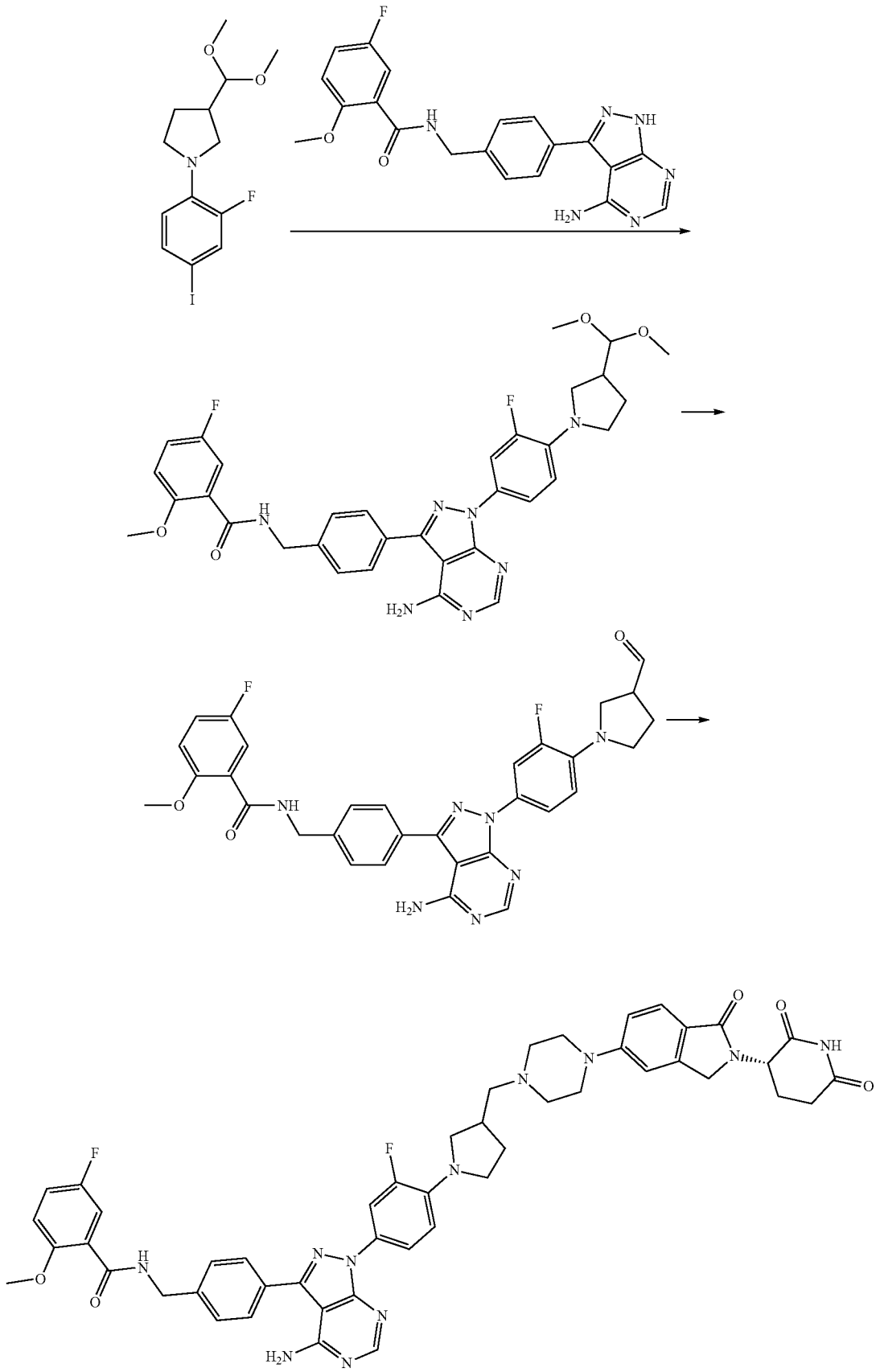

Step 1: Preparation of (1-(2-fluoro-4-nitrophenyl) pyrrolidin-3-yl)methanol

To a solution of 1,2-difluoro-4-nitrobenzene (2 g, 12.57 mmol) in CH$_3$CN (5 mL) was added pyrrolidin-3-ylmethanol (1.9 g, 13.83 mmol) and DIEA (4.9 g, 37.71 mmol). The reaction mixture was stirred at 80° C. for 3 hours. The solvent was removed in vacuum. The residue was purified by flash column chromatography with PE:EA=1:1 to afford the desired product (1.8 g, 59.6%) as a yellow solid. LC/MS: 241.1 [M+H]$^+$.

Step 2: Preparation of (1-(4-amino-2-fluorophenyl) pyrrolidin-3-yl)methanol

To a solution of (1-(2-fluoro-4-nitrophenyl)pyrrolidin-3-yl)methanol (1.8 g, 7.49 mmol) in MeOH (20 mL) was added Pd/C (180 mg, 10%). The reaction mixture was stirred at room temperature for 2 hours under H$_2$ at 1 atm. The catalyst was filtered out. The solution was concentrated in vacuum to afford the desired product (1.3 g, 82.5%) as a brown oil. LC/MS: 211.1 [M+H]$^+$.

Step 3: Preparation of (1-(2-fluoro-4-iodophenyl)pyrrolidin-3-yl)methanol

To a solution of (1-(4-amino-2-fluorophenyl)pyrrolidin-3-yl)methanol (1.3 g, 6.1 mmol) in CH$_3$CN (30 mL) was added 1.9 mL con. HCl (1.9 mL), NaNO$_2$ (630 mg, 9.13 mmol, dissolved in 8 mL H$_2$O) at 0° C. The mixture was stirred at 0° C. for 2 hours then KI (3.16 g, 19.03 mmol) was added. The reaction mixture was stirred at room temperature for 17 hours. The reaction was quenched by adding water (20 mL) and extracted with EA (20 mL×3). The organic phase was washed with brine and dried over Na$_2$SO$_4$. The solvent was removed in vacuum. The residue was purified by flash column chromatography with PE:EA=3:1 to afford the desired product (1.5 g, 75.5%) as a yellow solid. LC/MS: 321.9 [M+H]$^+$.

Step 4: Preparation of 1-(2-fluoro-4-iodophenyl) pyrrolidine-3-carbaldehyde

To a solution of oxalyl chloride (1.19 g, 9.34 mmol) in DCM (20 mL) was added DMSO (1.46 g, 18.68 mmol) at −78° C. The reaction mixture was stirred at −78° C. for 15 minutes then (1-(2-fluoro-4-iodophenyl)pyrrolidin-3-yl)methanol (1.5 g, 4.67 mmol) was added. The reaction mixture was stirred at −78° C. for the other 15 minutes. TEA (1.9 g, 18.68 mmol) was added at −78° C. The final mixture was stirred at −78° C. for 30 minutes. The reaction mixture was raised to room temperature and stirred for 1 hour. The reaction was quenched by adding water (20 mL) and extracted with DCM (20 mL×3). The organic phase was washed with brine and dried over Na$_2$SO$_4$. The solvent was removed in vacuum. The residue was purified by flash column chromatography with PE:EA=1:1 to afford the desired product (1.2 g, 80.5%) as a yellow solid. LC/MS: 319.8 [M+H]$^+$.

Step 5: Preparation of 3-(dimethoxymethyl)-1-(2-fluoro-4-iodophenyl)pyrrolidine To a solution of 1-(2-fluoro-4-iodophenyl)pyrrolidine-3-carbaldehyde (1.2 g, 3.76 mmol) in MeOH (20 mL) was added trimethoxymethane (600 mg, 5.46 mmol) and PTSA (97 mg, 1.36 mmol). The reaction was stirred at 60° C. for 12 hours. The solvent was removed in vacuum. The residue was dissolved in EA (20 mL), washed with NaHCO$_3$ solution and dried over Na$_2$SO$_4$. The organic phase was concentrated and purified by flash column chromatography with PE:EA=1:1 to afford the desired product (720 mg, 41.9%) as a yellow solid. LC/MS: 365.8 [M+H]$^+$.

Step 6: Preparation of N-(4-(4-amino-1-(4-(3-(dimethoxymethyl)pyrrolidin-1-yl)-3-fluorophenyl)-1H-pyrazolo[3,4-d]pyrimidin-3-yl)benzyl)-5-fluoro-2-methoxybenzamide To a solution of 3-(dimethoxymethyl)-1-(2-fluoro-4-iodophenyl)pyrrolidine (200 mg, 0.55 mmol) in 1,4-dioxane (5 mL) was added N-(4-(4-amino-1H-pyrazolo[3,4-d]pyrimidin-3-yl)benzyl)-5-fluoro-2-methoxybenzamide (429 mg, 1.09 mmol), Cs$_2$CO$_3$ (535 mg, 1.64 mmol), trans-N,N'-dimethylcyclohexane-1,2-diamine (156 mg, 1.09 mmol) and CuI (104 mg, 0.55 mmol). The reaction mixture was stirred at 100° C. for 17 hours under Ar. The solid was filtered out and the solution was concentered in vacuum. The residue was purified by Pre-TLC with DCM:MeOH=10:1 to afford the desired product (100 mg, 60% purity, 17.3% yield) as a white solid. LC/MS: 629.9 [M+H]$^+$.

Step 7: Preparation of N-(4-(4-amino-1-(3-fluoro-4-(3-formylpyrrolidin-1-yl)phenyl)-1H-pyrazolo[3,4-d]pyrimidin-3-yl)benzyl)-5-fluoro-2-methoxybenzamide To a solution of N-(4-(4-amino-1-(4-(3-(dimethoxymethyl)pyrrolidin-1-yl)-3-fluorophenyl)-1H-pyrazolo[3,4-d]pyrimidin-3-yl)benzyl)-5-fluoro-2-methoxybenzamide (80 mg, 60% purity, 0.076 mmol) in THF (2 mL) was added H$_2$SO$_4$ (4 mL, 3 M in water). The reaction was stirred at 70° C. for 2 hours. The reaction mixture was cooled to 0° C., neutralized with NaHCO$_3$ solution and extracted with EA (10 mL×3). The organic phase was washed with brine and dried over Na$_2$SO$_4$. The solution was concentered in vacuum to afford the desired product (40 mg, crude) as a yellow solid. LC/MS: 584.2 [M+H]$^+$.

Step 8: Preparation of N-(4-(4-amino-1-(4-(3-((4-(2-((S)-2,6-dioxopiperidin-3-yl)-1-oxoisoindolin-5-yl)piperazin-1-yl)methyl)pyrrolidin-1-yl)-3-fluorophenyl)-1H-pyrazolo[3,4-d]pyrimidin-3-yl)benzyl)-5-fluoro-2-methoxybenzamide To a solution of (S)-3-(1-oxo-5-(piperazin-1-yl)isoindolin-2-yl)piperidine-2,6-dione benzenesulfonic acid (11.26 mg, 0.034 mmol) in DMF (1 mL) and MeOH (1 mL) was added TEA (0.2 mL). The mixture was stirred at room temperature for 30 minutes. Then N-(4-(4-amino-1-(3-fluoro-4-(3-formylpyrrolidin-1-yl)phenyl)-1H-pyrazolo[3,4-d]pyrimidin-3-yl)benzyl)-5-fluoro-2-methoxybenzamide (40 mg, crude), HOAc (0.5 mL) and NaBH$_3$CN (21.55 mg, 0.343 mmol) was added. The reaction mixture was stirred at room temperature for 1 hour. The reaction was quenched by adding H$_2$O (10 mL) and extracted with EA (5 mL×3). The combined organic phase was washed with brine and dried over Na$_2$SO$_4$. The solution was concentrated in vacuum and the residue was purified by Pre-TLC with DCM:MeOH=10:1 to afford the desired product (6.9 mg, 10.1% for two steps) as a white solid. LC/MS: 896.5 [M+H]$^+$.

1H NMR (400 MHz, DMSO) δ 10.96 (s, 1H), 8.90 (t, J=6 Hz, 1H), 8.35 (s, 1H), 7.93 (d, J=15.3 Hz, 1H), 7.83 (d, J=8.8 Hz, 1H), 7.73 (d, J=8.1 Hz, 2H), 7.56-7.50 (m, 3H), 7.38-7.31 (m, 1H), 7.23-7.16 (m, 1H), 7.12-7.04 (m, 2H), 6.88 (t,

J=9.5 Hz, 1H), 5.05 (dd, J=13.3, 5.0 Hz, 1H), 4.60 (d, J=6.0 Hz, 2H), 4.36-4.17 (m, 2H), 3.91 (s, 2H), 3.57-3.49 (m, 1H), 3.48-3.40 (m, 2H), 3.31 (s, 3H), 3.22-3.15 (m, 1H), 2.93-2.83 (m, 1H), 2.66-2.53 (m, 4H), 2.45-2.30 (m, 3H), 2.13-1.90 (m, 3H), 1.73-1.66 (m, 1H), 1.50-1.40 (m, 1H), 1.27-1.17 (m, 5H).
Example 64: Preparation of N-(4-(4-amino-1-(6-(3-((4-(2-((S)-2,6-dioxopiperidin-3-yl)-1-oxoisoindolin-5-yl)piperazin-1-yl)methyl)pyrrolidin-1-yl)pyridin-3-yl)-1H-pyrazolo[3,4-d]pyrimidin-3-yl)benzyl)-5-fluoro-2-methoxybenzamide (Compound 66)
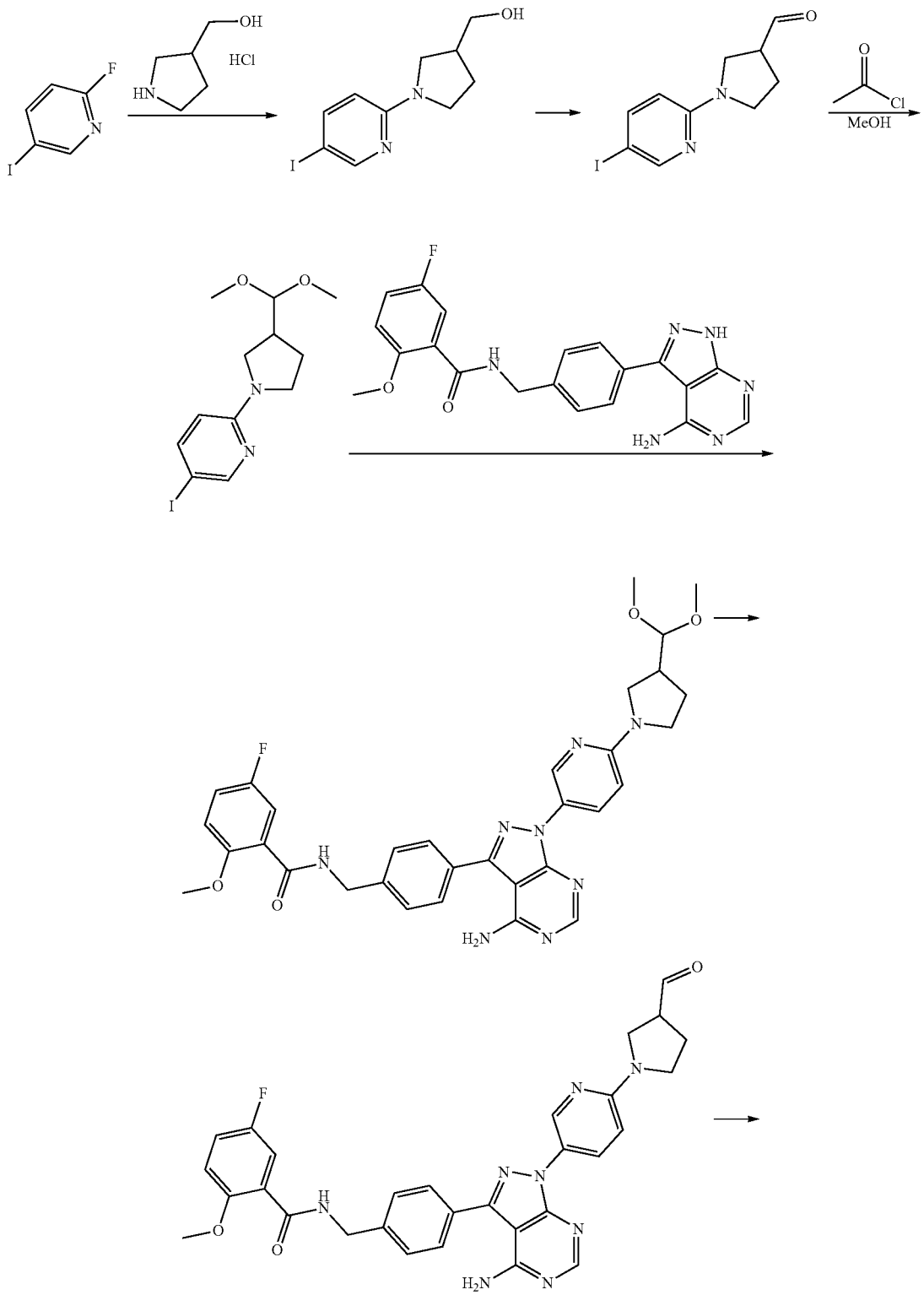

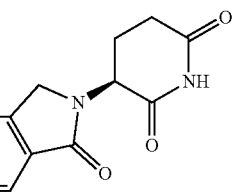
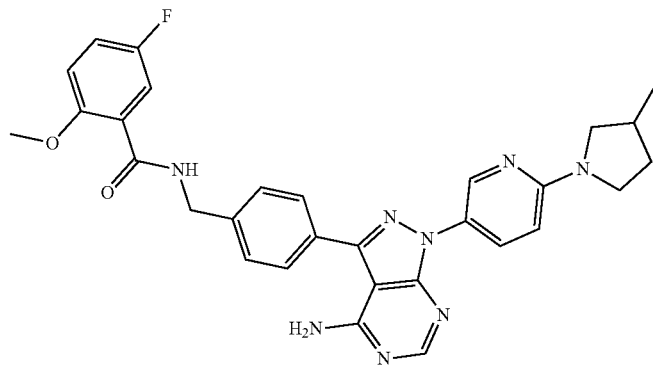

Step 1: Preparation of (1-(5-iodopyridin-2-yl)pyrrolidin-3-yl)methanol

To a solution of 2-fluoro-5-iodopyridine (2 g, 9 mmol) in DMF (20 mL) was added pyrrolidin-3-ylmethanol (1.09 g, 10.8 mmol) and potassium carbonate (3.73 g, 2.7 mmol). The reaction mixture was stirred at 100° C. for 2 hours. The reaction was quenched by adding water (50 mL) and extracted with EA (50 mL×3). The organic phase was washed with brine and dried over $Na_2SO_4$. The solvent was removed in vacuum and the residue was purified by flash column chromatography with PE:EA=5:1 to afford the desired product (2 g, 73.0%) as a yellow solid. LC/MS: 304.9 $[M+H]^+$.

Step 2: Preparation of 1-(5-iodopyridin-2-yl)pyrrolidine-3-carbaldehyde

To a solution of [1-(5-iodopyridin-2-yl)pyrrolidin-3-yl] methanol (2 g, 6.6 mmol) in DCM (30 mL) stirred under nitrogen at 0° C. was added Dess-Martin periodinane (4.2 g, 9.9 mmol) in portions. The reaction mixture was stirred at room temperature for 2 hours. The reaction was quenched by adding water (10 mL). The organic phase was washed with brine and dried over $Na_2SO_4$. The solvent was removed in vacuum to give the title compound (1.5 g, 75.7% yield) as a yellow solid. LC/MS: 302.9 $[M+H]^+$.

Step 3: Preparation of 2-(3-(dimethoxymethyl)pyrrolidin-1-yl)-5-iodopyridine To a solution of 1-(5-iodopyridin-2-yl)pyrrolidine-3-carbaldehyde (1.5 g, 5.0 mmol) in trimethoxy methane (20 mL) stirred under nitrogen at 25° C. was added TsOH (90 mg, 0.5 mmol). The reaction was stirred at 100° C. for 2 hours. The reaction mixture was concentrated in vacuum and the residue was purified by flash column chromatography with PE:EA=5:1 to afford the desired product (500 mg, 28.0%) as a yellow solid. LC/MS: 348.9 $[M+H]^+$.

Step 4: Preparation of N-(4-(4-amino-1-(6-(3-(dimethoxymethyl)pyrrolidin-1-yl)pyridin-3-yl)-1H-pyrazolo[3,4-d]pyrimidin-3-yl)benzyl)-5-fluoro-2-methoxybenzamide To a solution of 2-(3-(dimethoxymethyl)pyrrolidin-1-yl)-5-iodopyridine (120 mg, 0.34 mmol) in DMF (20 mL) was added N-(4-(4-amino-1H-pyrazolo[3,4-d]pyrimidin-3-yl) benzyl)-5-fluoro-2-methoxybenzamide (135 mg, 0.34 mmol), $Cs_2CO_3$ (336.8 mg, 1.03 mmol), Copper(I) iodide (65.3 mg, 0.34 mmol) and $N^1,N^1$-Dimethylcyclohexane-1,2-diamine (49.02 mg, 0.34 mmol). The reaction was stirred at 110° C. for 10 hours. The solid was filtered off and washed with DCM (10 mL×3). The solution was concentrated in vacuum and the residue was purified by flash column chromatography with DCM:MeOH=1:0~ 10:1 to afford the desired product (20 mg, 9.4%). LC/MS: 613.0 $[M+H]^+$.

Step 5: Preparation of N-(4-(4-amino-1-(6-(3-formylpyrrolidin-1-yl)pyridin-3-yl)-1H-pyrazolo [3,4-d] pyrimidin-3-yl)benzyl)-5-fluoro-2-methoxybenzamide A solution of N-(4-(4-amino-1-(6-(3-(dimethoxymethyl) pyrrolidin-1-yl)pyridin-3-yl)-1H-pyrazolo[3,4-d]pyrimidin-3-yl)benzyl)-5-fluoro-2-methoxybenzamide (15 mg, 0.025 mmol) in $H_2SO_4/H_2O/THF$ (1 mL, 1/3/2) was stirred under nitrogen at 70° C. for 1 hour. The mixture was diluted with EA (50 mL) and neutralized with NaOH (2 N). The organic phase was dried over $Na_2SO_4$. The solvent was removed in vacuum to give the title compound (12 mg, 86.5%) as a yellow solid. LC/MS: 567.0 $[M+H]^+$.

Step 6: Preparation of N-(4-(4-amino-1-(6-(3-((4-(2-((S)-2,6-dioxopiperidin-3-yl)-1-oxoisoindolin-5-yl)piperazin-1-yl)methyl)pyrrolidin-1-yl)pyridin-3-yl)-1H-pyrazolo[3,4-d]pyrimidin-3-yl) benzyl)-5-fluoro-2-methoxybenzamide To a solution of N-(4-(4-amino-1-(6-(3-formylpyrrolidin-1-yl)pyridin-3-yl)-1H-pyrazolo[3,4-d]pyrimidin-3-yl)benzyl)-5-fluoro-2-methoxybenzamide (12 mg, 0.02 mmol) in MeOH/DMF/HOAc (2 mL, 2:1:0.02) was added 2-(2,6-dioxopiperidin-3-yl)-5-(piperazin-1-yl)isoindole-1,3-dione (7 mg, 0.02 mmol), TEA (21.5 mg, 0.21 mmol) and $NaBH_3CN$ (6.6 mg, 0.106 mmol). The reaction was stirred at 60° C. for 1 hour. The reaction mixture was cooled to room temperature then quenched by adding water (5 mL) and extracted with DCM (5 mL×3). The organic phase was washed with brine and dried over $Na_2SO_4$. The solvent was removed in vacuum and the residue was purified by silica-gel column (DCM:MeOH=100:1-10:1) to afford the desired compound (10 mg, 53.7%). LC/MS: 878.9 $[M+H]^+$.

¹H NMR (400 MHz, DMSO) δ 10.96 (s, 1H), 8.90 (m, 1H), 8.67 (d, J=2.7 Hz, 1H), 8.31 (s, 2H), 8.07 (dd, J=9.0, 2.7 Hz, 1H), 7.72 (d, J=8.2 Hz, 2H), 7.58-7.50 (m, 3H), 7.38-7.30 (m, 1H), 7.21-7.18 (m, 1H), 7.10-7.05 (m, 2H), 6.62 (d, J=9.1 Hz, 1H), 5.09-5.03 (m, 1H), 4.60 (d, J=6.1 Hz, 2H), 4.33 (d, J=17.0 Hz, 1H), 4.21 (d, J=16.9 Hz, 1H), 3.91 (s, 3H), 3.74-3.61 (m, 2H), 3.59-3.53 (m, 2H), 3.32-3.25 (m, 6H), 3.22-3.14 (m, 2H), 2.92-2.85 (m, 1H), 2.62-2.55 (m, 4H), 2.43-2.31 (m, 3H), 2.13-2.10 (m, 1H), 2.01-1.91 (m, 1H), 1.80-1.72 (m, 1H).

Example 65: Preparation of 1-(5-(4-(6-(4-((5-(2-chloro-4-phenoxybenzoyl)-7H-pyrrolo[2,3-d]pyrimidin-4-yl)amino)piperidin-1-yl)-6-oxohexyl)piperazine-1-carbonyl)-2-methoxyphenyl) dihydropyrimidine-2,4(1H,3H)-dione (Compound 71)

The reaction was stirred at 90° C. for 17 hours. The solvent was evaporated under vacuum and the residue was purified by flash column chromatography with PE:EA=1:2 to afford the desired product (100 mg, 23%).

LC/MS: 502.8 [M+H]⁺.

Step 2: Preparation of 6-(4-(3-(2,4-dioxotetrahydro-pyrimidin-1(2H)-yl)-4-methoxybenzoyl)piperazin-1-yl)hexanoic acid To a solution of tert-butyl 6-(4-(3-(2,4-dioxotetrahydro-pyrimidin-1(2H)-yl)-4-methoxybenzoyl) piperazin-1-yl) hexanoate (100 mg, 0.2 mmol) in DCM (3 mL) was added TFA (1 mL). The mixture was stirred at room temperature for 2 hours. The solvent was removed under vacuum to afford the product (80 mg, crude). LC/MS: 446.7 [M+H]⁺.

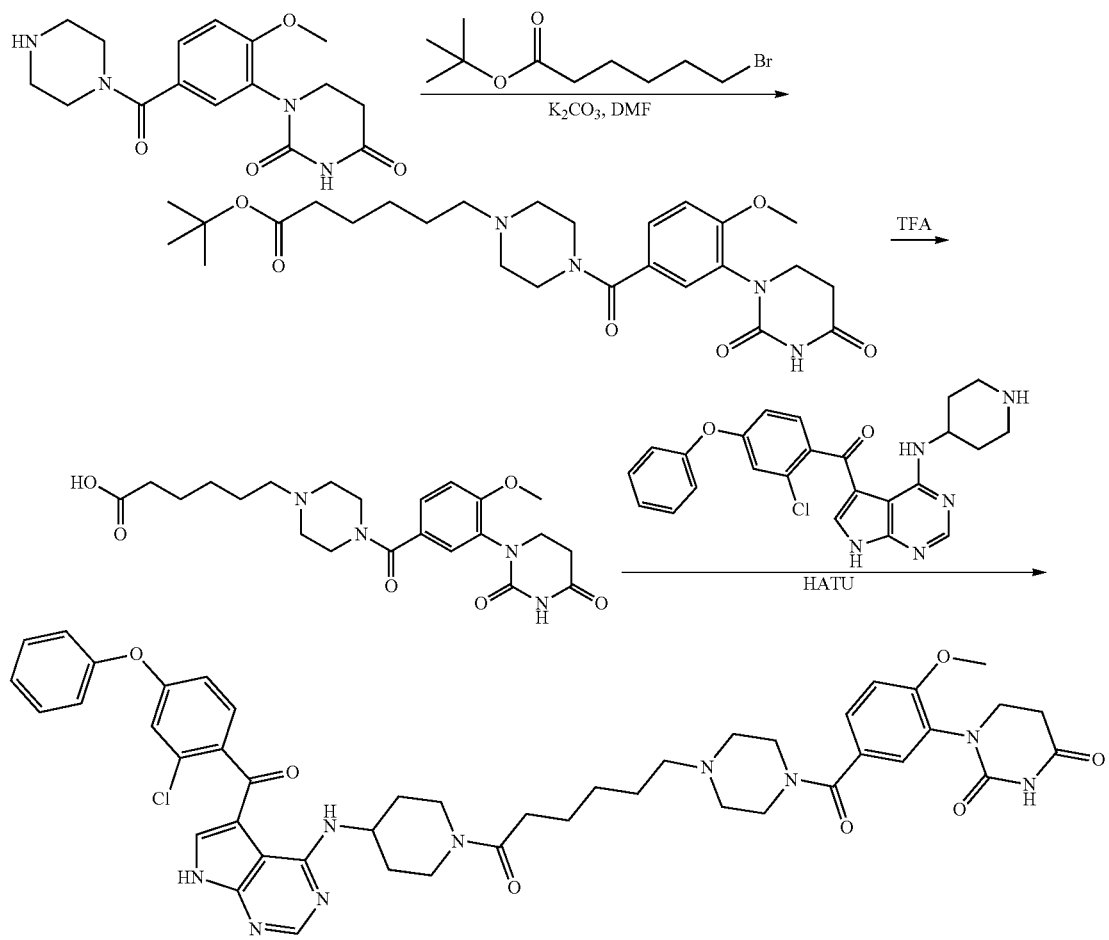

Step 1: Preparation of tert-butyl 6-(4-(3-(2,4-dioxo-tetrahydropyrimidin-1(2H)-yl)-4-methoxybenzoyl) piperazin-1-yl)hexanoate To a solution of tert-butyl 6-bromohexanoate (200 mg, 0.8 mmol) in DMF (10 mL) was added 1-(2-methoxy-5-(piperazine-1-carbonyl)phenyl)dihydropyrimidine-2,4(1H,3H)-dione (392 mg, 0.88 mmol) and K₂CO₃ (336 mg, 2.4 mmol).

Step 3: Preparation of 1-(5-(4-(6-(4-((5-(2-chloro-4-phenoxybenzoyl)-7H-pyrrolo[2,3-d]pyrimidin-4-yl) amino)piperidin-1-yl)-6-oxohexyl)piperazine-1-carbonyl)-2-methoxyphenyl)dihydropyrimidine-2,4(1H, 3H)-dione To a solution of 6-(4-(3-(2,4-dioxotetrahydropyrimidin-1 (2H)-yl)-4-methoxybenzoyl)piperazin-1-yl)hexanoic acid (80 mg, crude) in DCM (5 mL) was added HATU (102 mg, 0.27 mmol) and TEA (54 mg, 0.54 mmol). The mixture was stirred at room temperature for 5 minutes before (2-chloro-4-phenoxyphenyl)(4-(piperidin-4-ylamino)-7H-pyrrolo[2,3-d]pyrimidin-5-yl)methanone (80 mg, 0.18 mmol,) was added. The mixture was stirred at room temperature for 2 hours. The mixture was extracted with brine and concentrated in vacuum to give a crude product. The crude product was purified by Pre-TLC with DCM:MeOH=10:1 to afford the desired product. (19.5 mg, 11% for two steps). LC/MS: 876.1 [M+H]$^+$.

1H NMR (400 MHz, CDCl3) δ 9.12 (d, J=7.4 Hz, 1H), 8.37 (s, 1H), 7.46-7.37 (m, 5H), 7.33 (s, 1H), 7.23 (t, J=7.4 Hz, 1H), 7.12-7.06 (m, 3H), 7.02-6.93 (m, 2H), 4.40-4.48 (m, 1H), 4.31-4.38 (m, 1H), 3.89 (s, 3H), 3.77-3.87 (m, 2H), 3.71 (s, 4H), 3.34 (t, J=10.7 Hz, 1H), 3.20-3.12 (m, 1H), 2.87-2.81 (m, 2H), 2.70-2.52 (m, 5H), 2.36 (t, J=7.5 Hz, 2H), 2.11-2.21 (m, 2H), 1.53-1.75 (m, 8H), 1.40-1.25 (m, 2H).

Example 66: Preparation of 1-(5-(4-(5-(4-((5-(2-chloro-4-phenoxybenzoyl)-7H-pyrrolo[2,3-d]pyrimidin-4-yl)amino)piperidin-1-yl)-5-oxopentyl)piperazine-1-carbonyl)-2-methoxyphenyl) dihydropyrimidine-2,4(1H,3H)-dione (Compound 72)

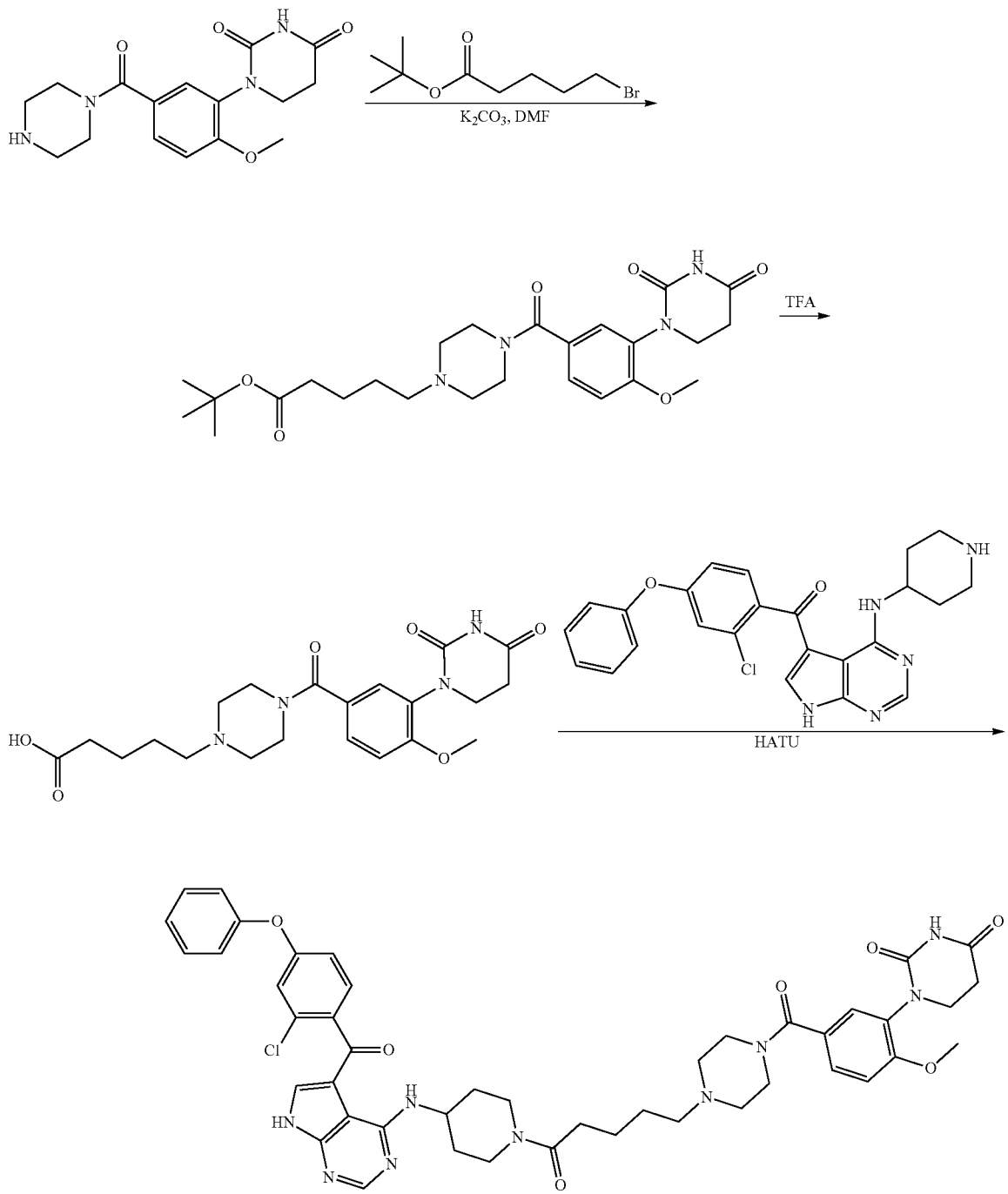

Step 1: Preparation of tert-butyl 5-(4-(3-(2,4-dioxo-tetrahydropyrimidin-1(2H)-yl)-4-methoxy benzoyl) piperazin-1-yl)pentanoate A solution of tert-butyl 5-bromopentanoate (380 mg, 1.60 mmol), 1-(2-methoxy-5-(piperazine-1-carbonyl)phenyl)dihydropyrimidine-2,4(1H,3H)-dione (1.07 g, 3.20 mmol), K₂CO₃ (1.11 g, 8.00 mmol), KI (266 mg, 1.60 mmol) in DMF (20 mL) was stirred at room temperature for 3 hours. The reaction mixture was diluted with water (50 mL) and extracted with EtOAc (50 mL×3). The combined organic layer was dried over Na₂SO₄, filtered and evaporated to afford a crude compound. The crude product was purified by column chromatography (DCM:MeOH=10:1) to obtain the desired product as a light yellow solid (130 mg, 17%). LC/MS: 488.7 [M+H]⁺.

Step 2: Preparation of 5-(4-(3-(2,4-dioxotetrahydro-pyrimidin-1(2H)-yl)-4-methoxybenzoyl) piperazin-1-yl)pentanoic acid A solution of tert-butyl 5-(4-(3-(2,4-dioxotetrahydropyrimidin-1(2H)-yl)-4-methoxy benzoyl)piperazin-1-yl)pentanoate (130 mg, 0.27 mmol) in DCM (12 mL) and TFA (9 mL) was stirred at room temperature for 2 hours. The mixture was concentrated in vacuum to give the desired compound as a yellow oil (115 mg, 98%). LC/MS: 432.8 [M+H]+

Step 3: Preparation of 1-(5-(4-(5-(4-((5-(2-chloro-4-phenoxybenzoyl)-7H-pyrrolo[2,3-d]pyrimidin-4-yl)amino)piperidin-1-yl)-5-oxopentyl)piperazine-1-carbonyl)-2-methoxyphenyl)dihydropyrimidine-2,4(1H,3H)-dione A solution of 5-(4-(3-(2,4-dioxotetrahydropyrimidin-1(2H)-yl)-4-methoxybenzoyl) piperazin-1-yl)pentanoic acid (115 mg, 0.27 mmol), (2-chloro-4-phenoxyphenyl)(4-(piperidin-4-ylamino)-7H-pyrrolo[2,3-d]pyrimidin-5-yl)methanone (133 mg, 0.30 mmol), HATU (154 mg, 0.41 mmol) and N,N-Diisopropylethylamine (174 mg, 1.35 mmol) in MeOH/DMF (2:1, 15 mL) was stirred at room temperature for 2 hours. The mixture was evaporated in vacuum and purified by Prep-TLC with MeOH:DCM=1:10 to give the title compound (40 mg, yield: 17%). LC/MS: 862.1 [M+H]⁺.

1H NMR (301 MHz, DMSO) δ 12.74 (s, 1H), 10.33 (s, 1H), 8.80 (s, 1H), 8.24 (d, J=3.6 Hz, 1H), 7.70-7.56 (m, 2H), 7.45 (d, J=7.7 Hz, 2H), 7.38-7.29 (m, 2H), 7.28-7.23 (m, 1H), 7.19-7.11 (m, 4H), 7.02-6.95 (m, 1H), 4.31-4.14 (m, 3H), 3.90-3.75 (m, 4H), 3.58-3.46 (m, 6H), 2.70-2.45 (m, 2H), 2.48-2.19 (m, 8H), 2.10-1.90 (m, 3H), 1.58-1.38 (m, 6H).

Example 67: Preparation of 1-(5-(4-(2-(4-((5-(2-chloro-4-phenoxybenzoyl)-7H-pyrrolo[2,3-d]pyrimidin-4-yl)amino)piperidin-1-yl)-2-oxoethyl)-[1,4'-bipiperidine]-1'-carbonyl)-2-methoxyphenyl)dihydropyrimidine-2,4(1H,3H)-dione (Compound 73)

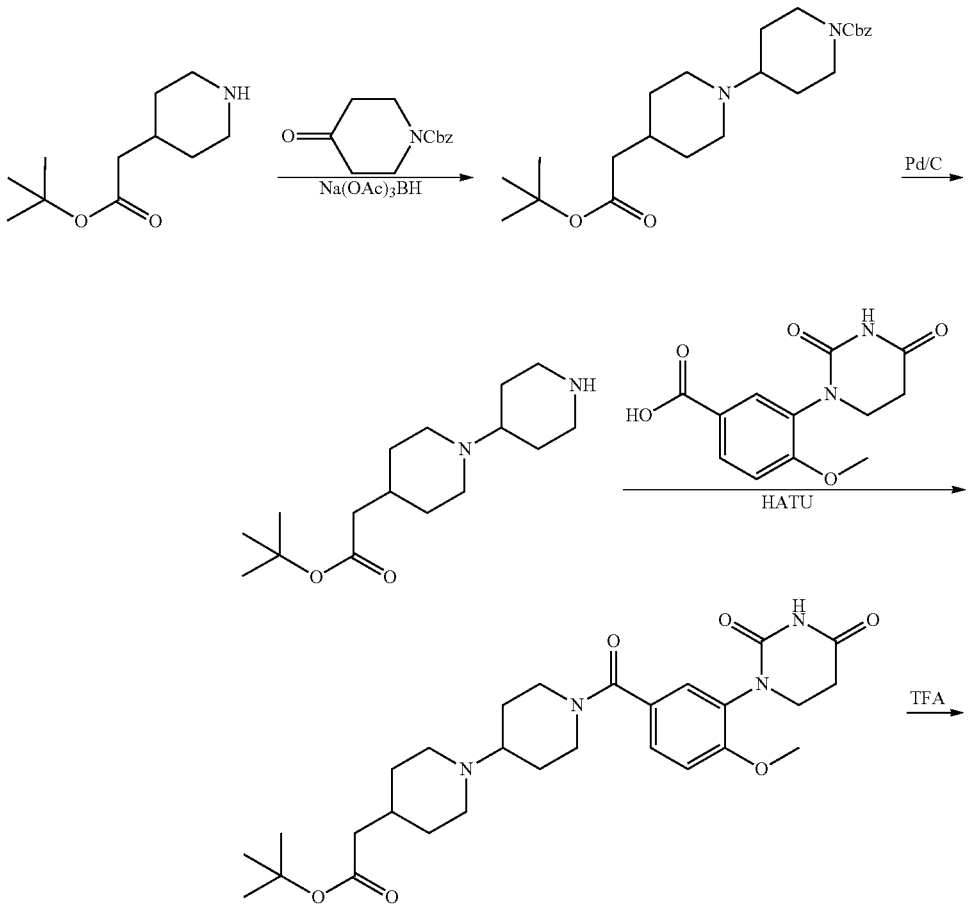

-continued

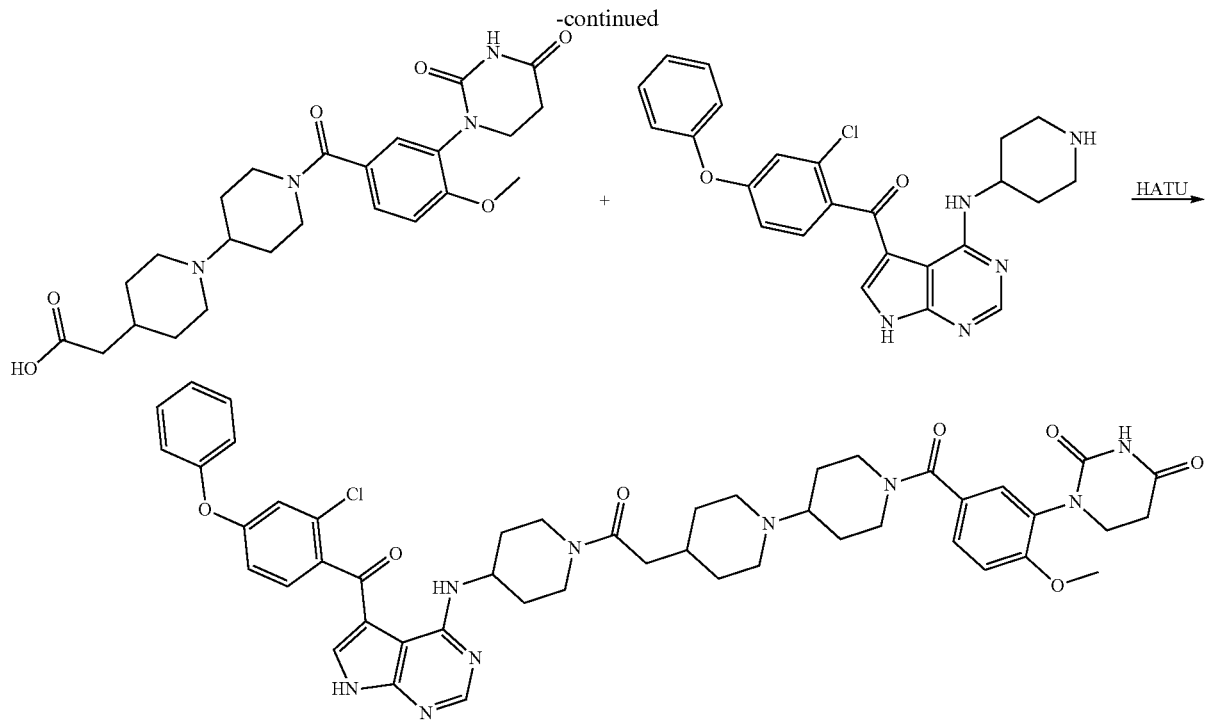

Step 1: Preparation of benzyl 4-(2-(tert-butoxy)-2-oxoethyl)-[1,4'-bipiperidine]-1'-carboxylate To a solution of tert-butyl 2-(piperidin-4-yl)acetate (500 mg, 2.51 mmol), benzyl 4-oxopiperidine-1-carboxylate (584.8 mg, 2.51 mmol), and TEA (507 mg, 5.02 mmol) in DCM (15 mL) was added MgSO$_4$ (3 g, 25.1 mmol). The reaction mixture was stirred at room temperature for 1 hour. NaBH(AcO)$_3$ (1.3 g, 6.27 mmol) was added portion-wise in 3 hours. The reaction mixture was stirred at room temperature overnight. The solid was filtered off and washed with DCM (20 mL×2). The solution was concentrated in vacuum to give a crude product. The crude product was purified by Prep-TLC with MeOH:DCM=1:10 to give the title compound as a white solid (850 mg, 80% purity, 65.1% yield). LC/MS: 417.2 [M+H]$^+$.

Step 2: Preparation of tert-butyl 2-([1,4'-bipiperidin]-4-yl)acetate

To a solution of benzyl 4-(2-(tert-butoxy)-2-oxoethyl)-[1,4'-bipiperidine]-1'-carboxylate (850 mg, 80% purity, 1.63 mmol) in dry t-BuOH (20 mL) was added Pd/C (100 mg). The mixture stirred at 20° C. for overnight under H$_2$. The catalyst was filtered off. The solution was concentrated in vacuum to afford the title product (320 mg, 90% purity, 62% yield) as a white solid. LC/MS: 227.1 [M−55]$^+$.

Step 3: Preparation of tert-butyl 2-(1'-(3-(2,4-dioxotetrahydropyrimidin-1(2H)-yl)-4-methoxy benzoyl)-[1,4'-bipiperidin]-4-yl)acetate A solution of tert-butyl 2-([1,4'-bipiperidin]-4-yl)acetate (320 mg, 90% purity, 1.02 mmol), 3-(2,4-dioxotetrahydropyrimidin-1(2H)-yl)-4-methoxybenzoic acid (269 mg, 1.02 mmol), HATU (463.6 mg, 1.22 mmol) and N,N-Diisopropylethylamine (197.4 mg, 1.53 mmol) in DMF (15 mL) was stirred at room temperature for 4 h. The mixture was evaporated in vacuo and purified by prep-TLC with MeOH:DCM=1:10 to give the title compound (30 mg, 5.5%) as a white solid. LC/MS: 529.2 [M+H]$^+$.

Step 4: Preparation of 2-(1'-(3-(2,4-dioxotetrahydropyrimidin-1(2H)-yl)-4-methoxybenzoyl)-[1,4'-bipiperidin]-4-yl)acetic acid A solution of tert-butyl 2-(1'-(3-(2,4-dioxotetrahydropyrimidin-1(2H)-yl)-4-methoxybenzoyl)-[1,4'-bipiperidin]-4-yl)acetate (30 mg, 0.056 mmol) in DCM (5 mL) and TFA (2 mL) was stirred at room temperature for 2 hours. The mixture was concentrated in vacuum to give the title compound (30 mg, 89.3% purity, 100% yield). LC/MS: 473.1 [M+H]$^+$.

Step 5: Preparation of 1-(5-(4-(2-(4-((5-(2-chloro-4-phenoxybenzoyl)-7H-pyrrolo[2,3-d]pyrimidin-4-yl)amino)piperidin-1-yl)-2-oxoethyl)-[1,4'-bipiperidine]-1'-carbonyl)-2-methoxyphenyl)dihydropyrimidine-2,4(1H,3H)-dione A solution of 2-(1'-(3-(2,4-dioxotetrahydropyrimidin-1(2H)-yl)-4-methoxybenzoyl)-[1,4'-bipiperidin]-4-yl)acetic acid (30 mg, 0.056 mmol), (2-chloro-4-phenoxyphenyl)(4-(piperidin-4-ylamino)-7H-pyrrolo[2,3-d]pyrimidin-5-yl)methanone (27.1 mg, 0.056 mmol), HATU (25.5 mg, 0.067 mmol) and N,N-Diisopropylethylamine (11 mg, 0.084 mmol) in DMF (10 mL) was stirred at room temperature for 4 hours. The mixture was evaporated in vacuum and purified by prep-TLC with MeOH:DCM=1:10 to give the title compound (15 mg, 29.4%) as a white solid. LC/MS: 901.5 [M+H]$^+$.

$^1$H NMR (400 MHz, DMSO) δ 12.89 (br, 1H), 10.35 (s, 1H), 9.36 (br, 1H), 9.00-8.92 (m, 1H), 8.29 (s, 1H), 7.68 (s, 1H), 7.58 (d, J=8.5 Hz, 1H), 7.49 (t, J=7.6 Hz, 2H), 7.42 (d,

J=8.4 Hz, 1H), 7.36 (s, 1H), 7.26 (t, J=7.3 Hz, 1H), 7.19 (d, J=8.1 Hz, 3H), 7.03 (d, J=8.3 Hz, 1H), 4.39-4.30 (m, 2H), 4.26-4.12 (m, 2H), 3.86 (s, 3H), 3.64-3.57 (m, 2H), 3.44 (d, J=8.7 Hz, 2H), 3.33-3.25 (m, 1H), 3.07-2.98 (m, 3H), 2.73-2.65 (m, 2H), 2.40-2.31 (m, 2H), 2.16-1.83 (m, 8H), 1.72-1.31 (m, 8H), 1.27-1.20 (m, 1H).

Example 68: Preparation of 1-(5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)piperazine-1-carbonyl)-2-methoxyphenyl)dihydropyrimidine-2,4(1H,3H)-dione (Compound 74)

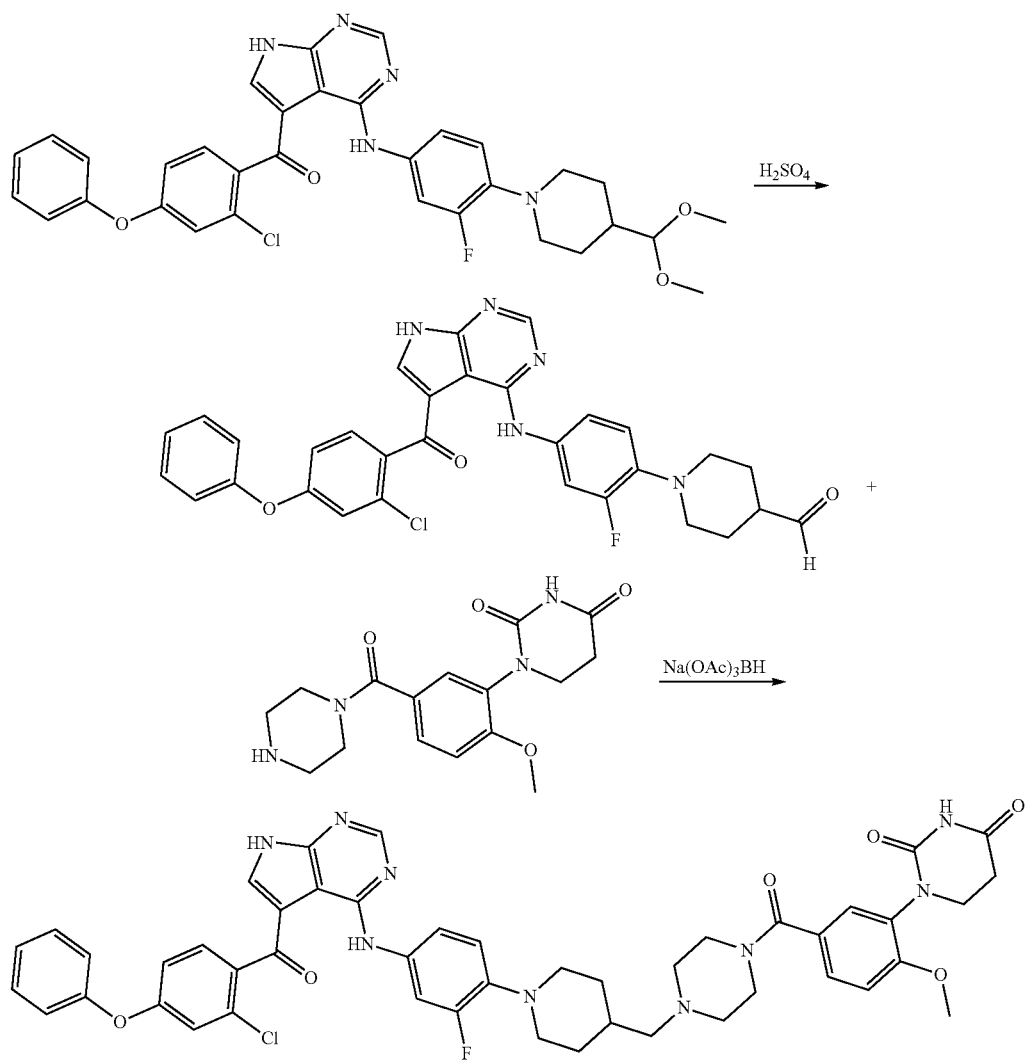

Step 1: Preparation of 1-(4-((5-(2-chloro-4-phenoxybenzoyl)-7H-pyrrolo[2,3-d]pyrimidin-4-yl)amino)-2-fluorophenyl)piperidine-4-carbaldehyde To a solution of (2-chloro-4-phenoxyphenyl)(4-((4-(4-(dimethoxymethyl)piperidin-1-yl)-3-fluorophenyl)amino)-7H-pyrrolo[2,3-d]pyrimidin-5-yl)methanone (200 mg, 0.33 mmol) in THF (5 mL) was added sulfuric acid (2M, 5 mL, 10 mmol). The mixture was stirred at 70° C. for 30 minutes. NaOH (1 M) was added to adjust pH=9 with and then extracted with ethyl acetate (20 mL×3). The combined organic layer was washed with brine, dried over Na$_2$SO$_4$ and concentrated in vacuum to give a crude product (152 mg, 81%). LC/MS: 569.6 [M+H]$^+$.

Step 2: Preparation of 1-(5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)piperazine-1-carbonyl)-2-methoxyphenyl)dihydropyrimidine-2,4(1H,3H)-dione To a solution of 1-(4-((5-(2-chloro-4-phenoxybenzoyl)-7H-pyrrolo[2,3-d]pyrimidin-4-yl)amino)-2-fluorophenyl)piperidine-4-carbaldehyde (90 mg, 0.16 mmol), 1-(2-methoxy-5-(piperazine-1-carbonyl)phenyl)dihydropyrimidine-2,4(1H,3H)-dione hydrochloride (53.1 mg, 0.16 mmol), and TEA (48.5 mg, 0.48 mmol) in DCM (15 mL) was added MgSO$_4$ (192 mg, 1.6 mmol). The reaction mixture was stirred at room temperature for 1 hour. NaBH(AcO)$_3$ (101.7 mg, 0.48 mmol) was added portion-wise in 3 hours. The reaction mixture was stirred at room temperature for 5 hours. The reaction mixture was concentrated under vacuum to give a crude product. The crude product was purified by Prep-TLC with MeOH:DCM=1:10 to give the title compound (40 mg, 98% purity, 25% yield). LC/MS: 885.4 [M+H]$^+$.

$^1$H NMR (301 MHz, DMSO) δ 13.04 (s, 1H), 11.12 (s, 1H), 10.35 (s, 1H), 8.44 (s, 1H), 8.02 (d, J=17.1 Hz, 1H), 7.83 (s, 1H), 7.63 (d, J=8.5 Hz, 1H), 7.53-7.43 (m, 2H), 7.40-7.12 (m, 7H), 7.10-6.99 (m, 2H), 3.83 (s, 3H), 3.60-3.35 (m, 6H), 3.29-3.20 (m, 2H), 2.70-2.55 (m, 5H), 2.40-2.32 (m, 3H), 2.21 (d, J=6.4 Hz, 2H), 1.80 (d, J=12.3 Hz, 2H), 1.70-1.62 (m, 1H), 1.40-1.27 (m, 3H).

Example 69: Preparation of 1-(5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)-1,4-diazepane-1-carbonyl)-2-methoxyphenyl)dihydropyrimidine-2,4(1H,3H)-dione (Compound 75)

was added HATU (862 mg, 2.268 mmol), DIEA (489 mg, 3.78 mmol) and tert-butyl (1,4-diazepan-1-yl)formate (380 mg, 1.89 mmol) at room temperature. The reaction mixture was stirred at room temperature for 12 hours. The mixture was poured into water (45 mL) and extracted with EtOAc (50 mL×2). The combined organic layer was washed with brine, dried over Na$_2$SO$_4$, and concentrated in vacuum to get a crude product. The crude product was purified by flash chromatography (MeOH/DCM=1:10) to give the desired product (1 g, 94.7%), LC/MS: 391.2 [M−55]$^+$.

Step 2: Preparation of 1-(5-(1,4-diazepane-1-carbonyl)-2-methoxyphenyl)dihydropyrimidine-2,4(1H,3H)-dione A solution of tert-butyl (4-{[3-(2,4-dioxo-1,3-diazinan-1-yl)-4-methoxyphenyl]carbonyl}-1,4-diazepan-1-yl)formate (1 g) in TFA/DCM (1:5, 12 mL) was stirred at room

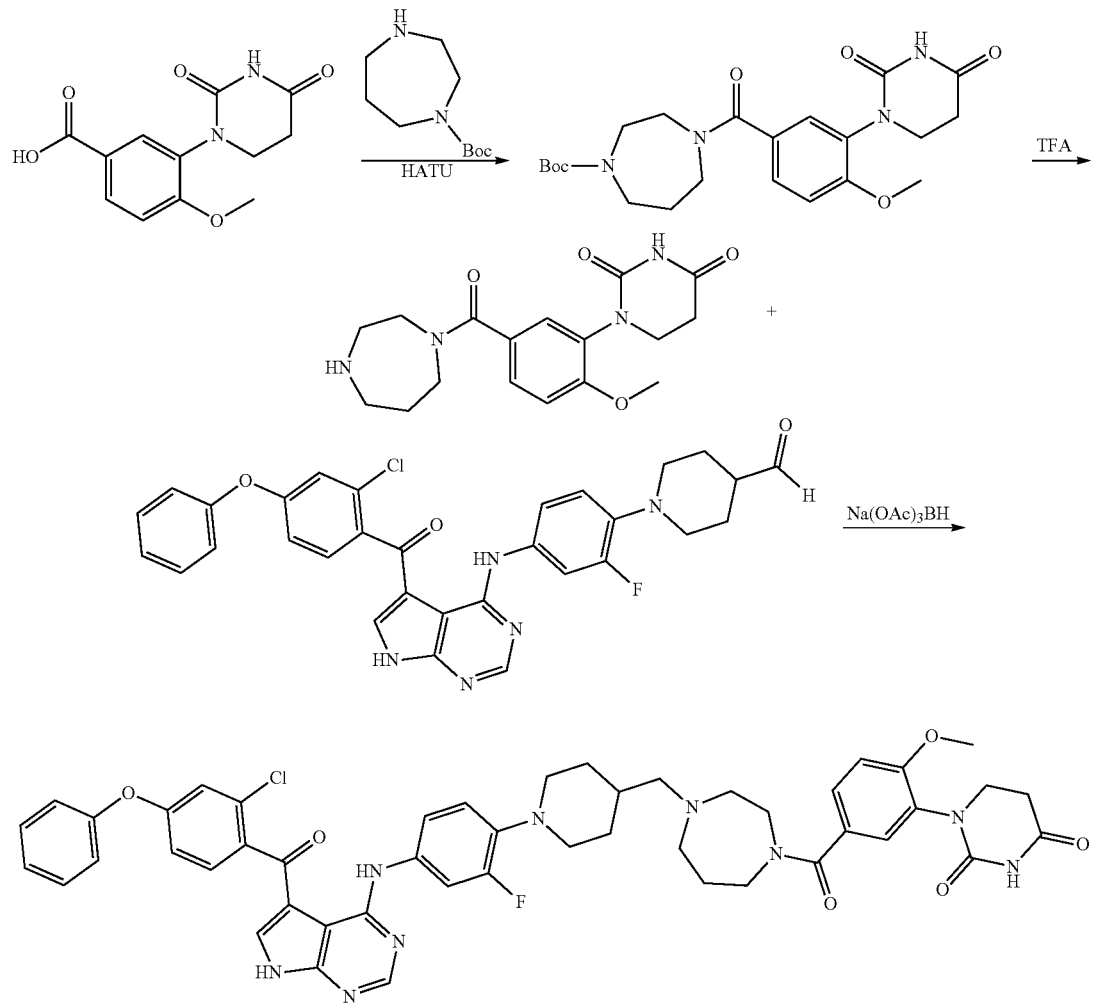

Step 1: Preparation of tert-butyl 4-(3-(2,4-dioxotetrahydropyrimidin-1(2H)-yl)-4-methoxybenzoyl)-1,4-diazepane-1-carboxylate To a solution of 3-(2,4-dioxo-1,3-diazinan-1-yl)-4-methoxybenzoic acid (500 mg, 1.89 mmol) in DMF (5 mL)

temperature for 2 hours. The solution was concentrated in vacuum. The residue was dissolved in DCM (50 mL), washed with saturated sodium bicarbonate solution and brine. The organic layer was dried over Na$_2$SO$_4$ and concentrated in vacuum to give the desired product (500 mg, 83.0%), LC/MS: 347.1 [M+H]$^+$.

Step 3: Preparation of 1-(5-(4-((1-(4-((5-(2-chloro-4-phenoxybenzoyl)-7H-pyrrolo[2,3-d]pyrimidin-4-yl)amino)-2-fluorophenyl)piperidin-4-yl)methyl)-1,4-diazepane-1-carbonyl)-2-methoxyphenyl)dihydropyrimidine-2,4(1H,3H)-dione To a solution of 1-(4-((5-(2-chloro-4-phenoxybenzoyl)-7H-pyrrolo[2,3-d]pyrimidin-4-yl)amino)-2-fluorophenyl)piperidine-4-carbaldehyde (80 mg, 0.14 mmol) in DCM (5 mL) was added 1-(5-(1,4-diazepane-1-carbonyl)-2-methoxyphenyl)dihydropyrimidine-2,4(1H,3H)-dione (97 mg, 0.28 mmol), Et₃N (28 mg, 0.28 mmol) and MgSO₄ (200 mg, 1.66 mmol) at room temperature. The mixture was stirred at room temperature for 30 minutes before NaBH(OAc)₃ (59 mg, 0.28 mmol) was added portion wise. The reaction mixture was stirred at room temperature for 1 hour. The mixture was filtered and the filtrate was concentrated in vacuum to give a crude product. The crude product was purified by Prep-TLC (MeOH/DCM=1:10) to give the desired product (80 mg, 63.5%). LC/MS: 900.1 [M+H]⁺.

¹H NMR (400 MHz, DMSO) δ 13.06 (br, 1H), 11.14 (s, 1H), 10.36 (s, 1H), 8.46 (s, 1H), 8.04 (d, J=14.8 Hz, 1H), 7.84 (s, 1H), 7.64 (d, J=8.4 Hz, 1H), 7.49 (t, J=7.6 Hz, 2H), 7.39-7.30 (m, 3H), 7.29-7.14 (m, 6H), 7.13-7.00 (m, 2H), 3.85 (s, 3H), 3.65-3.55 (m, 4H), 3.45-3.35 (m, 2H), 3.29-3.25 (m, 2H), 2.78-2.55 (m, 8H), 2.49-2.20 (m, 2H), 1.85-1.75 (m, 4H), 1.30-1.25 (m, 2H).

Example 70: Preparation of 1-(5-(4-(2-(1-(4-((5-(2-chloro-4-phenoxybenzoyl)-7H-pyrrolo[2,3-d]pyrimidin-4-yl)amino)-2-fluorophenyl)piperidin-4-yl)ethyl)piperazine-1-carbonyl)-2-methoxyphenyl)dihydropyrimidine-2,4(1H,3H)-dione (Compound 76)

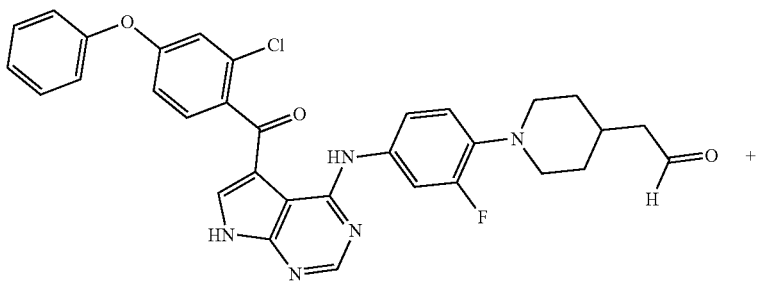

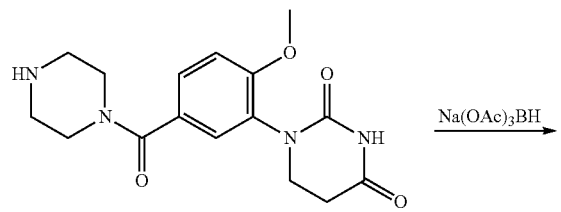

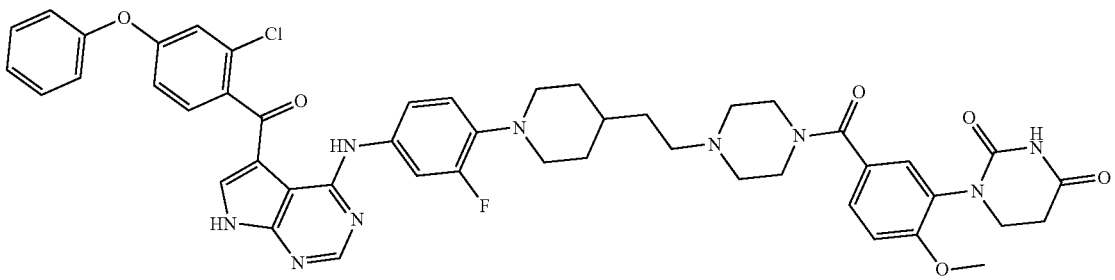

A solution of 2-(1-(4-((5-(2-chloro-4-phenoxybenzoyl)-7H-pyrrolo[2,3-d]pyrimidin-4-yl)amino)-2-fluorophenyl)piperidin-4-yl)acetaldehyde (140 mg, 0.24 mmol), 1-(2-methoxy-5-(piperazine-1-carbonyl)phenyl)dihydropyrimidine-2,4(1H,3H)-dione (80 mg, 0.24 mmol), TEA (121 mg, 1.2 mmol) and MgSO$_4$ (408 mg, 3.4 mmol) in DCM (20 mL) was stirred under nitrogen at room temperature for 30 minutes. Sodium triacetoxy borohydride (163 mg, 0.72 mmol) was added at 0° C. portion wise. The reaction mixture was stirred at room temperature for 2 hours. The reaction mixture was filtered. The organic layer was washed with water and concentrated in vacuum to give a crude product. The crude product was purified by Prep-TLC (MeOH:DCM=1:10) to give the desired product (55 mg, 25%) as a yellow solid.

LC/MS: 900.0[M+1]$^+$.

$^1$H NMR (400 MHz, DMSO) δ 13.06 (br, 1H), 11.14 (s, 1H), 10.36 (s, 1H), 10.05 (br, 1H), 8.46 (s, 1H), 8.04 (d, J=14.8 Hz, 1H), 7.84 (s, 1H), 7.64 (d, J=8.3 Hz, 1H), 7.49 (t, J=7.7 Hz, 2H), 7.45-7.37 (m, 1H), 7.33 (d, J=8.1 Hz, 1H), 7.30-7.24 (m, 1H), 7.23-7.11 (m, 3H), 7.09-7.04 (m, 1H), 3.86 (s, 2H), 3.67-3.56 (m, 2H), 3.52-3.39 (m, 2H), 3.38-3.24 (m, 4H), 3.22-2.96 (m, 2H), 2.91-2.56 (m, 4H), 2.45-1.88 (m, 5H), 1.85-1.45 (m, 4H), 1.42-0.87 (m, 5H).

Example 71: Preparation of (R)-1-(5-(4-(2-(3-((5-(2-chloro-4-phenoxybenzoyl)-7H-pyrrolo[2,3-d]pyrimidin-4-yl)amino)piperidin-1-yl)-2-oxoethyl)-[1,4'-bipiperidine]-1'-carbonyl)-2-methoxyphenyl)dihydropyrimidine-2,4(1H,3H)-dione (Compound 77)

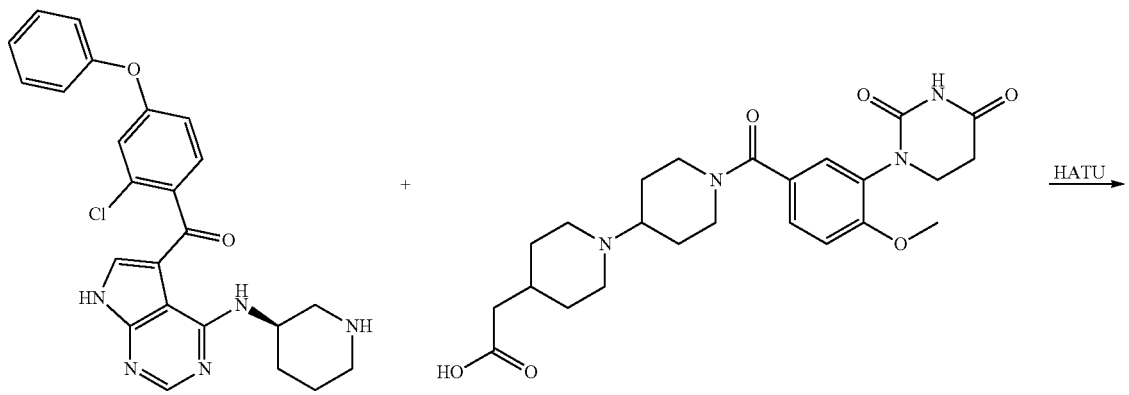

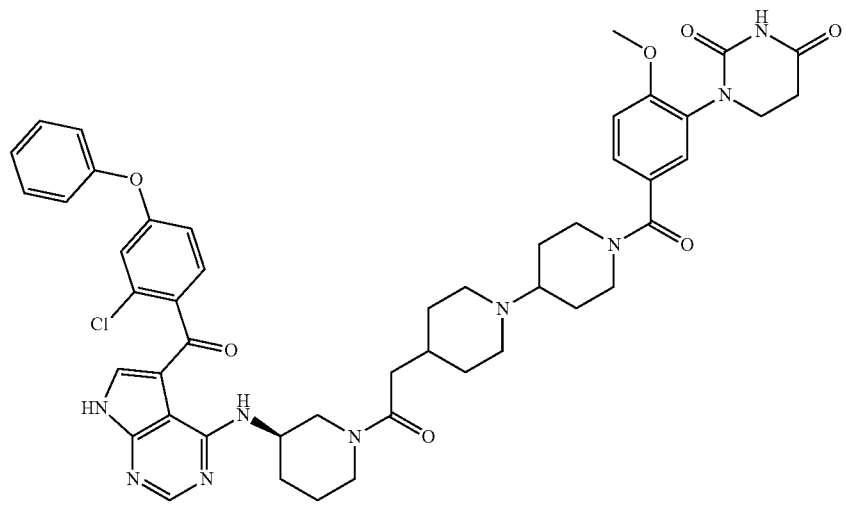

Step 1: Preparation of (R)-1-(5-(4-(2-(3-((5-(2-chloro-4-phenoxybenzoyl)-7H-pyrrolo[2,3-d]pyrimidin-4-yl)amino)piperidin-1-yl)-2-oxoethyl)-[1,4'-bipiperidine]-1'-carbonyl)-2-methoxyphenyl)dihydropyrimidine-2,4(1H,3H)-dione A solution of 2-(1'-(3-(2,4-dioxotetrahydropyrimidin-1(2H)-yl)-4-methoxybenzoyl)-[1,4'-bipiperidin]-4-yl)acetic acid (70 mg, 0.15 mmol), (R)-(2-chloro-4-phenoxyphenyl)(4-(piperidin-3-ylamino)-7H-pyrrolo[2,3-d]pyrimidin-5-yl)methanone (84 mg, 0.15 mmol), HATU (86 mg, 0.23 mmol) and N,N-Diisopropylethylamine (116 mg, 0.9 mmol) in DMF (10 mL) was stirred at room temperature for 4 hours. The mixture was evaporated in vacuum and purified by Prep-TLC with MeOH:DCM=1:10 to give the title compound (14 mg, 10%) as a white solid. LC/MS: 902.4 [M+H]⁺.

¹H NMR (301 MHz, DMSO) δ 12.86 (br, 1H), 10.37 (s, 1H), 8.87 (br, 1H), 8.32-8.24 (m, 1H), 7.67-7.62 (m, 1H), 7.60-7.52 (m, 1H), 7.51-7.43 (m, 2H), 7.42-7.34 (m, 2H), 7.29-7.12 (m, 5H), 7.05-6.98 (m, 1H), 4.32-4.21 (m, 1H), 4.20-4.13 (m, 1H), 3.84 (s, 3H), 3.63-3.53 (m, 3H), 3.33-3.24 (m, 2H), 3.21-3.13 (m, 1H), 3.07-3.01 (m, 1H), 2.94-2.77 (m, 3H), 2.67 (t, J=6.4 Hz, 2H), 2.35-2.23 (m, 2H), 2.10-1.70 (m, 10H), 1.67-1.46 (m, 6H), 1.19-1.15 (m, 1H).

Example 72: Preparation of 1-(5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazine-1-carbonyl)-2-methoxyphenyl)dihydropyrimidine-2,4(1H,3H)-dione (Compound 78)

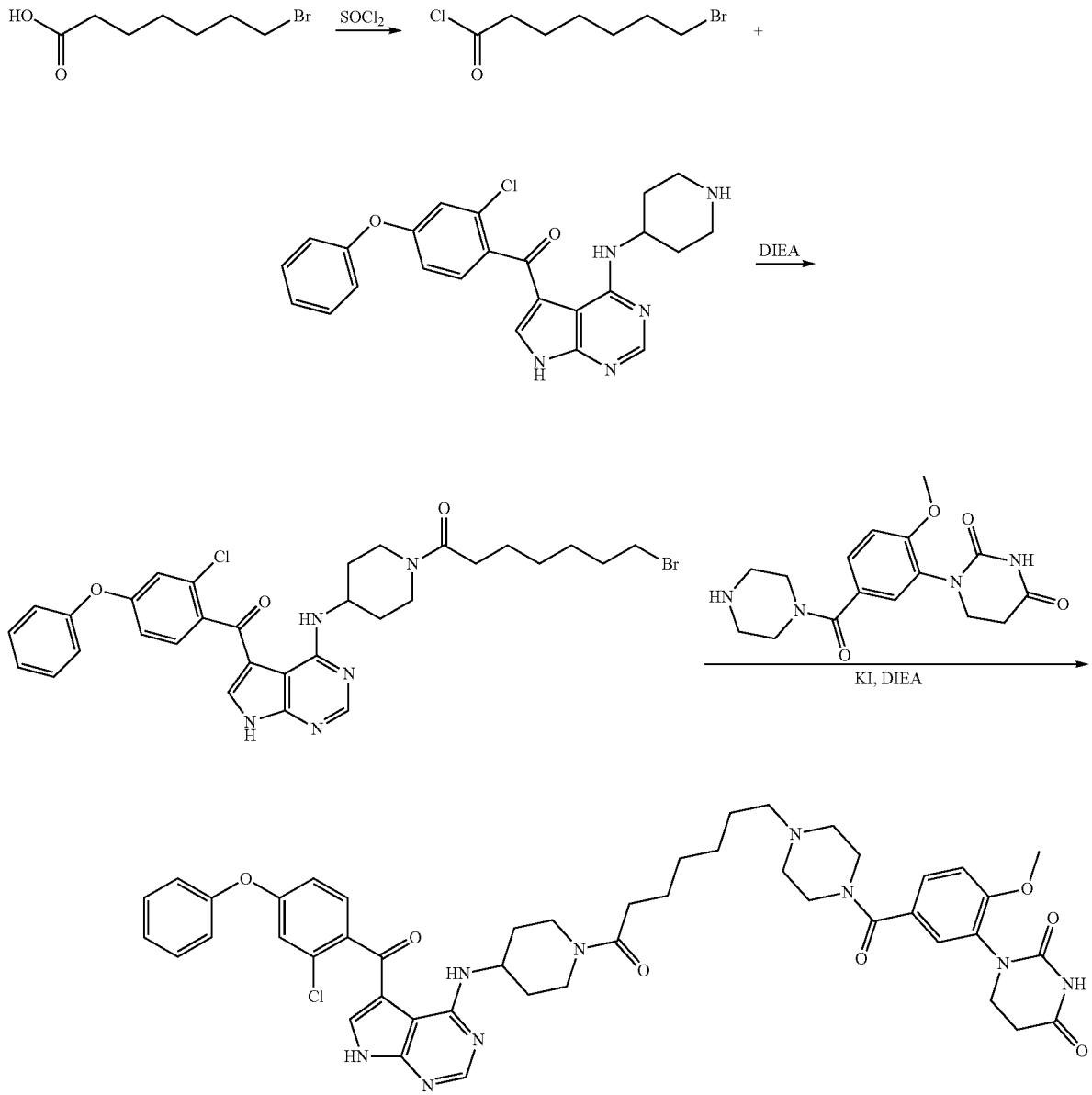

Step 1: Preparation of 7-bromoheptanoyl chloride

A solution of 7-bromoheptanoic acid (1 g, 4.8 mmol) in thionyl chloride (20 mL) was stirred at 70° C. for 5 hours. The reaction mixture was evaporated in vacuum to give the desired product as a brown oil (1 g, 91%). LC/MS: 223.0 [M+H]$^+$ (treated with MeOH).

Step 2: Preparation of 7-bromo-1-(4-((5-(2-chloro-4-phenoxybenzoyl)-7H-pyrrolo[2,3-d]pyrimidin-4-yl)amino)piperidin-1-yl)heptan-1-one To a solution of (2-chloro-4-phenoxyphenyl)(4-(piperidin-4-ylamino)-7H-pyrrolo[2,3-d]pyrimidin-5-yl)methanone (106 mg, 0.22 mmol) and N,N-Diisopropylethylamine (142.16 mg, 1.1 mmol) in ACN (10 mL) stirred under nitrogen at room temperature was added 7-bromoheptanoyl chloride (50 mg, 0.22 mmol). The mixture was stirred at room temperature for 5 hours. The solvent was removed in vacuum. The residue was partitioned between EtOAc and H$_2$O. The organic phase was dried over sodium sulfate and concentrated in vacuum to give a crude product. The crude product was purified by silica gel chromatography with CH$_2$Cl$_2$/MeOH (100:1-10:1) to afford the desired compound (60 mg, 41%) as a yellow solid. LC/MS: 637.9 [M+H]$^+$.

Step 3: Preparation of 1-(5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazine-1-carbonyl)-2-methoxyphenyl)dihydropyrimidine-2,4(1H,3H)-dione To a solution of 7-bromo-1-(4-((5-(2-chloro-4-phenoxybenzoyl)-7H-pyrrolo[2,3-d]pyrimidin-4-yl)amino)piperidin-1-yl)heptan-1-one (60 mg, 0.09 mmol), 1-{2-methoxy-5-[(piperazin-1-yl)carbonyl] phenyl}-1,3-diazinane (31.20 mg, 0.09 mmol) and N,N-Diisopropylethylamine (36.33 mg, 0.28 mmol] in ACN (10 mL) stirred under nitrogen at room temperature was added potassium iodide (3.1 mg, 0.02 mmol). The reaction mixture was stirred at 70° C. for 5 hours. The solvent was removed and the residue was purified by column chromatography (DCM/MeOH=50:1-10:1) to afford the product (21.3 mg, 0.024 mmol, 26%) as a yellow solid. LC/MS: 890.3 [M+H]$^+$.

$^1$H NMR (400 MHz, DMSO) δ 12.77 (s, 1H), 10.36 (s, 1H), 8.82 (d, J=7.4 Hz, 1H), 8.26 (s, 1H), 7.64 (s, 1H), 7.60-7.55 (m, 1H), 7.51-7.44 (m, 2H), 7.43-7.31 (m, 2H), 7.26 (t, J=7.4 Hz, 1H), 7.23-7.11 (m, 4H), 7.05-7.00 (m, 1H), 4.38-4.33 (m, 1H), 4.19-4.12 (m, 1H), 3.93-3.80 (m, 4H), 3.60 (t, J=6.6 Hz, 2H), 3.56-3.40 (m, 3H), 3.22-2.93 (m, 4H), 2.74-2.66 (m, 2H), 2.46-2.19 (m, 5H), 2.19-1.99 (m, 2H), 1.73-1.64 (m, 1H), 1.58-1.44 (m, 4H), 1.43-1.24 (m, 7H).

Example 73: Preparation of 1-(5-(4-(4-(4-((5-(2-chloro-4-phenoxybenzoyl)-7H-pyrrolo[2,3-d]pyrimidin-4-yl)amino)piperidine-1-carbonyl)benzyl)-1,4-diazepane-1-carbonyl)-2-methoxyphenyl)dihydropyrimidine-2,4(1H,3H)-dione (Compound 79)

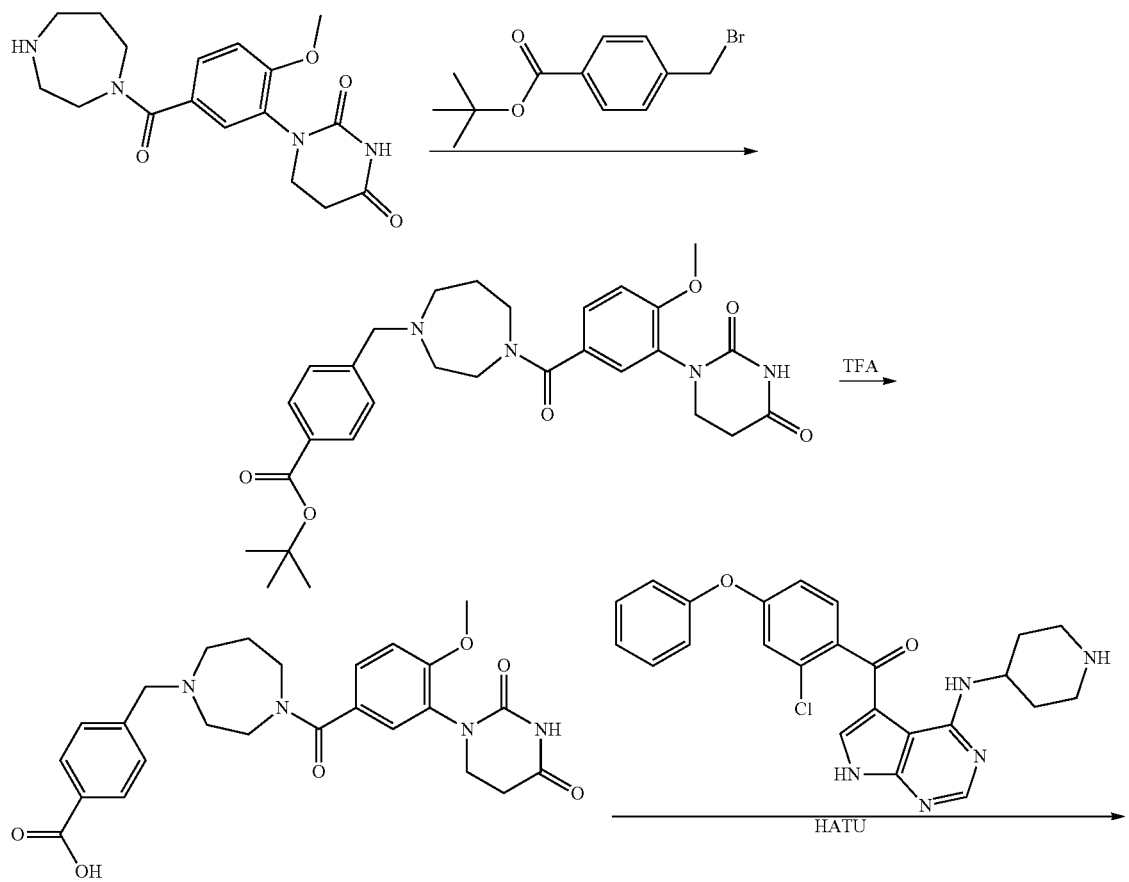

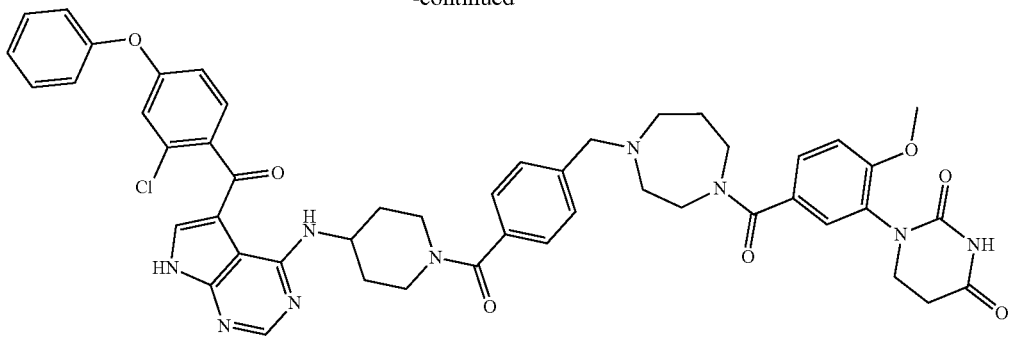

Step 1: Preparation of tert-butyl 4-((4-(3-(2,4-di-oxotetrahydropyrimidin-1(2H)-yl)-4-methoxy benzoyl)-1,4-diazepan-1-yl)methyl)benzoate To a solution of 1-(5-(1,4-diazepane-1-carbonyl)-2-methoxyphenyl)dihydropyrimidine-2,4(1H, 3H)-dione (80 mg, 0.23 mmol) in DMF (5 mL) was added tert-butyl 4-(bromomethyl)benzoate (69 mg, 0.25 mmol) and $K_2CO_3$ (64 mg, 0.46 mmol). The reaction was stirred at 75° C. for 17 hours. The solvent was removed under vacuum and the residue was purified by Pre-TLC with PE:EA=1:1 to afford the desired product (72 mg, 58%).

LC/MS: 537.2 $[M+H]^+$.

Step 2: Preparation of 4-((4-(3-(2,4-dioxotetrahydropyrimidin-1(2H)-yl)-4-methoxybenzoyl)-1,4-diazepan-1-yl)methyl)benzoic acid To a solution of tert-butyl 4-((4-(3-(2,4-dioxotetrahydropyrimidin-1(2H)-yl)-4-methoxybenzoyl)-1,4-diazepan-1-yl)methyl)benzoate (72 mg, 0.13 mmol) in DCM (3 mL) was added TFA (1 mL). The reaction was stirred at room temperature for 2 hours. The solvent was removed under vacuum to afford the product (80 mg) which was used in the next step without further purification. LC/MS: 481.0 $[M+H]^+$.

Step 3: Preparation of 1-(5-(4-(4-(4-(4-((5-(2-chloro-4-phenoxybenzoyl)-7H-pyrrolo[2,3-d]pyrimidin-4-yl)amino)piperidine-1-carbonyl)benzyl)-1,4-diazepane-1-carbonyl)-2-methoxyphenyl)dihydropyrimidine-2,4(1H,3H)-dione To a solution of 4-((4-(3-(2,4-dioxotetrahydropyrimidin-1(2H)-yl)-4-methoxybenzoyl)-1,4-diazepan-1-yl)methyl)benzoic acid (80 mg, crude) in DCM (5 mL) was added HATU (114 mg, 0.3 mmol) and DIEA (97 mg, 0.75 mmol). The mixture was stirred at room temperature for 5 minutes and (2-chloro-4-phenoxyphenyl)(4-(piperidin-4-ylamino)-7H-pyrrolo[2,3-d]pyrimidin-5-yl)methanone (73 mg, 0.15 mmol) was added. The mixture was stirred at room temperature for 2 hours. The mixture was washed with brine and concentrated in vacuum to give a crude product. The crude product was purified by Pre-TLC with DCM:MeOH=10:1 to afford the desired product. (25 mg, 21% for two steps). LC/MS: 910.1 $[M+H]^+$.

$^1$H NMR (400 MHz, DMSO) δ 12.77 (s, 1H), 10.34 (s, 1H), 8.85 (d, J=6.8 Hz, 1H), 8.25 (s, 1H), 7.64 (s, 1H), 7.58 (d, J=8.4 Hz, 1H), 7.48 (t, J=7.2 Hz, 2H), 7.44-7.31 (m, 6H), 7.26 (t, J=7.6 Hz, 1H), 7.23-7.17 (m, 3H), 7.16-7.11 (m, 1H), 7.03 (d, J=8.8 Hz, 1H), 4.42-4.20 (m, 2H), 3.83 (s, 3H), 3.68-3.53 (m, 6H), 3.46 (s, 2H), 3.27-3.13 (m, 2H), 2.75-2.60 (m, 4H), 2.59-2.53 (m, 1H), 2.23-1.92 (m, 3H), 1.86-1.66 (m, 3H), 1.60-1.48 (m, 2H).

Example 74: Preparation of 1-(5-(4-(4-(4-(4-((5-(2-chloro-4-phenoxybenzoyl)-7H-pyrrolo[2,3-d]pyrimidin-4-yl)amino)piperidine-1-carbonyl)benzyl)piperazine-1-carbonyl)-2-methoxyphenyl)dihydropyrimidine-2,4(1H,3H)-dione (Compound 80)

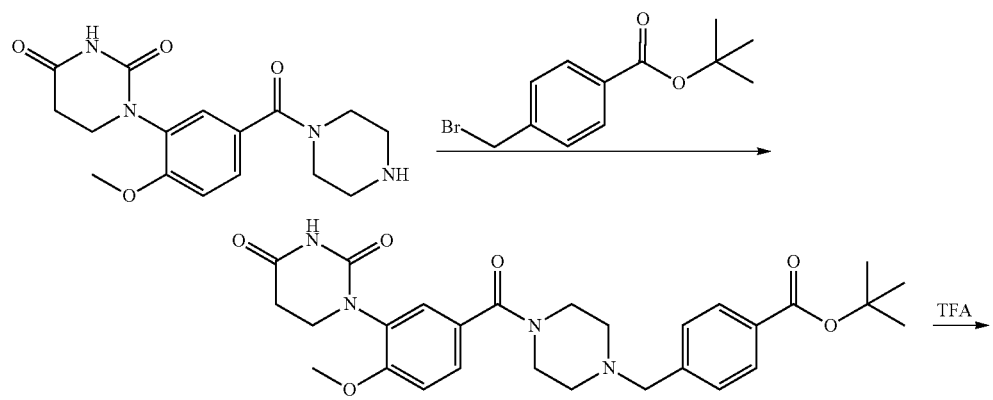

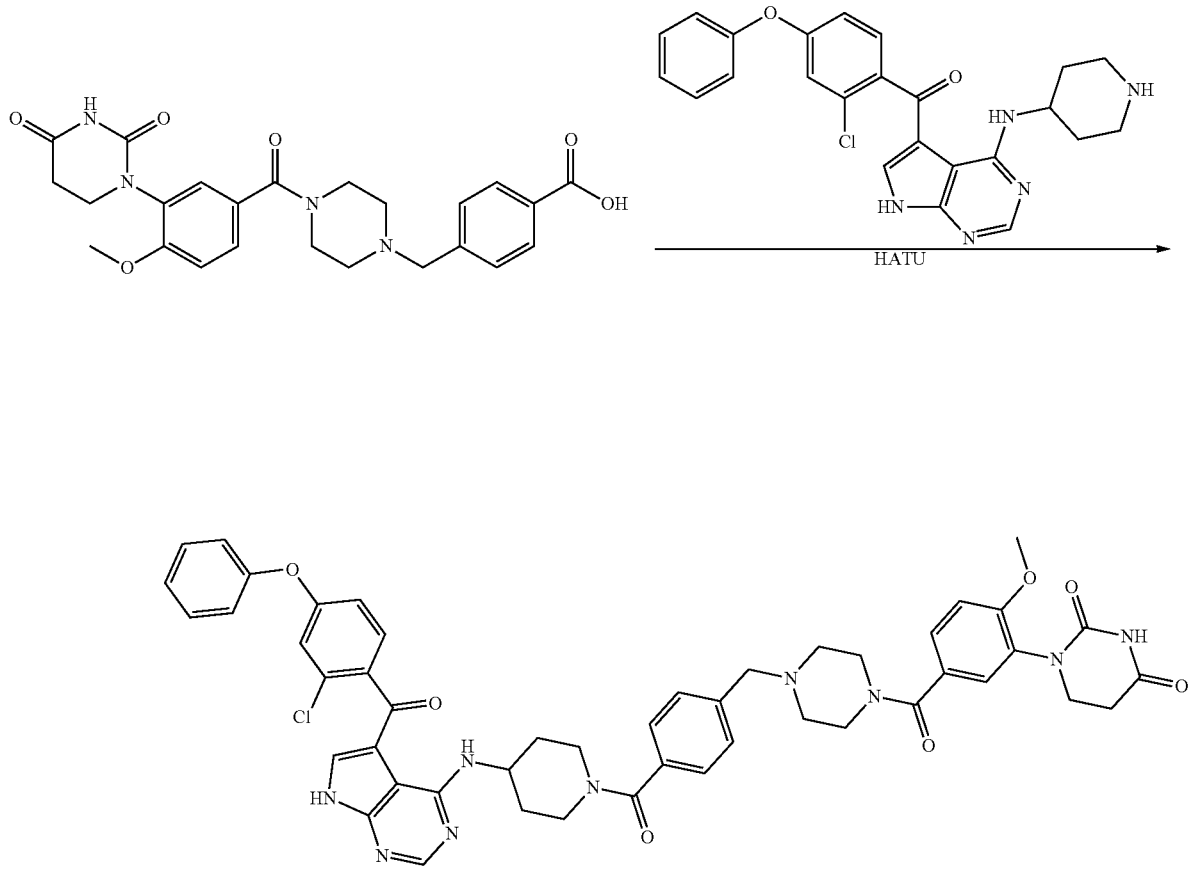

Step 1: Preparation of tert-butyl 4-((4-(3-(2,4-dioxotetrahydropyrimidin-1(2H)-yl)-4-methoxy benzoyl)piperazin-1-yl)methyl)benzoate A mixture of tert-butyl 4-(bromomethyl)benzoate (150 mg, 0.55 mmol), 1-(2-methoxy-5-(piperazine-1-carbonyl)phenyl)dihydropyrimidine-2,4(1H,3H)-dione (548 mg, 1.7 mmol) and DIEA (213 mg, 1.8 mmol) in DCM (20 mL) was stirred at room temperature for 4 hours. The solvent was removed under vacuum to give a crude product. The crude product was purified by Pre-TLC to give the product (160 mg, 50%) was obtained as yellow solid. LC/MS: 522.8 [M+H]$^+$.

Step 2: Preparation of 4-((4-(3-(2,4-dioxotetrahydropyrimidin-1(2H)-yl)-4-methoxybenzoyl)piperazin-1-yl)methyl)benzoic acid To a solution of tert-butyl 4-((4-(3-(2,4-dioxotetrahydropyrimidin-1(2H)-yl)-4-methoxybenzoyl) piperazin-1-yl) methyl)benzoate (160 mg) in DCM (20 mL) was added TFA (6 mL). The mixture was stirred at room temperature for 1 hour. The mixture was concentrated in vacuum to afford the crude compound (180 mg) which was used in the next step without further purification. LC/MS: 466.7 [M+H]$^+$.

Step 3: Preparation of 1-(5-(4-(4-(4-((5-(2-chloro-4-phenoxybenzoyl)-7H-pyrrolo[2,3-d]pyrimidin-4-yl)amino)piperidine-1-carbonyl)benzyl)piperazine-1-carbonyl)-2-methoxyphenyl)dihydro pyrimidine-2,4(1H,3H)-dione A solution of 4-((4-(3-(2,4-dioxotetrahydropyrimidin-1(2H)-yl)-4-methoxybenzoyl)piperazin-1-yl)methyl)benzoic acid (83 mg, purity: 70%, 0.12 mmol), (2-chloro-4-phenoxyphenyl)(4-(piperidin-4-ylamino)-7H-pyrrolo[2,3-d]pyrimidin-5-yl)methanone (60 mg, 0.12 mmol), HATU (57 mg, 0.15 mmol) and DIEA (48 mg, 0.37 MMOL) in DMF (10 mL) stirred at room temperature for 3 hours. The solvent was removed under vacuum to give a crude product. The crude product was purified by Pre-TLC to give the titled product (24 mg, 22%) as white solid. LC/MS: 895.5 [M+H]$^+$.

$^1$H NMR (400 MHz, DMSO) δ 12.75 (s, 1H), 10.33 (s, 1H), 8.85 (d, J=7.5 Hz, 1H), 8.26 (s, 1H), 7.63 (s, 1H), 7.58 (d, J=8.4 Hz, 1H), 7.50-7.46 (m, 2H), 7.42-7.36 (m, 4H), 7.34 (s, 1H), 7.26 (t, J=7.4 Hz, 1H), 7.22-7.10 (m, 4H), 7.05-7.00 (m, 1H), 4.36-4.31 (m, 2H), 3.84 (s, 3H), 3.65-3.45 (m, 8H), 3.32 (s, 3H), 3.29-3.17 (m, 2H), 2.67 (t, J=6.5 Hz, 2H), 2.46-2.37 (m, 3H), 2.15-2.00 (m, 2H), 1.62-1.52 (m, 2H).

Example 75: Preparation of (S)—N-(4-(4-amino-1-(4-(3-((4-(2-(2,6-dioxopiperidin-3-yl)-1-oxoisoindolin-5-yl)piperazin-1-yl)methyl)azetidin-1-yl)-3-fluorophenyl)-1H-pyrazolo[3,4-d]pyrimidin-3-yl)benzyl)-5-fluoro-2-methoxybenzamide (Compound 85)
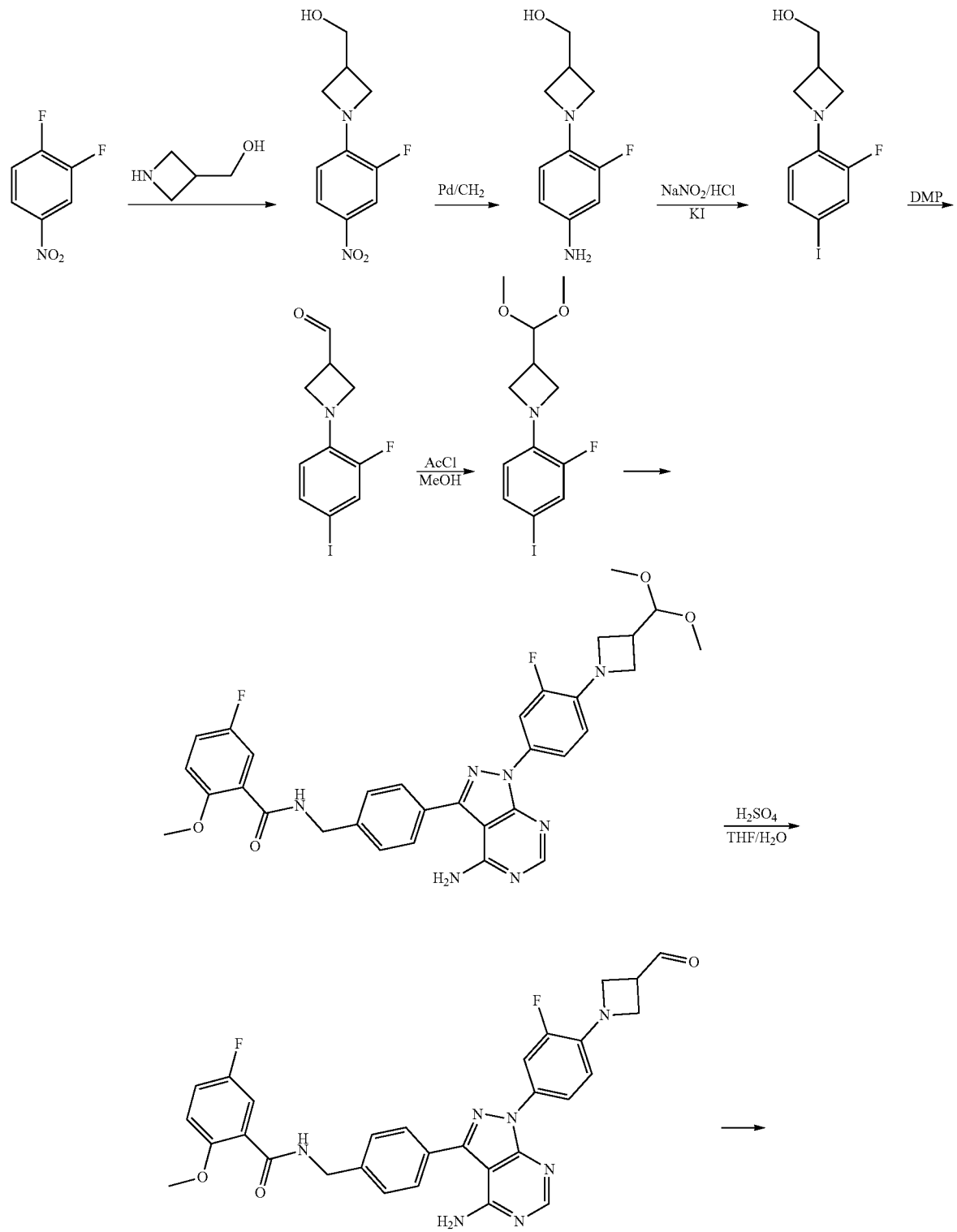

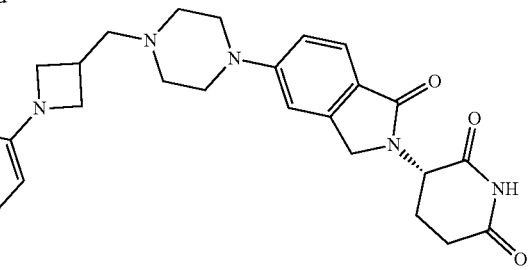
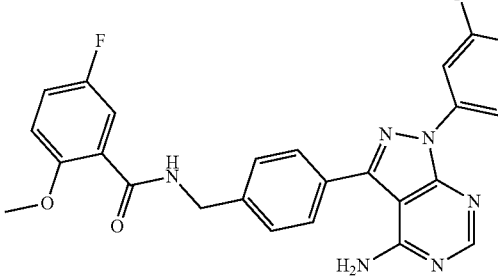

85

Step 1: Preparation of (1-(2-fluoro-4-nitrophenyl)azetidin-3-yl)methanol

The mixture of 1,2-difluoro-4-nitrobenzene (2.0 g, 12.6 mmol), azetidin-3-ylmethanol (1.3 g, 15.1 mmol) and DIEA (4.9 g, 37.8 mmol) in ACN (15 mL) was stirred at 80° C. for 3 hours. The solvent was removed in vacuum and the residue was purified by flash column chromatography with PE:EA=1:1 to afford the desired product (2.5 g, 88.1%). LC/MS: 227.0 [M+H]$^+$.

Step 2: Preparation of (1-(4-amino-2-fluorophenyl)azetidin-3-yl)methanol

To a solution of (1-(2-fluoro-4-nitrophenyl)azetidin-3-yl) methanol (2.5 g, 11.1 mmol) in MeOH (30 mL) was added Pd/C (0.25 g, 10%). The mixture was stirred at room temperature under $H_2$ at 1 atm for overnight. The catalyst was filtered off and the solution was concentrated in vacuum to give the product (2 g, 91.8%). LC/MS: 197.1 [M+H]$^+$.

Step 3: Preparation of (1-(2-fluoro-4-iodophenyl)azetidin-3-yl)methanol

To a solution of (1-(4-amino-2-fluorophenyl)azetidin-3-yl)methanol (2.0 g, 10.2 mmol) in ACN (40 mL) and con. HCl (3.5 mL) was added a solution of $NaNO_2$ (0.91 g, 13.2 mmol) in water (4 mL) at 0° C. The mixture was stirred at 0° C. for 2 hours then a solution of KI (4.3 g, 25.5 mmol) in water (6 mL) was added dropwise. The mixture was stirred at room temperature overnight. The mixture was diluted with water (15 mL) and extracted with DCM (40 mL×3). The combined organic layers were concentrated in vacuum and the residue was purified by purified by flash column chromatography with PE:EA=2:1 to afford the desired product (1.0 g, 31.3%). LC/MS: 308.0 [M+H]$^+$.

Step 4: Preparation of 1-(2-fluoro-4-iodophenyl)azetidine-3-carbaldehyde

To a solution of (1-(2-fluoro-4-iodophenyl)azetidin-3-yl) methanol (1.0 g, 3.3 mmol) in DCM (10 mL) stirred under nitrogen at 0° C. was added Dess-Martin periodinane (2.1 g, 4.9 mmol) in portions. The reaction mixture was stirred at room temperature for 2 hours. The reaction was quenched by adding water (10 mL). The organic phase was washed with brine and dried over $Na_2SO_4$. The solvent was removed in vacuum to give the desired product (0.8 g, 78.7% yield). LC/MS: 306.0 [M+H]$^+$.

Step 5: Preparation of 3-(dimethoxymethyl)-1-(2-fluoro-4-iodophenyl)azetidine To a solution of 1-(2-fluoro-4-iodophenyl)azetidine-3-carbaldehyde (800 mg, 2.6 mmol) in MeOH (10 mL) was added acetyl chloride (310 mg, 3.9 mmol) stirred under nitrogen at 0° C. The mixture was stirred at 25° C. for 2 hours. The reaction was quenched by adding TEA (1 mL). The solvent was removed in vacuum and the residue was purified by flash column chromatography with PE:EA=5:1 to afford the desired product (500 mg, 53.8%). LC/MS: 352.0 [M+H]$^+$.

Step 6: Preparation of N-(4-(4-amino-1-(4-(3-(dimethoxymethyl)azetidin-1-yl)-3-fluorophenyl)-1H-pyrazolo[3,4-d]pyrimidin-3-yl)benzyl)-5-fluoro-2-methoxybenzamide To a solution of 3-(dimethoxymethyl)-1-(2-fluoro-4-iodophenyl)azetidine (400 mg, 1.14 mmol) in DMSO (10 mL) was added N-(4-(4-amino-1H-pyrazolo[3,4-d]pyrimidin-3-yl)benzyl)-5-fluoro-2-methoxybenzamide (536.3 mg, 1.37 mmol), $K_2CO_3$ (472.3 mg, 3.41 mmol), copper(I) iodide (119.3 mg, 0.62 mmol) and N,N-dimethylglycine (129.2 mg, 1.25 mmol). The reaction was stirred at 110° C. for 16 hours. The solid was filtered off and washed with DCM (20 mL×3). The combined solution was concentrated in vacuum and the residue was purified by flash with DCM:MeOH=10:1 to afford the desired product (200 mg, 80% purity, 22.8% yield). LC/MS: 616.2 [M+H]$^+$.

Step 7: Preparation of N-(4-(4-amino-1-(3-fluoro-4-(3-formylazetidin-1-yl)phenyl)-1H-pyrazolo [3,4-d]pyrimidin-3-yl)benzyl)-5-fluoro-2-methoxybenzamide To a solution of N-(4-(4-amino-1-(4-(3-(dimethoxymethyl)azetidin-1-yl)-3-fluorophenyl)-1H-pyrazolo[3,4-d]pyrimidin-3-yl)benzyl)-5-fluoro-2-methoxybenzamide (200 mg, 80% purity, 0.26 mmol) was added $THF:H_2O:H_2SO_4$ (6 mL, 2:3:1). The mixture was stirred at room temperature for overnight. The solvent was removed in vacuum and the residue was diluted with DCM (20 mL). The organic phase was washed with saturated $NaHCO_3$ solution, brine and dried over Na₂SO₄. The solvent was removed in vacuum. The residue was purified by silica gel chromatography using PE/EA=1:1 to give the desired product (100 mg, 67.5%). LC/MS: 570.1 [M+H]⁺.

Step 8: Preparation of (S)—N-(4-(4-amino-1-(4-(3-((4-(2-(2,6-dioxopiperidin-3-yl)-1-oxoisoindolin-5-yl)piperazin-1-yl)methyl)azetidin-1-yl)-3-fluorophenyl)-1H-pyrazolo[3,4-d]pyrimidin-3-yl) benzyl)-5-fluoro-2-methoxybenzamide To a solution of N-(4-(4-amino-1-(3-fluoro-4-(3-formylazetidin-1-yl)phenyl)-1H-pyrazolo[3,4-d]pyrimidin-3-yl) benzyl)-5-fluoro-2-methoxybenzamide (100 mg, 0.17 mmol), (S)-3-(1-oxo-5-(piperazin-1-yl)isoindolin-2-yl)piperidine-2,6-dione (63.4 mg, 0.19 mmol) and TEA (88 mg, 0.87 mmol) in MeOH/DMF (6 mL, 2:1) was added AcOH (0.5 mL) and NaBH₃CN (44.1 mg, 0.70 mmol). The mixture was stirred at 60° C. for 1 hour. The reaction mixture was cooled to room temperature and quenched by adding water (5 mL). The mixture was extracted with DCM (15 mL×3). The organic phase was washed with brine and dried over Na₂SO₄. The solvent was removed and purified by Prep-HPLC to afford the desired compound (50 mg, 98.7% purity, 32.9% yield). LC/MS: 882.3[M+H]⁺.

¹H NMR (400 MHz, DMSO) δ 10.96 (s, 1H), 8.90 (t, J=6.2 Hz, 1H), 8.35 (s, 1H), 7.93-7.89 (m, 1H), 7.85-7.83 (m, 1H), 7.73 (d, J=8.1 Hz, 2H), 7.55-7.52 (m, 4H), 7.38-7.33 (m, 1H), 7.21-7.18 (m, 1H), 7.10-7.06 (m, 2H), 6.72 (t, J=9.3 Hz, 1H), 5.08-5.03 (dd, 1H), 4.60 (d, J=6.1 Hz, 2H), 4.34 (d, J=17.2 Hz, 1H), 4.22 (d, J=17.2 Hz, 1H), 4.12-4.10 (m, 2H), 3.91 (s, 3H), 3.69-3.63 (m, 2H), 3.32-3.27 (m, 3H), 3.04-2.85 (m, 3H), 2.68-2.55 (m, 6H), 2.39-2.33 (m, 2H), 1.96-1.91 (m, 1H).

Example 76: Preparation of N-(4-(4-amino-1-(1-(5-((4-(2-((S)-2,6-dioxopiperidin-3-yl)-1-oxoisoindolin-5-yl)piperazin-1-yl)methyl)pyridin-2-yl)pyrrolidin-3-yl)-1H-pyrazolo[3,4-d]pyrimidin-3-yl)benzyl)-5-fluoro-2-methoxybenzamide (Compound 92)

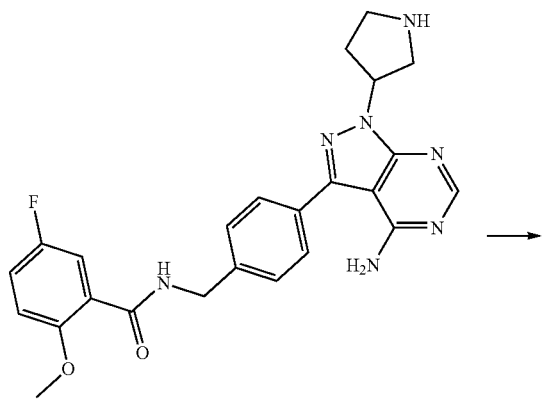

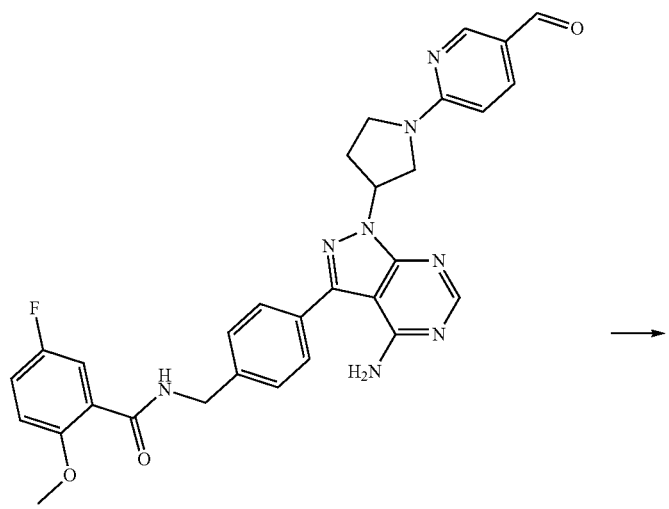

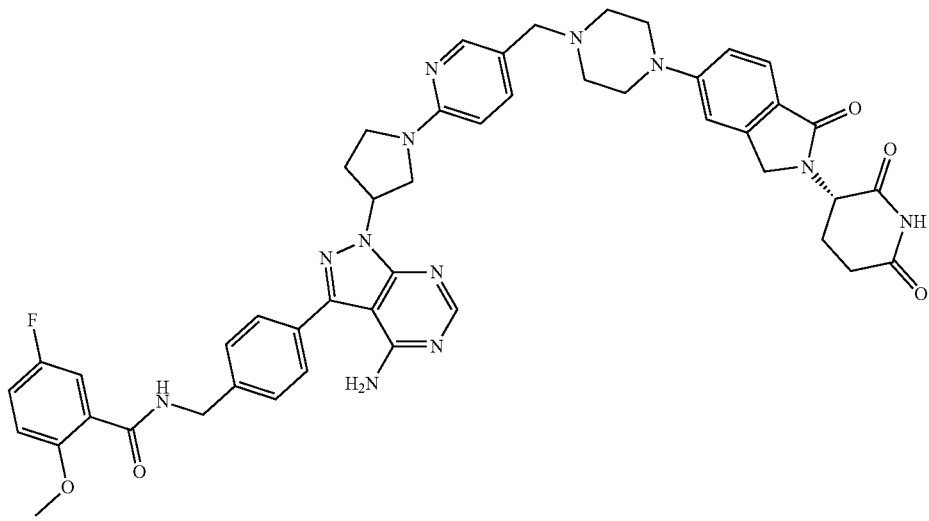

Step 1: Preparation of N-(4-(4-amino-1-(1-(5-formylpyridin-2-yl)pyrrolidin-3-yl)-1H-pyrazolo [3,4-d] pyrimidin-3-yl)benzyl)-5-fluoro-2-methoxybenzamide To a solution of N-({4-[4-amino-1-(pyrrolidin-3-yl)pyrazolo[3,4-d]pyrimidin-3-yl]phenyl}methyl)-5-fluoro-2-methoxybenzamide (200 mg, 0.43 mmol) in DMSO (5 mL) stirred at room temperature was added 6-bromopyridine-3-carbaldehyde (121 mg, 0.65 mmol) and K$_2$CO$_3$ (120 mg, 0.86 mmol). The reaction mixture was stirred at 80° C. for 12 hours. The reaction mixture was poured into water (100 mL) then extracted with EA (100 mL×2). The combined organic layers were washed with water, brine, dried over Na$_2$SO$_4$ and concentrated under vacuum to give a crude product. The crude product was purified by flash column chromatography (DCM/MeOH=10:1) to give the desired product (150 mg, 61.1%). LC/MS: 566.9 [M+H]$^+$.

Step 2: Preparation of N-(4-(4-amino-1-(1-(5-((4-(2-((S)-2,6-dioxopiperidin-3-yl)-1-oxoisoindolin-5-yl)piperazin-1-yl)methyl)pyridin-2-yl)pyrrolidin-3-yl)-1H-pyrazolo[3,4-d]pyrimidin-3-yl) benzyl)-5-fluoro-2-methoxybenzamide To a solution of N-(4-(4-amino-1-(1-(5-formylpyridin-2-yl)pyrrolidin-3-yl)-1H-pyrazolo[3,4-d]pyrimidin-3-yl)benzyl)-5-fluoro-2-methoxybenzamide (130 mg, 0.23 mmol) in MeOH/DMF/HOAc (12 mL, 2:1:0.05,) stirred at room temperature was added Et$_3$N (36 mg, 0.36 mmol), was added (S)-3-(1-oxo-5-(piperazin-1-yl)isoindolin-2-yl)piperidine-2,6-dione (86 mg, 0.18 mmol) and NaBH$_3$CN (45 mg, 0.72 mmol). The reaction mixture was stirred at 60° C. for 1 hours. The mixture was concentrated in vacuum then poured into water (50 mL) and extracted with EA (100 mL×2). The combined organic layers were washed with brine (200 mL), dried over Na$_2$SO$_4$ and concentrated under vacuum give a crude product. The crude product was purified by Prep-HPLC to give the desired product (18 mg, 8.9%). LC/MS: 879.0 [M+H]$^+$.

$^1$H NMR (400 MHz, DMSO) δ=10.94 (s, 1H), 8.85 (t, J=6.0 Hz, 1H), 8.28 (s, 1H), 8.18 (s, 1H), 7.99 (d, J=2.0 Hz, 1H), 7.61 (d, J=8.0 Hz, 2H), 7.53-7.45 (m, 5H), 7.36-7.31 (m, 1H), 7.18 (dd, J=9.2, 4.4 Hz, 1H), 7.05 (s, 1H), 7.03 (s, 1H), 6.50 (d, J=8.4 Hz, 2H), 5.62-5.57 (m, 1H), 5.04 (dd, J=13.2, 5.2 Hz, 1H), 4.57 (d, J=6.0 Hz, 2H), 4.32 (d, J=16.8 Hz, 1H), 4.19 (d, J=16.8 Hz, 1H), 4.01-3.91 (m, 2H), 3.89 (s, 3H), 3.86-3.72 (m, 3H), 3.65-3.55 (m, 2H), 3.38 (s, 2H), 3.32-3.25 (m, 4H), 2.94-2.84 (m, 2H), 2.62-2.58 (m, 1H), 2.56-2.52 (m, 3H), 1.98-1.92 (m, 1H).

Example 77: Preparation of N-(4-(4-amino-1-(6-((R)-3-((4-(2-((S)-2,6-dioxopiperidin-3-yl)-1-oxoisoindolin-5-yl)piperazin-1-yl)methyl)pyrrolidin-1-yl)pyridin-3-yl)-1H-pyrazolo[3,4-d]pyrimidin-3-yl)benzyl)-5-fluoro-2-methoxybenzamide (Compound 93)

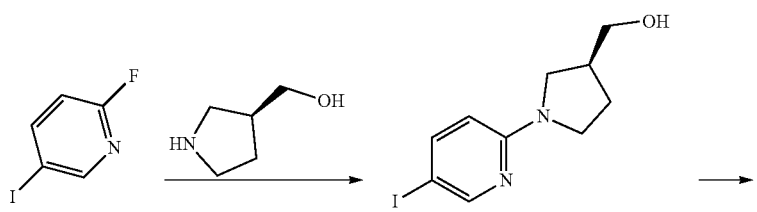

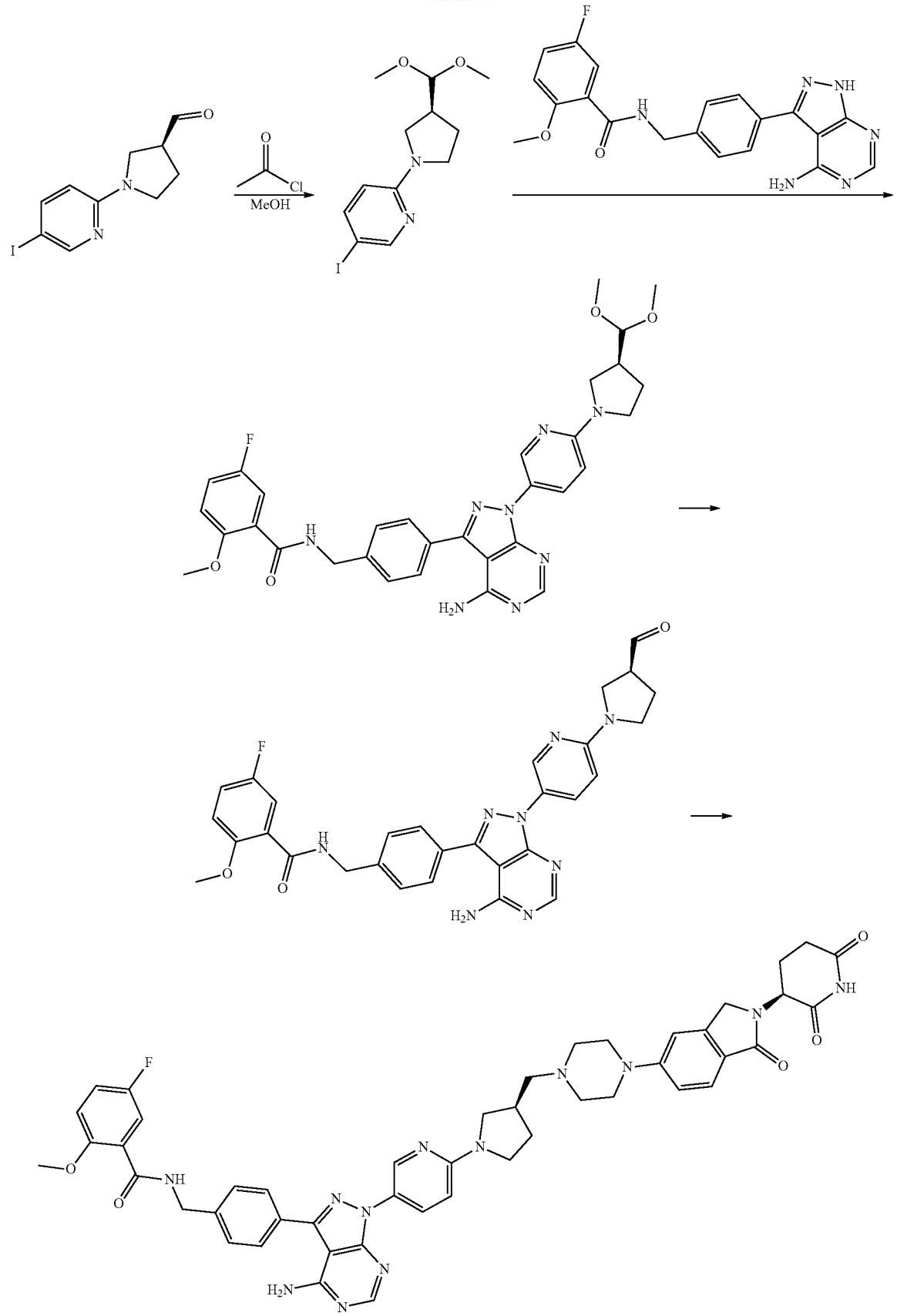

Compound 93 was prepared analogously with the procedure described for compound 66.

LC/MS: 878.8 [M+H]$^+$.

$^1$H NMR (400 MHz, DMSO) δ 10.96 (s, 1H), 8.93-8.86 (m, 1H), 8.67 (s, 1H), 8.31 (s, 1H), 8.08 (d, J=7.6 Hz, 1H), 7.72 (d, J=7.9 Hz, 2H), 7.59-7.49 (m, 4H), 7.38-7.32 (m, 1H), 7.20 (dd, J=9.1, 4.2 Hz, 1H), 7.14-7.04 (m, 2H), 6.62 (d, J=9.0 Hz, 1H), 5.06 (dd, J=13.0, 4.7 Hz, 1H), 4.60 (d, J=5.9 Hz, 2H), 4.34 (d, J=17.2 Hz, 1H), 4.21 (d, J=16.7 Hz, 1H), 3.91 (s, 3H), 3.71-3.50 (m, 3H), 3.49-3.36 (m, 3H), 3.27-3.15 (m, 2H), 2.89 (d, J=11.8 Hz, 1H), 2.70-2.53 (m, 6H), 2.48-2.41 (m, 4H), 2.17-2.10 (m, 1H), 1.99-1.94 (m, 1H), 1.80-1.72 (m, 1H).

Example 78: Preparation of N-(4-(4-amino-1-(6-((S)-3-((4-(2-((S)-2,6-dioxopiperidin-3-yl)-1-oxoisoindolin-5-yl) piperazin-1-yl)methyl)pyrrolidin-1-yl)pyridin-3-yl)-1H-pyrazolo[3,4-d]pyrimidin-3-yl)benzyl)-5-fluoro-2-methoxybenzamide (Compound 94)

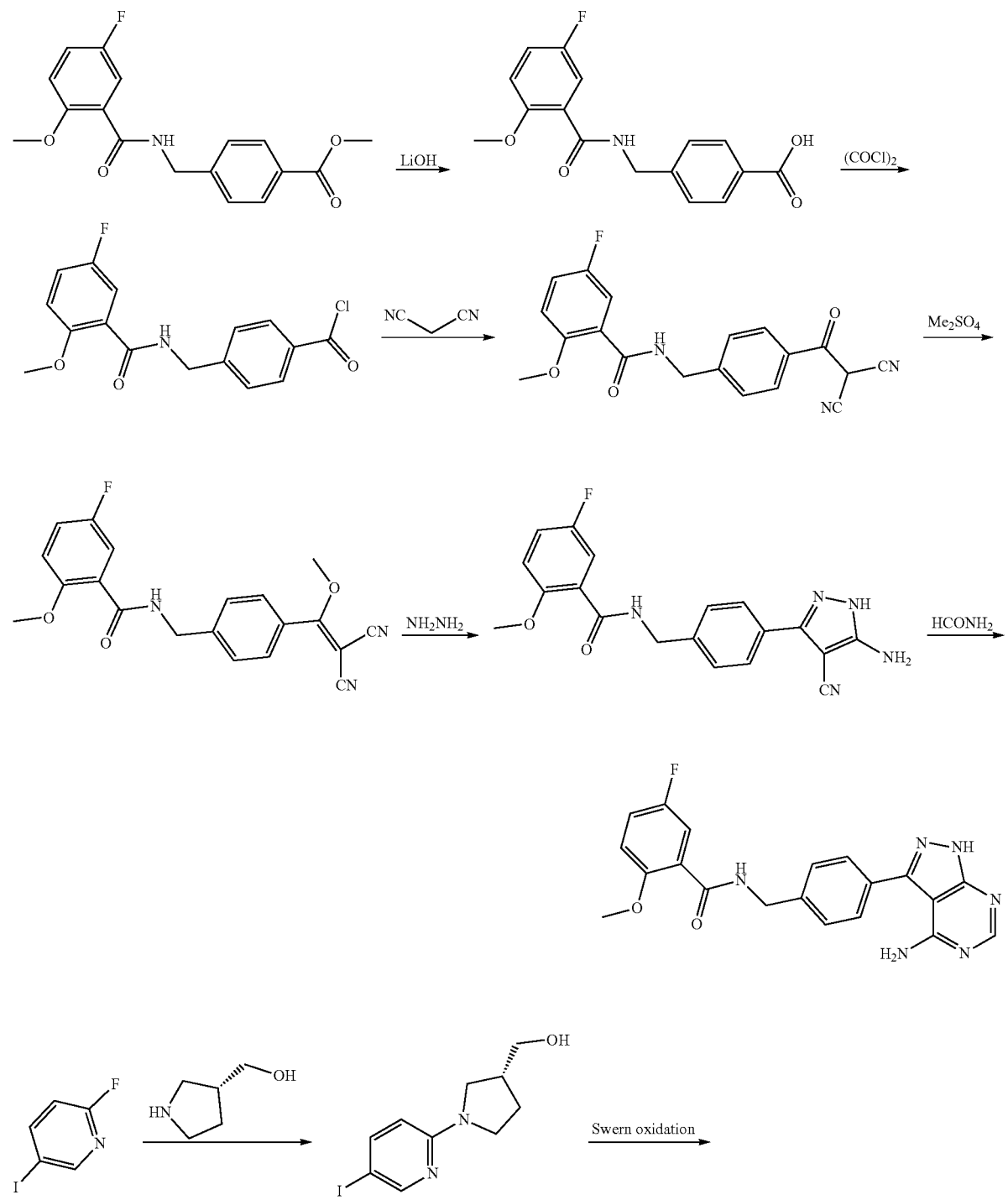

-continued
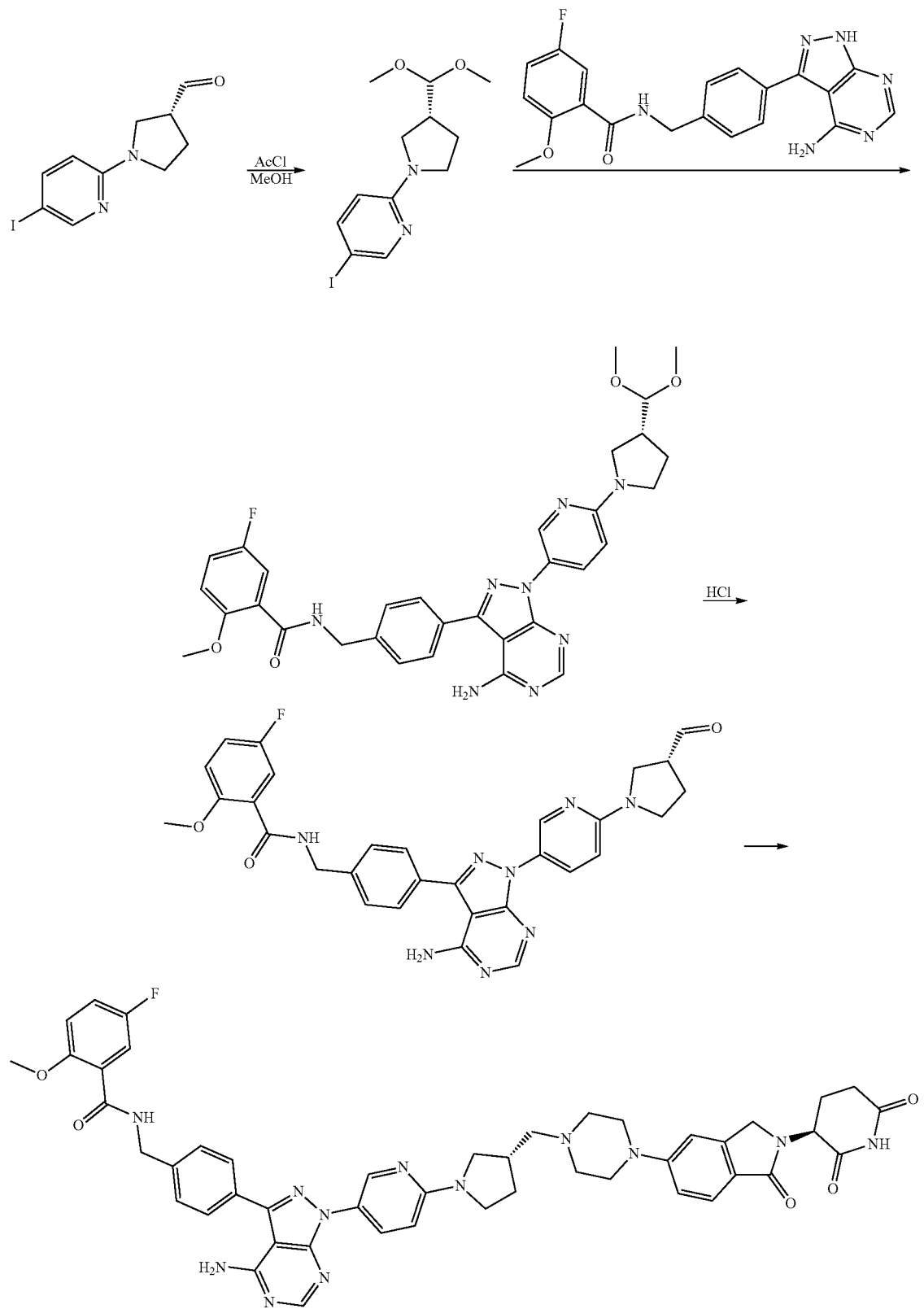

Step 1: Preparation of 4-((5-fluoro-2-methoxybenzamido)methyl)benzoic acid

To a solution of methyl 4-1{[(5-fluoro-2-methoxyphenyl)formamido]methyl}benzoate (7.1 g, 22.37 mmol) in THF/water (100 mL, 1:1) stirred at room temperature was added LiOH—H2O (4.7 g, 111.9 mmol). The reaction mixture was stirred at room temperature for 12 hours. The mixture was concentrated in vacuum to 50 mL and then acidified with HCl (5 M) until pH=5-6. The solid was filtered, washed with water and dried in vacuum to give the desired product (6 g, 88.42%). LC/MS: 304.0 [M+H]$^+$.

$^1$H NMR (400 MHz, DMSO) δ=8.89 (t, J=6.0 Hz, 1H), 7.91 (d, J=8.0 Hz, 2H), 7.50 (dd, J=9.2, 3.2 Hz, 1H), 7.43 (d, J=8.0 Hz, 2H), 7.37-7.31 (m, 1H), 7.18 (dd, J=9.2, 4.4 Hz, 1H), 4.56 (d, J=6.0 Hz, 2H), 3.89 (s, 3H).

Step 2: Preparation of 4-((5-fluoro-2-methoxybenzamido)methyl)benzoyl chloride To a solution of 4-{1[(5-fluoro-2-methoxyphenyl)formamido] methyl}benzoic acid (3.9 g, 12.86 mmol) in DCM (50 mL) stirred at room temperature was added oxalyl chloride (2.2 mL, 25.72 mmol). The reaction mixture was stirred at room temperature for 2 hours. The reaction mixture was concentrated under vacuum to give the title compound (4.0 g, crude) as a brown oil.

Step 3: Preparation of N-(4-(2,2-dicyanoacetyl)benzyl)-5-fluoro-2-methoxybenzamide To a solution of 4-{1[(5-fluoro-2-methoxyphenyl)formamido] methyl}benzoyl chloride (4 g, crude) and propanedinitrile (960 mg, 14.54 mmol) in acetone (40 mL) stirred at 5° C. was added NaOH (4 mL, 39.26 mmol, 40%) slowly. The reaction mixture was stirred at room temperature for 2 hours. The mixture was diluted with water (40 mL) and added HCl (5 M) was added to adjust to pH to 2-3. The solid was filtered, washed with water and dried in vacuum to give the desired product (3.8 g, 84.10% for two steps) as a white solid. LC/MS: 351.8 [M+H]$^+$.

$^1$H NMR (400 MHz, DMSO) δ=10.89 (s, 1H), 8.86 (t, J=6.0 Hz, 1H), 7.57 (d, J=8.0 Hz, 2H), 7.50 (dd, J=9.2, 3.2 Hz, 1H), 7.37-7.30 (m, 3H), 7.17 (dd, J=9.2, 4.4 Hz, 1H), 4.52 (d, J=6.0 Hz, 2H), 3.88 (s, 3H).

Step 4: Preparation of N-(4-(2,2-dicyano-1-methoxyvinyl)benzyl)-5-fluoro-2-methoxybenzamide To a solution of N-{[4-(2,2-dicyanoacetyl)phenyl]methyl}-5-fluoro-2-methoxybenzamide (3.14 g, 8.94 mmol) in dioxane (40 mL) stirred at room temperature was added NaHCO$_3$ (6.0 g, 71.52 mmol) and dimethyl sulfate (8.45 g, 67.05 mmol). The reaction mixture was stirred at 100° C. for 2.5 hours. The mixture was poured into water (60 mL) and extracted with EtOAc (100 mL×2). The combined organic layers were washed with brine (200 mL), dried over Na$_2$SO$_4$ and concentrated under vacuum to give the title compound (3.5 g, crude) as a brown oil. LC/MS: 366.0 [M+H]$^+$.

Step 5: Preparation of N-(4-(5-amino-4-cyano-1H-pyrazol-3-yl)benzyl)-5-fluoro-2-methoxybenzamide To a solution of N-{[4-(2,2-dicyano-1-methoxyeth-1-en-1-yl)phenyl]methyl}-5-fluoro-2-methoxybenzamide (6.2 g, crude) in MeOH/Water (20 mL, 2:1) in a sealed tube stirred at room temperature was added hydrazine (1.4 g, 34.16 mmol, 80%). The reaction mixture was stirred at 100° C. for 12 hours. The mixture was poured into water (100 mL) and extracted with EtOAc (100 mL×2). The combined organic layers were washed with brine (200 mL), dried over Na$_2$SO$_4$ and concentrated in vacuum. The residue was purified by flash chromatography (DCM:MeOH=10:1) to give the desired product (2.36 g, 36.1% for two steps). LC/MS: 366.0 [M+H]$^+$.

$^1$H NMR (400 MHz, DMSO) δ=12.12 (s, 1H), 8.84 (s, 1H), 7.74 (d, J=7.6 Hz, 2H), 7.51 (dd, J=9.2, 3.2 Hz, 1H), 7.42-7.38 (m, 2H), 7.36-7.30 (m, 1H), 7.18 (dd, J=9.2, 4.4 Hz, 1H), 6.46 (s, 1H), 4.53 (d, J=6.0 Hz, 2H), 3.89 (s, 3H).

Step 6: Preparation of N-(4-(4-amino-1H-pyrazolo[3,4-d]pyrimidin-3-yl)benzyl)-5-fluoro-2-methoxybenzamide N-{[4-(5-amino-4-cyano-1H-pyrazol-3-yl)phenyl]methyl}-5-fluoro-2-methoxybenzamide (2.36 g, 6.46 mmol) in formamide (30 mL) was stirred at 160° C. for 2 hours. The mixture was poured into water (100 mL) and extracted with EtOAc (100 mL×2). The combined organic layers were washed with brine (200 mL), dried over Na$_2$SO$_4$ and concentrated in vacuum. The residue was purified by flash chromatography (DCM:MeOH=10:1) to give the desired product (2.1 g, 82.8%). LC/MS: 393.0 [M+H]$^+$.

Step 7: Preparation of (R)-(1-(5-iodopyridin-2-yl)pyrrolidin-3-yl)methanol

To a solution of 2-fluoro-5-iodopyridine (3 g, 13.45 mmol) in DMF (30 mL) stirred at room temperature was added (3R)-pyrrolidin-3-ylmethanol (2.04 g, 20.18 mmol) and K$_2$CO$_3$ (5.6 g, 40.36 mmol). The reaction mixture was stirred at 100° C. for 12 hours. The mixture was poured into water (100 mL) and extracted with EtOAc (100 mL×2). The combined organic layers were washed with brine (200 mL), dried over Na$_2$SO$_4$ and concentrated in vacuum. The residue was purified by flash chromatography (PE:EtOAc=3:1) to give the desired product (3.0 g, 73.3%). LC/MS: 304.8 [M+H]$^+$.

Step 8: Preparation of (R)-1-(5-iodopyridin-2-yl)pyrrolidine-3-carbaldehyde

To a solution of oxalyl chloride (2.42 g, 19.07 mmol) in DCM (30 mL) stirred at −78° C. was added DMSO (3 g, 38.14 mmol) slowly at −78° C. for 15 minutes. Then a solution of [(3R)-1-(5-iodopyridin-2-yl)pyrrolidin-3-yl]methanol (2.9 g, 9.54 mmol) in DCM (5 mL) was added slowly. After 15 minutes Et$_3$N (3.86 g, 38.14 mmol) was added. The reaction mixture was stirred at −78° C. for 30 minutes then warmed to room temperature and stirred for 1 hour. The mixture was diluted with DCM (65 mL), washed with brine, dried over Na$_2$SO$_4$ and concentrated in vacuum to give the title compound (3.0 g, crude) as a brown solid. LC/MS: 302.7 [M+H]$^+$.

Step 9: Preparation of (R)-2-(3-(dimethoxymethyl)pyrrolidin-1-yl)-5-iodopyridine To a solution of (3R)-1-(5-iodopyridin-2-yl)pyrrolidine-3-carbaldehyde (3 g, crude) in MeOH (30 mL) stirred at 0° C. was added Acetyl chloride (1.56 g, 19.86 mmol). The reaction mixture was stirred at room temperature for 2 hours.

The reaction mixture was quenched with Et₃N (2 mL) and concentrated in vacuum. The residue was purified by flash chromatography (PE:EtOAc=5:1) to give the desired product (2.6 g, 78.3%). LC/MS: 348.7 [M+H]⁺.

¹H NMR (400 MHz, CDCl3) δ=8.28 (d, J=2.4 Hz, 1H), 7.61 (dd, J=8.8, 2.4 Hz, 1H), 6.21 (d, J=8.8 Hz, 1H), 4.29 (d, J=7.6 Hz, 1H), 3.59-3.51 (m, 2H), 3.42-3.34 (m, 7H), 3.25 (dd, J=10.8, 7.6 Hz, 1H), 2.73-2.63 (m, 1H), 2.16-2.05 (m, 1H), 1.94-1.84 (m, 1H).

Step 10: Preparation of (R)—N-(4-(4-amino-1-(6-(3-(dimethoxymethyl)pyrrolidin-1-yl)pyridin-3-yl)-1H-pyrazolo[3,4-d]pyrimidin-3-yl)benzyl)-5-fluoro-2-methoxybenzamide To a solution of (R)-2-(3-(dimethoxymethyl)pyrrolidin-1-yl)-5-iodopyridine (300 mg, 0.86 mmol) in DMSO (10 mL) was added N-(4-(4-amino-1H-pyrazolo[3,4-d]pyrimidin-3-yl)benzyl)-5-fluoro-2-methoxybenzamide (337 mg, 0.86 mmol), Na₂CO₃ (182 mg, 1.72 mmol), copper(I) iodide (82 mg, 0.43 mmol) and N, N-Dimethylglycine (89 mg, 0.86 mmol) stirred under nitrogen at 25° C. The reaction was stirred at 110° C. for 16 hours. The mixture was filtered and washed with DCM. The solution was concentrated in vacuum and the residue was purified by flash column chromatography (DCM:MeOH=10:1) to afford the desired product (460 mg, 87.2%) as a yellow solid. LC/MS: 612.7 [M+H]⁺.

Step 11: Preparation of (R)—N-(4-(4-amino-1-(6-(3-formylpyrrolidin-1-yl)pyridin-3-yl)-1H-pyrazolo[3,4-d]pyrimidin-3-yl)benzyl)-5-fluoro-2-methoxybenzamide To solution of (R)—N-(4-(4-amino-1-(6-(3-(dimethoxymethyl)pyrrolidin-1-yl)pyridin-3-yl)-1H-pyrazolo[3,4-d]pyrimidin-3-yl)benzyl)-5-fluoro-2-methoxybenzamide (460 mg, 0.75 mmol) in anhydrous THF (2.5 mL) was added HCl (4 N, 2.5 ml in the dioxane). The reaction mixture was stirred at room temperature for 4 hours. The solvent was removed in vacuum and the residue was dissolved with DCM. The organic phase was washed NaHCO₃, brine, dried over Na₂SO₄ and concentrated under vacuum to give the title compound (300 mg, crude) as a yellow solid. LC/MS: 566.8 [M+H]⁺.

Step 12: Preparation of N-(4-(4-amino-1-(6-((S)-3-((4-(2-((S)-2,6-dioxopiperidin-3-yl)-1-oxoisoindolin-5-yl)piperazin-1-yl)methyl)pyrrolidin-1-yl)pyridin-3-yl)-1H-pyrazolo[3,4-d]pyrimidin-3-yl)benzyl)-5-fluoro-2-methoxybenzamide To a solution of (R)—N-(4-(4-amino-1-(6-(3-formylpyrrolidin-1-yl)pyridin-3-yl)-1H-pyrazolo[3,4-d]pyrimidin-3-yl)benzyl)-5-fluoro-2-methoxybenzamide (300 mg, crude) in MeOH/DMF (12 mL, 2:1) stirred at room temperature was added (S)-3-(1-oxo-5-(piperazin-1-yl)isoindolin-2-yl)piperidine-2,6-dione (260 mg, 0.53 mmol) and Et₃N (107 mg, 1.06 mmol). The mixture was stirred at room temperature for 30 minutes then AcOH (1 mL) and NaBH₃CN (134 mg, 2.12 mmol) was added. The reaction mixture was stirred under nitrogen at 60° C. for 1 hour. The mixture was diluted with water and extracted with DCM. The organic phase was washed with brine, dried over Na₂SO₄ and concentrated in vacuum. The residue was purified by Prep-HPLC to afford the desired compound (30.5 mg, 6.9%). LC/MS: 878.8 [M+H]⁺.

¹H NMR (400 MHz, DMSO) δ=10.98 (s, 1H), 8.92 (t, J=6.0 Hz, 1H), 8.70 (d, J=2.4 Hz, 1H), 8.37 (s, 1H), 8.18 (d, J=8.8 Hz, 1H), 7.73 (d, J=8.0 Hz, 2H), 7.61 (d, J=8.4 Hz, 1H), 7.57-7.50 (m, 3H), 7.39-7.33 (m, 1H), 7.23-7.15 (m, 3H), 6.71 (d, J=8.8 Hz, 1H), 5.07 (dd, J=13.2, 4.8 Hz, 1H), 4.61 (d, J=6.0 Hz, 2H), 4.37 (d, J=17.2, 1H), 4.25 (d, J=17.2, 1H), 4.10-4.02 (m, 2H), 3.91 (s, 3H), 3.41-3.37 (m, 2H), 3.27-3.22 (m, 4H), 2.95-2.85 (m, 2H), 2.77 (d, J=5.2 Hz, 2H), 2.65-2.55 (m, 1H), 2.45-2.30 (m, 2H), 2.27-2.24 (m, 2H), 1.98-1.93 (m, 2H), 1.91-1.85 (m, 2H).

Example 79: Preparation of N-(4-(4-amino-1-(4-((R)-3-((4-(2-((S)-2,6-dioxopiperidin-3-yl)-1-oxoisoindolin-5-yl)piperazin-1-yl)methyl)pyrrolidin-1-yl)-3-fluorophenyl)-1H-pyrazolo[3,4-d]pyrimidin-3-yl)benzyl)-5-fluoro-2-methoxybenzamide
(Compound 95)

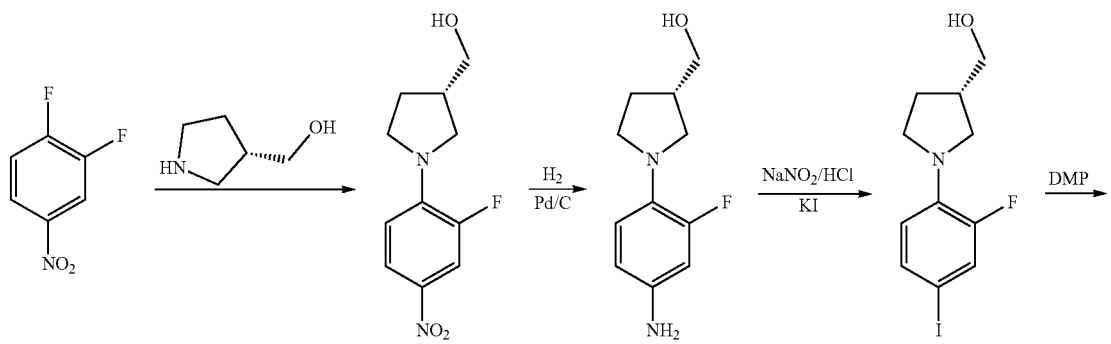

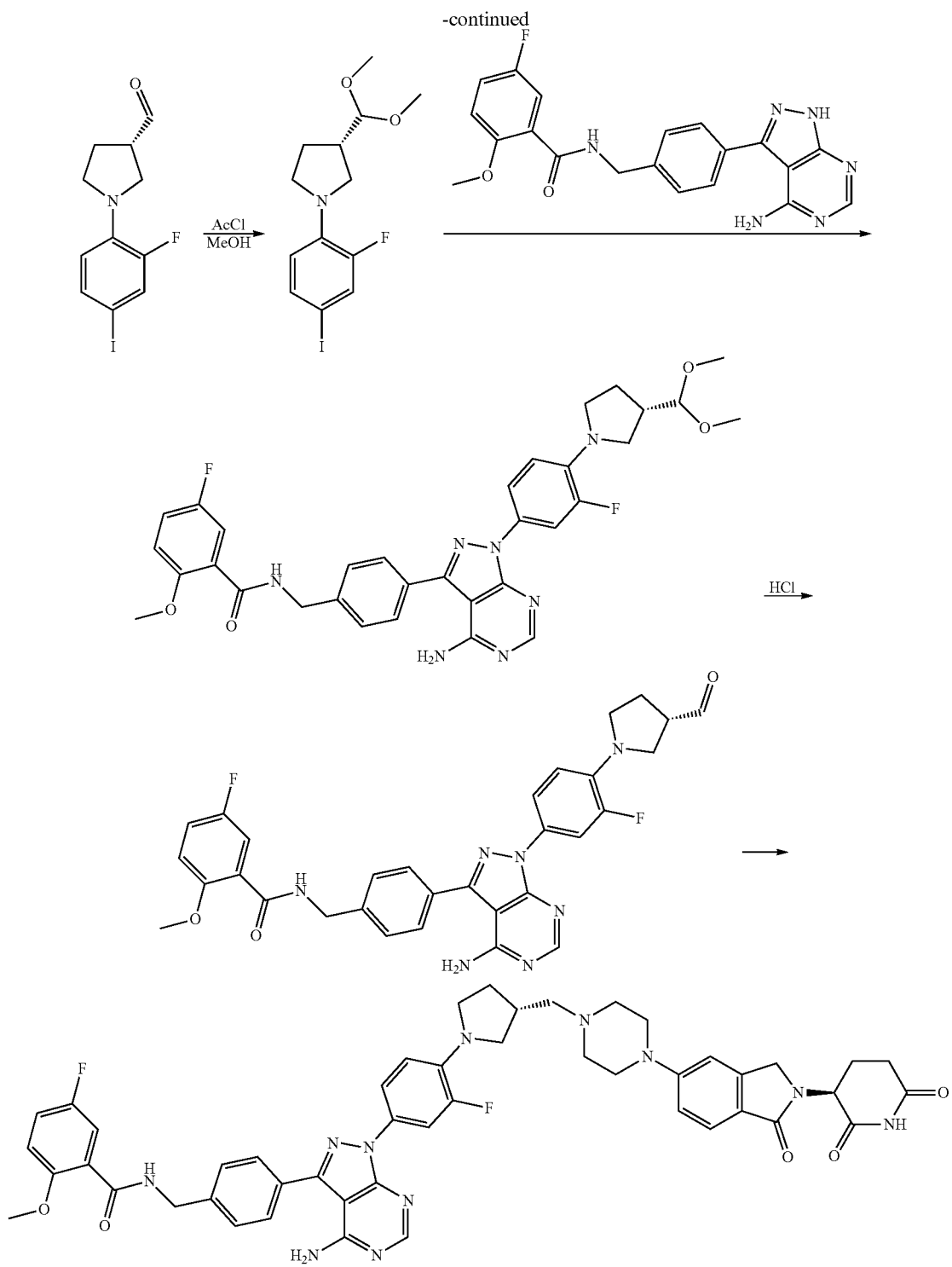

95

Step 1: Preparation of (S)-(1-(2-fluoro-4-nitrophenyl)pyrrolidin-3-yl)methanol To a solution of 1,2-difluoro-4-nitrobenzene (2.0 g, 12.6 mmol) in CH$_3$CN (30 mL) was added (3S)-pyrrolidin-3-ylmethanol hydrochloride (1.91 g, 13.8 mmol) and DIEA (4.89 g, 37.8 mmol). The reaction was stirred at 80° C. for 3 hours and then quenched by adding water. The mixture was extracted with EA, washed with brine and dried over Na$_2$SO$_4$. The solvent was removed in vacuum and the residue was purified by flash with PE:EA=1:1 to afford the desired product (2.8 g, 90% purity, 82.5% yield) as a yellow solid. LC/MS: 241.1 [M+H]$^+$.

Step 2: Preparation of (S)-(1-(4-amino-2-fluorophenyl)pyrrolidin-3-yl)methanol To a solution of (S)-(1-(2-fluoro-4-nitrophenyl)pyrrolidin-3-yl)methanol (2.8 g, 90% purity, 10.5 mmol) in methanol (40 mL) was added Pd/C (0.28 g, 10%). The reaction was stirred under H$_2$ atmosphere at 1 atm for 16 hours at 25° C. The catalyst was filtered off and washed with MeOH. The solution was concentrated in vacuum to afford the desired product (2.2 g, 99.6%) as a brown oil. LC/MS: 211.1 [M+H]$^+$.

Step 3: Preparation of (S)-(1-(2-fluoro-4-iodophenyl)pyrrolidin-3-yl)methanol To a solution of (S)-(1-(4-amino-2-fluorophenyl)pyrrolidin-3-yl)methanol (2.1 g, 9.98 mmol) in CH$_3$CN (30 mL) was added con. HCl (2.5 mL), NaNO$_2$ (827 mg, 11.98 mmol, dissolved in 5 mL H$_2$O) at 0° C. The mixture was stirred at 0° C. for 2 hours and KI (4.14 g, 24.97 mmol) was added. The reaction mixture was stirred at room temperature for 17 hours. The reaction was quenched by adding water (40 mL) and extracted with EA (40 mL×3). The organic phase was washed with brine and dried over Na$_2$SO$_4$. The solvent was removed in vacuum. The residue was purified by flash with PE:EA=3:1 to afford the desired product (2 g, 62.3%) as a yellow solid. LC/MS: 321.8 [M+H]$^+$.

Step 4: Preparation of (S)-1-(2-fluoro-4-iodophenyl)pyrrolidine-3-carbaldehyde To a solution of (S)-(1-(2-fluoro-4-iodophenyl)pyrrolidin-3-yl)methanol (1.9 g, 5.9 mmol) in DCM (20 mL) was added Dess-Martin periodinane (3.75 g, 8.8 mmol). The reaction was stirred at 25° C. for 2 hours. The reaction was quenched with saturated Na$_2$S$_2$O$_3$ solution then extracted with EA. The organic phase was washed with brine and dried over Na$_2$SO$_4$. The solvent was removed in vacuum and the residue was purified by flash with PE:EA=1:1 to afford the desired product (2 g, 80% purity, 84.9% yield) as a white solid. LC/MS: 319.8 [M+H]$^+$.

Step 5: Preparation of (S)-3-(dimethoxymethyl)-1-(2-fluoro-4-iodophenyl)pyrrolidine To a solution of (S)-1-(2-fluoro-4-iodophenyl)pyrrolidine-3-carbaldehyde (2.0 g, 80% purity, 5.0 mmol) in MeOH (20 mL) was added acetyl chloride (1.04 g, 13.2 mmol) stirred under nitrogen at 0° C. The reaction was stirred at 25° C. for 2 hours. The reaction was quenched with TEA and the solvent was removed in vacuum. The residue was purified by flash column chromatography with PE:EA=1:1 to afford the desired product (1.0 g, 90% purity, 49.2% yield) as a white solid. LC/MS: 365.7 [M+H]$^+$.

Step 6: Preparation of (S)—N-(4-(4-amino-1-(4-(3-(dimethoxymethyl)pyrrolidin-1-yl)-3-fluorophenyl)-1H-pyrazolo[3,4-d]pyrimidin-3-yl)benzyl)-5-fluoro-2-methoxybenzamide To a solution of (S)-3-(dimethoxymethyl)-1-(2-fluoro-4-iodophenyl)pyrrolidine (220 mg, 90% purity, 0.54 mmol) in DMSO (10 mL) was added N-[(4-{4-amino-1H-pyrazolo[3,4-d]pyrimidin-3-yl}phenyl)methyl]-5-fluoro-2-methoxybenzamide (257.89 mg, 0.65 mmol), Na$_2$CO$_3$ (127.72 mg, 1.2 mmol), copper(I) iodide (57.37 mg, 0.3 mmol) and N,N-dimethylglycine (62.13 mg, 0.6 mmol) stirred under nitrogen at 25° C. The reaction was stirred at 110° C. for 16 hours. The mixture was filtered and washed with DCM. The solvent was removed in vacuum and the residue was purified by flash with DCM:MeOH=10:1 to afford the desired product (170 mg, 90% purity, 44.1% yield) as a yellow solid. LC/MS: 629.8 [M+H]$^+$.

Step 7: Preparation of (S)—N-(4-(4-amino-1-(3-fluoro-4-(3-formylpyrrolidin-1-yl)phenyl)-1H-pyrazolo[3,4-d]pyrimidin-3-yl)benzyl)-5-fluoro-2-methoxybenzamide To a solution of (S)—N-(4-(4-amino-1-(4-(3-(dimethoxymethyl)pyrrolidin-1-yl)-3-fluorophenyl)-1H-pyrazolo[3,4-d]pyrimidin-3-yl)benzyl)-5-fluoro-2-methoxybenzamide (170 mg, 90% purity, 0.24 mmol) in DCM (4 mL) was added HCl (4N in the dioxane, 4 mL) stirred under nitrogen at 25° C. The reaction was stirred at 25° C. for 4 hours. The mixture was basified with saturated NaHCO$_3$ solution and extracted with DCM. The organic phase was washed with brine and dried over Na$_2$SO$_4$. The solution was concentrated in vacuum to afford the desired product (160 mg, crude) as a yellow solid. LC/MS: 583.8 [M+H]$^+$.

Step 8: Preparation of N-(4-(4-amino-1-(4-((R)-3-((4-(2-((S)-2,6-dioxopiperidin-3-yl)-1-oxoisoindolin-5-yl)piperazin-1-yl)methyl)pyrrolidin-1-yl)-3-fluorophenyl)-1H-pyrazolo[3,4-d]pyrimidin-3-yl)benzyl)-5-fluoro-2-methoxybenzamide To a solution of (S)-3-(1-oxo-5-(piperazin-1-yl)isoindolin-2-yl)piperidine-2,6-dione (150 mg, 0.3 mmol) in MeOH/DMF/AcOH (5 mL, 2:1:0.02) was added (S)—N-(4-(4-amino-1-(3-fluoro-4-(3-formylpyrrolidin-1-yl)phenyl)-1H-pyrazolo[3,4-d]pyrimidin-3-yl)benzyl)-5-fluoro-2-methoxybenzamide (150 mg, 0.25 mmol), TEA (52 mg, 0.51 mmol) and NaBH$_3$CN (48 mg, 0.77 mmol). The reaction was stirred at 60° C. for 1 hour. The reaction mixture was cooled to room temperature and then quenched with water. The mixture was extracted with DCM, washed with brine, dried over Na$_2$SO$_4$ and concentered in vacuum. The residue was purified by Prep-TLC with DCM:MeOH=10:1 to afford the desired product (60 mg, 26.0%) as a white solid. LC/MS: 896.7 [M+H]$^+$.

$^1$H NMR (400 MHz,) δ 10.92 (s, 1H), 8.86 (t, J=6.1 Hz, 1H), 8.32 (s, 1H), 7.89 (dd, J=15.2, 2.5 Hz, 1H), 7.79 (dd, J=8.8, 2.0 Hz, 1H), 7.69 (d, J=8.2 Hz, 2H), 7.52-7.47 (m, 4H), 7.34-7.28 (m, 1H), 7.16 (dd, J=9.1, 4.3 Hz, 1H), 7.03 (d, J=8.2 Hz, 2H), 6.84 (t, J=9.5 Hz, 1H), 5.02 (dd, J=13.3, 5.1 Hz, 1H), 4.57 (d, J=6.1 Hz, 2H), 4.30 (d, J=17.0 Hz, 1H), 4.17 (d, J=17.0 Hz, 1H), 3.88 (s, 3H), 3.51-3.45 (m, 1H), 3.42-3.37 (m, 2H), 3.27-3.25 (m, 3H), 3.21-3.11 (m, 2H), 2.90-2.81 (m, 1H), 2.60-2.52 (m, 6H), 2.41-2.24 (m, 4H), 2.07-2.01 (m, 1H), 1.95-1.89 (m, 1H), 1.69-1.62 (m, 1H).

Example 80: Preparation of N-(4-(4-amino-1-(4-((S)-3-((4-(2-((S)-2,6-dioxopiperidin-3-yl)-1-oxoisoindolin-5-yl)piperazin-1-yl)methyl)pyrrolidin-1-yl)-3-fluorophenyl)-1H-pyrazolo[3,4-d]pyrimidin-3-yl)benzyl)-5-fluoro-2-methoxybenzamide (Compound 96)
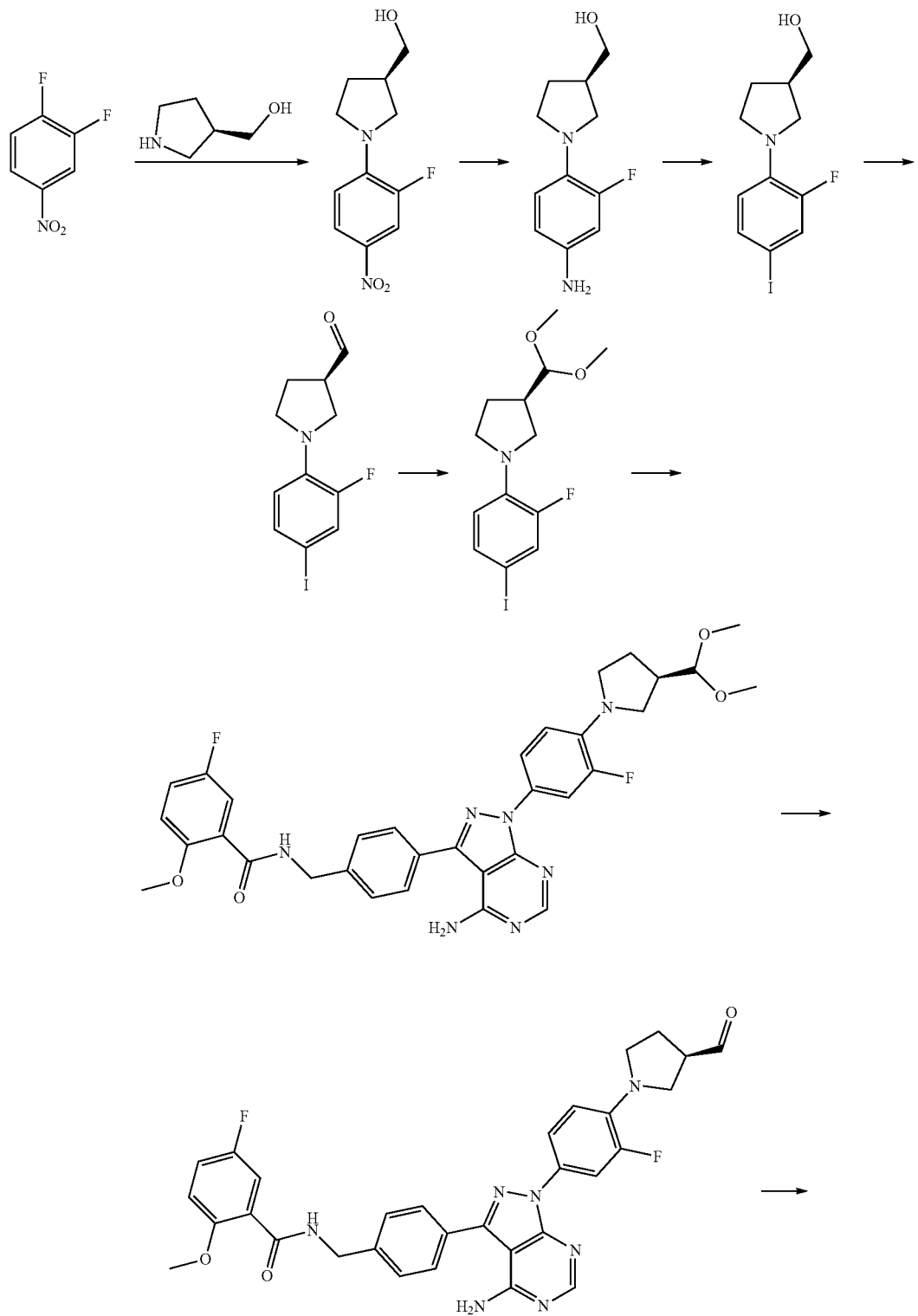

-continued

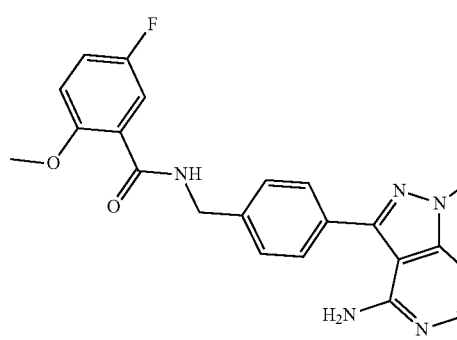

Compound 96 was prepared analogously with the procedure described for compound 95.

LC/MS: 896.6 [M+H]⁺.

1H NMR (400 MHz, DMSO) δ 10.98 (s, 1H), 9.61 (bs, 1H), 8.93-8.90 (m, 1H), 8.38 (s, 1H), 7.99-7.85 (m, 2H), 7.73 (d, J=8.2 Hz, 2H), 7.63-7.50 (m, 4H), 7.39-7.33 (m, 1H), 7.20 (m, 3H), 6.94-6.89 (m, 1H), 5.07 (m, 1H), 4.61 (d, J=6.1 Hz, 2H), 4.39-4.35 (m, 1H), 4.26-4.22 (m, 1H), 4.08-4.02 (m, 2H), 3.91 (s, 3H), 3.74-3.63 (m, 3H), 3.54-3.36 (m, 4H), 3.28-3.13 (m, 5H), 2.95-2.76 (m, 3H), 2.64-2.56 (m, 1H), 2.43-2.34 (m, 1H), 2.26-2.18 (m, 1H), 2.00-1.94 (m, 1H), 1.82-1.74 (m, 1H).

Example 81: Preparation of (S)—N-(4-(4-amino-1-(6-(3-((4-(2-(2,6-dioxopiperidin-3-yl)-1-oxoisoindolin-5-yl)piperazin-1-yl)methyl)azetidin-1-yl)pyridin-3-yl)-1H-pyrazolo[3,4-d]pyrimidin-3-yl)benzyl)-5-fluoro-2-methoxybenzamide (Compound 97)

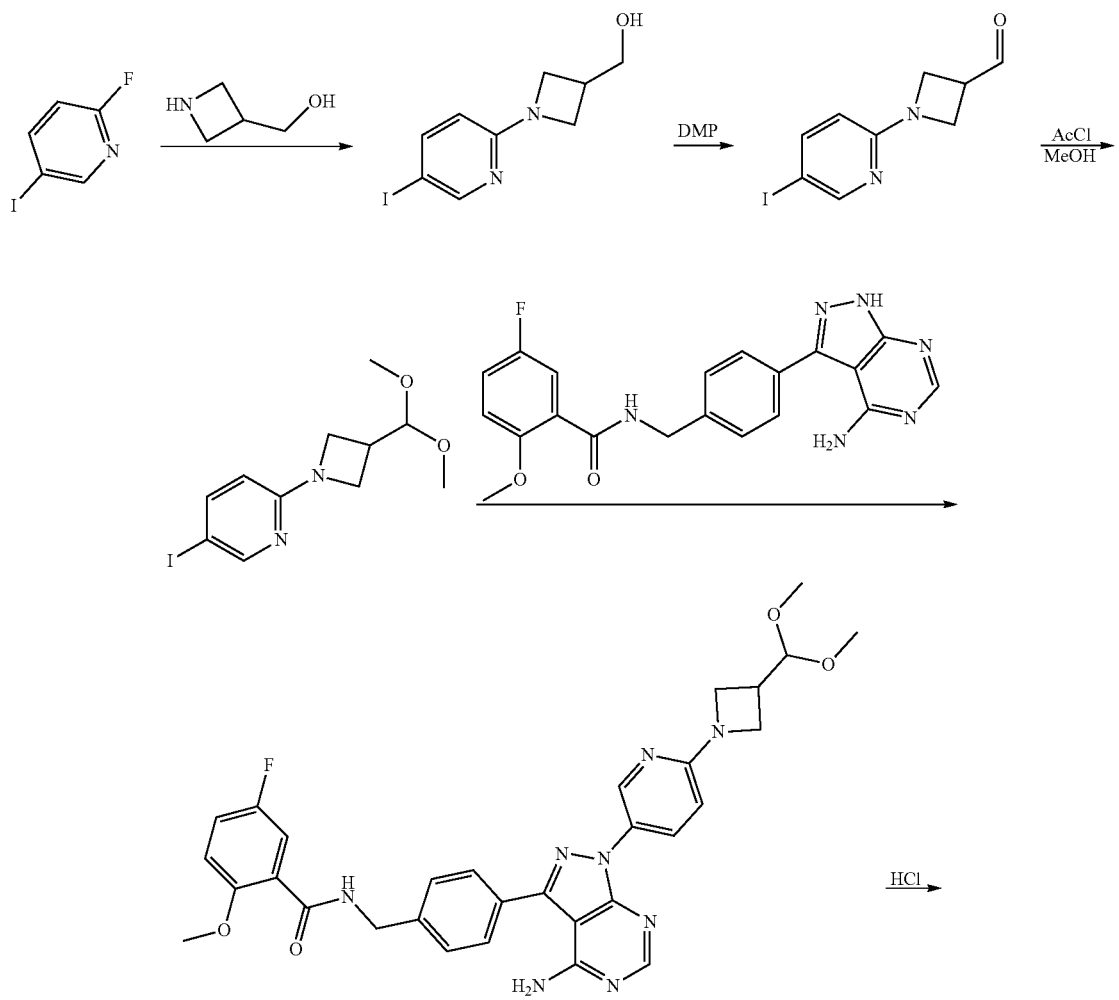

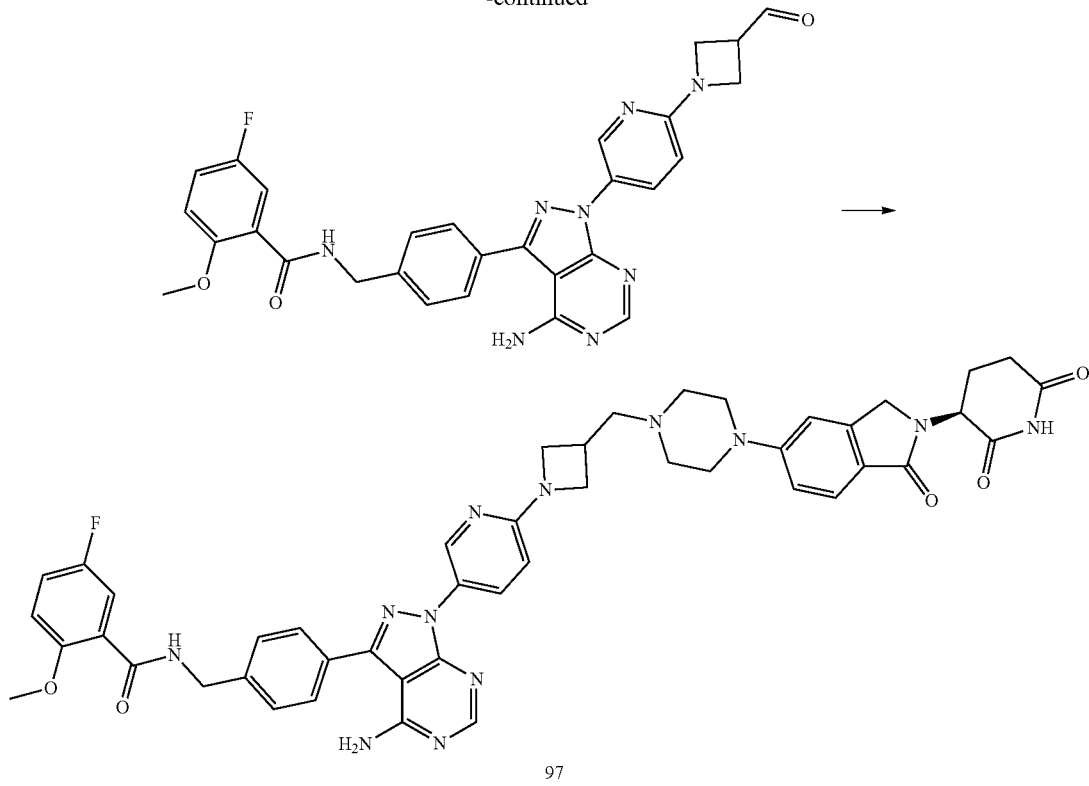

97

Step 1: Preparation of (1-(5-iodopyridin-2-yl)azetidin-3-yl)methanol

To a solution of 2-fluoro-5-iodopyridine (2.2 g, 9.86 mmol) in DMA (100 mL) stirred under argon at room temperature was added azetidin-3-ylmethanol (1.2 g, 9.86 mmol) and potassium carbonate (4.1 g, 29.59 mmol). The reaction mixture was stirred at 100° C. for overnight. The reaction was quenched by adding water (50 mL) and extracted with DCM (50 mL×3). The organic phase was washed with brine and dried over $Na_2SO_4$. The solvent was removed in vacuum and the residue was purified by flash column chromatography with PE:EA=5:1 to afford the desired product (1.5 g, 52.4%) as a yellow solid. LC/MS: 290.8 $[M+H]^+$.

Step 2: Preparation of 1-(5-iodopyridin-2-yl)azetidine-3-carbaldehyde

To a solution [1-(5-iodopyridin-2-yl)azetidin-3-yl]methanol (1.4 g, 4.82 mmol) in DCM (80 mL) stirred at room temperature was added Dess-Martin periodinane (3 g, 7.24 mmol). The reaction mixture was stirred at room temperature for 4 hours. The solvent was removed in vacuum and the residue was purified by flash with PE:EA=5:1 to afford the desired product (700 mg, 50.3%) as a yellow solid. LC/MS: 306.7 $[M+H_2O]^+$.

Step 3: Preparation of 2-(3-(dimethoxymethyl)azetidin-1-yl)-5-iodopyridine

To a solution of 1-(5-iodopyridin-2-yl) azetidine-3-carbaldehyde (700 mg, 2.42 mmol) in MeOH (10 mL) stirred under argon at 0° C. was added acetyl chloride (381 mg, 4.859 mmol). The reaction mixture was stirred at room temperature for 2 hours. The reaction was quenched with TEA (1 mL). The solvent was removed in vacuum and the residue was purified by flash column chromatography with PE:EA=5:1 to afford the desired product (400 mg, 49.2%). LC/MS: 334.8 $[M+H]^+$.

Step 4: Preparation of N-(4-(4-amino-1-(6-(3-(dimethoxymethyl)azetidin-1-yl)pyridin-3-yl)-1H-pyrazolo[3,4-d]pyrimidin-3-yl)benzyl)-5-fluoro-2-methoxybenzamide To a solution of 2-[3-(dimethoxymethyl)azetidin-1-yl]-5-iodopyridine (200 mg, 0.59 mmol) in DMSO (13 mL) was added N-[(4-{4-amino-1H-pyrazolo[3,4-d]pyrimidin-3-yl}phenyl)methyl]-5-fluoro-2-methoxybenzamide (282 mg, 0.71 mmol), $Na_2CO_3$ (139.5 mg, 1.31 mmol), copper(I) iodide (63 mg, 0.32 mmol) and N, N-dimethylglycine (67.89 mg, 0.65 mmol) stirred under nitrogen at 25° C. The reaction was stirred at 110° C. for overnight. The reaction was quenched by adding water (50 mL) and extracted with DCM (50 mL×3). The organic phase was washed with brine and dried over $Na_2SO_4$. The solvent was removed in vacuum and the residue was purified by flash column chromatography with DCM:MeOH=10:1 to afford the desired product (200 mg, 55.8%) as a white solid. LC/MS: 599.2 $[M+H]^+$.

Step 5: Preparation of N-(4-(4-amino-1-(6-(3-formylazetidin-1-yl)pyridin-3-yl)-1H-pyrazolo[3,4-d]pyrimidin-3-yl)benzyl)-5-fluoro-2-methoxybenzamide To a solution of N-{[4-(4-amino-1-{6-[3-(dimethoxymethyl)azetidin-1-yl]pyridin-3-yl}pyrazolo [3,4-d]pyrimidin- 3-yl)phenyl]methyl}-5-fluoro-2-methoxybenzamide (100 mg, 0.16 mmol) in DCM (10 mL) stirred at room temperature was added HCl/dioxane (10 mL). The reaction mixture was stirred at room temperature overnight. The solution was concentrated in vacuum to give the title compound (110 mg, crude) as a yellow solid. LC/MS: 553.2 [M+H]$^+$.

Step 6: Preparation of (S)—N-(4-(4-amino-1-(6-(3-((4-(2-(2,6-dioxopiperidin-3-yl)-1-oxoisoindolin-5-yl)piperazin-1-yl)methyl)azetidin-1-yl)pyridin-3-yl)-1H-pyrazolo[3,4-d]pyrimidin-3-yl) benzyl)-5-fluoro-2-methoxybenzamide To a solution of (S)-3-(1-oxo-5-(piperazin-1-yl)isoindolin-2-yl)piperidine-2,6-dione (105.6 mg, 0.217 mmol) in MeOH (6 mL)/DMF (3 mL) stirred under argon at room temperature was added TEA (37 mg, 0.36 mmol) and N-[(4-{4-amino-1-[6-(3-formylazetidin-1-yl)pyridin-3-yl]pyrazolo[3,4-d]pyrimidin-3-yl}phenyl)methyl]-5-fluoro-2-methoxybenzamide (100 mg, 0.181 mmol). Then NaBH$_3$CN (34 mg, 0.54 mmol) and AcOH (0.5 mL) was added. The reaction mixture was stirred at 60° C. for 1 hour. The reaction mixture was cooled to room temperature and quenched by adding water (10 mL). The mixture was extracted with DCM (10 mL×3). The combined organic phase was washed with brine and dried over Na$_2$SO$_4$. The solvent was removed in vacuum and the residue was purified by flash chromatography with DCM:MeOH=10:1 to afford the desired product (30 mg, 97.65% purity, 18.7% yield) as a white solid. LC/MS: 864.5 [M+H]$^+$.

$^1$H NMR (400 MHz, DMSO) δ 10.97 (s, 1H), 8.93 (t, J=6.0 Hz, 1H), 8.69 (s, 1H), 8.32 (s, 1H), 8.17-8.10 (m, 1H), 7.72 (d, J=8.4 Hz, 2H), 7.59-7.48 (m, 4H), 7.38-7.32 (m, 1H), 7.20 (dd, J=9.2, 4.3 Hz, 1H), 7.15-7.00 (m, 2H), 6.56 (d, J=9.2 Hz, 1H), 5.06 (dd, J=13.2, 5.1 Hz, 1H), 4.60 (d, J=6.0 Hz, 2H), 4.40-4.05 (m, 5H), 3.91 (s, 3H), 3.80-3.62 (m, 2H), 3.35-3.25 (m, 3H), 3.20-2.80 (m, 4H), 2.73-2.55 (m, 4H), 2.43-2.35 (m, 2H), 2.11-1.88 (m, 2H), 1.25-1.20 (m, 1H).

Testing of Compounds for BTK Activity

Example 82. BTK Degradative Activity of Exemplary Compounds of the Present Disclosure in a RAMOS Cell Line RAMOS (ATCC) cells were plated in 24-well plates at 8×10$^5$ cells/well in the RPMI growth medium containing 10% heat-inactivated FBS and 1× Penicillin Streptomycin, and then incubated at 37° C. overnight. The following day, the test compound was administered to the cells by using 1000× compound stock solution prepared in DMSO at various concentrations. After administration of the compound, the cells were then incubated at 37° C. for 6 hours.

Upon completion, the cells were collected by centrifugation and lysed in Laemmli sample buffer (1×; VWR International). Proteins in cell lysate were separated by SDS-PAGE and transferred to Odyssey nitrocellulose membranes (Licor) with Iblot® dry blotting transfer system (ThermoFisher). Nonspecific binding was blocked by incubating membranes with Intercept Blocking Buffer (Licor) for 1 hour at room temperature with gentle shaking. The membranes were then incubated overnight at 4° C. with primary antibodies anti-BTK (Cell signaling, cat. #8547) and anti-GAPDH (Cell signaling, cat. #5179) diluted in Intercept Blocking Buffer containing 0.1% Tween 20. After washing 3 times with TBS-T, the membranes were incubated with IRDye® 800CW goat anti-mouse IgG (1:20,000, Licor) or IRDye® 800CW goat anti-rabbit IgG (1:20,000, Licor) for 1 hour. After TBS-T washes, membranes were rinsed in TBS and scanned on Odyssey® CLx Imaging System (Licor). The bands were quantified using Image Studio™ Software (Licor).

Figure 2:
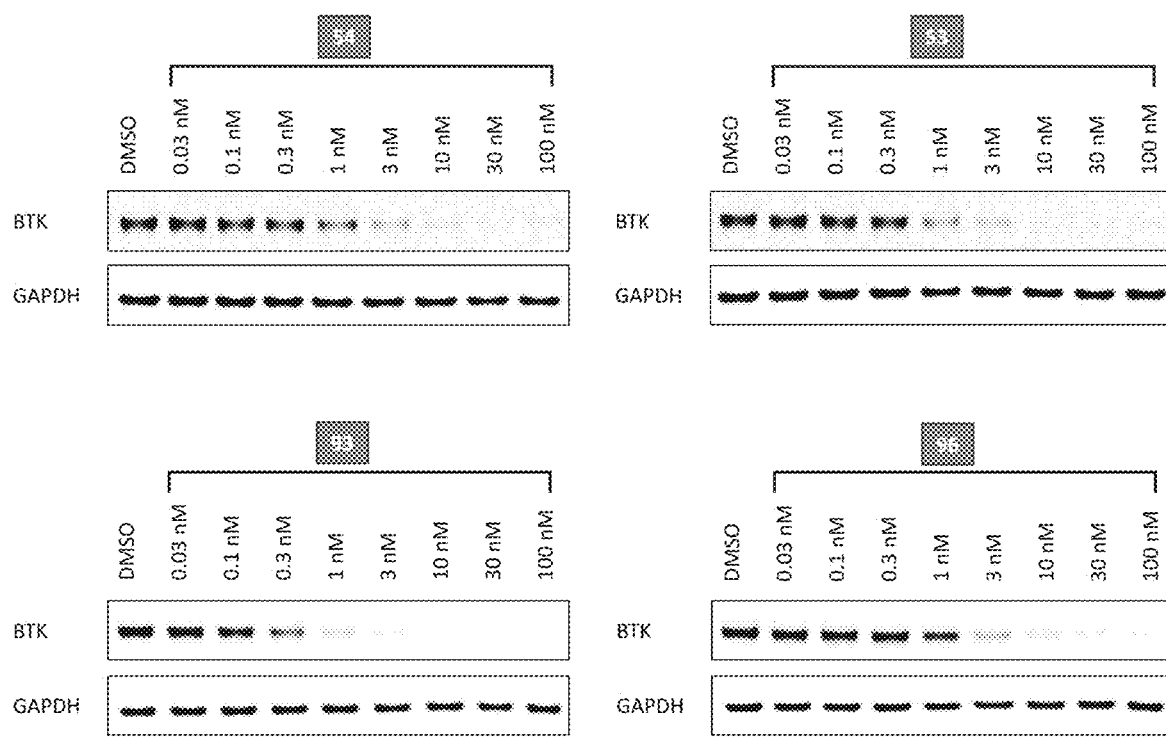
FIG. 2 illustrates the BTK degradative activity of compounds 53, 54, 93, and 96 in a RAMOS cell line 6 hours after administration.

FIG. 1 and FIG. 2 illustrate the BTK degradative activity of exemplary compounds 13, 25, 34, 42, 48, 49, 51, 53, 54, 78, 93 and 96 of the present disclosure in a RAMOS cell line 6 hours after administration.

Table 3 summarizes the BTK degradative activity of exemplary compounds of the present disclosure in a RAMOS cell line 6 hours after administration. The DC$_{50}$ values (i.e., the concentration of test compound at which 50% of the target protein is degraded) were calculated. A designation of "A" corresponds to a DC$_{50}$ value less than 10 nM. A designation of "B" corresponds to a DC$_{50}$ value greater than or equal to 10 nM and less than 100 nM. A designation of "C" corresponds to a DC$_{50}$ value greater than or equal to 100 nM.

TABLE 3

| Compound # | A: < 10 nM, B: ≥ 10 and < 100 nM, C: ≥ 100 nM<br>RAMOS BTK Degradation DC50 (nM) |
|---|---|
| 1 | C |
| 2 | C |
| 3 | C |
| 4 | C |
| 5 | C |
| 6 | C |
| 7 | B |
| 8 | B |
| 9 | B |
| 10 | C |
| 11 | B |
| 12 | B |
| 13 | A |
| 14 | B |
| 15 | C |
| 16 | B |
| 17 | B |
| 18 | C |
| 19 | B |
| 20 | B |
| 21 | B |
| 22 | B |
| 23 | B |
| 24 | B |
| 25 | A |
| 26 | B |
| 27 | B |
| 28 | B |
| 29 | B |
| 30 | C |
| 31 | B |
| 32 | B |
| 33 | B |
| 34 | A |
| 35 | C |
| 36 | C |
| 37 | B |
| 38 | C |
| 39 | C |
| 40 | C |
| 41 | C |
| 42 | A |
| 43 | A |
| 44 | C |
| 45 | C |
| 46 | C |
| 47 | C |
| 48 | A |
| 49 | A |
| 50 | B |
| 51 | A |

TABLE 3-continued

| Compound # | A: < 10 nM, B: ≥ 10 and < 100 nM, C: ≥ 100 nM RAMOS BTK Degradation DC50 (nM) |
|---|---|
| 52 | A |
| 53 | A |
| 54 | A |
| 55 | B |
| 58 | C |
| 60 | C |
| 61 | A |
| 62 | A |
| 63 | A |
| 64 | A |
| 65 | A |
| 66 | A |
| 71 | B |
| 72 | C |
| 73 | B |
| 74 | C |
| 75 | B |
| 76 | C |
| 77 | C |
| 78 | A |
| 79 | C |
| 80 | C |
| 85 | A |
| 92 | A |
| 93 | A |
| 94 | A |
| 95 | A |
| 96 | A |
| 97 | A |

Example 83. Generation of REC-1 BTK$^{C481S}$ Cell Line

The BTK gene in REC-1 cell line (ATCC) was edited by the CRISPR-Cas9 technology to create a C to S point mutation at residue 481 of BTK protein. For gene editing, first, gRNA complex was prepared with Alt-R CRISPR-Cas9 tracrRNA and crRNA BTK$^{C481S}$ (5'-GUAGUUCAG-GAGGCAGCCAU-3') (IDT-Integrated DNA Technologies), and then BTK$^{C481S}$ ribonucleoprotein (RNP) complex was prepared with gRNA complex and Alt-R S.p. Cas9 Nuclease V3 (IDT-Integrated DNA Technologies). Next, 1×10$^5$ REC-1 cells were electroporated with BTK$^{C481S}$ RNP complex, Alt-R Cas9 Electroporation Enhancer and BTKC481S Ultramer DNA Oligo (5'-AGCTGCT-GAGTCTGGAAGCGGTGGCGCATCTCCCTCAGA-TAGTTCAGGAGGGAGCC GTTGGC-CATGTACTCAGTGATGATGAAGATGGGGCGCTGCT-TGGTGCAG-3') (IDT-Integrated DNA Technologies) using Neon Transfection System (Thermo Fisher) under the condition of 1400 V, 10 ms, 3 pulses. Cells were then plated in a 96-well plate for 10 days and selected with 10 nM Ibrutinib for 5 passages. C481S mutation of BTK was further validated by Sanger Sequencing using gDNA extracted from these cells.

Growth Inhibitory Activity of Exemplary Compounds of the Present Disclosure in a BTK-Dependent REC-1 and REC-1 BTK$^{C481S}$ Cell Line.

REC-1 (ATCC) and REC-1 BTK$^{C481S}$ cells were plated in 96-well plates at 8,000 cells/well in 90 ul of RPMI growth medium containing 10% heat-inactivated FBS and 1× Penicillin Streptomycin, and then incubated at 37° C. overnight. The following day, the test compound was administered to the cells by using 10× compound stock solution prepared in growth medium at various concentrations. After administration of the compound, cells were then incubated at 37° C. for 6 days. Before CellTiter-Glo assay, the plates were equilibrated at room temperature for approximately 10 minutes. 100 ul of CellTiter-Glo® Reagent (Promega) was added to each well. The plates were then incubated at room temperature for 10 minutes and luminescence was recorded by EnSpire plate reader (PerkinElmer).

Table 4 summarizes the growth inhibitory activity of exemplary compounds of the present disclosure in a BTK-dependent REC-1 and REC1 BTK$^{C481S}$ cell line 6 days after administration.

The GI$_{50}$ values (i.e., the concentration of test compound at which 50% of cell growth are inhibited) were calculated. A designation of "A" corresponds to a DC$_{50}$ value less than 20 nM. A designation of "B" corresponds to a DC$_{50}$ value greater than or equal to 20 nM and less than 200 nM. A designation of "C" corresponds to a DC$_{50}$ value greater than or equal to 200 nM.

TABLE 4

| Compound # | A: < 20 nM, B: ≥ 20 and < 200 nM, C: ≥ 200 nM REC1 Cellular Grwoth Inhibition IC50 (nM) | A: < 20 nM, B: ≥ 20 and < 200 nM, C: ≥ 200 nM REC1 BTK$^{C481S}$ Cellular Grwoth Inhibition IC50 (nM) |
|---|---|---|
| 49 | A | A |
| 50 | A | N/A |
| 51 | A | N/A |
| 52 | A | N/A |
| 53 | A | N/A |
| 54 | A | N/A |
| 55 | C | N/A |
| 58 | C | N/A |
| 59 | A | A |
| 60 | B | N/A |
| 61 | A | N/A |
| 62 | B | N/A |
| 63 | B | N/A |
| 64 | B | N/A |
| 65 | A | A |
| 66 | A | A |
| 85 | A | A |
| 92 | B | N/A |
| 93 | A | A |
| 94 | A | A |
| 95 | A | A |
| 96 | A | A |
| 97 | A | A |

The many features and advantages of the present disclosure are apparent from the detailed specification, and thus it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described and accordingly, all suitable modifications and equivalents may be resorted to, falling within the scope of the present disclosure.

Moreover, those skilled in the art will appreciate that the conception upon which this disclosure is based may readily be used as a basis for designing other structures, methods, and systems for carrying out the several purposes of the present disclosure. Accordingly, the claims are not to be considered as limited by the foregoing description or examples.

What is claimed is:

1. A compound of Formula (I):

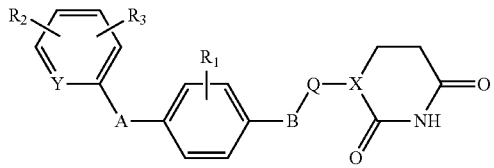

(I)

or a pharmaceutically acceptable salt, stereoisomer, deuterated isotope, or tautomer thereof,
wherein:
A is —C(O)NH(C$_1$-C$_5$ alkylene)-;
B is:

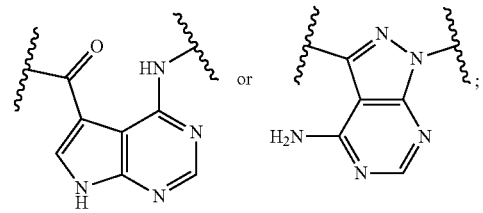 [SMILES: *Nc1ncnc2[nH]cc(C(*)=O)c12 ; *c1nn(*)c2ncnc(N)c12]

Q is -LW$_1$-;
L is a linker of the following formula:
-(heterocycloalkylene or arylene)-(heterocycloalkylene)-(C$_1$-C$_{17}$ alkylene)-(heterocycloalkylene)-,
wherein each heterocycloalkylene and arylene is optionally and independently substituted with 1, 2, or 3 independently selected R$_7$ substituents;
W$_1$ is:

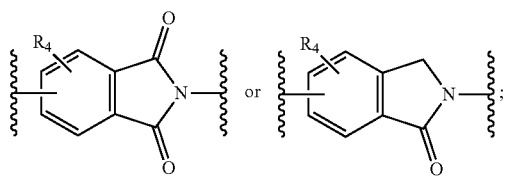

R$_1$ is H, halogen, CN, C$_1$-C$_3$ alkyl, C$_1$-C$_3$ haloalkyl, NH$_2$, N(alkyl)$_2$, OH, or OC$_1$-C$_4$ alkyl;
R$_2$ is H, halogen, CN, C$_1$-C$_5$ alkyl, C$_1$-C$_5$ deuteroalkyl, C$_1$-C$_5$ haloalkyl, N(alkyl)$_2$, OH, OC$_1$-C$_5$ alkyl, or OC$_1$-C$_5$ deuteroalkyl;
R$_3$ is H, halogen, CN, C$_1$-C$_5$ alkyl, C$_1$-C$_5$ deuteroalkyl, C$_1$-C$_5$ haloalkyl, N(alkyl)$_2$, OH, OC$_1$-C$_5$ alkyl, or OC$_1$-C$_5$ deuteroalkyl;
R$_4$ is H, halogen, CN, C$_1$-C$_5$ alkyl, C$_1$-C$_5$ haloalkyl, or OC$_1$-C$_5$ alkyl;
each R$_6$ is independently H, C$_1$-C$_3$ alkyl, C(O)C$_1$-C$_3$ alkyl, C(O)NHC$_1$-C$_3$ alkyl, or C(O)OC$_1$-C$_3$ alkyl, wherein each C$_1$-C$_3$ alkyl, C(O)C$_1$-C$_3$ alkyl, C(O)NHC$_1$-C$_3$ alkyl, and C(O)OC$_1$-C$_3$ alkyl is optionally and independently substituted with 1, 2, or 3 independently selected R$_7$ substituents;
each R$_7$ is independently halogen, CN, C$_1$-C$_3$ alkyl, C$_1$-C$_3$ haloalkyl, N(R$_6$)$_2$, OH, or OC$_1$-C$_3$ alkyl;

X is CH; and
Y is CH.

2. The compound according to claim 1, or a pharmaceutically acceptable salt, stereoisomer, deuterated isotope, or tautomer thereof, wherein A is —C(O)NHCH$_2$—.

3. The compound according to claim 1, or a pharmaceutically acceptable salt, stereoisomer, deuterated isotope, or tautomer thereof, wherein each heterocyclalkylene or arylene of L is independently selected from the group consisting of:

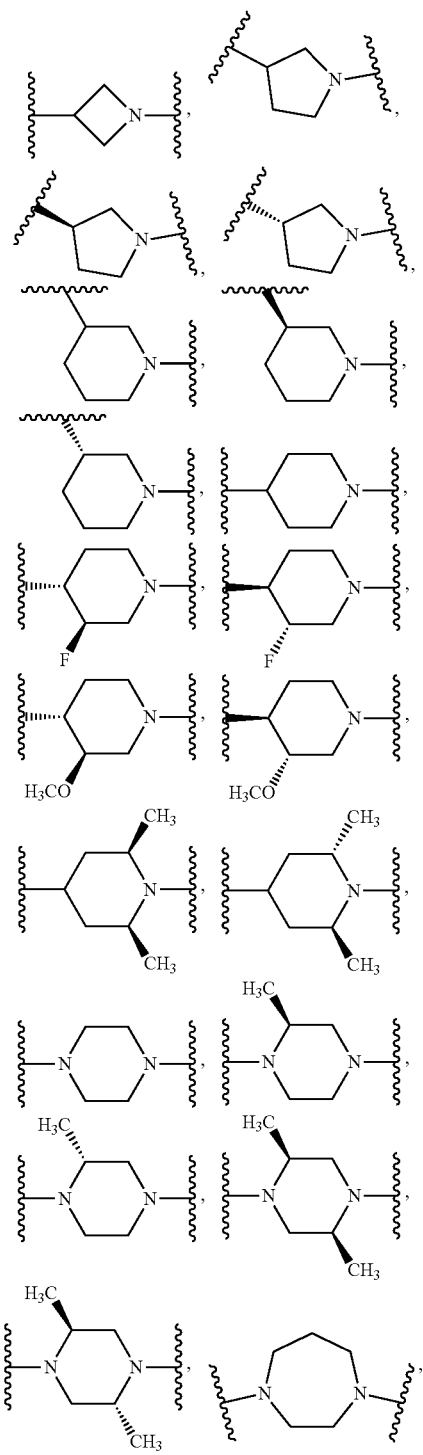

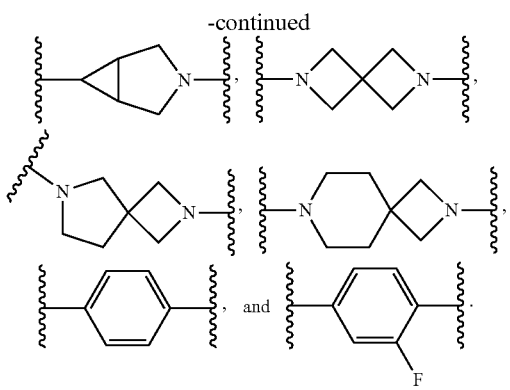

4. The compound according to claim 1, or a pharmaceutically acceptable salt, stereoisomer, deuterated isotope, or tautomer thereof, wherein $R_1$ is H, F, Cl, Br, I, $CH_3$, $CF_3$, or $CH(CH_3)_2$.

5. The compound according to claim 4, or a pharmaceutically acceptable salt, stereoisomer, deuterated isotope, or tautomer thereof, wherein $R_1$ is H, F, Cl, or Br.

6. The compound according to claim 1, or a pharmaceutically acceptable salt, stereoisomer, deuterated isotope, or tautomer thereof, wherein:
$R_2$ is H, halogen, $C_1$-$C_4$ alkyl, $CD_3$, $OC_1$-$C_4$ alkyl, or $OCD_3$; and
$R_3$ is H, halogen, $C_1$-$C_4$ alkyl, $CD_3$, $OC_1$-$C_4$ alkyl, or $OCD_3$.

7. The compound according to claim 6, or a pharmaceutically acceptable salt, stereoisomer, deuterated isotope, or tautomer thereof, wherein:
$R_2$ is F; and
$R_3$ is $OCH_3$.

8. The compound according to claim 6, or a pharmaceutically acceptable salt, stereoisomer, deuterated isotope, or tautomer thereof, wherein:
$R_2$ is $OCH_3$; and
$R_3$ is F.

9. The compound according to claim 1, or a pharmaceutically acceptable salt, stereoisomer, deuterated isotope, or tautomer thereof, wherein $R_4$ is H, halogen, CN, or $C_1$-$C_4$ haloalkyl.

10. The compound according to claim 9, or a pharmaceutically acceptable salt, stereoisomer, deuterated isotope, or tautomer thereof, wherein $R_4$ is H, F, Cl, Br, I, CN, or $C_1$-$C_4$ haloalkyl.

11. The compound according to claim 1, wherein the compound is of Formula (IB):

(IB)

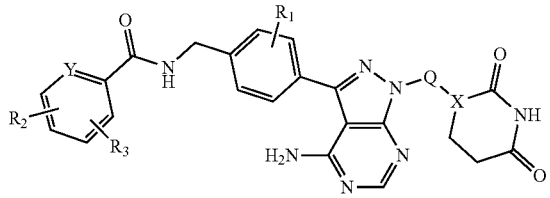

or a pharmaceutically acceptable salt, stereoisomer, deuterated isotope, or tautomer thereof.

12. A pharmaceutical composition comprising the compound according to claim 1, or a pharmaceutically acceptable salt, stereoisomer, deuterated isotope, or tautomer thereof, and at least one additional component selected from the group consisting of a pharmaceutical acceptable carrier, a pharmaceutically acceptable vehicle, and a pharmaceutically acceptable excipient.

13. A method for degrading Bruton's tyrosine kinase in a cell, wherein the method comprises contacting the cell with the compound according to claim 1, or a pharmaceutically acceptable salt, stereoisomer, deuterated isotope, or tautomer thereof.

14. A method for modulating Bruton's tyrosine kinase activity in a subject in need thereof, wherein the method comprises administering to the subject an effective amount of the compound according to claim 1, or a pharmaceutically acceptable salt, stereoisomer, deuterated isotope, or tautomer thereof.

15. The method according to claim 14, wherein the subject has a condition modulated by Bruton's tyrosine kinase selected from the group consisting of an autoimmune disease, cancer, an immunological disease, an inflammatory disorder, leukemia, and lymphoma.

16. The method according to claim 14, wherein the subject has a condition modulated by Bruton's tyrosine kinase selected from the group consisting of arthritis, B-cell lymphoma, B-cell malignancy, bone cancer, bone metastasis, chronic graft versus host disease, chronic lymphocytic leukemia, Crohn's disease, a disorder associated with renal transplant, follicular lymphoma, hairy cell leukemia, inflammatory bowel disease, irritable bowel syndrome, lupus, marginal zone lymphoma, mantle cell lymphoma, multiple myeloma, multiple sclerosis, non-Hodgkin lymphoma, osteoporosis, Sjogren's syndrome, small lymphocytic lymphoma, and Waldenström's macroglobulinemia.

17. The method according to claim 16, wherein the condition modulated by Bruton's tyrosine kinase is chronic graft versus host disease.

18. The method according to claim 16, wherein the condition modulated by Bruton's tyrosine kinase is chronic lymphocytic leukemia or small lymphocytic lymphoma.

19. The method according to claim 16, wherein the condition modulated by Bruton's tyrosine kinase is mantle cell lymphoma.

20. The method according to claim 16, wherein the condition modulated by Bruton's tyrosine kinase is marginal zone lymphoma.

21. The method according to claim 16, wherein the condition modulated by Bruton's tyrosine kinase is multiple sclerosis.

22. The method according to claim 16, wherein the condition modulated by Bruton's tyrosine kinase is Waldenström's macroglobulinemia.

23. The method according to claim 16, wherein the B-cell lymphoma is diffuse large B-cell lymphoma.

24. The method according to claim 16, wherein the non-Hodgkin lymphoma is B-cell non-Hodgkin lymphoma.

25. The method according to claim 14, wherein the method further comprises administering to the subject in need thereof an effective amount of the compound according to claim 1, or a pharmaceutically acceptable salt, stereoisomer, deuterated isotope, or tautomer thereof, in combination with at least one additional therapeutic agent.

26. The method according to claim 25, wherein the additional therapeutic agent is selected from the group consisting of bendamustine, bortezomib, chlorambucil, cyclophosphamide, dexamethasone, docetaxel, doxorubicin, endostatin, everolimus, fludarabine, fostamatinib, ibritumomab, idelalisib, ifosfamide, lenalidomide, mesalazine, ofatumumab, paclitaxel, pentostatin, prednisone, rituximab, temsirolimus, thalidomide, tositumomab, Venetoclax, and vincristine.

27. A method for modulating Bruton's tyrosine kinase activity in a subject in need thereof, wherein the method comprises administering to the subject an effective amount of the pharmaceutical composition according to claim 12.

28. A compound selected from the group consisting of:
(S)—N-(4-(4-amino-1-(4-(4-((4-(2-(2,6-dioxopiperidin-3-yl)-1-oxoisoindolin-5-yl)piperazin-1-yl)methyl)piperidin-1-yl)-3-fluorophenyl)-1H-pyrazolo[3,4-d]pyrimidin-3-yl)benzyl)-5-fluoro-2-methoxybenzamide;
N-(4-(4-amino-1-(4-(4-((4-(2-(2,6-dioxopiperidin-3-yl)-1,3-dioxoisoindolin-5-yl)piperazin-1-yl)methyl)piperidin-1-yl)-3-fluorophenyl)-1H-pyrazolo[3,4-d]pyrimidin-3-yl)benzyl)-5-fluoro-2-methoxybenzamide;
(S)—N-(4-(4-amino-1-(4-(4-((4-(2-(2,6-dioxopiperidin-3-yl)-6-fluoro-1-oxoisoindolin-5-yl)piperazin-1-yl)methyl)piperidin-1-yl)-3-fluorophenyl)-1H-pyrazolo[3,4-d]pyrimidin-3-yl)benzyl)-5-fluoro-2-methoxybenzamide;
(S)—N-(4-(4-amino-1-(1-(5-((4-(2-(2,6-dioxopiperidin-3-yl)-1-oxoisoindolin-5-yl)piperazin-1-yl)methyl)pyridin-2-yl)piperidin-4-yl)-1H-pyrazolo[3,4-d]pyrimidin-3-yl)benzyl)-5-fluoro-2-methoxybenzamide;
(S)—N-(4-(4-amino-1-(1-(4-((4-(2-(2,6-dioxopiperidin-3-yl)-1-oxoisoindolin-5-yl)piperazin-1-yl)methyl)phenyl)piperidin-4-yl)-1H-pyrazolo[3,4-d]pyrimidin-3-yl)benzyl)-5-fluoro-2-methoxybenzamide;
(S)—N-(4-(4-amino-1-(1-(5-((4-(2-(2,6-dioxopiperidin-3-yl)-1-oxoisoindolin-5-yl)piperazin-1-yl)methyl)pyridin-2-yl)azetidin-3-yl)-1H-pyrazolo[3,4-d]pyrimidin-3-yl)benzyl)-5-fluoro-2-methoxybenzamide;
N-(4-(4-amino-1-(1-(5-(4-(2-((S)-2,6-dioxopiperidin-3-yl)-1-oxoisoindolin-5-yl)piperazin-1-yl)pentanoyl)pyrrolidin-3-yl)-1H-pyrazolo[3,4-d]pyrimidin-3-yl)benzyl)-5-fluoro-2-methoxybenzamide;
N-(4-(4-amino-1-((S)-1-(5-((4-(2-((S)-2,6-dioxopiperidin-3-yl)-1-oxoisoindolin-5-yl)piperazin-1-yl)methyl)pyridin-2-yl)pyrrolidin-3-yl)-1H-pyrazolo[3,4-d]pyrimidin-3-yl)benzyl)-5-fluoro-2-methoxybenzamide;
N-(4-(4-amino-1-((R)-1-(5-((4-(2-((S)-2,6-dioxopiperidin-3-yl)-1-oxoisoindolin-5-yl)piperazin-1-yl)methyl)pyridin-2-yl)pyrrolidin-3-yl)-1H-pyrazolo[3,4-d]pyrimidin-3-yl)benzyl)-5-fluoro-2-methoxybenzamide;
N-(4-(4-amino-1-(1-(6-((4-(2-((S)-2,6-dioxopiperidin-3-yl)-1-oxoisoindolin-5-yl)piperazin-1-yl)methyl)pyridin-3-yl)pyrrolidin-3-yl)-1H-pyrazolo[3,4-d]pyrimidin-3-yl)benzyl)-5-fluoro-2-methoxybenzamide;
(S)—N-(4-(4-amino-1-(6-(4-((4-(2-(2,6-dioxopiperidin-3-yl)-1-oxoisoindolin-5-yl)piperazin-1-yl)methyl)piperidin-1-yl)pyridin-3-yl)-1H-pyrazolo[3,4-d]pyrimidin-3-yl)benzyl)-5-fluoro-2-methoxybenzamide;
N-(4-(4-amino-1-(1-(4-((4-(2-((S)-2,6-dioxopiperidin-3-yl)-1-oxoisoindolin-5-yl)piperazin-1-yl)methyl)phenyl)pyrrolidin-3-yl)-1H-pyrazolo[3,4-d]pyrimidin-3-yl)benzyl)-5-fluoro-2-methoxybenzamide;
(S)—N-(4-(4-amino-1-(1-(4-((4-(2-(2,6-dioxopiperidin-3-yl)-1-oxoisoindolin-5-yl)piperazin-1-yl)methyl)phenyl)azetidin-3-yl)-1H-pyrazolo[3,4-d]pyrimidin-3-yl)benzyl)-5-fluoro-2-methoxybenzamide;
(S)—N-(4-(4-amino-1-(1-(4-((4-(2-(2,6-dioxopiperidin-3-yl)-1-oxoisoindolin-5-yl)piperazin-1-yl)methyl)benzoyl)azetidin-3-yl)-1H-pyrazolo[3,4-d]pyrimidin-3-yl)benzyl)-5-fluoro-2-methoxybenzamide;
N-(4-(4-amino-1-(1-(4-((4-(2-((S)-2,6-dioxopiperidin-3-yl)-1-oxoisoindolin-5-yl)piperazin-1-yl)methyl)benzoyl)pyrrolidin-3-yl)-1H-pyrazolo[3,4-d]pyrimidin-3-yl)benzyl)-5-fluoro-2-methoxybenzamide;
N-(4-(4-amino-1-(1-(6-(4-((4-(2-((S)-2,6-dioxopiperidin-3-yl)-1-oxoisoindolin-5-yl)piperazin-1-yl)hexanoyl)pyrrolidin-3-yl)-1H-pyrazolo[3,4-d]pyrimidin-3-yl)benzyl)-5-fluoro-2-methoxybenzamide;
N-(4-(4-amino-1-(4-(3-((4-(2-((S)-2,6-dioxopiperidin-3-yl)-1-oxoisoindolin-5-yl)piperazin-1-yl)methyl)pyrrolidin-1-yl)-3-fluorophenyl)-1H-pyrazolo[3,4-d]pyrimidin-3-yl)benzyl)-5-fluoro-2-methoxybenzamide;
N-(4-(4-amino-1-(6-(3-((4-(2-((S)-2,6-dioxopiperidin-3-yl)-1-oxoisoindolin-5-yl)piperazin-1-yl)methyl)pyrrolidin-1-yl)pyridin-3-yl)-1H-pyrazolo[3,4-d]pyrimidin-3-yl)benzyl)-5-fluoro-2-methoxybenzamide;
N-(4-(4-amino-1-(4-(6-((4-(2-((S)-2,6-dioxopiperidin-3-yl)-1-oxoisoindolin-5-yl)piperazin-1-yl)methyl)-3-azabicyclo[3.1.0]hexan-3-yl)-3-fluorophenyl)-1H-pyrazolo[3,4-d]pyrimidin-3-yl)benzyl)-5-fluoro-2-methoxybenzamide;
N-(4-(4-amino-1-(4-((1R,5S,6s)-6-((4-(2-((S)-2,6-dioxopiperidin-3-yl)-1-oxoisoindolin-5-yl)piperazin-1-yl)methyl)-3-azabicyclo[3.1.0]hexan-3-yl)-3-fluorophenyl)-1H-pyrazolo[3,4-d]pyrimidin-3-yl)benzyl)-5-fluoro-2-methoxybenzamide;
N-(4-(4-amino-1-(4-((1R,5S,6r)-6-((4-(2-((S)-2,6-dioxopiperidin-3-yl)-1-oxoisoindolin-5-yl)piperazin-1-yl)methyl)-3-azabicyclo[3.1.0]hexan-3-yl)-3-fluorophenyl)-1H-pyrazolo[3,4-d]pyrimidin-3-yl)benzyl)-5-fluoro-2-methoxybenzamide;
(S)—N-(4-(4-amino-1-(4-(4-((4-(2-(2,6-dioxopiperidin-3-yl)-1-oxoisoindolin-5-yl)piperazin-1-yl)methyl)piperidin-1-yl)-3-fluorophenyl)-1H-pyrazolo[3,4-d]pyrimidin-3-yl)benzyl)picolinamide;
N-(4-(4-amino-1-(4-((R)-3-((4-(2-((S)-(2,6-dioxopiperidin-3-yl)-6-fluoro-1-oxoisoindolin-5-yl)piperazin-1-yl)methyl)pyrrolidin-1-yl)-3-fluorophenyl)-1H-pyrazolo[3,4-d]pyrimidin-3-yl)benzyl)picolinamide;
N-(4-(4-amino-1-(4-((S)-3-((4-(2-((S)-(2,6-dioxopiperidin-3-yl)-6-fluoro-1-oxoisoindolin-5-yl)piperazin-1-yl)methyl)pyrrolidin-1-yl)-3-fluorophenyl)-1H-pyrazolo[3,4-d]pyrimidin-3-yl)benzyl)picolinamide;
N-(4-(4-amino-1-(1-(1'-(2-(2,6-dioxopiperidin-3-yl)-1,3-dioxoisoindolin-5-yl)-[1,3'-biazetidin]-3-yl)piperidin-4-yl)-1H-pyrazolo[3,4-d]pyrimidin-3-yl)benzyl)-5-fluoro-2-methoxybenzamide;
N-(4-(4-amino-1-(1'-(1-(2-(2,6-dioxopiperidin-3-yl)-1,3-dioxoisoindolin-5-yl)azetidin-3-yl)-[1,4'-bipiperidin]-4-yl)-1H-pyrazolo[3,4-d]pyrimidin-3-yl)benzyl)-5-fluoro-2-methoxybenzamide;
(S)—N-(4-(4-amino-1-(4-(3-((4-(2-(2,6-dioxopiperidin-3-yl)-1-oxoisoindolin-5-yl)piperazin-1-yl)methyl)azetidin-1-yl)-3-fluorophenyl)-1H-pyrazolo[3,4-d]pyrimidin-3-yl)benzyl)-5-fluoro-2-methoxybenzamide;
(S)—N-(4-(4-amino-1-(1-(1-(2-(4-(2-(2,6-dioxopiperidin-3-yl)-1-oxoisoindolin-5-yl)piperazin-1-yl)ethyl)azetidin-3-yl)piperidin-4-yl)-1H-pyrazolo[3,4-d]pyrimidin-3-yl)benzyl)-5-fluoro-2-methoxybenzamide;
N-(4-(4-amino-1-(1-(1-(2-(4-(2-(2,6-dioxopiperidin-3-yl)-1,3-dioxoisoindolin-5-yl)piperazin-1-yl)ethyl)azetidin-3-yl)piperidin-4-yl)-1H-pyrazolo[3,4-d]pyrimidin-3-yl)benzyl)-5-fluoro-2-methoxybenzamide;
Trans-N-(4-(4-amino-1-(1-(3-(4-(2-(2,6-dioxopiperidin-3-yl)-1,3-dioxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide;
Cis-N-(4-(4-amino-1-(1-(3-(4-(2-(2,6-dioxopiperidin-3-yl)-1,3-dioxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide;

Trans-N-(4-(4-amino-1-(1-((1S,3r)-3-(4-(2-((S)-2,6-dioxopiperidin-3-yl)-1-oxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide;

Cis-N-(4-(4-amino-1-(1-(3-(4-(2-((S)-2,6-dioxopiperidin-3-yl)-1-oxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide;

N-(4-(4-amino-1-(1-(5-((4-(2-((S)-2,6-dioxopiperidin-3-yl)-1-oxoisoindolin-5-yl)piperazin-1-yl)methyl)pyridin-2-yl)pyrrolidin-3-yl)-1H-pyrazolo[3,4-d]pyrimidin-3-yl)benzyl)-5-fluoro-2-methoxybenzamide;

(S)—N-(4-(4-amino-1-(1-(1-(2-(4-(2-(2,6-dioxopiperidin-3-yl)-1-oxoisoindolin-5-yl)piperazin-1-yl)ethyl)azetidin-3-yl)piperidin-4-yl)-1H-pyrazolo[3,4-d]pyrimidin-3-yl)benzyl)-5-fluoro-2-methoxybenzamide;

N-(4-(4-amino-1-(1-(1-(2-(4-(2-(2,6-dioxopiperidin-3-yl)-1,3-dioxoisoindolin-5-yl)piperazin-1-yl)ethyl)azetidin-3-yl)piperidin-4-yl)-1H-pyrazolo[3,4-d]pyrimidin-3-yl)benzyl)-5-fluoro-2-methoxybenzamide;

Trans-N-(4-(4-amino-1-(1-(3-(4-(2-(2,6-dioxopiperidin-3-yl)-1,3-dioxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide;

Cis-N-(4-(4-amino-1-(1-(3-(4-(2-(2,6-dioxopiperidin-3-yl)-1,3-dioxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide;

Trans-N-(4-(4-amino-1-(1-((1S,3r)-3-(4-(2-((S)-2,6-dioxopiperidin-3-yl)-1-oxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide;

Cis-N-(4-(4-amino-1-(1-(3-(4-(2-((S)-2,6-dioxopiperidin-3-yl)-1-oxoisoindolin-5-yl)piperazin-1-yl)cyclobutyl)piperidin-4-yl)-1H-pyrazolo[3,4-d]pyrimidin-3-yl)benzyl)-5-fluoro-2-methoxybenzamide;

N-(4-(4-amino-1-(1-(5-((4-(2-((S)-2,6-dioxopiperidin-3-yl)-1-oxoisoindolin-5-yl)piperazin-1-yl)methyl)pyridin-2-yl)pyrrolidin-3-yl)-1H-pyrazolo[3,4-d]pyrimidin-3-yl)benzyl)-5-fluoro-2-methoxybenzamide;

(S)—N-(4-(4-amino-1-(1-(2-(4-(2-(2,6-dioxopiperidin-3-yl)-1-oxoisoindolin-5-yl)piperazin-1-yl)ethyl)piperidin-4-yl)-1H-pyrazolo[3,4-d]pyrimidin-3-yl)benzyl)-5-fluoro-2-methoxybenzamide;

(S)—N-(4-(4-amino-1-(1-(2-(4-(2-(2,6-dioxopiperidin-3-yl)-3-oxoisoindolin-5-yl)piperazin-1-yl)ethyl)piperidin-4-yl)-1H-pyrazolo[3,4-d]pyrimidin-3-yl)benzyl)-5-fluoro-2-methoxybenzamide;

(S)—N-(4-(4-amino-1-(4-(4-((4-(2-(2,6-dioxopiperidin-3-yl)-1-oxoisoindolin-5-yl)piperazin-1-yl)methyl)piperidin-1-yl)phenyl)-1H-pyrazolo[3,4-d]pyrimidin-3-yl)benzyl)-5-fluoro-2-methoxybenzamide;

N-(4-(4-amino-1-(4-(4-((1-(2-(2,6-dioxopiperidin-3-yl)-1,3-dioxoisoindolin-5-yl)azetidin-3-yl)methyl)piperazin-1-yl)phenyl)-1H-pyrazolo[3,4-d]pyrimidin-3-yl)benzyl)-5-fluoro-2-methoxybenzamide;

(S)—N-(4-(4-amino-1-(4-(3-((4-(2-(2,6-dioxopiperidin-3-yl)-1-oxoisoindolin-5-yl)piperazin-1-yl)methyl)azetidin-1-yl)phenyl)-1H-pyrazolo[3,4-d]pyrimidin-3-yl)benzyl)-5-fluoro-2-methoxybenzamide;

5-(4-((1-(4-(4-amino-3-(4-((5-fluoro-2-methoxybenzamido)methyl)phenyl)-1H-pyrazolo[3,4-d]pyrimidin-1-yl)phenyl)azetidin-3-yl)methyl)piperazin-1-yl)-N-(2,6-dioxopiperidin-3-yl)picolinamide;

5-(4-((1-(4-(4-amino-3-(4-((5-fluoro-2-methoxybenzamido)methyl)phenyl)-1H-pyrazolo[3,4-d]pyrimidin-1-yl)-2-fluorophenyl)azetidin-3-yl)methyl)piperazin-1-yl)-N-(2,6-dioxopiperidin-3-yl)picolinamide;

6-(4-((1-(4-(4-amino-3-(4-((5-fluoro-2-methoxybenzamido)methyl)phenyl)-1H-pyrazolo[3,4-d]pyrimidin-1-yl)-2-fluorophenyl)azetidin-3-yl)methyl)piperazin-1-yl)-N-(2,6-dioxopiperidin-3-yl)nicotinamide;

N-(4-(4-amino-1-(4-(3-((4-(4-(2,6-dioxopiperidin-3-yl)carbamoyl)phenyl)piperazin-1-yl)phenyl)azetidin-1-yl)phenyl-1H-pyrazolo[3,4-d]pyrimidin-3-yl)benzyl)-5-fluoro-2-methoxybenzamide; and 5-(4-((1-(4-(4-amino-3-(4-((5-fluoro-2-methoxybenzamido)methyl)phenyl)-1H-pyrazolo[3,4-d]pyrimidin-1-yl)-2-fluorophenyl)piperidin-4-yl)methyl)piperazin-1-yl)-N-(2,6-dioxopiperidin-3-yl)picolinamide;

or a pharmaceutically acceptable salt, deuterated isotope, or tautomer thereof.

29. A pharmaceutical composition comprising the compound according to claim 28, or a pharmaceutically acceptable salt, stereoisomer, deuterated isotope, or tautomer thereof, and at least one additional component selected from the group consisting of a pharmaceutical acceptable carrier, a pharmaceutically acceptable vehicle, and a pharmaceutically acceptable excipient.

30. A compound selected from the group consisting of:

5-((7-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)heptyl)oxy)-2-(2,6-dioxopiperidin-3-yl)isoindoline-1,3-dione;

5-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)-2-(2,6-dioxopiperidin-3-yl)isoindoline-1,3-dione;

5-((6-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)hexyl)oxy)-2-(2,6-dioxopiperidin-3-yl)isoindoline-1,3-dione;

5-(3-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)propoxy)-2-(2,6-dioxopiperidin-3-yl)isoindoline-1,3-dione;

5-(2-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)ethoxy)-2-(2,6-dioxopiperidin-3-yl)isoindoline-1,3-dione;

5-((5-(4-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperazin-1-yl)pentyl)oxy)-2-(2,6-dioxopiperidin-3-yl)isoindoline-1,3-dione;

5-(4-(6-((R)-3-((5-(2-chloro-4-phenoxybenzoyl)-7H-pyrrolo[2,3-d]pyrimidin-4-yl)amino)piperidin-1-yl)-6-oxohexyl)piperazin-1-yl)-2-(2,6-dioxopiperidin-3-yl)isoindoline-1,3-dione;

5-(4-(7-((R)-3-((5-(2-chloro-4-phenoxybenzoyl)-7H-pyrrolo[2,3-d]pyrimidin-4-yl)amino)piperidin-1-yl)-7-oxoheptyl)piperazin-1-yl)-2-(2,6-dioxopiperidin-3-yl)isoindoline-1,3-dione;

5-(4-((5-((R)-3-((5-(2-chloro-4-phenoxybenzoyl)-7H-pyrrolo[2,3-d]pyrimidin-4-yl)amino)piperidine-1-carbonyl)pyridin-2-yl)methyl)piperazin-1-yl)-2-(2,6-dioxopiperidin-3-yl)isoindoline-1,3-dione;

5-(4-((1-(5-((R)-3-((5-(2-chloro-4-phenoxybenzoyl)-7H-pyrrolo[2,3-d]pyrimidin-4-yl)amino)piperidine-1-carbonyl)pyridin-2-yl)piperidin-4-yl)methyl)piperazin-1-yl)-2-(2,6-dioxopiperidin-3-yl)isoindoline-1,3-dione;

5-(4-(5-((R)-3-((5-(2-chloro-4-phenoxybenzoyl)-7H-pyr-rolo[2,3-d]pyrimidin-4-yl)amino)piperidin-1-yl)-5-oxopentyl)piperazin-1-yl)-2-(2,6-dioxopiperidin-3-yl)isoindoline-1,3-dione;

5-(4-(7-(4-((5-(2-chloro-4-phenoxybenzoyl)-7H-pyrrolo[2,3-d]pyrimidin-4-yl)amino)piperidin-1-yl)heptyl)piperazin-1-yl)-2-(2,6-dioxopiperidin-3-yl)isoindoline-1,3-dione;

(S)-3-(5-(4-(6-(4-((5-(2-chloro-4-phenoxybenzoyl)-7H-pyrrolo[2,3-d]pyrimidin-4-yl)amino)piperidin-1-yl)-6-oxohexyl)piperazin-1-yl)-1-oxoisoindolin-2-yl)piperidine-2,6-dione;

(S)-3-(5-(4-(5-((R)-3-((5-(2-chloro-4-phenoxybenzoyl)-7H-pyrrolo[2,3-d]pyrimidin-4-yl)amino)piperidin-1-yl)-5-oxopentyl)piperazin-1-yl)-1-oxoisoindolin-2-yl)piperidine-2,6-dione;

5-(4-(6-((R)-3-((5-(2-chloro-4-phenoxybenzoyl)-7H-pyrrolo[2,3-d]pyrimidin-4-yl)amino)piperidin-1-yl)hexyl)piperazin-1-yl)-2-(2,6-dioxopiperidin-3-yl)isoindoline-1,3-dione;

(S)-3-(5-(4-(6-((R)-3-((5-(2-chloro-4-phenoxybenzoyl)-7H-pyrrolo[2,3-d]pyrimidin-4-yl)amino)piperidin-1-yl)-6-oxohexyl)piperazin-1-yl)-1-oxoisoindolin-2-yl)piperidine-2,6-dione;

3-(5-(4-(7-((R)-3-((5-(2-chloro-4-phenoxybenzoyl)-7H-pyrrolo[2,3-d]pyrimidin-4-yl)amino)piperidin-1-yl)-7-oxoheptyl)piperazin-1-yl)-1-oxoisoindolin-2-yl)piperidine-2,6-dione;

5-(4-(6-(4-((5-(2-chloro-4-phenoxybenzoyl)-7H-pyrrolo[2,3-d]pyrimidin-4-yl)amino)piperidin-1-yl)hexyl)piperazin-1-yl)-2-(2,6-dioxopiperidin-3-yl)isoindoline-1,3-dione;

5-(4-(4-((R)-3-((5-(2-chloro-4-phenoxybenzoyl)-7H-pyrrolo[2,3-d]pyrimidin-4-yl)amino)piperidin-1-yl)-4-oxobutyl)piperazin-1-yl)-2-(2,6-dioxopiperidin-3-yl)isoindoline-1,3-dione;

(S)-3-(5-(4-(4-((R)-3-((5-(2-chloro-4-phenoxybenzoyl)-7H-pyrrolo[2,3-d]pyrimidin-4-yl)amino)piperidin-1-yl)-4-oxobutyl)piperazin-1-yl)-1-oxoisoindolin-2-yl)piperidine-2,6-dione;

(S)-3-(5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazin-1-yl)-1-oxoisoindolin-2-yl)piperidine-2,6-dione;

5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazin-1-yl)-2-(2,6-dioxopiperidin-3-yl)isoindoline-1,3-dione;

5-(4-(4-(4-((5-(2-chloro-4-phenoxybenzoyl)-7H-pyrrolo[2,3-d]pyrimidin-4-yl)amino)piperidin-1-yl)-4-oxobutyl)piperazin-1-yl)-2-(2,6-dioxopiperidin-3-yl)isoindoline-1,3-dione;

(S)-3-(5-(4-(4-(4-((5-(2-chloro-4-phenoxybenzoyl)-7H-pyrrolo[2,3-d]pyrimidin-4-yl)amino)piperidin-1-yl)-4-oxobutyl)piperazin-1-yl)-1-oxoisoindolin-2-yl)piperidine-2,6-dione;

(S)-3-(5-(4-(5-(4-((5-(2-chloro-4-phenoxybenzoyl)-7H-pyrrolo[2,3-d]pyrimidin-4-yl)amino)piperidin-1-yl)-5-oxopentyl)piperazin-1-yl)-1-oxoisoindolin-2-yl)piperidine-2,6-dione;

5-(4-(3-(4-((5-(2-chloro-4-phenoxybenzoyl)-7H-pyrrolo[2,3-d]pyrimidin-4-yl)amino)piperidin-1-yl)propyl)piperazin-1-yl)-2-(2,6-dioxopiperidin-3-yl)isoindoline-1,3-dione;

5-(4-(4-(4-((5-(2-chloro-4-phenoxybenzoyl)-7H-pyrrolo[2,3-d]pyrimidin-4-yl)amino)piperidin-1-yl)butyl)piperazin-1-yl)-2-(2,6-dioxopiperidin-3-yl)isoindoline-1,3-dione;

5-(4-(6-(4-((5-(2-chloro-4-phenoxybenzoyl)-7H-pyrrolo[2,3-d]pyrimidin-4-yl)amino)piperidin-1-yl)-6-oxohexyl)piperazin-1-yl)-2-(2,6-dioxopiperidin-3-yl)isoindoline-1,3-dione;

5-(4-(7-((R)-3-((5-(2-chloro-4-phenoxybenzoyl)-7H-pyrrolo[2,3-d]pyrimidin-4-yl)amino)piperidin-1-yl)heptyl)piperazin-1-yl)-2-(2,6-dioxopiperidin-3-yl)isoindoline-1,3-dione;

5-(4-(5-((R)-3-((5-(2-chloro-4-phenoxybenzoyl)-7H-pyrrolo[2,3-d]pyrimidin-4-yl)amino)piperidin-1-yl)pentyl)piperazin-1-yl)-2-(2,6-dioxopiperidin-3-yl)isoindoline-1,3-dione;

5-(4-(5-(4-((5-(2-chloro-4-phenoxybenzoyl)-7H-pyrrolo[2,3-d]pyrimidin-4-yl)amino)piperidin-1-yl)-5-oxopentyl)piperazin-1-yl)-2-(2,6-dioxopiperidin-3-yl)isoindoline-1,3-dione;

(S)-3-(5-(4-((1-((R)-3-((5-(2-chloro-4-phenoxybenzoyl)-7H-pyrrolo[2,3-d]pyrimidin-4-yl)amino)piperidine-1-carbonyl)piperidin-4-yl)methyl)piperazin-1-yl)-1-oxoisoindolin-2-yl)piperidine-2,6-dione;

5-(4-((1-((R)-3-((5-(2-chloro-4-phenoxybenzoyl)-7H-pyrrolo[2,3-d]pyrimidin-4-yl)amino)piperidine-1-carbonyl)piperidin-4-yl)methyl)piperazin-1-yl)-2-(2,6-dioxopiperidin-3-yl)isoindoline-1,3-dione;

5-(4-(5-(4-((5-(2-chloro-4-phenoxybenzoyl)-7H-pyrrolo[2,3-d]pyrimidin-4-yl)amino)piperidin-1-yl)pentyl)piperazin-1-yl)-2-(2,6-dioxopiperidin-3-yl)isoindoline-1,3-dione;

4-(9-(4-((5-(2-chloro-4-phenoxybenzoyl)-7H-pyrrolo[2,3-d]pyrimidin-4-yl)amino)piperidin-1-yl)-9-oxonon-1-yn-1-yl)-2-(2,6-dioxopiperidin-3-yl)isoindoline-1,3-dione;

4-(7-(4-((5-(2-chloro-4-phenoxybenzoyl)-7H-pyrrolo[2,3-d]pyrimidin-4-yl)amino)piperidin-1-yl)-7-oxohept-1-yn-1-yl)-2-(2,6-dioxopiperidin-3-yl)isoindoline-1,3-dione;

5-(4-(3-(2-(4-((5-(2-chloro-4-phenoxybenzoyl)-7H-pyrrolo[2,3-d]pyrimidin-4-yl)amino)piperidin-1-yl)-2-oxoethyl)cyclobutyl)piperazin-1-yl)-2-(2,6-dioxopiperidin-3-yl)isoindoline-1,3-dione;

4-(8-(4-((5-(2-chloro-4-phenoxybenzoyl)-7H-pyrrolo[2,3-d]pyrimidin-4-yl)amino)piperidin-1-yl)-8-oxooct-1-yn-1-yl)-2-(2,6-dioxopiperidin-3-yl)isoindoline-1,3-dione;

3-(4-(9-(4-((5-(2-chloro-4-phenoxybenzoyl)-7H-pyrrolo[2,3-d]pyrimidin-4-yl)amino)piperidin-1-yl)-9-oxonon-1-yn-1-yl)-1-oxoisoindolin-2-yl)piperidine-2,6-dione;

3-(4-(8-(4-((5-(2-chloro-4-phenoxybenzoyl)-7H-pyrrolo[2,3-d]pyrimidin-4-yl)amino) piperidin-1-yl)-8-oxooct-1-yn-1-yl)-1-oxoisoindolin-2-yl)piperidine-2,6-dione;

3-(4-(7-(4-((5-(2-chloro-4-phenoxybenzoyl)-7H-pyrrolo[2,3-d]pyrimidin-4-yl)amino)piperidin-1-yl)-7-oxohept-1-yn-1-yl)-1-oxoisoindolin-2-yl)piperidine-2,6-dione;

(S)-3-(5-(4-(3-(2-(4-((5-(2-chloro-4-phenoxybenzoyl)-7H-pyrrolo[2,3-d]pyrimidin-4-yl)amino)piperidin-1-yl)-2-oxoethyl)cyclobutyl)piperazin-1-yl)-1-oxoisoindolin-2-yl)piperidine-2,6-dione;

5-(4-(3-(2-((R)-3-((5-(2-chloro-4-phenoxybenzoyl)-7H-pyrrolo[2,3-d]pyrimidin-4-yl)amino)piperidin-1-yl)-2- oxoethyl)cyclobutyl)piperazin-1-yl)-2-(2,6-dioxopiperidin-3-yl)isoindoline-1,3-dione;

5-(4-(2-(1-(4-(((5-(2-chloro-4-phenoxybenzoyl)-7H-pyrrolo[2,3-d]pyrimidin-4-yl)amino)-2-fluorophenyl)piperidin-4-yl)ethyl)piperazin-1-yl)-2-(2,6-dioxopiperidin-3-yl)isoindoline-1,3-dione;

(S)-3-(5-(4-(2-(1-(4-(((5-(2-chloro-4-phenoxybenzoyl)-7H-pyrrolo[2,3-d]pyrimidin-4-yl)amino)-2-fluorophenyl)piperidin-4-yl)ethyl)piperazin-1-yl)-1-oxoisoindolin-2-yl)piperidine-2,6-dione;

(S)-3-(5-(4-((1-(4-(((5-(2-chloro-4-phenoxybenzoyl)-7H-pyrrolo[2,3-d]pyrimidin-4-yl)amino)-2-fluorophenyl)piperidin-4-yl)methyl)piperazin-1-yl)-1-oxoisoindolin-2-yl)piperidine-2,6-dione;

5-(4-((1-(4-(((5-(2-chloro-4-phenoxybenzoyl)-7H-pyrrolo[2,3-d]pyrimidin-4-yl)amino)-2-fluorophenyl)piperidin-4-yl)methyl)piperazin-1-yl)-2-(2,6-dioxopiperidin-3-yl)isoindoline-1,3-dione;

5-(4-(3-(2-(4-(((5-(2-chloro-4-phenoxybenzoyl)-7H-pyrrolo[2,3-d]pyrimidin-4-yl)amino)piperidin-1-yl)-2-oxoethyl)azetidin-1-yl)piperidin-1-yl)-2-(2,6-dioxopiperidin-3-yl)isoindoline-1,3-dione;

1-(5-(4-(6-(4-((5-(2-chloro-4-phenoxybenzoyl)-7H-pyrrolo[2,3-d]pyrimidin-4-yl)amino)piperidin-1-yl)-6-oxohexyl)piperazine-1-carbonyl)-2-methoxyphenyl)dihydropyrimidine-2,4(1H,3H)-dione;

1-(5-(4-(5-(4-((5-(2-chloro-4-phenoxybenzoyl)-7H-pyrrolo[2,3-d]pyrimidin-4-yl)amino)piperidin-1-yl)-5-oxopentyl)piperazine-1-carbonyl)-2-methoxyphenyl)dihydropyrimidine-2,4(1H,3H)-dione;

1-(5-(4-(2-(4-((5-(2-chloro-4-phenoxybenzoyl)-7H-pyrrolo[2,3-d]pyrimidin-4-yl)amino)piperidin-1-yl)-2-oxoethyl)-[1,4'-bipiperidine]-1'-carbonyl)-2-methoxyphenyl)dihydropyrimidine-2,4(1H,3H)-dione;

1-(5-(4-((1-(4-(((5-(2-chloro-4-phenoxybenzoyl)-7H-pyrrolo[2,3-d]pyrimidin-4-yl)amino)-2-fluorophenyl)piperidin-4-yl)methyl)piperazine-1-carbonyl)-2-methoxyphenyl)dihydropyrimidine-2,4(1H,3H)-dione;

1-(5-(4-((1-(4-(((5-(2-chloro-4-phenoxybenzoyl)-7H-pyrrolo[2,3-d]pyrimidin-4-yl)amino)-2-fluorophenyl)piperidin-4-yl)methyl)-1,4-diazepane-1-carbonyl)-2-methoxyphenyl)dihydropyrimidine-2,4(1H,3H)-dione;

1-(5-(4-(2-(1-(4-(((5-(2-chloro-4-phenoxybenzoyl)-7H-pyrrolo[2,3-d]pyrimidin-4-yl)amino)-2-fluorophenyl)piperidin-4-yl)ethyl)piperazine-1-carbonyl)-2-methoxyphenyl)dihydropyrimidine-2,4(1H,3H)-dione;

(R)-1-(5-(4-(2-(3-((5-(2-chloro-4-phenoxybenzoyl)-7H-pyrrolo[2,3-d]pyrimidin-4-yl)amino)piperidin-1-yl)-2-oxoethyl)-[1,4'-bipiperidine]-1'-carbonyl)-2-methoxyphenyl)dihydropyrimidine-2,4(1H,3H)-dione;

1-(5-(4-(7-(4-((5-(2-chloro-4-phenoxybenzoyl)-7H-pyrrolo[2,3-d]pyrimidin-4-yl)amino)piperidin-1-yl)-7-oxoheptyl)piperazine-1-carbonyl)-2-methoxyphenyl)dihydropyrimidine-2,4(1H,3H)-dione;

1-(5-(4-(4-(4-((5-(2-chloro-4-phenoxybenzoyl)-7H-pyrrolo[2,3-d]pyrimidin-4-yl)amino)piperidine-1-carbonyl)benzyl)-1,4-diazepane-1-carbonyl)-2-methoxyphenyl)dihydropyrimidine-2,4(1H,3H)-dione;

1-(5-(4-(4-(4-((5-(2-chloro-4-phenoxybenzoyl)-7H-pyrrolo[2,3-d]pyrimidin-4-yl)amino)piperidine-1-carbonyl)benzyl)piperazine-1-carbonyl)-2-methoxyphenyl)dihydropyrimidine-2,4(1H,3H)-dione;

or a pharmaceutically acceptable salt, deuterated isotope, or tautomer thereof.

\* \* \* \* \*

UNITED STATES PATENT AND TRADEMARK OFFICE
CERTIFICATE OF CORRECTION

PATENT NO. : 11,530,222 B2
APPLICATION NO. : 17/591051
DATED : December 20, 2022
INVENTOR(S) : Yimin Qian et al.

It is certified that error appears in the above-identified patent and that said Letters Patent is hereby corrected as shown below:

In the Claims

In Claim 3, Column 354, Line 8, "heterocyclalkylene" should read --heterocycloalkylene--.

In Claim 12, Column 356, Line 3, "a pharmaceutical acceptable carrier," should read --a pharmaceutically acceptable carrier,--.

In Claim 28, Column 360, Lines 9-12, "N-(4-(4-amino-1-(4-(3-((4-(4-(2,6-dioxopiperidin-3-yl)carbamoyl)phenyl)piperazin-1-yl)phenyl)azetidin-1-yl)phenyl-1H-pyrazolo[3,4-d]pyrimidin-3-yl)benzyl)-5-fluoro-2-methoxybenzamide;" should read --N-(4-(4-amino-1-(4-(3-((4-(4-((2,6-dioxopiperidin-3-yl)carbamoyl)phenyl)piperazin-1-yl)methyl)azetidin-1-yl)phenyl)-1H-pyrazolo [3,4-d]pyrimidin-3-yl)benzyl)-5-fluoro-2-methoxybenzamide;--.

In Claim 29, Column 360, Line 24, "a pharmaceutical acceptable carrier," should read --a pharmaceutically acceptable carrier,--.

Signed and Sealed this
Seventh Day of March, 2023

Katherine Kelly Vidal
*Director of the United States Patent and Trademark Office*